(12) United States Patent
Cronin et al.

(10) Patent No.: US 7,507,552 B1
(45) Date of Patent: Mar. 24, 2009

(54) CRYSTALLIZATION OF HISTONE DEACETYLASE 2

(75) Inventors: Ciaran N. Cronin, San Diego, CA (US);
Mark T. Hilgers, San Diego, CA (US);
Mark W. Knuth, El Cajon, CA (US);
Marc E. Navre, Encinitas, CA (US); Bi Ching Sang, San Diego, CA (US);
Robert J. Skene, San Diego, CA (US);
Leslie W. Tari, San Diego, CA (US);
Keith P. Wilson, La Jolla, CA (US);
Darbi Witmer, Encinitas, CA (US);
Hua Zou, San Diego, CA (US)

(73) Assignee: Takeda San Diego, Inc., San Diego, CA (US)

( * ) Notice: Subject to any disclaimer, the term of this patent is extended or adjusted under 35 U.S.C. 154(b) by 138 days.

(21) Appl. No.: 10/826,170

(22) Filed: Apr. 16, 2004

(51) Int. Cl.
*C12Q 1/34* (2006.01)
*C12N 9/78* (2006.01)
*G01N 33/483* (2006.01)
*G01N 31/00* (2006.01)
*G06G 7/58* (2006.01)

(52) U.S. Cl. ............... 435/18; 435/227; 702/27; 703/11; 436/4

(58) Field of Classification Search ............ None
See application file for complete search history.

(56) References Cited

U.S. PATENT DOCUMENTS

| | | | |
|---|---|---|---|
| 4,263,010 A | 4/1981 | Randolph | |
| 4,668,584 A | 5/1987 | Uzgiris et al. | |
| 4,755,363 A | 7/1988 | Fujita et al. | |
| 4,833,233 A | 5/1989 | Carter | |
| 4,886,646 A | 12/1989 | Carter et al. | |
| 4,919,899 A | 4/1990 | Herrmann et al. | |
| 5,078,975 A | 1/1992 | Rhodes et al. | |
| 5,096,676 A | 3/1992 | McPherson et al. | |
| 5,130,105 A | 7/1992 | Carter et al. | |
| 5,221,410 A | 6/1993 | Kushner et al. | |
| 5,400,741 A | 3/1995 | DeTitta et al. | |
| 5,419,278 A | 5/1995 | Carter | |
| 5,641,681 A | 6/1997 | Carter | |
| 5,643,540 A | 7/1997 | Carter et al. | |
| 5,728,559 A | 3/1998 | Nilsson et al. | |
| 6,812,339 B1 * | 11/2004 | Venter et al. | 536/24.31 |
| 7,169,801 B2 * | 1/2007 | Bressi et al. | 514/394 |
| 2004/0137518 A1 * | 7/2004 | Lambert et al. | 435/7.1 |

FOREIGN PATENT DOCUMENTS

| | | |
|---|---|---|
| WO | WO 99/23885 | 5/1999 |
| WO | WO 00/60345 | 10/2000 |
| WO | WO 02/08931 A1 | 1/2002 |
| WO | WO 03/035208 A1 | 5/2003 |
| WO | WO 03/064047 A1 | 8/2003 |

OTHER PUBLICATIONS

"Introduction to Protein Structure Second Edition," Branden and Tooze, Garland Publishing Inc., New York, 1999, pp. 374-375.*
"Principles of X-ray Crystallography," Drenth, Springer, New York, 1995, p. 1.*
Kierzek et al. Biophys Chem 91:1-20, 2001.*
GenBank Accession No. Q92769, GI:3023939, Feb. 1998.*
Wang et al. J Med Chem 48:6936-6947, 2005.*
Flower, "Drug Design, Cutting Edge Approaches," Royal Society of Chemistry, Cambridge, UK, 2002, 21-27.*
Branden et al., "Introduction to Protein Structure Second Edition", Garland Publishing Inc., New York, 1999, p. 382.*
Definition of "trimer" at Stedman's Online Medical Dictionary, www.stedmans.com, last viewed on Apr. 30, 2007, 1 page.*
"Developing using Crystallographic Maps" at www.ysbl.york.ac.uk/~cowtan/clipper/doc/p_develop_map.html, last viewed on Jan. 6, 2008.*
Skarzynski et al., "Industrial perspective on X-ray data collection and analysis", Acta Crystallogr D Biol Crystallogr D62:102-107, 2006.*
Finnin, Michael S. et al. "Structures of a histone deacetylase homologue bound to the TSA and SAHA inhibitors" Letters to Nature, vol. 401, Sep. 9, 1999.
Gililand, Gary L. et al. "Crystallization of biological macromolecules for X-ray diffraction studies" Current Opinion in Stuctural Bilogy 1996, 595-603.
Ke, Ailong et al. "Crystallization of RNA and RNA-protein complexes" Methods 34 (2004) 408-414.
Somaza, John R. et al. "Structure snapshots of human HDAC8 provide insights into the class I histone deascetylases" Structure, vol. 12, 1325-1334, Jul. 2004.
Wiencek, J.M. et al. "New structure for protein crystal growth" Annu. Rev. Biomed. Eng. 1999. 01-:505-534.
Stoddard et al. "Molecular recognition analayzed by docking simulations: The aspartae receptor and isocitrate dehydrogenase from *Eschericia coli*" Proc. Natl. Acad. Sci. USA (1992) vol. 90, pp. 1146-1153.
Brunger et al. "Crystallography & NMR System: A new Software Suite for Macromolecular Structure Determination" Acta Cryst, (1998), pp. 905-921.

* cited by examiner

*Primary Examiner*—David J Steadman
(74) *Attorney, Agent, or Firm*—David J. Weitz

(57) ABSTRACT

Provided are crystals relating to histone deacetylase 2 (HDAC-2) and its various uses.

11 Claims, 172 Drawing Sheets

FIGURE 1A

Amino acid sequence for full length human HDAC-2
[SEQ ID NO:1]

```
----MAYSQGGGKKKVCYYYDGDIGNYYYGQGHPMKPHRIRMTHNLLLNYGLYRKMEIYR      60
PHKATAEEMTKYHSDEYIKFLRSIRPDNMSEYSKQMQRFNVGEDCPVFDGLFEFCQLSTG     120
GSVAGAVKLNRQQTDMAVNWAGGLHHAKKSEASGFCYVNDIVLAILELLKYHQRVLYIDI     180
DIHHGDGVEEAFYTTDRVMTVSFHKYGEYFPGTGDLRDIGAGKGKYYAVNFPMRDGIDDE     240
SYGQIFKPIISKVMEMYQPSAVVLQCGADSLSGDRLGCFNLTVKGHAKCVEVVKTFNLPL     300
LMLGGGGYTIRNVARCWTYETAVALDCEIPNELPYNDYFEYFGPDFKLHISPSNMTNQNT     360
PEYMEKIKQRLFENLRMLPHAPGVQMQAIPEDAVHEDSGDEDGEDPDKRISIRASDKRIA     420
CDEEFSDSEDEGEGGRRNVADHKKGAKKARIEEDKKETEDKKTDVKEEDKSKDNSGEKTD     480
TKGTKSEQLSNP                                                    488
```

Human cDNA sequence encoding HDAC-2
[SEQ ID NO:2]

```
ATGGGATCCATGGCGTACAGTCAAGGAGGCGGCAAAAAAAAGTCTGCTACTACTACGAC      60
GGTGATATTGGAAATTATTATTATGGACAGGGTCATCCCATGAAGCCTCATAGAATCCGC     120
ATGACCCATAACTTGCTGTTAAATTATGGCTTATACAGAAAAATGGAAATATATAGGCCC     180
CATAAAGCCACTGCCGAAGAAATGACAAAATATCACAGTGATGAGTATATCAAATTTCTA     240
CGGTCAATAAGACCAGATAACATGTCTGAGTATAGTAAGCAGATGCAGAGATTTAATGTT     300
GGAGAAGATTGTCCAGTGTTTGATGGACTCTTTGAGTTTTGTCAGCTCTCAACTGGCGGT     360
TCAGTTGCTGGAGCTGTGAAGTTAAACCGACAACAGACTGATATGGCTGTTAATTGGGCT     420
GGAGGATTACATCATGCTAAGAAATCAGAAGCATCAGGATTCTGTTACGTTAATGATATT     480
GTGCTTGCCATCCTTGAATTACTAAAGTATCATCAGAGAGTCTTATATATTGATATAGAT     540
ATTCATCATGGTGATGGTGTTGAAGAAGCTTTTTATACAACAGATCGTGTAATGACGGTA     600
TCATTCCATAAATATGGGGAATACTTTCCTGGCACAGGAGACTTGAGGGATATTGGTGCT     660
GGAAAAGGCAAATACTATGCTGTCAATTTTCCAATGAGAGATGGTATAGATGATGAGTCA     720
TATGGGCAGATATTTAAGCCTATTATCTCAAAGGTGATGGAGATGTATCAACCTAGTGCT     780
GTGGTATTACAGTGTGGTGCAGACTCATTATCTGGTGATAGACTGGGTTGTTTCAATCTA     840
ACAGTCAAAGGTCATGCTAAATGTGTAGAAGTTGTAAAAACTTTTAACTTACCATTACTG     900
ATGCTTGGAGGAGGTGGCTACACAATCCGTAATGTTGCTCGATGTTGGACATATGAGACT     960
GCAGTTGCCCTTGATTGTGAGATTCCCAATGAGTTGCCATATAATGATTACTTTGAGTAT    1020
TTTGGACCAGACTTCAAACTGCATATTAGTCCTTCAAACATGACAAACCAGAACACTCCA    1080
GAATATATGGAAAAGATAAAACAGCGTTTGTTTGAAAATTTGCGCATGTTACCTCATGCA    1140
CCTGGTGTCCAGATGCAAGCTATTCCAGAAGATGCTGTTCATGAAGACAGTGGAGATGAA    1200
GATGGAGAAGATCCAGACAAGAGAATTTCTATTCGAGCATCAGACAAGCGGATAGCTTGT    1260
GATGAAGAATTCTCAGATTCTGAGGATGAAGGAGAAGGAGGTCGAAGAAATGTGGCTGAT    1320
CATAAGAAAGGAGCAAAGAAGCTAGAATTGAAGAAGATAAGAAAGAAACAGAGGACAAA    1480
AAAACAGACGTTAAGGAAGAAGATAAATCCAAGGACAACAGTGGTGAAAAAACAGATACC    1540
AAAGGAACCAAATCAGAACAGCTCAGCAACCCCGGGCATCACCATCACCATCACTAA      1597
```

FIGURE 1B

Amino acid sequence for full length human HDAC-2 with a C-terminal 6x-histidine tag
[SEQ ID NO:3]
(6x-histidine tag is underlined)

```
----MAYSQGGGKKKVCYYYDGDIGNYYYGQGHPMKPHRIRMTHNLLLNYGLYRKMEIYR    60
PHKATAEEMTKYHSDEYIKFLRSIRPDNMSEYSKQMQRFNVGEDCPVFDGLFEFCQLSTG   120
GSVAGAVKLNRQQTDMAVNWAGGLHHAKKSEASGFCYVNDIVLAILELLKYHQRVLYIDI   180
DIHHGDGVEEAFYTTDRVMTVSFHKYGEYFPGTGDLRDIGAGKGKYYAVNFPMRDGIDDE   240
SYGQIFKPIISKVMEMYQPSAVVLQCGADSLSGDRLGCFNLTVKGHAKCVEVVKTFNLPL   300
LMLGGGGYTIRNVARCWTYETAVALDCEIPNELPYNDYFEYFGPDFKLHISPSNMTNQNT   360
PEYMEKIKQRLFENLRMLPHAPGVQMQAIPEDAVHEDSGDEDGEDPDKRISIRASDKRIA   420
CDEEFSDSEDEGEGGRRNVADHKKGAKKARIEEDKKETEDKKTDVKEEDKSKDNSGEKTD   480
TKGTKSEQLSNPGHHHHHH                                           495
```

Amino acid sequence for CLEC fragment of human HDAC-2
[SEQ ID NO:4]

```
-------SQGGGKKKVCYYYDGDIGNYYYGQGHPMKPHRIRMTHNLLLNYGLYRKMEIYR    60
PHKATAEEMTKYHSDEYIKFLRSIRPDNMSEYSKQMQRFNVGEDCPVFDGLFEFCQLSTG   120
GSVAGAVKLNRQQTDMAVNWAGGLHHAKKSEASGFCYVNDIVLAILELLKYHQRVLYIDI   180
DIHHGDGVEEAFYTTDRVMTVSFHKYGEYFPGTGDLRDIGAGKGKYYAVNFPMRDGIDDE   240
SYGQIFKPIISKVMEMYQPSAVVLQCGADSLSGDRLGCFNLTVKGHAKCVEVVKTFNLPL   300
LMLGGGGYTIRNVARCWTYETAVALDCEIPNELPYNDYFEYFGPDFKLHISPSNMTNQNT   360
PEYMEKIKQRLFENLRMLPHAPGVQ                                     381
```

Amino acid sequence for immobilized Trypsin fragment of human HDAC-2
[SEQ ID NO:5]

```
----MAYSQGGGKKKVCYYYDGDIGNYYYGQGHPMKPHRIRMTHNLLLNYGLYRKMEIYR    60
PHKATAEEMTKYHSDEYIKFLRSIRPDNMSEYSKQMQRFNVGEDCPVFDGLFEFCQLSTG   120
GSVAGAVKLNRQQTDMAVNWAGGLHHAKKSEASGFCYVNDIVLAILELLKYHQRVLYIDI   180
DIHHGDGVEEAFYTTDRVMTVSFHKYGEYFPGTGDLRDIGAGKGKYYAVNFPMRDGIDDE   240
SYGQIFKPIISKVMEMYQPSAVVLQCGADSLSGDRLGCFNLTVKGHAKCVEVVKTFNLPL   300
LMLGGGGYTIRNVARCWTYETAVALDCEIPNELPYNDYFEYFGPDFKLHISPSNMTNQNT   360
PEYMEKIKQRLFENLRMLPHAPGVQMQAIPEDAVHEDSGDEDGEDPDKR             405
```

FIGURE 3A

LEGEND

Column headings from left to right are (A) 'ATOMNumber', (B) 'ATOMType', (C) 'Amino Acid', (D) 'Chain Identifier', (E) 'Amino Acid Number', (F) 'X Coordinate', (G) 'Y Coordinate', (H) 'Z Coordinate', (I) 'Occupancy' (OCC), (J) 'B factor' and (K) 'atom type'.

| | A | B | C | D | E | F | G | H | I | J | K |
|---|---|---|---|---|---|---|---|---|---|---|---|
| ATOM | 1 | N | GLY | A | 12 | -10.934 | 21.875 | -7.883 | 1.00 | 33.38 | N |
| ATOM | 2 | CA | GLY | A | 12 | -11.554 | 22.914 | -7.002 | 1.00 | 32.88 | C |
| ATOM | 3 | C | GLY | A | 12 | -10.561 | 23.520 | -6.029 | 1.00 | 35.11 | C |
| ATOM | 4 | O | GLY | A | 12 | -9.351 | 23.417 | -6.239 | 1.00 | 32.05 | O |
| ATOM | 5 | N | LYS | A | 13 | -11.079 | 24.160 | -4.978 | 1.00 | 34.94 | N |
| ATOM | 6 | CA | LYS | A | 13 | -10.259 | 24.721 | -3.902 | 1.00 | 35.84 | C |
| ATOM | 7 | CB | LYS | A | 13 | -11.097 | 25.602 | -2.975 | 1.00 | 35.62 | C |
| ATOM | 8 | CG | LYS | A | 13 | -11.498 | 26.956 | -3.561 | 1.00 | 39.36 | C |
| ATOM | 9 | CD | LYS | A | 13 | -10.965 | 28.120 | -2.737 | 1.00 | 45.43 | C |
| ATOM | 10 | CE | LYS | A | 13 | -11.669 | 28.247 | -1.394 | 1.00 | 50.50 | C |
| ATOM | 11 | NZ | LYS | A | 13 | -11.738 | 29.662 | -0.931 | 1.00 | 55.04 | N |
| ATOM | 12 | C | LYS | A | 13 | -9.640 | 23.590 | -3.095 | 1.00 | 37.36 | C |
| ATOM | 13 | O | LYS | A | 13 | -10.219 | 22.508 | -2.978 | 1.00 | 37.04 | O |
| ATOM | 14 | N | LYS | A | 14 | -8.468 | 23.837 | -2.525 | 1.00 | 36.44 | N |
| ATOM | 15 | CA | LYS | A | 14 | -7.742 | 22.763 | -1.861 | 1.00 | 36.93 | C |
| ATOM | 16 | CB | LYS | A | 14 | -6.377 | 22.563 | -2.524 | 1.00 | 43.40 | C |
| ATOM | 17 | CG | LYS | A | 14 | -6.434 | 21.757 | -3.823 | 1.00 | 47.48 | C |
| ATOM | 18 | CD | LYS | A | 14 | -6.187 | 22.633 | -5.041 | 1.00 | 53.17 | C |
| ATOM | 19 | CE | LYS | A | 14 | -5.489 | 21.861 | -6.154 | 1.00 | 53.51 | C |
| ATOM | 20 | NZ | LYS | A | 14 | -4.068 | 21.523 | -5.834 | 1.00 | 55.26 | N |
| ATOM | 21 | C | LYS | A | 14 | -7.606 | 22.961 | -0.355 | 1.00 | 33.27 | C |
| ATOM | 22 | O | LYS | A | 14 | -7.598 | 24.094 | 0.135 | 1.00 | 30.92 | O |
| ATOM | 23 | N | LYS | A | 15 | -7.522 | 21.850 | 0.372 | 1.00 | 28.55 | N |
| ATOM | 24 | CA | LYS | A | 15 | -7.203 | 21.894 | 1.794 | 1.00 | 30.03 | C |
| ATOM | 25 | CB | LYS | A | 15 | -7.570 | 20.584 | 2.493 | 1.00 | 31.98 | C |
| ATOM | 26 | CG | LYS | A | 15 | -7.978 | 20.777 | 3.941 | 1.00 | 38.76 | C |
| ATOM | 27 | CD | LYS | A | 15 | -7.800 | 19.517 | 4.765 | 1.00 | 41.81 | C |
| ATOM | 28 | CE | LYS | A | 15 | -7.132 | 19.840 | 6.094 | 1.00 | 45.73 | C |
| ATOM | 29 | NZ | LYS | A | 15 | -7.614 | 18.967 | 7.199 | 1.00 | 48.16 | N |
| ATOM | 30 | C | LYS | A | 15 | -5.715 | 22.188 | 1.968 | 1.00 | 26.95 | C |
| ATOM | 31 | O | LYS | A | 15 | -4.867 | 21.492 | 1.409 | 1.00 | 24.84 | O |
| ATOM | 32 | N | VAL | A | 16 | -5.414 | 23.227 | 2.739 | 1.00 | 26.40 | N |
| ATOM | 33 | CA | VAL | A | 16 | -4.033 | 23.639 | 2.992 | 1.00 | 23.42 | C |
| ATOM | 34 | CB | VAL | A | 16 | -3.786 | 25.104 | 2.528 | 1.00 | 21.46 | C |
| ATOM | 35 | CG1 | VAL | A | 16 | -2.358 | 25.543 | 2.832 | 1.00 | 21.08 | C |
| ATOM | 36 | CG2 | VAL | A | 16 | -4.087 | 25.271 | 1.034 | 1.00 | 24.77 | C |
| ATOM | 37 | C | VAL | A | 16 | -3.712 | 23.513 | 4.480 | 1.00 | 20.74 | C |
| ATOM | 38 | O | VAL | A | 16 | -4.437 | 24.045 | 5.325 | 1.00 | 20.94 | O |
| ATOM | 39 | N | CYS | A | 17 | -2.629 | 22.806 | 4.792 | 1.00 | 21.17 | N |
| ATOM | 40 | CA | CYS | A | 17 | -2.110 | 22.737 | 6.152 | 1.00 | 18.02 | C |
| ATOM | 41 | CB | CYS | A | 17 | -1.921 | 21.291 | 6.596 | 1.00 | 26.27 | C |
| ATOM | 42 | SG | CYS | A | 17 | -3.490 | 20.425 | 6.865 | 1.00 | 32.95 | S |
| ATOM | 43 | C | CYS | A | 17 | -0.785 | 23.484 | 6.181 | 1.00 | 20.58 | C |
| ATOM | 44 | O | CYS | A | 17 | 0.053 | 23.298 | 5.304 | 1.00 | 21.14 | O |
| ATOM | 45 | N | TYR | A | 18 | -0.606 | 24.312 | 7.200 | 1.00 | 16.48 | N |
| ATOM | 46 | CA | TYR | A | 18 | 0.499 | 25.260 | 7.253 | 1.00 | 15.92 | C |
| ATOM | 47 | CB | TYR | A | 18 | -0.088 | 26.667 | 7.066 | 1.00 | 18.52 | C |

FIGURE 3B

```
ATOM     48  CG  TYR A  18       0.783  27.857   7.402  1.00 17.99           C
ATOM     49  CD1 TYR A  18       1.004  28.228   8.725  1.00 21.27           C
ATOM     50  CE1 TYR A  18       1.775  29.334   9.039  1.00 22.51           C
ATOM     51  CZ  TYR A  18       2.325  30.094   8.025  1.00 20.40           C
ATOM     52  OH  TYR A  18       3.080  31.191   8.351  1.00 24.81           O
ATOM     53  CE2 TYR A  18       2.110  29.763   6.701  1.00 20.69           C
ATOM     54  CD2 TYR A  18       1.331  28.647   6.395  1.00 20.51           C
ATOM     55  C   TYR A  18       1.271  25.095   8.567  1.00 17.76           C
ATOM     56  O   TYR A  18       0.679  25.031   9.654  1.00 16.61           O
ATOM     57  N   TYR A  19       2.598  25.025   8.458  1.00 15.66           N
ATOM     58  CA  TYR A  19       3.449  24.724   9.601  1.00 16.08           C
ATOM     59  CB  TYR A  19       4.357  23.528   9.300  1.00 19.83           C
ATOM     60  CG  TYR A  19       3.556  22.260   9.158  1.00 23.49           C
ATOM     61  CD1 TYR A  19       2.996  21.908   7.934  1.00 24.37           C
ATOM     62  CE1 TYR A  19       2.233  20.765   7.798  1.00 28.59           C
ATOM     63  CZ  TYR A  19       2.021  19.949   8.893  1.00 28.87           C
ATOM     64  OH  TYR A  19       1.263  18.815   8.732  1.00 33.13           O
ATOM     65  CE2 TYR A  19       2.559  20.270  10.128  1.00 26.44           C
ATOM     66  CD2 TYR A  19       3.322  21.429  10.260  1.00 25.61           C
ATOM     67  C   TYR A  19       4.269  25.925  10.029  1.00 20.65           C
ATOM     68  O   TYR A  19       4.959  26.548   9.220  1.00 21.70           O
ATOM     69  N   TYR A  20       4.175  26.245  11.311  1.00 19.23           N
ATOM     70  CA  TYR A  20       4.866  27.402  11.852  1.00 20.20           C
ATOM     71  CB  TYR A  20       4.019  28.661  11.654  1.00 18.21           C
ATOM     72  CG  TYR A  20       4.614  29.908  12.270  1.00 24.20           C
ATOM     73  CD1 TYR A  20       4.075  30.451  13.440  1.00 22.89           C
ATOM     74  CE1 TYR A  20       4.614  31.605  14.016  1.00 24.32           C
ATOM     75  CZ  TYR A  20       5.699  32.219  13.416  1.00 25.74           C
ATOM     76  OH  TYR A  20       6.229  33.351  13.978  1.00 26.57           O
ATOM     77  CE2 TYR A  20       6.257  31.699  12.254  1.00 21.08           C
ATOM     78  CD2 TYR A  20       5.716  30.546  11.686  1.00 18.99           C
ATOM     79  C   TYR A  20       5.181  27.215  13.322  1.00 20.24           C
ATOM     80  O   TYR A  20       4.327  26.789  14.103  1.00 20.13           O
ATOM     81  N   ASP A  21       6.419  27.528  13.686  1.00 20.92           N
ATOM     82  CA  ASP A  21       6.807  27.609  15.084  1.00 21.80           C
ATOM     83  CB  ASP A  21       7.927  26.620  15.411  1.00 24.77           C
ATOM     84  CG  ASP A  21       8.132  26.460  16.901  1.00 27.98           C
ATOM     85  OD1 ASP A  21       8.099  25.314  17.401  1.00 29.26           O
ATOM     86  OD2 ASP A  21       8.307  27.436  17.656  1.00 28.43           O
ATOM     87  C   ASP A  21       7.237  29.023  15.423  1.00 26.07           C
ATOM     88  O   ASP A  21       8.187  29.545  14.836  1.00 26.99           O
ATOM     89  N   GLY A  22       6.540  29.630  16.384  1.00 27.58           N
ATOM     90  CA  GLY A  22       6.792  31.004  16.797  1.00 31.26           C
ATOM     91  C   GLY A  22       8.191  31.288  17.321  1.00 33.32           C
ATOM     92  O   GLY A  22       8.607  32.448  17.384  1.00 39.03           O
ATOM     93  N   ASP A  23       8.916  30.231  17.684  1.00 26.95           N
ATOM     94  CA  ASP A  23      10.280  30.350  18.200  1.00 28.38           C
ATOM     95  CB  ASP A  23      10.626  29.143  19.079  1.00 31.55           C
ATOM     96  CG  ASP A  23       9.761  29.055  20.324  1.00 40.64           C
ATOM     97  OD1 ASP A  23       9.641  27.941  20.888  1.00 43.66           O
ATOM     98  OD2 ASP A  23       9.166  30.041  20.815  1.00 40.36           O
ATOM     99  C   ASP A  23      11.331  30.495  17.099  1.00 26.66           C
ATOM    100  O   ASP A  23      12.457  30.933  17.373  1.00 24.70           O
ATOM    101  N   ILE A  24      10.971  30.119  15.868  1.00 26.24           N
ATOM    102  CA  ILE A  24      11.893  30.169  14.724  1.00 27.74           C
ATOM    103  CB  ILE A  24      11.192  29.692  13.407  1.00 31.85           C
ATOM    104  CG1 ILE A  24      12.223  29.270  12.353  1.00 33.00           C
```

FIGURE 3C

| | | | | | | | | | | |
|---|---|---|---|---|---|---|---|---|---|---|
| ATOM | 105 | CD1 | ILE | A | 24 | 12.745 | 27.849 | 12.528 | 1.00 36.31 | C |
| ATOM | 106 | CG2 | ILE | A | 24 | 10.254 | 30.772 | 12.846 | 1.00 30.58 | C |
| ATOM | 107 | C | ILE | A | 24 | 12.554 | 31.536 | 14.522 | 1.00 25.65 | C |
| ATOM | 108 | O | ILE | A | 24 | 13.734 | 31.611 | 14.184 | 1.00 27.69 | O |
| ATOM | 109 | N | GLY | A | 25 | 11.788 | 32.606 | 14.730 | 1.00 27.57 | N |
| ATOM | 110 | CA | GLY | A | 25 | 12.267 | 33.960 | 14.510 | 1.00 28.06 | C |
| ATOM | 111 | C | GLY | A | 25 | 13.326 | 34.442 | 15.486 | 1.00 32.62 | C |
| ATOM | 112 | O | GLY | A | 25 | 13.925 | 35.491 | 15.266 | 1.00 33.18 | O |
| ATOM | 113 | N | ASN | A | 26 | 13.554 | 33.680 | 16.556 | 1.00 29.29 | N |
| ATOM | 114 | CA | ASN | A | 26 | 14.520 | 34.047 | 17.588 | 1.00 32.21 | C |
| ATOM | 115 | CB | ASN | A | 26 | 14.039 | 33.584 | 18.969 | 1.00 36.54 | C |
| ATOM | 116 | CG | ASN | A | 26 | 12.740 | 34.256 | 19.399 | 1.00 38.26 | C |
| ATOM | 117 | OD1 | ASN | A | 26 | 12.432 | 35.374 | 18.984 | 1.00 40.40 | O |
| ATOM | 118 | ND2 | ASN | A | 26 | 11.975 | 33.572 | 20.243 | 1.00 41.23 | N |
| ATOM | 119 | C | ASN | A | 26 | 15.936 | 33.524 | 17.329 | 1.00 29.78 | C |
| ATOM | 120 | O | ASN | A | 26 | 16.870 | 33.858 | 18.062 | 1.00 29.28 | O |
| ATOM | 121 | N | TYR | A | 27 | 16.093 | 32.694 | 16.302 | 1.00 22.93 | N |
| ATOM | 122 | CA | TYR | A | 27 | 17.409 | 32.170 | 15.957 | 1.00 24.38 | C |
| ATOM | 123 | CB | TYR | A | 27 | 17.289 | 30.822 | 15.240 | 1.00 23.89 | C |
| ATOM | 124 | CG | TYR | A | 27 | 16.742 | 29.744 | 16.153 | 1.00 25.58 | C |
| ATOM | 125 | CD1 | TYR | A | 27 | 15.384 | 29.428 | 16.155 | 1.00 26.62 | C |
| ATOM | 126 | CE1 | TYR | A | 27 | 14.873 | 28.456 | 17.005 | 1.00 27.47 | C |
| ATOM | 127 | CZ | TYR | A | 27 | 15.717 | 27.795 | 17.875 | 1.00 30.04 | C |
| ATOM | 128 | OH | TYR | A | 27 | 15.214 | 26.829 | 18.720 | 1.00 30.17 | O |
| ATOM | 129 | CE2 | TYR | A | 27 | 17.068 | 28.100 | 17.904 | 1.00 28.43 | C |
| ATOM | 130 | CD2 | TYR | A | 27 | 17.573 | 29.070 | 17.044 | 1.00 25.97 | C |
| ATOM | 131 | C | TYR | A | 27 | 18.163 | 33.204 | 15.130 | 1.00 25.10 | C |
| ATOM | 132 | O | TYR | A | 27 | 17.574 | 33.889 | 14.301 | 1.00 25.59 | O |
| ATOM | 133 | N | TYR | A | 28 | 19.464 | 33.316 | 15.372 | 1.00 25.63 | N |
| ATOM | 134 | CA | TYR | A | 28 | 20.260 | 34.403 | 14.817 | 1.00 26.96 | C |
| ATOM | 135 | CB | TYR | A | 28 | 20.485 | 35.464 | 15.901 | 1.00 26.97 | C |
| ATOM | 136 | CG | TYR | A | 28 | 21.145 | 36.749 | 15.444 | 1.00 31.50 | C |
| ATOM | 137 | CD1 | TYR | A | 28 | 20.567 | 37.549 | 14.458 | 1.00 32.89 | C |
| ATOM | 138 | CE1 | TYR | A | 28 | 21.175 | 38.745 | 14.052 | 1.00 37.38 | C |
| ATOM | 139 | CZ | TYR | A | 28 | 22.365 | 39.140 | 14.648 | 1.00 38.32 | C |
| ATOM | 140 | OH | TYR | A | 28 | 22.977 | 40.311 | 14.261 | 1.00 42.88 | O |
| ATOM | 141 | CE2 | TYR | A | 28 | 22.950 | 38.363 | 15.631 | 1.00 37.22 | C |
| ATOM | 142 | CD2 | TYR | A | 28 | 22.338 | 37.178 | 16.026 | 1.00 33.60 | C |
| ATOM | 143 | C | TYR | A | 28 | 21.591 | 33.876 | 14.300 | 1.00 26.09 | C |
| ATOM | 144 | O | TYR | A | 28 | 22.396 | 33.350 | 15.068 | 1.00 25.01 | O |
| ATOM | 145 | N | TYR | A | 29 | 21.816 | 34.018 | 12.996 | 1.00 23.10 | N |
| ATOM | 146 | CA | TYR | A | 29 | 23.039 | 33.524 | 12.365 | 1.00 24.24 | C |
| ATOM | 147 | CB | TYR | A | 29 | 22.902 | 33.517 | 10.842 | 1.00 20.78 | C |
| ATOM | 148 | CG | TYR | A | 29 | 22.228 | 32.300 | 10.239 | 1.00 21.17 | C |
| ATOM | 149 | CD1 | TYR | A | 29 | 22.904 | 31.505 | 9.312 | 1.00 20.94 | C |
| ATOM | 150 | CE1 | TYR | A | 29 | 22.299 | 30.392 | 8.732 | 1.00 21.73 | C |
| ATOM | 151 | CZ | TYR | A | 29 | 20.996 | 30.057 | 9.068 | 1.00 20.67 | C |
| ATOM | 152 | OH | TYR | A | 29 | 20.414 | 28.959 | 8.465 | 1.00 18.73 | O |
| ATOM | 153 | CE2 | TYR | A | 29 | 20.292 | 30.826 | 9.982 | 1.00 22.03 | C |
| ATOM | 154 | CD2 | TYR | A | 29 | 20.911 | 31.955 | 10.564 | 1.00 22.31 | C |
| ATOM | 155 | C | TYR | A | 29 | 24.280 | 34.331 | 12.759 | 1.00 24.93 | C |
| ATOM | 156 | O | TYR | A | 29 | 25.397 | 33.825 | 12.686 | 1.00 30.10 | O |
| ATOM | 157 | N | GLY | A | 30 | 24.083 | 35.581 | 13.170 | 1.00 25.85 | N |
| ATOM | 158 | CA | GLY | A | 30 | 25.185 | 36.421 | 13.601 | 1.00 24.94 | C |
| ATOM | 159 | C | GLY | A | 30 | 25.193 | 37.753 | 12.891 | 1.00 27.68 | C |
| ATOM | 160 | O | GLY | A | 30 | 24.529 | 37.924 | 11.865 | 1.00 24.31 | O |
| ATOM | 161 | N | GLN | A | 31 | 25.954 | 38.698 | 13.437 | 1.00 32.35 | N |

FIGURE 3D

```
ATOM    162  CA   GLN A  31      26.024  40.056  12.903  1.00 36.84           C
ATOM    163  CB   GLN A  31      26.956  40.917  13.761  1.00 42.74           C
ATOM    164  CG   GLN A  31      26.826  42.411  13.524  1.00 47.99           C
ATOM    165  CD   GLN A  31      27.419  43.229  14.657  1.00 53.94           C
ATOM    166  OE1  GLN A  31      28.638  43.245  14.847  1.00 54.68           O
ATOM    167  NE2  GLN A  31      26.560  43.904  15.416  1.00 54.72           N
ATOM    168  C    GLN A  31      26.490  40.067  11.451  1.00 33.05           C
ATOM    169  O    GLN A  31      27.519  39.483  11.120  1.00 34.31           O
ATOM    170  N    GLY A  32      25.718  40.723  10.594  1.00 31.96           N
ATOM    171  CA   GLY A  32      26.056  40.827   9.187  1.00 32.47           C
ATOM    172  C    GLY A  32      25.672  39.645   8.305  1.00 29.76           C
ATOM    173  O    GLY A  32      25.779  39.743   7.086  1.00 28.79           O
ATOM    174  N    HIS A  33      25.237  38.532   8.898  1.00 27.05           N
ATOM    175  CA   HIS A  33      24.827  37.369   8.102  1.00 24.71           C
ATOM    176  CB   HIS A  33      24.767  36.099   8.952  1.00 23.18           C
ATOM    177  CG   HIS A  33      24.859  34.844   8.144  1.00 22.69           C
ATOM    178  ND1  HIS A  33      23.854  34.432   7.292  1.00 18.66           N
ATOM    179  CE1  HIS A  33      24.223  33.313   6.695  1.00 22.66           C
ATOM    180  NE2  HIS A  33      25.430  32.986   7.125  1.00 21.22           N
ATOM    181  CD2  HIS A  33      25.851  33.930   8.029  1.00 22.71           C
ATOM    182  C    HIS A  33      23.476  37.619   7.422  1.00 21.92           C
ATOM    183  O    HIS A  33      22.515  37.998   8.088  1.00 22.85           O
ATOM    184  N    PRO A  34      23.405  37.422   6.103  1.00 22.53           N
ATOM    185  CA   PRO A  34      22.191  37.750   5.345  1.00 22.87           C
ATOM    186  CB   PRO A  34      22.626  37.581   3.883  1.00 25.21           C
ATOM    187  CG   PRO A  34      23.781  36.651   3.927  1.00 22.98           C
ATOM    188  CD   PRO A  34      24.477  36.903   5.232  1.00 21.75           C
ATOM    189  C    PRO A  34      20.980  36.866   5.653  1.00 17.77           C
ATOM    190  O    PRO A  34      19.853  37.304   5.400  1.00 22.49           O
ATOM    191  N    MET A  35      21.197  35.666   6.186  1.00 16.87           N
ATOM    192  CA   MET A  35      20.076  34.770   6.474  1.00 21.27           C
ATOM    193  CB   MET A  35      20.513  33.303   6.462  1.00 19.13           C
ATOM    194  CG   MET A  35      19.398  32.310   6.801  1.00 22.02           C
ATOM    195  SD   MET A  35      17.972  32.372   5.677  1.00 26.90           S
ATOM    196  CE   MET A  35      18.493  31.246   4.395  1.00 23.80           C
ATOM    197  C    MET A  35      19.447  35.148   7.814  1.00 19.95           C
ATOM    198  O    MET A  35      20.097  35.075   8.861  1.00 20.46           O
ATOM    199  N    LYS A  36      18.181  35.552   7.766  1.00 19.74           N
ATOM    200  CA   LYS A  36      17.497  36.083   8.937  1.00 18.06           C
ATOM    201  CB   LYS A  36      17.205  37.577   8.742  1.00 20.07           C
ATOM    202  CG   LYS A  36      18.481  38.434   8.710  1.00 25.82           C
ATOM    203  CD   LYS A  36      18.240  39.814   8.146  1.00 30.73           C
ATOM    204  CE   LYS A  36      19.559  40.556   7.986  1.00 34.11           C
ATOM    205  NZ   LYS A  36      19.345  42.024   7.846  1.00 42.02           N
ATOM    206  C    LYS A  36      16.210  35.301   9.194  1.00 19.19           C
ATOM    207  O    LYS A  36      15.195  35.574   8.562  1.00 17.85           O
ATOM    208  N    PRO A  37      16.256  34.316  10.098  1.00 19.64           N
ATOM    209  CA   PRO A  37      15.077  33.498  10.423  1.00 18.87           C
ATOM    210  CB   PRO A  37      15.569  32.650  11.595  1.00 19.36           C
ATOM    211  CG   PRO A  37      17.031  32.469  11.283  1.00 18.04           C
ATOM    212  CD   PRO A  37      17.447  33.867  10.848  1.00 19.76           C
ATOM    213  C    PRO A  37      13.837  34.304  10.807  1.00 21.11           C
ATOM    214  O    PRO A  37      12.721  33.817  10.635  1.00 19.76           O
ATOM    215  N    HIS A  38      14.056  35.520  11.305  1.00 20.44           N
ATOM    216  CA   HIS A  38      13.014  36.514  11.574  1.00 24.68           C
ATOM    217  CB   HIS A  38      13.706  37.832  11.959  1.00 30.82           C
ATOM    218  CG   HIS A  38      12.774  38.946  12.313  1.00 37.66           C
```

FIGURE 3E

| ATOM | 219 | ND1 | HIS | A | 38 | 12.862 | 40.196 | 11.737 | 1.00 | 39.92 | N |
|------|-----|-----|-----|---|----|--------|--------|--------|------|-------|---|
| ATOM | 220 | CE1 | HIS | A | 38 | 11.928 | 40.979 | 12.245 | 1.00 | 40.67 | C |
| ATOM | 221 | NE2 | HIS | A | 38 | 11.244 | 40.286 | 13.137 | 1.00 | 42.93 | N |
| ATOM | 222 | CD2 | HIS | A | 38 | 11.754 | 39.012 | 13.201 | 1.00 | 42.01 | C |
| ATOM | 223 | C | HIS | A | 38 | 12.051 | 36.727 | 10.396 | 1.00 | 21.58 | C |
| ATOM | 224 | O | HIS | A | 38 | 10.869 | 37.030 | 10.594 | 1.00 | 19.93 | O |
| ATOM | 225 | N | ARG | A | 39 | 12.540 | 36.556 | 9.168 | 1.00 | 19.61 | N |
| ATOM | 226 | CA | ARG | A | 39 | 11.668 | 36.671 | 7.994 | 1.00 | 15.49 | C |
| ATOM | 227 | CB | ARG | A | 39 | 12.465 | 36.510 | 6.688 | 1.00 | 17.51 | C |
| ATOM | 228 | CG | ARG | A | 39 | 12.875 | 35.079 | 6.395 | 1.00 | 16.16 | C |
| ATOM | 229 | CD | ARG | A | 39 | 14.171 | 34.884 | 5.591 | 1.00 | 19.34 | C |
| ATOM | 230 | NE | ARG | A | 39 | 14.395 | 33.444 | 5.551 | 1.00 | 18.36 | N |
| ATOM | 231 | CZ | ARG | A | 39 | 14.563 | 32.723 | 4.462 | 1.00 | 22.50 | C |
| ATOM | 232 | NH1 | ARG | A | 39 | 14.641 | 33.302 | 3.266 | 1.00 | 21.04 | N |
| ATOM | 233 | NH2 | ARG | A | 39 | 14.679 | 31.406 | 4.577 | 1.00 | 18.37 | N |
| ATOM | 234 | C | ARG | A | 39 | 10.463 | 35.701 | 8.027 | 1.00 | 15.22 | C |
| ATOM | 235 | O | ARG | A | 39 | 9.421 | 36.001 | 7.453 | 1.00 | 16.67 | O |
| ATOM | 236 | N | ILE | A | 40 | 10.610 | 34.549 | 8.687 | 1.00 | 16.84 | N |
| ATOM | 237 | CA | ILE | A | 40 | 9.507 | 33.577 | 8.802 | 1.00 | 15.88 | C |
| ATOM | 238 | CB | ILE | A | 40 | 10.006 | 32.200 | 9.352 | 1.00 | 18.90 | C |
| ATOM | 239 | CG1 | ILE | A | 40 | 11.233 | 31.682 | 8.582 | 1.00 | 19.03 | C |
| ATOM | 240 | CD1 | ILE | A | 40 | 11.060 | 31.608 | 7.057 | 1.00 | 22.57 | C |
| ATOM | 241 | CG2 | ILE | A | 40 | 8.868 | 31.145 | 9.357 | 1.00 | 19.23 | C |
| ATOM | 242 | C | ILE | A | 40 | 8.408 | 34.135 | 9.708 | 1.00 | 19.64 | C |
| ATOM | 243 | O | ILE | A | 40 | 7.212 | 33.972 | 9.439 | 1.00 | 17.38 | O |
| ATOM | 244 | N | ARG | A | 41 | 8.831 | 34.772 | 10.796 | 1.00 | 17.65 | N |
| ATOM | 245 | CA | ARG | A | 41 | 7.915 | 35.409 | 11.736 | 1.00 | 18.92 | C |
| ATOM | 246 | CB | ARG | A | 41 | 8.670 | 35.883 | 12.984 | 1.00 | 17.52 | C |
| ATOM | 247 | CG | ARG | A | 41 | 7.772 | 36.434 | 14.105 | 1.00 | 26.88 | C |
| ATOM | 248 | CD | ARG | A | 41 | 8.451 | 36.496 | 15.481 | 1.00 | 33.14 | C |
| ATOM | 249 | NE | ARG | A | 41 | 9.806 | 37.042 | 15.396 | 1.00 | 41.48 | N |
| ATOM | 250 | CZ | ARG | A | 41 | 10.624 | 37.237 | 16.431 | 1.00 | 46.61 | C |
| ATOM | 251 | NH1 | ARG | A | 41 | 10.243 | 36.932 | 17.667 | 1.00 | 46.68 | N |
| ATOM | 252 | NH2 | ARG | A | 41 | 11.836 | 37.742 | 16.225 | 1.00 | 47.05 | N |
| ATOM | 253 | C | ARG | A | 41 | 7.198 | 36.578 | 11.064 | 1.00 | 17.60 | C |
| ATOM | 254 | O | ARG | A | 41 | 6.000 | 36.766 | 11.261 | 1.00 | 17.02 | O |
| ATOM | 255 | N | MET | A | 42 | 7.936 | 37.353 | 10.266 | 1.00 | 17.83 | N |
| ATOM | 256 | CA | MET | A | 42 | 7.349 | 38.440 | 9.475 | 1.00 | 17.23 | C |
| ATOM | 257 | CB | MET | A | 42 | 8.429 | 39.170 | 8.683 | 1.00 | 17.73 | C |
| ATOM | 258 | CG | MET | A | 42 | 9.261 | 40.137 | 9.494 | 1.00 | 24.20 | C |
| ATOM | 259 | SD | MET | A | 42 | 10.568 | 40.862 | 8.460 | 1.00 | 29.51 | S |
| ATOM | 260 | CE | MET | A | 42 | 9.588 | 41.776 | 7.275 | 1.00 | 17.90 | C |
| ATOM | 261 | C | MET | A | 42 | 6.282 | 37.935 | 8.514 | 1.00 | 18.80 | C |
| ATOM | 262 | O | MET | A | 42 | 5.180 | 38.491 | 8.447 | 1.00 | 16.34 | O |
| ATOM | 263 | N | THR | A | 43 | 6.622 | 36.888 | 7.758 | 1.00 | 17.87 | N |
| ATOM | 264 | CA | THR | A | 43 | 5.676 | 36.247 | 6.847 | 1.00 | 16.55 | C |
| ATOM | 265 | CB | THR | A | 43 | 6.324 | 35.000 | 6.218 | 1.00 | 17.33 | C |
| ATOM | 266 | OG1 | THR | A | 43 | 7.452 | 35.392 | 5.431 | 1.00 | 17.62 | O |
| ATOM | 267 | CG2 | THR | A | 43 | 5.373 | 34.333 | 5.232 | 1.00 | 16.92 | C |
| ATOM | 268 | C | THR | A | 43 | 4.401 | 35.839 | 7.580 | 1.00 | 15.77 | C |
| ATOM | 269 | O | THR | A | 43 | 3.293 | 36.169 | 7.148 | 1.00 | 17.70 | O |
| ATOM | 270 | N | HIS | A | 44 | 4.569 | 35.113 | 8.682 | 1.00 | 16.86 | N |
| ATOM | 271 | CA | HIS | A | 44 | 3.444 | 34.637 | 9.479 | 1.00 | 18.12 | C |
| ATOM | 272 | CB | HIS | A | 44 | 3.945 | 33.839 | 10.679 | 1.00 | 18.26 | C |
| ATOM | 273 | CG | HIS | A | 44 | 2.851 | 33.160 | 11.440 | 1.00 | 21.55 | C |
| ATOM | 274 | ND1 | HIS | A | 44 | 2.139 | 32.098 | 10.925 | 1.00 | 20.89 | N |
| ATOM | 275 | CE1 | HIS | A | 44 | 1.238 | 31.705 | 11.808 | 1.00 | 22.53 | C |

FIGURE 3F

| | | | | | | | | | |
|---|---|---|---|---|---|---|---|---|---|
| ATOM | 276 | NE2 | HIS | A | 44 | 1.340 | 32.474 | 12.878 | 1.00 21.32 | N |
| ATOM | 277 | CD2 | HIS | A | 44 | 2.338 | 33.396 | 12.671 | 1.00 23.23 | C |
| ATOM | 278 | C | HIS | A | 44 | 2.568 | 35.783 | 9.988 | 1.00 14.96 | C |
| ATOM | 279 | O | HIS | A | 44 | 1.347 | 35.714 | 9.925 | 1.00 15.26 | O |
| ATOM | 280 | N | ASN | A | 45 | 3.206 | 36.827 | 10.499 | 1.00 17.89 | N |
| ATOM | 281 | CA | ASN | A | 45 | 2.468 | 37.982 | 11.020 | 1.00 18.49 | C |
| ATOM | 282 | CB | ASN | A | 45 | 3.421 | 38.954 | 11.701 | 1.00 19.18 | C |
| ATOM | 283 | CG | ASN | A | 45 | 2.690 | 40.006 | 12.499 | 1.00 19.96 | C |
| ATOM | 284 | OD1 | ASN | A | 45 | 2.550 | 41.137 | 12.058 | 1.00 20.10 | O |
| ATOM | 285 | ND2 | ASN | A | 45 | 2.197 | 39.627 | 13.672 | 1.00 21.68 | N |
| ATOM | 286 | C | ASN | A | 45 | 1.652 | 38.694 | 9.944 | 1.00 16.41 | C |
| ATOM | 287 | O | ASN | A | 45 | 0.512 | 39.108 | 10.178 | 1.00 16.69 | O |
| ATOM | 288 | N | LEU | A | 46 | 2.231 | 38.824 | 8.754 | 1.00 15.77 | N |
| ATOM | 289 | CA | LEU | A | 46 | 1.524 | 39.445 | 7.638 | 1.00 18.43 | C |
| ATOM | 290 | CB | LEU | A | 46 | 2.483 | 39.657 | 6.459 | 1.00 18.86 | C |
| ATOM | 291 | CG | LEU | A | 46 | 1.972 | 40.468 | 5.268 | 1.00 20.80 | C |
| ATOM | 292 | CD1 | LEU | A | 46 | 1.292 | 41.790 | 5.699 | 1.00 22.33 | C |
| ATOM | 293 | CD2 | LEU | A | 46 | 3.128 | 40.721 | 4.310 | 1.00 16.54 | C |
| ATOM | 294 | C | LEU | A | 46 | 0.325 | 38.587 | 7.238 | 1.00 20.27 | C |
| ATOM | 295 | O | LEU | A | 46 | -0.786 | 39.082 | 7.072 | 1.00 16.74 | O |
| ATOM | 296 | N | LEU | A | 47 | 0.582 | 37.288 | 7.107 | 1.00 18.76 | N |
| ATOM | 297 | CA | LEU | A | 47 | -0.410 | 36.252 | 6.857 | 1.00 23.38 | C |
| ATOM | 298 | CB | LEU | A | 47 | 0.297 | 34.916 | 7.069 | 1.00 29.13 | C |
| ATOM | 299 | CG | LEU | A | 47 | 0.089 | 33.722 | 6.182 | 1.00 34.93 | C |
| ATOM | 300 | CD1 | LEU | A | 47 | 1.443 | 33.224 | 5.721 | 1.00 30.00 | C |
| ATOM | 301 | CD2 | LEU | A | 47 | -0.595 | 32.700 | 7.045 | 1.00 36.15 | C |
| ATOM | 302 | C | LEU | A | 47 | -1.605 | 36.319 | 7.804 | 1.00 22.40 | C |
| ATOM | 303 | O | LEU | A | 47 | -2.768 | 36.278 | 7.372 | 1.00 22.88 | O |
| ATOM | 304 | N | LEU | A | 48 | -1.310 | 36.401 | 9.098 | 1.00 21.20 | N |
| ATOM | 305 | CA | LEU | A | 48 | -2.340 | 36.469 | 10.133 | 1.00 23.56 | C |
| ATOM | 306 | CB | LEU | A | 48 | -1.713 | 36.414 | 11.535 | 1.00 22.57 | C |
| ATOM | 307 | CG | LEU | A | 48 | -1.069 | 35.093 | 11.967 | 1.00 26.40 | C |
| ATOM | 308 | CD1 | LEU | A | 48 | -0.596 | 35.173 | 13.410 | 1.00 28.25 | C |
| ATOM | 309 | CD2 | LEU | A | 48 | -2.007 | 33.898 | 11.763 | 1.00 30.15 | C |
| ATOM | 310 | C | LEU | A | 48 | -3.182 | 37.729 | 9.994 | 1.00 22.55 | C |
| ATOM | 311 | O | LEU | A | 48 | -4.405 | 37.690 | 10.154 | 1.00 20.82 | O |
| ATOM | 312 | N | ASN | A | 49 | -2.525 | 38.842 | 9.680 | 1.00 20.25 | N |
| ATOM | 313 | CA | ASN | A | 49 | -3.223 | 40.118 | 9.578 | 1.00 20.48 | C |
| ATOM | 314 | CB | ASN | A | 49 | -2.251 | 41.277 | 9.754 | 1.00 18.74 | C |
| ATOM | 315 | CG | ASN | A | 49 | -1.943 | 41.519 | 11.205 | 1.00 21.43 | C |
| ATOM | 316 | OD1 | ASN | A | 49 | -2.803 | 41.994 | 11.954 | 1.00 19.85 | O |
| ATOM | 317 | ND2 | ASN | A | 49 | -0.738 | 41.148 | 11.631 | 1.00 17.29 | N |
| ATOM | 318 | C | ASN | A | 49 | -4.084 | 40.279 | 8.339 | 1.00 24.12 | C |
| ATOM | 319 | O | ASN | A | 49 | -5.007 | 41.096 | 8.318 | 1.00 22.21 | O |
| ATOM | 320 | N | TYR | A | 50 | -3.785 | 39.485 | 7.317 | 1.00 19.55 | N |
| ATOM | 321 | CA | TYR | A | 50 | -4.646 | 39.376 | 6.150 | 1.00 24.04 | C |
| ATOM | 322 | CB | TYR | A | 50 | -3.843 | 38.846 | 4.969 | 1.00 18.75 | C |
| ATOM | 323 | CG | TYR | A | 50 | -3.283 | 39.901 | 4.042 | 1.00 19.07 | C |
| ATOM | 324 | CD1 | TYR | A | 50 | -4.124 | 40.687 | 3.259 | 1.00 17.18 | C |
| ATOM | 325 | CE1 | TYR | A | 50 | -3.611 | 41.634 | 2.385 | 1.00 18.52 | C |
| ATOM | 326 | CZ | TYR | A | 50 | -2.241 | 41.788 | 2.283 | 1.00 15.23 | C |
| ATOM | 327 | OH | TYR | A | 50 | -1.726 | 42.714 | 1.422 | 1.00 17.51 | O |
| ATOM | 328 | CE2 | TYR | A | 50 | -1.384 | 41.007 | 3.039 | 1.00 17.62 | C |
| ATOM | 329 | CD2 | TYR | A | 50 | -1.909 | 40.076 | 3.916 | 1.00 14.97 | C |
| ATOM | 330 | C | TYR | A | 50 | -5.838 | 38.448 | 6.415 | 1.00 24.79 | C |
| ATOM | 331 | O | TYR | A | 50 | -6.763 | 38.365 | 5.603 | 1.00 28.69 | O |
| ATOM | 332 | N | GLY | A | 51 | -5.801 | 37.745 | 7.542 | 1.00 22.50 | N |

FIGURE 3G

| | | | | | | | | | |
|---|---|---|---|---|---|---|---|---|---|
| ATOM | 333 | CA  | GLY A | 51 | -6.876  | 36.851 | 7.948  | 1.00 25.51 | C |
| ATOM | 334 | C   | GLY A | 51 | -6.859  | 35.475 | 7.299  | 1.00 27.37 | C |
| ATOM | 335 | O   | GLY A | 51 | -7.883  | 34.786 | 7.272  | 1.00 28.23 | O |
| ATOM | 336 | N   | LEU A | 52 | -5.697  | 35.057 | 6.798  | 1.00 23.48 | N |
| ATOM | 337 | CA  | LEU A | 52 | -5.590  | 33.787 | 6.076  | 1.00 21.82 | C |
| ATOM | 338 | CB  | LEU A | 52 | -4.338  | 33.770 | 5.182  | 1.00 22.63 | C |
| ATOM | 339 | CG  | LEU A | 52 | -4.271  | 34.858 | 4.096  | 1.00 25.27 | C |
| ATOM | 340 | CD1 | LEU A | 52 | -2.984  | 34.748 | 3.273  | 1.00 26.86 | C |
| ATOM | 341 | CD2 | LEU A | 52 | -5.483  | 34.843 | 3.177  | 1.00 26.70 | C |
| ATOM | 342 | C   | LEU A | 52 | -5.662  | 32.553 | 6.974  | 1.00 22.25 | C |
| ATOM | 343 | O   | LEU A | 52 | -5.921  | 31.443 | 6.490  | 1.00 27.62 | O |
| ATOM | 344 | N   | TYR A | 53 | -5.468  | 32.750 | 8.278  | 1.00 21.13 | N |
| ATOM | 345 | CA  | TYR A | 53 | -5.650  | 31.688 | 9.270  | 1.00 26.98 | C |
| ATOM | 346 | CB  | TYR A | 53 | -5.264  | 32.171 | 10.678 | 1.00 28.47 | C |
| ATOM | 347 | CG  | TYR A | 53 | -6.126  | 33.296 | 11.219 | 1.00 31.97 | C |
| ATOM | 348 | CD1 | TYR A | 53 | -7.239  | 33.029 | 12.018 | 1.00 35.07 | C |
| ATOM | 349 | CE1 | TYR A | 53 | -8.038  | 34.064 | 12.514 | 1.00 35.75 | C |
| ATOM | 350 | CZ  | TYR A | 53 | -7.712  | 35.378 | 12.214 | 1.00 37.70 | C |
| ATOM | 351 | OH  | TYR A | 53 | -8.486  | 36.407 | 12.695 | 1.00 40.14 | O |
| ATOM | 352 | CE2 | TYR A | 53 | -6.607  | 35.665 | 11.428 | 1.00 34.10 | C |
| ATOM | 353 | CD2 | TYR A | 53 | -5.823  | 34.628 | 10.937 | 1.00 30.37 | C |
| ATOM | 354 | C   | TYR A | 53 | -7.081  | 31.143 | 9.273  | 1.00 29.52 | C |
| ATOM | 355 | O   | TYR A | 53 | -7.314  | 30.002 | 9.668  | 1.00 31.10 | O |
| ATOM | 356 | N   | ARG A | 54 | -8.030  | 31.965 | 8.832  | 1.00 29.73 | N |
| ATOM | 357 | CA  | ARG A | 54 | -9.429  | 31.546 | 8.702  | 1.00 33.07 | C |
| ATOM | 358 | CB  | ARG A | 54 | -10.325 | 32.753 | 8.402  | 1.00 38.00 | C |
| ATOM | 359 | CG  | ARG A | 54 | -10.607 | 33.640 | 9.605  | 1.00 45.73 | C |
| ATOM | 360 | CD  | ARG A | 54 | -11.625 | 34.738 | 9.339  | 1.00 53.38 | C |
| ATOM | 361 | NE  | ARG A | 54 | -11.010 | 36.066 | 9.348  | 1.00 59.05 | N |
| ATOM | 362 | CZ  | ARG A | 54 | -11.575 | 37.168 | 8.859  | 1.00 62.15 | C |
| ATOM | 363 | NH1 | ARG A | 54 | -12.784 | 37.124 | 8.309  | 1.00 63.52 | N |
| ATOM | 364 | NH2 | ARG A | 54 | -10.925 | 38.323 | 8.920  | 1.00 62.31 | N |
| ATOM | 365 | C   | ARG A | 54 | -9.650  | 30.468 | 7.630  | 1.00 33.81 | C |
| ATOM | 366 | O   | ARG A | 54 | -10.668 | 29.772 | 7.655  | 1.00 32.94 | O |
| ATOM | 367 | N   | LYS A | 55 | -8.705  | 30.333 | 6.699  | 1.00 29.14 | N |
| ATOM | 368 | CA  | LYS A | 55 | -8.886  | 29.469 | 5.530  | 1.00 30.85 | C |
| ATOM | 369 | CB  | LYS A | 55 | -8.616  | 30.244 | 4.232  | 1.00 35.92 | C |
| ATOM | 370 | CG  | LYS A | 55 | -9.214  | 31.644 | 4.183  | 1.00 42.07 | C |
| ATOM | 371 | CD  | LYS A | 55 | -10.415 | 31.706 | 3.257  | 1.00 45.41 | C |
| ATOM | 372 | CE  | LYS A | 55 | -10.921 | 33.136 | 3.113  | 1.00 51.15 | C |
| ATOM | 373 | NZ  | LYS A | 55 | -11.676 | 33.594 | 4.321  | 1.00 51.35 | N |
| ATOM | 374 | C   | LYS A | 55 | -8.036  | 28.198 | 5.550  | 1.00 28.94 | C |
| ATOM | 375 | O   | LYS A | 55 | -8.193  | 27.332 | 4.685  | 1.00 27.40 | O |
| ATOM | 376 | N   | MET A | 56 | -7.135  | 28.084 | 6.520  | 1.00 28.92 | N |
| ATOM | 377 | CA  | MET A | 56 | -6.244  | 26.923 | 6.579  | 1.00 28.44 | C |
| ATOM | 378 | CB  | MET A | 56 | -4.923  | 27.206 | 5.849  | 1.00 31.07 | C |
| ATOM | 379 | CG  | MET A | 56 | -4.334  | 28.556 | 6.139  | 1.00 31.85 | C |
| ATOM | 380 | SD  | MET A | 56 | -2.661  | 28.791 | 5.491  | 1.00 29.08 | S |
| ATOM | 381 | CE  | MET A | 56 | -2.114  | 29.915 | 6.690  | 1.00 25.68 | C |
| ATOM | 382 | C   | MET A | 56 | -5.970  | 26.475 | 8.001  | 1.00 27.32 | C |
| ATOM | 383 | O   | MET A | 56 | -6.130  | 27.247 | 8.943  | 1.00 31.86 | O |
| ATOM | 384 | N   | GLU A | 57 | -5.557  | 25.219 | 8.147  | 1.00 27.77 | N |
| ATOM | 385 | CA  | GLU A | 57 | -5.182  | 24.681 | 9.446  | 1.00 28.19 | C |
| ATOM | 386 | CB  | GLU A | 57 | -5.350  | 23.159 | 9.466  | 1.00 33.68 | C |
| ATOM | 387 | CG  | GLU A | 57 | -6.649  | 22.675 | 10.092 | 1.00 43.84 | C |
| ATOM | 388 | CD  | GLU A | 57 | -7.179  | 21.416 | 9.429  | 1.00 48.30 | C |
| ATOM | 389 | OE1 | GLU A | 57 | -6.475  | 20.383 | 9.450  | 1.00 49.75 | O |

FIGURE 3H

| | | | | | | | | | |
|---|---|---|---|---|---|---|---|---|---|
| ATOM | 390 | OE2 | GLU A | 57 | -8.302 | 21.458 | 8.885 | 1.00 53.23 | O |
| ATOM | 391 | C | GLU A | 57 | -3.733 | 25.046 | 9.714 | 1.00 27.14 | C |
| ATOM | 392 | O | GLU A | 57 | -2.867 | 24.806 | 8.871 | 1.00 26.43 | O |
| ATOM | 393 | N | ILE A | 58 | -3.470 | 25.629 | 10.879 | 1.00 23.96 | N |
| ATOM | 394 | CA | ILE A | 58 | -2.103 | 25.966 | 11.255 | 1.00 23.30 | C |
| ATOM | 395 | CB | ILE A | 58 | -2.005 | 27.439 | 11.729 | 1.00 25.42 | C |
| ATOM | 396 | CG1 | ILE A | 58 | -2.341 | 28.389 | 10.572 | 1.00 26.37 | C |
| ATOM | 397 | CD1 | ILE A | 58 | -2.385 | 29.866 | 10.965 | 1.00 28.44 | C |
| ATOM | 398 | CG2 | ILE A | 58 | -0.611 | 27.740 | 12.293 | 1.00 21.56 | C |
| ATOM | 399 | C | ILE A | 58 | -1.606 | 24.985 | 12.317 | 1.00 23.73 | C |
| ATOM | 400 | O | ILE A | 58 | -2.246 | 24.793 | 13.354 | 1.00 25.27 | O |
| ATOM | 401 | N | TYR A | 59 | -0.478 | 24.347 | 12.028 | 1.00 21.51 | N |
| ATOM | 402 | CA | TYR A | 59 | 0.137 | 23.368 | 12.915 | 1.00 21.20 | C |
| ATOM | 403 | CB | TYR A | 59 | 0.285 | 22.025 | 12.205 | 1.00 24.78 | C |
| ATOM | 404 | CG | TYR A | 59 | -1.015 | 21.329 | 11.893 | 1.00 30.40 | C |
| ATOM | 405 | CD1 | TYR A | 59 | -1.638 | 20.517 | 12.842 | 1.00 35.62 | C |
| ATOM | 406 | CE1 | TYR A | 59 | -2.834 | 19.866 | 12.559 | 1.00 37.26 | C |
| ATOM | 407 | CZ | TYR A | 59 | -3.417 | 20.024 | 11.314 | 1.00 39.08 | C |
| ATOM | 408 | OH | TYR A | 59 | -4.600 | 19.381 | 11.028 | 1.00 43.75 | O |
| ATOM | 409 | CE2 | TYR A | 59 | -2.816 | 20.820 | 10.352 | 1.00 37.62 | C |
| ATOM | 410 | CD2 | TYR A | 59 | -1.616 | 21.466 | 10.645 | 1.00 34.35 | C |
| ATOM | 411 | C | TYR A | 59 | 1.516 | 23.818 | 13.337 | 1.00 22.46 | C |
| ATOM | 412 | O | TYR A | 59 | 2.257 | 24.415 | 12.553 | 1.00 21.64 | O |
| ATOM | 413 | N | ARG A | 60 | 1.875 | 23.504 | 14.573 | 1.00 20.21 | N |
| ATOM | 414 | CA | ARG A | 60 | 3.241 | 23.689 | 15.018 | 1.00 22.73 | C |
| ATOM | 415 | CB | ARG A | 60 | 3.264 | 23.993 | 16.509 | 1.00 27.65 | C |
| ATOM | 416 | CG | ARG A | 60 | 4.580 | 24.532 | 17.001 | 1.00 26.76 | C |
| ATOM | 417 | CD | ARG A | 60 | 4.622 | 24.755 | 18.496 | 1.00 28.10 | C |
| ATOM | 418 | NE | ARG A | 60 | 5.630 | 25.743 | 18.837 | 1.00 26.39 | N |
| ATOM | 419 | CZ | ARG A | 60 | 5.473 | 26.706 | 19.727 | 1.00 28.18 | C |
| ATOM | 420 | NH1 | ARG A | 60 | 4.335 | 26.818 | 20.409 | 1.00 27.35 | N |
| ATOM | 421 | NH2 | ARG A | 60 | 6.464 | 27.560 | 19.935 | 1.00 26.95 | N |
| ATOM | 422 | C | ARG A | 60 | 4.017 | 22.408 | 14.702 | 1.00 24.37 | C |
| ATOM | 423 | O | ARG A | 60 | 3.558 | 21.318 | 15.029 | 1.00 23.42 | O |
| ATOM | 424 | N | PRO A | 61 | 5.174 | 22.523 | 14.047 | 1.00 26.28 | N |
| ATOM | 425 | CA | PRO A | 61 | 5.977 | 21.337 | 13.730 | 1.00 26.84 | C |
| ATOM | 426 | CB | PRO A | 61 | 7.118 | 21.910 | 12.887 | 1.00 24.71 | C |
| ATOM | 427 | CG | PRO A | 61 | 7.239 | 23.321 | 13.333 | 1.00 30.02 | C |
| ATOM | 428 | CD | PRO A | 61 | 5.818 | 23.761 | 13.572 | 1.00 24.64 | C |
| ATOM | 429 | C | PRO A | 61 | 6.547 | 20.716 | 15.004 | 1.00 23.34 | C |
| ATOM | 430 | O | PRO A | 61 | 6.787 | 21.431 | 15.975 | 1.00 22.07 | O |
| ATOM | 431 | N | HIS A | 62 | 6.756 | 19.404 | 14.992 | 1.00 22.91 | N |
| ATOM | 432 | CA | HIS A | 62 | 7.558 | 18.767 | 16.024 | 1.00 22.92 | C |
| ATOM | 433 | CB | HIS A | 62 | 7.326 | 17.253 | 16.020 | 1.00 25.21 | C |
| ATOM | 434 | CG | HIS A | 62 | 7.839 | 16.571 | 14.791 | 1.00 23.64 | C |
| ATOM | 435 | ND1 | HIS A | 62 | 7.200 | 16.649 | 13.573 | 1.00 26.11 | N |
| ATOM | 436 | CE1 | HIS A | 62 | 7.882 | 15.960 | 12.676 | 1.00 27.75 | C |
| ATOM | 437 | NE2 | HIS A | 62 | 8.946 | 15.447 | 13.266 | 1.00 24.33 | N |
| ATOM | 438 | CD2 | HIS A | 62 | 8.941 | 15.810 | 14.590 | 1.00 23.21 | C |
| ATOM | 439 | C | HIS A | 62 | 9.027 | 19.079 | 15.725 | 1.00 24.85 | C |
| ATOM | 440 | O | HIS A | 62 | 9.372 | 19.485 | 14.609 | 1.00 23.85 | O |
| ATOM | 441 | N | LYS A | 63 | 9.885 | 18.897 | 16.719 | 1.00 21.34 | N |
| ATOM | 442 | CA | LYS A | 63 | 11.321 | 18.931 | 16.489 | 1.00 21.51 | C |
| ATOM | 443 | CB | LYS A | 63 | 12.074 | 19.240 | 17.781 | 1.00 22.01 | C |
| ATOM | 444 | CG | LYS A | 63 | 11.922 | 20.661 | 18.283 | 1.00 27.78 | C |
| ATOM | 445 | CD | LYS A | 63 | 12.644 | 20.834 | 19.610 | 1.00 35.80 | C |
| ATOM | 446 | CE | LYS A | 63 | 12.118 | 22.038 | 20.381 | 1.00 40.35 | C |

FIGURE 3I

| ATOM | 447 | NZ | LYS | A | 63 | 12.551 | 23.320 | 19.765 | 1.00 | 44.02 | N |
|---|---|---|---|---|---|---|---|---|---|---|---|
| ATOM | 448 | C | LYS | A | 63 | 11.752 | 17.573 | 15.941 | 1.00 | 27.78 | C |
| ATOM | 449 | O | LYS | A | 63 | 11.701 | 16.560 | 16.654 | 1.00 | 28.26 | O |
| ATOM | 450 | N | ALA | A | 64 | 12.160 | 17.544 | 14.674 | 1.00 | 21.91 | N |
| ATOM | 451 | CA | ALA | A | 64 | 12.664 | 16.313 | 14.064 | 1.00 | 21.78 | C |
| ATOM | 452 | CB | ALA | A | 64 | 13.080 | 16.564 | 12.617 | 1.00 | 24.55 | C |
| ATOM | 453 | C | ALA | A | 64 | 13.838 | 15.754 | 14.874 | 1.00 | 19.76 | C |
| ATOM | 454 | O | ALA | A | 64 | 14.667 | 16.507 | 15.375 | 1.00 | 20.06 | O |
| ATOM | 455 | N | THR | A | 65 | 13.900 | 14.435 | 15.025 | 1.00 | 18.07 | N |
| ATOM | 456 | CA | THR | A | 65 | 14.960 | 13.831 | 15.832 | 1.00 | 21.15 | C |
| ATOM | 457 | CB | THR | A | 65 | 14.431 | 12.589 | 16.565 | 1.00 | 22.77 | C |
| ATOM | 458 | OG1 | THR | A | 65 | 14.090 | 11.587 | 15.595 | 1.00 | 19.46 | O |
| ATOM | 459 | CG2 | THR | A | 65 | 13.107 | 12.897 | 17.276 | 1.00 | 23.54 | C |
| ATOM | 460 | C | THR | A | 65 | 16.161 | 13.421 | 14.984 | 1.00 | 21.80 | C |
| ATOM | 461 | O | THR | A | 65 | 16.088 | 13.413 | 13.755 | 1.00 | 22.04 | O |
| ATOM | 462 | N | ALA | A | 66 | 17.252 | 13.054 | 15.655 | 1.00 | 25.80 | N |
| ATOM | 463 | CA | ALA | A | 66 | 18.428 | 12.469 | 15.002 | 1.00 | 28.82 | C |
| ATOM | 464 | CB | ALA | A | 66 | 19.514 | 12.159 | 16.036 | 1.00 | 29.20 | C |
| ATOM | 465 | C | ALA | A | 66 | 18.083 | 11.219 | 14.192 | 1.00 | 34.57 | C |
| ATOM | 466 | O | ALA | A | 66 | 18.640 | 10.995 | 13.114 | 1.00 | 37.46 | O |
| ATOM | 467 | N | GLU | A | 67 | 17.151 | 10.418 | 14.708 | 1.00 | 36.04 | N |
| ATOM | 468 | CA | GLU | A | 67 | 16.640 | 9.249 | 13.994 | 1.00 | 34.03 | C |
| ATOM | 469 | CB | GLU | A | 67 | 15.579 | 8.522 | 14.835 | 1.00 | 37.03 | C |
| ATOM | 470 | CG | GLU | A | 67 | 16.030 | 7.184 | 15.404 | 1.00 | 38.13 | C |
| ATOM | 471 | CD | GLU | A | 67 | 14.929 | 6.447 | 16.154 | 1.00 | 39.99 | C |
| ATOM | 472 | OE1 | GLU | A | 67 | 13.735 | 6.629 | 15.827 | 1.00 | 40.99 | O |
| ATOM | 473 | OE2 | GLU | A | 67 | 15.258 | 5.674 | 17.078 | 1.00 | 38.90 | O |
| ATOM | 474 | C | GLU | A | 67 | 16.047 | 9.652 | 12.646 | 1.00 | 33.82 | C |
| ATOM | 475 | O | GLU | A | 67 | 16.303 | 9.009 | 11.624 | 1.00 | 34.42 | O |
| ATOM | 476 | N | GLU | A | 68 | 15.249 | 10.716 | 12.653 | 1.00 | 24.65 | N |
| ATOM | 477 | CA | GLU | A | 68 | 14.639 | 11.228 | 11.434 | 1.00 | 24.62 | C |
| ATOM | 478 | CB | GLU | A | 68 | 13.604 | 12.316 | 11.761 | 1.00 | 25.86 | C |
| ATOM | 479 | CG | GLU | A | 68 | 12.262 | 11.759 | 12.225 | 1.00 | 33.44 | C |
| ATOM | 480 | CD | GLU | A | 68 | 11.314 | 12.834 | 12.739 | 1.00 | 36.80 | C |
| ATOM | 481 | OE1 | GLU | A | 68 | 10.428 | 13.265 | 11.971 | 1.00 | 38.84 | O |
| ATOM | 482 | OE2 | GLU | A | 68 | 11.452 | 13.243 | 13.913 | 1.00 | 34.68 | O |
| ATOM | 483 | C | GLU | A | 68 | 15.707 | 11.766 | 10.477 | 1.00 | 22.14 | C |
| ATOM | 484 | O | GLU | A | 68 | 15.662 | 11.497 | 9.273 | 1.00 | 23.63 | O |
| ATOM | 485 | N | MET | A | 69 | 16.669 | 12.507 | 11.017 | 1.00 | 20.21 | N |
| ATOM | 486 | CA | MET | A | 69 | 17.688 | 13.154 | 10.180 | 1.00 | 21.75 | C |
| ATOM | 487 | CB | MET | A | 69 | 18.489 | 14.185 | 10.971 | 1.00 | 24.48 | C |
| ATOM | 488 | CG | MET | A | 69 | 17.701 | 15.453 | 11.260 | 1.00 | 24.04 | C |
| ATOM | 489 | SD | MET | A | 69 | 18.576 | 16.503 | 12.376 | 1.00 | 23.98 | S |
| ATOM | 490 | CE | MET | A | 69 | 17.309 | 17.708 | 12.749 | 1.00 | 24.60 | C |
| ATOM | 491 | C | MET | A | 69 | 18.631 | 12.160 | 9.510 | 1.00 | 25.36 | C |
| ATOM | 492 | O | MET | A | 69 | 19.060 | 12.386 | 8.383 | 1.00 | 21.00 | O |
| ATOM | 493 | N | THR | A | 70 | 18.934 | 11.059 | 10.197 | 1.00 | 24.31 | N |
| ATOM | 494 | CA | THR | A | 70 | 19.865 | 10.065 | 9.660 | 1.00 | 24.75 | C |
| ATOM | 495 | CB | THR | A | 70 | 20.629 | 9.314 | 10.787 | 1.00 | 26.67 | C |
| ATOM | 496 | OG1 | THR | A | 70 | 19.695 | 8.724 | 11.698 | 1.00 | 24.61 | O |
| ATOM | 497 | CG2 | THR | A | 70 | 21.440 | 10.294 | 11.643 | 1.00 | 21.95 | C |
| ATOM | 498 | C | THR | A | 70 | 19.217 | 9.086 | 8.679 | 1.00 | 25.39 | C |
| ATOM | 499 | O | THR | A | 70 | 19.863 | 8.132 | 8.242 | 1.00 | 25.68 | O |
| ATOM | 500 | N | LYS | A | 71 | 17.954 | 9.329 | 8.318 | 1.00 | 22.05 | N |
| ATOM | 501 | CA | LYS | A | 71 | 17.362 | 8.662 | 7.158 | 1.00 | 24.95 | C |
| ATOM | 502 | CB | LYS | A | 71 | 15.869 | 8.970 | 7.024 | 1.00 | 25.63 | C |
| ATOM | 503 | CG | LYS | A | 71 | 14.984 | 8.325 | 8.104 | 1.00 | 33.74 | C |

FIGURE 3J

| ATOM | 504 | CD  | LYS | A | 71 | 14.588 | 6.891  | 7.750  | 1.00 | 40.72 | C |
|------|-----|-----|-----|---|----|--------|--------|--------|------|-------|---|
| ATOM | 505 | CE  | LYS | A | 71 | 13.277 | 6.841  | 6.957  | 1.00 | 45.97 | C |
| ATOM | 506 | NZ  | LYS | A | 71 | 13.430 | 6.156  | 5.632  | 1.00 | 48.35 | N |
| ATOM | 507 | C   | LYS | A | 71 | 18.116 | 9.091  | 5.891  | 1.00 | 25.46 | C |
| ATOM | 508 | O   | LYS | A | 71 | 18.066 | 8.409  | 4.870  | 1.00 | 27.11 | O |
| ATOM | 509 | N   | TYR | A | 72 | 18.826 | 10.215 | 5.978  | 1.00 | 26.15 | N |
| ATOM | 510 | CA  | TYR | A | 72 | 19.674 | 10.677 | 4.879  | 1.00 | 23.70 | C |
| ATOM | 511 | CB  | TYR | A | 72 | 19.027 | 11.840 | 4.116  | 1.00 | 24.13 | C |
| ATOM | 512 | CG  | TYR | A | 72 | 19.928 | 12.364 | 3.019  | 1.00 | 25.76 | C |
| ATOM | 513 | CD1 | TYR | A | 72 | 20.469 | 13.645 | 3.086  | 1.00 | 26.87 | C |
| ATOM | 514 | CE1 | TYR | A | 72 | 21.307 | 14.121 | 2.076  | 1.00 | 29.16 | C |
| ATOM | 515 | CZ  | TYR | A | 72 | 21.616 | 13.299 | 1.006  | 1.00 | 28.81 | C |
| ATOM | 516 | OH  | TYR | A | 72 | 22.448 | 13.748 | 0.008  | 1.00 | 33.17 | O |
| ATOM | 517 | CE2 | TYR | A | 72 | 21.099 | 12.021 | 0.928  | 1.00 | 30.58 | C |
| ATOM | 518 | CD2 | TYR | A | 72 | 20.261 | 11.561 | 1.928  | 1.00 | 27.65 | C |
| ATOM | 519 | C   | TYR | A | 72 | 21.087 | 11.050 | 5.312  | 1.00 | 24.87 | C |
| ATOM | 520 | O   | TYR | A | 72 | 22.064 | 10.593 | 4.717  | 1.00 | 27.21 | O |
| ATOM | 521 | N   | HIS | A | 73 | 21.197 | 11.898 | 6.332  | 1.00 | 21.31 | N |
| ATOM | 522 | CA  | HIS | A | 73 | 22.495 | 12.381 | 6.775  | 1.00 | 20.08 | C |
| ATOM | 523 | CB  | HIS | A | 73 | 22.336 | 13.642 | 7.623  | 1.00 | 18.64 | C |
| ATOM | 524 | CG  | HIS | A | 73 | 21.788 | 14.808 | 6.859  | 1.00 | 21.71 | C |
| ATOM | 525 | ND1 | HIS | A | 73 | 22.569 | 15.586 | 6.032  | 1.00 | 17.90 | N |
| ATOM | 526 | CE1 | HIS | A | 73 | 21.824 | 16.534 | 5.491  | 1.00 | 19.15 | C |
| ATOM | 527 | NE2 | HIS | A | 73 | 20.587 | 16.395 | 5.932  | 1.00 | 19.73 | N |
| ATOM | 528 | CD2 | HIS | A | 73 | 20.536 | 15.321 | 6.788  | 1.00 | 19.88 | C |
| ATOM | 529 | C   | HIS | A | 73 | 23.280 | 11.325 | 7.537  | 1.00 | 22.98 | C |
| ATOM | 530 | O   | HIS | A | 73 | 22.698 | 10.440 | 8.165  | 1.00 | 21.15 | O |
| ATOM | 531 | N   | SER | A | 74 | 24.606 | 11.420 | 7.471  | 1.00 | 23.80 | N |
| ATOM | 532 | CA  | SER | A | 74 | 25.470 | 10.491 | 8.195  | 1.00 | 28.28 | C |
| ATOM | 533 | CB  | SER | A | 74 | 26.928 | 10.638 | 7.751  | 1.00 | 26.06 | C |
| ATOM | 534 | OG  | SER | A | 74 | 27.504 | 11.822 | 8.270  | 1.00 | 29.56 | O |
| ATOM | 535 | C   | SER | A | 74 | 25.351 | 10.705 | 9.698  | 1.00 | 27.37 | C |
| ATOM | 536 | O   | SER | A | 74 | 25.118 | 11.823 | 10.158 | 1.00 | 26.14 | O |
| ATOM | 537 | N   | ASP | A | 75 | 25.510 | 9.622  | 10.453 | 1.00 | 25.53 | N |
| ATOM | 538 | CA  | ASP | A | 75 | 25.470 | 9.679  | 11.910 | 1.00 | 31.71 | C |
| ATOM | 539 | CB  | ASP | A | 75 | 25.616 | 8.280  | 12.514 | 1.00 | 37.16 | C |
| ATOM | 540 | CG  | ASP | A | 75 | 24.361 | 7.448  | 12.361 | 1.00 | 44.25 | C |
| ATOM | 541 | OD1 | ASP | A | 75 | 24.392 | 6.467  | 11.589 | 1.00 | 49.21 | O |
| ATOM | 542 | OD2 | ASP | A | 75 | 23.298 | 7.693  | 12.973 | 1.00 | 47.55 | O |
| ATOM | 543 | C   | ASP | A | 75 | 26.524 | 10.618 | 12.488 | 1.00 | 26.63 | C |
| ATOM | 544 | O   | ASP | A | 75 | 26.250 | 11.328 | 13.448 | 1.00 | 25.73 | O |
| ATOM | 545 | N   | GLU | A | 76 | 27.719 | 10.631 | 11.897 | 1.00 | 26.99 | N |
| ATOM | 546 | CA  | GLU | A | 76 | 28.814 | 11.481 | 12.378 | 1.00 | 27.92 | C |
| ATOM | 547 | CB  | GLU | A | 76 | 30.116 | 11.190 | 11.615 | 1.00 | 33.59 | C |
| ATOM | 548 | CG  | GLU | A | 76 | 30.407 | 9.710  | 11.377 | 1.00 | 41.55 | C |
| ATOM | 549 | CD  | GLU | A | 76 | 29.741 | 9.169  | 10.118 | 1.00 | 46.86 | C |
| ATOM | 550 | OE1 | GLU | A | 76 | 30.160 | 9.560  | 9.005  | 1.00 | 50.59 | O |
| ATOM | 551 | OE2 | GLU | A | 76 | 28.795 | 8.355  | 10.240 | 1.00 | 44.87 | O |
| ATOM | 552 | C   | GLU | A | 76 | 28.467 | 12.963 | 12.255 | 1.00 | 23.53 | C |
| ATOM | 553 | O   | GLU | A | 76 | 28.761 | 13.763 | 13.151 | 1.00 | 26.19 | O |
| ATOM | 554 | N   | TYR | A | 77 | 27.840 | 13.323 | 11.138 | 1.00 | 22.98 | N |
| ATOM | 555 | CA  | TYR | A | 77 | 27.482 | 14.714 | 10.872 | 1.00 | 21.25 | C |
| ATOM | 556 | CB  | TYR | A | 77 | 27.084 | 14.895 | 9.392  | 1.00 | 20.56 | C |
| ATOM | 557 | CG  | TYR | A | 77 | 26.601 | 16.286 | 9.034  | 1.00 | 20.54 | C |
| ATOM | 558 | CD1 | TYR | A | 77 | 27.345 | 17.421 | 9.372  | 1.00 | 21.01 | C |
| ATOM | 559 | CE1 | TYR | A | 77 | 26.890 | 18.703 | 9.054  | 1.00 | 21.63 | C |
| ATOM | 560 | CZ  | TYR | A | 77 | 25.686 | 18.848 | 8.385  | 1.00 | 19.11 | C |

FIGURE 3K

| ATOM | 561 | OH  | TYR | A | 77 | 25.228 | 20.107 | 8.059  | 1.00 | 20.20 | O |
|------|-----|-----|-----|---|----|--------|--------|--------|------|-------|---|
| ATOM | 562 | CE2 | TYR | A | 77 | 24.936 | 17.735 | 8.031  | 1.00 | 20.31 | C |
| ATOM | 563 | CD2 | TYR | A | 77 | 25.392 | 16.465 | 8.357  | 1.00 | 19.49 | C |
| ATOM | 564 | C   | TYR | A | 77 | 26.375 | 15.190 | 11.826 | 1.00 | 19.07 | C |
| ATOM | 565 | O   | TYR | A | 77 | 26.469 | 16.276 | 12.397 | 1.00 | 22.28 | O |
| ATOM | 566 | N   | ILE | A | 78 | 25.344 | 14.373 | 12.007 | 1.00 | 21.41 | N |
| ATOM | 567 | CA  | ILE | A | 78 | 24.239 | 14.745 | 12.900 | 1.00 | 23.46 | C |
| ATOM | 568 | CB  | ILE | A | 78 | 23.020 | 13.801 | 12.704 | 1.00 | 21.24 | C |
| ATOM | 569 | CG1 | ILE | A | 78 | 22.453 | 13.935 | 11.281 | 1.00 | 24.33 | C |
| ATOM | 570 | CD1 | ILE | A | 78 | 22.186 | 15.393 | 10.814 | 1.00 | 21.45 | C |
| ATOM | 571 | CG2 | ILE | A | 78 | 21.926 | 14.066 | 13.750 | 1.00 | 24.33 | C |
| ATOM | 572 | C   | ILE | A | 78 | 24.713 | 14.807 | 14.358 | 1.00 | 22.03 | C |
| ATOM | 573 | O   | ILE | A | 78 | 24.315 | 15.706 | 15.117 | 1.00 | 25.61 | O |
| ATOM | 574 | N   | LYS | A | 79 | 25.587 | 13.869 | 14.729 | 1.00 | 24.02 | N |
| ATOM | 575 | CA  | LYS | A | 79 | 26.220 | 13.867 | 16.047 | 1.00 | 29.57 | C |
| ATOM | 576 | CB  | LYS | A | 79 | 27.173 | 12.675 | 16.176 | 1.00 | 34.77 | C |
| ATOM | 577 | CG  | LYS | A | 79 | 27.529 | 12.291 | 17.600 | 1.00 | 43.13 | C |
| ATOM | 578 | CD  | LYS | A | 79 | 27.915 | 10.813 | 17.689 | 1.00 | 47.35 | C |
| ATOM | 579 | CE  | LYS | A | 79 | 29.370 | 10.581 | 17.282 | 1.00 | 51.68 | C |
| ATOM | 580 | NZ  | LYS | A | 79 | 30.135 | 9.823  | 18.318 | 1.00 | 55.12 | N |
| ATOM | 581 | C   | LYS | A | 79 | 26.970 | 15.176 | 16.286 | 1.00 | 28.32 | C |
| ATOM | 582 | O   | LYS | A | 79 | 26.893 | 15.755 | 17.380 | 1.00 | 27.46 | O |
| ATOM | 583 | N   | PHE | A | 80 | 27.681 | 15.643 | 15.258 | 1.00 | 24.91 | N |
| ATOM | 584 | CA  | PHE | A | 80 | 28.402 | 16.917 | 15.315 | 1.00 | 24.74 | C |
| ATOM | 585 | CB  | PHE | A | 80 | 29.296 | 17.098 | 14.076 | 1.00 | 24.37 | C |
| ATOM | 586 | CG  | PHE | A | 80 | 29.817 | 18.502 | 13.897 | 1.00 | 24.98 | C |
| ATOM | 587 | CD1 | PHE | A | 80 | 29.237 | 19.358 | 12.963 | 1.00 | 26.01 | C |
| ATOM | 588 | CE1 | PHE | A | 80 | 29.708 | 20.654 | 12.800 | 1.00 | 24.31 | C |
| ATOM | 589 | CZ  | PHE | A | 80 | 30.767 | 21.109 | 13.568 | 1.00 | 25.79 | C |
| ATOM | 590 | CE2 | PHE | A | 80 | 31.356 | 20.264 | 14.505 | 1.00 | 27.71 | C |
| ATOM | 591 | CD2 | PHE | A | 80 | 30.881 | 18.969 | 14.662 | 1.00 | 26.48 | C |
| ATOM | 592 | C   | PHE | A | 80 | 27.448 | 18.109 | 15.475 | 1.00 | 20.54 | C |
| ATOM | 593 | O   | PHE | A | 80 | 27.670 | 18.975 | 16.327 | 1.00 | 25.28 | O |
| ATOM | 594 | N   | LEU | A | 81 | 26.397 | 18.154 | 14.654 | 1.00 | 23.25 | N |
| ATOM | 595 | CA  | LEU | A | 81 | 25.404 | 19.230 | 14.739 | 1.00 | 20.55 | C |
| ATOM | 596 | CB  | LEU | A | 81 | 24.320 | 19.077 | 13.663 | 1.00 | 21.77 | C |
| ATOM | 597 | CG  | LEU | A | 81 | 24.717 | 19.380 | 12.213 | 1.00 | 23.78 | C |
| ATOM | 598 | CD1 | LEU | A | 81 | 23.505 | 19.230 | 11.307 | 1.00 | 24.12 | C |
| ATOM | 599 | CD2 | LEU | A | 81 | 25.326 | 20.779 | 12.061 | 1.00 | 20.40 | C |
| ATOM | 600 | C   | LEU | A | 81 | 24.775 | 19.304 | 16.131 | 1.00 | 23.82 | C |
| ATOM | 601 | O   | LEU | A | 81 | 24.549 | 20.395 | 16.659 | 1.00 | 23.23 | O |
| ATOM | 602 | N   | ARG | A | 82 | 24.533 | 18.135 | 16.722 | 1.00 | 24.11 | N |
| ATOM | 603 | CA  | ARG | A | 82 | 24.014 | 18.008 | 18.088 | 1.00 | 31.57 | C |
| ATOM | 604 | CB  | ARG | A | 82 | 23.739 | 16.538 | 18.394 | 1.00 | 33.37 | C |
| ATOM | 605 | CG  | ARG | A | 82 | 22.400 | 16.047 | 17.951 | 1.00 | 39.51 | C |
| ATOM | 606 | CD  | ARG | A | 82 | 21.733 | 15.145 | 18.967 | 1.00 | 44.81 | C |
| ATOM | 607 | NE  | ARG | A | 82 | 21.938 | 13.738 | 18.644 | 1.00 | 47.74 | N |
| ATOM | 608 | CZ  | ARG | A | 82 | 21.639 | 12.727 | 19.451 | 1.00 | 48.73 | C |
| ATOM | 609 | NH1 | ARG | A | 82 | 21.863 | 11.482 | 19.058 | 1.00 | 48.37 | N |
| ATOM | 610 | NH2 | ARG | A | 82 | 21.117 | 12.954 | 20.651 | 1.00 | 49.98 | N |
| ATOM | 611 | C   | ARG | A | 82 | 24.965 | 18.541 | 19.163 | 1.00 | 33.99 | C |
| ATOM | 612 | O   | ARG | A | 82 | 24.522 | 18.964 | 20.236 | 1.00 | 36.10 | O |
| ATOM | 613 | N   | SER | A | 83 | 26.265 | 18.501 | 18.877 | 1.00 | 33.49 | N |
| ATOM | 614 | CA  | SER | A | 83 | 27.302 | 18.786 | 19.872 | 1.00 | 33.19 | C |
| ATOM | 615 | CB  | SER | A | 83 | 28.468 | 17.804 | 19.722 | 1.00 | 31.42 | C |
| ATOM | 616 | OG  | SER | A | 83 | 28.002 | 16.474 | 19.645 | 1.00 | 33.45 | O |
| ATOM | 617 | C   | SER | A | 83 | 27.849 | 20.201 | 19.818 | 1.00 | 31.55 | C |

FIGURE 3L

```
ATOM    618  O    SER A   83      28.182  20.776  20.853  1.00 34.62           O
ATOM    619  N    ILE A   84      27.942  20.757  18.612  1.00 30.92           N
ATOM    620  CA   ILE A   84      28.625  22.033  18.386  1.00 29.61           C
ATOM    621  CB   ILE A   84      28.991  22.204  16.863  1.00 30.29           C
ATOM    622  CG1  ILE A   84      29.954  23.376  16.646  1.00 32.44           C
ATOM    623  CD1  ILE A   84      31.317  23.187  17.253  1.00 33.42           C
ATOM    624  CG2  ILE A   84      27.739  22.350  15.983  1.00 28.46           C
ATOM    625  C    ILE A   84      27.885  23.252  18.953  1.00 31.08           C
ATOM    626  O    ILE A   84      26.679  23.412  18.757  1.00 30.35           O
ATOM    627  N    ARG A   85      28.627  24.095  19.668  1.00 30.63           N
ATOM    628  CA   ARG A   85      28.093  25.296  20.314  1.00 33.14           C
ATOM    629  CB   ARG A   85      27.779  25.009  21.784  1.00 38.41           C
ATOM    630  CG   ARG A   85      26.480  24.273  22.039  1.00 44.89           C
ATOM    631  CD   ARG A   85      26.270  23.909  23.500  1.00 49.36           C
ATOM    632  NE   ARG A   85      26.715  22.546  23.783  1.00 54.43           N
ATOM    633  CZ   ARG A   85      27.779  22.232  24.515  1.00 55.40           C
ATOM    634  NH1  ARG A   85      28.092  20.958  24.704  1.00 56.76           N
ATOM    635  NH2  ARG A   85      28.531  23.180  25.061  1.00 55.60           N
ATOM    636  C    ARG A   85      29.133  26.412  20.234  1.00 28.72           C
ATOM    637  O    ARG A   85      30.323  26.129  20.097  1.00 33.33           O
ATOM    638  N    PRO A   86      28.708  27.675  20.310  1.00 32.35           N
ATOM    639  CA   PRO A   86      29.658  28.798  20.327  1.00 33.28           C
ATOM    640  CB   PRO A   86      28.757  30.011  20.551  1.00 36.65           C
ATOM    641  CG   PRO A   86      27.445  29.592  19.993  1.00 34.96           C
ATOM    642  CD   PRO A   86      27.309  28.143  20.358  1.00 33.12           C
ATOM    643  C    PRO A   86      30.708  28.700  21.445  1.00 40.50           C
ATOM    644  O    PRO A   86      31.807  29.234  21.280  1.00 40.71           O
ATOM    645  N    ASP A   87      30.376  28.012  22.538  1.00 43.67           N
ATOM    646  CA   ASP A   87      31.260  27.898  23.703  1.00 48.56           C
ATOM    647  CB   ASP A   87      30.439  27.763  24.998  1.00 53.81           C
ATOM    648  CG   ASP A   87      29.646  26.468  25.063  1.00 56.89           C
ATOM    649  OD1  ASP A   87      28.439  26.490  24.736  1.00 60.09           O
ATOM    650  OD2  ASP A   87      30.140  25.382  25.437  1.00 57.39           O
ATOM    651  C    ASP A   87      32.308  26.781  23.611  1.00 47.82           C
ATOM    652  O    ASP A   87      33.293  26.799  24.350  1.00 47.19           O
ATOM    653  N    ASN A   88      32.092  25.816  22.718  1.00 47.17           N
ATOM    654  CA   ASN A   88      33.035  24.706  22.535  1.00 43.00           C
ATOM    655  CB   ASN A   88      32.398  23.368  22.952  1.00 41.44           C
ATOM    656  CG   ASN A   88      31.275  22.914  22.014  1.00 40.42           C
ATOM    657  OD1  ASN A   88      31.081  23.464  20.929  1.00 38.05           O
ATOM    658  ND2  ASN A   88      30.538  21.895  22.437  1.00 38.90           N
ATOM    659  C    ASN A   88      33.631  24.626  21.123  1.00 42.50           C
ATOM    660  O    ASN A   88      34.150  23.583  20.716  1.00 44.02           O
ATOM    661  N    MET A   89      33.557  25.739  20.396  1.00 44.68           N
ATOM    662  CA   MET A   89      34.004  25.829  19.003  1.00 47.95           C
ATOM    663  CB   MET A   89      33.747  27.237  18.466  1.00 48.59           C
ATOM    664  CG   MET A   89      32.677  27.323  17.404  1.00 48.75           C
ATOM    665  SD   MET A   89      32.197  29.029  17.117  1.00 49.61           S
ATOM    666  CE   MET A   89      33.377  29.523  15.854  1.00 54.00           C
ATOM    667  C    MET A   89      35.478  25.477  18.807  1.00 51.22           C
ATOM    668  O    MET A   89      35.819  24.657  17.950  1.00 49.28           O
ATOM    669  N    SER A   90      36.343  26.101  19.607  1.00 55.04           N
ATOM    670  CA   SER A   90      37.794  25.917  19.502  1.00 58.87           C
ATOM    671  CB   SER A   90      38.525  26.828  20.491  1.00 60.51           C
ATOM    672  OG   SER A   90      37.894  26.813  21.761  1.00 63.53           O
ATOM    673  C    SER A   90      38.228  24.464  19.697  1.00 58.74           C
ATOM    674  O    SER A   90      39.259  24.043  19.173  1.00 60.21           O
```

FIGURE 3M

```
ATOM    675  N    GLU A  91      37.427  23.706  20.442  1.00 59.55           N
ATOM    676  CA   GLU A  91      37.673  22.283  20.659  1.00 60.08           C
ATOM    677  CB   GLU A  91      36.924  21.794  21.901  1.00 62.80           C
ATOM    678  CG   GLU A  91      37.538  22.252  23.213  1.00 66.98           C
ATOM    679  CD   GLU A  91      36.725  21.816  24.415  1.00 70.22           C
ATOM    680  OE1  GLU A  91      35.815  22.569  24.825  1.00 71.48           O
ATOM    681  OE2  GLU A  91      36.996  20.720  24.948  1.00 70.70           O
ATOM    682  C    GLU A  91      37.284  21.434  19.449  1.00 56.93           C
ATOM    683  O    GLU A  91      37.817  20.340  19.258  1.00 57.11           O
ATOM    684  N    TYR A  92      36.356  21.943  18.639  1.00 53.39           N
ATOM    685  CA   TYR A  92      35.848  21.218  17.472  1.00 49.17           C
ATOM    686  CB   TYR A  92      34.313  21.235  17.467  1.00 49.27           C
ATOM    687  CG   TYR A  92      33.652  20.259  18.422  1.00 50.80           C
ATOM    688  CD1  TYR A  92      33.329  20.637  19.726  1.00 50.43           C
ATOM    689  CE1  TYR A  92      32.716  19.745  20.603  1.00 51.79           C
ATOM    690  CZ   TYR A  92      32.415  18.462  20.173  1.00 52.46           C
ATOM    691  OH   TYR A  92      31.809  17.575  21.031  1.00 54.33           O
ATOM    692  CE2  TYR A  92      32.718  18.065  18.882  1.00 52.06           C
ATOM    693  CD2  TYR A  92      33.331  18.963  18.014  1.00 51.22           C
ATOM    694  C    TYR A  92      36.374  21.792  16.149  1.00 46.37           C
ATOM    695  O    TYR A  92      35.807  21.529  15.087  1.00 40.05           O
ATOM    696  N    SER A  93      37.457  22.565  16.221  1.00 45.63           N
ATOM    697  CA   SER A  93      38.010  23.287  15.070  1.00 47.51           C
ATOM    698  CB   SER A  93      39.319  23.982  15.454  1.00 48.34           C
ATOM    699  OG   SER A  93      40.373  23.041  15.583  1.00 52.68           O
ATOM    700  C    SER A  93      38.216  22.430  13.814  1.00 47.08           C
ATOM    701  O    SER A  93      37.954  22.885  12.698  1.00 45.68           O
ATOM    702  N    LYS A  94      38.674  21.194  14.008  1.00 47.43           N
ATOM    703  CA   LYS A  94      38.946  20.269  12.905  1.00 46.11           C
ATOM    704  CB   LYS A  94      39.875  19.137  13.365  1.00 49.41           C
ATOM    705  CG   LYS A  94      41.219  19.617  13.937  1.00 54.56           C
ATOM    706  CD   LYS A  94      42.061  18.463  14.490  1.00 57.10           C
ATOM    707  CE   LYS A  94      42.915  18.907  15.676  1.00 59.72           C
ATOM    708  NZ   LYS A  94      44.276  19.368  15.265  1.00 59.90           N
ATOM    709  C    LYS A  94      37.663  19.694  12.305  1.00 44.73           C
ATOM    710  O    LYS A  94      37.575  19.482  11.092  1.00 39.71           O
ATOM    711  N    GLN A  95      36.675  19.440  13.162  1.00 42.62           N
ATOM    712  CA   GLN A  95      35.387  18.890  12.739  1.00 40.29           C
ATOM    713  CB   GLN A  95      34.601  18.371  13.947  1.00 44.66           C
ATOM    714  CG   GLN A  95      35.045  16.999  14.447  1.00 48.96           C
ATOM    715  CD   GLN A  95      36.414  17.015  15.124  1.00 52.54           C
ATOM    716  OE1  GLN A  95      36.850  18.043  15.653  1.00 53.11           O
ATOM    717  NE2  GLN A  95      37.095  15.873  15.101  1.00 56.39           N
ATOM    718  C    GLN A  95      34.565  19.933  11.991  1.00 31.97           C
ATOM    719  O    GLN A  95      33.834  19.611  11.060  1.00 30.53           O
ATOM    720  N    MET A  96      34.696  21.185  12.410  1.00 27.10           N
ATOM    721  CA   MET A  96      34.029  22.299  11.751  1.00 29.37           C
ATOM    722  CB   MET A  96      34.334  23.596  12.488  1.00 29.10           C
ATOM    723  CG   MET A  96      33.552  23.756  13.791  1.00 32.82           C
ATOM    724  SD   MET A  96      34.072  25.224  14.687  1.00 40.99           S
ATOM    725  CE   MET A  96      33.349  26.507  13.709  1.00 35.80           C
ATOM    726  C    MET A  96      34.437  22.412  10.281  1.00 31.38           C
ATOM    727  O    MET A  96      33.604  22.673   9.413  1.00 23.48           O
ATOM    728  N    GLN A  97      35.720  22.198  10.003  1.00 29.95           N
ATOM    729  CA   GLN A  97      36.213  22.283   8.631  1.00 29.24           C
ATOM    730  CB   GLN A  97      37.741  22.423   8.605  1.00 28.31           C
ATOM    731  CG   GLN A  97      38.230  23.582   9.459  1.00 33.77           C
```

FIGURE 3N

| ATOM | 732 | CD  | GLN A | 97  | 39.641 | 24.026 | 9.131  | 1.00 | 36.64 | C |
|------|-----|-----|-------|-----|--------|--------|--------|------|-------|---|
| ATOM | 733 | OE1 | GLN A | 97  | 39.871 | 25.201 | 8.843  | 1.00 | 40.09 | O |
| ATOM | 734 | NE2 | GLN A | 97  | 40.585 | 23.099 | 9.190  | 1.00 | 34.75 | N |
| ATOM | 735 | C   | GLN A | 97  | 35.722 | 21.112 | 7.791  | 1.00 | 28.13 | C |
| ATOM | 736 | O   | GLN A | 97  | 35.273 | 21.307 | 6.660  | 1.00 | 28.89 | O |
| ATOM | 737 | N   | ARG A | 98  | 35.769 | 19.908 | 8.363  | 1.00 | 26.86 | N |
| ATOM | 738 | CA  | ARG A | 98  | 35.295 | 18.696 | 7.693  | 1.00 | 28.01 | C |
| ATOM | 739 | CB  | ARG A | 98  | 35.537 | 17.476 | 8.586  | 1.00 | 35.34 | C |
| ATOM | 740 | CG  | ARG A | 98  | 35.623 | 16.156 | 7.839  | 1.00 | 43.39 | C |
| ATOM | 741 | CD  | ARG A | 98  | 34.705 | 15.075 | 8.383  | 1.00 | 51.56 | C |
| ATOM | 742 | NE  | ARG A | 98  | 35.073 | 14.657 | 9.737  | 1.00 | 56.66 | N |
| ATOM | 743 | CZ  | ARG A | 98  | 34.962 | 13.416 | 10.203 | 1.00 | 60.29 | C |
| ATOM | 744 | NH1 | ARG A | 98  | 35.319 | 13.145 | 11.452 | 1.00 | 60.97 | N |
| ATOM | 745 | NH2 | ARG A | 98  | 34.496 | 12.443 | 9.428  | 1.00 | 62.22 | N |
| ATOM | 746 | C   | ARG A | 98  | 33.812 | 18.762 | 7.295  | 1.00 | 28.93 | C |
| ATOM | 747 | O   | ARG A | 98  | 33.425 | 18.280 | 6.230  | 1.00 | 27.55 | O |
| ATOM | 748 | N   | PHE A | 99  | 32.991 | 19.352 | 8.162  | 1.00 | 26.78 | N |
| ATOM | 749 | CA  | PHE A | 99  | 31.545 | 19.424 | 7.937  | 1.00 | 22.03 | C |
| ATOM | 750 | CB  | PHE A | 99  | 30.797 | 19.112 | 9.240  | 1.00 | 22.34 | C |
| ATOM | 751 | CG  | PHE A | 99  | 31.047 | 17.724 | 9.765  | 1.00 | 21.45 | C |
| ATOM | 752 | CD1 | PHE A | 99  | 30.825 | 16.613 | 8.965  | 1.00 | 22.29 | C |
| ATOM | 753 | CE1 | PHE A | 99  | 31.063 | 15.328 | 9.446  | 1.00 | 25.12 | C |
| ATOM | 754 | CZ  | PHE A | 99  | 31.529 | 15.150 | 10.741 | 1.00 | 26.43 | C |
| ATOM | 755 | CE2 | PHE A | 99  | 31.761 | 16.249 | 11.550 | 1.00 | 27.29 | C |
| ATOM | 756 | CD2 | PHE A | 99  | 31.523 | 17.533 | 11.060 | 1.00 | 25.68 | C |
| ATOM | 757 | C   | PHE A | 99  | 31.093 | 20.772 | 7.364  | 1.00 | 24.51 | C |
| ATOM | 758 | O   | PHE A | 99  | 29.892 | 21.024 | 7.240  | 1.00 | 24.49 | O |
| ATOM | 759 | N   | ASN A | 100 | 32.062 | 21.619 | 7.010  | 1.00 | 23.01 | N |
| ATOM | 760 | CA  | ASN A | 100 | 31.819 | 22.946 | 6.417  | 1.00 | 24.31 | C |
| ATOM | 761 | CB  | ASN A | 100 | 31.255 | 22.832 | 4.993  | 1.00 | 22.20 | C |
| ATOM | 762 | CG  | ASN A | 100 | 31.330 | 24.146 | 4.227  | 1.00 | 28.03 | C |
| ATOM | 763 | OD1 | ASN A | 100 | 32.274 | 24.915 | 4.390  | 1.00 | 24.26 | O |
| ATOM | 764 | ND2 | ASN A | 100 | 30.322 | 24.414 | 3.398  | 1.00 | 25.70 | N |
| ATOM | 765 | C   | ASN A | 100 | 30.954 | 23.890 | 7.268  | 1.00 | 25.05 | C |
| ATOM | 766 | O   | ASN A | 100 | 30.050 | 24.565 | 6.761  | 1.00 | 23.93 | O |
| ATOM | 767 | N   | VAL A | 101 | 31.241 | 23.927 | 8.561  | 1.00 | 24.26 | N |
| ATOM | 768 | CA  | VAL A | 101 | 30.550 | 24.829 | 9.472  | 1.00 | 27.01 | C |
| ATOM | 769 | CB  | VAL A | 101 | 29.897 | 24.032 | 10.639 | 1.00 | 29.13 | C |
| ATOM | 770 | CG1 | VAL A | 101 | 29.439 | 24.944 | 11.754 | 1.00 | 31.06 | C |
| ATOM | 771 | CG2 | VAL A | 101 | 28.720 | 23.209 | 10.118 | 1.00 | 24.73 | C |
| ATOM | 772 | C   | VAL A | 101 | 31.536 | 25.891 | 9.962  | 1.00 | 30.21 | C |
| ATOM | 773 | O   | VAL A | 101 | 32.674 | 25.573 | 10.316 | 1.00 | 34.62 | O |
| ATOM | 774 | N   | GLY A | 102 | 31.121 | 27.155 | 9.946  | 1.00 | 31.63 | N |
| ATOM | 775 | CA  | GLY A | 102 | 31.953 | 28.213 | 10.495 | 1.00 | 34.41 | C |
| ATOM | 776 | C   | GLY A | 102 | 32.093 | 29.512 | 9.725  | 1.00 | 36.47 | C |
| ATOM | 777 | O   | GLY A | 102 | 32.550 | 30.506 | 10.297 | 1.00 | 39.67 | O |
| ATOM | 778 | N   | GLU A | 103 | 31.735 | 29.518 | 8.442  | 1.00 | 37.59 | N |
| ATOM | 779 | CA  | GLU A | 103 | 31.738 | 30.761 | 7.657  | 1.00 | 39.54 | C |
| ATOM | 780 | CB  | GLU A | 103 | 32.776 | 30.742 | 6.515  | 1.00 | 47.84 | C |
| ATOM | 781 | CG  | GLU A | 103 | 33.439 | 29.395 | 6.254  | 1.00 | 57.12 | C |
| ATOM | 782 | CD  | GLU A | 103 | 34.707 | 29.494 | 5.416  | 1.00 | 62.56 | C |
| ATOM | 783 | OE1 | GLU A | 103 | 35.148 | 28.448 | 4.884  | 1.00 | 63.73 | O |
| ATOM | 784 | OE2 | GLU A | 103 | 35.268 | 30.606 | 5.285  | 1.00 | 63.86 | O |
| ATOM | 785 | C   | GLU A | 103 | 30.343 | 31.094 | 7.133  | 1.00 | 35.88 | C |
| ATOM | 786 | O   | GLU A | 103 | 29.620 | 31.870 | 7.758  | 1.00 | 36.79 | O |
| ATOM | 787 | N   | ASP A | 104 | 29.969 | 30.503 | 5.997  | 1.00 | 30.21 | N |
| ATOM | 788 | CA  | ASP A | 104 | 28.626 | 30.657 | 5.436  | 1.00 | 32.67 | C |

FIGURE 30

```
ATOM    789  CB  ASP A 104      28.532  29.970   4.071  1.00 36.26           C
ATOM    790  CG  ASP A 104      29.047  30.835   2.932  1.00 39.98           C
ATOM    791  OD1 ASP A 104      29.618  31.917   3.193  1.00 41.69           O
ATOM    792  OD2 ASP A 104      28.924  30.503   1.733  1.00 43.71           O
ATOM    793  C   ASP A 104      27.586  30.044   6.363  1.00 27.12           C
ATOM    794  O   ASP A 104      26.473  30.547   6.486  1.00 27.91           O
ATOM    795  N   CYS A 105      27.963  28.938   6.998  1.00 25.15           N
ATOM    796  CA  CYS A 105      27.087  28.214   7.902  1.00 23.97           C
ATOM    797  CB  CYS A 105      26.918  26.764   7.428  1.00 24.52           C
ATOM    798  SG  CYS A 105      26.536  26.592   5.658  1.00 28.15           S
ATOM    799  C   CYS A 105      27.694  28.287   9.303  1.00 22.93           C
ATOM    800  O   CYS A 105      28.385  27.364   9.738  1.00 20.50           O
ATOM    801  N   PRO A 106      27.456  29.393  10.010  1.00 21.50           N
ATOM    802  CA  PRO A 106      28.108  29.603  11.306  1.00 21.74           C
ATOM    803  CB  PRO A 106      27.823  31.079  11.605  1.00 24.94           C
ATOM    804  CG  PRO A 106      26.551  31.374  10.877  1.00 23.33           C
ATOM    805  CD  PRO A 106      26.571  30.515   9.650  1.00 23.08           C
ATOM    806  C   PRO A 106      27.519  28.726  12.399  1.00 23.61           C
ATOM    807  O   PRO A 106      26.446  28.127  12.227  1.00 21.20           O
ATOM    808  N   VAL A 107      28.253  28.635  13.501  1.00 26.40           N
ATOM    809  CA  VAL A 107      27.750  28.040  14.727  1.00 26.92           C
ATOM    810  CB  VAL A 107      28.889  27.463  15.603  1.00 26.44           C
ATOM    811  CG1 VAL A 107      28.327  26.760  16.826  1.00 27.92           C
ATOM    812  CG2 VAL A 107      29.744  26.494  14.807  1.00 26.88           C
ATOM    813  C   VAL A 107      27.050  29.159  15.481  1.00 27.76           C
ATOM    814  O   VAL A 107      27.638  30.220  15.735  1.00 27.02           O
ATOM    815  N   PHE A 108      25.787  28.932  15.819  1.00 24.54           N
ATOM    816  CA  PHE A 108      25.050  29.882  16.643  1.00 25.54           C
ATOM    817  CB  PHE A 108      24.147  30.795  15.792  1.00 24.92           C
ATOM    818  CG  PHE A 108      23.190  30.060  14.874  1.00 24.09           C
ATOM    819  CD1 PHE A 108      23.535  29.799  13.552  1.00 23.93           C
ATOM    820  CE1 PHE A 108      22.652  29.144  12.695  1.00 23.69           C
ATOM    821  CZ  PHE A 108      21.392  28.749  13.162  1.00 24.59           C
ATOM    822  CE2 PHE A 108      21.034  29.012  14.482  1.00 22.49           C
ATOM    823  CD2 PHE A 108      21.930  29.671  15.324  1.00 21.84           C
ATOM    824  C   PHE A 108      24.271  29.150  17.723  1.00 25.72           C
ATOM    825  O   PHE A 108      24.072  27.937  17.629  1.00 25.11           O
ATOM    826  N   ASP A 109      23.861  29.883  18.754  1.00 28.56           N
ATOM    827  CA  ASP A 109      23.079  29.314  19.848  1.00 29.52           C
ATOM    828  CB  ASP A 109      22.791  30.372  20.919  1.00 35.51           C
ATOM    829  CG  ASP A 109      24.036  30.785  21.687  1.00 42.56           C
ATOM    830  OD1 ASP A 109      24.710  29.904  22.267  1.00 47.41           O
ATOM    831  OD2 ASP A 109      24.412  31.973  21.773  1.00 45.72           O
ATOM    832  C   ASP A 109      21.769  28.738  19.320  1.00 27.06           C
ATOM    833  O   ASP A 109      21.024  29.425  18.613  1.00 26.92           O
ATOM    834  N   GLY A 110      21.516  27.473  19.648  1.00 22.47           N
ATOM    835  CA  GLY A 110      20.289  26.802  19.259  1.00 26.60           C
ATOM    836  C   GLY A 110      20.303  26.242  17.850  1.00 24.61           C
ATOM    837  O   GLY A 110      19.251  25.886  17.317  1.00 24.16           O
ATOM    838  N   LEU A 111      21.496  26.152  17.256  1.00 25.45           N
ATOM    839  CA  LEU A 111      21.665  25.627  15.898  1.00 22.65           C
ATOM    840  CB  LEU A 111      23.152  25.456  15.556  1.00 25.46           C
ATOM    841  CG  LEU A 111      23.542  24.765  14.247  1.00 25.97           C
ATOM    842  CD1 LEU A 111      22.826  25.389  13.061  1.00 26.11           C
ATOM    843  CD2 LEU A 111      25.055  24.826  14.053  1.00 24.48           C
ATOM    844  C   LEU A 111      20.911  24.323  15.654  1.00 22.25           C
ATOM    845  O   LEU A 111      20.131  24.231  14.708  1.00 20.01           O
```

FIGURE 3P

| | | | | | | | | | | |
|---|---|---|---|---|---|---|---|---|---|---|
| ATOM | 846 | N | PHE | A | 112 | 21.140 | 23.314 | 16.495 | 1.00 21.78 | N |
| ATOM | 847 | CA | PHE | A | 112 | 20.473 | 22.036 | 16.278 | 1.00 19.97 | C |
| ATOM | 848 | CB | PHE | A | 112 | 21.014 | 20.917 | 17.179 | 1.00 22.58 | C |
| ATOM | 849 | CG | PHE | A | 112 | 20.541 | 19.547 | 16.765 | 1.00 21.88 | C |
| ATOM | 850 | CD1 | PHE | A | 112 | 20.960 | 18.990 | 15.563 | 1.00 24.96 | C |
| ATOM | 851 | CE1 | PHE | A | 112 | 20.505 | 17.737 | 15.160 | 1.00 25.01 | C |
| ATOM | 852 | CZ | PHE | A | 112 | 19.608 | 17.033 | 15.960 | 1.00 27.92 | C |
| ATOM | 853 | CE2 | PHE | A | 112 | 19.175 | 17.585 | 17.154 | 1.00 25.93 | C |
| ATOM | 854 | CD2 | PHE | A | 112 | 19.632 | 18.841 | 17.548 | 1.00 25.29 | C |
| ATOM | 855 | C | PHE | A | 112 | 18.948 | 22.138 | 16.386 | 1.00 20.44 | C |
| ATOM | 856 | O | PHE | A | 112 | 18.237 | 21.567 | 15.563 | 1.00 21.44 | O |
| ATOM | 857 | N | GLU | A | 113 | 18.462 | 22.860 | 17.395 | 1.00 19.79 | N |
| ATOM | 858 | CA | GLU | A | 113 | 17.025 | 23.078 | 17.585 | 1.00 23.27 | C |
| ATOM | 859 | CB | GLU | A | 113 | 16.773 | 23.917 | 18.844 | 1.00 28.94 | C |
| ATOM | 860 | CG | GLU | A | 113 | 16.734 | 23.123 | 20.139 | 1.00 41.80 | C |
| ATOM | 861 | CD | GLU | A | 113 | 16.053 | 23.880 | 21.268 | 1.00 51.45 | C |
| ATOM | 862 | OE1 | GLU | A | 113 | 14.887 | 23.548 | 21.587 | 1.00 55.07 | O |
| ATOM | 863 | OE2 | GLU | A | 113 | 16.681 | 24.805 | 21.837 | 1.00 55.95 | O |
| ATOM | 864 | C | GLU | A | 113 | 16.400 | 23.769 | 16.373 | 1.00 20.04 | C |
| ATOM | 865 | O | GLU | A | 113 | 15.296 | 23.422 | 15.950 | 1.00 19.05 | O |
| ATOM | 866 | N | PHE | A | 114 | 17.110 | 24.763 | 15.838 | 1.00 21.15 | N |
| ATOM | 867 | CA | PHE | A | 114 | 16.719 | 25.458 | 14.609 | 1.00 21.75 | C |
| ATOM | 868 | CB | PHE | A | 114 | 17.764 | 26.539 | 14.274 | 1.00 22.89 | C |
| ATOM | 869 | CG | PHE | A | 114 | 17.587 | 27.185 | 12.923 | 1.00 26.73 | C |
| ATOM | 870 | CD1 | PHE | A | 114 | 18.426 | 26.846 | 11.860 | 1.00 29.48 | C |
| ATOM | 871 | CE1 | PHE | A | 114 | 18.274 | 27.450 | 10.613 | 1.00 30.99 | C |
| ATOM | 872 | CZ | PHE | A | 114 | 17.278 | 28.408 | 10.422 | 1.00 30.97 | C |
| ATOM | 873 | CE2 | PHE | A | 114 | 16.444 | 28.756 | 11.474 | 1.00 28.22 | C |
| ATOM | 874 | CD2 | PHE | A | 114 | 16.606 | 28.148 | 12.718 | 1.00 25.48 | C |
| ATOM | 875 | C | PHE | A | 114 | 16.542 | 24.460 | 13.458 | 1.00 21.61 | C |
| ATOM | 876 | O | PHE | A | 114 | 15.524 | 24.479 | 12.768 | 1.00 21.11 | O |
| ATOM | 877 | N | CYS | A | 115 | 17.526 | 23.577 | 13.271 | 1.00 18.25 | N |
| ATOM | 878 | CA | CYS | A | 115 | 17.435 | 22.528 | 12.261 | 1.00 19.52 | C |
| ATOM | 879 | CB | CYS | A | 115 | 18.719 | 21.700 | 12.226 | 1.00 22.06 | C |
| ATOM | 880 | SG | CYS | A | 115 | 20.158 | 22.667 | 11.742 | 1.00 26.02 | S |
| ATOM | 881 | C | CYS | A | 115 | 16.252 | 21.606 | 12.514 | 1.00 16.78 | C |
| ATOM | 882 | O | CYS | A | 115 | 15.552 | 21.227 | 11.585 | 1.00 18.66 | O |
| ATOM | 883 | N | GLN | A | 116 | 16.047 | 21.245 | 13.777 | 1.00 16.08 | N |
| ATOM | 884 | CA | GLN | A | 116 | 14.959 | 20.333 | 14.148 | 1.00 19.01 | C |
| ATOM | 885 | CB | GLN | A | 116 | 14.988 | 20.041 | 15.647 | 1.00 20.96 | C |
| ATOM | 886 | CG | GLN | A | 116 | 16.140 | 19.188 | 16.130 | 1.00 19.64 | C |
| ATOM | 887 | CD | GLN | A | 116 | 16.007 | 18.886 | 17.614 | 1.00 21.49 | C |
| ATOM | 888 | OE1 | GLN | A | 116 | 16.306 | 19.739 | 18.457 | 1.00 21.33 | O |
| ATOM | 889 | NE2 | GLN | A | 116 | 15.519 | 17.692 | 17.935 | 1.00 20.46 | N |
| ATOM | 890 | C | GLN | A | 116 | 13.597 | 20.906 | 13.787 | 1.00 19.03 | C |
| ATOM | 891 | O | GLN | A | 116 | 12.720 | 20.184 | 13.318 | 1.00 21.06 | O |
| ATOM | 892 | N | LEU | A | 117 | 13.433 | 22.203 | 14.018 | 1.00 18.71 | N |
| ATOM | 893 | CA | LEU | A | 117 | 12.167 | 22.898 | 13.768 | 1.00 21.30 | C |
| ATOM | 894 | CB | LEU | A | 117 | 12.159 | 24.268 | 14.454 | 1.00 24.70 | C |
| ATOM | 895 | CG | LEU | A | 117 | 11.908 | 24.268 | 15.961 | 1.00 29.00 | C |
| ATOM | 896 | CD1 | LEU | A | 117 | 12.011 | 25.688 | 16.512 | 1.00 33.08 | C |
| ATOM | 897 | CD2 | LEU | A | 117 | 10.554 | 23.650 | 16.292 | 1.00 33.00 | C |
| ATOM | 898 | C | LEU | A | 117 | 11.893 | 23.073 | 12.286 | 1.00 21.23 | C |
| ATOM | 899 | O | LEU | A | 117 | 10.777 | 22.833 | 11.823 | 1.00 21.72 | O |
| ATOM | 900 | N | SER | A | 118 | 12.919 | 23.501 | 11.555 | 1.00 19.10 | N |
| ATOM | 901 | CA | SER | A | 118 | 12.850 | 23.658 | 10.106 | 1.00 21.36 | C |
| ATOM | 902 | CB | SER | A | 118 | 14.194 | 24.195 | 9.593 | 1.00 22.78 | C |

FIGURE 3Q

| | | | | | | | | | |
|---|---|---|---|---|---|---|---|---|---|
| ATOM | 903 | OG | SER A 118 | 14.250 | 24.187 | 8.181 | 1.00 | 30.56 | O |
| ATOM | 904 | C | SER A 118 | 12.502 | 22.323 | 9.438 | 1.00 | 20.55 | C |
| ATOM | 905 | O | SER A 118 | 11.612 | 22.246 | 8.588 | 1.00 | 22.01 | O |
| ATOM | 906 | N | THR A 119 | 13.197 | 21.270 | 9.850 | 1.00 | 20.36 | N |
| ATOM | 907 | CA | THR A 119 | 12.986 | 19.930 | 9.312 | 1.00 | 19.89 | C |
| ATOM | 908 | CB | THR A 119 | 14.122 | 19.000 | 9.775 | 1.00 | 21.72 | C |
| ATOM | 909 | OG1 | THR A 119 | 15.366 | 19.492 | 9.261 | 1.00 | 23.16 | O |
| ATOM | 910 | CG2 | THR A 119 | 13.993 | 17.618 | 9.153 | 1.00 | 24.56 | C |
| ATOM | 911 | C | THR A 119 | 11.629 | 19.344 | 9.707 | 1.00 | 20.94 | C |
| ATOM | 912 | O | THR A 119 | 10.954 | 18.740 | 8.876 | 1.00 | 18.19 | O |
| ATOM | 913 | N | GLY A 120 | 11.246 | 19.516 | 10.970 | 1.00 | 20.37 | N |
| ATOM | 914 | CA | GLY A 120 | 9.993 | 18.961 | 11.472 | 1.00 | 18.50 | C |
| ATOM | 915 | C | GLY A 120 | 8.791 | 19.353 | 10.632 | 1.00 | 19.37 | C |
| ATOM | 916 | O | GLY A 120 | 7.937 | 18.514 | 10.343 | 1.00 | 18.97 | O |
| ATOM | 917 | N | GLY A 121 | 8.736 | 20.621 | 10.221 | 1.00 | 16.56 | N |
| ATOM | 918 | CA | GLY A 121 | 7.656 | 21.110 | 9.378 | 1.00 | 19.64 | C |
| ATOM | 919 | C | GLY A 121 | 7.545 | 20.412 | 8.030 | 1.00 | 15.61 | C |
| ATOM | 920 | O | GLY A 121 | 6.445 | 20.073 | 7.586 | 1.00 | 16.06 | O |
| ATOM | 921 | N | SER A 122 | 8.684 | 20.191 | 7.377 | 1.00 | 13.94 | N |
| ATOM | 922 | CA | SER A 122 | 8.706 | 19.551 | 6.063 | 1.00 | 16.13 | C |
| ATOM | 923 | CB | SER A 122 | 10.093 | 19.700 | 5.430 | 1.00 | 17.73 | C |
| ATOM | 924 | OG | SER A 122 | 10.429 | 21.079 | 5.348 | 1.00 | 17.56 | O |
| ATOM | 925 | C | SER A 122 | 8.300 | 18.077 | 6.147 | 1.00 | 17.26 | C |
| ATOM | 926 | O | SER A 122 | 7.477 | 17.609 | 5.359 | 1.00 | 16.70 | O |
| ATOM | 927 | N | VAL A 123 | 8.867 | 17.364 | 7.113 | 1.00 | 19.13 | N |
| ATOM | 928 | CA | VAL A 123 | 8.544 | 15.946 | 7.318 | 1.00 | 22.48 | C |
| ATOM | 929 | CB | VAL A 123 | 9.558 | 15.271 | 8.278 | 1.00 | 23.49 | C |
| ATOM | 930 | CG1 | VAL A 123 | 9.094 | 13.867 | 8.707 | 1.00 | 28.65 | C |
| ATOM | 931 | CG2 | VAL A 123 | 10.931 | 15.188 | 7.615 | 1.00 | 22.94 | C |
| ATOM | 932 | C | VAL A 123 | 7.084 | 15.768 | 7.781 | 1.00 | 21.22 | C |
| ATOM | 933 | O | VAL A 123 | 6.377 | 14.880 | 7.296 | 1.00 | 19.57 | O |
| ATOM | 934 | N | ALA A 124 | 6.632 | 16.630 | 8.689 | 1.00 | 21.25 | N |
| ATOM | 935 | CA | ALA A 124 | 5.231 | 16.615 | 9.126 | 1.00 | 20.58 | C |
| ATOM | 936 | CB | ALA A 124 | 4.993 | 17.643 | 10.232 | 1.00 | 20.68 | C |
| ATOM | 937 | C | ALA A 124 | 4.271 | 16.853 | 7.963 | 1.00 | 19.99 | C |
| ATOM | 938 | O | ALA A 124 | 3.238 | 16.184 | 7.852 | 1.00 | 19.08 | O |
| ATOM | 939 | N | GLY A 125 | 4.613 | 17.805 | 7.100 | 1.00 | 19.56 | N |
| ATOM | 940 | CA | GLY A 125 | 3.831 | 18.071 | 5.905 | 1.00 | 15.04 | C |
| ATOM | 941 | C | GLY A 125 | 3.743 | 16.871 | 4.971 | 1.00 | 15.60 | C |
| ATOM | 942 | O | GLY A 125 | 2.668 | 16.554 | 4.453 | 1.00 | 16.85 | O |
| ATOM | 943 | N | ALA A 126 | 4.875 | 16.205 | 4.755 | 1.00 | 17.63 | N |
| ATOM | 944 | CA | ALA A 126 | 4.914 | 15.003 | 3.919 | 1.00 | 16.88 | C |
| ATOM | 945 | CB | ALA A 126 | 6.357 | 14.518 | 3.740 | 1.00 | 18.31 | C |
| ATOM | 946 | C | ALA A 126 | 4.032 | 13.886 | 4.484 | 1.00 | 18.39 | C |
| ATOM | 947 | O | ALA A 126 | 3.315 | 13.225 | 3.733 | 1.00 | 18.76 | O |
| ATOM | 948 | N | VAL A 127 | 4.089 | 13.687 | 5.803 | 1.00 | 21.04 | N |
| ATOM | 949 | CA | VAL A 127 | 3.254 | 12.687 | 6.483 | 1.00 | 20.07 | C |
| ATOM | 950 | CB | VAL A 127 | 3.597 | 12.566 | 8.000 | 1.00 | 21.55 | C |
| ATOM | 951 | CG1 | VAL A 127 | 2.570 | 11.686 | 8.741 | 1.00 | 21.33 | C |
| ATOM | 952 | CG2 | VAL A 127 | 5.014 | 12.015 | 8.203 | 1.00 | 23.06 | C |
| ATOM | 953 | C | VAL A 127 | 1.770 | 12.990 | 6.284 | 1.00 | 23.14 | C |
| ATOM | 954 | O | VAL A 127 | 0.992 | 12.092 | 5.953 | 1.00 | 22.48 | O |
| ATOM | 955 | N | LYS A 128 | 1.388 | 14.256 | 6.463 | 1.00 | 20.92 | N |
| ATOM | 956 | CA | LYS A 128 | 0.000 | 14.685 | 6.262 | 1.00 | 22.14 | C |
| ATOM | 957 | CB | LYS A 128 | -0.151 | 16.164 | 6.638 | 1.00 | 25.68 | C |
| ATOM | 958 | CG | LYS A 128 | -1.577 | 16.593 | 6.963 | 1.00 | 33.83 | C |
| ATOM | 959 | CD | LYS A 128 | -1.898 | 16.433 | 8.440 | 1.00 | 37.22 | C |

FIGURE 3R

```
ATOM    960  CE  LYS A 128      -3.245  17.062   8.767  1.00 39.54           C
ATOM    961  NZ  LYS A 128      -4.117  16.134   9.537  1.00 43.32           N
ATOM    962  C   LYS A 128      -0.474  14.441   4.817  1.00 21.94           C
ATOM    963  O   LYS A 128      -1.617  14.025   4.575  1.00 19.05           O
ATOM    964  N   LEU A 129       0.413  14.697   3.863  1.00 17.99           N
ATOM    965  CA  LEU A 129       0.140  14.436   2.456  1.00 20.30           C
ATOM    966  CB  LEU A 129       1.270  15.006   1.589  1.00 21.72           C
ATOM    967  CG  LEU A 129       1.199  16.344   0.832  1.00 27.04           C
ATOM    968  CD1 LEU A 129      -0.022  17.198   1.108  1.00 25.71           C
ATOM    969  CD2 LEU A 129       2.485  17.133   1.030  1.00 21.20           C
ATOM    970  C   LEU A 129      -0.031  12.930   2.196  1.00 21.81           C
ATOM    971  O   LEU A 129      -0.985  12.520   1.530  1.00 24.50           O
ATOM    972  N   ASN A 130       0.886  12.125   2.733  1.00 21.13           N
ATOM    973  CA  ASN A 130       0.831  10.663   2.619  1.00 22.34           C
ATOM    974  CB  ASN A 130       1.978  10.009   3.399  1.00 23.20           C
ATOM    975  CG  ASN A 130       3.299  10.005   2.633  1.00 21.83           C
ATOM    976  OD1 ASN A 130       3.340  10.275   1.439  1.00 21.99           O
ATOM    977  ND2 ASN A 130       4.379   9.683   3.328  1.00 20.89           N
ATOM    978  C   ASN A 130      -0.491  10.093   3.129  1.00 26.11           C
ATOM    979  O   ASN A 130      -1.044   9.159   2.550  1.00 23.82           O
ATOM    980  N   ARG A 131      -0.980  10.670   4.222  1.00 25.03           N
ATOM    981  CA  ARG A 131      -2.192  10.197   4.883  1.00 25.63           C
ATOM    982  CB  ARG A 131      -2.177  10.633   6.345  1.00 26.07           C
ATOM    983  CG  ARG A 131      -1.129   9.907   7.157  1.00 24.82           C
ATOM    984  CD  ARG A 131      -1.019  10.388   8.578  1.00 32.37           C
ATOM    985  NE  ARG A 131      -2.138   9.910   9.382  1.00 37.96           N
ATOM    986  CZ  ARG A 131      -2.471  10.400  10.570  1.00 42.32           C
ATOM    987  NH1 ARG A 131      -3.508   9.891  11.227  1.00 38.26           N
ATOM    988  NH2 ARG A 131      -1.772  11.402  11.097  1.00 37.14           N
ATOM    989  C   ARG A 131      -3.456  10.680   4.193  1.00 27.74           C
ATOM    990  O   ARG A 131      -4.566  10.322   4.599  1.00 30.63           O
ATOM    991  N   GLN A 132      -3.279  11.484   3.145  1.00 24.76           N
ATOM    992  CA  GLN A 132      -4.378  12.072   2.385  1.00 30.81           C
ATOM    993  CB  GLN A 132      -5.199  10.988   1.667  1.00 33.63           C
ATOM    994  CG  GLN A 132      -4.550  10.446   0.397  1.00 39.49           C
ATOM    995  CD  GLN A 132      -5.352   9.317  -0.238  1.00 43.85           C
ATOM    996  OE1 GLN A 132      -4.824   8.231  -0.469  1.00 46.84           O
ATOM    997  NE2 GLN A 132      -6.624   9.572  -0.519  1.00 46.68           N
ATOM    998  C   GLN A 132      -5.265  12.944   3.276  1.00 30.21           C
ATOM    999  O   GLN A 132      -6.481  13.008   3.095  1.00 32.07           O
ATOM   1000  N   GLN A 133      -4.636  13.621   4.231  1.00 26.05           N
ATOM   1001  CA  GLN A 133      -5.346  14.484   5.165  1.00 29.85           C
ATOM   1002  CB  GLN A 133      -4.771  14.316   6.569  1.00 30.51           C
ATOM   1003  CG  GLN A 133      -5.507  13.280   7.386  1.00 38.40           C
ATOM   1004  CD  GLN A 133      -4.703  12.773   8.563  1.00 40.74           C
ATOM   1005  OE1 GLN A 133      -3.731  13.402   8.983  1.00 46.48           O
ATOM   1006  NE2 GLN A 133      -5.110  11.632   9.103  1.00 43.48           N
ATOM   1007  C   GLN A 133      -5.317  15.950   4.739  1.00 28.10           C
ATOM   1008  O   GLN A 133      -5.995  16.788   5.329  1.00 27.85           O
ATOM   1009  N   THR A 134      -4.524  16.247   3.713  1.00 23.27           N
ATOM   1010  CA  THR A 134      -4.472  17.581   3.124  1.00 23.70           C
ATOM   1011  CB  THR A 134      -3.500  18.509   3.931  1.00 24.37           C
ATOM   1012  OG1 THR A 134      -3.623  19.870   3.485  1.00 24.13           O
ATOM   1013  CG2 THR A 134      -2.026  18.158   3.679  1.00 20.83           C
ATOM   1014  C   THR A 134      -4.104  17.471   1.641  1.00 24.29           C
ATOM   1015  O   THR A 134      -3.558  16.448   1.203  1.00 24.52           O
ATOM   1016  N   ASP A 135      -4.437  18.501   0.868  1.00 20.92           N
```

FIGURE 3S

```
ATOM   1017  CA   ASP A 135      -4.024   18.587   -0.529  1.00  26.62           C
ATOM   1018  CB   ASP A 135      -5.079   19.315   -1.361  1.00  31.75           C
ATOM   1019  CG   ASP A 135      -6.437   18.634   -1.309  1.00  38.60           C
ATOM   1020  OD1  ASP A 135      -7.441   19.328   -1.027  1.00  40.99           O
ATOM   1021  OD2  ASP A 135      -6.592   17.412   -1.521  1.00  37.56           O
ATOM   1022  C    ASP A 135      -2.679   19.300   -0.664  1.00  25.09           C
ATOM   1023  O    ASP A 135      -1.881   18.978   -1.550  1.00  20.41           O
ATOM   1024  N    MET A 136      -2.447   20.283    0.206  1.00  21.71           N
ATOM   1025  CA   MET A 136      -1.201   21.047    0.202  1.00  20.14           C
ATOM   1026  CB   MET A 136      -1.412   22.429   -0.420  1.00  23.48           C
ATOM   1027  CG   MET A 136      -1.680   22.417   -1.912  1.00  32.17           C
ATOM   1028  SD   MET A 136      -1.809   24.086   -2.554  1.00  37.36           S
ATOM   1029  CE   MET A 136      -3.466   24.097   -3.021  1.00  41.85           C
ATOM   1030  C    MET A 136      -0.685   21.212    1.626  1.00  20.21           C
ATOM   1031  O    MET A 136      -1.475   21.420    2.555  1.00  22.55           O
ATOM   1032  N    ALA A 137       0.631   21.101    1.801  1.00  16.32           N
ATOM   1033  CA   ALA A 137       1.244   21.414    3.083  1.00  15.44           C
ATOM   1034  CB   ALA A 137       1.878   20.198    3.711  1.00  17.40           C
ATOM   1035  C    ALA A 137       2.277   22.492    2.817  1.00  19.12           C
ATOM   1036  O    ALA A 137       2.951   22.467    1.788  1.00  18.34           O
ATOM   1037  N    VAL A 138       2.370   23.450    3.729  1.00  16.61           N
ATOM   1038  CA   VAL A 138       3.250   24.599    3.544  1.00  14.47           C
ATOM   1039  CB   VAL A 138       2.438   25.918    3.414  1.00  17.61           C
ATOM   1040  CG1  VAL A 138       3.376   27.113    3.208  1.00  16.01           C
ATOM   1041  CG2  VAL A 138       1.426   25.835    2.276  1.00  16.78           C
ATOM   1042  C    VAL A 138       4.201   24.701    4.731  1.00  16.38           C
ATOM   1043  O    VAL A 138       3.773   24.697    5.890  1.00  18.24           O
ATOM   1044  N    ASN A 139       5.498   24.781    4.443  1.00  15.01           N
ATOM   1045  CA   ASN A 139       6.495   25.027    5.475  1.00  15.07           C
ATOM   1046  CB   ASN A 139       7.222   23.735    5.897  1.00  15.17           C
ATOM   1047  CG   ASN A 139       8.280   23.984    6.980  1.00  14.94           C
ATOM   1048  OD1  ASN A 139       8.146   24.902    7.802  1.00  18.91           O
ATOM   1049  ND2  ASN A 139       9.341   23.192    6.968  1.00  15.99           N
ATOM   1050  C    ASN A 139       7.500   26.066    4.987  1.00  15.11           C
ATOM   1051  O    ASN A 139       8.507   25.714    4.376  1.00  14.44           O
ATOM   1052  N    TRP A 140       7.232   27.341    5.268  1.00  14.16           N
ATOM   1053  CA   TRP A 140       8.138   28.408    4.825  1.00  13.67           C
ATOM   1054  CB   TRP A 140       7.497   29.793    5.011  1.00  14.98           C
ATOM   1055  CG   TRP A 140       6.281   30.003    4.173  1.00  14.68           C
ATOM   1056  CD1  TRP A 140       5.067   30.474    4.600  1.00  12.91           C
ATOM   1057  NE1  TRP A 140       4.187   30.526    3.544  1.00  13.63           N
ATOM   1058  CE2  TRP A 140       4.813   30.088    2.407  1.00  14.14           C
ATOM   1059  CD2  TRP A 140       6.137   29.746    2.762  1.00  14.44           C
ATOM   1060  CE3  TRP A 140       6.997   29.261    1.757  1.00  15.69           C
ATOM   1061  CZ3  TRP A 140       6.513   29.141    0.451  1.00  18.55           C
ATOM   1062  CH2  TRP A 140       5.186   29.492    0.134  1.00  19.80           C
ATOM   1063  CZ2  TRP A 140       4.324   29.963    1.096  1.00  15.78           C
ATOM   1064  C    TRP A 140       9.517   28.357    5.489  1.00  16.54           C
ATOM   1065  O    TRP A 140      10.482   28.896    4.946  1.00  16.42           O
ATOM   1066  N    ALA A 141       9.609   27.713    6.653  1.00  14.30           N
ATOM   1067  CA   ALA A 141      10.888   27.563    7.361  1.00  18.35           C
ATOM   1068  CB   ALA A 141      10.649   27.294    8.852  1.00  16.95           C
ATOM   1069  C    ALA A 141      11.783   26.470    6.772  1.00  19.52           C
ATOM   1070  O    ALA A 141      12.931   26.310    7.195  1.00  22.93           O
ATOM   1071  N    GLY A 142      11.251   25.711    5.821  1.00  18.06           N
ATOM   1072  CA   GLY A 142      12.000   24.650    5.168  1.00  19.80           C
ATOM   1073  C    GLY A 142      12.572   25.107    3.839  1.00  20.07           C
```

FIGURE 3T

| ATOM | 1074 | O   | GLY | A | 142 | 12.682 | 26.311 | 3.582  | 1.00 | 17.45 | O |
|------|------|-----|-----|---|-----|--------|--------|--------|------|-------|---|
| ATOM | 1075 | N   | GLY | A | 143 | 12.942 | 24.147 | 2.996  | 1.00 | 17.28 | N |
| ATOM | 1076 | CA  | GLY | A | 143 | 13.480 | 24.452 | 1.680  | 1.00 | 18.17 | C |
| ATOM | 1077 | C   | GLY | A | 143 | 14.990 | 24.625 | 1.647  | 1.00 | 17.63 | C |
| ATOM | 1078 | O   | GLY | A | 143 | 15.526 | 25.257 | 0.738  | 1.00 | 21.53 | O |
| ATOM | 1079 | N   | LEU | A | 144 | 15.682 | 24.034 | 2.617  | 1.00 | 17.85 | N |
| ATOM | 1080 | CA  | LEU | A | 144 | 17.132 | 24.221 | 2.752  | 1.00 | 21.55 | C |
| ATOM | 1081 | CB  | LEU | A | 144 | 17.554 | 24.087 | 4.219  | 1.00 | 23.94 | C |
| ATOM | 1082 | CG  | LEU | A | 144 | 16.980 | 25.175 | 5.147  | 1.00 | 28.94 | C |
| ATOM | 1083 | CD1 | LEU | A | 144 | 17.667 | 25.151 | 6.494  | 1.00 | 36.38 | C |
| ATOM | 1084 | CD2 | LEU | A | 144 | 17.067 | 26.580 | 4.536  | 1.00 | 35.47 | C |
| ATOM | 1085 | C   | LEU | A | 144 | 17.908 | 23.280 | 1.816  | 1.00 | 20.95 | C |
| ATOM | 1086 | O   | LEU | A | 144 | 18.480 | 22.270 | 2.238  | 1.00 | 23.16 | O |
| ATOM | 1087 | N   | HIS | A | 145 | 17.932 | 23.656 | 0.541  | 1.00 | 16.60 | N |
| ATOM | 1088 | CA  | HIS | A | 145 | 18.267 | 22.733 | -0.546 | 1.00 | 17.45 | C |
| ATOM | 1089 | CB  | HIS | A | 145 | 17.630 | 23.189 | -1.872 | 1.00 | 17.38 | C |
| ATOM | 1090 | CG  | HIS | A | 145 | 18.024 | 24.571 | -2.308 | 1.00 | 16.70 | C |
| ATOM | 1091 | ND1 | HIS | A | 145 | 17.706 | 25.070 | -3.563 | 1.00 | 17.91 | N |
| ATOM | 1092 | CE1 | HIS | A | 145 | 18.175 | 26.300 | -3.667 | 1.00 | 16.58 | C |
| ATOM | 1093 | NE2 | HIS | A | 145 | 18.775 | 26.622 | -2.537 | 1.00 | 20.69 | N |
| ATOM | 1094 | CD2 | HIS | A | 145 | 18.704 | 25.555 | -1.674 | 1.00 | 18.17 | C |
| ATOM | 1095 | C   | HIS | A | 145 | 19.754 | 22.427 | -0.755 | 1.00 | 17.73 | C |
| ATOM | 1096 | O   | HIS | A | 145 | 20.076 | 21.534 | -1.542 | 1.00 | 19.50 | O |
| ATOM | 1097 | N   | HIS | A | 146 | 20.639 | 23.150 | -0.059 | 1.00 | 17.35 | N |
| ATOM | 1098 | CA  | HIS | A | 146 | 22.092 | 23.003 | -0.251 | 1.00 | 16.90 | C |
| ATOM | 1099 | CB  | HIS | A | 146 | 22.826 | 24.340 | -0.053 | 1.00 | 17.59 | C |
| ATOM | 1100 | CG  | HIS | A | 146 | 22.461 | 25.387 | -1.056 | 1.00 | 18.37 | C |
| ATOM | 1101 | ND1 | HIS | A | 146 | 22.535 | 25.174 | -2.415 | 1.00 | 17.89 | N |
| ATOM | 1102 | CE1 | HIS | A | 146 | 22.149 | 26.266 | -3.050 | 1.00 | 20.39 | C |
| ATOM | 1103 | NE2 | HIS | A | 146 | 21.825 | 27.178 | -2.152 | 1.00 | 19.46 | N |
| ATOM | 1104 | CD2 | HIS | A | 146 | 22.007 | 26.653 | -0.897 | 1.00 | 16.79 | C |
| ATOM | 1105 | C   | HIS | A | 146 | 22.754 | 21.960 | 0.633  | 1.00 | 20.58 | C |
| ATOM | 1106 | O   | HIS | A | 146 | 23.854 | 21.505 | 0.314  | 1.00 | 19.56 | O |
| ATOM | 1107 | N   | ALA | A | 147 | 22.108 | 21.597 | 1.741  | 1.00 | 17.31 | N |
| ATOM | 1108 | CA  | ALA | A | 147 | 22.710 | 20.670 | 2.699  | 1.00 | 21.31 | C |
| ATOM | 1109 | CB  | ALA | A | 147 | 21.842 | 20.541 | 3.959  | 1.00 | 19.41 | C |
| ATOM | 1110 | C   | ALA | A | 147 | 22.983 | 19.304 | 2.077  | 1.00 | 18.97 | C |
| ATOM | 1111 | O   | ALA | A | 147 | 22.154 | 18.773 | 1.341  | 1.00 | 20.21 | O |
| ATOM | 1112 | N   | LYS | A | 148 | 24.161 | 18.759 | 2.380  | 1.00 | 19.00 | N |
| ATOM | 1113 | CA  | LYS | A | 148 | 24.614 | 17.486 | 1.833  | 1.00 | 22.65 | C |
| ATOM | 1114 | CB  | LYS | A | 148 | 26.044 | 17.621 | 1.279  | 1.00 | 25.83 | C |
| ATOM | 1115 | CG  | LYS | A | 148 | 26.282 | 18.852 | 0.401  | 1.00 | 31.00 | C |
| ATOM | 1116 | CD  | LYS | A | 148 | 25.540 | 18.763 | -0.932 | 1.00 | 34.70 | C |
| ATOM | 1117 | CE  | LYS | A | 148 | 26.064 | 19.799 | -1.938 | 1.00 | 35.04 | C |
| ATOM | 1118 | NZ  | LYS | A | 148 | 25.991 | 21.204 | -1.416 | 1.00 | 33.54 | N |
| ATOM | 1119 | C   | LYS | A | 148 | 24.585 | 16.402 | 2.897  | 1.00 | 22.37 | C |
| ATOM | 1120 | O   | LYS | A | 148 | 24.394 | 16.692 | 4.076  | 1.00 | 19.93 | O |
| ATOM | 1121 | N   | LYS | A | 149 | 24.816 | 15.158 | 2.483  | 1.00 | 22.46 | N |
| ATOM | 1122 | CA  | LYS | A | 149 | 24.790 | 14.024 | 3.411  | 1.00 | 23.66 | C |
| ATOM | 1123 | CB  | LYS | A | 149 | 25.242 | 12.742 | 2.698  | 1.00 | 26.03 | C |
| ATOM | 1124 | CG  | LYS | A | 149 | 25.092 | 11.479 | 3.533  | 1.00 | 32.98 | C |
| ATOM | 1125 | CD  | LYS | A | 149 | 25.502 | 10.235 | 2.755  | 1.00 | 36.94 | C |
| ATOM | 1126 | CE  | LYS | A | 149 | 24.542 | 9.082  | 3.009  | 1.00 | 44.27 | C |
| ATOM | 1127 | NZ  | LYS | A | 149 | 24.860 | 8.328  | 4.262  | 1.00 | 47.40 | N |
| ATOM | 1128 | C   | LYS | A | 149 | 25.640 | 14.260 | 4.661  | 1.00 | 23.28 | C |
| ATOM | 1129 | O   | LYS | A | 149 | 25.188 | 14.018 | 5.788  | 1.00 | 22.43 | O |
| ATOM | 1130 | N   | SER | A | 150 | 26.870 | 14.726 | 4.464  | 1.00 | 20.84 | N |

FIGURE 3U

| ATOM | 1131 | CA  | SER  | A | 150 | 27.788 | 14.933 | 5.578  | 1.00 | 25.33 | C |
|------|------|-----|------|---|-----|--------|--------|--------|------|-------|---|
| ATOM | 1132 | CB  | ASER | A | 150 | 28.879 | 13.858 | 5.565  | 0.65 | 24.25 | C |
| ATOM | 1133 | OG  | ASER | A | 150 | 28.302 | 12.566 | 5.538  | 0.65 | 28.66 | O |
| ATOM | 1134 | C   | SER  | A | 150 | 28.420 | 16.321 | 5.576  | 1.00 | 25.44 | C |
| ATOM | 1135 | O   | SER  | A | 150 | 29.575 | 16.481 | 5.973  | 1.00 | 25.98 | O |
| ATOM | 1136 | N   | GLU  | A | 151 | 27.661 | 17.328 | 5.147  | 1.00 | 23.39 | N |
| ATOM | 1137 | CA  | GLU  | A | 151 | 28.209 | 18.672 | 5.014  | 1.00 | 25.81 | C |
| ATOM | 1138 | CB  | GLU  | A | 151 | 28.997 | 18.769 | 3.704  | 1.00 | 31.29 | C |
| ATOM | 1139 | CG  | GLU  | A | 151 | 30.347 | 19.436 | 3.836  | 1.00 | 42.38 | C |
| ATOM | 1140 | CD  | GLU  | A | 151 | 31.243 | 19.155 | 2.647  | 1.00 | 48.42 | C |
| ATOM | 1141 | OE1 | GLU  | A | 151 | 30.864 | 19.523 | 1.512  | 1.00 | 48.92 | O |
| ATOM | 1142 | OE2 | GLU  | A | 151 | 32.327 | 18.564 | 2.852  | 1.00 | 54.47 | O |
| ATOM | 1143 | C   | GLU  | A | 151 | 27.136 | 19.741 | 5.000  | 1.00 | 20.26 | C |
| ATOM | 1144 | O   | GLU  | A | 151 | 26.137 | 19.606 | 4.305  | 1.00 | 22.28 | O |
| ATOM | 1145 | N   | ALA  | A | 152 | 27.359 | 20.808 | 5.759  | 1.00 | 19.32 | N |
| ATOM | 1146 | CA  | ALA  | A | 152 | 26.555 | 22.015 | 5.646  | 1.00 | 19.28 | C |
| ATOM | 1147 | CB  | ALA  | A | 152 | 26.752 | 22.900 | 6.867  | 1.00 | 17.50 | C |
| ATOM | 1148 | C   | ALA  | A | 152 | 26.985 | 22.758 | 4.387  | 1.00 | 20.88 | C |
| ATOM | 1149 | O   | ALA  | A | 152 | 28.112 | 22.585 | 3.924  | 1.00 | 20.72 | O |
| ATOM | 1150 | N   | SER  | A | 153 | 26.095 | 23.580 | 3.837  | 1.00 | 22.15 | N |
| ATOM | 1151 | CA  | SER  | A | 153 | 26.431 | 24.406 | 2.681  | 1.00 | 21.33 | C |
| ATOM | 1152 | CB  | SER  | A | 153 | 26.579 | 23.542 | 1.422  | 1.00 | 18.71 | C |
| ATOM | 1153 | OG  | SER  | A | 153 | 26.648 | 24.332 | 0.249  | 1.00 | 23.59 | O |
| ATOM | 1154 | C   | SER  | A | 153 | 25.382 | 25.486 | 2.467  | 1.00 | 18.89 | C |
| ATOM | 1155 | O   | SER  | A | 153 | 24.194 | 25.248 | 2.674  | 1.00 | 18.58 | O |
| ATOM | 1156 | N   | GLY  | A | 154 | 25.830 | 26.677 | 2.072  | 1.00 | 18.52 | N |
| ATOM | 1157 | CA  | GLY  | A | 154 | 24.921 | 27.729 | 1.645  | 1.00 | 20.64 | C |
| ATOM | 1158 | C   | GLY  | A | 154 | 23.832 | 28.092 | 2.646  | 1.00 | 19.62 | C |
| ATOM | 1159 | O   | GLY  | A | 154 | 22.664 | 28.268 | 2.280  | 1.00 | 18.83 | O |
| ATOM | 1160 | N   | PHE  | A | 155 | 24.226 | 28.210 | 3.911  | 1.00 | 17.50 | N |
| ATOM | 1161 | CA  | PHE  | A | 155 | 23.329 | 28.567 | 5.017  | 1.00 | 17.61 | C |
| ATOM | 1162 | CB  | PHE  | A | 155 | 22.431 | 29.784 | 4.691  | 1.00 | 19.27 | C |
| ATOM | 1163 | CG  | PHE  | A | 155 | 23.151 | 30.951 | 4.046  | 1.00 | 19.64 | C |
| ATOM | 1164 | CD1 | PHE  | A | 155 | 24.519 | 31.159 | 4.231  | 1.00 | 20.04 | C |
| ATOM | 1165 | CE1 | PHE  | A | 155 | 25.167 | 32.248 | 3.635  | 1.00 | 21.58 | C |
| ATOM | 1166 | CZ  | PHE  | A | 155 | 24.444 | 33.138 | 2.851  | 1.00 | 20.38 | C |
| ATOM | 1167 | CE2 | PHE  | A | 155 | 23.075 | 32.941 | 2.658  | 1.00 | 20.98 | C |
| ATOM | 1168 | CD2 | PHE  | A | 155 | 22.439 | 31.855 | 3.260  | 1.00 | 19.95 | C |
| ATOM | 1169 | C   | PHE  | A | 155 | 22.448 | 27.390 | 5.487  | 1.00 | 18.57 | C |
| ATOM | 1170 | O   | PHE  | A | 155 | 21.671 | 27.542 | 6.429  | 1.00 | 17.44 | O |
| ATOM | 1171 | N   | CYS  | A | 156 | 22.575 | 26.238 | 4.828  | 1.00 | 19.84 | N |
| ATOM | 1172 | CA  | CYS  | A | 156 | 21.763 | 25.048 | 5.127  | 1.00 | 19.05 | C |
| ATOM | 1173 | CB  | CYS  | A | 156 | 21.271 | 24.390 | 3.837  | 1.00 | 20.24 | C |
| ATOM | 1174 | SG  | CYS  | A | 156 | 20.437 | 25.486 | 2.678  | 1.00 | 24.69 | S |
| ATOM | 1175 | C   | CYS  | A | 156 | 22.590 | 24.018 | 5.882  | 1.00 | 20.51 | C |
| ATOM | 1176 | O   | CYS  | A | 156 | 23.752 | 23.809 | 5.555  | 1.00 | 17.67 | O |
| ATOM | 1177 | N   | TYR  | A | 157 | 21.976 | 23.353 | 6.861  | 1.00 | 16.75 | N |
| ATOM | 1178 | CA  | TYR  | A | 157 | 22.669 | 22.367 | 7.690  | 1.00 | 16.33 | C |
| ATOM | 1179 | CB  | TYR  | A | 157 | 22.619 | 22.778 | 9.164  | 1.00 | 19.56 | C |
| ATOM | 1180 | CG  | TYR  | A | 157 | 23.177 | 24.156 | 9.455  | 1.00 | 19.61 | C |
| ATOM | 1181 | CD1 | TYR  | A | 157 | 22.379 | 25.293 | 9.331  | 1.00 | 19.53 | C |
| ATOM | 1182 | CE1 | TYR  | A | 157 | 22.881 | 26.562 | 9.613  | 1.00 | 20.19 | C |
| ATOM | 1183 | CZ  | TYR  | A | 157 | 24.199 | 26.704 | 10.028 | 1.00 | 19.40 | C |
| ATOM | 1184 | OH  | TYR  | A | 157 | 24.679 | 27.966 | 10.296 | 1.00 | 21.72 | O |
| ATOM | 1185 | CE2 | TYR  | A | 157 | 25.011 | 25.590 | 10.174 | 1.00 | 17.45 | C |
| ATOM | 1186 | CD2 | TYR  | A | 157 | 24.497 | 24.320 | 9.882  | 1.00 | 19.69 | C |
| ATOM | 1187 | C   | TYR  | A | 157 | 22.059 | 20.982 | 7.522  | 1.00 | 18.10 | C |

FIGURE 3V

| ATOM | 1188 | O   | TYR | A | 157 | 22.775 | 19.981 | 7.395  | 1.00 | 20.48 | O |
|------|------|-----|-----|---|-----|--------|--------|--------|------|-------|---|
| ATOM | 1189 | N   | VAL | A | 158 | 20.733 | 20.931 | 7.529  | 1.00 | 17.10 | N |
| ATOM | 1190 | CA  | VAL | A | 158 | 20.004 | 19.675 | 7.359  | 1.00 | 17.50 | C |
| ATOM | 1191 | CB  | VAL | A | 158 | 19.182 | 19.332 | 8.620  | 1.00 | 20.14 | C |
| ATOM | 1192 | CG1 | VAL | A | 158 | 18.349 | 18.076 | 8.416  | 1.00 | 20.38 | C |
| ATOM | 1193 | CG2 | VAL | A | 158 | 20.098 | 19.161 | 9.832  | 1.00 | 19.84 | C |
| ATOM | 1194 | C   | VAL | A | 158 | 19.098 | 19.817 | 6.141  | 1.00 | 17.83 | C |
| ATOM | 1195 | O   | VAL | A | 158 | 18.403 | 20.831 | 5.989  | 1.00 | 17.51 | O |
| ATOM | 1196 | N   | ASN | A | 159 | 19.124 | 18.821 | 5.261  | 1.00 | 17.97 | N |
| ATOM | 1197 | CA  | ASN | A | 159 | 18.319 | 18.890 | 4.058  | 1.00 | 15.25 | C |
| ATOM | 1198 | CB  | ASN | A | 159 | 18.955 | 18.156 | 2.872  | 1.00 | 16.37 | C |
| ATOM | 1199 | CG  | ASN | A | 159 | 18.466 | 18.704 | 1.546  | 1.00 | 16.45 | C |
| ATOM | 1200 | OD1 | ASN | A | 159 | 17.260 | 18.824 | 1.324  | 1.00 | 15.26 | O |
| ATOM | 1201 | ND2 | ASN | A | 159 | 19.392 | 19.056 | 0.668  | 1.00 | 17.55 | N |
| ATOM | 1202 | C   | ASN | A | 159 | 16.898 | 18.403 | 4.301  | 1.00 | 17.19 | C |
| ATOM | 1203 | O   | ASN | A | 159 | 16.572 | 17.239 | 4.058  | 1.00 | 16.07 | O |
| ATOM | 1204 | N   | ASP | A | 160 | 16.058 | 19.310 | 4.791  | 1.00 | 17.69 | N |
| ATOM | 1205 | CA  | ASP | A | 160 | 14.656 | 18.995 | 5.073  | 1.00 | 19.65 | C |
| ATOM | 1206 | CB  | ASP | A | 160 | 13.940 | 20.211 | 5.668  | 1.00 | 22.13 | C |
| ATOM | 1207 | CG  | ASP | A | 160 | 13.804 | 21.350 | 4.674  | 1.00 | 26.96 | C |
| ATOM | 1208 | OD1 | ASP | A | 160 | 14.837 | 21.983 | 4.359  | 1.00 | 28.95 | O |
| ATOM | 1209 | OD2 | ASP | A | 160 | 12.714 | 21.669 | 4.141  | 1.00 | 25.72 | O |
| ATOM | 1210 | C   | ASP | A | 160 | 13.905 | 18.505 | 3.834  | 1.00 | 19.66 | C |
| ATOM | 1211 | O   | ASP | A | 160 | 12.984 | 17.686 | 3.949  | 1.00 | 16.76 | O |
| ATOM | 1212 | N   | ILE | A | 161 | 14.292 | 19.004 | 2.658  | 1.00 | 16.72 | N |
| ATOM | 1213 | CA  | ILE | A | 161 | 13.635 | 18.606 | 1.412  | 1.00 | 16.23 | C |
| ATOM | 1214 | CB  | ILE | A | 161 | 14.118 | 19.453 | 0.222  | 1.00 | 15.43 | C |
| ATOM | 1215 | CG1 | ILE | A | 161 | 13.944 | 20.939 | 0.508  | 1.00 | 19.11 | C |
| ATOM | 1216 | CD1 | ILE | A | 161 | 14.594 | 21.809 | -0.520 | 1.00 | 18.48 | C |
| ATOM | 1217 | CG2 | ILE | A | 161 | 13.367 | 19.037 | -1.060 | 1.00 | 16.63 | C |
| ATOM | 1218 | C   | ILE | A | 161 | 13.867 | 17.129 | 1.112  | 1.00 | 14.56 | C |
| ATOM | 1219 | O   | ILE | A | 161 | 12.921 | 16.388 | 0.829  | 1.00 | 17.23 | O |
| ATOM | 1220 | N   | VAL | A | 162 | 15.129 | 16.711 | 1.177  | 1.00 | 15.36 | N |
| ATOM | 1221 | CA  | VAL | A | 162 | 15.479 | 15.311 | 0.943  | 1.00 | 16.11 | C |
| ATOM | 1222 | CB  | VAL | A | 162 | 16.999 | 15.090 | 1.005  | 1.00 | 16.48 | C |
| ATOM | 1223 | CG1 | VAL | A | 162 | 17.343 | 13.591 | 1.041  | 1.00 | 17.80 | C |
| ATOM | 1224 | CG2 | VAL | A | 162 | 17.683 | 15.772 | -0.203 | 1.00 | 16.81 | C |
| ATOM | 1225 | C   | VAL | A | 162 | 14.740 | 14.413 | 1.947  | 1.00 | 17.75 | C |
| ATOM | 1226 | O   | VAL | A | 162 | 14.203 | 13.369 | 1.572  | 1.00 | 20.01 | O |
| ATOM | 1227 | N   | LEU | A | 163 | 14.710 | 14.834 | 3.208  | 1.00 | 18.36 | N |
| ATOM | 1228 | CA  | LEU | A | 163 | 14.018 | 14.087 | 4.260  | 1.00 | 16.36 | C |
| ATOM | 1229 | CB  | LEU | A | 163 | 14.325 | 14.683 | 5.640  | 1.00 | 15.85 | C |
| ATOM | 1230 | CG  | LEU | A | 163 | 15.792 | 14.540 | 6.069  | 1.00 | 17.78 | C |
| ATOM | 1231 | CD1 | LEU | A | 163 | 16.082 | 15.374 | 7.310  | 1.00 | 18.63 | C |
| ATOM | 1232 | CD2 | LEU | A | 163 | 16.195 | 13.065 | 6.295  | 1.00 | 19.14 | C |
| ATOM | 1233 | C   | LEU | A | 163 | 12.516 | 13.999 | 3.999  | 1.00 | 18.06 | C |
| ATOM | 1234 | O   | LEU | A | 163 | 11.916 | 12.935 | 4.162  | 1.00 | 15.72 | O |
| ATOM | 1235 | N   | ALA | A | 164 | 11.916 | 15.101 | 3.553  | 1.00 | 13.65 | N |
| ATOM | 1236 | CA  | ALA | A | 164 | 10.491 | 15.105 | 3.215  | 1.00 | 15.83 | C |
| ATOM | 1237 | CB  | ALA | A | 164 | 9.983  | 16.530 | 3.027  | 1.00 | 16.67 | C |
| ATOM | 1238 | C   | ALA | A | 164 | 10.166 | 14.245 | 1.988  | 1.00 | 20.37 | C |
| ATOM | 1239 | O   | ALA | A | 164 | 9.133  | 13.565 | 1.964  | 1.00 | 18.76 | O |
| ATOM | 1240 | N   | ILE | A | 165 | 11.040 | 14.268 | 0.980  | 1.00 | 15.92 | N |
| ATOM | 1241 | CA  | ILE | A | 165 | 10.836 | 13.449 | -0.222 | 1.00 | 16.40 | C |
| ATOM | 1242 | CB  | ILE | A | 165 | 11.786 | 13.887 | -1.375 | 1.00 | 17.82 | C |
| ATOM | 1243 | CG1 | ILE | A | 165 | 11.346 | 15.245 | -1.941 | 1.00 | 16.79 | C |
| ATOM | 1244 | CD1 | ILE | A | 165 | 12.424 | 15.918 | -2.839 | 1.00 | 16.89 | C |

FIGURE 3W

| | | | | | | | | | |
|---|---|---|---|---|---|---|---|---|---|
| ATOM | 1245 | CG2 | ILE A 165 | 11.805 | 12.839 | -2.515 | 1.00 | 16.11 | C |
| ATOM | 1246 | C | ILE A 165 | 10.972 | 11.953 | 0.098 | 1.00 | 16.87 | C |
| ATOM | 1247 | O | ILE A 165 | 10.192 | 11.134 | -0.396 | 1.00 | 18.97 | O |
| ATOM | 1248 | N | LEU A 166 | 11.942 | 11.612 | 0.944 | 1.00 | 16.77 | N |
| ATOM | 1249 | CA | LEU A 166 | 12.099 | 10.237 | 1.427 | 1.00 | 18.24 | C |
| ATOM | 1250 | CB | LEU A 166 | 13.329 | 10.105 | 2.321 | 1.00 | 18.14 | C |
| ATOM | 1251 | CG | LEU A 166 | 14.696 | 10.149 | 1.622 | 1.00 | 21.00 | C |
| ATOM | 1252 | CD1 | LEU A 166 | 15.807 | 10.139 | 2.664 | 1.00 | 22.82 | C |
| ATOM | 1253 | CD2 | LEU A 166 | 14.881 | 9.007 | 0.607 | 1.00 | 22.10 | C |
| ATOM | 1254 | C | LEU A 166 | 10.846 | 9.738 | 2.148 | 1.00 | 21.97 | C |
| ATOM | 1255 | O | LEU A 166 | 10.476 | 8.568 | 2.022 | 1.00 | 21.97 | O |
| ATOM | 1256 | N | GLU A 167 | 10.180 | 10.632 | 2.873 | 1.00 | 19.05 | N |
| ATOM | 1257 | CA | GLU A 167 | 8.898 | 10.300 | 3.500 | 1.00 | 22.91 | C |
| ATOM | 1258 | CB | GLU A 167 | 8.472 | 11.381 | 4.503 | 1.00 | 24.95 | C |
| ATOM | 1259 | CG | GLU A 167 | 7.147 | 11.105 | 5.202 | 1.00 | 33.84 | C |
| ATOM | 1260 | CD | GLU A 167 | 7.204 | 9.913 | 6.151 | 1.00 | 40.30 | C |
| ATOM | 1261 | OE1 | GLU A 167 | 6.150 | 9.272 | 6.357 | 1.00 | 48.14 | O |
| ATOM | 1262 | OE2 | GLU A 167 | 8.292 | 9.615 | 6.696 | 1.00 | 44.28 | O |
| ATOM | 1263 | C | GLU A 167 | 7.816 | 10.079 | 2.451 | 1.00 | 21.93 | C |
| ATOM | 1264 | O | GLU A 167 | 7.062 | 9.110 | 2.536 | 1.00 | 22.13 | O |
| ATOM | 1265 | N | LEU A 168 | 7.748 | 10.959 | 1.450 | 1.00 | 17.90 | N |
| ATOM | 1266 | CA | LEU A 168 | 6.775 | 10.802 | 0.365 | 1.00 | 20.78 | C |
| ATOM | 1267 | CB | LEU A 168 | 6.816 | 11.989 | -0.601 | 1.00 | 17.36 | C |
| ATOM | 1268 | CG | LEU A 168 | 6.283 | 13.336 | -0.096 | 1.00 | 19.88 | C |
| ATOM | 1269 | CD1 | LEU A 168 | 6.633 | 14.437 | -1.104 | 1.00 | 19.43 | C |
| ATOM | 1270 | CD2 | LEU A 168 | 4.774 | 13.293 | 0.161 | 1.00 | 20.09 | C |
| ATOM | 1271 | C | LEU A 168 | 6.966 | 9.499 | -0.409 | 1.00 | 20.26 | C |
| ATOM | 1272 | O | LEU A 168 | 5.988 | 8.878 | -0.831 | 1.00 | 22.71 | O |
| ATOM | 1273 | N | LEU A 169 | 8.220 | 9.084 | -0.568 | 1.00 | 19.15 | N |
| ATOM | 1274 | CA | LEU A 169 | 8.554 | 7.870 | -1.319 | 1.00 | 22.58 | C |
| ATOM | 1275 | CB | LEU A 169 | 10.067 | 7.777 | -1.549 | 1.00 | 20.95 | C |
| ATOM | 1276 | CG | LEU A 169 | 10.634 | 8.779 | -2.563 | 1.00 | 20.49 | C |
| ATOM | 1277 | CD1 | LEU A 169 | 12.147 | 8.818 | -2.513 | 1.00 | 23.93 | C |
| ATOM | 1278 | CD2 | LEU A 169 | 10.135 | 8.472 | -3.983 | 1.00 | 20.46 | C |
| ATOM | 1279 | C | LEU A 169 | 8.024 | 6.584 | -0.670 | 1.00 | 24.96 | C |
| ATOM | 1280 | O | LEU A 169 | 7.946 | 5.542 | -1.321 | 1.00 | 22.88 | O |
| ATOM | 1281 | N | LYS A 170 | 7.659 | 6.665 | 0.608 | 1.00 | 24.70 | N |
| ATOM | 1282 | CA | LYS A 170 | 7.016 | 5.547 | 1.299 | 1.00 | 28.63 | C |
| ATOM | 1283 | CB | LYS A 170 | 6.772 | 5.886 | 2.774 | 1.00 | 27.24 | C |
| ATOM | 1284 | CG | LYS A 170 | 8.012 | 5.877 | 3.643 | 1.00 | 31.04 | C |
| ATOM | 1285 | CD | LYS A 170 | 7.687 | 6.377 | 5.047 | 1.00 | 34.25 | C |
| ATOM | 1286 | CE | LYS A 170 | 8.910 | 6.323 | 5.946 | 1.00 | 40.49 | C |
| ATOM | 1287 | NZ | LYS A 170 | 8.604 | 6.778 | 7.338 | 1.00 | 44.46 | N |
| ATOM | 1288 | C | LYS A 170 | 5.688 | 5.186 | 0.632 | 1.00 | 29.03 | C |
| ATOM | 1289 | O | LYS A 170 | 5.301 | 4.020 | 0.611 | 1.00 | 33.31 | O |
| ATOM | 1290 | N | TYR A 171 | 5.003 | 6.184 | 0.071 | 1.00 | 29.59 | N |
| ATOM | 1291 | CA | TYR A 171 | 3.660 | 5.979 | -0.480 | 1.00 | 32.85 | C |
| ATOM | 1292 | CB | TYR A 171 | 2.618 | 6.683 | 0.395 | 1.00 | 36.13 | C |
| ATOM | 1293 | CG | TYR A 171 | 2.454 | 6.049 | 1.753 | 1.00 | 42.78 | C |
| ATOM | 1294 | CD1 | TYR A 171 | 1.588 | 4.960 | 1.934 | 1.00 | 46.42 | C |
| ATOM | 1295 | CE1 | TYR A 171 | 1.441 | 4.356 | 3.181 | 1.00 | 47.32 | C |
| ATOM | 1296 | CZ | TYR A 171 | 2.168 | 4.830 | 4.259 | 1.00 | 47.90 | C |
| ATOM | 1297 | OH | TYR A 171 | 2.020 | 4.232 | 5.489 | 1.00 | 50.54 | O |
| ATOM | 1298 | CE2 | TYR A 171 | 3.040 | 5.899 | 4.106 | 1.00 | 44.30 | C |
| ATOM | 1299 | CD2 | TYR A 171 | 3.180 | 6.496 | 2.856 | 1.00 | 42.09 | C |
| ATOM | 1300 | C | TYR A 171 | 3.507 | 6.405 | -1.940 | 1.00 | 34.44 | C |
| ATOM | 1301 | O | TYR A 171 | 2.458 | 6.173 | -2.551 | 1.00 | 34.55 | O |

FIGURE 3X

```
ATOM   1302  N    HIS A 172       4.549   7.032  -2.486  1.00 28.65           N
ATOM   1303  CA   HIS A 172       4.531   7.521  -3.861  1.00 27.46           C
ATOM   1304  CB   HIS A 172       4.601   9.055  -3.889  1.00 25.29           C
ATOM   1305  CG   HIS A 172       3.397   9.719  -3.308  1.00 21.86           C
ATOM   1306  ND1  HIS A 172       3.294  10.034  -1.970  1.00 23.01           N
ATOM   1307  CE1  HIS A 172       2.127  10.606  -1.744  1.00 21.77           C
ATOM   1308  NE2  HIS A 172       1.465  10.666  -2.883  1.00 23.11           N
ATOM   1309  CD2  HIS A 172       2.233  10.109  -3.876  1.00 20.59           C
ATOM   1310  C    HIS A 172       5.681   6.934  -4.668  1.00 23.87           C
ATOM   1311  O    HIS A 172       6.840   7.006  -4.258  1.00 26.78           O
ATOM   1312  N    GLN A 173       5.349   6.352  -5.816  1.00 24.60           N
ATOM   1313  CA   GLN A 173       6.348   5.740  -6.685  1.00 27.68           C
ATOM   1314  CB   GLN A 173       5.667   4.922  -7.793  1.00 32.24           C
ATOM   1315  CG   GLN A 173       6.622   4.092  -8.670  1.00 41.86           C
ATOM   1316  CD   GLN A 173       7.498   3.125  -7.880  1.00 47.23           C
ATOM   1317  OE1  GLN A 173       8.713   3.076  -8.085  1.00 50.35           O
ATOM   1318  NE2  GLN A 173       6.884   2.351  -6.986  1.00 48.31           N
ATOM   1319  C    GLN A 173       7.272   6.798  -7.288  1.00 24.56           C
ATOM   1320  O    GLN A 173       8.491   6.610  -7.323  1.00 23.93           O
ATOM   1321  N    ARG A 174       6.678   7.908  -7.735  1.00 23.66           N
ATOM   1322  CA   ARG A 174       7.417   8.990  -8.390  1.00 24.60           C
ATOM   1323  CB   ARG A 174       7.074   9.033  -9.881  1.00 25.62           C
ATOM   1324  CG   ARG A 174       7.707   7.907 -10.708  1.00 27.68           C
ATOM   1325  CD   ARG A 174       7.273   7.886 -12.174  1.00 27.56           C
ATOM   1326  NE   ARG A 174       5.819   7.951 -12.335  1.00 29.57           N
ATOM   1327  CZ   ARG A 174       4.998   6.904 -12.275  1.00 34.44           C
ATOM   1328  NH1  ARG A 174       3.692   7.077 -12.427  1.00 32.20           N
ATOM   1329  NH2  ARG A 174       5.472   5.682 -12.062  1.00 34.97           N
ATOM   1330  C    ARG A 174       7.105  10.346  -7.753  1.00 20.48           C
ATOM   1331  O    ARG A 174       5.941  10.720  -7.615  1.00 23.38           O
ATOM   1332  N    VAL A 175       8.155  11.074  -7.378  1.00 19.52           N
ATOM   1333  CA   VAL A 175       8.007  12.396  -6.771  1.00 17.00           C
ATOM   1334  CB   VAL A 175       8.580  12.436  -5.335  1.00 16.29           C
ATOM   1335  CG1  VAL A 175       8.505  13.855  -4.748  1.00 21.13           C
ATOM   1336  CG2  VAL A 175       7.846  11.447  -4.416  1.00 17.62           C
ATOM   1337  C    VAL A 175       8.729  13.431  -7.638  1.00 15.52           C
ATOM   1338  O    VAL A 175       9.869  13.222  -8.045  1.00 18.40           O
ATOM   1339  N    LEU A 176       8.056  14.538  -7.910  1.00 14.21           N
ATOM   1340  CA   LEU A 176       8.656  15.624  -8.678  1.00 15.81           C
ATOM   1341  CB   LEU A 176       7.663  16.144  -9.719  1.00 16.50           C
ATOM   1342  CG   LEU A 176       8.072  17.381 -10.532  1.00 17.21           C
ATOM   1343  CD1  LEU A 176       9.359  17.133 -11.329  1.00 17.36           C
ATOM   1344  CD2  LEU A 176       6.929  17.823 -11.441  1.00 17.85           C
ATOM   1345  C    LEU A 176       9.088  16.748  -7.741  1.00 15.84           C
ATOM   1346  O    LEU A 176       8.300  17.214  -6.929  1.00 17.58           O
ATOM   1347  N    TYR A 177      10.346  17.165  -7.860  1.00 15.24           N
ATOM   1348  CA   TYR A 177      10.870  18.289  -7.089  1.00 15.94           C
ATOM   1349  CB   TYR A 177      12.172  17.899  -6.384  1.00 15.18           C
ATOM   1350  CG   TYR A 177      12.881  19.075  -5.730  1.00 15.93           C
ATOM   1351  CD1  TYR A 177      12.333  19.704  -4.609  1.00 16.32           C
ATOM   1352  CE1  TYR A 177      12.965  20.797  -4.010  1.00 15.92           C
ATOM   1353  CZ   TYR A 177      14.157  21.270  -4.528  1.00 16.44           C
ATOM   1354  OH   TYR A 177      14.768  22.348  -3.911  1.00 16.61           O
ATOM   1355  CE2  TYR A 177      14.728  20.669  -5.639  1.00 15.74           C
ATOM   1356  CD2  TYR A 177      14.080  19.575  -6.246  1.00 17.11           C
ATOM   1357  C    TYR A 177      11.118  19.445  -8.061  1.00 17.59           C
ATOM   1358  O    TYR A 177      11.740  19.246  -9.104  1.00 15.50           O
```

FIGURE 3Y

```
ATOM   1359  N    ILE A 178      10.596  20.623  -7.725  1.00 14.85           N
ATOM   1360  CA   ILE A 178      10.739  21.837  -8.530  1.00 13.73           C
ATOM   1361  CB   ILE A 178       9.377  22.290  -9.126  1.00 15.33           C
ATOM   1362  CG1  ILE A 178       8.719  21.183  -9.968  1.00 18.64           C
ATOM   1363  CD1  ILE A 178       7.221  21.419 -10.211  1.00 17.95           C
ATOM   1364  CG2  ILE A 178       9.565  23.560  -9.969  1.00 16.11           C
ATOM   1365  C    ILE A 178      11.299  22.947  -7.646  1.00 15.96           C
ATOM   1366  O    ILE A 178      10.818  23.167  -6.535  1.00 16.99           O
ATOM   1367  N    ASP A 179      12.300  23.658  -8.159  1.00 16.05           N
ATOM   1368  CA   ASP A 179      13.099  24.562  -7.354  1.00 17.54           C
ATOM   1369  CB   ASP A 179      14.462  23.892  -7.157  1.00 16.49           C
ATOM   1370  CG   ASP A 179      15.339  24.596  -6.154  1.00 18.79           C
ATOM   1371  OD1  ASP A 179      15.355  25.847  -6.120  1.00 17.74           O
ATOM   1372  OD2  ASP A 179      16.077  23.965  -5.369  1.00 20.41           O
ATOM   1373  C    ASP A 179      13.221  25.906  -8.091  1.00 18.01           C
ATOM   1374  O    ASP A 179      13.918  25.994  -9.110  1.00 17.86           O
ATOM   1375  N    ILE A 180      12.539  26.938  -7.590  1.00 14.57           N
ATOM   1376  CA   ILE A 180      12.560  28.271  -8.231  1.00 15.26           C
ATOM   1377  CB   ILE A 180      11.122  28.795  -8.550  1.00 18.76           C
ATOM   1378  CG1  ILE A 180      10.300  29.004  -7.270  1.00 16.38           C
ATOM   1379  CD1  ILE A 180       8.981  29.755  -7.489  1.00 20.08           C
ATOM   1380  CG2  ILE A 180      10.416  27.873  -9.549  1.00 19.83           C
ATOM   1381  C    ILE A 180      13.377  29.310  -7.456  1.00 16.08           C
ATOM   1382  O    ILE A 180      13.335  30.510  -7.769  1.00 15.61           O
ATOM   1383  N    ASP A 181      14.106  28.840  -6.444  1.00 14.42           N
ATOM   1384  CA   ASP A 181      15.191  29.606  -5.814  1.00 16.61           C
ATOM   1385  CB   ASP A 181      15.907  28.692  -4.818  1.00 16.09           C
ATOM   1386  CG   ASP A 181      16.795  29.436  -3.838  1.00 17.78           C
ATOM   1387  OD1  ASP A 181      16.411  29.589  -2.656  1.00 16.75           O
ATOM   1388  OD2  ASP A 181      17.922  29.868  -4.144  1.00 14.76           O
ATOM   1389  C    ASP A 181      16.161  30.064  -6.921  1.00 14.28           C
ATOM   1390  O    ASP A 181      16.332  29.366  -7.923  1.00 15.81           O
ATOM   1391  N    ILE A 182      16.793  31.221  -6.751  1.00 16.89           N
ATOM   1392  CA   ILE A 182      17.766  31.695  -7.736  1.00 16.34           C
ATOM   1393  CB   ILE A 182      18.174  33.179  -7.450  1.00 14.73           C
ATOM   1394  CG1  ILE A 182      18.801  33.804  -8.702  1.00 17.97           C
ATOM   1395  CD1  ILE A 182      19.099  35.282  -8.568  1.00 18.21           C
ATOM   1396  CG2  ILE A 182      19.124  33.282  -6.241  1.00 15.16           C
ATOM   1397  C    ILE A 182      18.982  30.763  -7.842  1.00 15.08           C
ATOM   1398  O    ILE A 182      19.653  30.717  -8.877  1.00 14.98           O
ATOM   1399  N    HIS A 183      19.243  29.999  -6.779  1.00 15.16           N
ATOM   1400  CA   HIS A 183      20.383  29.090  -6.740  1.00 14.82           C
ATOM   1401  CB   HIS A 183      21.013  29.067  -5.344  1.00 16.59           C
ATOM   1402  CG   HIS A 183      21.525  30.397  -4.897  1.00 18.85           C
ATOM   1403  ND1  HIS A 183      20.840  31.196  -4.007  1.00 19.91           N
ATOM   1404  CE1  HIS A 183      21.517  32.315  -3.815  1.00 22.22           C
ATOM   1405  NE2  HIS A 183      22.619  32.268  -4.544  1.00 19.70           N
ATOM   1406  CD2  HIS A 183      22.643  31.082  -5.238  1.00 17.77           C
ATOM   1407  C    HIS A 183      19.979  27.678  -7.117  1.00 14.67           C
ATOM   1408  O    HIS A 183      18.842  27.264  -6.888  1.00 14.27           O
ATOM   1409  N    HIS A 184      20.931  26.941  -7.681  1.00 15.82           N
ATOM   1410  CA   HIS A 184      20.727  25.543  -8.023  1.00 16.81           C
ATOM   1411  CB   HIS A 184      21.953  25.002  -8.762  1.00 15.59           C
ATOM   1412  CG   HIS A 184      21.847  23.554  -9.111  1.00 16.97           C
ATOM   1413  ND1  HIS A 184      22.828  22.641  -8.799  1.00 19.83           N
ATOM   1414  CE1  HIS A 184      22.463  21.443  -9.217  1.00 18.05           C
ATOM   1415  NE2  HIS A 184      21.276  21.546  -9.784  1.00 19.59           N
```

FIGURE 3Z

```
ATOM   1416  CD2 HIS A 184      20.865  22.855  -9.726  1.00 18.12           C
ATOM   1417  C   HIS A 184      20.495  24.711  -6.758  1.00 17.51           C
ATOM   1418  O   HIS A 184      21.238  24.836  -5.798  1.00 17.92           O
ATOM   1419  N   GLY A 185      19.467  23.865  -6.770  1.00 19.54           N
ATOM   1420  CA  GLY A 185      19.184  22.990  -5.641  1.00 20.77           C
ATOM   1421  C   GLY A 185      20.098  21.775  -5.642  1.00 22.30           C
ATOM   1422  O   GLY A 185      19.662  20.645  -5.893  1.00 17.69           O
ATOM   1423  N   ASP A 186      21.370  22.013  -5.351  1.00 20.58           N
ATOM   1424  CA  ASP A 186      22.394  20.994  -5.544  1.00 19.99           C
ATOM   1425  CB  ASP A 186      23.802  21.613  -5.548  1.00 18.86           C
ATOM   1426  CG  ASP A 186      24.151  22.315  -4.245  1.00 27.79           C
ATOM   1427  OD1 ASP A 186      25.356  22.380  -3.913  1.00 25.32           O
ATOM   1428  OD2 ASP A 186      23.303  22.835  -3.492  1.00 24.20           O
ATOM   1429  C   ASP A 186      22.283  19.821  -4.565  1.00 19.34           C
ATOM   1430  O   ASP A 186      22.519  18.671  -4.943  1.00 18.81           O
ATOM   1431  N   GLY A 187      21.911  20.110  -3.323  1.00 17.32           N
ATOM   1432  CA  GLY A 187      21.805  19.074  -2.303  1.00 18.98           C
ATOM   1433  C   GLY A 187      20.698  18.084  -2.606  1.00 16.48           C
ATOM   1434  O   GLY A 187      20.853  16.883  -2.355  1.00 21.55           O
ATOM   1435  N   VAL A 188      19.586  18.578  -3.152  1.00 17.28           N
ATOM   1436  CA  VAL A 188      18.469  17.710  -3.543  1.00 17.23           C
ATOM   1437  CB  VAL A 188      17.150  18.507  -3.733  1.00 18.26           C
ATOM   1438  CG1 VAL A 188      15.970  17.563  -3.940  1.00 18.70           C
ATOM   1439  CG2 VAL A 188      16.892  19.409  -2.526  1.00 18.57           C
ATOM   1440  C   VAL A 188      18.801  16.915  -4.817  1.00 18.53           C
ATOM   1441  O   VAL A 188      18.561  15.700  -4.892  1.00 19.38           O
ATOM   1442  N   GLU A 189      19.354  17.600  -5.814  1.00 17.91           N
ATOM   1443  CA  GLU A 189      19.773  16.932  -7.047  1.00 20.74           C
ATOM   1444  CB  GLU A 189      20.378  17.940  -8.026  1.00 22.94           C
ATOM   1445  CG  GLU A 189      20.714  17.351  -9.384  1.00 23.87           C
ATOM   1446  CD  GLU A 189      21.408  18.354 -10.274  1.00 28.15           C
ATOM   1447  OE1 GLU A 189      20.708  19.152 -10.921  1.00 28.55           O
ATOM   1448  OE2 GLU A 189      22.655  18.358 -10.302  1.00 31.71           O
ATOM   1449  C   GLU A 189      20.773  15.811  -6.751  1.00 20.69           C
ATOM   1450  O   GLU A 189      20.653  14.709  -7.294  1.00 21.72           O
ATOM   1451  N   GLU A 190      21.733  16.093  -5.875  1.00 21.20           N
ATOM   1452  CA  GLU A 190      22.759  15.121  -5.498  1.00 23.71           C
ATOM   1453  CB  GLU A 190      23.806  15.766  -4.595  1.00 27.15           C
ATOM   1454  CG  GLU A 190      24.866  14.797  -4.096  1.00 33.60           C
ATOM   1455  CD  GLU A 190      26.015  15.498  -3.406  1.00 39.29           C
ATOM   1456  OE1 GLU A 190      26.012  15.554  -2.159  1.00 38.80           O
ATOM   1457  OE2 GLU A 190      26.916  15.995  -4.113  1.00 41.58           O
ATOM   1458  C   GLU A 190      22.186  13.862  -4.829  1.00 23.84           C
ATOM   1459  O   GLU A 190      22.549  12.744  -5.195  1.00 23.03           O
ATOM   1460  N   ALA A 191      21.307  14.056  -3.848  1.00 21.78           N
ATOM   1461  CA  ALA A 191      20.637  12.946  -3.169  1.00 21.73           C
ATOM   1462  CB  ALA A 191      19.644  13.475  -2.139  1.00 20.82           C
ATOM   1463  C   ALA A 191      19.927  12.001  -4.137  1.00 21.86           C
ATOM   1464  O   ALA A 191      19.944  10.788  -3.941  1.00 21.48           O
ATOM   1465  N   PHE A 192      19.306  12.555  -5.176  1.00 18.51           N
ATOM   1466  CA  PHE A 192      18.440  11.766  -6.047  1.00 18.52           C
ATOM   1467  CB  PHE A 192      17.018  12.331  -6.002  1.00 19.97           C
ATOM   1468  CG  PHE A 192      16.415  12.332  -4.615  1.00 19.49           C
ATOM   1469  CD1 PHE A 192      16.084  13.529  -3.982  1.00 19.40           C
ATOM   1470  CE1 PHE A 192      15.518  13.534  -2.698  1.00 17.83           C
ATOM   1471  CZ  PHE A 192      15.286  12.322  -2.037  1.00 18.49           C
ATOM   1472  CE2 PHE A 192      15.612  11.118  -2.665  1.00 20.32           C
```

FIGURE 3AA

```
ATOM   1473  CD2 PHE A 192      16.176  11.129  -3.946  1.00 20.98           C
ATOM   1474  C   PHE A 192      18.949  11.628  -7.489  1.00 17.91           C
ATOM   1475  O   PHE A 192      18.198  11.266  -8.395  1.00 20.26           O
ATOM   1476  N   TYR A 193      20.236  11.899  -7.669  1.00 18.12           N
ATOM   1477  CA  TYR A 193      20.855  11.949  -8.988  1.00 20.43           C
ATOM   1478  CB  TYR A 193      22.309  12.401  -8.864  1.00 18.97           C
ATOM   1479  CG  TYR A 193      22.829  13.104 -10.098  1.00 25.14           C
ATOM   1480  CD1 TYR A 193      23.906  12.580 -10.816  1.00 26.82           C
ATOM   1481  CE1 TYR A 193      24.391  13.220 -11.953  1.00 25.58           C
ATOM   1482  CZ  TYR A 193      23.800  14.398 -12.381  1.00 28.04           C
ATOM   1483  OH  TYR A 193      24.282  15.023 -13.508  1.00 26.87           O
ATOM   1484  CE2 TYR A 193      22.721  14.942 -11.685  1.00 26.11           C
ATOM   1485  CD2 TYR A 193      22.245  14.294 -10.550  1.00 24.50           C
ATOM   1486  C   TYR A 193      20.799  10.614  -9.732  1.00 20.60           C
ATOM   1487  O   TYR A 193      20.717  10.599 -10.959  1.00 22.30           O
ATOM   1488  N   THR A 194      20.837   9.514  -8.979  1.00 23.58           N
ATOM   1489  CA  THR A 194      20.913   8.171  -9.562  1.00 24.93           C
ATOM   1490  CB  THR A 194      22.079   7.371  -8.937  1.00 27.22           C
ATOM   1491  OG1 THR A 194      21.931   7.344  -7.514  1.00 29.93           O
ATOM   1492  CG2 THR A 194      23.410   8.083  -9.150  1.00 26.13           C
ATOM   1493  C   THR A 194      19.621   7.369  -9.448  1.00 29.26           C
ATOM   1494  O   THR A 194      19.633   6.140  -9.588  1.00 27.61           O
ATOM   1495  N   THR A 195      18.507   8.049  -9.186  1.00 25.50           N
ATOM   1496  CA  THR A 195      17.219   7.363  -9.150  1.00 24.50           C
ATOM   1497  CB  THR A 195      16.685   7.211  -7.697  1.00 28.02           C
ATOM   1498  OG1 THR A 195      15.432   6.512  -7.722  1.00 22.50           O
ATOM   1499  CG2 THR A 195      16.321   8.571  -7.086  1.00 24.35           C
ATOM   1500  C   THR A 195      16.192   8.017 -10.056  1.00 22.49           C
ATOM   1501  O   THR A 195      16.181   9.240 -10.235  1.00 20.65           O
ATOM   1502  N   ASP A 196      15.344   7.184 -10.651  1.00 22.60           N
ATOM   1503  CA  ASP A 196      14.211   7.659 -11.429  1.00 23.27           C
ATOM   1504  CB  ASP A 196      13.918   6.708 -12.598  1.00 29.45           C
ATOM   1505  CG  ASP A 196      13.620   5.279 -12.156  1.00 33.81           C
ATOM   1506  OD1 ASP A 196      13.877   4.915 -10.987  1.00 31.42           O
ATOM   1507  OD2 ASP A 196      13.128   4.439 -12.939  1.00 34.95           O
ATOM   1508  C   ASP A 196      12.955   7.865 -10.578  1.00 24.43           C
ATOM   1509  O   ASP A 196      11.909   8.259 -11.091  1.00 24.57           O
ATOM   1510  N   ARG A 197      13.056   7.604  -9.278  1.00 22.66           N
ATOM   1511  CA  ARG A 197      11.898   7.752  -8.399  1.00 19.73           C
ATOM   1512  CB  ARG A 197      12.000   6.816  -7.200  1.00 24.14           C
ATOM   1513  CG  ARG A 197      11.654   5.368  -7.557  1.00 27.30           C
ATOM   1514  CD  ARG A 197      11.405   4.472  -6.370  1.00 30.31           C
ATOM   1515  NE  ARG A 197      10.176   4.840  -5.669  1.00 30.94           N
ATOM   1516  CZ  ARG A 197       9.962   4.640  -4.374  1.00 29.96           C
ATOM   1517  NH1 ARG A 197       8.816   5.022  -3.831  1.00 27.04           N
ATOM   1518  NH2 ARG A 197      10.890   4.067  -3.618  1.00 30.73           N
ATOM   1519  C   ARG A 197      11.693   9.206  -7.971  1.00 20.11           C
ATOM   1520  O   ARG A 197      10.622   9.578  -7.501  1.00 20.16           O
ATOM   1521  N   VAL A 198      12.722  10.026  -8.158  1.00 20.30           N
ATOM   1522  CA  VAL A 198      12.600  11.468  -7.947  1.00 17.11           C
ATOM   1523  CB  VAL A 198      13.358  11.927  -6.685  1.00 17.05           C
ATOM   1524  CG1 VAL A 198      13.217  13.443  -6.472  1.00 18.68           C
ATOM   1525  CG2 VAL A 198      12.895  11.141  -5.438  1.00 17.58           C
ATOM   1526  C   VAL A 198      13.173  12.194  -9.155  1.00 18.44           C
ATOM   1527  O   VAL A 198      14.322  11.970  -9.518  1.00 20.49           O
ATOM   1528  N   MET A 199      12.367  13.043  -9.781  1.00 16.26           N
ATOM   1529  CA  MET A 199      12.869  13.920 -10.834  1.00 19.54           C
```

FIGURE 3BB

| ATOM | 1530 | CB | MET | A | 199 | 11.897 | 13.986 | -12.007 | 1.00 | 19.84 | C |
|---|---|---|---|---|---|---|---|---|---|---|---|
| ATOM | 1531 | CG | MET | A | 199 | 12.281 | 15.033 | -13.049 | 1.00 | 26.01 | C |
| ATOM | 1532 | SD | MET | A | 199 | 11.244 | 14.972 | -14.499 | 1.00 | 36.88 | S |
| ATOM | 1533 | CE | MET | A | 199 | 11.942 | 13.614 | -15.311 | 1.00 | 30.73 | C |
| ATOM | 1534 | C | MET | A | 199 | 13.055 | 15.312 | -10.257 | 1.00 | 21.01 | C |
| ATOM | 1535 | O | MET | A | 199 | 12.131 | 15.853 | -9.646 | 1.00 | 18.64 | O |
| ATOM | 1536 | N | THR | A | 200 | 14.243 | 15.884 | -10.446 | 1.00 | 18.60 | N |
| ATOM | 1537 | CA | THR | A | 200 | 14.524 | 17.230 | -9.934 | 1.00 | 17.54 | C |
| ATOM | 1538 | CB | THR | A | 200 | 15.848 | 17.275 | -9.141 | 1.00 | 20.37 | C |
| ATOM | 1539 | OG1 | THR | A | 200 | 16.917 | 16.734 | -9.935 | 1.00 | 20.99 | O |
| ATOM | 1540 | CG2 | THR | A | 200 | 15.795 | 16.363 | -7.909 | 1.00 | 20.47 | C |
| ATOM | 1541 | C | THR | A | 200 | 14.570 | 18.232 | -11.083 | 1.00 | 21.03 | C |
| ATOM | 1542 | O | THR | A | 200 | 15.188 | 17.975 | -12.121 | 1.00 | 20.83 | O |
| ATOM | 1543 | N | VAL | A | 201 | 13.893 | 19.362 | -10.899 | 1.00 | 15.55 | N |
| ATOM | 1544 | CA | VAL | A | 201 | 13.834 | 20.409 | -11.910 | 1.00 | 15.86 | C |
| ATOM | 1545 | CB | VAL | A | 201 | 12.414 | 20.568 | -12.508 | 1.00 | 15.57 | C |
| ATOM | 1546 | CG1 | VAL | A | 201 | 12.400 | 21.660 | -13.582 | 1.00 | 18.15 | C |
| ATOM | 1547 | CG2 | VAL | A | 201 | 11.902 | 19.246 | -13.088 | 1.00 | 21.36 | C |
| ATOM | 1548 | C | VAL | A | 201 | 14.228 | 21.718 | -11.244 | 1.00 | 17.55 | C |
| ATOM | 1549 | O | VAL | A | 201 | 13.516 | 22.205 | -10.365 | 1.00 | 17.25 | O |
| ATOM | 1550 | N | SER | A | 202 | 15.364 | 22.274 | -11.645 | 1.00 | 16.83 | N |
| ATOM | 1551 | CA | SER | A | 202 | 15.816 | 23.528 | -11.051 | 1.00 | 18.01 | C |
| ATOM | 1552 | CB | SER | A | 202 | 17.117 | 23.326 | -10.274 | 1.00 | 16.01 | C |
| ATOM | 1553 | OG | SER | A | 202 | 17.571 | 24.548 | -9.712 | 1.00 | 17.20 | O |
| ATOM | 1554 | C | SER | A | 202 | 15.997 | 24.603 | -12.108 | 1.00 | 15.17 | C |
| ATOM | 1555 | O | SER | A | 202 | 16.571 | 24.354 | -13.173 | 1.00 | 13.35 | O |
| ATOM | 1556 | N | PHE | A | 203 | 15.482 | 25.789 | -11.800 | 1.00 | 13.63 | N |
| ATOM | 1557 | CA | PHE | A | 203 | 15.681 | 26.984 | -12.611 | 1.00 | 14.43 | C |
| ATOM | 1558 | CB | PHE | A | 203 | 14.341 | 27.689 | -12.884 | 1.00 | 12.50 | C |
| ATOM | 1559 | CG | PHE | A | 203 | 13.319 | 26.823 | -13.564 | 1.00 | 17.96 | C |
| ATOM | 1560 | CD1 | PHE | A | 203 | 12.491 | 25.980 | -12.823 | 1.00 | 18.22 | C |
| ATOM | 1561 | CE1 | PHE | A | 203 | 11.543 | 25.167 | -13.457 | 1.00 | 19.51 | C |
| ATOM | 1562 | CZ | PHE | A | 203 | 11.426 | 25.199 | -14.829 | 1.00 | 18.12 | C |
| ATOM | 1563 | CE2 | PHE | A | 203 | 12.247 | 26.045 | -15.581 | 1.00 | 17.58 | C |
| ATOM | 1564 | CD2 | PHE | A | 203 | 13.181 | 26.849 | -14.945 | 1.00 | 18.57 | C |
| ATOM | 1565 | C | PHE | A | 203 | 16.555 | 27.887 | -11.751 | 1.00 | 17.92 | C |
| ATOM | 1566 | O | PHE | A | 203 | 16.214 | 28.147 | -10.597 | 1.00 | 17.77 | O |
| ATOM | 1567 | N | HIS | A | 204 | 17.680 | 28.357 | -12.285 | 1.00 | 16.64 | N |
| ATOM | 1568 | CA | HIS | A | 204 | 18.642 | 29.075 | -11.450 | 1.00 | 14.96 | C |
| ATOM | 1569 | CB | HIS | A | 204 | 19.456 | 28.087 | -10.610 | 1.00 | 15.86 | C |
| ATOM | 1570 | CG | HIS | A | 204 | 19.984 | 26.940 | -11.404 | 1.00 | 21.07 | C |
| ATOM | 1571 | ND1 | HIS | A | 204 | 19.304 | 25.746 | -11.522 | 1.00 | 18.75 | N |
| ATOM | 1572 | CE1 | HIS | A | 204 | 19.991 | 24.930 | -12.303 | 1.00 | 19.04 | C |
| ATOM | 1573 | NE2 | HIS | A | 204 | 21.087 | 25.555 | -12.701 | 1.00 | 21.96 | N |
| ATOM | 1574 | CD2 | HIS | A | 204 | 21.105 | 26.816 | -12.157 | 1.00 | 18.24 | C |
| ATOM | 1575 | C | HIS | A | 204 | 19.610 | 29.898 | -12.273 | 1.00 | 17.04 | C |
| ATOM | 1576 | O | HIS | A | 204 | 19.838 | 29.621 | -13.459 | 1.00 | 14.82 | O |
| ATOM | 1577 | N | LYS | A | 205 | 20.189 | 30.901 | -11.623 | 1.00 | 17.40 | N |
| ATOM | 1578 | CA | LYS | A | 205 | 21.297 | 31.636 | -12.210 | 1.00 | 17.49 | C |
| ATOM | 1579 | CB | LYS | A | 205 | 21.636 | 32.886 | -11.399 | 1.00 | 21.73 | C |
| ATOM | 1580 | CG | LYS | A | 205 | 22.628 | 33.786 | -12.143 | 1.00 | 31.19 | C |
| ATOM | 1581 | CD | LYS | A | 205 | 23.181 | 34.896 | -11.283 | 1.00 | 36.11 | C |
| ATOM | 1582 | CE | LYS | A | 205 | 24.621 | 35.239 | -11.675 | 1.00 | 40.39 | C |
| ATOM | 1583 | NZ | LYS | A | 205 | 24.784 | 35.565 | -13.120 | 1.00 | 42.98 | N |
| ATOM | 1584 | C | LYS | A | 205 | 22.510 | 30.724 | -12.296 | 1.00 | 19.26 | C |
| ATOM | 1585 | O | LYS | A | 205 | 22.808 | 29.979 | -11.365 | 1.00 | 17.53 | O |
| ATOM | 1586 | N | TYR | A | 206 | 23.200 | 30.776 | -13.429 | 1.00 | 17.36 | N |

FIGURE 3CC

```
ATOM   1587  CA   TYR A 206      24.329  29.895 -13.658  1.00 19.17           C
ATOM   1588  CB   TYR A 206      23.908  28.711 -14.528  1.00 17.57           C
ATOM   1589  CG   TYR A 206      25.002  27.701 -14.754  1.00 18.73           C
ATOM   1590  CD1  TYR A 206      25.712  27.668 -15.957  1.00 24.25           C
ATOM   1591  CE1  TYR A 206      26.732  26.728 -16.167  1.00 24.83           C
ATOM   1592  CZ   TYR A 206      27.046  25.831 -15.162  1.00 26.02           C
ATOM   1593  OH   TYR A 206      28.048  24.908 -15.350  1.00 31.27           O
ATOM   1594  CE2  TYR A 206      26.355  25.849 -13.957  1.00 24.51           C
ATOM   1595  CD2  TYR A 206      25.341  26.782 -13.761  1.00 22.18           C
ATOM   1596  C    TYR A 206      25.459  30.657 -14.322  1.00 22.31           C
ATOM   1597  O    TYR A 206      25.219  31.487 -15.203  1.00 23.88           O
ATOM   1598  N    GLY A 207      26.683  30.358 -13.895  1.00 23.60           N
ATOM   1599  CA   GLY A 207      27.873  31.007 -14.420  1.00 29.41           C
ATOM   1600  C    GLY A 207      28.553  31.830 -13.345  1.00 31.65           C
ATOM   1601  O    GLY A 207      28.117  32.940 -13.045  1.00 35.65           O
ATOM   1602  N    GLU A 208      29.607  31.268 -12.756  1.00 35.44           N
ATOM   1603  CA   GLU A 208      30.389  31.930 -11.702  1.00 41.06           C
ATOM   1604  CB   GLU A 208      31.165  33.135 -12.260  1.00 47.95           C
ATOM   1605  CG   GLU A 208      32.227  32.798 -13.298  1.00 54.90           C
ATOM   1606  CD   GLU A 208      32.643  34.010 -14.115  1.00 59.50           C
ATOM   1607  OE1  GLU A 208      32.234  34.105 -15.295  1.00 61.75           O
ATOM   1608  OE2  GLU A 208      33.376  34.872 -13.578  1.00 60.18           O
ATOM   1609  C    GLU A 208      29.506  32.362 -10.529  1.00 37.16           C
ATOM   1610  O    GLU A 208      29.701  33.431  -9.947  1.00 39.40           O
ATOM   1611  N    TYR A 209      28.530  31.523 -10.192  1.00 28.29           N
ATOM   1612  CA   TYR A 209      27.542  31.849  -9.170  1.00 26.43           C
ATOM   1613  CB   TYR A 209      26.214  32.204  -9.849  1.00 27.37           C
ATOM   1614  CG   TYR A 209      25.257  33.027  -9.018  1.00 30.36           C
ATOM   1615  CD1  TYR A 209      24.021  32.510  -8.642  1.00 29.81           C
ATOM   1616  CE1  TYR A 209      23.122  33.262  -7.895  1.00 29.75           C
ATOM   1617  CZ   TYR A 209      23.455  34.547  -7.515  1.00 32.87           C
ATOM   1618  OH   TYR A 209      22.556  35.272  -6.767  1.00 37.37           O
ATOM   1619  CE2  TYR A 209      24.677  35.093  -7.876  1.00 31.58           C
ATOM   1620  CD2  TYR A 209      25.571  34.334  -8.629  1.00 31.47           C
ATOM   1621  C    TYR A 209      27.365  30.637  -8.258  1.00 24.01           C
ATOM   1622  O    TYR A 209      27.505  29.498  -8.706  1.00 25.82           O
ATOM   1623  N    PHE A 210      27.084  30.887  -6.983  1.00 22.19           N
ATOM   1624  CA   PHE A 210      26.877  29.813  -6.008  1.00 20.48           C
ATOM   1625  CB   PHE A 210      26.626  30.397  -4.609  1.00 19.79           C
ATOM   1626  CG   PHE A 210      26.586  29.357  -3.522  1.00 21.43           C
ATOM   1627  CD1  PHE A 210      25.376  28.784  -3.128  1.00 21.27           C
ATOM   1628  CE1  PHE A 210      25.346  27.799  -2.139  1.00 19.48           C
ATOM   1629  CZ   PHE A 210      26.530  27.380  -1.540  1.00 23.72           C
ATOM   1630  CE2  PHE A 210      27.741  27.940  -1.924  1.00 22.23           C
ATOM   1631  CD2  PHE A 210      27.766  28.920  -2.918  1.00 21.03           C
ATOM   1632  C    PHE A 210      25.683  28.958  -6.439  1.00 16.90           C
ATOM   1633  O    PHE A 210      24.673  29.515  -6.873  1.00 21.77           O
ATOM   1634  N    PRO A 211      25.755  27.628  -6.315  1.00 20.08           N
ATOM   1635  CA   PRO A 211      26.927  26.882  -5.835  1.00 22.14           C
ATOM   1636  CB   PRO A 211      26.281  25.664  -5.166  1.00 22.51           C
ATOM   1637  CG   PRO A 211      25.024  25.409  -5.972  1.00 20.64           C
ATOM   1638  CD   PRO A 211      24.621  26.729  -6.596  1.00 18.17           C
ATOM   1639  C    PRO A 211      27.895  26.410  -6.935  1.00 25.02           C
ATOM   1640  O    PRO A 211      28.841  25.684  -6.624  1.00 25.95           O
ATOM   1641  N    GLY A 212      27.655  26.798  -8.185  1.00 22.58           N
ATOM   1642  CA   GLY A 212      28.538  26.440  -9.288  1.00 24.23           C
ATOM   1643  C    GLY A 212      28.116  25.217 -10.085  1.00 24.46           C
```

FIGURE 3DD

| ATOM | 1644 | O | GLY | A | 212 | 28.773 | 24.844 | -11.058 | 1.00 | 27.79 | O |
|---|---|---|---|---|---|---|---|---|---|---|---|
| ATOM | 1645 | N | THR | A | 213 | 27.021 | 24.590 | -9.672 | 1.00 | 23.23 | N |
| ATOM | 1646 | CA | THR | A | 213 | 26.481 | 23.414 | -10.359 | 1.00 | 22.43 | C |
| ATOM | 1647 | CB | THR | A | 213 | 26.238 | 22.281 | -9.351 | 1.00 | 26.37 | C |
| ATOM | 1648 | OG1 | THR | A | 213 | 25.504 | 22.798 | -8.235 | 1.00 | 25.20 | O |
| ATOM | 1649 | CG2 | THR | A | 213 | 27.557 | 21.790 | -8.745 | 1.00 | 30.24 | C |
| ATOM | 1650 | C | THR | A | 213 | 25.169 | 23.747 | -11.068 | 1.00 | 21.10 | C |
| ATOM | 1651 | O | THR | A | 213 | 24.715 | 24.886 | -11.046 | 1.00 | 22.73 | O |
| ATOM | 1652 | N | GLY | A | 214 | 24.552 | 22.742 | -11.679 | 1.00 | 18.42 | N |
| ATOM | 1653 | CA | GLY | A | 214 | 23.302 | 22.944 | -12.388 | 1.00 | 16.00 | C |
| ATOM | 1654 | C | GLY | A | 214 | 23.478 | 23.372 | -13.836 | 1.00 | 15.48 | C |
| ATOM | 1655 | O | GLY | A | 214 | 22.665 | 24.123 | -14.368 | 1.00 | 15.75 | O |
| ATOM | 1656 | N | ASP | A | 215 | 24.533 | 22.874 | -14.474 | 1.00 | 19.81 | N |
| ATOM | 1657 | CA | ASP | A | 215 | 24.698 | 23.001 | -15.922 | 1.00 | 21.08 | C |
| ATOM | 1658 | CB | ASP | A | 215 | 26.037 | 22.387 | -16.358 | 1.00 | 22.08 | C |
| ATOM | 1659 | CG | ASP | A | 215 | 26.436 | 22.788 | -17.770 | 1.00 | 24.99 | C |
| ATOM | 1660 | OD1 | ASP | A | 215 | 25.795 | 22.323 | -18.729 | 1.00 | 24.51 | O |
| ATOM | 1661 | OD2 | ASP | A | 215 | 27.369 | 23.576 | -18.017 | 1.00 | 28.31 | O |
| ATOM | 1662 | C | ASP | A | 215 | 23.548 | 22.285 | -16.634 | 1.00 | 21.85 | C |
| ATOM | 1663 | O | ASP | A | 215 | 23.021 | 21.293 | -16.136 | 1.00 | 20.21 | O |
| ATOM | 1664 | N | LEU | A | 216 | 23.166 | 22.811 | -17.795 | 1.00 | 19.05 | N |
| ATOM | 1665 | CA | LEU | A | 216 | 22.198 | 22.192 | -18.694 | 1.00 | 22.13 | C |
| ATOM | 1666 | CB | LEU | A | 216 | 22.241 | 22.951 | -20.033 | 1.00 | 28.03 | C |
| ATOM | 1667 | CG | LEU | A | 216 | 21.293 | 22.605 | -21.171 | 1.00 | 28.87 | C |
| ATOM | 1668 | CD1 | LEU | A | 216 | 19.858 | 22.855 | -20.753 | 1.00 | 32.10 | C |
| ATOM | 1669 | CD2 | LEU | A | 216 | 21.640 | 23.444 | -22.390 | 1.00 | 29.15 | C |
| ATOM | 1670 | C | LEU | A | 216 | 22.486 | 20.702 | -18.935 | 1.00 | 22.08 | C |
| ATOM | 1671 | O | LEU | A | 216 | 21.564 | 19.883 | -19.038 | 1.00 | 19.37 | O |
| ATOM | 1672 | N | ARG | A | 217 | 23.771 | 20.362 | -19.005 | 1.00 | 20.19 | N |
| ATOM | 1673 | CA | ARG | A | 217 | 24.203 | 19.009 | -19.359 | 1.00 | 20.92 | C |
| ATOM | 1674 | CB | ARG | A | 217 | 25.578 | 19.062 | -20.040 | 1.00 | 20.98 | C |
| ATOM | 1675 | CG | ARG | A | 217 | 25.597 | 19.872 | -21.320 | 1.00 | 26.58 | C |
| ATOM | 1676 | CD | ARG | A | 217 | 26.314 | 21.203 | -21.158 | 1.00 | 36.86 | C |
| ATOM | 1677 | NE | ARG | A | 217 | 27.581 | 21.233 | -21.860 | 1.00 | 39.02 | N |
| ATOM | 1678 | CZ | ARG | A | 217 | 28.563 | 22.101 | -21.642 | 1.00 | 36.04 | C |
| ATOM | 1679 | NH1 | ARG | A | 217 | 28.474 | 23.039 | -20.703 | 1.00 | 30.86 | N |
| ATOM | 1680 | NH2 | ARG | A | 217 | 29.659 | 22.013 | -22.377 | 1.00 | 35.11 | N |
| ATOM | 1681 | C | ARG | A | 217 | 24.243 | 18.042 | -18.175 | 1.00 | 22.68 | C |
| ATOM | 1682 | O | ARG | A | 217 | 24.562 | 16.865 | -18.349 | 1.00 | 21.50 | O |
| ATOM | 1683 | N | ASP | A | 218 | 23.933 | 18.535 | -16.976 | 1.00 | 20.38 | N |
| ATOM | 1684 | CA | ASP | A | 218 | 23.826 | 17.674 | -15.802 | 1.00 | 22.85 | C |
| ATOM | 1685 | CB | ASP | A | 218 | 24.100 | 18.468 | -14.515 | 1.00 | 22.39 | C |
| ATOM | 1686 | CG | ASP | A | 218 | 25.551 | 18.904 | -14.393 | 1.00 | 29.80 | C |
| ATOM | 1687 | OD1 | ASP | A | 218 | 25.822 | 19.914 | -13.704 | 1.00 | 28.12 | O |
| ATOM | 1688 | OD2 | ASP | A | 218 | 26.494 | 18.298 | -14.948 | 1.00 | 29.63 | O |
| ATOM | 1689 | C | ASP | A | 218 | 22.422 | 17.085 | -15.799 | 1.00 | 24.07 | C |
| ATOM | 1690 | O | ASP | A | 218 | 21.459 | 17.770 | -15.461 | 1.00 | 25.32 | O |
| ATOM | 1691 | N | ILE | A | 219 | 22.305 | 15.820 | -16.200 | 1.00 | 20.97 | N |
| ATOM | 1692 | CA | ILE | A | 219 | 20.994 | 15.232 | -16.482 | 1.00 | 20.57 | C |
| ATOM | 1693 | CB | ILE | A | 219 | 20.865 | 14.887 | -17.990 | 1.00 | 24.89 | C |
| ATOM | 1694 | CG1 | ILE | A | 219 | 22.005 | 13.957 | -18.434 | 1.00 | 26.25 | C |
| ATOM | 1695 | CD1 | ILE | A | 219 | 21.657 | 13.077 | -19.619 | 1.00 | 31.15 | C |
| ATOM | 1696 | CG2 | ILE | A | 219 | 20.819 | 16.164 | -18.837 | 1.00 | 24.18 | C |
| ATOM | 1697 | C | ILE | A | 219 | 20.658 | 14.005 | -15.624 | 1.00 | 19.23 | C |
| ATOM | 1698 | O | ILE | A | 219 | 19.632 | 13.367 | -15.835 | 1.00 | 21.70 | O |
| ATOM | 1699 | N | GLY | A | 220 | 21.512 | 13.698 | -14.657 | 1.00 | 20.51 | N |
| ATOM | 1700 | CA | GLY | A | 220 | 21.353 | 12.507 | -13.840 | 1.00 | 19.86 | C |

FIGURE 3EE

| | | | | | | | | | | |
|---|---|---|---|---|---|---|---|---|---|---|
| ATOM | 1701 | C | GLY | A | 220 | 22.316 | 11.431 | -14.291 | 1.00 24.42 | C |
| ATOM | 1702 | O | GLY | A | 220 | 22.991 | 11.592 | -15.312 | 1.00 22.93 | O |
| ATOM | 1703 | N | ALA | A | 221 | 22.380 | 10.340 | -13.530 | 1.00 23.56 | N |
| ATOM | 1704 | CA | ALA | A | 221 | 23.274 | 9.227 | -13.833 | 1.00 26.17 | C |
| ATOM | 1705 | CB | ALA | A | 221 | 24.561 | 9.353 | -13.038 | 1.00 28.69 | C |
| ATOM | 1706 | C | ALA | A | 221 | 22.590 | 7.901 | -13.533 | 1.00 28.50 | C |
| ATOM | 1707 | O | ALA | A | 221 | 21.687 | 7.833 | -12.690 | 1.00 25.84 | O |
| ATOM | 1708 | N | GLY | A | 222 | 23.024 | 6.851 | -14.231 | 1.00 29.61 | N |
| ATOM | 1709 | CA | GLY | A | 222 | 22.475 | 5.516 | -14.065 | 1.00 27.35 | C |
| ATOM | 1710 | C | GLY | A | 222 | 20.983 | 5.460 | -14.308 | 1.00 26.35 | C |
| ATOM | 1711 | O | GLY | A | 222 | 20.488 | 5.968 | -15.317 | 1.00 28.77 | O |
| ATOM | 1712 | N | LYS | A | 223 | 20.265 | 4.848 | -13.369 | 1.00 28.08 | N |
| ATOM | 1713 | CA | LYS | A | 223 | 18.804 | 4.798 | -13.403 | 1.00 29.76 | C |
| ATOM | 1714 | CB | LYS | A | 223 | 18.281 | 4.005 | -12.203 | 1.00 33.86 | C |
| ATOM | 1715 | CG | LYS | A | 223 | 16.987 | 3.263 | -12.453 | 1.00 43.52 | C |
| ATOM | 1716 | CD | LYS | A | 223 | 16.789 | 2.163 | -11.419 | 1.00 47.26 | C |
| ATOM | 1717 | CE | LYS | A | 223 | 16.109 | 0.951 | -12.032 | 1.00 51.41 | C |
| ATOM | 1718 | NZ | LYS | A | 223 | 14.764 | 0.712 | -11.430 | 1.00 53.95 | N |
| ATOM | 1719 | C | LYS | A | 223 | 18.196 | 6.201 | -13.393 | 1.00 25.53 | C |
| ATOM | 1720 | O | LYS | A | 223 | 17.078 | 6.403 | -13.865 | 1.00 25.76 | O |
| ATOM | 1721 | N | GLY | A | 224 | 18.942 | 7.160 | -12.853 | 1.00 24.20 | N |
| ATOM | 1722 | CA | GLY | A | 224 | 18.483 | 8.539 | -12.793 | 1.00 26.21 | C |
| ATOM | 1723 | C | GLY | A | 224 | 18.809 | 9.399 | -14.006 | 1.00 23.96 | C |
| ATOM | 1724 | O | GLY | A | 224 | 18.490 | 10.588 | -14.010 | 1.00 22.79 | O |
| ATOM | 1725 | N | LYS | A | 225 | 19.445 | 8.822 | -15.030 | 1.00 24.46 | N |
| ATOM | 1726 | CA | LYS | A | 225 | 19.758 | 9.583 | -16.250 | 1.00 25.07 | C |
| ATOM | 1727 | CB | LYS | A | 225 | 20.605 | 8.753 | -17.228 | 1.00 30.14 | C |
| ATOM | 1728 | CG | LYS | A | 225 | 21.169 | 9.556 | -18.397 | 1.00 30.67 | C |
| ATOM | 1729 | CD | LYS | A | 225 | 21.867 | 8.656 | -19.417 | 1.00 34.91 | C |
| ATOM | 1730 | CE | LYS | A | 225 | 23.093 | 9.341 | -20.010 | 1.00 37.53 | C |
| ATOM | 1731 | NZ | LYS | A | 225 | 23.245 | 9.059 | -21.470 | 1.00 40.99 | N |
| ATOM | 1732 | C | LYS | A | 225 | 18.494 | 10.096 | -16.944 | 1.00 22.39 | C |
| ATOM | 1733 | O | LYS | A | 225 | 17.572 | 9.327 | -17.219 | 1.00 26.02 | O |
| ATOM | 1734 | N | TYR | A | 226 | 18.481 | 11.399 | -17.234 | 1.00 20.80 | N |
| ATOM | 1735 | CA | TYR | A | 226 | 17.327 | 12.130 | -17.775 | 1.00 21.39 | C |
| ATOM | 1736 | CB | TYR | A | 226 | 16.680 | 11.408 | -18.969 | 1.00 27.46 | C |
| ATOM | 1737 | CG | TYR | A | 226 | 17.644 | 11.160 | -20.110 | 1.00 34.32 | C |
| ATOM | 1738 | CD1 | TYR | A | 226 | 18.193 | 12.223 | -20.831 | 1.00 34.28 | C |
| ATOM | 1739 | CE1 | TYR | A | 226 | 19.085 | 11.997 | -21.882 | 1.00 38.95 | C |
| ATOM | 1740 | CZ | TYR | A | 226 | 19.438 | 10.697 | -22.208 | 1.00 40.15 | C |
| ATOM | 1741 | OH | TYR | A | 226 | 20.320 | 10.470 | -23.238 | 1.00 47.70 | O |
| ATOM | 1742 | CE2 | TYR | A | 226 | 18.908 | 9.626 | -21.506 | 1.00 39.33 | C |
| ATOM | 1743 | CD2 | TYR | A | 226 | 18.017 | 9.861 | -20.461 | 1.00 35.12 | C |
| ATOM | 1744 | C | TYR | A | 226 | 16.273 | 12.533 | -16.733 | 1.00 21.34 | C |
| ATOM | 1745 | O | TYR | A | 226 | 15.256 | 13.130 | -17.082 | 1.00 23.47 | O |
| ATOM | 1746 | N | TYR | A | 227 | 16.533 | 12.236 | -15.464 | 1.00 21.67 | N |
| ATOM | 1747 | CA | TYR | A | 227 | 15.610 | 12.608 | -14.386 | 1.00 21.88 | C |
| ATOM | 1748 | CB | TYR | A | 227 | 15.293 | 11.397 | -13.496 | 1.00 20.41 | C |
| ATOM | 1749 | CG | TYR | A | 227 | 14.556 | 10.315 | -14.247 | 1.00 21.92 | C |
| ATOM | 1750 | CD1 | TYR | A | 227 | 15.252 | 9.310 | -14.924 | 1.00 24.45 | C |
| ATOM | 1751 | CE1 | TYR | A | 227 | 14.576 | 8.324 | -15.636 | 1.00 26.10 | C |
| ATOM | 1752 | CZ | TYR | A | 227 | 13.195 | 8.340 | -15.670 | 1.00 26.27 | C |
| ATOM | 1753 | OH | TYR | A | 227 | 12.516 | 7.367 | -16.358 | 1.00 29.33 | O |
| ATOM | 1754 | CE2 | TYR | A | 227 | 12.483 | 9.325 | -15.010 | 1.00 26.51 | C |
| ATOM | 1755 | CD2 | TYR | A | 227 | 13.169 | 10.310 | -14.305 | 1.00 24.03 | C |
| ATOM | 1756 | C | TYR | A | 227 | 16.105 | 13.793 | -13.555 | 1.00 22.89 | C |
| ATOM | 1757 | O | TYR | A | 227 | 15.544 | 14.096 | -12.501 | 1.00 22.20 | O |

FIGURE 3FF

```
ATOM   1758  N    ALA A 228      17.170  14.443 -14.018  1.00 18.20           N
ATOM   1759  CA   ALA A 228      17.564  15.736 -13.471  1.00 19.12           C
ATOM   1760  CB   ALA A 228      18.976  15.696 -12.876  1.00 19.55           C
ATOM   1761  C    ALA A 228      17.459  16.748 -14.602  1.00 22.76           C
ATOM   1762  O    ALA A 228      17.926  16.498 -15.715  1.00 21.07           O
ATOM   1763  N    VAL A 229      16.798  17.868 -14.325  1.00 20.83           N
ATOM   1764  CA   VAL A 229      16.540  18.889 -15.333  1.00 18.59           C
ATOM   1765  CB   VAL A 229      15.021  18.972 -15.684  1.00 19.99           C
ATOM   1766  CG1  VAL A 229      14.735  20.056 -16.717  1.00 20.33           C
ATOM   1767  CG2  VAL A 229      14.496  17.622 -16.191  1.00 21.82           C
ATOM   1768  C    VAL A 229      17.054  20.215 -14.775  1.00 18.84           C
ATOM   1769  O    VAL A 229      16.675  20.615 -13.678  1.00 19.22           O
ATOM   1770  N    ASN A 230      17.936  20.872 -15.522  1.00 17.19           N
ATOM   1771  CA   ASN A 230      18.523  22.132 -15.085  1.00 16.98           C
ATOM   1772  CB   ASN A 230      20.013  21.935 -14.770  1.00 18.78           C
ATOM   1773  CG   ASN A 230      20.230  21.134 -13.494  1.00 20.85           C
ATOM   1774  OD1  ASN A 230      19.797  21.544 -12.419  1.00 21.17           O
ATOM   1775  ND2  ASN A 230      20.874  19.976 -13.613  1.00 19.36           N
ATOM   1776  C    ASN A 230      18.327  23.196 -16.149  1.00 18.42           C
ATOM   1777  O    ASN A 230      18.668  22.975 -17.309  1.00 18.47           O
ATOM   1778  N    PHE A 231      17.747  24.330 -15.754  1.00 17.18           N
ATOM   1779  CA   PHE A 231      17.548  25.464 -16.654  1.00 12.60           C
ATOM   1780  CB   PHE A 231      16.065  25.876 -16.702  1.00 16.28           C
ATOM   1781  CG   PHE A 231      15.694  26.676 -17.932  1.00 17.90           C
ATOM   1782  CD1  PHE A 231      14.694  26.234 -18.793  1.00 19.55           C
ATOM   1783  CE1  PHE A 231      14.361  26.957 -19.935  1.00 22.20           C
ATOM   1784  CZ   PHE A 231      15.029  28.146 -20.219  1.00 20.26           C
ATOM   1785  CE2  PHE A 231      16.021  28.604 -19.365  1.00 21.19           C
ATOM   1786  CD2  PHE A 231      16.352  27.870 -18.227  1.00 15.75           C
ATOM   1787  C    PHE A 231      18.430  26.625 -16.175  1.00 16.05           C
ATOM   1788  O    PHE A 231      18.024  27.403 -15.307  1.00 15.64           O
ATOM   1789  N    PRO A 232      19.646  26.720 -16.712  1.00 17.02           N
ATOM   1790  CA   PRO A 232      20.567  27.793 -16.320  1.00 16.50           C
ATOM   1791  CB   PRO A 232      21.912  27.341 -16.912  1.00 17.28           C
ATOM   1792  CG   PRO A 232      21.564  26.449 -18.040  1.00 17.71           C
ATOM   1793  CD   PRO A 232      20.240  25.820 -17.720  1.00 16.67           C
ATOM   1794  C    PRO A 232      20.127  29.116 -16.926  1.00 18.05           C
ATOM   1795  O    PRO A 232      19.744  29.162 -18.101  1.00 19.34           O
ATOM   1796  N    MET A 233      20.180  30.177 -16.127  1.00 17.23           N
ATOM   1797  CA   MET A 233      19.758  31.496 -16.573  1.00 16.00           C
ATOM   1798  CB   MET A 233      18.442  31.902 -15.892  1.00 16.71           C
ATOM   1799  CG   MET A 233      17.215  31.093 -16.298  1.00 22.44           C
ATOM   1800  SD   MET A 233      15.915  31.226 -15.043  1.00 28.75           S
ATOM   1801  CE   MET A 233      14.623  30.205 -15.795  1.00 29.76           C
ATOM   1802  C    MET A 233      20.832  32.532 -16.248  1.00 16.91           C
ATOM   1803  O    MET A 233      21.754  32.276 -15.471  1.00 17.92           O
ATOM   1804  N    ARG A 234      20.688  33.705 -16.845  1.00 15.79           N
ATOM   1805  CA   ARG A 234      21.584  34.831 -16.611  1.00 18.92           C
ATOM   1806  CB   ARG A 234      22.000  35.455 -17.949  1.00 20.22           C
ATOM   1807  CG   ARG A 234      22.547  34.461 -18.969  1.00 17.81           C
ATOM   1808  CD   ARG A 234      24.040  34.207 -18.849  1.00 30.06           C
ATOM   1809  NE   ARG A 234      24.316  32.934 -18.204  1.00 36.21           N
ATOM   1810  CZ   ARG A 234      24.812  31.858 -18.809  1.00 33.40           C
ATOM   1811  NH1  ARG A 234      25.014  30.764 -18.101  1.00 35.66           N
ATOM   1812  NH2  ARG A 234      25.111  31.863 -20.102  1.00 33.37           N
ATOM   1813  C    ARG A 234      20.893  35.885 -15.750  1.00 20.84           C
ATOM   1814  O    ARG A 234      19.697  35.779 -15.463  1.00 17.66           O
```

FIGURE 3GG

```
ATOM   1815  N    ASP A 235      21.658  36.905 -15.355  1.00 21.16           N
ATOM   1816  CA   ASP A 235      21.143  38.052 -14.608  1.00 23.37           C
ATOM   1817  CB   ASP A 235      22.202  39.160 -14.558  1.00 30.77           C
ATOM   1818  CG   ASP A 235      23.296  38.884 -13.561  1.00 37.64           C
ATOM   1819  OD1  ASP A 235      23.263  37.824 -12.910  1.00 41.12           O
ATOM   1820  OD2  ASP A 235      24.239  39.678 -13.360  1.00 42.19           O
ATOM   1821  C    ASP A 235      19.893  38.658 -15.226  1.00 22.18           C
ATOM   1822  O    ASP A 235      19.751  38.705 -16.453  1.00 20.28           O
ATOM   1823  N    GLY A 236      18.998  39.127 -14.361  1.00 19.53           N
ATOM   1824  CA   GLY A 236      17.950  40.051 -14.755  1.00 21.05           C
ATOM   1825  C    GLY A 236      16.701  39.502 -15.395  1.00 20.67           C
ATOM   1826  O    GLY A 236      15.948  40.262 -15.994  1.00 20.77           O
ATOM   1827  N    ILE A 237      16.460  38.196 -15.275  1.00 20.86           N
ATOM   1828  CA   ILE A 237      15.252  37.611 -15.852  1.00 20.82           C
ATOM   1829  CB   ILE A 237      15.223  36.060 -15.703  1.00 25.44           C
ATOM   1830  CG1  ILE A 237      14.125  35.464 -16.588  1.00 25.50           C
ATOM   1831  CD1  ILE A 237      14.374  34.035 -17.002  1.00 29.42           C
ATOM   1832  CG2  ILE A 237      15.035  35.642 -14.246  1.00 18.29           C
ATOM   1833  C    ILE A 237      14.013  38.261 -15.245  1.00 20.54           C
ATOM   1834  O    ILE A 237      13.990  38.586 -14.053  1.00 21.69           O
ATOM   1835  N    ASP A 238      13.004  38.472 -16.079  1.00 20.91           N
ATOM   1836  CA   ASP A 238      11.770  39.111 -15.651  1.00 25.19           C
ATOM   1837  CB   ASP A 238      11.508  40.409 -16.433  1.00 28.05           C
ATOM   1838  CG   ASP A 238      11.508  40.214 -17.944  1.00 35.95           C
ATOM   1839  OD1  ASP A 238      11.142  39.125 -18.440  1.00 32.33           O
ATOM   1840  OD2  ASP A 238      11.855  41.126 -18.724  1.00 42.70           O
ATOM   1841  C    ASP A 238      10.588  38.153 -15.730  1.00 24.19           C
ATOM   1842  O    ASP A 238      10.745  37.002 -16.153  1.00 25.52           O
ATOM   1843  N    ASP A 239       9.419  38.625 -15.300  1.00 19.70           N
ATOM   1844  CA   ASP A 239       8.215  37.794 -15.205  1.00 20.84           C
ATOM   1845  CB   ASP A 239       7.017  38.636 -14.763  1.00 22.23           C
ATOM   1846  CG   ASP A 239       7.119  39.098 -13.325  1.00 28.33           C
ATOM   1847  OD1  ASP A 239       8.008  38.607 -12.588  1.00 24.75           O
ATOM   1848  OD2  ASP A 239       6.332  39.947 -12.845  1.00 27.66           O
ATOM   1849  C    ASP A 239       7.863  37.111 -16.525  1.00 27.97           C
ATOM   1850  O    ASP A 239       7.538  35.918 -16.550  1.00 22.92           O
ATOM   1851  N    GLU A 240       7.929  37.879 -17.611  1.00 30.52           N
ATOM   1852  CA   GLU A 240       7.500  37.408 -18.926  1.00 36.04           C
ATOM   1853  CB   GLU A 240       7.346  38.578 -19.895  1.00 40.85           C
ATOM   1854  CG   GLU A 240       6.248  38.375 -20.927  1.00 50.92           C
ATOM   1855  CD   GLU A 240       6.239  39.462 -21.986  1.00 56.38           C
ATOM   1856  OE1  GLU A 240       7.090  39.413 -22.901  1.00 58.92           O
ATOM   1857  OE2  GLU A 240       5.383  40.370 -21.902  1.00 57.05           O
ATOM   1858  C    GLU A 240       8.436  36.349 -19.503  1.00 30.43           C
ATOM   1859  O    GLU A 240       7.974  35.346 -20.042  1.00 34.94           O
ATOM   1860  N    SER A 241       9.741  36.576 -19.388  1.00 27.70           N
ATOM   1861  CA   SER A 241      10.737  35.599 -19.823  1.00 30.76           C
ATOM   1862  CB   SER A 241      12.142  36.191 -19.745  1.00 33.64           C
ATOM   1863  OG   SER A 241      12.201  37.427 -20.436  1.00 41.91           O
ATOM   1864  C    SER A 241      10.658  34.298 -19.013  1.00 28.78           C
ATOM   1865  O    SER A 241      10.735  33.204 -19.579  1.00 27.67           O
ATOM   1866  N    TYR A 242      10.483  34.425 -17.698  1.00 22.39           N
ATOM   1867  CA   TYR A 242      10.365  33.264 -16.815  1.00 23.43           C
ATOM   1868  CB   TYR A 242      10.383  33.706 -15.350  1.00 21.16           C
ATOM   1869  CG   TYR A 242      10.898  32.682 -14.363  1.00 21.53           C
ATOM   1870  CD1  TYR A 242      12.206  32.758 -13.862  1.00 21.03           C
ATOM   1871  CE1  TYR A 242      12.683  31.837 -12.932  1.00 21.15           C
```

FIGURE 3HH

| | | | | | | | | |
|---|---|---|---|---|---|---|---|---|
| ATOM | 1872 | CZ  | TYR A 242 | 11.846 | 30.825 | -12.478 | 1.00 20.20 | C |
| ATOM | 1873 | OH  | TYR A 242 | 12.315 | 29.921 | -11.554 | 1.00 19.17 | O |
| ATOM | 1874 | CE2 | TYR A 242 | 10.540 | 30.733 | -12.940 | 1.00 24.73 | C |
| ATOM | 1875 | CD2 | TYR A 242 | 10.070 | 31.666 | -13.868 | 1.00 24.54 | C |
| ATOM | 1876 | C   | TYR A 242 | 9.089  | 32.479 | -17.105 | 1.00 21.69 | C |
| ATOM | 1877 | O   | TYR A 242 | 9.136  | 31.264 | -17.268 | 1.00 24.85 | O |
| ATOM | 1878 | N   | GLY A 243 | 7.958  | 33.179 | -17.170 | 1.00 26.58 | N |
| ATOM | 1879 | CA  | GLY A 243 | 6.654  | 32.552 | -17.351 | 1.00 31.83 | C |
| ATOM | 1880 | C   | GLY A 243 | 6.478  | 31.786 | -18.653 | 1.00 34.44 | C |
| ATOM | 1881 | O   | GLY A 243 | 5.811  | 30.742 | -18.683 | 1.00 34.46 | O |
| ATOM | 1882 | N   | GLN A 244 | 7.093  | 32.304 | -19.717 | 1.00 31.10 | N |
| ATOM | 1883 | CA  | GLN A 244 | 7.055  | 31.698 | -21.048 | 1.00 37.32 | C |
| ATOM | 1884 | CB  | GLN A 244 | 7.591  | 32.682 | -22.096 | 1.00 43.14 | C |
| ATOM | 1885 | CG  | GLN A 244 | 6.605  | 33.775 | -22.518 | 1.00 51.70 | C |
| ATOM | 1886 | CD  | GLN A 244 | 5.498  | 33.262 | -23.424 | 1.00 56.17 | C |
| ATOM | 1887 | OE1 | GLN A 244 | 5.756  | 32.840 | -24.555 | 1.00 57.52 | O |
| ATOM | 1888 | NE2 | GLN A 244 | 4.262  | 33.296 | -22.929 | 1.00 56.84 | N |
| ATOM | 1889 | C   | GLN A 244 | 7.860  | 30.400 | -21.115 | 1.00 35.19 | C |
| ATOM | 1890 | O   | GLN A 244 | 7.784  | 29.662 | -22.096 | 1.00 34.27 | O |
| ATOM | 1891 | N   | ILE A 245 | 8.629  | 30.133 | -20.066 | 1.00 26.66 | N |
| ATOM | 1892 | CA  | ILE A 245 | 9.464  | 28.950 | -20.000 | 1.00 25.55 | C |
| ATOM | 1893 | CB  | ILE A 245 | 10.952 | 29.398 | -19.856 | 1.00 29.44 | C |
| ATOM | 1894 | CG1 | ILE A 245 | 11.706 | 29.061 | -21.140 | 1.00 29.51 | C |
| ATOM | 1895 | CD1 | ILE A 245 | 11.168 | 29.777 | -22.370 | 1.00 30.51 | C |
| ATOM | 1896 | CG2 | ILE A 245 | 11.622 | 28.888 | -18.563 | 1.00 30.64 | C |
| ATOM | 1897 | C   | ILE A 245 | 9.012  | 27.958 | -18.926 | 1.00 24.16 | C |
| ATOM | 1898 | O   | ILE A 245 | 9.061  | 26.743 | -19.127 | 1.00 22.55 | O |
| ATOM | 1899 | N   | PHE A 246 | 8.535  | 28.479 | -17.802 | 1.00 21.41 | N |
| ATOM | 1900 | CA  | PHE A 246 | 8.164  | 27.632 | -16.672 | 1.00 20.29 | C |
| ATOM | 1901 | CB  | PHE A 246 | 7.861  | 28.495 | -15.437 | 1.00 18.73 | C |
| ATOM | 1902 | CG  | PHE A 246 | 7.621  | 27.699 | -14.196 | 1.00 19.99 | C |
| ATOM | 1903 | CD1 | PHE A 246 | 6.319  | 27.385 | -13.797 | 1.00 21.10 | C |
| ATOM | 1904 | CE1 | PHE A 246 | 6.090  | 26.629 | -12.649 | 1.00 21.90 | C |
| ATOM | 1905 | CZ  | PHE A 246 | 7.172  | 26.195 | -11.879 | 1.00 18.69 | C |
| ATOM | 1906 | CE2 | PHE A 246 | 8.476  | 26.504 | -12.274 | 1.00 17.44 | C |
| ATOM | 1907 | CD2 | PHE A 246 | 8.692  | 27.251 | -13.429 | 1.00 19.85 | C |
| ATOM | 1908 | C   | PHE A 246 | 6.972  | 26.724 | -17.008 | 1.00 21.04 | C |
| ATOM | 1909 | O   | PHE A 246 | 7.055  | 25.499 | -16.868 | 1.00 20.55 | O |
| ATOM | 1910 | N   | LYS A 247 | 5.873  | 27.323 | -17.456 | 1.00 17.93 | N |
| ATOM | 1911 | CA  | LYS A 247 | 4.664  | 26.549 | -17.758 | 1.00 22.59 | C |
| ATOM | 1912 | CB  | LYS A 247 | 3.493  | 27.459 | -18.160 | 1.00 26.10 | C |
| ATOM | 1913 | CG  | LYS A 247 | 2.143  | 26.746 | -18.151 | 1.00 34.13 | C |
| ATOM | 1914 | CD  | LYS A 247 | 1.001  | 27.682 | -18.485 | 1.00 40.97 | C |
| ATOM | 1915 | CE  | LYS A 247 | -0.319 | 26.920 | -18.531 | 1.00 46.16 | C |
| ATOM | 1916 | NZ  | LYS A 247 | -1.190 | 27.402 | -19.640 | 1.00 50.07 | N |
| ATOM | 1917 | C   | LYS A 247 | 4.896  | 25.411 | -18.781 | 1.00 22.35 | C |
| ATOM | 1918 | O   | LYS A 247 | 4.552  | 24.265 | -18.487 | 1.00 23.32 | O |
| ATOM | 1919 | N   | PRO A 248 | 5.485  | 25.698 | -19.949 | 1.00 22.62 | N |
| ATOM | 1920 | CA  | PRO A 248 | 5.805  | 24.632 | -20.918 | 1.00 22.76 | C |
| ATOM | 1921 | CB  | PRO A 248 | 6.490  | 25.388 | -22.066 | 1.00 25.89 | C |
| ATOM | 1922 | CG  | PRO A 248 | 6.025  | 26.800 | -21.931 | 1.00 24.41 | C |
| ATOM | 1923 | CD  | PRO A 248 | 5.860  | 27.031 | -20.463 | 1.00 22.52 | C |
| ATOM | 1924 | C   | PRO A 248 | 6.728  | 23.525 | -20.384 | 1.00 24.03 | C |
| ATOM | 1925 | O   | PRO A 248 | 6.478  | 22.353 | -20.681 | 1.00 24.67 | O |
| ATOM | 1926 | N   | ILE A 249 | 7.772  | 23.875 | -19.629 | 1.00 18.03 | N |
| ATOM | 1927 | CA  | ILE A 249 | 8.669  | 22.863 | -19.073 | 1.00 18.27 | C |
| ATOM | 1928 | CB  | ILE A 249 | 9.959  | 23.489 | -18.469 | 1.00 20.02 | C |

FIGURE 3II

| ATOM | 1929 | CG1 | ILE | A | 249 | 10.841 | 24.113 | -19.564 | 1.00 | 22.35 | C |
| --- | --- | --- | --- | --- | --- | --- | --- | --- | --- | --- | --- |
| ATOM | 1930 | CD1 | ILE | A | 249 | 11.665 | 23.118 | -20.385 | 1.00 | 32.72 | C |
| ATOM | 1931 | CG2 | ILE | A | 249 | 10.746 | 22.452 | -17.647 | 1.00 | 18.35 | C |
| ATOM | 1932 | C | ILE | A | 249 | 7.952 | 21.977 | -18.049 | 1.00 | 21.23 | C |
| ATOM | 1933 | O | ILE | A | 249 | 8.059 | 20.748 | -18.105 | 1.00 | 20.10 | O |
| ATOM | 1934 | N | ILE | A | 250 | 7.219 | 22.599 | -17.129 | 1.00 | 17.71 | N |
| ATOM | 1935 | CA | ILE | A | 250 | 6.513 | 21.849 | -16.086 | 1.00 | 16.89 | C |
| ATOM | 1936 | CB | ILE | A | 250 | 5.975 | 22.790 | -14.970 | 1.00 | 21.22 | C |
| ATOM | 1937 | CG1 | ILE | A | 250 | 7.142 | 23.465 | -14.219 | 1.00 | 20.72 | C |
| ATOM | 1938 | CD1 | ILE | A | 250 | 8.282 | 22.522 | -13.781 | 1.00 | 19.49 | C |
| ATOM | 1939 | CG2 | ILE | A | 250 | 5.085 | 22.022 | -13.972 | 1.00 | 23.08 | C |
| ATOM | 1940 | C | ILE | A | 250 | 5.409 | 20.982 | -16.702 | 1.00 | 19.54 | C |
| ATOM | 1941 | O | ILE | A | 250 | 5.250 | 19.824 | -16.313 | 1.00 | 19.99 | O |
| ATOM | 1942 | N | SER | A | 251 | 4.691 | 21.524 | -17.683 | 1.00 | 19.28 | N |
| ATOM | 1943 | CA | SER | A | 251 | 3.637 | 20.762 | -18.357 | 1.00 | 23.94 | C |
| ATOM | 1944 | CB | SER | A | 251 | 2.897 | 21.617 | -19.381 | 1.00 | 23.65 | C |
| ATOM | 1945 | OG | SER | A | 251 | 2.339 | 22.762 | -18.762 | 1.00 | 31.13 | O |
| ATOM | 1946 | C | SER | A | 251 | 4.203 | 19.512 | -19.025 | 1.00 | 21.56 | C |
| ATOM | 1947 | O | SER | A | 251 | 3.610 | 18.437 | -18.937 | 1.00 | 25.09 | O |
| ATOM | 1948 | N | LYS | A | 252 | 5.351 | 19.661 | -19.680 | 1.00 | 23.02 | N |
| ATOM | 1949 | CA | LYS | A | 252 | 6.010 | 18.542 | -20.351 | 1.00 | 25.65 | C |
| ATOM | 1950 | CB | LYS | A | 252 | 7.147 | 19.044 | -21.245 | 1.00 | 30.10 | C |
| ATOM | 1951 | CG | LYS | A | 252 | 7.721 | 17.989 | -22.203 | 1.00 | 34.38 | C |
| ATOM | 1952 | CD | LYS | A | 252 | 6.720 | 17.582 | -23.284 | 1.00 | 39.91 | C |
| ATOM | 1953 | CE | LYS | A | 252 | 6.698 | 18.580 | -24.436 | 1.00 | 45.84 | C |
| ATOM | 1954 | NZ | LYS | A | 252 | 5.633 | 18.256 | -25.431 | 1.00 | 50.28 | N |
| ATOM | 1955 | C | LYS | A | 252 | 6.540 | 17.514 | -19.354 | 1.00 | 26.73 | C |
| ATOM | 1956 | O | LYS | A | 252 | 6.435 | 16.296 | -19.576 | 1.00 | 21.80 | O |
| ATOM | 1957 | N | VAL | A | 253 | 7.113 | 18.010 | -18.259 | 1.00 | 20.90 | N |
| ATOM | 1958 | CA | VAL | A | 253 | 7.596 | 17.153 | -17.189 | 1.00 | 21.20 | C |
| ATOM | 1959 | CB | VAL | A | 253 | 8.332 | 17.967 | -16.086 | 1.00 | 22.54 | C |
| ATOM | 1960 | CG1 | VAL | A | 253 | 8.493 | 17.156 | -14.818 | 1.00 | 27.03 | C |
| ATOM | 1961 | CG2 | VAL | A | 253 | 9.700 | 18.439 | -16.585 | 1.00 | 23.61 | C |
| ATOM | 1962 | C | VAL | A | 253 | 6.440 | 16.337 | -16.603 | 1.00 | 21.75 | C |
| ATOM | 1963 | O | VAL | A | 253 | 6.562 | 15.115 | -16.438 | 1.00 | 28.18 | O |
| ATOM | 1964 | N | MET | A | 254 | 5.329 | 17.010 | -16.310 | 1.00 | 20.96 | N |
| ATOM | 1965 | CA | MET | A | 254 | 4.129 | 16.355 | -15.780 | 1.00 | 23.23 | C |
| ATOM | 1966 | CB | MET | A | 254 | 3.026 | 17.378 | -15.512 | 1.00 | 24.89 | C |
| ATOM | 1967 | CG | MET | A | 254 | 3.301 | 18.306 | -14.333 | 1.00 | 25.26 | C |
| ATOM | 1968 | SD | MET | A | 254 | 3.211 | 17.475 | -12.749 | 1.00 | 27.71 | S |
| ATOM | 1969 | CE | MET | A | 254 | 3.201 | 18.922 | -11.638 | 1.00 | 24.41 | C |
| ATOM | 1970 | C | MET | A | 254 | 3.606 | 15.265 | -16.719 | 1.00 | 27.64 | C |
| ATOM | 1971 | O | MET | A | 254 | 3.236 | 14.179 | -16.267 | 1.00 | 28.34 | O |
| ATOM | 1972 | N | GLU | A | 255 | 3.591 | 15.562 | -18.018 | 1.00 | 28.31 | N |
| ATOM | 1973 | CA | GLU | A | 255 | 3.119 | 14.624 | -19.040 | 1.00 | 31.47 | C |
| ATOM | 1974 | CB | GLU | A | 255 | 2.969 | 15.338 | -20.398 | 1.00 | 35.10 | C |
| ATOM | 1975 | CG | GLU | A | 255 | 2.919 | 14.411 | -21.609 | 1.00 | 46.02 | C |
| ATOM | 1976 | CD | GLU | A | 255 | 2.706 | 15.145 | -22.925 | 1.00 | 51.56 | C |
| ATOM | 1977 | OE1 | GLU | A | 255 | 3.696 | 15.644 | -23.506 | 1.00 | 52.84 | O |
| ATOM | 1978 | OE2 | GLU | A | 255 | 1.547 | 15.212 | -23.386 | 1.00 | 54.42 | O |
| ATOM | 1979 | C | GLU | A | 255 | 4.032 | 13.395 | -19.157 | 1.00 | 29.19 | C |
| ATOM | 1980 | O | GLU | A | 255 | 3.553 | 12.258 | -19.216 | 1.00 | 29.05 | O |
| ATOM | 1981 | N | MET | A | 256 | 5.340 | 13.635 | -19.177 | 1.00 | 25.93 | N |
| ATOM | 1982 | CA | MET | A | 256 | 6.329 | 12.576 | -19.358 | 1.00 | 24.95 | C |
| ATOM | 1983 | CB | MET | A | 256 | 7.660 | 13.150 | -19.866 | 1.00 | 28.00 | C |
| ATOM | 1984 | CG | MET | A | 256 | 7.609 | 13.797 | -21.247 | 1.00 | 32.79 | C |
| ATOM | 1985 | SD | MET | A | 256 | 6.953 | 12.713 | -22.541 | 1.00 | 40.01 | S |

FIGURE 3JJ

```
ATOM   1986  CE   MET A 256       8.174   11.379  -22.544  1.00 37.27           C
ATOM   1987  C    MET A 256       6.575   11.758  -18.095  1.00 27.45           C
ATOM   1988  O    MET A 256       6.674   10.530  -18.159  1.00 27.18           O
ATOM   1989  N    TYR A 257       6.681   12.434  -16.951  1.00 24.08           N
ATOM   1990  CA   TYR A 257       7.103   11.782  -15.709  1.00 24.72           C
ATOM   1991  CB   TYR A 257       7.964   12.728  -14.862  1.00 23.35           C
ATOM   1992  CG   TYR A 257       8.598   12.082  -13.650  1.00 20.86           C
ATOM   1993  CD1  TYR A 257       8.373   12.597  -12.373  1.00 22.18           C
ATOM   1994  CE1  TYR A 257       8.949   12.014  -11.253  1.00 18.84           C
ATOM   1995  CZ   TYR A 257       9.758   10.909  -11.400  1.00 22.57           C
ATOM   1996  OH   TYR A 257      10.325   10.342  -10.290  1.00 23.25           O
ATOM   1997  CE2  TYR A 257       9.999   10.366  -12.658  1.00 19.50           C
ATOM   1998  CD2  TYR A 257       9.422   10.959  -13.774  1.00 19.95           C
ATOM   1999  C    TYR A 257       5.952   11.230  -14.872  1.00 21.11           C
ATOM   2000  O    TYR A 257       6.130   10.253  -14.144  1.00 23.78           O
ATOM   2001  N    GLN A 258       4.786   11.862  -14.978  1.00 22.41           N
ATOM   2002  CA   GLN A 258       3.575   11.443  -14.257  1.00 24.97           C
ATOM   2003  CB   GLN A 258       2.964   10.200  -14.919  1.00 28.34           C
ATOM   2004  CG   GLN A 258       2.686   10.361  -16.390  1.00 35.90           C
ATOM   2005  CD   GLN A 258       1.225   10.187  -16.695  1.00 43.07           C
ATOM   2006  OE1  GLN A 258       0.770    9.069  -16.945  1.00 42.69           O
ATOM   2007  NE2  GLN A 258       0.476   11.284  -16.655  1.00 45.07           N
ATOM   2008  C    GLN A 258       3.816   11.174  -12.768  1.00 24.15           C
ATOM   2009  O    GLN A 258       3.580   10.054  -12.290  1.00 23.95           O
ATOM   2010  N    PRO A 259       4.278   12.191  -12.032  1.00 23.20           N
ATOM   2011  CA   PRO A 259       4.542   12.031  -10.598  1.00 20.98           C
ATOM   2012  CB   PRO A 259       5.246   13.346  -10.222  1.00 20.31           C
ATOM   2013  CG   PRO A 259       4.722   14.349  -11.209  1.00 21.72           C
ATOM   2014  CD   PRO A 259       4.544   13.570  -12.491  1.00 23.26           C
ATOM   2015  C    PRO A 259       3.223   11.907   -9.851  1.00 19.65           C
ATOM   2016  O    PRO A 259       2.195   12.342  -10.371  1.00 20.26           O
ATOM   2017  N    SER A 260       3.240   11.324   -8.655  1.00 22.29           N
ATOM   2018  CA   SER A 260       2.029   11.303   -7.841  1.00 21.87           C
ATOM   2019  CB   SER A 260       1.728    9.889   -7.338  1.00 22.63           C
ATOM   2020  OG   SER A 260       2.886    9.301   -6.795  1.00 28.12           O
ATOM   2021  C    SER A 260       2.096   12.305   -6.677  1.00 23.40           C
ATOM   2022  O    SER A 260       1.120   12.475   -5.937  1.00 19.22           O
ATOM   2023  N    ALA A 261       3.247   12.960   -6.517  1.00 20.90           N
ATOM   2024  CA   ALA A 261       3.399   14.033   -5.531  1.00 18.31           C
ATOM.  2025  CB   ALA A 261       3.771   13.485   -4.171  1.00 19.24           C
ATOM   2026  C    ALA A 261       4.444   15.033   -5.998  1.00 18.83           C
ATOM   2027  O    ALA A 261       5.348   14.690   -6.765  1.00 18.33           O
ATOM   2028  N    VAL A 262       4.309   16.268   -5.530  1.00 17.08           N
ATOM   2029  CA   VAL A 262       5.192   17.355   -5.950  1.00 14.45           C
ATOM   2030  CB   VAL A 262       4.467   18.335   -6.899  1.00 17.87           C
ATOM   2031  CG1  VAL A 262       5.425   19.448   -7.402  1.00 17.67           C
ATOM   2032  CG2  VAL A 262       3.850   17.597   -8.083  1.00 20.33           C
ATOM   2033  C    VAL A 262       5.726   18.108   -4.732  1.00 15.66           C
ATOM   2034  O    VAL A 262       4.993   18.354   -3.776  1.00 16.13           O
ATOM   2035  N    VAL A 263       7.010   18.452   -4.771  1.00 13.90           N
ATOM   2036  CA   VAL A 263       7.610   19.316   -3.757  1.00 16.19           C
ATOM   2037  CB   VAL A 263       8.761   18.612   -3.000  1.00 15.30           C
ATOM   2038  CG1  VAL A 263       9.442   19.559   -2.010  1.00 13.82           C
ATOM   2039  CG2  VAL A 263       8.245   17.387   -2.264  1.00 17.44           C
ATOM   2040  C    VAL A 263       8.112   20.557   -4.495  1.00 18.19           C
ATOM   2041  O    VAL A 263       8.906   20.447   -5.436  1.00 16.67           O
ATOM   2042  N    LEU A 264       7.624   21.722   -4.080  1.00 15.22           N
```

FIGURE 3KK

```
ATOM   2043  CA   LEU A 264       8.000  22.985  -4.700  1.00 14.01           C
ATOM   2044  CB   LEU A 264       6.754  23.716  -5.227  1.00 14.88           C
ATOM   2045  CG   LEU A 264       6.954  25.096  -5.875  1.00 17.21           C
ATOM   2046  CD1  LEU A 264       7.772  24.986  -7.161  1.00 15.60           C
ATOM   2047  CD2  LEU A 264       5.595  25.735  -6.169  1.00 18.91           C
ATOM   2048  C    LEU A 264       8.769  23.843  -3.694  1.00 17.32           C
ATOM   2049  O    LEU A 264       8.234  24.218  -2.643  1.00 15.70           O
ATOM   2050  N    GLN A 265      10.039  24.105  -4.005  1.00 14.65           N
ATOM   2051  CA   GLN A 265      10.867  25.009  -3.215  1.00 13.14           C
ATOM   2052  CB   GLN A 265      12.334  24.545  -3.252  1.00 15.15           C
ATOM   2053  CG   GLN A 265      13.230  25.077  -2.130  1.00 14.21           C
ATOM   2054  CD   GLN A 265      13.991  26.327  -2.535  1.00 15.72           C
ATOM   2055  OE1  GLN A 265      13.563  27.053  -3.441  1.00 20.01           O
ATOM   2056  NE2  GLN A 265      15.115  26.587  -1.870  1.00 15.52           N
ATOM   2057  C    GLN A 265      10.680  26.413  -3.813  1.00 15.15           C
ATOM   2058  O    GLN A 265      10.887  26.617  -5.014  1.00 14.45           O
ATOM   2059  N    CYS A 266      10.253  27.367  -2.983  1.00 12.99           N
ATOM   2060  CA   CYS A 266       9.863  28.692  -3.468  1.00 14.78           C
ATOM   2061  CB   CYS A 266       8.445  29.049  -2.997  1.00 18.11           C
ATOM   2062  SG   CYS A 266       7.164  27.838  -3.408  1.00 21.88           S
ATOM   2063  C    CYS A 266      10.814  29.766  -2.972  1.00 16.35           C
ATOM   2064  O    CYS A 266      10.368  30.823  -2.512  1.00 18.50           O
ATOM   2065  N    GLY A 267      12.114  29.502  -3.063  1.00 16.88           N
ATOM   2066  CA   GLY A 267      13.118  30.468  -2.639  1.00 15.76           C
ATOM   2067  C    GLY A 267      12.830  31.851  -3.200  1.00 15.57           C
ATOM   2068  O    GLY A 267      12.658  32.010  -4.410  1.00 18.40           O
ATOM   2069  N    ALA A 268      12.763  32.844  -2.316  1.00 16.62           N
ATOM   2070  CA   ALA A 268      12.361  34.201  -2.684  1.00 15.89           C
ATOM   2071  CB   ALA A 268      11.556  34.848  -1.535  1.00 16.08           C
ATOM   2072  C    ALA A 268      13.549  35.083  -3.081  1.00 16.55           C
ATOM   2073  O    ALA A 268      13.386  36.280  -3.326  1.00 17.81           O
ATOM   2074  N    ASP A 269      14.737  34.493  -3.170  1.00 15.03           N
ATOM   2075  CA   ASP A 269      15.899  35.245  -3.634  1.00 14.24           C
ATOM   2076  CB   ASP A 269      17.215  34.685  -3.072  1.00 13.50           C
ATOM   2077  CG   ASP A 269      17.361  33.196  -3.272  1.00 18.62           C
ATOM   2078  OD1  ASP A 269      16.544  32.581  -3.999  1.00 15.42           O
ATOM   2079  OD2  ASP A 269      18.293  32.559  -2.738  1.00 17.13           O
ATOM   2080  C    ASP A 269      15.951  35.439  -5.157  1.00 17.65           C
ATOM   2081  O    ASP A 269      16.858  36.084  -5.677  1.00 15.85           O
ATOM   2082  N    SER A 270      14.961  34.894  -5.861  1.00 15.27           N
ATOM   2083  CA   SER A 270      14.793  35.154  -7.288  1.00 16.54           C
ATOM   2084  CB   SER A 270      14.186  33.940  -7.997  1.00 19.60           C
ATOM   2085  OG   SER A 270      13.184  33.341  -7.199  1.00 20.56           O
ATOM   2086  C    SER A 270      13.950  36.410  -7.558  1.00 19.77           C
ATOM   2087  O    SER A 270      13.647  36.727  -8.719  1.00 17.26           O
ATOM   2088  N    LEU A 271      13.578  37.126  -6.493  1.00 16.74           N
ATOM   2089  CA   LEU A 271      12.815  38.366  -6.631  1.00 17.79           C
ATOM   2090  CB   LEU A 271      12.014  38.672  -5.361  1.00 15.78           C
ATOM   2091  CG   LEU A 271      10.886  37.701  -4.989  1.00 18.28           C
ATOM   2092  CD1  LEU A 271      10.391  38.013  -3.572  1.00 16.29           C
ATOM   2093  CD2  LEU A 271       9.732  37.736  -6.004  1.00 17.72           C
ATOM   2094  C    LEU A 271      13.691  39.569  -6.929  1.00 18.08           C
ATOM   2095  O    LEU A 271      14.836  39.661  -6.465  1.00 18.83           O
ATOM   2096  N    SER A 272      13.119  40.492  -7.693  1.00 20.22           N
ATOM   2097  CA   SER A 272      13.682  41.822  -7.899  1.00 22.06           C
ATOM   2098  CB   SER A 272      12.652  42.711  -8.594  1.00 22.22           C
ATOM   2099  OG   SER A 272      13.131  44.040  -8.702  1.00 27.40           O
```

FIGURE 3LL

```
ATOM   2100  C    SER A 272      14.060  42.450  -6.564  1.00 24.05           C
ATOM   2101  O    SER A 272      13.283  42.389  -5.600  1.00 21.60           O
ATOM   2102  N    GLY A 273      15.256  43.035  -6.518  1.00 23.09           N
ATOM   2103  CA   GLY A 273      15.729  43.736  -5.336  1.00 24.52           C
ATOM   2104  C    GLY A 273      16.285  42.867  -4.220  1.00 20.60           C
ATOM   2105  O    GLY A 273      16.557  43.372  -3.131  1.00 21.43           O
ATOM   2106  N    ASP A 274      16.458  41.568  -4.461  1.00 17.81           N
ATOM   2107  CA   ASP A 274      17.041  40.721  -3.429  1.00 19.13           C
ATOM   2108  CB   ASP A 274      16.992  39.241  -3.792  1.00 18.22           C
ATOM   2109  CG   ASP A 274      17.419  38.369  -2.640  1.00 22.92           C
ATOM   2110  OD1  ASP A 274      16.576  38.125  -1.745  1.00 20.07           O
ATOM   2111  OD2  ASP A 274      18.587  37.930  -2.521  1.00 24.08           O
ATOM   2112  C    ASP A 274      18.482  41.126  -3.152  1.00 21.68           C
ATOM   2113  O    ASP A 274      19.229  41.457  -4.078  1.00 23.24           O
ATOM   2114  N    ARG A 275      18.857  41.099  -1.877  1.00 21.43           N
ATOM   2115  CA   ARG A 275      20.196  41.500  -1.441  1.00 24.72           C
ATOM   2116  CB   ARG A 275      20.317  41.395   0.085  1.00 27.55           C
ATOM   2117  CG   ARG A 275      19.865  42.630   0.853  1.00 37.75           C
ATOM   2118  CD   ARG A 275      20.260  42.632   2.334  1.00 42.19           C
ATOM   2119  NE   ARG A 275      21.629  42.155   2.564  1.00 49.44           N
ATOM   2120  CZ   ARG A 275      22.137  41.810   3.739  1.00 51.16           C
ATOM   2121  NH1  ARG A 275      21.401  41.884   4.843  1.00 49.94           N
ATOM   2122  NH2  ARG A 275      23.393  41.389   3.821  1.00 50.89           N
ATOM   2123  C    ARG A 275      21.301  40.673  -2.085  1.00 23.16           C
ATOM   2124  O    ARG A 275      22.381  41.192  -2.368  1.00 23.33           O
ATOM   2125  N    LEU A 276      21.047  39.380  -2.287  1.00 20.45           N
ATOM   2126  CA   LEU A 276      22.061  38.482  -2.840  1.00 21.95           C
ATOM   2127  CB   LEU A 276      22.224  37.227  -1.965  1.00 22.48           C
ATOM   2128  CG   LEU A 276      22.605  37.409  -0.486  1.00 24.23           C
ATOM   2129  CD1  LEU A 276      22.829  36.056   0.183  1.00 22.94           C
ATOM   2130  CD2  LEU A 276      23.831  38.314  -0.287  1.00 27.10           C
ATOM   2131  C    LEU A 276      21.798  38.082  -4.290  1.00 25.48           C
ATOM   2132  O    LEU A 276      22.727  37.768  -5.028  1.00 31.92           O
ATOM   2133  N    GLY A 277      20.537  38.094  -4.697  1.00 23.11           N
ATOM   2134  CA   GLY A 277      20.163  37.631  -6.023  1.00 22.99           C
ATOM   2135  C    GLY A 277      20.168  38.711  -7.085  1.00 26.70           C
ATOM   2136  O    GLY A 277      20.081  39.900  -6.769  1.00 27.37           O
ATOM   2137  N    CYS A 278      20.253  38.294  -8.347  1.00 21.60           N
ATOM   2138  CA   CYS A 278      20.279  39.224  -9.474  1.00 23.23           C
ATOM   2139  CB   CYS A 278      21.661  39.240 -10.143  1.00 34.11           C
ATOM   2140  SG   CYS A 278      22.657  37.764  -9.852  1.00 51.68           S
ATOM   2141  C    CYS A 278      19.189  38.975 -10.514  1.00 22.32           C
ATOM   2142  O    CYS A 278      19.360  39.303 -11.686  1.00 23.23           O
ATOM   2143  N    PHE A 279      18.068  38.399 -10.087  1.00 18.03           N
ATOM   2144  CA   PHE A 279      16.906  38.260 -10.956  1.00 19.54           C
ATOM   2145  CB   PHE A 279      16.122  36.986 -10.604  1.00 16.66           C
ATOM   2146  CG   PHE A 279      16.669  35.711 -11.217  1.00 18.32           C
ATOM   2147  CD1  PHE A 279      15.979  34.512 -11.035  1.00 16.29           C
ATOM   2148  CE1  PHE A 279      16.445  33.320 -11.585  1.00 20.37           C
ATOM   2149  CZ   PHE A 279      17.618  33.316 -12.343  1.00 20.84           C
ATOM   2150  CE2  PHE A 279      18.323  34.502 -12.536  1.00 21.46           C
ATOM   2151  CD2  PHE A 279      17.843  35.697 -11.977  1.00 20.00           C
ATOM   2152  C    PHE A 279      15.997  39.487 -10.808  1.00 18.03           C
ATOM   2153  O    PHE A 279      16.214  40.337  -9.935  1.00 19.64           O
ATOM   2154  N    ASN A 280      14.970  39.567 -11.647  1.00 16.97           N
ATOM   2155  CA   ASN A 280      14.077  40.721 -11.673  1.00 17.94           C
ATOM   2156  CB   ASN A 280      14.399  41.605 -12.895  1.00 18.63           C
```

FIGURE 3MM

```
ATOM   2157  CG  ASN A 280      13.993  43.070 -12.695  1.00 23.74           C
ATOM   2158  OD1 ASN A 280      13.755  43.516 -11.576  1.00 23.83           O
ATOM   2159  ND2 ASN A 280      13.915  43.819 -13.792  1.00 23.81           N
ATOM   2160  C   ASN A 280      12.600  40.316 -11.655  1.00 17.84           C
ATOM   2161  O   ASN A 280      11.759  40.973 -12.272  1.00 20.01           O
ATOM   2162  N   LEU A 281      12.286  39.229 -10.947  1.00 15.89           N
ATOM   2163  CA  LEU A 281      10.898  38.776 -10.834  1.00 18.39           C
ATOM   2164  CB  LEU A 281      10.834  37.301 -10.409  1.00 18.59           C
ATOM   2165  CG  LEU A 281      11.469  36.224 -11.292  1.00 21.18           C
ATOM   2166  CD1 LEU A 281      11.195  34.839 -10.691  1.00 22.17           C
ATOM   2167  CD2 LEU A 281      10.953  36.311 -12.723  1.00 23.67           C
ATOM   2168  C   LEU A 281      10.113  39.592  -9.818  1.00 17.32           C
ATOM   2169  O   LEU A 281      10.660  40.000  -8.792  1.00 20.69           O
ATOM   2170  N   THR A 282       8.827  39.793 -10.092  1.00 18.66           N
ATOM   2171  CA  THR A 282       7.921  40.344  -9.089  1.00 19.21           C
ATOM   2172  CB  THR A 282       6.800  41.207  -9.726  1.00 19.92           C
ATOM   2173  OG1 THR A 282       5.901  40.376 -10.478  1.00 20.49           O
ATOM   2174  CG2 THR A 282       7.371  42.186 -10.752  1.00 23.25           C
ATOM   2175  C   THR A 282       7.307  39.214  -8.278  1.00 18.64           C
ATOM   2176  O   THR A 282       7.497  38.038  -8.587  1.00 17.52           O
ATOM   2177  N   VAL A 283       6.576  39.584  -7.233  1.00 19.80           N
ATOM   2178  CA  VAL A 283       5.849  38.619  -6.429  1.00 20.55           C
ATOM   2179  CB  VAL A 283       5.254  39.292  -5.171  1.00 22.86           C
ATOM   2180  CG1 VAL A 283       4.207  38.407  -4.511  1.00 24.37           C
ATOM   2181  CG2 VAL A 283       6.385  39.616  -4.182  1.00 20.76           C
ATOM   2182  C   VAL A 283       4.799  37.891  -7.276  1.00 21.86           C
ATOM   2183  O   VAL A 283       4.641  36.681  -7.149  1.00 18.51           O
ATOM   2184  N   LYS A 284       4.106  38.622  -8.152  1.00 20.33           N
ATOM   2185  CA  LYS A 284       3.137  38.014  -9.073  1.00 22.74           C
ATOM   2186  CB  LYS A 284       2.383  39.087  -9.868  1.00 27.52           C
ATOM   2187  CG  LYS A 284       1.128  39.606  -9.193  1.00 36.73           C
ATOM   2188  CD  LYS A 284       0.296  40.458 -10.152  1.00 41.16           C
ATOM   2189  CE  LYS A 284      -0.088  41.800  -9.529  1.00 46.57           C
ATOM   2190  NZ  LYS A 284      -0.683  42.752 -10.524  1.00 46.00           N
ATOM   2191  C   LYS A 284       3.788  37.022 -10.040  1.00 20.71           C
ATOM   2192  O   LYS A 284       3.226  35.963 -10.314  1.00 22.30           O
ATOM   2193  N   GLY A 285       4.965  37.372 -10.559  1.00 19.78           N
ATOM   2194  CA  GLY A 285       5.691  36.497 -11.467  1.00 20.86           C
ATOM   2195  C   GLY A 285       6.170  35.243 -10.763  1.00 23.10           C
ATOM   2196  O   GLY A 285       6.082  34.130 -11.293  1.00 22.87           O
ATOM   2197  N   HIS A 286       6.684  35.435  -9.554  1.00 19.16           N
ATOM   2198  CA  HIS A 286       7.119  34.338  -8.703  1.00 20.45           C
ATOM   2199  CB  HIS A 286       7.712  34.903  -7.409  1.00 19.10           C
ATOM   2200  CG  HIS A 286       8.626  33.960  -6.697  1.00 17.27           C
ATOM   2201  ND1 HIS A 286       8.178  33.077  -5.741  1.00 18.78           N
ATOM   2202  CE1 HIS A 286       9.201  32.388  -5.267  1.00 16.80           C
ATOM   2203  NE2 HIS A 286      10.299  32.798  -5.878  1.00 17.36           N
ATOM   2204  CD2 HIS A 286       9.968  33.784  -6.775  1.00 15.55           C
ATOM   2205  C   HIS A 286       5.960  33.399  -8.389  1.00 19.49           C
ATOM   2206  O   HIS A 286       6.069  32.185  -8.573  1.00 22.26           O
ATOM   2207  N   ALA A 287       4.849  33.981  -7.941  1.00 18.03           N
ATOM   2208  CA  ALA A 287       3.661  33.238  -7.549  1.00 18.07           C
ATOM   2209  CB  ALA A 287       2.680  34.161  -6.859  1.00 19.83           C
ATOM   2210  C   ALA A 287       2.969  32.512  -8.699  1.00 21.64           C
ATOM   2211  O   ALA A 287       2.258  31.531  -8.469  1.00 22.98           O
ATOM   2212  N   LYS A 288       3.165  33.002  -9.922  1.00 21.97           N
ATOM   2213  CA  LYS A 288       2.655  32.341 -11.121  1.00 25.80           C
```

FIGURE 3NN

```
ATOM   2214  CB   LYS A 288       3.095  33.097 -12.379  1.00 31.30           C
ATOM   2215  CG   LYS A 288       2.294  32.757 -13.637  1.00 39.56           C
ATOM   2216  CD   LYS A 288       2.345  33.889 -14.656  1.00 47.76           C
ATOM   2217  CE   LYS A 288       3.545  33.758 -15.598  1.00 52.05           C
ATOM   2218  NZ   LYS A 288       4.545  34.862 -15.407  1.00 50.53           N
ATOM   2219  C    LYS A 288       3.120  30.885 -11.186  1.00 25.80           C
ATOM   2220  O    LYS A 288       2.371  30.012 -11.638  1.00 21.58           O
ATOM   2221  N    CYS A 289       4.352  30.630 -10.731  1.00 21.02           N
ATOM   2222  CA   CYS A 289       4.890  29.270 -10.666  1.00 21.57           C
ATOM   2223  CB   CYS A 289       6.331  29.277 -10.169  1.00 22.62           C
ATOM   2224  SG   CYS A 289       7.416  30.243 -11.219  1.00 25.70           S
ATOM   2225  C    CYS A 289       4.051  28.385  -9.764  1.00 22.17           C
ATOM   2226  O    CYS A 289       3.772  27.241 -10.102  1.00 18.49           O
ATOM   2227  N    VAL A 290       3.657  28.924  -8.614  1.00 20.65           N
ATOM   2228  CA   VAL A 290       2.820  28.201  -7.663  1.00 22.50           C
ATOM   2229  CB   VAL A 290       2.630  29.005  -6.353  1.00 19.70           C
ATOM   2230  CG1  VAL A 290       1.704  28.266  -5.404  1.00 20.56           C
ATOM   2231  CG2  VAL A 290       3.981  29.271  -5.694  1.00 22.63           C
ATOM   2232  C    VAL A 290       1.462  27.897  -8.290  1.00 23.73           C
ATOM   2233  O    VAL A 290       0.970  26.767  -8.205  1.00 22.30           O
ATOM   2234  N    GLU A 291       0.868  28.911  -8.918  1.00 21.47           N
ATOM   2235  CA   GLU A 291      -0.396  28.752  -9.640  1.00 25.72           C
ATOM   2236  CB   GLU A 291      -0.772  30.061 -10.337  1.00 34.02           C
ATOM   2237  CG   GLU A 291      -2.262  30.246 -10.575  1.00 45.25           C
ATOM   2238  CD   GLU A 291      -2.637  31.699 -10.814  1.00 52.35           C
ATOM   2239  OE1  GLU A 291      -3.563  31.949 -11.614  1.00 56.56           O
ATOM   2240  OE2  GLU A 291      -2.009  32.596 -10.204  1.00 55.25           O
ATOM   2241  C    GLU A 291      -0.319  27.624 -10.675  1.00 23.85           C
ATOM   2242  O    GLU A 291      -1.213  26.784 -10.749  1.00 23.65           O
ATOM   2243  N    VAL A 292       0.763  27.603 -11.452  1.00 20.68           N
ATOM   2244  CA   VAL A 292       0.961  26.590 -12.489  1.00 20.98           C
ATOM   2245  CB   VAL A 292       2.228  26.888 -13.338  1.00 21.90           C
ATOM   2246  CG1  VAL A 292       2.685  25.650 -14.119  1.00 23.43           C
ATOM   2247  CG2  VAL A 292       1.965  28.052 -14.288  1.00 24.95           C
ATOM   2248  C    VAL A 292       1.018  25.174 -11.898  1.00 21.34           C
ATOM   2249  O    VAL A 292       0.305  24.274 -12.351  1.00 23.32           O
ATOM   2250  N    VAL A 293       1.849  24.986 -10.879  1.00 17.97           N
ATOM   2251  CA   VAL A 293       2.000  23.668 -10.248  1.00 21.44           C
ATOM   2252  CB   VAL A 293       3.146  23.658  -9.222  1.00 17.29           C
ATOM   2253  CG1  VAL A 293       3.251  22.296  -8.524  1.00 21.43           C
ATOM   2254  CG2  VAL A 293       4.469  24.016  -9.906  1.00 21.04           C
ATOM   2255  C    VAL A 293       0.689  23.214  -9.607  1.00 22.90           C
ATOM   2256  O    VAL A 293       0.325  22.035  -9.677  1.00 22.65           O
ATOM   2257  N    LYS A 294      -0.024  24.164  -9.007  1.00 24.39           N
ATOM   2258  CA   LYS A 294      -1.322  23.907  -8.384  1.00 28.31           C
ATOM   2259  CB   LYS A 294      -1.910  25.215  -7.854  1.00 32.06           C
ATOM   2260  CG   LYS A 294      -2.169  25.216  -6.375  1.00 38.62           C
ATOM   2261  CD   LYS A 294      -2.730  26.553  -5.931  1.00 38.29           C
ATOM   2262  CE   LYS A 294      -4.230  26.478  -5.717  1.00 38.96           C
ATOM   2263  NZ   LYS A 294      -4.933  27.428  -6.612  1.00 44.27           N
ATOM   2264  C    LYS A 294      -2.341  23.258  -9.319  1.00 26.09           C
ATOM   2265  O    LYS A 294      -3.114  22.394  -8.891  1.00 27.27           O
ATOM   2266  N    THR A 295      -2.352  23.679 -10.584  1.00 26.99           N
ATOM   2267  CA   THR A 295      -3.386  23.241 -11.526  1.00 29.22           C
ATOM   2268  CB   THR A 295      -3.355  24.053 -12.849  1.00 31.61           C
ATOM   2269  OG1  THR A 295      -2.082  23.897 -13.491  1.00 34.70           O
ATOM   2270  CG2  THR A 295      -3.453  25.544 -12.573  1.00 33.92           C
```

FIGURE 300

```
ATOM   2271  C   THR A 295      -3.350  21.742 -11.828  1.00 29.22           C
ATOM   2272  O   THR A 295      -4.350  21.181 -12.263  1.00 26.76           O
ATOM   2273  N   PHE A 296      -2.212  21.097 -11.575  1.00 24.19           N
ATOM   2274  CA  PHE A 296      -2.065  19.675 -11.864  1.00 25.40           C
ATOM   2275  CB  PHE A 296      -0.589  19.311 -12.083  1.00 24.15           C
ATOM   2276  CG  PHE A 296      -0.026  19.878 -13.349  1.00 25.84           C
ATOM   2277  CD1 PHE A 296      -0.218  19.224 -14.566  1.00 28.23           C
ATOM   2278  CE1 PHE A 296       0.284  19.759 -15.746  1.00 28.38           C
ATOM   2279  CZ  PHE A 296       0.981  20.968 -15.716  1.00 28.63           C
ATOM   2280  CE2 PHE A 296       1.165  21.631 -14.510  1.00 25.00           C
ATOM   2281  CD2 PHE A 296       0.660  21.091 -13.338  1.00 25.04           C
ATOM   2282  C   PHE A 296      -2.735  18.783 -10.819  1.00 23.20           C
ATOM   2283  O   PHE A 296      -2.760  17.563 -10.971  1.00 25.82           O
ATOM   2284  N   ASN A 297      -3.277  19.406  -9.772  1.00 25.09           N
ATOM   2285  CA  ASN A 297      -4.079  18.729  -8.747  1.00 27.46           C
ATOM   2286  CB BASN A 297      -5.472  18.366  -9.295  0.35 26.30           C
ATOM   2287  CB AASN A 297      -5.458  18.324  -9.302  0.65 31.74           C
ATOM   2288  CG BASN A 297      -6.516  18.220  -8.199  0.35 25.49           C
ATOM   2289  CG AASN A 297      -6.301  19.514  -9.709  0.65 36.04           C
ATOM   2290  OD1BASN A 297      -6.413  18.833  -7.136  0.35 27.01           O
ATOM   2291  OD1AASN A 297      -6.630  20.371  -8.888  0.65 36.86           O
ATOM   2292  ND2BASN A 297      -7.532  17.403  -8.457  0.35 25.03           N
ATOM   2293  ND2AASN A 297      -6.668  19.565 -10.986  0.65 38.33           N
ATOM   2294  C   ASN A 297      -3.382  17.507  -8.158  1.00 26.62           C
ATOM   2295  O   ASN A 297      -3.969  16.426  -8.041  1.00 27.10           O
ATOM   2296  N   LEU A 298      -2.108  17.679  -7.819  1.00 24.04           N
ATOM   2297  CA  LEU A 298      -1.347  16.633  -7.149  1.00 21.55           C
ATOM   2298  CB  LEU A 298      -0.031  16.365  -7.883  1.00 22.65           C
ATOM   2299  CG  LEU A 298      -0.185  15.710  -9.257  1.00 27.56           C
ATOM   2300  CD1 LEU A 298       1.133  15.741 -10.013  1.00 27.42           C
ATOM   2301  CD2 LEU A 298      -0.728  14.271  -9.114  1.00 25.31           C
ATOM   2302  C   LEU A 298      -1.061  17.071  -5.728  1.00 21.11           C
ATOM   2303  O   LEU A 298      -0.990  18.276  -5.472  1.00 22.86           O
ATOM   2304  N   PRO A 299      -0.910  16.111  -4.808  1.00 21.63           N
ATOM   2305  CA  PRO A 299      -0.465  16.421  -3.443  1.00 22.31           C
ATOM   2306  CB  PRO A 299      -0.137  15.049  -2.848  1.00 24.00           C
ATOM   2307  CG  PRO A 299      -0.931  14.053  -3.657  1.00 26.20           C
ATOM   2308  CD  PRO A 299      -1.166  14.671  -5.000  1.00 24.45           C
ATOM   2309  C   PRO A 299       0.798  17.266  -3.544  1.00 21.00           C
ATOM   2310  O   PRO A 299       1.714  16.888  -4.277  1.00 18.60           O
ATOM   2311  N   LEU A 300       0.822  18.399  -2.848  1.00 17.58           N
ATOM   2312  CA  LEU A 300       1.887  19.385  -3.026  1.00 17.59           C
ATOM   2313  CB  LEU A 300       1.346  20.580  -3.816  1.00 18.61           C
ATOM   2314  CG  LEU A 300       2.223  21.809  -4.072  1.00 21.05           C
ATOM   2315  CD1 LEU A 300       3.544  21.456  -4.782  1.00 19.32           C
ATOM   2316  CD2 LEU A 300       1.423  22.816  -4.887  1.00 23.02           C
ATOM   2317  C   LEU A 300       2.466  19.849  -1.691  1.00 17.37           C
ATOM   2318  O   LEU A 300       1.728  20.257  -0.794  1.00 18.03           O
ATOM   2319  N   LEU A 301       3.788  19.786  -1.575  1.00 15.41           N
ATOM   2320  CA  LEU A 301       4.491  20.330  -0.427  1.00 16.84           C
ATOM   2321  CB  LEU A 301       5.476  19.298   0.134  1.00 18.57           C
ATOM   2322  CG  LEU A 301       6.382  19.715   1.301  1.00 20.01           C
ATOM   2323  CD1 LEU A 301       5.572  20.042   2.564  1.00 17.00           C
ATOM   2324  CD2 LEU A 301       7.384  18.607   1.576  1.00 19.26           C
ATOM   2325  C   LEU A 301       5.220  21.589  -0.882  1.00 17.23           C
ATOM   2326  O   LEU A 301       6.066  21.531  -1.780  1.00 15.65           O
ATOM   2327  N   MET A 302       4.859  22.722  -0.285  1.00 15.68           N
```

FIGURE 3PP

```
ATOM   2328  CA   MET A 302       5.467  24.004  -0.621  1.00 18.04           C
ATOM   2329  CB   MET A 302       4.389  25.058  -0.853  1.00 16.95           C
ATOM   2330  CG   MET A 302       3.599  24.868  -2.124  1.00 24.30           C
ATOM   2331  SD   MET A 302       2.172  25.964  -2.085  1.00 34.45           S
ATOM   2332  CE   MET A 302       3.039  27.555  -2.079  1.00 18.28           C
ATOM   2333  C    MET A 302       6.409  24.458   0.486  1.00 14.71           C
ATOM   2334  O    MET A 302       6.025  24.556   1.657  1.00 16.36           O
ATOM   2335  N    LEU A 303       7.650  24.735   0.109  1.00 15.14           N
ATOM   2336  CA   LEU A 303       8.679  25.076   1.074  1.00 13.21           C
ATOM   2337  CB   LEU A 303       9.758  23.983   1.122  1.00 13.92           C
ATOM   2338  CG   LEU A 303       9.244  22.545   1.316  1.00 14.09           C
ATOM   2339  CD1  LEU A 303      10.369  21.551   1.048  1.00 17.23           C
ATOM   2340  CD2  LEU A 303       8.697  22.370   2.731  1.00 14.49           C
ATOM   2341  C    LEU A 303       9.310  26.413   0.735  1.00 13.53           C
ATOM   2342  O    LEU A 303       9.156  26.916  -0.381  1.00 15.22           O
ATOM   2343  N    GLY A 304      10.002  26.985   1.715  1.00 14.89           N
ATOM   2344  CA   GLY A 304      10.698  28.246   1.532  1.00 16.21           C
ATOM   2345  C    GLY A 304      12.052  28.036   0.877  1.00 18.29           C
ATOM   2346  O    GLY A 304      12.196  27.205  -0.024  1.00 19.36           O
ATOM   2347  N    GLY A 305      13.045  28.795   1.328  1.00 19.16           N
ATOM   2348  CA   GLY A 305      14.401  28.704   0.806  1.00 20.73           C
ATOM   2349  C    GLY A 305      15.105  30.030   1.003  1.00 21.04           C
ATOM   2350  O    GLY A 305      14.904  30.691   2.020  1.00 18.74           O
ATOM   2351  N    GLY A 306      15.919  30.427   0.030  1.00 17.08           N
ATOM   2352  CA   GLY A 306      16.608  31.708   0.096  1.00 18.20           C
ATOM   2353  C    GLY A 306      15.658  32.897   0.071  1.00 19.52           C
ATOM   2354  O    GLY A 306      14.465  32.758  -0.198  1.00 21.40           O
ATOM   2355  N    GLY A 307      16.194  34.078   0.358  1.00 19.00           N
ATOM   2356  CA   GLY A 307      15.407  35.292   0.355  1.00 15.92           C
ATOM   2357  C    GLY A 307      16.006  36.220   1.392  1.00 16.42           C
ATOM   2358  O    GLY A 307      15.967  35.918   2.589  1.00 15.69           O
ATOM   2359  N    TYR A 308      16.568  37.335   0.931  1.00 17.62           N
ATOM   2360  CA   TYR A 308      17.451  38.164   1.777  1.00 14.95           C
ATOM   2361  CB   TYR A 308      18.922  37.973   1.351  1.00 19.46           C
ATOM   2362  CG   TYR A 308      19.235  36.506   1.309  1.00 17.69           C
ATOM   2363  CD1  TYR A 308      19.202  35.799   0.106  1.00 20.53           C
ATOM   2364  CE1  TYR A 308      19.435  34.426   0.083  1.00 20.77           C
ATOM   2365  CZ   TYR A 308      19.671  33.760   1.273  1.00 19.18           C
ATOM   2366  OH   TYR A 308      19.894  32.404   1.288  1.00 19.96           O
ATOM   2367  CE2  TYR A 308      19.685  34.441   2.473  1.00 21.66           C
ATOM   2368  CD2  TYR A 308      19.460  35.802   2.484  1.00 17.80           C
ATOM   2369  C    TYR A 308      17.057  39.636   1.862  1.00 20.28           C
ATOM   2370  O    TYR A 308      17.656  40.405   2.610  1.00 19.45           O
ATOM   2371  N    THR A 309      16.045  40.025   1.103  1.00 17.89           N
ATOM   2372  CA   THR A 309      15.403  41.320   1.311  1.00 17.30           C
ATOM   2373  CB   THR A 309      15.205  42.034  -0.026  1.00 17.32           C
ATOM   2374  OG1  THR A 309      16.497  42.351  -0.560  1.00 19.88           O
ATOM   2375  CG2  THR A 309      14.551  43.401   0.164  1.00 16.71           C
ATOM   2376  C    THR A 309      14.097  40.969   2.000  1.00 16.23           C
ATOM   2377  O    THR A 309      13.120  40.610   1.348  1.00 17.53           O
ATOM   2378  N    ILE A 310      14.101  41.029   3.328  1.00 16.67           N
ATOM   2379  CA   ILE A 310      13.076  40.306   4.082  1.00 15.50           C
ATOM   2380  CB   ILE A 310      13.515  40.012   5.540  1.00 20.65           C
ATOM   2381  CG1  ILE A 310      13.753  41.306   6.331  1.00 21.95           C
ATOM   2382  CD1  ILE A 310      14.146  41.072   7.801  1.00 23.95           C
ATOM   2383  CG2  ILE A 310      14.786  39.147   5.523  1.00 24.23           C
ATOM   2384  C    ILE A 310      11.664  40.859   3.955  1.00 14.90           C
```

FIGURE 3QQ

```
ATOM   2385  O    ILE A 310     10.702  40.108   4.077  1.00  17.74           O
ATOM   2386  N    ARG A 311     11.526  42.155   3.676  1.00  15.56           N
ATOM   2387  CA   ARG A 311     10.202  42.692   3.373  1.00  15.31           C
ATOM   2388  CB   ARG A 311     10.221  44.221   3.203  1.00  18.73           C
ATOM   2389  CG   ARG A 311     11.045  44.729   2.025  1.00  19.66           C
ATOM   2390  CD   ARG A 311     11.215  46.242   2.002  1.00  19.64           C
ATOM   2391  NE   ARG A 311     11.984  46.663   0.834  1.00  24.45           N
ATOM   2392  CZ   ARG A 311     13.308  46.759   0.803  1.00  26.23           C
ATOM   2393  NH1  ARG A 311     13.915  47.139  -0.313  1.00  29.95           N
ATOM   2394  NH2  ARG A 311     14.029  46.486   1.885  1.00  29.19           N
ATOM   2395  C    ARG A 311      9.611  42.006   2.133  1.00  19.24           C
ATOM   2396  O    ARG A 311      8.421  41.731   2.081  1.00  17.02           O
ATOM   2397  N    ASN A 312     10.450  41.706   1.146  1.00  14.90           N
ATOM   2398  CA   ASN A 312      9.938  41.084  -0.073  1.00  17.77           C
ATOM   2399  CB   ASN A 312     10.857  41.381  -1.253  1.00  17.73           C
ATOM   2400  CG   ASN A 312     10.862  42.860  -1.617  1.00  19.08           C
ATOM   2401  OD1  ASN A 312      9.905  43.587  -1.328  1.00  20.36           O
ATOM   2402  ND2  ASN A 312     11.936  43.310  -2.254  1.00  19.11           N
ATOM   2403  C    ASN A 312      9.696  39.591   0.086  1.00  15.53           C
ATOM   2404  O    ASN A 312      8.828  39.026  -0.588  1.00  15.71           O
ATOM   2405  N    VAL A 313     10.470  38.964   0.972  1.00  16.92           N
ATOM   2406  CA   VAL A 313     10.248  37.564   1.335  1.00  14.92           C
ATOM   2407  CB   VAL A 313     11.336  37.047   2.302  1.00  16.71           C
ATOM   2408  CG1  VAL A 313     11.073  35.606   2.697  1.00  20.63           C
ATOM   2409  CG2  VAL A 313     12.715  37.165   1.683  1.00  15.17           C
ATOM   2410  C    VAL A 313      8.858  37.424   1.958  1.00  15.55           C
ATOM   2411  O    VAL A 313      8.058  36.575   1.546  1.00  15.59           O
ATOM   2412  N    ALA A 314      8.569  38.281   2.937  1.00  14.21           N
ATOM   2413  CA   ALA A 314      7.271  38.284   3.610  1.00  15.47           C
ATOM   2414  CB   ALA A 314      7.252  39.358   4.718  1.00  12.66           C
ATOM   2415  C    ALA A 314      6.107  38.475   2.629  1.00  16.75           C
ATOM   2416  O    ALA A 314      5.104  37.764   2.700  1.00  14.92           O
ATOM   2417  N    ARG A 315      6.254  39.422   1.706  1.00  13.66           N
ATOM   2418  CA   ARG A 315      5.238  39.673   0.685  1.00  15.79           C
ATOM   2419  CB   ARG A 315      5.667  40.828  -0.229  1.00  14.83           C
ATOM   2420  CG   ARG A 315      5.695  42.207   0.414  1.00  14.92           C
ATOM   2421  CD   ARG A 315      6.417  43.239  -0.433  1.00  18.36           C
ATOM   2422  NE   ARG A 315      5.953  44.589  -0.125  1.00  19.80           N
ATOM   2423  CZ   ARG A 315      6.741  45.603   0.198  1.00  22.16           C
ATOM   2424  NH1  ARG A 315      6.199  46.786   0.478  1.00  20.79           N
ATOM   2425  NH2  ARG A 315      8.062  45.449   0.249  1.00  19.49           N
ATOM   2426  C    ARG A 315      5.034  38.444  -0.194  1.00  14.58           C
ATOM   2427  O    ARG A 315      3.910  38.038  -0.463  1.00  16.44           O
ATOM   2428  N    CYS A 316      6.145  37.883  -0.657  1.00  11.83           N
ATOM   2429  CA   CYS A 316      6.122  36.771  -1.602  1.00  14.91           C
ATOM   2430  CB   CYS A 316      7.554  36.426  -2.004  1.00  16.47           C
ATOM   2431  SG   CYS A 316      7.689  35.273  -3.381  1.00  19.01           S
ATOM   2432  C    CYS A 316      5.429  35.549  -1.005  1.00  15.14           C
ATOM   2433  O    CYS A 316      4.530  34.969  -1.613  1.00  15.78           O
ATOM   2434  N    TRP A 317      5.837  35.174   0.198  1.00  12.13           N
ATOM   2435  CA   TRP A 317      5.305  33.964   0.814  1.00  12.79           C
ATOM   2436  CB   TRP A 317      6.281  33.421   1.854  1.00  11.60           C
ATOM   2437  CG   TRP A 317      7.532  32.867   1.228  1.00  15.48           C
ATOM   2438  CD1  TRP A 317      7.714  32.524  -0.091  1.00  14.60           C
ATOM   2439  NE1  TRP A 317      8.992  32.052  -0.286  1.00  15.24           N
ATOM   2440  CE2  TRP A 317      9.659  32.075   0.912  1.00  14.69           C
ATOM   2441  CD2  TRP A 317      8.768  32.584   1.885  1.00  15.39           C
```

FIGURE 3RR

| | | | | | | | | | |
|---|---|---|---|---|---|---|---|---|---|
| ATOM | 2442 | CE3 | TRP A 317 | 9.220 | 32.700 | 3.210 | 1.00 | 15.90 | C |
| ATOM | 2443 | CZ3 | TRP A 317 | 10.532 | 32.311 | 3.510 | 1.00 | 16.00 | C |
| ATOM | 2444 | CH2 | TRP A 317 | 11.387 | 31.823 | 2.515 | 1.00 | 16.28 | C |
| ATOM | 2445 | CZ2 | TRP A 317 | 10.973 | 31.696 | 1.216 | 1.00 | 15.73 | C |
| ATOM | 2446 | C | TRP A 317 | 3.885 | 34.150 | 1.352 | 1.00 | 18.05 | C |
| ATOM | 2447 | O | TRP A 317 | 3.109 | 33.196 | 1.397 | 1.00 | 14.92 | O |
| ATOM | 2448 | N | THR A 318 | 3.533 | 35.381 | 1.724 | 1.00 | 13.33 | N |
| ATOM | 2449 | CA | THR A 318 | 2.143 | 35.684 | 2.072 | 1.00 | 12.98 | C |
| ATOM | 2450 | CB | THR A 318 | 2.029 | 37.117 | 2.632 | 1.00 | 17.01 | C |
| ATOM | 2451 | OG1 | THR A 318 | 2.661 | 37.171 | 3.918 | 1.00 | 16.66 | O |
| ATOM | 2452 | CG2 | THR A 318 | 0.579 | 37.480 | 2.930 | 1.00 | 19.95 | C |
| ATOM | 2453 | C | THR A 318 | 1.242 | 35.506 | 0.840 | 1.00 | 14.23 | C |
| ATOM | 2454 | O | THR A 318 | 0.195 | 34.850 | 0.904 | 1.00 | 16.36 | O |
| ATOM | 2455 | N | TYR A 319 | 1.661 | 36.088 | -0.277 | 1.00 | 15.42 | N |
| ATOM | 2456 | CA | TYR A 319 | 0.881 | 36.009 | -1.507 | 1.00 | 17.96 | C |
| ATOM | 2457 | CB | TYR A 319 | 1.456 | 36.921 | -2.582 | 1.00 | 16.59 | C |
| ATOM | 2458 | CG | TYR A 319 | 0.561 | 37.044 | -3.793 | 1.00 | 19.29 | C |
| ATOM | 2459 | CD1 | TYR A 319 | -0.731 | 37.564 | -3.683 | 1.00 | 21.38 | C |
| ATOM | 2460 | CE1 | TYR A 319 | -1.565 | 37.667 | -4.799 | 1.00 | 25.09 | C |
| ATOM | 2461 | CZ | TYR A 319 | -1.103 | 37.239 | -6.028 | 1.00 | 26.19 | C |
| ATOM | 2462 | OH | TYR A 319 | -1.914 | 37.338 | -7.136 | 1.00 | 29.55 | O |
| ATOM | 2463 | CE2 | TYR A 319 | 0.172 | 36.716 | -6.158 | 1.00 | 24.01 | C |
| ATOM | 2464 | CD2 | TYR A 319 | 0.993 | 36.614 | -5.044 | 1.00 | 20.66 | C |
| ATOM | 2465 | C | TYR A 319 | 0.784 | 34.567 | -2.006 | 1.00 | 18.47 | C |
| ATOM | 2466 | O | TYR A 319 | -0.275 | 34.129 | -2.444 | 1.00 | 17.21 | O |
| ATOM | 2467 | N | GLU A 320 | 1.875 | 33.820 | -1.884 | 1.00 | 18.09 | N |
| ATOM | 2468 | CA | GLU A 320 | 1.882 | 32.423 | -2.328 | 1.00 | 17.91 | C |
| ATOM | 2469 | CB | GLU A 320 | 3.321 | 31.917 | -2.503 | 1.00 | 16.67 | C |
| ATOM | 2470 | CG | GLU A 320 | 3.909 | 32.618 | -3.718 | 1.00 | 16.41 | C |
| ATOM | 2471 | CD | GLU A 320 | 5.366 | 32.358 | -4.008 | 1.00 | 20.32 | C |
| ATOM | 2472 | OE1 | GLU A 320 | 6.125 | 31.939 | -3.116 | 1.00 | 21.09 | O |
| ATOM | 2473 | OE2 | GLU A 320 | 5.746 | 32.613 | -5.168 | 1.00 | 23.67 | O |
| ATOM | 2474 | C | GLU A 320 | 1.009 | 31.518 | -1.462 | 1.00 | 17.98 | C |
| ATOM | 2475 | O | GLU A 320 | 0.423 | 30.553 | -1.958 | 1.00 | 16.96 | O |
| ATOM | 2476 | N | THR A 321 | 0.896 | 31.853 | -0.182 | 1.00 | 15.23 | N |
| ATOM | 2477 | CA | THR A 321 | -0.067 | 31.200 | 0.697 | 1.00 | 18.07 | C |
| ATOM | 2478 | CB | THR A 321 | 0.129 | 31.672 | 2.144 | 1.00 | 19.69 | C |
| ATOM | 2479 | OG1 | THR A 321 | 1.483 | 31.429 | 2.551 | 1.00 | 20.60 | O |
| ATOM | 2480 | CG2 | THR A 321 | -0.696 | 30.820 | 3.097 | 1.00 | 17.93 | C |
| ATOM | 2481 | C | THR A 321 | -1.502 | 31.497 | 0.225 | 1.00 | 18.74 | C |
| ATOM | 2482 | O | THR A 321 | -2.335 | 30.587 | 0.103 | 1.00 | 18.53 | O |
| ATOM | 2483 | N | ALA A 322 | -1.776 | 32.770 | -0.044 | 1.00 | 15.67 | N |
| ATOM | 2484 | CA | ALA A 322 | -3.073 | 33.188 | -0.577 | 1.00 | 17.52 | C |
| ATOM | 2485 | CB | ALA A 322 | -3.133 | 34.706 | -0.693 | 1.00 | 18.65 | C |
| ATOM | 2486 | C | ALA A 322 | -3.388 | 32.510 | -1.923 | 1.00 | 18.13 | C |
| ATOM | 2487 | O | ALA A 322 | -4.531 | 32.122 | -2.171 | 1.00 | 22.33 | O |
| ATOM | 2488 | N | VAL A 323 | -2.368 | 32.354 | -2.769 | 1.00 | 17.72 | N |
| ATOM | 2489 | CA | VAL A 323 | -2.489 | 31.607 | -4.031 | 1.00 | 21.30 | C |
| ATOM | 2490 | CB | VAL A 323 | -1.199 | 31.713 | -4.903 | 1.00 | 19.86 | C |
| ATOM | 2491 | CG1 | VAL A 323 | -1.216 | 30.708 | -6.060 | 1.00 | 19.69 | C |
| ATOM | 2492 | CG2 | VAL A 323 | -1.039 | 33.134 | -5.448 | 1.00 | 20.19 | C |
| ATOM | 2493 | C | VAL A 323 | -2.869 | 30.143 | -3.774 | 1.00 | 19.47 | C |
| ATOM | 2494 | O | VAL A 323 | -3.774 | 29.610 | -4.426 | 1.00 | 20.19 | O |
| ATOM | 2495 | N | ALA A 324 | -2.203 | 29.511 | -2.809 | 1.00 | 16.79 | N |
| ATOM | 2496 | CA | ALA A 324 | -2.512 | 28.133 | -2.428 | 1.00 | 21.38 | C |
| ATOM | 2497 | CB | ALA A 324 | -1.594 | 27.670 | -1.312 | 1.00 | 21.34 | C |
| ATOM | 2498 | C | ALA A 324 | -3.973 | 27.992 | -1.996 | 1.00 | 22.64 | C |

FIGURE 3SS

```
ATOM   2499  O    ALA A 324      -4.610   26.971   -2.258  1.00 22.66           O
ATOM   2500  N    LEU A 325      -4.488   29.030   -1.342  1.00 20.95           N
ATOM   2501  CA   LEU A 325      -5.848   29.037   -0.809  1.00 22.35           C
ATOM   2502  CB   LEU A 325      -5.906   29.903    0.459  1.00 20.30           C
ATOM   2503  CG   LEU A 325      -5.173   29.415    1.712  1.00 21.72           C
ATOM   2504  CD1  LEU A 325      -4.975   30.571    2.686  1.00 22.94           C
ATOM   2505  CD2  LEU A 325      -5.938   28.273    2.371  1.00 27.72           C
ATOM   2506  C    LEU A 325      -6.885   29.543   -1.811  1.00 25.97           C
ATOM   2507  O    LEU A 325      -8.085   29.527   -1.518  1.00 27.53           O
ATOM   2508  N    ASP A 326      -6.415   29.984   -2.979  1.00 25.12           N
ATOM   2509  CA   ASP A 326      -7.236   30.658   -3.996  1.00 27.86           C
ATOM   2510  CB   ASP A 326      -8.202   29.677   -4.661  1.00 30.06           C
ATOM   2511  CG   ASP A 326      -7.508   28.767   -5.633  1.00 30.53           C
ATOM   2512  OD1  ASP A 326      -7.379   27.562   -5.333  1.00 32.21           O
ATOM   2513  OD2  ASP A 326      -7.041   29.175   -6.716  1.00 36.90           O
ATOM   2514  C    ASP A 326      -7.990   31.848   -3.417  1.00 31.17           C
ATOM   2515  O    ASP A 326      -9.166   32.072   -3.722  1.00 30.83           O
ATOM   2516  N    CYS A 327      -7.295   32.607   -2.578  1.00 29.52           N
ATOM   2517  CA   CYS A 327      -7.897   33.718   -1.861  1.00 32.25           C
ATOM   2518  CB   CYS A 327      -7.704   33.526   -0.350  1.00 35.59           C
ATOM   2519  SG   CYS A 327      -8.381   34.836    0.688  1.00 44.40           S
ATOM   2520  C    CYS A 327      -7.276   35.020   -2.348  1.00 36.43           C
ATOM   2521  O    CYS A 327      -6.069   35.247   -2.194  1.00 34.18           O
ATOM   2522  N    GLU A 328      -8.101   35.856   -2.976  1.00 34.43           N
ATOM   2523  CA   GLU A 328      -7.666   37.170   -3.421  1.00 38.24           C
ATOM   2524  CB   GLU A 328      -8.703   37.799   -4.354  1.00 46.35           C
ATOM   2525  CG   GLU A 328      -8.635   37.326   -5.796  1.00 55.57           C
ATOM   2526  CD   GLU A 328      -9.974   37.436   -6.508  1.00 61.43           C
ATOM   2527  OE1  GLU A 328     -10.386   38.570   -6.844  1.00 62.00           O
ATOM   2528  OE2  GLU A 328     -10.616   36.387   -6.732  1.00 64.79           O
ATOM   2529  C    GLU A 328      -7.483   38.048   -2.192  1.00 36.90           C
ATOM   2530  O    GLU A 328      -8.394   38.164   -1.365  1.00 34.82           O
ATOM   2531  N    ILE A 329      -6.301   38.639   -2.055  1.00 29.58           N
ATOM   2532  CA   ILE A 329      -6.047   39.575   -0.963  1.00 28.65           C
ATOM   2533  CB   ILE A 329      -4.948   39.046    0.010  1.00 24.52           C
ATOM   2534  CG1  ILE A 329      -3.641   38.714   -0.725  1.00 22.15           C
ATOM   2535  CD1  ILE A 329      -2.472   38.398    0.224  1.00 21.80           C
ATOM   2536  CG2  ILE A 329      -5.486   37.855    0.815  1.00 28.06           C
ATOM   2537  C    ILE A 329      -5.707   40.960   -1.508  1.00 24.70           C
ATOM   2538  O    ILE A 329      -5.108   41.064   -2.582  1.00 26.56           O
ATOM   2539  N    PRO A 330      -6.104   42.017   -0.789  1.00 26.09           N
ATOM   2540  CA   PRO A 330      -5.852   43.394   -1.241  1.00 24.62           C
ATOM   2541  CB   PRO A 330      -6.513   44.276   -0.162  1.00 24.43           C
ATOM   2542  CG   PRO A 330      -7.058   43.384    0.873  1.00 26.00           C
ATOM   2543  CD   PRO A 330      -6.846   41.967    0.484  1.00 24.77           C
ATOM   2544  C    PRO A 330      -4.368   43.733   -1.344  1.00 26.85           C
ATOM   2545  O    PRO A 330      -3.545   43.201   -0.595  1.00 24.09           O
ATOM   2546  N    ASN A 331      -4.044   44.621   -2.275  1.00 22.23           N
ATOM   2547  CA   ASN A 331      -2.678   45.100   -2.444  1.00 24.07           C
ATOM   2548  CB   ASN A 331      -2.532   45.859   -3.765  1.00 22.95           C
ATOM   2549  CG   ASN A 331      -1.079   46.141   -4.126  1.00 25.02           C
ATOM   2550  OD1  ASN A 331      -0.182   45.333   -3.858  1.00 23.98           O
ATOM   2551  ND2  ASN A 331      -0.841   47.292   -4.741  1.00 27.18           N
ATOM   2552  C    ASN A 331      -2.258   45.980   -1.273  1.00 23.16           C
ATOM   2553  O    ASN A 331      -1.094   45.995   -0.892  1.00 22.84           O
ATOM   2554  N    GLU A 332      -3.216   46.701   -0.695  1.00 24.58           N
ATOM   2555  CA   GLU A 332      -2.941   47.540    0.471  1.00 24.60           C
```

FIGURE 3TT

```
ATOM   2556  CB   GLU A 332      -4.137  48.461   0.756  1.00 30.07           C
ATOM   2557  CG   GLU A 332      -4.028  49.278   2.039  1.00 40.95           C
ATOM   2558  CD   GLU A 332      -3.246  50.576   1.872  1.00 47.94           C
ATOM   2559  OE1  GLU A 332      -2.804  50.888   0.740  1.00 51.17           O
ATOM   2560  OE2  GLU A 332      -3.074  51.293   2.884  1.00 47.40           O
ATOM   2561  C    GLU A 332      -2.646  46.629   1.662  1.00 20.10           C
ATOM   2562  O    GLU A 332      -3.490  45.817   2.042  1.00 18.10           O
ATOM   2563  N    LEU A 333      -1.443  46.741   2.230  1.00 19.40           N
ATOM   2564  CA   LEU A 333      -1.069  45.895   3.374  1.00 20.17           C
ATOM   2565  CB   LEU A 333       0.418  46.020   3.705  1.00 20.71           C
ATOM   2566  CG   LEU A 333       1.448  45.487   2.715  1.00 21.40           C
ATOM   2567  CD1  LEU A 333       2.807  45.878   3.211  1.00 20.37           C
ATOM   2568  CD2  LEU A 333       1.373  43.972   2.547  1.00 18.52           C
ATOM   2569  C    LEU A 333      -1.875  46.233   4.621  1.00 21.83           C
ATOM   2570  O    LEU A 333      -2.099  47.414   4.913  1.00 18.82           O
ATOM   2571  N    PRO A 334      -2.313  45.213   5.361  1.00 22.61           N
ATOM   2572  CA   PRO A 334      -2.968  45.459   6.644  1.00 20.85           C
ATOM   2573  CB   PRO A 334      -3.535  44.089   7.021  1.00 22.66           C
ATOM   2574  CG   PRO A 334      -2.587  43.109   6.374  1.00 23.31           C
ATOM   2575  CD   PRO A 334      -2.209  43.771   5.062  1.00 20.74           C
ATOM   2576  C    PRO A 334      -1.907  45.875   7.645  1.00 18.84           C
ATOM   2577  O    PRO A 334      -0.738  45.535   7.470  1.00 17.25           O
ATOM   2578  N    TYR A 335      -2.302  46.594   8.691  1.00 19.45           N
ATOM   2579  CA   TYR A 335      -1.380  46.858   9.773  1.00 17.47           C
ATOM   2580  CB   TYR A 335      -2.017  47.724  10.864  1.00 20.62           C
ATOM   2581  CG   TYR A 335      -0.991  48.141  11.882  1.00 20.65           C
ATOM   2582  CD1  TYR A 335      -0.922  47.517  13.120  1.00 22.70           C
ATOM   2583  CE1  TYR A 335       0.049  47.873  14.049  1.00 25.15           C
ATOM   2584  CZ   TYR A 335       0.969  48.852  13.733  1.00 23.26           C
ATOM   2585  OH   TYR A 335       1.936  49.209  14.649  1.00 26.39           O
ATOM   2586  CE2  TYR A 335       0.932  49.479  12.500  1.00 25.52           C
ATOM   2587  CD2  TYR A 335      -0.040  49.113  11.577  1.00 20.57           C
ATOM   2588  C    TYR A 335      -0.863  45.530  10.347  1.00 18.95           C
ATOM   2589  O    TYR A 335      -1.585  44.535  10.387  1.00 19.32           O
ATOM   2590  N    ASN A 336       0.401  45.517  10.745  1.00 18.97           N
ATOM   2591  CA   ASN A 336       1.039  44.323  11.297  1.00 18.38           C
ATOM   2592  CB   ASN A 336       1.473  43.369  10.163  1.00 17.29           C
ATOM   2593  CG   ASN A 336       2.480  43.999   9.221  1.00 19.41           C
ATOM   2594  OD1  ASN A 336       3.679  43.964   9.473  1.00 19.73           O
ATOM   2595  ND2  ASN A 336       1.996  44.578   8.130  1.00 19.89           N
ATOM   2596  C    ASN A 336       2.229  44.721  12.177  1.00 20.27           C
ATOM   2597  O    ASN A 336       2.611  45.895  12.215  1.00 18.23           O
ATOM   2598  N    ASP A 337       2.810  43.751  12.882  1.00 16.96           N
ATOM   2599  CA   ASP A 337       3.905  44.018  13.826  1.00 20.61           C
ATOM   2600  CB   ASP A 337       4.242  42.752  14.624  1.00 21.73           C
ATOM   2601  CG   ASP A 337       3.253  42.482  15.740  1.00 30.64           C
ATOM   2602  OD1  ASP A 337       2.347  43.314  15.965  1.00 30.84           O
ATOM   2603  OD2  ASP A 337       3.309  41.459  16.452  1.00 35.21           O
ATOM   2604  C    ASP A 337       5.180  44.548  13.168  1.00 19.90           C
ATOM   2605  O    ASP A 337       6.077  45.047  13.849  1.00 19.36           O
ATOM   2606  N    TYR A 338       5.253  44.434  11.846  1.00 19.12           N
ATOM   2607  CA   TYR A 338       6.452  44.783  11.096  1.00 18.90           C
ATOM   2608  CB   TYR A 338       7.070  43.512  10.497  1.00 20.47           C
ATOM   2609  CG   TYR A 338       7.354  42.487  11.560  1.00 24.05           C
ATOM   2610  CD1  TYR A 338       6.495  41.407  11.766  1.00 23.90           C
ATOM   2611  CE1  TYR A 338       6.747  40.470  12.763  1.00 24.65           C
ATOM   2612  CZ   TYR A 338       7.863  40.623  13.567  1.00 28.97           C
```

FIGURE 3UU

| | | | | | | | | | |
|---|---|---|---|---|---|---|---|---|---|
| ATOM | 2613 | OH | TYR | A 338 | 8.143 | 39.712 | 14.557 | 1.00 31.47 | O |
| ATOM | 2614 | CE2 | TYR | A 338 | 8.720 | 41.697 | 13.391 | 1.00 31.27 | C |
| ATOM | 2615 | CD2 | TYR | A 338 | 8.463 | 42.619 | 12.390 | 1.00 28.08 | C |
| ATOM | 2616 | C | TYR | A 338 | 6.140 | 45.797 | 10.007 | 1.00 17.36 | C |
| ATOM | 2617 | O | TYR | A 338 | 6.884 | 45.916 | 9.034 | 1.00 18.26 | O |
| ATOM | 2618 | N | PHE | A 339 | 5.051 | 46.543 | 10.201 | 1.00 15.77 | N |
| ATOM | 2619 | CA | PHE | A 339 | 4.530 | 47.469 | 9.199 | 1.00 16.64 | C |
| ATOM | 2620 | CB | PHE | A 339 | 3.370 | 48.291 | 9.786 | 1.00 18.97 | C |
| ATOM | 2621 | CG | PHE | A 339 | 2.498 | 48.950 | 8.747 | 1.00 20.81 | C |
| ATOM | 2622 | CD1 | PHE | A 339 | 2.461 | 50.336 | 8.635 | 1.00 17.50 | C |
| ATOM | 2623 | CE1 | PHE | A 339 | 1.656 | 50.953 | 7.689 | 1.00 17.50 | C |
| ATOM | 2624 | CZ | PHE | A 339 | 0.867 | 50.190 | 6.829 | 1.00 19.43 | C |
| ATOM | 2625 | CE2 | PHE | A 339 | 0.893 | 48.804 | 6.924 | 1.00 18.38 | C |
| ATOM | 2626 | CD2 | PHE | A 339 | 1.708 | 48.188 | 7.884 | 1.00 17.46 | C |
| ATOM | 2627 | C | PHE | A 339 | 5.592 | 48.393 | 8.608 | 1.00 18.46 | C |
| ATOM | 2628 | O | PHE | A 339 | 5.572 | 48.663 | 7.409 | 1.00 19.75 | O |
| ATOM | 2629 | N | GLU | A 340 | 6.521 | 48.859 | 9.444 | 1.00 17.11 | N |
| ATOM | 2630 | CA | GLU | A 340 | 7.569 | 49.793 | 9.013 | 1.00 20.80 | C |
| ATOM | 2631 | CB | GLU | A 340 | 8.310 | 50.366 | 10.233 | 1.00 21.99 | C |
| ATOM | 2632 | CG | GLU | A 340 | 9.292 | 49.410 | 10.905 | 1.00 24.24 | C |
| ATOM | 2633 | CD | GLU | A 340 | 8.662 | 48.489 | 11.948 | 1.00 28.00 | C |
| ATOM | 2634 | OE1 | GLU | A 340 | 7.425 | 48.272 | 11.942 | 1.00 25.13 | O |
| ATOM | 2635 | OE2 | GLU | A 340 | 9.421 | 47.970 | 12.791 | 1.00 27.42 | O |
| ATOM | 2636 | C | GLU | A 340 | 8.568 | 49.203 | 8.000 | 1.00 19.31 | C |
| ATOM | 2637 | O | GLU | A 340 | 9.215 | 49.942 | 7.248 | 1.00 19.06 | O |
| ATOM | 2638 | N | TYR | A 341 | 8.700 | 47.879 | 7.996 | 1.00 19.00 | N |
| ATOM | 2639 | CA | TYR | A 341 | 9.561 | 47.195 | 7.034 | 1.00 20.65 | C |
| ATOM | 2640 | CB | TYR | A 341 | 9.691 | 45.707 | 7.390 | 1.00 21.48 | C |
| ATOM | 2641 | CG | TYR | A 341 | 10.606 | 45.396 | 8.556 | 1.00 26.26 | C |
| ATOM | 2642 | CD1 | TYR | A 341 | 10.228 | 45.698 | 9.865 | 1.00 26.93 | C |
| ATOM | 2643 | CE1 | TYR | A 341 | 11.051 | 45.402 | 10.941 | 1.00 31.95 | C |
| ATOM | 2644 | CZ | TYR | A 341 | 12.267 | 44.777 | 10.724 | 1.00 35.99 | C |
| ATOM | 2645 | OH | TYR | A 341 | 13.073 | 44.492 | 11.806 | 1.00 40.28 | O |
| ATOM | 2646 | CE2 | TYR | A 341 | 12.669 | 44.449 | 9.436 | 1.00 35.69 | C |
| ATOM | 2647 | CD2 | TYR | A 341 | 11.833 | 44.754 | 8.357 | 1.00 32.67 | C |
| ATOM | 2648 | C | TYR | A 341 | 9.038 | 47.333 | 5.600 | 1.00 18.89 | C |
| ATOM | 2649 | O | TYR | A 341 | 9.794 | 47.169 | 4.649 | 1.00 18.54 | O |
| ATOM | 2650 | N | PHE | A 342 | 7.752 | 47.645 | 5.449 | 1.00 17.23 | N |
| ATOM | 2651 | CA | PHE | A 342 | 7.106 | 47.618 | 4.136 | 1.00 19.66 | C |
| ATOM | 2652 | CB | PHE | A 342 | 5.754 | 46.916 | 4.219 | 1.00 18.65 | C |
| ATOM | 2653 | CG | PHE | A 342 | 5.842 | 45.520 | 4.747 | 1.00 19.44 | C |
| ATOM | 2654 | CD1 | PHE | A 342 | 5.526 | 45.244 | 6.077 | 1.00 18.93 | C |
| ATOM | 2655 | CE1 | PHE | A 342 | 5.624 | 43.941 | 6.580 | 1.00 17.64 | C |
| ATOM | 2656 | CZ | PHE | A 342 | 6.031 | 42.896 | 5.738 | 1.00 17.63 | C |
| ATOM | 2657 | CE2 | PHE | A 342 | 6.348 | 43.162 | 4.407 | 1.00 17.86 | C |
| ATOM | 2658 | CD2 | PHE | A 342 | 6.254 | 44.472 | 3.916 | 1.00 18.76 | C |
| ATOM | 2659 | C | PHE | A 342 | 6.966 | 48.982 | 3.467 | 1.00 20.45 | C |
| ATOM | 2660 | O | PHE | A 342 | 6.323 | 49.101 | 2.423 | 1.00 21.45 | O |
| ATOM | 2661 | N | GLY | A 343 | 7.579 | 50.001 | 4.059 | 1.00 21.30 | N |
| ATOM | 2662 | CA | GLY | A 343 | 7.641 | 51.313 | 3.434 | 1.00 21.86 | C |
| ATOM | 2663 | C | GLY | A 343 | 8.605 | 51.309 | 2.255 | 1.00 22.99 | C |
| ATOM | 2664 | O | GLY | A 343 | 9.386 | 50.367 | 2.111 | 1.00 23.25 | O |
| ATOM | 2665 | N | PRO | A 344 | 8.584 | 52.354 | 1.428 | 1.00 24.95 | N |
| ATOM | 2666 | CA | PRO | A 344 | 7.714 | 53.530 | 1.612 | 1.00 27.61 | C |
| ATOM | 2667 | CB | PRO | A 344 | 8.443 | 54.613 | 0.809 | 1.00 28.17 | C |
| ATOM | 2668 | CG | PRO | A 344 | 9.119 | 53.854 | -0.304 | 1.00 28.28 | C |
| ATOM | 2669 | CD | PRO | A 344 | 9.464 | 52.495 | 0.250 | 1.00 26.01 | C |

FIGURE 3VV

```
ATOM   2670  C    PRO A 344       6.287  53.383   1.077  1.00  28.17           C
ATOM   2671  O    PRO A 344       5.483  54.297   1.258  1.00  33.00           O
ATOM   2672  N    ASP A 345       5.982  52.254   0.443  1.00  26.00           N
ATOM   2673  CA   ASP A 345       4.713  52.072  -0.259  1.00  26.27           C
ATOM   2674  CB   ASP A 345       4.953  51.280  -1.545  1.00  25.27           C
ATOM   2675  CG   ASP A 345       5.642  49.965  -1.281  1.00  26.12           C
ATOM   2676  OD1  ASP A 345       6.864  49.981  -1.020  1.00  27.45           O
ATOM   2677  OD2  ASP A 345       5.028  48.876  -1.258  1.00  24.52           O
ATOM   2678  C    ASP A 345       3.617  51.387   0.563  1.00  23.18           C
ATOM   2679  O    ASP A 345       2.436  51.670   0.367  1.00  24.72           O
ATOM   2680  N    PHE A 346       4.006  50.481   1.461  1.00  19.75           N
ATOM   2681  CA   PHE A 346       3.063  49.669   2.248  1.00  19.35           C
ATOM   2682  CB   PHE A 346       2.383  50.504   3.351  1.00  23.34           C
ATOM   2683  CG   PHE A 346       3.351  51.338   4.143  1.00  20.31           C
ATOM   2684  CD1  PHE A 346       3.528  52.687   3.851  1.00  22.21           C
ATOM   2685  CE1  PHE A 346       4.452  53.458   4.564  1.00  21.26           C
ATOM   2686  CZ   PHE A 346       5.202  52.881   5.575  1.00  20.06           C
ATOM   2687  CE2  PHE A 346       5.045  51.528   5.870  1.00  19.62           C
ATOM   2688  CD2  PHE A 346       4.125  50.764   5.150  1.00  19.13           C
ATOM   2689  C    PHE A 346       2.052  48.914   1.380  1.00  20.13           C
ATOM   2690  O    PHE A 346       0.876  48.755   1.745  1.00  18.78           O
ATOM   2691  N    LYS A 347       2.540  48.438   0.233  1.00  17.85           N
ATOM   2692  CA   LYS A 347       1.763  47.590  -0.665  1.00  19.19           C
ATOM   2693  CB   LYS A 347       1.730  48.180  -2.083  1.00  23.26           C
ATOM   2694  CG   LYS A 347       1.197  49.610  -2.171  1.00  29.07           C
ATOM   2695  CD   LYS A 347      -0.320  49.652  -2.162  1.00  38.93           C
ATOM   2696  CE   LYS A 347      -0.842  50.884  -2.895  1.00  42.65           C
ATOM   2697  NZ   LYS A 347      -2.330  50.854  -3.022  1.00  46.69           N
ATOM   2698  C    LYS A 347       2.335  46.176  -0.711  1.00  18.84           C
ATOM   2699  O    LYS A 347       3.510  45.964  -0.409  1.00  21.54           O
ATOM   2700  N    LEU A 348       1.499  45.218  -1.106  1.00  19.07           N
ATOM   2701  CA   LEU A 348       1.900  43.811  -1.165  1.00  21.21           C
ATOM   2702  CB   LEU A 348       0.665  42.903  -1.206  1.00  20.29           C
ATOM   2703  CG   LEU A 348       0.926  41.391  -1.297  1.00  21.84           C
ATOM   2704  CD1  LEU A 348       1.596  40.862  -0.025  1.00  20.89           C
ATOM   2705  CD2  LEU A 348      -0.371  40.644  -1.580  1.00  20.79           C
ATOM   2706  C    LEU A 348       2.785  43.524  -2.372  1.00  21.85           C
ATOM   2707  O    LEU A 348       3.805  42.832  -2.271  1.00  21.12           O
ATOM   2708  N    HIS A 349       2.384  44.045  -3.522  1.00  23.57           N
ATOM   2709  CA   HIS A 349       3.105  43.764  -4.755  1.00  23.74           C
ATOM   2710  CB   HIS A 349       2.127  43.723  -5.928  1.00  25.29           C
ATOM   2711  CG   HIS A 349       1.179  42.575  -5.829  1.00  26.39           C
ATOM   2712  ND1  HIS A 349       1.583  41.271  -6.021  1.00  28.08           N
ATOM   2713  CE1  HIS A 349       0.556  40.463  -5.825  1.00  27.79           C
ATOM   2714  NE2  HIS A 349      -0.492  41.194  -5.488  1.00  27.73           N
ATOM   2715  CD2  HIS A 349      -0.124  42.518  -5.466  1.00  27.58           C
ATOM   2716  C    HIS A 349       4.288  44.688  -4.974  1.00  26.46           C
ATOM   2717  O    HIS A 349       4.323  45.798  -4.444  1.00  29.51           O
ATOM   2718  N    ILE A 350       5.273  44.196  -5.722  1.00  23.31           N
ATOM   2719  CA   ILE A 350       6.508  44.922  -5.970  1.00  23.76           C
ATOM   2720  CB   ILE A 350       7.736  44.148  -5.397  1.00  24.59           C
ATOM   2721  CG1  ILE A 350       7.981  42.833  -6.158  1.00  20.59           C
ATOM   2722  CD1  ILE A 350       9.267  42.105  -5.731  1.00  25.42           C
ATOM   2723  CG2  ILE A 350       7.568  43.896  -3.888  1.00  27.88           C
ATOM   2724  C    ILE A 350       6.690  45.206  -7.459  1.00  24.16           C
ATOM   2725  O    ILE A 350       6.159  44.492  -8.309  1.00  24.06           O
ATOM   2726  N    SER A 351       7.441  46.257  -7.763  1.00  29.61           N
```

FIGURE 3WW

```
ATOM   2727  CA   SER A 351       7.779  46.593  -9.141  1.00 32.20           C
ATOM   2728  CB   SER A 351       7.793  48.114  -9.326  1.00 37.24           C
ATOM   2729  OG   SER A 351       6.475  48.630  -9.344  1.00 42.67           O
ATOM   2730  C    SER A 351       9.142  46.012  -9.491  1.00 28.67           C
ATOM   2731  O    SER A 351      10.004  45.893  -8.617  1.00 29.69           O
ATOM   2732  N    PRO A 352       9.344  45.643 -10.758  1.00 27.95           N
ATOM   2733  CA   PRO A 352      10.670  45.223 -11.225  1.00 27.35           C
ATOM   2734  CB   PRO A 352      10.426  44.741 -12.664  1.00 31.09           C
ATOM   2735  CG   PRO A 352       8.973  44.897 -12.949  1.00 29.85           C
ATOM   2736  CD   PRO A 352       8.327  45.608 -11.823  1.00 27.43           C
ATOM   2737  C    PRO A 352      11.664  46.388 -11.237  1.00 31.80           C
ATOM   2738  O    PRO A 352      11.252  47.551 -11.292  1.00 31.55           O
ATOM   2739  N    SER A 353      12.953  46.071 -11.168  1.00 33.57           N
ATOM   2740  CA   SER A 353      14.007  47.057 -11.383  1.00 39.63           C
ATOM   2741  CB   SER A 353      15.340  46.548 -10.834  1.00 42.74           C
ATOM   2742  OG   SER A 353      15.214  46.115  -9.490  1.00 52.90           O
ATOM   2743  C    SER A 353      14.136  47.332 -12.879  1.00 40.03           C
ATOM   2744  O    SER A 353      13.595  46.592 -13.704  1.00 39.35           O
ATOM   2745  N    ASN A 354      14.855  48.395 -13.231  1.00 44.94           N
ATOM   2746  CA   ASN A 354      15.108  48.703 -14.637  1.00 46.36           C
ATOM   2747  CB   ASN A 354      15.158  50.223 -14.867  1.00 52.83           C
ATOM   2748  CG   ASN A 354      16.472  50.852 -14.425  1.00 55.85           C
ATOM   2749  OD1  ASN A 354      17.050  51.663 -15.148  1.00 61.44           O
ATOM   2750  ND2  ASN A 354      16.942  50.496 -13.232  1.00 57.99           N
ATOM   2751  C    ASN A 354      16.359  47.993 -15.174  1.00 45.20           C
ATOM   2752  O    ASN A 354      16.826  48.289 -16.280  1.00 46.54           O
ATOM   2753  N    MET A 355      16.882  47.054 -14.382  1.00 38.35           N
ATOM   2754  CA   MET A 355      18.056  46.258 -14.744  1.00 33.94           C
ATOM   2755  CB   MET A 355      18.421  45.287 -13.613  1.00 36.48           C
ATOM   2756  CG   MET A 355      17.620  43.980 -13.600  1.00 34.52           C
ATOM   2757  SD   MET A 355      18.043  42.858 -12.243  1.00 33.88           S
ATOM   2758  CE   MET A 355      19.753  42.482 -12.614  1.00 32.61           C
ATOM   2759  C    MET A 355      17.861  45.500 -16.054  1.00 31.33           C
ATOM   2760  O    MET A 355      16.748  45.089 -16.394  1.00 31.45           O
ATOM   2761  N    THR A 356      18.953  45.313 -16.784  1.00 30.09           N
ATOM   2762  CA   THR A 356      18.880  44.665 -18.085  1.00 32.93           C
ATOM   2763  CB   THR A 356      20.135  44.966 -18.931  1.00 36.71           C
ATOM   2764  OG1  THR A 356      21.284  44.379 -18.311  1.00 45.58           O
ATOM   2765  CG2  THR A 356      20.453  46.459 -18.913  1.00 35.37           C
ATOM   2766  C    THR A 356      18.688  43.163 -17.925  1.00 27.66           C
ATOM   2767  O    THR A 356      19.286  42.538 -17.049  1.00 29.92           O
ATOM   2768  N    ASN A 357      17.827  42.608 -18.764  1.00 25.97           N
ATOM   2769  CA   ASN A 357      17.646  41.171 -18.843  1.00 28.31           C
ATOM   2770  CB   ASN A 357      16.223  40.848 -19.293  1.00 26.07           C
ATOM   2771  CG   ASN A 357      15.923  39.362 -19.260  1.00 25.50           C
ATOM   2772  OD1  ASN A 357      16.752  38.550 -18.839  1.00 25.35           O
ATOM   2773  ND2  ASN A 357      14.731  38.998 -19.697  1.00 25.56           N
ATOM   2774  C    ASN A 357      18.667  40.550 -19.795  1.00 30.76           C
ATOM   2775  O    ASN A 357      18.570  40.718 -21.012  1.00 31.12           O
ATOM   2776  N    GLN A 358      19.640  39.837 -19.226  1.00 28.37           N
ATOM   2777  CA   GLN A 358      20.686  39.161 -20.001  1.00 28.86           C
ATOM   2778  CB   GLN A 358      21.885  38.829 -19.107  1.00 32.14           C
ATOM   2779  CG   GLN A 358      22.643  40.048 -18.606  1.00 41.84           C
ATOM   2780  CD   GLN A 358      23.755  40.467 -19.551  1.00 46.63           C
ATOM   2781  OE1  GLN A 358      24.935  40.291 -19.242  1.00 52.74           O
ATOM   2782  NE2  GLN A 358      23.385  41.015 -20.703  1.00 45.33           N
ATOM   2783  C    GLN A 358      20.193  37.903 -20.724  1.00 26.56           C
```

FIGURE 3XX

| | | | | | | | | | | |
|---|---|---|---|---|---|---|---|---|---|---|
| ATOM | 2784 | O | GLN | A | 358 | 20.892 | 37.363 | -21.591 | 1.00 28.17 | O |
| ATOM | 2785 | N | ASN | A | 359 | 18.992 | 37.450 | -20.366 | 1.00 22.56 | N |
| ATOM | 2786 | CA | ASN | A | 359 | 18.337 | 36.319 | -21.018 | 1.00 25.42 | C |
| ATOM | 2787 | CB | ASN | A | 359 | 17.416 | 35.586 | -20.044 | 1.00 21.45 | C |
| ATOM | 2788 | CG | ASN | A | 359 | 18.102 | 35.248 | -18.753 | 1.00 24.75 | C |
| ATOM | 2789 | OD1 | ASN | A | 359 | 18.064 | 36.024 | -17.798 | 1.00 23.96 | O |
| ATOM | 2790 | ND2 | ASN | A | 359 | 18.761 | 34.101 | -18.722 | 1.00 20.30 | N |
| ATOM | 2791 | C | ASN | A | 359 | 17.515 | 36.757 | -22.218 | 1.00 27.85 | C |
| ATOM | 2792 | O | ASN | A | 359 | 16.381 | 37.220 | -22.067 | 1.00 31.99 | O |
| ATOM | 2793 | N | THR | A | 360 | 18.072 | 36.596 | -23.410 | 1.00 19.23 | N |
| ATOM | 2794 | CA | THR | A | 360 | 17.335 | 36.941 | -24.620 | 1.00 20.22 | C |
| ATOM | 2795 | CB | THR | A | 360 | 18.252 | 36.913 | -25.858 | 1.00 21.73 | C |
| ATOM | 2796 | OG1 | THR | A | 360 | 18.693 | 35.568 | -26.086 | 1.00 18.55 | O |
| ATOM | 2797 | CG2 | THR | A | 360 | 19.550 | 37.695 | -25.601 | 1.00 23.09 | C |
| ATOM | 2798 | C | THR | A | 360 | 16.197 | 35.931 | -24.782 | 1.00 17.88 | C |
| ATOM | 2799 | O | THR | A | 360 | 16.295 | 34.811 | -24.288 | 1.00 17.25 | O |
| ATOM | 2800 | N | PRO | A | 361 | 15.115 | 36.324 | -25.446 | 1.00 20.23 | N |
| ATOM | 2801 | CA | PRO | A | 361 | 14.045 | 35.377 | -25.782 | 1.00 20.50 | C |
| ATOM | 2802 | CB | PRO | A | 361 | 13.115 | 36.209 | -26.666 | 1.00 22.82 | C |
| ATOM | 2803 | CG | PRO | A | 361 | 13.340 | 37.628 | -26.197 | 1.00 21.88 | C |
| ATOM | 2804 | CD | PRO | A | 361 | 14.806 | 37.698 | -25.895 | 1.00 21.04 | C |
| ATOM | 2805 | C | PRO | A | 361 | 14.580 | 34.151 | -26.538 | 1.00 20.52 | C |
| ATOM | 2806 | O | PRO | A | 361 | 14.125 | 33.030 | -26.276 | 1.00 20.98 | O |
| ATOM | 2807 | N | GLU | A | 362 | 15.552 | 34.355 | -27.433 | 1.00 19.45 | N |
| ATOM | 2808 | CA | GLU | A | 362 | 16.156 | 33.246 | -28.184 | 1.00 22.31 | C |
| ATOM | 2809 | CB | GLU | A | 362 | 17.120 | 33.770 | -29.257 | 1.00 24.75 | C |
| ATOM | 2810 | CG | GLU | A | 362 | 16.418 | 34.443 | -30.423 | 1.00 29.42 | C |
| ATOM | 2811 | CD | GLU | A | 362 | 16.063 | 35.898 | -30.161 | 1.00 34.08 | C |
| ATOM | 2812 | OE1 | GLU | A | 362 | 16.583 | 36.501 | -29.194 | 1.00 29.05 | O |
| ATOM | 2813 | OE2 | GLU | A | 362 | 15.249 | 36.442 | -30.936 | 1.00 41.75 | O |
| ATOM | 2814 | C | GLU | A | 362 | 16.888 | 32.267 | -27.283 | 1.00 15.74 | C |
| ATOM | 2815 | O | GLU | A | 362 | 16.793 | 31.053 | -27.471 | 1.00 17.88 | O |
| ATOM | 2816 | N | TYR | A | 363 | 17.641 | 32.801 | -26.322 | 1.00 16.09 | N |
| ATOM | 2817 | CA | TYR | A | 363 | 18.317 | 31.985 | -25.321 | 1.00 17.78 | C |
| ATOM | 2818 | CB | TYR | A | 363 | 19.116 | 32.883 | -24.361 | 1.00 17.31 | C |
| ATOM | 2819 | CG | TYR | A | 363 | 19.753 | 32.159 | -23.199 | 1.00 17.40 | C |
| ATOM | 2820 | CD1 | TYR | A | 363 | 19.051 | 31.967 | -22.004 | 1.00 18.41 | C |
| ATOM | 2821 | CE1 | TYR | A | 363 | 19.625 | 31.307 | -20.933 | 1.00 18.41 | C |
| ATOM | 2822 | CZ | TYR | A | 363 | 20.922 | 30.826 | -21.046 | 1.00 20.35 | C |
| ATOM | 2823 | OH | TYR | A | 363 | 21.499 | 30.168 | -19.986 | 1.00 19.63 | O |
| ATOM | 2824 | CE2 | TYR | A | 363 | 21.645 | 31.008 | -22.217 | 1.00 19.48 | C |
| ATOM | 2825 | CD2 | TYR | A | 363 | 21.059 | 31.671 | -23.287 | 1.00 18.21 | C |
| ATOM | 2826 | C | TYR | A | 363 | 17.301 | 31.114 | -24.570 | 1.00 17.82 | C |
| ATOM | 2827 | O | TYR | A | 363 | 17.487 | 29.899 | -24.445 | 1.00 17.03 | O |
| ATOM | 2828 | N | MET | A | 364 | 16.223 | 31.736 | -24.095 | 1.00 17.48 | N |
| ATOM | 2829 | CA | MET | A | 364 | 15.189 | 31.025 | -23.331 | 1.00 20.72 | C |
| ATOM | 2830 | CB | MET | A | 364 | 14.089 | 31.984 | -22.852 | 1.00 20.54 | C |
| ATOM | 2831 | CG | MET | A | 364 | 14.560 | 33.078 | -21.873 | 1.00 21.57 | C |
| ATOM | 2832 | SD | MET | A | 364 | 15.488 | 32.503 | -20.435 | 1.00 26.70 | S |
| ATOM | 2833 | CE | MET | A | 364 | 14.164 | 31.679 | -19.482 | 1.00 28.90 | C |
| ATOM | 2834 | C | MET | A | 364 | 14.584 | 29.886 | -24.144 | 1.00 20.54 | C |
| ATOM | 2835 | O | MET | A | 364 | 14.468 | 28.754 | -23.658 | 1.00 19.59 | O |
| ATOM | 2836 | N | GLU | A | 365 | 14.221 | 30.182 | -25.388 | 1.00 19.90 | N |
| ATOM | 2837 | CA | GLU | A | 365 | 13.648 | 29.175 | -26.278 | 1.00 23.25 | C |
| ATOM | 2838 | CB | GLU | A | 365 | 13.093 | 29.830 | -27.546 | 1.00 28.88 | C |
| ATOM | 2839 | CG | GLU | A | 365 | 12.422 | 28.857 | -28.499 | 1.00 40.27 | C |
| ATOM | 2840 | CD | GLU | A | 365 | 10.943 | 28.637 | -28.211 | 1.00 46.89 | C |

FIGURE 3YY

| | | | | | | | | | |
|---|---|---|---|---|---|---|---|---|---|
| ATOM | 2841 | OE1 | GLU | A | 365 | 10.250 | 28.093 | -29.104 | 1.00 50.72 | O |
| ATOM | 2842 | OE2 | GLU | A | 365 | 10.471 | 29.001 | -27.109 | 1.00 47.40 | O |
| ATOM | 2843 | C | GLU | A | 365 | 14.645 | 28.056 | -26.621 | 1.00 22.96 | C |
| ATOM | 2844 | O | GLU | A | 365 | 14.268 | 26.883 | -26.679 | 1.00 21.73 | O |
| ATOM | 2845 | N | LYS | A | 366 | 15.908 | 28.416 | -26.836 | 1.00 17.70 | N |
| ATOM | 2846 | CA | LYS | A | 366 | 16.937 | 27.414 | -27.127 | 1.00 19.86 | C |
| ATOM | 2847 | CB | LYS | A | 366 | 18.253 | 28.079 | -27.545 | 1.00 20.09 | C |
| ATOM | 2848 | CG | LYS | A | 366 | 19.332 | 27.110 | -28.031 | 1.00 20.27 | C |
| ATOM | 2849 | CD | LYS | A | 366 | 18.985 | 26.494 | -29.387 | 1.00 28.82 | C |
| ATOM | 2850 | CE | LYS | A | 366 | 19.918 | 25.341 | -29.704 | 1.00 32.20 | C |
| ATOM | 2851 | NZ | LYS | A | 366 | 19.372 | 24.478 | -30.785 | 1.00 33.92 | N |
| ATOM | 2852 | C | LYS | A | 366 | 17.156 | 26.435 | -25.967 | 1.00 18.69 | C |
| ATOM | 2853 | O | LYS | A | 366 | 17.182 | 25.215 | -26.173 | 1.00 20.87 | O |
| ATOM | 2854 | N | ILE | A | 367 | 17.314 | 26.956 | -24.750 | 1.00 18.62 | N |
| ATOM | 2855 | CA | ILE | A | 367 | 17.493 | 26.090 | -23.584 | 1.00 18.87 | C |
| ATOM | 2856 | CB | ILE | A | 367 | 17.772 | 26.906 | -22.283 | 1.00 19.32 | C |
| ATOM | 2857 | CG1 | ILE | A | 367 | 19.033 | 27.788 | -22.420 | 1.00 20.31 | C |
| ATOM | 2858 | CD1 | ILE | A | 367 | 20.302 | 27.057 | -22.853 | 1.00 25.23 | C |
| ATOM | 2859 | CG2 | ILE | A | 367 | 17.871 | 25.981 | -21.062 | 1.00 17.94 | C |
| ATOM | 2860 | C | ILE | A | 367 | 16.274 | 25.178 | -23.421 | 1.00 18.84 | C |
| ATOM | 2861 | O | ILE | A | 367 | 16.421 | 23.978 | -23.180 | 1.00 20.73 | O |
| ATOM | 2862 | N | LYS | A | 368 | 15.083 | 25.744 | -23.586 | 1.00 19.07 | N |
| ATOM | 2863 | CA | LYS | A | 368 | 13.843 | 24.971 | -23.467 | 1.00 20.86 | C |
| ATOM | 2864 | CB | LYS | A | 368 | 12.627 | 25.876 | -23.684 | 1.00 21.72 | C |
| ATOM | 2865 | CG | LYS | A | 368 | 11.280 | 25.145 | -23.649 | 1.00 26.38 | C |
| ATOM | 2866 | CD | LYS | A | 368 | 10.106 | 26.092 | -23.394 | 1.00 29.95 | C |
| ATOM | 2867 | CE | LYS | A | 368 | 9.904 | 27.098 | -24.522 | 1.00 34.33 | C |
| ATOM | 2868 | NZ | LYS | A | 368 | 9.620 | 26.446 | -25.833 | 1.00 39.15 | N |
| ATOM | 2869 | C | LYS | A | 368 | 13.829 | 23.807 | -24.462 | 1.00 20.78 | C |
| ATOM | 2870 | O | LYS | A | 368 | 13.515 | 22.668 | -24.102 | 1.00 21.74 | O |
| ATOM | 2871 | N | GLN | A | 369 | 14.192 | 24.105 | -25.706 | 1.00 22.39 | N |
| ATOM | 2872 | CA | GLN | A | 369 | 14.265 | 23.101 | -26.763 | 1.00 25.02 | C |
| ATOM | 2873 | CB | GLN | A | 369 | 14.624 | 23.761 | -28.097 | 1.00 31.98 | C |
| ATOM | 2874 | CG | GLN | A | 369 | 13.423 | 24.433 | -28.774 | 1.00 41.37 | C |
| ATOM | 2875 | CD | GLN | A | 369 | 13.807 | 25.435 | -29.860 | 1.00 46.86 | C |
| ATOM | 2876 | OE1 | GLN | A | 369 | 12.950 | 26.166 | -30.360 | 1.00 48.54 | O |
| ATOM | 2877 | NE2 | GLN | A | 369 | 15.087 | 25.472 | -30.223 | 1.00 50.00 | N |
| ATOM | 2878 | C | GLN | A | 369 | 15.242 | 21.969 | -26.432 | 1.00 24.58 | C |
| ATOM | 2879 | O | GLN | A | 369 | 14.936 | 20.795 | -26.667 | 1.00 23.89 | O |
| ATOM | 2880 | N | ARG | A | 370 | 16.403 | 22.324 | -25.883 | 1.00 20.59 | N |
| ATOM | 2881 | CA | ARG | A | 370 | 17.388 | 21.338 | -25.455 | 1.00 25.30 | C |
| ATOM | 2882 | CB | ARG | A | 370 | 18.699 | 22.011 | -25.052 | 1.00 29.96 | C |
| ATOM | 2883 | CG | ARG | A | 370 | 19.914 | 21.435 | -25.764 | 1.00 42.70 | C |
| ATOM | 2884 | CD | ARG | A | 370 | 20.570 | 22.380 | -26.763 | 1.00 45.37 | C |
| ATOM | 2885 | NE | ARG | A | 370 | 21.890 | 22.796 | -26.297 | 1.00 49.29 | N |
| ATOM | 2886 | CZ | ARG | A | 370 | 22.828 | 23.364 | -27.048 | 1.00 46.53 | C |
| ATOM | 2887 | NH1 | ARG | A | 370 | 23.983 | 23.692 | -26.499 | 1.00 44.59 | N |
| ATOM | 2888 | NH2 | ARG | A | 370 | 22.624 | 23.608 | -28.336 | 1.00 46.94 | N |
| ATOM | 2889 | C | ARG | A | 370 | 16.858 | 20.451 | -24.320 | 1.00 27.79 | C |
| ATOM | 2890 | O | ARG | A | 370 | 17.082 | 19.236 | -24.323 | 1.00 22.64 | O |
| ATOM | 2891 | N | LEU | A | 371 | 16.138 | 21.053 | -23.373 | 1.00 24.05 | N |
| ATOM | 2892 | CA | LEU | A | 371 | 15.540 | 20.297 | -22.269 | 1.00 26.11 | C |
| ATOM | 2893 | CB | LEU | A | 371 | 15.020 | 21.237 | -21.172 | 1.00 25.58 | C |
| ATOM | 2894 | CG | LEU | A | 371 | 16.063 | 22.031 | -20.373 | 1.00 26.45 | C |
| ATOM | 2895 | CD1 | LEU | A | 371 | 15.369 | 22.895 | -19.332 | 1.00 25.24 | C |
| ATOM | 2896 | CD2 | LEU | A | 371 | 17.056 | 21.105 | -19.708 | 1.00 28.24 | C |
| ATOM | 2897 | C | LEU | A | 371 | 14.416 | 19.386 | -22.757 | 1.00 23.65 | C |

FIGURE 3ZZ

```
ATOM   2898  O    LEU A 371      14.277  18.259 -22.276  1.00 23.19           O
ATOM   2899  N    PHE A 372      13.625  19.878 -23.711  1.00 22.83           N
ATOM   2900  CA   PHE A 372      12.574  19.086 -24.354  1.00 23.96           C
ATOM   2901  CB   PHE A 372      11.836  19.918 -25.409  1.00 27.20           C
ATOM   2902  CG   PHE A 372      10.724  20.784 -24.858  1.00 30.62           C
ATOM   2903  CD1  PHE A 372      10.483  20.877 -23.486  1.00 34.59           C
ATOM   2904  CE1  PHE A 372       9.452  21.684 -22.988  1.00 32.18           C
ATOM   2905  CZ   PHE A 372       8.651  22.404 -23.864  1.00 35.53           C
ATOM   2906  CE2  PHE A 372       8.883  22.323 -25.240  1.00 38.21           C
ATOM   2907  CD2  PHE A 372       9.918  21.516 -25.725  1.00 35.56           C
ATOM   2908  C    PHE A 372      13.159  17.836 -25.011  1.00 28.24           C
ATOM   2909  O    PHE A 372      12.542  16.768 -24.989  1.00 27.97           O
ATOM   2910  N    GLU A 373      14.354  17.980 -25.584  1.00 28.42           N
ATOM   2911  CA   GLU A 373      15.062  16.870 -26.216  1.00 31.37           C
ATOM   2912  CB   GLU A 373      16.310  17.375 -26.948  1.00 33.53           C
ATOM   2913  CG   GLU A 373      16.934  16.360 -27.894  1.00 42.69           C
ATOM   2914  CD   GLU A 373      17.915  16.975 -28.882  1.00 47.76           C
ATOM   2915  OE1  GLU A 373      18.494  16.208 -29.681  1.00 48.13           O
ATOM   2916  OE2  GLU A 373      18.111  18.215 -28.868  1.00 51.21           O
ATOM   2917  C    GLU A 373      15.435  15.796 -25.190  1.00 31.95           C
ATOM   2918  O    GLU A 373      15.324  14.602 -25.469  1.00 29.44           O
ATOM   2919  N    ASN A 374      15.871  16.223 -24.007  1.00 25.68           N
ATOM   2920  CA   ASN A 374      16.187  15.288 -22.928  1.00 25.03           C
ATOM   2921  CB   ASN A 374      16.911  15.997 -21.783  1.00 26.09           C
ATOM   2922  CG   ASN A 374      18.309  16.470 -22.172  1.00 31.20           C
ATOM   2923  OD1  ASN A 374      18.915  15.960 -23.116  1.00 30.95           O
ATOM   2924  ND2  ASN A 374      18.822  17.454 -21.442  1.00 28.88           N
ATOM   2925  C    ASN A 374      14.943  14.573 -22.402  1.00 24.97           C
ATOM   2926  O    ASN A 374      14.990  13.383 -22.087  1.00 27.63           O
ATOM   2927  N    LEU A 375      13.836  15.308 -22.330  1.00 24.23           N
ATOM   2928  CA   LEU A 375      12.568  14.795 -21.816  1.00 28.02           C
ATOM   2929  CB   LEU A 375      11.567  15.938 -21.638  1.00 28.86           C
ATOM   2930  CG   LEU A 375      11.309  16.540 -20.246  1.00 32.84           C
ATOM   2931  CD1  LEU A 375      12.378  16.196 -19.220  1.00 32.55           C
ATOM   2932  CD2  LEU A 375      11.125  18.042 -20.343  1.00 33.10           C
ATOM   2933  C    LEU A 375      11.942  13.703 -22.687  1.00 32.42           C
ATOM   2934  O    LEU A 375      11.200  12.857 -22.179  1.00 30.92           O
ATOM   2935  N    ARG A 376      12.231  13.711 -23.988  1.00 29.56           N
ATOM   2936  CA   ARG A 376      11.667  12.678 -24.864  1.00 35.62           C
ATOM   2937  CB   ARG A 376      11.472  13.178 -26.306  1.00 40.97           C
ATOM   2938  CG   ARG A 376      12.727  13.533 -27.065  1.00 45.87           C
ATOM   2939  CD   ARG A 376      12.464  13.934 -28.510  1.00 51.03           C
ATOM   2940  NE   ARG A 376      12.334  15.380 -28.675  1.00 53.66           N
ATOM   2941  CZ   ARG A 376      13.178  16.148 -29.361  1.00 54.53           C
ATOM   2942  NH1  ARG A 376      14.239  15.623 -29.967  1.00 53.84           N
ATOM   2943  NH2  ARG A 376      12.957  17.453 -29.444  1.00 56.10           N
ATOM   2944  C    ARG A 376      12.433  11.348 -24.789  1.00 34.04           C
ATOM   2945  O    ARG A 376      12.033  10.353 -25.405  1.00 34.00           O
ATOM   2946  N    MET A 377      13.520  11.350 -24.017  1.00 26.29           N
ATOM   2947  CA   MET A 377      14.269  10.146 -23.672  1.00 32.77           C
ATOM   2948  CB   MET A 377      15.722  10.494 -23.325  1.00 34.46           C
ATOM   2949  CG   MET A 377      16.557  11.004 -24.487  1.00 39.11           C
ATOM   2950  SD   MET A 377      16.306  10.063 -25.995  1.00 39.81           S
ATOM   2951  CE   MET A 377      17.086   8.474 -25.570  1.00 42.82           C
ATOM   2952  C    MET A 377      13.637   9.378 -22.507  1.00 34.00           C
ATOM   2953  O    MET A 377      14.109   8.296 -22.150  1.00 35.60           O
ATOM   2954  N    LEU A 378      12.585   9.938 -21.910  1.00 35.22           N
```

FIGURE 3AAA

```
ATOM   2955  CA   LEU A 378      11.848   9.255 -20.848  1.00 39.58           C
ATOM   2956  CB   LEU A 378      10.923  10.225 -20.105  1.00 37.47           C
ATOM   2957  CG   LEU A 378      11.454  11.236 -19.077  1.00 39.01           C
ATOM   2958  CD1  LEU A 378      10.451  11.373 -17.935  1.00 37.35           C
ATOM   2959  CD2  LEU A 378      12.845  10.904 -18.535  1.00 37.58           C
ATOM   2960  C    LEU A 378      11.030   8.097 -21.424  1.00 41.28           C
ATOM   2961  O    LEU A 378      10.796   7.094 -20.748  1.00 46.82           O
ATOM   2962  ZN   ZN  A 379      19.053  30.794  -2.957  1.00 19.11          ZN
ATOM   2963  NA   NA  A 380      16.532  26.900  -8.341  1.00  7.53          NA
ATOM   2964  O3   TSS A 381      26.560  35.845  -1.374  1.00 30.84           O
ATOM   2965  C9   TSS A 381      26.821  34.998  -0.538  1.00 29.67           C
ATOM   2966  C10  TSS A 381      27.173  35.422   0.860  1.00 30.43           C
ATOM   2967  C11  TSS A 381      27.552  34.478   1.816  1.00 29.52           C
ATOM   2968  C12  TSS A 381      27.872  34.891   3.109  1.00 32.84           C
ATOM   2969  C13  TSS A 381      27.814  36.244   3.459  1.00 32.66           C
ATOM   2970  N2   TSS A 381      28.138  36.658   4.770  1.00 34.23           N
ATOM   2971  C17  TSS A 381      28.270  38.073   5.094  1.00 35.80           C
ATOM   2972  C16  TSS A 381      28.339  35.673   5.826  1.00 33.26           C
ATOM   2973  C14  TSS A 381      27.429  37.184   2.499  1.00 31.75           C
ATOM   2974  C15  TSS A 381      27.115  36.776   1.205  1.00 32.43           C
ATOM   2975  C2   TSS A 381      26.756  33.540  -0.906  1.00 30.30           C
ATOM   2976  C1   TSS A 381      27.513  33.302  -2.211  1.00 31.69           C
ATOM   2977  C3   TSS A 381      25.295  33.142  -1.037  1.00 31.43           C
ATOM   2978  C4   TSS A 381      24.734  32.016  -0.547  1.00 28.97           C
ATOM   2979  C5   TSS A 381      25.560  31.004   0.196  1.00 30.38           C
ATOM   2980  C6   TSS A 381      23.280  31.810  -0.780  1.00 29.11           C
ATOM   2981  C7   TSS A 381      22.601  30.679  -0.533  1.00 30.26           C
ATOM   2982  C8   TSS A 381      21.140  30.616  -0.824  1.00 34.30           C
ATOM   2983  O1   TSS A 381      20.529  31.655  -0.988  1.00 33.99           O
ATOM   2984  N1   TSS A 381      20.493  29.446  -0.918  1.00 39.82           N
ATOM   2985  O2   TSS A 381      19.604  29.233  -1.781  1.00 28.30           O
ATOM   2986  N    LYS B  14      50.323  15.582 -35.191  1.00 51.80           N
ATOM   2987  CA   LYS B  14      50.848  16.978 -35.108  1.00 50.24           C
ATOM   2988  CB   LYS B  14      50.366  17.807 -36.303  1.00 54.02           C
ATOM   2989  CG   LYS B  14      51.103  17.508 -37.605  1.00 56.04           C
ATOM   2990  CD   LYS B  14      51.096  18.707 -38.532  1.00 57.82           C
ATOM   2991  CE   LYS B  14      51.995  18.481 -39.737  1.00 59.21           C
ATOM   2992  NZ   LYS B  14      51.576  19.327 -40.891  1.00 61.17           N
ATOM   2993  C    LYS B  14      50.457  17.647 -33.788  1.00 47.13           C
ATOM   2994  O    LYS B  14      49.270  17.772 -33.467  1.00 45.65           O
ATOM   2995  N    LYS B  15      51.469  18.069 -33.030  1.00 39.99           N
ATOM   2996  CA   LYS B  15      51.271  18.657 -31.711  1.00 34.39           C
ATOM   2997  CB   LYS B  15      52.545  18.514 -30.874  1.00 35.90           C
ATOM   2998  CG   LYS B  15      52.369  18.880 -29.406  1.00 41.66           C
ATOM   2999  CD   LYS B  15      53.505  18.345 -28.567  1.00 44.32           C
ATOM   3000  CE   LYS B  15      53.240  18.564 -27.089  1.00 47.55           C
ATOM   3001  NZ   LYS B  15      54.494  18.501 -26.289  1.00 49.77           N
ATOM   3002  C    LYS B  15      50.867  20.131 -31.802  1.00 31.11           C
ATOM   3003  O    LYS B  15      51.446  20.893 -32.577  1.00 29.11           O
ATOM   3004  N    VAL B  16      49.876  20.515 -31.000  1.00 24.52           N
ATOM   3005  CA   VAL B  16      49.434  21.902 -30.910  1.00 22.76           C
ATOM   3006  CB   VAL B  16      47.969  22.065 -31.390  1.00 23.04           C
ATOM   3007  CG1  VAL B  16      47.478  23.504 -31.176  1.00 25.92           C
ATOM   3008  CG2  VAL B  16      47.820  21.642 -32.852  1.00 25.01           C
ATOM   3009  C    VAL B  16      49.555  22.397 -29.474  1.00 20.81           C
ATOM   3010  O    VAL B  16      48.994  21.795 -28.558  1.00 24.15           O
ATOM   3011  N    CYS B  17      50.300  23.484 -29.277  1.00 17.41           N
```

FIGURE 3BBB

```
ATOM   3012  CA   CYS  B   17      50.360  24.148 -27.980  1.00 18.48           C
ATOM   3013  CB   BCYS B   17      51.790  24.285 -27.459  0.35 22.45           C
ATOM   3014  CB   ACYS B   17      51.818  24.443 -27.601  0.65 20.21           C
ATOM   3015  SG   BCYS B   17      52.741  25.645 -28.133  0.35 23.89           S
ATOM   3016  SG   ACYS B   17      52.853  23.001 -27.210  0.65 23.09           S
ATOM   3017  C    CYS  B   17      49.623  25.481 -28.056  1.00 21.96           C
ATOM   3018  O    CYS  B   17      49.727  26.205 -29.044  1.00 22.77           O
ATOM   3019  N    TYR  B   18      48.888  25.797 -27.002  1.00 17.18           N
ATOM   3020  CA   TYR  B   18      47.931  26.891 -27.039  1.00 17.25           C
ATOM   3021  CB   TYR  B   18      46.523  26.289 -27.138  1.00 15.54           C
ATOM   3022  CG   TYR  B   18      45.343  27.185 -26.827  1.00 18.67           C
ATOM   3023  CD1  TYR  B   18      44.981  27.456 -25.514  1.00 20.20           C
ATOM   3024  CE1  TYR  B   18      43.886  28.249 -25.219  1.00 20.26           C
ATOM   3025  CZ   TYR  B   18      43.128  28.767 -26.243  1.00 18.48           C
ATOM   3026  OH   TYR  B   18      42.041  29.533 -25.918  1.00 21.90           O
ATOM   3027  CE2  TYR  B   18      43.441  28.495 -27.564  1.00 20.99           C
ATOM   3028  CD2  TYR  B   18      44.547  27.703 -27.852  1.00 20.60           C
ATOM   3029  C    TYR  B   18      48.134  27.704 -25.777  1.00 14.77           C
ATOM   3030  O    TYR  B   18      48.245  27.142 -24.685  1.00 14.94           O
ATOM   3031  N    TYR  B   19      48.205  29.022 -25.937  1.00 13.05           N
ATOM   3032  CA   TYR  B   19      48.430  29.932 -24.816  1.00 13.85           C
ATOM   3033  CB   TYR  B   19      49.549  30.915 -25.142  1.00 16.58           C
ATOM   3034  CG   TYR  B   19      50.878  30.224 -25.168  1.00 19.18           C
ATOM   3035  CD1  TYR  B   19      51.322  29.583 -26.323  1.00 22.65           C
ATOM   3036  CE1  TYR  B   19      52.543  28.918 -26.347  1.00 27.72           C
ATOM   3037  CZ   TYR  B   19      53.324  28.893 -25.207  1.00 26.45           C
ATOM   3038  OH   TYR  B   19      54.532  28.239 -25.234  1.00 31.65           O
ATOM   3039  CE2  TYR  B   19      52.902  29.518 -24.044  1.00 23.98           C
ATOM   3040  CD2  TYR  B   19      51.678  30.177 -24.028  1.00 19.88           C
ATOM   3041  C    TYR  B   19      47.195  30.688 -24.393  1.00 16.78           C
ATOM   3042  O    TYR  B   19      46.464  31.215 -25.225  1.00 15.60           O
ATOM   3043  N    TYR  B   20      46.969  30.733 -23.084  1.00 15.74           N
ATOM   3044  CA   TYR  B   20      45.857  31.489 -22.527  1.00 16.70           C
ATOM   3045  CB   TYR  B   20      44.566  30.677 -22.586  1.00 18.23           C
ATOM   3046  CG   TYR  B   20      43.364  31.357 -21.958  1.00 17.55           C
ATOM   3047  CD1  TYR  B   20      42.869  30.940 -20.715  1.00 20.04           C
ATOM   3048  CE1  TYR  B   20      41.755  31.567 -20.135  1.00 20.94           C
ATOM   3049  CZ   TYR  B   20      41.126  32.603 -20.820  1.00 20.53           C
ATOM   3050  OH   TYR  B   20      40.022  33.230 -20.285  1.00 22.42           O
ATOM   3051  CE2  TYR  B   20      41.597  33.023 -22.047  1.00 16.20           C
ATOM   3052  CD2  TYR  B   20      42.707  32.396 -22.614  1.00 18.73           C
ATOM   3053  C    TYR  B   20      46.133  31.848 -21.091  1.00 18.34           C
ATOM   3054  O    TYR  B   20      46.519  30.993 -20.290  1.00 16.36           O
ATOM   3055  N    ASP  B   21      45.922  33.118 -20.769  1.00 17.66           N
ATOM   3056  CA   ASP  B   21      45.899  33.545 -19.381  1.00 21.06           C
ATOM   3057  CB   ASP  B   21      46.890  34.679 -19.135  1.00 22.10           C
ATOM   3058  CG   ASP  B   21      47.009  35.023 -17.669  1.00 30.63           C
ATOM   3059  OD1  ASP  B   21      47.969  34.558 -17.019  1.00 32.60           O
ATOM   3060  OD2  ASP  B   21      46.171  35.730 -17.076  1.00 27.90           O
ATOM   3061  C    ASP  B   21      44.491  33.987 -19.006  1.00 21.45           C
ATOM   3062  O    ASP  B   21      43.889  34.822 -19.692  1.00 19.73           O
ATOM   3063  N    GLY  B   22      43.995  33.442 -17.897  1.00 21.84           N
ATOM   3064  CA   GLY  B   22      42.667  33.738 -17.393  1.00 23.46           C
ATOM   3065  C    GLY  B   22      42.364  35.196 -17.104  1.00 25.27           C
ATOM   3066  O    GLY  B   22      41.200  35.566 -16.984  1.00 26.54           O
ATOM   3067  N    ASP  B   23      43.398  36.024 -16.990  1.00 22.26           N
ATOM   3068  CA   ASP  B   23      43.198  37.437 -16.686  1.00 24.80           C
```

FIGURE 3CCC

```
ATOM   3069  CB   ASP B  23      44.305  37.951 -15.776  1.00 31.31           C
ATOM   3070  CG   ASP B  23      43.969  37.771 -14.321  1.00 38.00           C
ATOM   3071  OD1  ASP B  23      44.790  37.169 -13.607  1.00 37.96           O
ATOM   3072  OD2  ASP B  23      42.897  38.182 -13.815  1.00 39.84           O
ATOM   3073  C    ASP B  23      43.092  38.326 -17.915  1.00 23.01           C
ATOM   3074  O    ASP B  23      42.695  39.488 -17.805  1.00 21.92           O
ATOM   3075  N    ILE B  24      43.438  37.778 -19.080  1.00 21.13           N
ATOM   3076  CA   ILE B  24      43.468  38.565 -20.308  1.00 21.45           C
ATOM   3077  CB   ILE B  24      43.966  37.723 -21.517  1.00 23.79           C
ATOM   3078  CG1  ILE B  24      44.466  38.643 -22.639  1.00 27.39           C
ATOM   3079  CD1  ILE B  24      45.900  39.166 -22.407  1.00 30.99           C
ATOM   3080  CG2  ILE B  24      42.888  36.744 -22.014  1.00 22.75           C
ATOM   3081  C    ILE B  24      42.128  39.259 -20.576  1.00 21.93           C
ATOM   3082  O    ILE B  24      42.103  40.420 -20.987  1.00 21.23           O
ATOM   3083  N    GLY B  25      41.031  38.562 -20.284  1.00 19.89           N
ATOM   3084  CA   GLY B  25      39.694  39.082 -20.513  1.00 21.42           C
ATOM   3085  C    GLY B  25      39.256  40.181 -19.562  1.00 23.69           C
ATOM   3086  O    GLY B  25      38.212  40.791 -19.779  1.00 24.43           O
ATOM   3087  N    ASN B  26      40.047  40.441 -18.520  1.00 19.98           N
ATOM   3088  CA   ASN B  26      39.684  41.435 -17.511  1.00 25.72           C
ATOM   3089  CB   ASN B  26      40.064  40.952 -16.107  1.00 27.49           C
ATOM   3090  CG   ASN B  26      39.302  39.704 -15.693  1.00 30.56           C
ATOM   3091  OD1  ASN B  26      38.108  39.571 -15.966  1.00 34.41           O
ATOM   3092  ND2  ASN B  26      39.992  38.782 -15.031  1.00 32.47           N
ATOM   3093  C    ASN B  26      40.245  42.833 -17.765  1.00 26.16           C
ATOM   3094  O    ASN B  26      39.881  43.783 -17.068  1.00 26.56           O
ATOM   3095  N    TYR B  27      41.122  42.956 -18.758  1.00 19.89           N
ATOM   3096  CA   TYR B  27      41.658  44.259 -19.139  1.00 22.37           C
ATOM   3097  CB   TYR B  27      43.019  44.121 -19.829  1.00 20.95           C
ATOM   3098  CG   TYR B  27      44.059  43.535 -18.902  1.00 21.65           C
ATOM   3099  CD1  TYR B  27      44.326  42.170 -18.909  1.00 21.34           C
ATOM   3100  CE1  TYR B  27      45.258  41.618 -18.049  1.00 24.27           C
ATOM   3101  CZ   TYR B  27      45.938  42.433 -17.162  1.00 28.40           C
ATOM   3102  OH   TYR B  27      46.861  41.870 -16.319  1.00 29.25           O
ATOM   3103  CE2  TYR B  27      45.692  43.798 -17.123  1.00 26.37           C
ATOM   3104  CD2  TYR B  27      44.748  44.341 -17.991  1.00 23.32           C
ATOM   3105  C    TYR B  27      40.637  44.957 -20.012  1.00 22.54           C
ATOM   3106  O    TYR B  27      39.944  44.316 -20.802  1.00 23.64           O
ATOM   3107  N    TYR B  28      40.531  46.268 -19.849  1.00 22.07           N
ATOM   3108  CA   TYR B  28      39.422  47.016 -20.420  1.00 21.64           C
ATOM   3109  CB   TYR B  28      38.378  47.266 -19.332  1.00 25.47           C
ATOM   3110  CG   TYR B  28      37.092  47.906 -19.792  1.00 28.96           C
ATOM   3111  CD1  TYR B  28      36.310  47.322 -20.791  1.00 31.80           C
ATOM   3112  CE1  TYR B  28      35.117  47.913 -21.206  1.00 33.40           C
ATOM   3113  CZ   TYR B  28      34.699  49.092 -20.607  1.00 33.32           C
ATOM   3114  OH   TYR B  28      33.522  49.683 -21.003  1.00 39.34           O
ATOM   3115  CE2  TYR B  28      35.456  49.689 -19.612  1.00 32.14           C
ATOM   3116  CD2  TYR B  28      36.644  49.092 -19.207  1.00 31.49           C
ATOM   3117  C    TYR B  28      39.909  48.320 -21.021  1.00 21.39           C
ATOM   3118  O    TYR B  28      40.462  49.178 -20.317  1.00 19.23           O
ATOM   3119  N    TYR B  29      39.715  48.458 -22.333  1.00 18.91           N
ATOM   3120  CA   TYR B  29      40.189  49.636 -23.063  1.00 19.68           C
ATOM   3121  CB   TYR B  29      40.127  49.390 -24.570  1.00 17.54           C
ATOM   3122  CG   TYR B  29      41.346  48.710 -25.167  1.00 16.08           C
ATOM   3123  CD1  TYR B  29      42.125  49.355 -26.128  1.00 17.57           C
ATOM   3124  CE1  TYR B  29      43.238  48.727 -26.703  1.00 16.59           C
ATOM   3125  CZ   TYR B  29      43.575  47.440 -26.301  1.00 18.46           C
```

FIGURE 3DDD

| ATOM | 3126 | OH  | TYR | B | 29 | 44.668 | 46.814 | -26.859 | 1.00 | 19.77 | O |
|------|------|-----|-----|---|----|--------|--------|---------|------|-------|---|
| ATOM | 3127 | CE2 | TYR | B | 29 | 42.819 | 46.782 | -25.349 | 1.00 | 19.43 | C |
| ATOM | 3128 | CD2 | TYR | B | 29 | 41.709 | 47.418 | -24.785 | 1.00 | 19.55 | C |
| ATOM | 3129 | C   | TYR | B | 29 | 39.406 | 50.910 | -22.726 | 1.00 | 23.36 | C |
| ATOM | 3130 | O   | TYR | B | 29 | 39.890 | 52.013 | -22.966 | 1.00 | 27.73 | O |
| ATOM | 3131 | N   | GLY | B | 30 | 38.200 | 50.756 | -22.188 | 1.00 | 24.71 | N |
| ATOM | 3132 | CA  | GLY | B | 30 | 37.378 | 51.900 | -21.837 | 1.00 | 25.50 | C |
| ATOM | 3133 | C   | GLY | B | 30 | 36.042 | 51.872 | -22.543 | 1.00 | 26.39 | C |
| ATOM | 3134 | O   | GLY | B | 30 | 35.876 | 51.182 | -23.552 | 1.00 | 24.07 | O |
| ATOM | 3135 | N   | GLN | B | 31 | 35.080 | 52.621 | -22.011 | 1.00 | 29.26 | N |
| ATOM | 3136 | CA  | GLN | B | 31 | 33.730 | 52.659 | -22.578 | 1.00 | 31.59 | C |
| ATOM | 3137 | CB  | GLN | B | 31 | 32.810 | 53.538 | -21.723 | 1.00 | 36.77 | C |
| ATOM | 3138 | CG  | GLN | B | 31 | 31.326 | 53.295 | -21.951 | 1.00 | 43.29 | C |
| ATOM | 3139 | CD  | GLN | B | 31 | 30.463 | 53.876 | -20.844 | 1.00 | 46.50 | C |
| ATOM | 3140 | OE1 | GLN | B | 31 | 30.325 | 55.096 | -20.733 | 1.00 | 50.54 | O |
| ATOM | 3141 | NE2 | GLN | B | 31 | 29.883 | 53.006 | -20.023 | 1.00 | 46.22 | N |
| ATOM | 3142 | C   | GLN | B | 31 | 33.739 | 53.145 | -24.027 | 1.00 | 27.93 | C |
| ATOM | 3143 | O   | GLN | B | 31 | 34.385 | 54.139 | -24.351 | 1.00 | 30.21 | O |
| ATOM | 3144 | N   | GLY | B | 32 | 33.043 | 52.416 | -24.894 | 1.00 | 27.86 | N |
| ATOM | 3145 | CA  | GLY | B | 32 | 32.940 | 52.777 | -26.298 | 1.00 | 29.95 | C |
| ATOM | 3146 | C   | GLY | B | 32 | 34.095 | 52.315 | -27.174 | 1.00 | 25.89 | C |
| ATOM | 3147 | O   | GLY | B | 32 | 34.038 | 52.459 | -28.396 | 1.00 | 26.27 | O |
| ATOM | 3148 | N   | HIS | B | 33 | 35.143 | 51.761 | -26.568 | 1.00 | 21.74 | N |
| ATOM | 3149 | CA  | HIS | B | 33 | 36.288 | 51.312 | -27.356 | 1.00 | 19.54 | C |
| ATOM | 3150 | CB  | HIS | B | 33 | 37.567 | 51.262 | -26.521 | 1.00 | 18.99 | C |
| ATOM | 3151 | CG  | HIS | B | 33 | 38.815 | 51.289 | -27.347 | 1.00 | 20.07 | C |
| ATOM | 3152 | ND1 | HIS | B | 33 | 39.202 | 50.229 | -28.142 | 1.00 | 19.52 | N |
| ATOM | 3153 | CE1 | HIS | B | 33 | 40.322 | 50.537 | -28.766 | 1.00 | 20.05 | C |
| ATOM | 3154 | NE2 | HIS | B | 33 | 40.676 | 51.760 | -28.410 | 1.00 | 21.63 | N |
| ATOM | 3155 | CD2 | HIS | B | 33 | 39.747 | 52.255 | -27.526 | 1.00 | 19.75 | C |
| ATOM | 3156 | C   | HIS | B | 33 | 35.979 | 49.946 | -27.964 | 1.00 | 18.55 | C |
| ATOM | 3157 | O   | HIS | B | 33 | 35.560 | 49.029 | -27.251 | 1.00 | 21.21 | O |
| ATOM | 3158 | N   | PRO | B | 34 | 36.164 | 49.813 | -29.276 | 1.00 | 20.37 | N |
| ATOM | 3159 | CA  | PRO | B | 34 | 35.811 | 48.566 | -29.965 | 1.00 | 20.22 | C |
| ATOM | 3160 | CB  | PRO | B | 34 | 35.963 | 48.912 | -31.453 | 1.00 | 20.65 | C |
| ATOM | 3161 | CG  | PRO | B | 34 | 36.780 | 50.137 | -31.514 | 1.00 | 23.26 | C |
| ATOM | 3162 | CD  | PRO | B | 34 | 36.681 | 50.840 | -30.200 | 1.00 | 20.22 | C |
| ATOM | 3163 | C   | PRO | B | 34 | 36.696 | 47.369 | -29.596 | 1.00 | 16.58 | C |
| ATOM | 3164 | O   | PRO | B | 34 | 36.256 | 46.240 | -29.801 | 1.00 | 15.53 | O |
| ATOM | 3165 | N   | MET | B | 35 | 37.913 | 47.602 | -29.105 | 1.00 | 14.38 | N |
| ATOM | 3166 | CA  | MET | B | 35 | 38.796 | 46.483 | -28.741 | 1.00 | 18.29 | C |
| ATOM | 3167 | CB  | MET | B | 35 | 40.271 | 46.923 | -28.743 | 1.00 | 14.94 | C |
| ATOM | 3168 | CG  | MET | B | 35 | 41.287 | 45.805 | -28.449 | 1.00 | 21.90 | C |
| ATOM | 3169 | SD  | MET | B | 35 | 41.050 | 44.277 | -29.401 | 1.00 | 25.35 | S |
| ATOM | 3170 | CE  | MET | B | 35 | 42.057 | 44.597 | -30.837 | 1.00 | 24.31 | C |
| ATOM | 3171 | C   | MET | B | 35 | 38.382 | 45.907 | -27.381 | 1.00 | 17.08 | C |
| ATOM | 3172 | O   | MET | B | 35 | 38.429 | 46.602 | -26.367 | 1.00 | 18.24 | O |
| ATOM | 3173 | N   | LYS | B | 36 | 37.972 | 44.637 | -27.368 | 1.00 | 15.39 | N |
| ATOM | 3174 | CA  | LYS | B | 36 | 37.438 | 44.015 | -26.162 | 1.00 | 15.49 | C |
| ATOM | 3175 | CB  | LYS | B | 36 | 35.944 | 43.712 | -26.334 | 1.00 | 18.66 | C |
| ATOM | 3176 | CG  | LYS | B | 36 | 35.062 | 44.958 | -26.439 | 1.00 | 24.64 | C |
| ATOM | 3177 | CD  | LYS | B | 36 | 33.744 | 44.627 | -27.115 | 1.00 | 28.78 | C |
| ATOM | 3178 | CE  | LYS | B | 36 | 32.934 | 45.882 | -27.447 | 1.00 | 34.51 | C |
| ATOM | 3179 | NZ  | LYS | B | 36 | 32.983 | 46.926 | -26.389 | 1.00 | 37.35 | N |
| ATOM | 3180 | C   | LYS | B | 36 | 38.183 | 42.722 | -25.822 | 1.00 | 15.82 | C |
| ATOM | 3181 | O   | LYS | B | 36 | 37.858 | 41.673 | -26.362 | 1.00 | 15.92 | O |
| ATOM | 3182 | N   | PRO | B | 37 | 39.183 | 42.794 | -24.948 | 1.00 | 16.12 | N |

FIGURE 3EEE

| | | | | | | | | | | |
|---|---|---|---|---|---|---|---|---|---|---|
| ATOM | 3183 | CA | PRO | B | 37 | 39.950 | 41.601 | -24.556 | 1.00 18.00 | C |
| ATOM | 3184 | CB | PRO | B | 37 | 40.831 | 42.126 | -23.426 | 1.00 16.18 | C |
| ATOM | 3185 | CG | PRO | B | 37 | 41.091 | 43.559 | -23.844 | 1.00 16.69 | C |
| ATOM | 3186 | CD | PRO | B | 37 | 39.718 | 44.017 | -24.313 | 1.00 16.61 | C |
| ATOM | 3187 | C | PRO | B | 37 | 39.086 | 40.424 | -24.084 | 1.00 17.51 | C |
| ATOM | 3188 | O | PRO | B | 37 | 39.538 | 39.280 | -24.150 | 1.00 18.82 | O |
| ATOM | 3189 | N | HIS | B | 38 | 37.868 | 40.714 | -23.624 | 1.00 17.95 | N |
| ATOM | 3190 | CA | HIS | B | 38 | 36.898 | 39.700 | -23.202 | 1.00 16.18 | C |
| ATOM | 3191 | CB | HIS | B | 38 | 35.586 | 40.391 | -22.816 | 1.00 23.69 | C |
| ATOM | 3192 | CG | HIS | B | 38 | 34.554 | 39.464 | -22.261 | 1.00 28.89 | C |
| ATOM | 3193 | ND1 | HIS | B | 38 | 33.281 | 39.371 | -22.782 | 1.00 35.54 | N |
| ATOM | 3194 | CE1 | HIS | B | 38 | 32.591 | 38.480 | -22.091 | 1.00 33.51 | C |
| ATOM | 3195 | NE2 | HIS | B | 38 | 33.372 | 37.994 | -21.141 | 1.00 35.94 | N |
| ATOM | 3196 | CD2 | HIS | B | 38 | 34.605 | 38.590 | -21.228 | 1.00 27.90 | C |
| ATOM | 3197 | C | HIS | B | 38 | 36.633 | 38.648 | -24.288 | 1.00 17.96 | C |
| ATOM | 3198 | O | HIS | B | 38 | 36.290 | 37.492 | -23.990 | 1.00 17.83 | O |
| ATOM | 3199 | N | ARG | B | 39 | 36.791 | 39.052 | -25.548 | 1.00 16.39 | N |
| ATOM | 3200 | CA | ARG | B | 39 | 36.621 | 38.141 | -26.679 | 1.00 14.98 | C |
| ATOM | 3201 | CB | ARG | B | 39 | 36.797 | 38.886 | -28.017 | 1.00 16.89 | C |
| ATOM | 3202 | CG | ARG | B | 39 | 38.246 | 39.199 | -28.383 | 1.00 16.83 | C |
| ATOM | 3203 | CD | ARG | B | 39 | 38.460 | 40.439 | -29.248 | 1.00 17.98 | C |
| ATOM | 3204 | NE | ARG | B | 39 | 39.904 | 40.659 | -29.335 | 1.00 18.74 | N |
| ATOM | 3205 | CZ | ARG | B | 39 | 40.591 | 40.774 | -30.457 | 1.00 22.41 | C |
| ATOM | 3206 | NH1 | ARG | B | 39 | 39.968 | 40.778 | -31.635 | 1.00 20.23 | N |
| ATOM | 3207 | NH2 | ARG | B | 39 | 41.911 | 40.923 | -30.399 | 1.00 20.02 | N |
| ATOM | 3208 | C | ARG | B | 39 | 37.558 | 36.930 | -26.594 | 1.00 14.04 | C |
| ATOM | 3209 | O | ARG | B | 39 | 37.216 | 35.858 | -27.088 | 1.00 16.91 | O |
| ATOM | 3210 | N | ILE | B | 40 | 38.725 | 37.099 | -25.963 | 1.00 13.87 | N |
| ATOM | 3211 | CA | ILE | B | 40 | 39.688 | 35.993 | -25.845 | 1.00 13.96 | C |
| ATOM | 3212 | CB | ILE | B | 40 | 41.096 | 36.515 | -25.439 | 1.00 15.30 | C |
| ATOM | 3213 | CG1 | ILE | B | 40 | 41.613 | 37.517 | -26.482 | 1.00 21.15 | C |
| ATOM | 3214 | CD1 | ILE | B | 40 | 42.409 | 38.630 | -25.877 | 1.00 31.64 | C |
| ATOM | 3215 | CG2 | ILE | B | 40 | 42.104 | 35.357 | -25.284 | 1.00 17.86 | C |
| ATOM | 3216 | C | ILE | B | 40 | 39.157 | 34.961 | -24.846 | 1.00 16.80 | C |
| ATOM | 3217 | O | ILE | B | 40 | 39.290 | 33.750 | -25.058 | 1.00 16.33 | O |
| ATOM | 3218 | N | ARG | B | 41 | 38.547 | 35.456 | -23.772 | 1.00 15.85 | N |
| ATOM | 3219 | CA | ARG | B | 41 | 37.914 | 34.601 | -22.776 | 1.00 17.53 | C |
| ATOM | 3220 | CB | ARG | B | 41 | 37.475 | 35.410 | -21.552 | 1.00 18.35 | C |
| ATOM | 3221 | CG | ARG | B | 41 | 36.813 | 34.560 | -20.459 | 1.00 24.94 | C |
| ATOM | 3222 | CD | ARG | B | 41 | 36.730 | 35.228 | -19.090 | 1.00 30.95 | C |
| ATOM | 3223 | NE | ARG | B | 41 | 36.331 | 36.629 | -19.191 | 1.00 35.13 | N |
| ATOM | 3224 | CZ | ARG | B | 41 | 36.679 | 37.574 | -18.326 | 1.00 39.51 | C |
| ATOM | 3225 | NH1 | ARG | B | 41 | 37.439 | 37.278 | -17.279 | 1.00 40.29 | N |
| ATOM | 3226 | NH2 | ARG | B | 41 | 36.264 | 38.821 | -18.508 | 1.00 40.45 | N |
| ATOM | 3227 | C | ARG | B | 41 | 36.719 | 33.874 | -23.393 | 1.00 17.35 | C |
| ATOM | 3228 | O | ARG | B | 41 | 36.518 | 32.692 | -23.134 | 1.00 14.42 | O |
| ATOM | 3229 | N | MET | B | 42 | 35.939 | 34.574 | -24.216 | 1.00 13.95 | N |
| ATOM | 3230 | CA | MET | B | 42 | 34.806 | 33.937 | -24.908 | 1.00 15.13 | C |
| ATOM | 3231 | CB | MET | B | 42 | 34.011 | 34.958 | -25.718 | 1.00 16.57 | C |
| ATOM | 3232 | CG | MET | B | 42 | 33.248 | 35.957 | -24.882 | 1.00 22.55 | C |
| ATOM | 3233 | SD | MET | B | 42 | 32.491 | 37.188 | -25.967 | 1.00 27.39 | S |
| ATOM | 3234 | CE | MET | B | 42 | 31.358 | 36.118 | -26.937 | 1.00 19.76 | C |
| ATOM | 3235 | C | MET | B | 42 | 35.254 | 32.797 | -25.813 | 1.00 15.40 | C |
| ATOM | 3236 | O | MET | B | 42 | 34.642 | 31.724 | -25.823 | 1.00 16.48 | O |
| ATOM | 3237 | N | THR | B | 43 | 36.331 | 33.040 | -26.559 | 1.00 15.35 | N |
| ATOM | 3238 | CA | THR | B | 43 | 36.963 | 32.038 | -27.409 | 1.00 15.79 | C |
| ATOM | 3239 | CB | THR | B | 43 | 38.202 | 32.659 | -28.101 | 1.00 16.45 | C |

FIGURE 3FFF

| ATOM | 3240 | OG1 | THR | B | 43 | 37.789 | 33.743 | -28.943 | 1.00 | 16.25 | O |
|---|---|---|---|---|---|---|---|---|---|---|---|
| ATOM | 3241 | CG2 | THR | B | 43 | 38.862 | 31.663 | -29.043 | 1.00 | 16.42 | C |
| ATOM | 3242 | C | THR | B | 43 | 37.406 | 30.827 | -26.599 | 1.00 | 14.88 | C |
| ATOM | 3243 | O | THR | B | 43 | 37.103 | 29.681 | -26.949 | 1.00 | 13.01 | O |
| ATOM | 3244 | N | HIS | B | 44 | 38.144 | 31.086 | -25.527 | 1.00 | 16.50 | N |
| ATOM | 3245 | CA | HIS | B | 44 | 38.633 | 30.014 | -24.667 | 1.00 | 17.55 | C |
| ATOM | 3246 | CB | HIS | B | 44 | 39.468 | 30.598 | -23.528 | 1.00 | 15.58 | C |
| ATOM | 3247 | CG | HIS | B | 44 | 40.152 | 29.562 | -22.697 | 1.00 | 18.57 | C |
| ATOM | 3248 | ND1 | HIS | B | 44 | 41.199 | 28.806 | -23.172 | 1.00 | 19.42 | N |
| ATOM | 3249 | CE1 | HIS | B | 44 | 41.609 | 27.981 | -22.226 | 1.00 | 20.26 | C |
| ATOM | 3250 | NE2 | HIS | B | 44 | 40.865 | 28.177 | -21.153 | 1.00 | 19.48 | N |
| ATOM | 3251 | CD2 | HIS | B | 44 | 39.943 | 29.160 | -21.422 | 1.00 | 19.18 | C |
| ATOM | 3252 | C | HIS | B | 44 | 37.478 | 29.188 | -24.111 | 1.00 | 15.76 | C |
| ATOM | 3253 | O | HIS | B | 44 | 37.495 | 27.957 | -24.167 | 1.00 | 16.07 | O |
| ATOM | 3254 | N | ASN | B | 45 | 36.461 | 29.871 | -23.594 | 1.00 | 15.87 | N |
| ATOM | 3255 | CA | ASN | B | 45 | 35.306 | 29.186 | -23.011 | 1.00 | 18.20 | C |
| ATOM | 3256 | CB | ASN | B | 45 | 34.358 | 30.195 | -22.362 | 1.00 | 16.63 | C |
| ATOM | 3257 | CG | ASN | B | 45 | 33.273 | 29.527 | -21.548 | 1.00 | 22.63 | C |
| ATOM | 3258 | OD1 | ASN | B | 45 | 32.143 | 29.391 | -22.006 | 1.00 | 21.45 | O |
| ATOM | 3259 | ND2 | ASN | B | 45 | 33.614 | 29.099 | -20.337 | 1.00 | 21.84 | N |
| ATOM | 3260 | C | ASN | B | 45 | 34.562 | 28.301 | -24.024 | 1.00 | 18.20 | C |
| ATOM | 3261 | O | ASN | B | 45 | 34.139 | 27.186 | -23.699 | 1.00 | 14.66 | O |
| ATOM | 3262 | N | LEU | B | 46 | 34.430 | 28.784 | -25.254 | 1.00 | 14.22 | N |
| ATOM | 3263 | CA | LEU | B | 46 | 33.782 | 28.002 | -26.310 | 1.00 | 17.00 | C |
| ATOM | 3264 | CB | LEU | B | 46 | 33.601 | 28.851 | -27.578 | 1.00 | 16.73 | C |
| ATOM | 3265 | CG | LEU | B | 46 | 32.249 | 28.883 | -28.300 | 1.00 | 25.32 | C |
| ATOM | 3266 | CD1 | LEU | B | 46 | 32.439 | 29.295 | -29.770 | 1.00 | 18.98 | C |
| ATOM | 3267 | CD2 | LEU | B | 46 | 31.419 | 27.592 | -28.160 | 1.00 | 17.55 | C |
| ATOM | 3268 | C | LEU | B | 46 | 34.594 | 26.757 | -26.634 | 1.00 | 17.29 | C |
| ATOM | 3269 | O | LEU | B | 46 | 34.050 | 25.659 | -26.748 | 1.00 | 15.95 | O |
| ATOM | 3270 | N | LEU | B | 47 | 35.904 | 26.948 | -26.780 | 1.00 | 18.12 | N |
| ATOM | 3271 | CA | LEU | B | 47 | 36.841 | 25.878 | -27.089 | 1.00 | 20.12 | C |
| ATOM | 3272 | CB | BLEU | B | 47 | 38.242 | 26.480 | -27.249 | 0.35 | 24.84 | C |
| ATOM | 3273 | CB | ALEU | B | 47 | 38.267 | 26.434 | -27.218 | 0.65 | 23.54 | C |
| ATOM | 3274 | CG | BLEU | B | 47 | 39.495 | 25.640 | -27.036 | 0.35 | 26.90 | C |
| ATOM | 3275 | CG | ALEU | B | 47 | 38.644 | 27.074 | -28.548 | 0.65 | 24.19 | C |
| ATOM | 3276 | CD1 | BLEU | B | 47 | 40.395 | 25.853 | -28.218 | 0.35 | 28.65 | C |
| ATOM | 3277 | CD1 | ALEU | B | 47 | 39.915 | 27.895 | -28.405 | 0.65 | 21.58 | C |
| ATOM | 3278 | CD2 | BLEU | B | 47 | 40.193 | 26.033 | -25.749 | 0.35 | 29.19 | C |
| ATOM | 3279 | CD2 | ALEU | B | 47 | 38.816 | 26.008 | -29.600 | 0.65 | 25.26 | C |
| ATOM | 3280 | C | LEU | B | 47 | 36.835 | 24.791 | -26.023 | 1.00 | 21.46 | C |
| ATOM | 3281 | O | LEU | B | 47 | 36.868 | 23.595 | -26.335 | 1.00 | 20.57 | O |
| ATOM | 3282 | N | LEU | B | 48 | 36.823 | 25.216 | -24.765 | 1.00 | 17.70 | N |
| ATOM | 3283 | CA | LEU | B | 48 | 36.763 | 24.288 | -23.642 | 1.00 | 19.47 | C |
| ATOM | 3284 | CB | LEU | B | 48 | 36.847 | 25.037 | -22.309 | 1.00 | 22.03 | C |
| ATOM | 3285 | CG | LEU | B | 48 | 38.204 | 25.577 | -21.827 | 1.00 | 25.01 | C |
| ATOM | 3286 | CD1 | LEU | B | 48 | 38.120 | 25.977 | -20.358 | 1.00 | 26.72 | C |
| ATOM | 3287 | CD2 | LEU | B | 48 | 39.347 | 24.589 | -22.044 | 1.00 | 26.26 | C |
| ATOM | 3288 | C | LEU | B | 48 | 35.473 | 23.480 | -23.699 | 1.00 | 19.56 | C |
| ATOM | 3289 | O | LEU | B | 48 | 35.489 | 22.273 | -23.493 | 1.00 | 19.16 | O |
| ATOM | 3290 | N | ASN | B | 49 | 34.361 | 24.151 | -23.995 | 1.00 | 14.22 | N |
| ATOM | 3291 | CA | ASN | B | 49 | 33.071 | 23.468 | -24.062 | 1.00 | 16.89 | C |
| ATOM | 3292 | CB | ASN | B | 49 | 31.932 | 24.470 | -23.915 | 1.00 | 15.73 | C |
| ATOM | 3293 | CG | ASN | B | 49 | 31.686 | 24.834 | -22.465 | 1.00 | 16.91 | C |
| ATOM | 3294 | OD1 | ASN | B | 49 | 31.191 | 24.014 | -21.698 | 1.00 | 20.28 | O |
| ATOM | 3295 | ND2 | ASN | B | 49 | 32.060 | 26.048 | -22.075 | 1.00 | 15.59 | N |
| ATOM | 3296 | C | ASN | B | 49 | 32.884 | 22.554 | -25.276 | 1.00 | 19.55 | C |

FIGURE 3GGG

| ATOM | 3297 | O   | ASN | B | 49 | 32.022 | 21.674 | -25.267 | 1.00 | 18.78 | O |
|------|------|-----|-----|---|----|--------|--------|---------|------|-------|---|
| ATOM | 3298 | N   | TYR | B | 50 | 33.704 | 22.754 | -26.308 | 1.00 | 17.90 | N |
| ATOM | 3299 | CA  | TYR | B | 50 | 33.775 | 21.815 | -27.430 | 1.00 | 20.30 | C |
| ATOM | 3300 | CB  | TYR | B | 50 | 34.329 | 22.516 | -28.669 | 1.00 | 18.47 | C |
| ATOM | 3301 | CG  | TYR | B | 50 | 33.278 | 23.059 | -29.614 | 1.00 | 16.02 | C |
| ATOM | 3302 | CD1 | TYR | B | 50 | 32.473 | 22.192 | -30.362 | 1.00 | 16.98 | C |
| ATOM | 3303 | CE1 | TYR | B | 50 | 31.507 | 22.689 | -31.240 | 1.00 | 16.48 | C |
| ATOM | 3304 | CZ  | TYR | B | 50 | 31.364 | 24.068 | -31.396 | 1.00 | 18.51 | C |
| ATOM | 3305 | OH  | TYR | B | 50 | 30.422 | 24.545 | -32.268 | 1.00 | 17.03 | O |
| ATOM | 3306 | CE2 | TYR | B | 50 | 32.153 | 24.953 | -30.671 | 1.00 | 15.64 | C |
| ATOM | 3307 | CD2 | TYR | B | 50 | 33.109 | 24.443 | -29.785 | 1.00 | 17.94 | C |
| ATOM | 3308 | C   | TYR | B | 50 | 34.650 | 20.601 | -27.095 | 1.00 | 21.42 | C |
| ATOM | 3309 | O   | TYR | B | 50 | 34.677 | 19.610 | -27.839 | 1.00 | 22.64 | O |
| ATOM | 3310 | N   | GLY | B | 51 | 35.381 | 20.699 | -25.992 | 1.00 | 19.41 | N |
| ATOM | 3311 | CA  | GLY | B | 51 | 36.262 | 19.637 | -25.528 | 1.00 | 24.87 | C |
| ATOM | 3312 | C   | GLY | B | 51 | 37.629 | 19.612 | -26.188 | 1.00 | 26.32 | C |
| ATOM | 3313 | O   | GLY | B | 51 | 38.341 | 18.605 | -26.116 | 1.00 | 28.08 | O |
| ATOM | 3314 | N   | LEU | B | 52 | 38.008 | 20.716 | -26.830 | 1.00 | 23.50 | N |
| ATOM | 3315 | CA  | LEU | B | 52 | 39.271 | 20.767 | -27.568 | 1.00 | 22.03 | C |
| ATOM | 3316 | CB  | LEU | B | 52 | 39.293 | 21.963 | -28.531 | 1.00 | 22.15 | C |
| ATOM | 3317 | CG  | LEU | B | 52 | 38.307 | 21.931 | -29.714 | 1.00 | 26.16 | C |
| ATOM | 3318 | CD1 | LEU | B | 52 | 38.611 | 23.046 | -30.692 | 1.00 | 30.60 | C |
| ATOM | 3319 | CD2 | LEU | B | 52 | 38.305 | 20.593 | -30.440 | 1.00 | 28.55 | C |
| ATOM | 3320 | C   | LEU | B | 52 | 40.520 | 20.742 | -26.670 | 1.00 | 20.59 | C |
| ATOM | 3321 | O   | LEU | B | 52 | 41.629 | 20.510 | -27.152 | 1.00 | 23.95 | O |
| ATOM | 3322 | N   | TYR | B | 53 | 40.338 | 20.965 | -25.369 | 1.00 | 21.65 | N |
| ATOM | 3323 | CA  | TYR | B | 53 | 41.433 | 20.847 | -24.398 | 1.00 | 22.91 | C |
| ATOM | 3324 | CB  | TYR | B | 53 | 40.996 | 21.325 | -23.010 | 1.00 | 25.41 | C |
| ATOM | 3325 | CG  | TYR | B | 53 | 39.918 | 20.481 | -22.384 | 1.00 | 28.97 | C |
| ATOM | 3326 | CD1 | TYR | B | 53 | 40.245 | 19.362 | -21.614 | 1.00 | 27.77 | C |
| ATOM | 3327 | CE1 | TYR | B | 53 | 39.259 | 18.576 | -21.049 | 1.00 | 33.46 | C |
| ATOM | 3328 | CZ  | TYR | B | 53 | 37.926 | 18.906 | -21.245 | 1.00 | 31.95 | C |
| ATOM | 3329 | OH  | TYR | B | 53 | 36.951 | 18.125 | -20.677 | 1.00 | 35.08 | O |
| ATOM | 3330 | CE2 | TYR | B | 53 | 37.572 | 20.016 | -22.001 | 1.00 | 28.45 | C |
| ATOM | 3331 | CD2 | TYR | B | 53 | 38.566 | 20.792 | -22.569 | 1.00 | 25.31 | C |
| ATOM | 3332 | C   | TYR | B | 53 | 41.983 | 19.417 | -24.318 | 1.00 | 27.33 | C |
| ATOM | 3333 | O   | TYR | B | 53 | 43.115 | 19.198 | -23.888 | 1.00 | 28.15 | O |
| ATOM | 3334 | N   | ARG | B | 54 | 41.173 | 18.449 | -24.737 | 1.00 | 27.45 | N |
| ATOM | 3335 | CA  | ARG | B | 54 | 41.571 | 17.042 | -24.718 | 1.00 | 31.82 | C |
| ATOM | 3336 | CB  | ARG | B | 54 | 40.352 | 16.142 | -24.947 | 1.00 | 36.39 | C |
| ATOM | 3337 | CG  | ARG | B | 54 | 39.310 | 16.221 | -23.847 | 1.00 | 43.10 | C |
| ATOM | 3338 | CD  | ARG | B | 54 | 38.821 | 14.868 | -23.360 | 1.00 | 52.75 | C |
| ATOM | 3339 | NE  | ARG | B | 54 | 37.770 | 14.332 | -24.222 | 1.00 | 58.08 | N |
| ATOM | 3340 | CZ  | ARG | B | 54 | 37.173 | 13.158 | -24.046 | 1.00 | 61.98 | C |
| ATOM | 3341 | NH1 | ARG | B | 54 | 37.515 | 12.373 | -23.029 | 1.00 | 64.87 | N |
| ATOM | 3342 | NH2 | ARG | B | 54 | 36.228 | 12.764 | -24.890 | 1.00 | 62.91 | N |
| ATOM | 3343 | C   | ARG | B | 54 | 42.654 | 16.724 | -25.748 | 1.00 | 32.69 | C |
| ATOM | 3344 | O   | ARG | B | 54 | 43.331 | 15.697 | -25.643 | 1.00 | 34.25 | O |
| ATOM | 3345 | N   | LYS | B | 55 | 42.825 | 17.610 | -26.730 | 1.00 | 27.21 | N |
| ATOM | 3346 | CA  | LYS | B | 55 | 43.661 | 17.318 | -27.894 | 1.00 | 27.88 | C |
| ATOM | 3347 | CB  | LYS | B | 55 | 42.817 | 17.339 | -29.174 | 1.00 | 32.14 | C |
| ATOM | 3348 | CG  | LYS | B | 55 | 41.777 | 16.230 | -29.255 | 1.00 | 37.82 | C |
| ATOM | 3349 | CD  | LYS | B | 55 | 41.049 | 16.251 | -30.587 | 1.00 | 42.53 | C |
| ATOM | 3350 | CE  | LYS | B | 55 | 39.633 | 16.774 | -30.422 | 1.00 | 47.03 | C |
| ATOM | 3351 | NZ  | LYS | B | 55 | 38.664 | 16.010 | -31.257 | 1.00 | 49.45 | N |
| ATOM | 3352 | C   | LYS | B | 55 | 44.862 | 18.248 | -28.049 | 1.00 | 27.53 | C |
| ATOM | 3353 | O   | LYS | B | 55 | 45.658 | 18.081 | -28.965 | 1.00 | 28.94 | O |

FIGURE 3HHH

| ATOM | 3354 | N   | MET | B | 56 | 44.992 | 19.228 | -27.161 | 1.00 | 27.07 | N |
|------|------|-----|-----|---|----|--------|--------|---------|------|-------|---|
| ATOM | 3355 | CA  | MET | B | 56 | 46.132 | 20.134 | -27.228 | 1.00 | 29.60 | C |
| ATOM | 3356 | CB  | MET | B | 56 | 45.786 | 21.415 | -27.997 | 1.00 | 31.09 | C |
| ATOM | 3357 | CG  | MET | B | 56 | 44.578 | 22.146 | -27.495 | 1.00 | 31.93 | C |
| ATOM | 3358 | SD  | MET | B | 56 | 44.269 | 23.678 | -28.399 | 1.00 | 31.43 | S |
| ATOM | 3359 | CE  | MET | B | 56 | 43.187 | 24.360 | -27.294 | 1.00 | 21.31 | C |
| ATOM | 3360 | C   | MET | B | 56 | 46.700 | 20.463 | -25.861 | 1.00 | 27.84 | C |
| ATOM | 3361 | O   | MET | B | 56 | 46.023 | 20.321 | -24.845 | 1.00 | 30.56 | O |
| ATOM | 3362 | N   | GLU | B | 57 | 47.959 | 20.890 | -25.856 | 1.00 | 26.94 | N |
| ATOM | 3363 | CA  | GLU | B | 57 | 48.623 | 21.331 | -24.644 | 1.00 | 28.52 | C |
| ATOM | 3364 | CB  | GLU | B | 57 | 50.135 | 21.146 | -24.784 | 1.00 | 34.68 | C |
| ATOM | 3365 | CG  | GLU | B | 57 | 50.855 | 20.691 | -23.520 | 1.00 | 45.60 | C |
| ATOM | 3366 | CD  | GLU | B | 57 | 50.357 | 19.364 | -22.979 | 1.00 | 48.40 | C |
| ATOM | 3367 | OE1 | GLU | B | 57 | 50.687 | 18.315 | -23.575 | 1.00 | 52.76 | O |
| ATOM | 3368 | OE2 | GLU | B | 57 | 49.639 | 19.372 | -21.954 | 1.00 | 52.02 | O |
| ATOM | 3369 | C   | GLU | B | 57 | 48.264 | 22.798 | -24.406 | 1.00 | 25.40 | C |
| ATOM | 3370 | O   | GLU | B | 57 | 48.465 | 23.642 | -25.277 | 1.00 | 23.67 | O |
| ATOM | 3371 | N   | ILE | B | 58 | 47.702 | 23.088 | -23.241 | 1.00 | 20.81 | N |
| ATOM | 3372 | CA  | ILE | B | 58 | 47.343 | 24.458 | -22.890 | 1.00 | 22.40 | C |
| ATOM | 3373 | CB  | ILE | B | 58 | 45.898 | 24.510 | -22.337 | 1.00 | 20.66 | C |
| ATOM | 3374 | CG1 | ILE | B | 58 | 44.901 | 24.116 | -23.438 | 1.00 | 20.24 | C |
| ATOM | 3375 | CD1 | ILE | B | 58 | 43.480 | 23.988 | -22.968 | 1.00 | 25.11 | C |
| ATOM | 3376 | CG2 | ILE | B | 58 | 45.581 | 25.896 | -21.765 | 1.00 | 20.94 | C |
| ATOM | 3377 | C   | ILE | B | 58 | 48.351 | 25.018 | -21.890 | 1.00 | 24.61 | C |
| ATOM | 3378 | O   | ILE | B | 58 | 48.560 | 24.436 | -20.822 | 1.00 | 21.26 | O |
| ATOM | 3379 | N   | TYR | B | 59 | 48.981 | 26.135 | -22.250 | 1.00 | 19.63 | N |
| ATOM | 3380 | CA  | TYR | B | 59 | 49.950 | 26.809 | -21.383 | 1.00 | 17.24 | C |
| ATOM | 3381 | CB  | TYR | B | 59 | 51.302 | 26.947 | -22.075 | 1.00 | 20.03 | C |
| ATOM | 3382 | CG  | TYR | B | 59 | 51.983 | 25.656 | -22.405 | 1.00 | 25.16 | C |
| ATOM | 3383 | CD1 | TYR | B | 59 | 52.915 | 25.092 | -21.533 | 1.00 | 29.01 | C |
| ATOM | 3384 | CE1 | TYR | B | 59 | 53.554 | 23.892 | -21.845 | 1.00 | 28.47 | C |
| ATOM | 3385 | CZ  | TYR | B | 59 | 53.259 | 23.259 | -23.037 | 1.00 | 32.39 | C |
| ATOM | 3386 | OH  | TYR | B | 59 | 53.884 | 22.078 | -23.363 | 1.00 | 39.74 | O |
| ATOM | 3387 | CE2 | TYR | B | 59 | 52.340 | 23.804 | -23.914 | 1.00 | 33.76 | C |
| ATOM | 3388 | CD2 | TYR | B | 59 | 51.713 | 24.997 | -23.600 | 1.00 | 31.07 | C |
| ATOM | 3389 | C   | TYR | B | 59 | 49.482 | 28.202 | -21.026 | 1.00 | 23.22 | C |
| ATOM | 3390 | O   | TYR | B | 59 | 48.775 | 28.845 | -21.802 | 1.00 | 21.39 | O |
| ATOM | 3391 | N   | ARG | B | 60 | 49.900 | 28.669 | -19.855 | 1.00 | 20.34 | N |
| ATOM | 3392 | CA  | ARG | B | 60 | 49.746 | 30.065 | -19.501 | 1.00 | 22.17 | C |
| ATOM | 3393 | CB  | ARG | B | 60 | 49.583 | 30.217 | -17.993 | 1.00 | 26.38 | C |
| ATOM | 3394 | CG  | ARG | B | 60 | 48.163 | 29.966 | -17.503 | 1.00 | 38.28 | C |
| ATOM | 3395 | CD  | ARG | B | 60 | 47.926 | 30.341 | -16.046 | 1.00 | 44.18 | C |
| ATOM | 3396 | NE  | ARG | B | 60 | 48.760 | 31.465 | -15.616 | 1.00 | 51.42 | N |
| ATOM | 3397 | CZ  | ARG | B | 60 | 49.318 | 31.573 | -14.413 | 1.00 | 55.15 | C |
| ATOM | 3398 | NH1 | ARG | B | 60 | 50.061 | 32.634 | -14.121 | 1.00 | 53.06 | N |
| ATOM | 3399 | NH2 | ARG | B | 60 | 49.135 | 30.624 | -13.499 | 1.00 | 55.99 | N |
| ATOM | 3400 | C   | ARG | B | 60 | 51.002 | 30.788 | -19.984 | 1.00 | 21.73 | C |
| ATOM | 3401 | O   | ARG | B | 60 | 52.110 | 30.275 | -19.822 | 1.00 | 24.70 | O |
| ATOM | 3402 | N   | PRO | B | 61 | 50.840 | 31.960 | -20.596 | 1.00 | 19.86 | N |
| ATOM | 3403 | CA  | PRO | B | 61 | 51.997 | 32.752 | -21.013 | 1.00 | 16.68 | C |
| ATOM | 3404 | CB  | PRO | B | 61 | 51.367 | 33.880 | -21.840 | 1.00 | 16.23 | C |
| ATOM | 3405 | CG  | PRO | B | 61 | 50.004 | 34.059 | -21.237 | 1.00 | 16.66 | C |
| ATOM | 3406 | CD  | PRO | B | 61 | 49.565 | 32.634 | -20.916 | 1.00 | 16.50 | C |
| ATOM | 3407 | C   | PRO | B | 61 | 52.720 | 33.324 | -19.796 | 1.00 | 16.83 | C |
| ATOM | 3408 | O   | PRO | B | 61 | 52.093 | 33.581 | -18.767 | 1.00 | 19.68 | O |
| ATOM | 3409 | N   | HIS | B | 62 | 54.031 | 33.501 | -19.917 | 1.00 | 18.43 | N |
| ATOM | 3410 | CA  | HIS | B | 62 | 54.783 | 34.279 | -18.943 | 1.00 | 21.06 | C |

FIGURE 3III

```
ATOM   3411  CB   HIS B  62      56.282  33.980 -19.059  1.00 18.85           C
ATOM   3412  CG   HIS B  62      56.895  34.447 -20.346  1.00 22.39           C
ATOM   3413  ND1  HIS B  62      56.701  33.794 -21.543  1.00 22.41           N
ATOM   3414  CE1  HIS B  62      57.361  34.422 -22.499  1.00 26.00           C
ATOM   3415  NE2  HIS B  62      57.974  35.464 -21.966  1.00 24.24           N
ATOM   3416  CD2  HIS B  62      57.701  35.500 -20.619  1.00 20.17           C
ATOM   3417  C    HIS B  62      54.522  35.755 -19.243  1.00 21.34           C
ATOM   3418  O    HIS B  62      54.012  36.095 -20.316  1.00 17.66           O
ATOM   3419  N    LYS B  63      54.857  36.627 -18.299  1.00 19.72           N
ATOM   3420  CA   LYS B  63      54.788  38.055 -18.550  1.00 19.52           C
ATOM   3421  CB   LYS B  63      54.613  38.823 -17.238  1.00 24.85           C
ATOM   3422  CG   LYS B  63      53.202  38.735 -16.647  1.00 29.04           C
ATOM   3423  CD   LYS B  63      53.061  39.574 -15.386  1.00 33.47           C
ATOM   3424  CE   LYS B  63      53.798  38.950 -14.207  1.00 42.07           C
ATOM   3425  NZ   LYS B  63      52.875  38.583 -13.088  1.00 47.76           N
ATOM   3426  C    LYS B  63      56.075  38.466 -19.255  1.00 21.13           C
ATOM   3427  O    LYS B  63      57.138  38.498 -18.636  1.00 21.15           O
ATOM   3428  N    ALA B  64      55.986  38.742 -20.555  1.00 21.04           N
ATOM   3429  CA   ALA B  64      57.154  39.150 -21.336  1.00 21.09           C
ATOM   3430  CB   ALA B  64      56.729  39.604 -22.736  1.00 19.54           C
ATOM   3431  C    ALA B  64      57.933  40.258 -20.622  1.00 18.19           C
ATOM   3432  O    ALA B  64      57.342  41.205 -20.112  1.00 18.95           O
ATOM   3433  N    THR B  65      59.257  40.131 -20.578  1.00 18.50           N
ATOM   3434  CA   THR B  65      60.075  41.084 -19.831  1.00 22.79           C
ATOM   3435  CB   THR B  65      61.390  40.428 -19.344  1.00 24.58           C
ATOM   3436  OG1  THR B  65      62.113  39.914 -20.465  1.00 25.80           O
ATOM   3437  CG2  THR B  65      61.106  39.187 -18.507  1.00 24.76           C
ATOM   3438  C    THR B  65      60.401  42.311 -20.673  1.00 24.47           C
ATOM   3439  O    THR B  65      60.291  42.277 -21.892  1.00 20.57           O
ATOM   3440  N    ALA B  66      60.813  43.387 -20.009  1.00 26.12           N
ATOM   3441  CA   ALA B  66      61.344  44.558 -20.701  1.00 27.77           C
ATOM   3442  CB   ALA B  66      61.762  45.632 -19.695  1.00 27.63           C
ATOM   3443  C    ALA B  66      62.510  44.166 -21.616  1.00 26.98           C
ATOM   3444  O    ALA B  66      62.609  44.656 -22.742  1.00 30.33           O
ATOM   3445  N    GLU B  67      63.366  43.259 -21.145  1.00 24.08           N
ATOM   3446  CA   GLU B  67      64.467  42.733 -21.952  1.00 28.07           C
ATOM   3447  CB   GLU B  67      65.407  41.849 -21.115  1.00 37.69           C
ATOM   3448  CG   GLU B  67      65.217  40.347 -21.266  1.00 48.38           C
ATOM   3449  CD   GLU B  67      66.474  39.631 -21.720  1.00 54.67           C
ATOM   3450  OE1  GLU B  67      66.492  39.129 -22.865  1.00 56.59           O
ATOM   3451  OE2  GLU B  67      67.441  39.561 -20.929  1.00 58.10           O
ATOM   3452  C    GLU B  67      63.989  42.028 -23.229  1.00 26.99           C
ATOM   3453  O    GLU B  67      64.609  42.170 -24.277  1.00 25.93           O
ATOM   3454  N    GLU B  68      62.881  41.290 -23.146  1.00 23.66           N
ATOM   3455  CA   GLU B  68      62.310  40.638 -24.322  1.00 23.59           C
ATOM   3456  CB   GLU B  68      61.200  39.658 -23.923  1.00 25.21           C
ATOM   3457  CG   GLU B  68      61.695  38.325 -23.384  1.00 33.01           C
ATOM   3458  CD   GLU B  68      60.569  37.475 -22.822  1.00 34.12           C
ATOM   3459  OE1  GLU B  68      59.944  36.729 -23.603  1.00 37.57           O
ATOM   3460  OE2  GLU B  68      60.302  37.562 -21.607  1.00 35.49           O
ATOM   3461  C    GLU B  68      61.762  41.677 -25.302  1.00 18.20           C
ATOM   3462  O    GLU B  68      62.010  41.593 -26.497  1.00 21.51           O
ATOM   3463  N    MET B  69      61.026  42.655 -24.784  1.00 20.38           N
ATOM   3464  CA   MET B  69      60.372  43.661 -25.631  1.00 20.01           C
ATOM   3465  CB   MET B  69      59.373  44.484 -24.828  1.00 19.58           C
ATOM   3466  CG   MET B  69      58.209  43.670 -24.293  1.00 20.19           C
ATOM   3467  SD   MET B  69      57.113  44.696 -23.329  1.00 26.93           S
```

FIGURE 3JJJ

| ATOM | 3468 | CE  | MET  | B | 69 | 55.888 | 43.490 | -22.897 | 1.00 | 25.63 | C |
|------|------|-----|------|---|----|--------|--------|---------|------|-------|---|
| ATOM | 3469 | C   | MET  | B | 69 | 61.359 | 44.589 | -26.330 | 1.00 | 23.56 | C |
| ATOM | 3470 | O   | MET  | B | 69 | 61.112 | 45.011 | -27.466 | 1.00 | 20.41 | O |
| ATOM | 3471 | N   | THR  | B | 70 | 62.473 | 44.900 | -25.663 | 1.00 | 20.42 | N |
| ATOM | 3472 | CA  | THR  | B | 70 | 63.462 | 45.812 | -26.250 | 1.00 | 23.60 | C |
| ATOM | 3473 | CB  | THR  | B | 70 | 64.304 | 46.566 | -25.179 | 1.00 | 22.88 | C |
| ATOM | 3474 | OG1 | THR  | B | 70 | 64.913 | 45.626 | -24.292 | 1.00 | 24.59 | O |
| ATOM | 3475 | CG2 | THR  | B | 70 | 63.422 | 47.424 | -24.288 | 1.00 | 23.08 | C |
| ATOM | 3476 | C   | THR  | B | 70 | 64.379 | 45.143 | -27.268 | 1.00 | 23.91 | C |
| ATOM | 3477 | O   | THR  | B | 70 | 65.309 | 45.776 | -27.772 | 1.00 | 25.37 | O |
| ATOM | 3478 | N   | LYS  | B | 71 | 64.128 | 43.870 | -27.569 | 1.00 | 20.75 | N |
| ATOM | 3479 | CA  | LYS  | B | 71 | 64.771 | 43.227 | -28.712 | 1.00 | 23.78 | C |
| ATOM | 3480 | CB  | LYS  | B | 71 | 64.467 | 41.720 | -28.777 | 1.00 | 26.41 | C |
| ATOM | 3481 | CG  | BLYS | B | 71 | 64.977 | 40.913 | -27.576 | 0.35 | 27.69 | C |
| ATOM | 3482 | CG  | ALYS | B | 71 | 65.260 | 40.877 | -27.781 | 0.65 | 34.84 | C |
| ATOM | 3483 | CD  | BLYS | B | 71 | 66.500 | 40.874 | -27.505 | 0.35 | 27.54 | C |
| ATOM | 3484 | CD  | ALYS | B | 71 | 66.472 | 40.228 | -28.440 | 0.65 | 39.51 | C |
| ATOM | 3485 | CE  | BLYS | B | 71 | 66.970 | 40.010 | -26.344 | 0.35 | 28.95 | C |
| ATOM | 3486 | CE  | ALYS | B | 71 | 66.942 | 39.003 | -27.664 | 0.65 | 42.90 | C |
| ATOM | 3487 | NZ  | BLYS | B | 71 | 67.314 | 40.828 | -25.150 | 0.35 | 28.38 | N |
| ATOM | 3488 | NZ  | ALYS | B | 71 | 66.135 | 37.786 | -27.973 | 0.65 | 43.44 | N |
| ATOM | 3489 | C   | LYS  | B | 71 | 64.333 | 43.924 | -29.998 | 1.00 | 23.39 | C |
| ATOM | 3490 | O   | LYS  | B | 71 | 65.031 | 43.871 | -31.012 | 1.00 | 27.51 | O |
| ATOM | 3491 | N   | TYR  | B | 72 | 63.173 | 44.578 | -29.943 | 1.00 | 22.08 | N |
| ATOM | 3492 | CA  | TYR  | B | 72 | 62.691 | 45.391 | -31.054 | 1.00 | 21.13 | C |
| ATOM | 3493 | CB  | TYR  | B | 72 | 61.450 | 44.765 | -31.700 | 1.00 | 22.47 | C |
| ATOM | 3494 | CG  | TYR  | B | 72 | 60.928 | 45.609 | -32.837 | 1.00 | 21.07 | C |
| ATOM | 3495 | CD1 | TYR  | B | 72 | 59.652 | 46.171 | -32.787 | 1.00 | 24.78 | C |
| ATOM | 3496 | CE1 | TYR  | B | 72 | 59.175 | 46.963 | -33.836 | 1.00 | 26.14 | C |
| ATOM | 3497 | CZ  | TYR  | B | 72 | 59.987 | 47.201 | -34.931 | 1.00 | 27.13 | C |
| ATOM | 3498 | OH  | TYR  | B | 72 | 59.530 | 47.974 | -35.975 | 1.00 | 30.14 | O |
| ATOM | 3499 | CE2 | TYR  | B | 72 | 61.261 | 46.658 | -34.998 | 1.00 | 26.15 | C |
| ATOM | 3500 | CD2 | TYR  | B | 72 | 61.726 | 45.870 | -33.951 | 1.00 | 24.21 | C |
| ATOM | 3501 | C   | TYR  | B | 72 | 62.391 | 46.847 | -30.670 | 1.00 | 20.76 | C |
| ATOM | 3502 | O   | TYR  | B | 72 | 62.883 | 47.786 | -31.313 | 1.00 | 21.88 | O |
| ATOM | 3503 | N   | HIS  | B | 73 | 61.556 | 47.024 | -29.652 | 1.00 | 17.63 | N |
| ATOM | 3504 | CA  | HIS  | B | 73 | 61.102 | 48.343 | -29.228 | 1.00 | 16.93 | C |
| ATOM | 3505 | CB  | HIS  | B | 73 | 59.898 | 48.217 | -28.306 | 1.00 | 16.05 | C |
| ATOM | 3506 | CG  | HIS  | B | 73 | 58.681 | 47.692 | -28.993 | 1.00 | 18.71 | C |
| ATOM | 3507 | ND1 | HIS  | B | 73 | 57.883 | 48.485 | -29.788 | 1.00 | 17.52 | N |
| ATOM | 3508 | CE1 | HIS  | B | 73 | 56.893 | 47.756 | -30.276 | 1.00 | 17.77 | C |
| ATOM | 3509 | NE2 | HIS  | B | 73 | 57.026 | 46.521 | -29.830 | 1.00 | 17.71 | N |
| ATOM | 3510 | CD2 | HIS  | B | 73 | 58.138 | 46.452 | -29.025 | 1.00 | 18.64 | C |
| ATOM | 3511 | C   | HIS  | B | 73 | 62.198 | 49.128 | -28.527 | 1.00 | 20.19 | C |
| ATOM | 3512 | O   | HIS  | B | 73 | 63.105 | 48.554 | -27.939 | 1.00 | 19.93 | O |
| ATOM | 3513 | N   | SER  | B | 74 | 62.100 | 50.447 | -28.595 | 1.00 | 19.75 | N |
| ATOM | 3514 | CA  | SER  | B | 74 | 63.065 | 51.305 | -27.919 | 1.00 | 24.58 | C |
| ATOM | 3515 | CB  | SER  | B | 74 | 62.972 | 52.743 | -28.449 | 1.00 | 27.25 | C |
| ATOM | 3516 | OG  | SER  | B | 74 | 61.854 | 53.429 | -27.913 | 1.00 | 29.10 | O |
| ATOM | 3517 | C   | SER  | B | 74 | 62.899 | 51.243 | -26.397 | 1.00 | 25.32 | C |
| ATOM | 3518 | O   | SER  | B | 74 | 61.786 | 51.098 | -25.886 | 1.00 | 21.76 | O |
| ATOM | 3519 | N   | ASP  | B | 75 | 64.030 | 51.323 | -25.693 | 1.00 | 25.20 | N |
| ATOM | 3520 | CA  | ASP  | B | 75 | 64.095 | 51.336 | -24.231 | 1.00 | 31.82 | C |
| ATOM | 3521 | CB  | ASP  | B | 75 | 65.521 | 51.699 | -23.788 | 1.00 | 39.80 | C |
| ATOM | 3522 | CG  | ASP  | B | 75 | 66.362 | 50.489 | -23.442 | 1.00 | 46.47 | C |
| ATOM | 3523 | OD1 | ASP  | B | 75 | 67.238 | 50.621 | -22.562 | 1.00 | 52.62 | O |
| ATOM | 3524 | OD2 | ASP  | B | 75 | 66.234 | 49.374 | -23.990 | 1.00 | 50.68 | O |

FIGURE 3KKK

```
ATOM   3525  C   ASP B  75      63.151  52.370 -23.646  1.00 27.40           C
ATOM   3526  O   ASP B  75      62.435  52.105 -22.676  1.00 25.69           O
ATOM   3527  N   GLU B  76      63.175  53.556 -24.246  1.00 24.85           N
ATOM   3528  CA  GLU B  76      62.421  54.704 -23.765  1.00 26.81           C
ATOM   3529  CB  GLU B  76      62.841  55.968 -24.530  1.00 28.67           C
ATOM   3530  CG  GLU B  76      64.358  56.150 -24.661  1.00 37.57           C
ATOM   3531  CD  GLU B  76      64.920  55.651 -25.995  1.00 41.29           C
ATOM   3532  OE1 GLU B  76      65.087  56.477 -26.924  1.00 41.83           O
ATOM   3533  OE2 GLU B  76      65.211  54.435 -26.118  1.00 31.65           O
ATOM   3534  C   GLU B  76      60.912  54.463 -23.870  1.00 25.40           C
ATOM   3535  O   GLU B  76      60.165  54.802 -22.953  1.00 24.36           O
ATOM   3536  N   TYR B  77      60.482  53.856 -24.978  1.00 22.01           N
ATOM   3537  CA  TYR B  77      59.068  53.537 -25.187  1.00 21.94           C
ATOM   3538  CB  TYR B  77      58.825  53.076 -26.630  1.00 20.32           C
ATOM   3539  CG  TYR B  77      57.403  52.620 -26.928  1.00 19.95           C
ATOM   3540  CD1 TYR B  77      56.305  53.392 -26.557  1.00 18.65           C
ATOM   3541  CE1 TYR B  77      54.993  52.972 -26.826  1.00 20.24           C
ATOM   3542  CZ  TYR B  77      54.787  51.765 -27.484  1.00 19.44           C
ATOM   3543  OH  TYR B  77      53.505  51.353 -27.752  1.00 16.65           O
ATOM   3544  CE2 TYR B  77      55.866  50.976 -27.859  1.00 17.99           C
ATOM   3545  CD2 TYR B  77      57.167  51.411 -27.583  1.00 19.29           C
ATOM   3546  C   TYR B  77      58.576  52.493 -24.172  1.00 19.36           C
ATOM   3547  O   TYR B  77      57.529  52.668 -23.550  1.00 20.98           O
ATOM   3548  N   ILE B  78      59.347  51.427 -23.999  1.00 19.81           N
ATOM   3549  CA  ILE B  78      58.987  50.370 -23.051  1.00 19.78           C
ATOM   3550  CB  ILE B  78      59.921  49.143 -23.215  1.00 18.93           C
ATOM   3551  CG1 ILE B  78      59.768  48.522 -24.617  1.00 20.13           C
ATOM   3552  CD1 ILE B  78      58.291  48.337 -25.099  1.00 19.21           C
ATOM   3553  CG2 ILE B  78      59.661  48.087 -22.120  1.00 21.07           C
ATOM   3554  C   ILE B  78      58.952  50.900 -21.611  1.00 22.72           C
ATOM   3555  O   ILE B  78      58.036  50.574 -20.844  1.00 22.35           O
ATOM   3556  N   LYS B  79      59.927  51.738 -21.256  1.00 23.14           N
ATOM   3557  CA  LYS B  79      59.931  52.389 -19.942  1.00 25.94           C
ATOM   3558  CB  LYS B  79      61.167  53.284 -19.771  1.00 27.71           C
ATOM   3559  CG  LYS B  79      61.400  53.741 -18.333  1.00 37.39           C
ATOM   3560  CD  LYS B  79      62.488  54.804 -18.256  1.00 42.72           C
ATOM   3561  CE  LYS B  79      62.485  55.501 -16.901  1.00 45.68           C
ATOM   3562  NZ  LYS B  79      63.199  56.812 -16.967  1.00 50.52           N
ATOM   3563  C   LYS B  79      58.654  53.203 -19.736  1.00 22.38           C
ATOM   3564  O   LYS B  79      58.063  53.181 -18.656  1.00 23.65           O
ATOM   3565  N   PHE B  80      58.235  53.916 -20.780  1.00 23.07           N
ATOM   3566  CA  PHE B  80      57.013  54.704 -20.726  1.00 21.95           C
ATOM   3567  CB  PHE B  80      56.850  55.540 -21.995  1.00 22.14           C
ATOM   3568  CG  PHE B  80      55.474  56.077 -22.181  1.00 22.61           C
ATOM   3569  CD1 PHE B  80      54.597  55.484 -23.085  1.00 21.50           C
ATOM   3570  CE1 PHE B  80      53.305  55.977 -23.245  1.00 21.26           C
ATOM   3571  CZ  PHE B  80      52.886  57.066 -22.493  1.00 24.11           C
ATOM   3572  CE2 PHE B  80      53.749  57.656 -21.590  1.00 23.49           C
ATOM   3573  CD2 PHE B  80      55.035  57.162 -21.433  1.00 24.45           C
ATOM   3574  C   PHE B  80      55.773  53.830 -20.490  1.00 21.24           C
ATOM   3575  O   PHE B  80      54.938  54.150 -19.642  1.00 22.04           O
ATOM   3576  N   LEU B  81      55.672  52.719 -21.219  1.00 22.25           N
ATOM   3577  CA  LEU B  81      54.528  51.814 -21.074  1.00 20.38           C
ATOM   3578  CB  LEU B  81      54.590  50.685 -22.111  1.00 18.71           C
ATOM   3579  CG  LEU B  81      54.341  51.003 -23.588  1.00 21.37           C
ATOM   3580  CD1 LEU B  81      54.428  49.715 -24.407  1.00 18.65           C
ATOM   3581  CD2 LEU B  81      52.995  51.711 -23.837  1.00 19.80           C
```

FIGURE 3LLL

```
ATOM   3582  C   LEU B  81      54.456  51.230 -19.668  1.00 24.31           C
ATOM   3583  O   LEU B  81      53.367  51.015 -19.132  1.00 22.50           O
ATOM   3584  N   ARG B  82      55.629  50.993 -19.081  1.00 23.28           N
ATOM   3585  CA  ARG B  82      55.755  50.451 -17.731  1.00 28.34           C
ATOM   3586  CB  ARG B  82      57.180  49.918 -17.514  1.00 30.66           C
ATOM   3587  CG  ARG B  82      57.374  49.128 -16.217  1.00 41.46           C
ATOM   3588  CD  ARG B  82      58.251  47.893 -16.348  1.00 45.54           C
ATOM   3589  NE  ARG B  82      59.652  48.227 -16.597  1.00 50.40           N
ATOM   3590  CZ  ARG B  82      60.637  47.337 -16.666  1.00 51.99           C
ATOM   3591  NH1 ARG B  82      61.877  47.745 -16.899  1.00 49.38           N
ATOM   3592  NH2 ARG B  82      60.388  46.039 -16.506  1.00 51.90           N
ATOM   3593  C   ARG B  82      55.389  51.474 -16.649  1.00 27.54           C
ATOM   3594  O   ARG B  82      55.101  51.099 -15.516  1.00 30.28           O
ATOM   3595  N   SER B  83      55.380  52.755 -17.012  1.00 28.13           N
ATOM   3596  CA  SER B  83      55.181  53.848 -16.054  1.00 28.02           C
ATOM   3597  CB  SER B  83      56.214  54.957 -16.295  1.00 30.12           C
ATOM   3598  OG  SER B  83      57.539  54.463 -16.203  1.00 33.57           O
ATOM   3599  C   SER B  83      53.786  54.463 -16.093  1.00 30.36           C
ATOM   3600  O   SER B  83      53.259  54.883 -15.054  1.00 27.73           O
ATOM   3601  N   ILE B  84      53.205  54.531 -17.292  1.00 26.01           N
ATOM   3602  CA  ILE B  84      51.955  55.250 -17.523  1.00 27.19           C
ATOM   3603  CB  ILE B  84      51.723  55.515 -19.058  1.00 27.26           C
ATOM   3604  CG1 ILE B  84      50.584  56.514 -19.280  1.00 28.02           C
ATOM   3605  CD1 ILE B  84      50.993  57.965 -19.159  1.00 30.20           C
ATOM   3606  CG2 ILE B  84      51.445  54.219 -19.830  1.00 24.93           C
ATOM   3607  C   ILE B  84      50.741  54.589 -16.858  1.00 29.56           C
ATOM   3608  O   ILE B  84      50.505  53.391 -17.009  1.00 28.40           O
ATOM   3609  N   ARG B  85      49.989  55.387 -16.106  1.00 30.15           N
ATOM   3610  CA  ARG B  85      48.783  54.916 -15.428  1.00 31.78           C
ATOM   3611  CB  ARG B  85      49.094  54.614 -13.954  1.00 35.34           C
ATOM   3612  CG  ARG B  85      50.009  53.416 -13.742  1.00 41.11           C
ATOM   3613  CD  ARG B  85      50.324  53.111 -12.294  1.00 47.83           C
ATOM   3614  NE  ARG B  85      51.541  53.792 -11.859  1.00 54.73           N
ATOM   3615  CZ  ARG B  85      51.567  54.817 -11.015  1.00 56.25           C
ATOM   3616  NH1 ARG B  85      52.725  55.371 -10.682  1.00 57.28           N
ATOM   3617  NH2 ARG B  85      50.441  55.290 -10.499  1.00 56.82           N
ATOM   3618  C   ARG B  85      47.702  55.994 -15.567  1.00 31.26           C
ATOM   3619  O   ARG B  85      48.034  57.149 -15.841  1.00 32.69           O
ATOM   3620  N   PRO B  86      46.420  55.642 -15.421  1.00 32.32           N
ATOM   3621  CA  PRO B  86      45.352  56.651 -15.490  1.00 34.00           C
ATOM   3622  CB  PRO B  86      44.092  55.854 -15.142  1.00 35.01           C
ATOM   3623  CG  PRO B  86      44.417  54.466 -15.558  1.00 32.36           C
ATOM   3624  CD  PRO B  86      45.874  54.287 -15.214  1.00 32.80           C
ATOM   3625  C   PRO B  86      45.558  57.800 -14.497  1.00 36.79           C
ATOM   3626  O   PRO B  86      45.228  58.936 -14.826  1.00 37.86           O
ATOM   3627  N   ASP B  87      46.129  57.505 -13.330  1.00 38.39           N
ATOM   3628  CA  ASP B  87      46.309  58.500 -12.270  1.00 43.54           C
ATOM   3629  CB  ASP B  87      46.376  57.812 -10.900  1.00 45.90           C
ATOM   3630  CG  ASP B  87      47.540  56.849 -10.787  1.00 49.62           C
ATOM   3631  OD1 ASP B  87      47.363  55.653 -11.099  1.00 53.63           O
ATOM   3632  OD2 ASP B  87      48.672  57.200 -10.401  1.00 52.23           O
ATOM   3633  C   ASP B  87      47.504  59.455 -12.457  1.00 43.84           C
ATOM   3634  O   ASP B  87      47.589  60.472 -11.764  1.00 44.37           O
ATOM   3635  N   ASN B  88      48.417  59.139 -13.376  1.00 40.42           N
ATOM   3636  CA  ASN B  88      49.554  60.026 -13.657  1.00 38.99           C
ATOM   3637  CB  ASN B  88      50.884  59.371 -13.242  1.00 38.63           C
ATOM   3638  CG  ASN B  88      51.231  58.137 -14.074  1.00 36.47           C
```

FIGURE 3MMM

| | | | | | | | | | | |
|---|---|---|---|---|---|---|---|---|---|---|
| ATOM | 3639 | OD1 | ASN | B | 88 | 50.714 | 57.940 | -15.173 | 1.00 33.52 | O |
| ATOM | 3640 | ND2 | ASN | B | 88 | 52.123 | 57.309 | -13.546 | 1.00 33.11 | N |
| ATOM | 3641 | C | ASN | B | 88 | 49.631 | 60.565 | -15.094 | 1.00 39.39 | C |
| ATOM | 3642 | O | ASN | B | 88 | 50.683 | 61.039 | -15.533 | 1.00 39.80 | O |
| ATOM | 3643 | N | MET | B | 89 | 48.514 | 60.495 | -15.814 | 1.00 38.90 | N |
| ATOM | 3644 | CA | MET | B | 89 | 48.441 | 60.938 | -17.208 | 1.00 43.18 | C |
| ATOM | 3645 | CB | MET | B | 89 | 47.044 | 60.688 | -17.771 | 1.00 45.41 | C |
| ATOM | 3646 | CG | MET | B | 89 | 46.848 | 59.310 | -18.358 | 1.00 43.97 | C |
| ATOM | 3647 | SD | MET | B | 89 | 45.109 | 58.992 | -18.684 | 1.00 46.76 | S |
| ATOM | 3648 | CE | MET | B | 89 | 44.900 | 59.748 | -20.265 | 1.00 47.46 | C |
| ATOM | 3649 | C | MET | B | 89 | 48.812 | 62.404 | -17.418 | 1.00 45.70 | C |
| ATOM | 3650 | O | MET | B | 89 | 49.435 | 62.747 | -18.425 | 1.00 47.55 | O |
| ATOM | 3651 | N | SER | B | 90 | 48.423 | 63.262 | -16.474 | 1.00 47.30 | N |
| ATOM | 3652 | CA | SER | B | 90 | 48.698 | 64.697 | -16.564 | 1.00 48.59 | C |
| ATOM | 3653 | CB | SER | B | 90 | 47.984 | 65.458 | -15.443 | 1.00 51.96 | C |
| ATOM | 3654 | OG | SER | B | 90 | 48.370 | 64.968 | -14.170 | 1.00 53.49 | O |
| ATOM | 3655 | C | SER | B | 90 | 50.198 | 64.994 | -16.542 | 1.00 47.56 | C |
| ATOM | 3656 | O | SER | B | 90 | 50.670 | 65.875 | -17.261 | 1.00 50.40 | O |
| ATOM | 3657 | N | GLU | B | 91 | 50.938 | 64.240 | -15.731 | 1.00 45.97 | N |
| ATOM | 3658 | CA | GLU | B | 91 | 52.391 | 64.378 | -15.628 | 1.00 46.68 | C |
| ATOM | 3659 | CB | GLU | B | 91 | 52.911 | 63.613 | -14.403 | 1.00 52.70 | C |
| ATOM | 3660 | CG | GLU | B | 91 | 52.508 | 64.225 | -13.067 | 1.00 59.06 | C |
| ATOM | 3661 | CD | GLU | B | 91 | 52.581 | 63.239 | -11.913 | 1.00 63.48 | C |
| ATOM | 3662 | OE1 | GLU | B | 91 | 53.463 | 63.408 | -11.041 | 1.00 65.35 | O |
| ATOM | 3663 | OE2 | GLU | B | 91 | 51.754 | 62.302 | -11.866 | 1.00 64.70 | O |
| ATOM | 3664 | C | GLU | B | 91 | 53.134 | 63.913 | -16.887 | 1.00 45.33 | C |
| ATOM | 3665 | O | GLU | B | 91 | 54.260 | 64.349 | -17.145 | 1.00 44.94 | O |
| ATOM | 3666 | N | TYR | B | 92 | 52.498 | 63.042 | -17.669 | 1.00 40.26 | N |
| ATOM | 3667 | CA | TYR | B | 92 | 53.149 | 62.391 | -18.806 | 1.00 38.09 | C |
| ATOM | 3668 | CB | TYR | B | 92 | 53.011 | 60.873 | -18.671 | 1.00 37.64 | C |
| ATOM | 3669 | CG | TYR | B | 92 | 54.007 | 60.218 | -17.754 | 1.00 37.03 | C |
| ATOM | 3670 | CD1 | TYR | B | 92 | 53.664 | 59.897 | -16.442 | 1.00 36.95 | C |
| ATOM | 3671 | CE1 | TYR | B | 92 | 54.580 | 59.284 | -15.589 | 1.00 38.80 | C |
| ATOM | 3672 | CZ | TYR | B | 92 | 55.850 | 58.984 | -16.052 | 1.00 39.58 | C |
| ATOM | 3673 | OH | TYR | B | 92 | 56.756 | 58.379 | -15.215 | 1.00 41.35 | O |
| ATOM | 3674 | CE2 | TYR | B | 92 | 56.215 | 59.290 | -17.355 | 1.00 39.34 | C |
| ATOM | 3675 | CD2 | TYR | B | 92 | 55.292 | 59.904 | -18.199 | 1.00 39.18 | C |
| ATOM | 3676 | C | TYR | B | 92 | 52.595 | 62.808 | -20.172 | 1.00 39.81 | C |
| ATOM | 3677 | O | TYR | B | 92 | 52.831 | 62.115 | -21.171 | 1.00 37.66 | O |
| ATOM | 3678 | N | SER | B | 93 | 51.875 | 63.930 | -20.220 | 1.00 38.31 | N |
| ATOM | 3679 | CA | SER | B | 93 | 51.174 | 64.363 | -21.437 | 1.00 40.95 | C |
| ATOM | 3680 | CB | SER | B | 93 | 50.385 | 65.658 | -21.193 | 1.00 42.77 | C |
| ATOM | 3681 | OG | SER | B | 93 | 51.243 | 66.786 | -21.164 | 1.00 46.96 | O |
| ATOM | 3682 | C | SER | B | 93 | 52.073 | 64.493 | -22.675 | 1.00 38.73 | C |
| ATOM | 3683 | O | SER | B | 93 | 51.666 | 64.128 | -23.777 | 1.00 38.49 | O |
| ATOM | 3684 | N | LYS | B | 94 | 53.288 | 65.008 | -22.486 | 1.00 38.57 | N |
| ATOM | 3685 | CA | LYS | B | 94 | 54.257 | 65.139 | -23.577 | 1.00 39.39 | C |
| ATOM | 3686 | CB | LYS | B | 94 | 55.458 | 65.985 | -23.142 | 1.00 46.48 | C |
| ATOM | 3687 | CG | LYS | B | 94 | 55.192 | 67.489 | -23.144 | 1.00 53.56 | C |
| ATOM | 3688 | CD | LYS | B | 94 | 56.003 | 68.204 | -24.221 | 1.00 58.64 | C |
| ATOM | 3689 | CE | LYS | B | 94 | 55.742 | 69.710 | -24.202 | 1.00 61.26 | C |
| ATOM | 3690 | NZ | LYS | B | 94 | 54.833 | 70.136 | -25.312 | 1.00 61.77 | N |
| ATOM | 3691 | C | LYS | B | 94 | 54.731 | 63.777 | -24.088 | 1.00 35.28 | C |
| ATOM | 3692 | O | LYS | B | 94 | 54.956 | 63.593 | -25.286 | 1.00 31.75 | O |
| ATOM | 3693 | N | GLN | B | 95 | 54.879 | 62.826 | -23.173 | 1.00 28.67 | N |
| ATOM | 3694 | CA | GLN | B | 95 | 55.291 | 61.476 | -23.543 | 1.00 31.51 | C |
| ATOM | 3695 | CB | GLN | B | 95 | 55.869 | 60.733 | -22.340 | 1.00 35.30 | C |

FIGURE 3NNN

| | | | | | | | | | | |
|---|---|---|---|---|---|---|---|---|---|---|
| ATOM | 3696 | CG | GLN | B | 95 | 57.329 | 61.096 | -22.061 | 1.00 42.05 | C |
| ATOM | 3697 | CD | GLN | B | 95 | 57.940 | 60.299 | -20.923 | 1.00 47.50 | C |
| ATOM | 3698 | OE1 | GLN | B | 95 | 58.234 | 59.110 | -21.072 | 1.00 49.63 | O |
| ATOM | 3699 | NE2 | GLN | B | 95 | 58.146 | 60.956 | -19.786 | 1.00 50.71 | N |
| ATOM | 3700 | C | GLN | B | 95 | 54.143 | 60.702 | -24.191 | 1.00 26.02 | C |
| ATOM | 3701 | O | GLN | B | 95 | 54.362 | 59.925 | -25.116 | 1.00 26.70 | O |
| ATOM | 3702 | N | MET | B | 96 | 52.920 | 60.935 | -23.721 | 1.00 24.97 | N |
| ATOM | 3703 | CA | MET | B | 96 | 51.735 | 60.358 | -24.356 | 1.00 28.04 | C |
| ATOM | 3704 | CB | MET | B | 96 | 50.470 | 60.759 | -23.602 | 1.00 29.05 | C |
| ATOM | 3705 | CG | MET | B | 96 | 50.232 | 59.958 | -22.324 | 1.00 30.36 | C |
| ATOM | 3706 | SD | MET | B | 96 | 48.837 | 60.567 | -21.358 | 1.00 35.97 | S |
| ATOM | 3707 | CE | MET | B | 96 | 47.507 | 60.511 | -22.579 | 1.00 37.95 | C |
| ATOM | 3708 | C | MET | B | 96 | 51.627 | 60.754 | -25.834 | 1.00 30.20 | C |
| ATOM | 3709 | O | MET | B | 96 | 51.266 | 59.933 | -26.679 | 1.00 26.92 | O |
| ATOM | 3710 | N | GLN | B | 97 | 51.950 | 62.011 | -26.138 | 1.00 28.90 | N |
| ATOM | 3711 | CA | GLN | B | 97 | 51.916 | 62.504 | -27.510 | 1.00 28.29 | C |
| ATOM | 3712 | CB | GLN | B | 97 | 52.020 | 64.034 | -27.538 | 1.00 34.33 | C |
| ATOM | 3713 | CG | GLN | B | 97 | 50.662 | 64.725 | -27.557 | 1.00 43.73 | C |
| ATOM | 3714 | CD | GLN | B | 97 | 50.763 | 66.242 | -27.501 | 1.00 49.73 | C |
| ATOM | 3715 | OE1 | GLN | B | 97 | 51.303 | 66.870 | -28.417 | 1.00 49.03 | O |
| ATOM | 3716 | NE2 | GLN | B | 97 | 50.235 | 66.833 | -26.432 | 1.00 51.93 | N |
| ATOM | 3717 | C | GLN | B | 97 | 53.014 | 61.875 | -28.363 | 1.00 27.81 | C |
| ATOM | 3718 | O | GLN | B | 97 | 52.758 | 61.442 | -29.492 | 1.00 26.49 | O |
| ATOM | 3719 | N | ARG | B | 98 | 54.229 | 61.827 | -27.815 | 1.00 21.97 | N |
| ATOM | 3720 | CA | ARG | B | 98 | 55.379 | 61.239 | -28.495 | 1.00 28.18 | C |
| ATOM | 3721 | CB | ARG | B | 98 | 56.645 | 61.399 | -27.651 | 1.00 27.45 | C |
| ATOM | 3722 | CG | ARG | B | 98 | 57.941 | 61.284 | -28.449 | 1.00 39.21 | C |
| ATOM | 3723 | CD | ARG | B | 98 | 58.900 | 60.206 | -27.962 | 1.00 46.95 | C |
| ATOM | 3724 | NE | ARG | B | 98 | 59.591 | 60.579 | -26.725 | 1.00 54.26 | N |
| ATOM | 3725 | CZ | ARG | B | 98 | 60.880 | 60.344 | -26.468 | 1.00 57.63 | C |
| ATOM | 3726 | NH1 | ARG | B | 98 | 61.399 | 60.724 | -25.306 | 1.00 57.98 | N |
| ATOM | 3727 | NH2 | ARG | B | 98 | 61.655 | 59.734 | -27.362 | 1.00 57.97 | N |
| ATOM | 3728 | C | ARG | B | 98 | 55.168 | 59.757 | -28.822 | 1.00 25.70 | C |
| ATOM | 3729 | O | ARG | B | 98 | 55.491 | 59.308 | -29.923 | 1.00 22.83 | O |
| ATOM | 3730 | N | PHE | B | 99 | 54.623 | 59.013 | -27.866 | 1.00 23.87 | N |
| ATOM | 3731 | CA | PHE | B | 99 | 54.465 | 57.564 | -28.018 | 1.00 24.00 | C |
| ATOM | 3732 | CB | PHE | B | 99 | 54.814 | 56.861 | -26.701 | 1.00 22.59 | C |
| ATOM | 3733 | CG | PHE | B | 99 | 56.249 | 57.070 | -26.263 | 1.00 19.84 | C |
| ATOM | 3734 | CD1 | PHE | B | 99 | 57.303 | 56.719 | -27.099 | 1.00 24.39 | C |
| ATOM | 3735 | CE1 | PHE | B | 99 | 58.631 | 56.910 | -26.700 | 1.00 24.66 | C |
| ATOM | 3736 | CZ | PHE | B | 99 | 58.905 | 57.459 | -25.460 | 1.00 22.67 | C |
| ATOM | 3737 | CE2 | PHE | B | 99 | 57.861 | 57.813 | -24.617 | 1.00 22.78 | C |
| ATOM | 3738 | CD2 | PHE | B | 99 | 56.542 | 57.617 | -25.020 | 1.00 19.47 | C |
| ATOM | 3739 | C | PHE | B | 99 | 53.083 | 57.161 | -28.541 | 1.00 26.48 | C |
| ATOM | 3740 | O | PHE | B | 99 | 52.764 | 55.968 | -28.633 | 1.00 26.29 | O |
| ATOM | 3741 | N | ASN | B | 100 | 52.279 | 58.163 | -28.895 | 1.00 23.02 | N |
| ATOM | 3742 | CA | ASN | B | 100 | 50.948 | 57.972 | -29.481 | 1.00 27.67 | C |
| ATOM | 3743 | CB | ASN | B | 100 | 51.056 | 57.379 | -30.899 | 1.00 26.88 | C |
| ATOM | 3744 | CG | ASN | B | 100 | 49.788 | 57.566 | -31.714 | 1.00 33.11 | C |
| ATOM | 3745 | OD1 | ASN | B | 100 | 49.134 | 58.604 | -31.637 | 1.00 36.56 | O |
| ATOM | 3746 | ND2 | ASN | B | 100 | 49.434 | 56.551 | -32.502 | 1.00 30.74 | N |
| ATOM | 3747 | C | ASN | B | 100 | 49.990 | 57.158 | -28.606 | 1.00 25.82 | C |
| ATOM | 3748 | O | ASN | B | 100 | 49.220 | 56.337 | -29.103 | 1.00 25.22 | O |
| ATOM | 3749 | N | VAL | B | 101 | 50.046 | 57.395 | -27.300 | 1.00 25.74 | N |
| ATOM | 3750 | CA | VAL | B | 101 | 49.158 | 56.728 | -26.356 | 1.00 28.70 | C |
| ATOM | 3751 | CB | VAL | B | 101 | 49.966 | 56.020 | -25.240 | 1.00 26.89 | C |
| ATOM | 3752 | CG1 | VAL | B | 101 | 49.060 | 55.471 | -24.146 | 1.00 29.25 | C |

FIGURE 3000

```
ATOM   3753  CG2 VAL B 101      50.811  54.887 -25.823  1.00 28.28           C
ATOM   3754  C   VAL B 101      48.161  57.746 -25.790  1.00 32.53           C
ATOM   3755  O   VAL B 101      48.534  58.878 -25.472  1.00 33.68           O
ATOM   3756  N   GLY B 102      46.892  57.352 -25.699  1.00 30.69           N
ATOM   3757  CA  GLY B 102      45.874  58.194 -25.093  1.00 33.26           C
ATOM   3758  C   GLY B 102      44.616  58.422 -25.913  1.00 36.91           C
ATOM   3759  O   GLY B 102      43.634  58.950 -25.388  1.00 37.99           O
ATOM   3760  N   GLU B 103      44.643  58.039 -27.190  1.00 38.27           N
ATOM   3761  CA  GLU B 103      43.477  58.159 -28.070  1.00 39.23           C
ATOM   3762  CB  GLU B 103      43.797  59.055 -29.275  1.00 47.00           C
ATOM   3763  CG  GLU B 103      42.574  59.611 -29.995  1.00 55.49           C
ATOM   3764  CD  GLU B 103      42.527  61.131 -30.001  1.00 60.39           C
ATOM   3765  OE1 GLU B 103      43.382  61.757 -30.670  1.00 62.33           O
ATOM   3766  OE2 GLU B 103      41.629  61.699 -29.340  1.00 62.58           O
ATOM   3767  C   GLU B 103      42.979  56.773 -28.508  1.00 35.60           C
ATOM   3768  O   GLU B 103      42.297  56.086 -27.743  1.00 35.59           O
ATOM   3769  N   ASP B 104      43.332  56.365 -29.726  1.00 32.63           N
ATOM   3770  CA  ASP B 104      43.011  55.031 -30.230  1.00 33.21           C
ATOM   3771  CB  ASP B 104      43.509  54.865 -31.669  1.00 39.42           C
ATOM   3772  CG  ASP B 104      42.546  55.441 -32.700  1.00 44.91           C
ATOM   3773  OD1 ASP B 104      41.536  56.070 -32.311  1.00 47.54           O
ATOM   3774  OD2 ASP B 104      42.727  55.313 -33.931  1.00 48.52           O
ATOM   3775  C   ASP B 104      43.635  53.957 -29.349  1.00 27.18           C
ATOM   3776  O   ASP B 104      43.079  52.869 -29.198  1.00 27.61           O
ATOM   3777  N   CYS B 105      44.801  54.277 -28.788  1.00 22.25           N
ATOM   3778  CA  CYS B 105      45.506  53.408 -27.848  1.00 22.86           C
ATOM   3779  CB  CYS B 105      46.944  53.167 -28.325  1.00 22.68           C
ATOM   3780  SG  CYS B 105      47.087  52.658 -30.058  1.00 24.45           S
ATOM   3781  C   CYS B 105      45.492  54.049 -26.453  1.00 23.09           C
ATOM   3782  O   CYS B 105      46.458  54.716 -26.057  1.00 21.09           O
ATOM   3783  N   PRO B 106      44.402  53.834 -25.711  1.00 22.20           N
ATOM   3784  CA  PRO B 106      44.182  54.517 -24.432  1.00 22.98           C
ATOM   3785  CB  PRO B 106      42.733  54.156 -24.099  1.00 24.50           C
ATOM   3786  CG  PRO B 106      42.536  52.822 -24.740  1.00 23.13           C
ATOM   3787  CD  PRO B 106      43.292  52.915 -26.030  1.00 22.99           C
ATOM   3788  C   PRO B 106      45.098  54.017 -23.329  1.00 26.78           C
ATOM   3789  O   PRO B 106      45.698  52.938 -23.443  1.00 22.39           O
ATOM   3790  N   VAL B 107      45.217  54.824 -22.280  1.00 24.05           N
ATOM   3791  CA  VAL B 107      45.806  54.382 -21.030  1.00 25.91           C
ATOM   3792  CB  VAL B 107      46.393  55.563 -20.224  1.00 29.94           C
ATOM   3793  CG1 VAL B 107      47.055  55.060 -18.938  1.00 29.48           C
ATOM   3794  CG2 VAL B 107      47.388  56.354 -21.071  1.00 26.91           C
ATOM   3795  C   VAL B 107      44.698  53.720 -20.221  1.00 28.65           C
ATOM   3796  O   VAL B 107      43.628  54.301 -20.028  1.00 32.50           O
ATOM   3797  N   PHE B 108      44.946  52.499 -19.767  1.00 26.52           N
ATOM   3798  CA  PHE B 108      44.020  51.834 -18.858  1.00 27.03           C
ATOM   3799  CB  PHE B 108      43.036  50.915 -19.610  1.00 27.04           C
ATOM   3800  CG  PHE B 108      43.693  49.882 -20.495  1.00 24.17           C
ATOM   3801  CD1 PHE B 108      43.865  50.120 -21.859  1.00 21.94           C
ATOM   3802  CE1 PHE B 108      44.450  49.149 -22.690  1.00 21.20           C
ATOM   3803  CZ  PHE B 108      44.855  47.931 -22.152  1.00 21.92           C
ATOM   3804  CE2 PHE B 108      44.679  47.683 -20.794  1.00 20.80           C
ATOM   3805  CD2 PHE B 108      44.092  48.652 -19.977  1.00 23.64           C
ATOM   3806  C   PHE B 108      44.772  51.085 -17.777  1.00 27.15           C
ATOM   3807  O   PHE B 108      45.976  50.852 -17.909  1.00 23.41           O
ATOM   3808  N   ASP B 109      44.061  50.720 -16.709  1.00 25.29           N
ATOM   3809  CA  ASP B 109      44.655  50.011 -15.579  1.00 29.38           C
```

FIGURE 3PPP

```
ATOM   3810  CB   ASP B 109      43.620  49.783 -14.469  1.00 35.81           C
ATOM   3811  CG   ASP B 109      43.108  51.074 -13.860  1.00 42.40           C
ATOM   3812  OD1  ASP B 109      43.933  51.899 -13.410  1.00 46.68           O
ATOM   3813  OD2  ASP B 109      41.891  51.342 -13.782  1.00 42.75           O
ATOM   3814  C    ASP B 109      45.209  48.664 -16.019  1.00 26.93           C
ATOM   3815  O    ASP B 109      44.501  47.870 -16.634  1.00 28.44           O
ATOM   3816  N    GLY B 110      46.478  48.420 -15.703  1.00 24.67           N
ATOM   3817  CA   GLY B 110      47.122  47.161 -16.028  1.00 25.00           C
ATOM   3818  C    GLY B 110      47.599  47.064 -17.466  1.00 22.64           C
ATOM   3819  O    GLY B 110      47.890  45.968 -17.954  1.00 21.40           O
ATOM   3820  N    LEU B 111      47.688  48.207 -18.143  1.00 22.41           N
ATOM   3821  CA   LEU B 111      48.113  48.252 -19.540  1.00 22.94           C
ATOM   3822  CB   LEU B 111      48.301  49.709 -20.007  1.00 22.49           C
ATOM   3823  CG   LEU B 111      49.035  49.942 -21.332  1.00 25.88           C
ATOM   3824  CD1  LEU B 111      48.310  49.270 -22.493  1.00 24.86           C
ATOM   3825  CD2  LEU B 111      49.225  51.434 -21.607  1.00 29.70           C
ATOM   3826  C    LEU B 111      49.389  47.447 -19.786  1.00 20.23           C
ATOM   3827  O    LEU B 111      49.445  46.613 -20.693  1.00 20.50           O
ATOM   3828  N    PHE B 112      50.415  47.694 -18.980  1.00 19.98           N
ATOM   3829  CA   PHE B 112      51.690  47.039 -19.220  1.00 21.15           C
ATOM   3830  CB   PHE B 112      52.810  47.649 -18.382  1.00 23.45           C
ATOM   3831  CG   PHE B 112      54.165  47.106 -18.722  1.00 24.50           C
ATOM   3832  CD1  PHE B 112      54.762  47.414 -19.941  1.00 25.47           C
ATOM   3833  CE1  PHE B 112      56.014  46.903 -20.276  1.00 25.04           C
ATOM   3834  CZ   PHE B 112      56.677  46.076 -19.389  1.00 26.87           C
ATOM   3835  CE2  PHE B 112      56.091  45.755 -18.166  1.00 26.90           C
ATOM   3836  CD2  PHE B 112      54.835  46.269 -17.838  1.00 25.95           C
ATOM   3837  C    PHE B 112      51.607  45.531 -19.006  1.00 21.35           C
ATOM   3838  O    PHE B 112      52.142  44.765 -19.802  1.00 21.34           O
ATOM   3839  N    GLU B 113      50.917  45.119 -17.944  1.00 19.54           N
ATOM   3840  CA   GLU B 113      50.694  43.701 -17.654  1.00 21.92           C
ATOM   3841  CB   GLU B 113      49.888  43.573 -16.367  1.00 25.06           C
ATOM   3842  CG   GLU B 113      50.082  42.274 -15.608  1.00 37.10           C
ATOM   3843  CD   GLU B 113      49.379  42.296 -14.259  1.00 44.22           C
ATOM   3844  OE1  GLU B 113      50.025  41.946 -13.247  1.00 47.14           O
ATOM   3845  OE2  GLU B 113      48.180  42.673 -14.207  1.00 45.31           O
ATOM   3846  C    GLU B 113      49.958  43.008 -18.810  1.00 21.30           C
ATOM   3847  O    GLU B 113      50.308  41.894 -19.208  1.00 18.89           O
ATOM   3848  N    PHE B 114      48.943  43.688 -19.340  1.00 18.64           N
ATOM   3849  CA   PHE B 114      48.199  43.233 -20.513  1.00 20.59           C
ATOM   3850  CB   PHE B 114      47.085  44.244 -20.818  1.00 22.45           C
ATOM   3851  CG   PHE B 114      46.373  44.014 -22.124  1.00 23.54           C
ATOM   3852  CD1  PHE B 114      46.608  44.852 -23.214  1.00 23.31           C
ATOM   3853  CE1  PHE B 114      45.938  44.663 -24.423  1.00 26.03           C
ATOM   3854  CZ   PHE B 114      45.009  43.622 -24.548  1.00 23.58           C
ATOM   3855  CE2  PHE B 114      44.761  42.784 -23.460  1.00 28.45           C
ATOM   3856  CD2  PHE B 114      45.443  42.987 -22.252  1.00 23.61           C
ATOM   3857  C    PHE B 114      49.126  43.036 -21.721  1.00 20.37           C
ATOM   3858  O    PHE B 114      49.047  42.027 -22.414  1.00 17.39           O
ATOM   3859  N    CYS B 115      50.020  43.994 -21.957  1.00 16.81           N
ATOM   3860  CA   CYS B 115      51.011  43.858 -23.022  1.00 18.66           C
ATOM   3861  CB   CYS B 115      51.807  45.152 -23.193  1.00 19.67           C
ATOM   3862  SG   CYS B 115      50.777  46.522 -23.773  1.00 25.59           S
ATOM   3863  C    CYS B 115      51.955  42.684 -22.755  1.00 16.14           C
ATOM   3864  O    CYS B 115      52.314  41.952 -23.670  1.00 14.44           O
ATOM   3865  N    GLN B 116      52.363  42.515 -21.504  1.00 15.60           N
ATOM   3866  CA   GLN B 116      53.258  41.415 -21.143  1.00 16.04           C
```

FIGURE 3QQQ

```
ATOM   3867  CB   GLN B 116      53.613  41.496 -19.662  1.00 16.36           C
ATOM   3868  CG   GLN B 116      54.544  42.640 -19.334  1.00 21.18           C
ATOM   3869  CD   GLN B 116      54.936  42.633 -17.886  1.00 21.58           C
ATOM   3870  OE1  GLN B 116      54.114  42.929 -17.025  1.00 22.21           O
ATOM   3871  NE2  GLN B 116      56.189  42.295 -17.609  1.00 20.60           N
ATOM   3872  C    GLN B 116      52.660  40.042 -21.459  1.00 15.67           C
ATOM   3873  O    GLN B 116      53.350  39.166 -21.979  1.00 16.35           O
ATOM   3874  N    LEU B 117      51.381  39.868 -21.136  1.00 17.14           N
ATOM   3875  CA   LEU B 117      50.709  38.577 -21.291  1.00 20.53           C
ATOM   3876  CB   LEU B 117      49.425  38.540 -20.465  1.00 19.75           C
ATOM   3877  CG   LEU B 117      49.563  38.511 -18.941  1.00 22.04           C
ATOM   3878  CD1  LEU B 117      48.212  38.828 -18.320  1.00 22.30           C
ATOM   3879  CD2  LEU B 117      50.086  37.157 -18.445  1.00 25.76           C
ATOM   3880  C    LEU B 117      50.399  38.250 -22.748  1.00 19.48           C
ATOM   3881  O    LEU B 117      50.577  37.112 -23.191  1.00 19.72           O
ATOM   3882  N    SER B 118      49.928  39.256 -23.482  1.00 19.36           N
ATOM   3883  CA   SER B 118      49.709  39.132 -24.917  1.00 19.40           C
ATOM   3884  CB   SER B 118      49.130  40.446 -25.469  1.00 23.00           C
ATOM   3885  OG   SER B 118      49.238  40.502 -26.880  1.00 30.79           O
ATOM   3886  C    SER B 118      51.009  38.748 -25.633  1.00 20.79           C
ATOM   3887  O    SER B 118      51.040  37.810 -26.422  1.00 21.29           O
ATOM   3888  N    THR B 119      52.088  39.462 -25.329  1.00 16.68           N
ATOM   3889  CA   THR B 119      53.379  39.218 -25.959  1.00 14.73           C
ATOM   3890  CB   THR B 119      54.339  40.354 -25.612  1.00 19.24           C
ATOM   3891  OG1  THR B 119      53.803  41.584 -26.120  1.00 21.82           O
ATOM   3892  CG2  THR B 119      55.666  40.194 -26.343  1.00 21.43           C
ATOM   3893  C    THR B 119      53.983  37.879 -25.535  1.00 17.98           C
ATOM   3894  O    THR B 119      54.554  37.174 -26.357  1.00 18.62           O
ATOM   3895  N    GLY B 120      53.851  37.555 -24.250  1.00 17.52           N
ATOM   3896  CA   GLY B 120      54.447  36.357 -23.679  1.00 20.03           C
ATOM   3897  C    GLY B 120      54.059  35.115 -24.444  1.00 17.91           C
ATOM   3898  O    GLY B 120      54.915  34.290 -24.760  1.00 19.65           O
ATOM   3899  N    GLY B 121      52.772  35.002 -24.771  1.00 17.34           N
ATOM   3900  CA   GLY B 121      52.268  33.855 -25.508  1.00 18.21           C
ATOM   3901  C    GLY B 121      52.889  33.697 -26.885  1.00 17.26           C
ATOM   3902  O    GLY B 121      53.154  32.585 -27.336  1.00 17.34           O
ATOM   3903  N    SER B 122      53.122  34.816 -27.563  1.00 13.65           N
ATOM   3904  CA   SER B 122      53.682  34.788 -28.904  1.00 13.70           C
ATOM   3905  CB   SER B 122      53.522  36.167 -29.554  1.00 14.35           C
ATOM   3906  OG   SER B 122      52.141  36.466 -29.681  1.00 16.20           O
ATOM   3907  C    SER B 122      55.154  34.387 -28.885  1.00 13.23           C
ATOM   3908  O    SER B 122      55.584  33.547 -29.681  1.00 16.76           O
ATOM   3909  N    VAL B 123      55.923  35.005 -27.995  1.00 14.37           N
ATOM   3910  CA   VAL B 123      57.351  34.667 -27.871  1.00 18.24           C
ATOM   3911  CB   VAL B 123      58.118  35.709 -27.032  1.00 21.06           C
ATOM   3912  CG1  VAL B 123      59.558  35.262 -26.793  1.00 25.46           C
ATOM   3913  CG2  VAL B 123      58.109  37.078 -27.753  1.00 19.67           C
ATOM   3914  C    VAL B 123      57.557  33.233 -27.342  1.00 18.72           C
ATOM   3915  O    VAL B 123      58.415  32.496 -27.840  1.00 20.70           O
ATOM   3916  N    ALA B 124      56.753  32.833 -26.361  1.00 20.16           N
ATOM   3917  CA   ALA B 124      56.818  31.466 -25.835  1.00 20.13           C
ATOM   3918  CB   ALA B 124      55.908  31.303 -24.618  1.00 21.23           C
ATOM   3919  C    ALA B 124      56.487  30.425 -26.906  1.00 18.79           C
ATOM   3920  O    ALA B 124      57.119  29.380 -26.970  1.00 18.16           O
ATOM   3921  N    GLY B 125      55.499  30.721 -27.750  1.00 16.98           N
ATOM   3922  CA   GLY B 125      55.176  29.861 -28.882  1.00 16.45           C
ATOM   3923  C    GLY B 125      56.327  29.718 -29.862  1.00 20.50           C
```

FIGURE 3RRR

| ATOM | 3924 | O   | GLY | B | 125 | 56.641 | 28.609 | -30.308 | 1.00 | 17.74 | O |
|------|------|-----|-----|---|-----|--------|--------|---------|------|-------|---|
| ATOM | 3925 | N   | ALA | B | 126 | 56.960 | 30.840 | -30.200 | 1.00 | 17.13 | N |
| ATOM | 3926 | CA  | ALA | B | 126 | 58.136 | 30.818 | -31.069 | 1.00 | 18.25 | C |
| ATOM | 3927 | CB  | ALA | B | 126 | 58.633 | 32.244 | -31.341 | 1.00 | 15.94 | C |
| ATOM | 3928 | C   | ALA | B | 126 | 59.266 | 29.952 | -30.497 | 1.00 | 18.93 | C |
| ATOM | 3929 | O   | ALA | B | 126 | 59.914 | 29.204 | -31.237 | 1.00 | 21.73 | O |
| ATOM | 3930 | N   | VAL | B | 127 | 59.482 | 30.051 | -29.186 | 1.00 | 21.36 | N |
| ATOM | 3931 | CA  | VAL | B | 127 | 60.499 | 29.247 | -28.496 | 1.00 | 22.04 | C |
| ATOM | 3932 | CB  | VAL | B | 127 | 60.631 | 29.655 | -27.000 | 1.00 | 25.66 | C |
| ATOM | 3933 | CG1 | VAL | B | 127 | 61.496 | 28.647 | -26.214 | 1.00 | 27.11 | C |
| ATOM | 3934 | CG2 | VAL | B | 127 | 61.212 | 31.059 | -26.885 | 1.00 | 25.48 | C |
| ATOM | 3935 | C   | VAL | B | 127 | 60.180 | 27.753 | -28.633 | 1.00 | 22.14 | C |
| ATOM | 3936 | O   | VAL | B | 127 | 61.061 | 26.944 | -28.963 | 1.00 | 24.31 | O |
| ATOM | 3937 | N   | LYS | B | 128 | 58.918 | 27.401 | -28.393 | 1.00 | 21.33 | N |
| ATOM | 3938 | CA  | LYS | B | 128 | 58.435 | 26.026 | -28.544 | 1.00 | 25.19 | C |
| ATOM | 3939 | CB  | LYS | B | 128 | 56.954 | 25.947 | -28.156 | 1.00 | 29.86 | C |
| ATOM | 3940 | CG  | LYS | B | 128 | 56.633 | 24.961 | -27.045 | 1.00 | 40.74 | C |
| ATOM | 3941 | CD  | LYS | B | 128 | 56.802 | 25.569 | -25.664 | 1.00 | 43.55 | C |
| ATOM | 3942 | CE  | LYS | B | 128 | 56.632 | 24.509 | -24.582 | 1.00 | 46.91 | C |
| ATOM | 3943 | NZ  | LYS | B | 128 | 57.093 | 24.984 | -23.246 | 1.00 | 49.85 | N |
| ATOM | 3944 | C   | LYS | B | 128 | 58.656 | 25.477 | -29.960 | 1.00 | 25.18 | C |
| ATOM | 3945 | O   | LYS | B | 128 | 59.101 | 24.332 | -30.134 | 1.00 | 22.99 | O |
| ATOM | 3946 | N   | LEU | B | 129 | 58.355 | 26.295 | -30.968 | 1.00 | 16.26 | N |
| ATOM | 3947 | CA  | LEU | B | 129 | 58.586 | 25.929 | -32.363 | 1.00 | 18.49 | C |
| ATOM | 3948 | CB  | LEU | B | 129 | 58.048 | 27.024 | -33.307 | 1.00 | 17.39 | C |
| ATOM | 3949 | CG  | LEU | B | 129 | 56.678 | 26.957 | -34.010 | 1.00 | 27.07 | C |
| ATOM | 3950 | CD1 | LEU | B | 129 | 55.848 | 25.735 | -33.691 | 1.00 | 20.03 | C |
| ATOM | 3951 | CD2 | LEU | B | 129 | 55.864 | 28.238 | -33.789 | 1.00 | 22.35 | C |
| ATOM | 3952 | C   | LEU | B | 129 | 60.081 | 25.723 | -32.626 | 1.00 | 20.22 | C |
| ATOM | 3953 | O   | LEU | B | 129 | 60.467 | 24.737 | -33.257 | 1.00 | 23.10 | O |
| ATOM | 3954 | N   | ASN | B | 130 | 60.902 | 26.655 | -32.141 | 1.00 | 22.03 | N |
| ATOM | 3955 | CA  | ASN | B | 130 | 62.358 | 26.607 | -32.309 | 1.00 | 24.60 | C |
| ATOM | 3956 | CB  | ASN | B | 130 | 63.018 | 27.813 | -31.633 | 1.00 | 21.92 | C |
| ATOM | 3957 | CG  | ASN | B | 130 | 63.070 | 29.044 | -32.531 | 1.00 | 20.30 | C |
| ATOM | 3958 | OD1 | ASN | B | 130 | 62.811 | 28.969 | -33.728 | 1.00 | 20.60 | O |
| ATOM | 3959 | ND2 | ASN | B | 130 | 63.430 | 30.178 | -31.948 | 1.00 | 20.79 | N |
| ATOM | 3960 | C   | ASN | B | 130 | 62.956 | 25.335 | -31.712 | 1.00 | 30.46 | C |
| ATOM | 3961 | O   | ASN | B | 130 | 63.796 | 24.680 | -32.332 | 1.00 | 34.15 | O |
| ATOM | 3962 | N   | ARG | B | 131 | 62.513 | 25.002 | -30.503 | 1.00 | 30.95 | N |
| ATOM | 3963 | CA  | ARG | B | 131 | 62.998 | 23.826 | -29.778 | 1.00 | 32.51 | C |
| ATOM | 3964 | CB  | ARG | B | 131 | 62.758 | 24.002 | -28.274 | 1.00 | 33.41 | C |
| ATOM | 3965 | CG  | ARG | B | 131 | 63.820 | 24.865 | -27.596 | 1.00 | 39.19 | C |
| ATOM | 3966 | CD  | ARG | B | 131 | 63.447 | 25.393 | -26.221 | 1.00 | 44.79 | C |
| ATOM | 3967 | NE  | ARG | B | 131 | 64.388 | 26.421 | -25.769 | 1.00 | 48.21 | N |
| ATOM | 3968 | CZ  | ARG | B | 131 | 64.337 | 27.038 | -24.591 | 1.00 | 50.60 | C |
| ATOM | 3969 | NH1 | ARG | B | 131 | 65.244 | 27.958 | -24.292 | 1.00 | 52.87 | N |
| ATOM | 3970 | NH2 | ARG | B | 131 | 63.386 | 26.748 | -23.709 | 1.00 | 52.91 | N |
| ATOM | 3971 | C   | ARG | B | 131 | 62.381 | 22.525 | -30.295 | 1.00 | 32.58 | C |
| ATOM | 3972 | O   | ARG | B | 131 | 62.685 | 21.440 | -29.793 | 1.00 | 34.72 | O |
| ATOM | 3973 | N   | GLN | B | 132 | 61.527 | 22.646 | -31.312 | 1.00 | 26.94 | N |
| ATOM | 3974 | CA  | GLN | B | 132 | 60.831 | 21.519 | -31.930 | 1.00 | 31.69 | C |
| ATOM | 3975 | CB  | GLN | B | 132 | 61.808 | 20.633 | -32.719 | 1.00 | 36.27 | C |
| ATOM | 3976 | CG  | GLN | B | 132 | 62.235 | 21.219 | -34.063 | 1.00 | 38.78 | C |
| ATOM | 3977 | CD  | GLN | B | 132 | 63.450 | 20.522 | -34.662 | 1.00 | 42.94 | C |
| ATOM | 3978 | OE1 | GLN | B | 132 | 64.284 | 21.164 | -35.303 | 1.00 | 44.92 | O |
| ATOM | 3979 | NE2 | GLN | B | 132 | 63.550 | 19.213 | -34.460 | 1.00 | 41.23 | N |
| ATOM | 3980 | C   | GLN | B | 132 | 60.025 | 20.705 | -30.913 | 1.00 | 33.82 | C |

FIGURE 3SSS

| | | | | | | | | | | |
|---|---|---|---|---|---|---|---|---|---|---|
| ATOM | 3981 | C | GLN | B | 132 | 59.881 | 19.487 | -31.048 | 1.00 36.32 | O |
| ATOM | 3982 | N | GLN | B | 133 | 59.495 | 21.392 | -29.903 | 1.00 32.89 | N |
| ATOM | 3983 | CA | GLN | B | 133 | 58.649 | 20.763 | -28.885 | 1.00 34.79 | C |
| ATOM | 3984 | CB | GLN | B | 133 | 58.800 | 21.481 | -27.537 | 1.00 37.78 | C |
| ATOM | 3985 | CG | GLN | B | 133 | 60.201 | 21.374 | -26.928 | 1.00 43.56 | C |
| ATOM | 3986 | CD | GLN | B | 133 | 60.415 | 22.283 | -25.726 | 1.00 48.81 | C |
| ATOM | 3987 | OE1 | GLN | B | 133 | 59.971 | 23.432 | -25.713 | 1.00 53.11 | O |
| ATOM | 3988 | NE2 | GLN | B | 133 | 61.110 | 21.770 | -24.718 | 1.00 51.66 | N |
| ATOM | 3989 | C | GLN | B | 133 | 57.181 | 20.725 | -29.325 | 1.00 34.71 | C |
| ATOM | 3990 | O | GLN | B | 133 | 56.356 | 20.046 | -28.709 | 1.00 34.73 | O |
| ATOM | 3991 | N | THR | B | 134 | 56.872 | 21.452 | -30.398 | 1.00 28.47 | N |
| ATOM | 3992 | CA | THR | B | 134 | 55.533 | 21.496 | -30.979 | 1.00 25.62 | C |
| ATOM | 3993 | CB | THR | B | 134 | 54.665 | 22.574 | -30.258 | 1.00 26.34 | C |
| ATOM | 3994 | OG1 | THR | B | 134 | 53.295 | 22.429 | -30.639 | 1.00 24.49 | O |
| ATOM | 3995 | CG2 | THR | B | 134 | 55.015 | 23.994 | -30.719 | 1.00 21.48 | C |
| ATOM | 3996 | C | THR | B | 134 | 55.603 | 21.760 | -32.484 | 1.00 24.55 | C |
| ATOM | 3997 | O | THR | B | 134 | 56.600 | 22.285 | -32.978 | 1.00 24.86 | O |
| ATOM | 3998 | N | ASP | B | 135 | 54.547 | 21.391 | -33.204 | 1.00 22.82 | N |
| ATOM | 3999 | CA | ASP | B | 135 | 54.426 | 21.700 | -34.629 | 1.00 26.17 | C |
| ATOM | 4000 | CB | ASP | B | 135 | 53.735 | 20.561 | -35.369 | 1.00 30.90 | C |
| ATOM | 4001 | CG | ASP | B | 135 | 54.516 | 19.270 | -35.294 | 1.00 38.55 | C |
| ATOM | 4002 | OD1 | ASP | B | 135 | 54.005 | 18.299 | -34.690 | 1.00 39.83 | O |
| ATOM | 4003 | OD2 | ASP | B | 135 | 55.652 | 19.146 | -35.797 | 1.00 40.51 | O |
| ATOM | 4004 | C | ASP | B | 135 | 53.662 | 22.998 | -34.886 | 1.00 22.57 | C |
| ATOM | 4005 | O | ASP | B | 135 | 53.888 | 23.672 | -35.890 | 1.00 21.86 | O |
| ATOM | 4006 | N | MET | B | 136 | 52.720 | 23.302 | -34.000 | 1.00 21.85 | N |
| ATOM | 4007 | CA | MET | B | 136 | 51.919 | 24.515 | -34.103 | 1.00 21.45 | C |
| ATOM | 4008 | CB | MET | B | 136 | 50.520 | 24.205 | -34.647 | 1.00 23.65 | C |
| ATOM | 4009 | CG | MET | B | 136 | 50.469 | 23.979 | -36.151 | 1.00 31.21 | C |
| ATOM | 4010 | SD | MET | B | 136 | 48.910 | 23.252 | -36.696 | 1.00 32.86 | S |
| ATOM | 4011 | CE | MET | B | 136 | 49.292 | 21.484 | -36.512 | 1.00 37.13 | C |
| ATOM | 4012 | C | MET | B | 136 | 51.806 | 25.129 | -32.722 | 1.00 16.87 | C |
| ATOM | 4013 | O | MET | B | 136 | 51.682 | 24.418 | -31.723 | 1.00 20.63 | O |
| ATOM | 4014 | N | ALA | B | 137 | 51.866 | 26.454 | -32.664 | 1.00 15.54 | N |
| ATOM | 4015 | CA | ALA | B | 137 | 51.622 | 27.166 | -31.422 | 1.00 13.08 | C |
| ATOM | 4016 | CB | ALA | B | 137 | 52.875 | 27.855 | -30.932 | 1.00 16.27 | C |
| ATOM | 4017 | C | ALA | B | 137 | 50.544 | 28.191 | -31.733 | 1.00 16.34 | C |
| ATOM | 4018 | O | ALA | B | 137 | 50.535 | 28.772 | -32.824 | 1.00 15.54 | O |
| ATOM | 4019 | N | VAL | B | 138 | 49.639 | 28.392 | -30.784 | 1.00 15.63 | N |
| ATOM | 4020 | CA | VAL | B | 138 | 48.497 | 29.292 | -30.978 | 1.00 13.83 | C |
| ATOM | 4021 | CB | VAL | B | 138 | 47.162 | 28.506 | -31.025 | 1.00 17.28 | C |
| ATOM | 4022 | CG1 | VAL | B | 138 | 45.970 | 29.474 | -31.210 | 1.00 14.69 | C |
| ATOM | 4023 | CG2 | VAL | B | 138 | 47.174 | 27.465 | -32.130 | 1.00 17.51 | C |
| ATOM | 4024 | C | VAL | B | 138 | 48.436 | 30.300 | -29.835 | 1.00 13.92 | C |
| ATOM | 4025 | O | VAL | B | 138 | 48.483 | 29.924 | -28.665 | 1.00 15.45 | O |
| ATOM | 4026 | N | ASN | B | 139 | 48.336 | 31.585 | -30.165 | 1.00 13.25 | N |
| ATOM | 4027 | CA | ASN | B | 139 | 48.131 | 32.611 | -29.144 | 1.00 11.58 | C |
| ATOM | 4028 | CB | ASN | B | 139 | 49.449 | 33.321 | -28.789 | 1.00 12.41 | C |
| ATOM | 4029 | CG | ASN | B | 139 | 49.256 | 34.455 | -27.780 | 1.00 14.95 | C |
| ATOM | 4030 | OD1 | ASN | B | 139 | 48.411 | 34.373 | -26.892 | 1.00 15.82 | O |
| ATOM | 4031 | ND2 | ASN | B | 139 | 50.049 | 35.520 | -27.917 | 1.00 18.63 | N |
| ATOM | 4032 | C | ASN | B | 139 | 47.125 | 33.621 | -29.648 | 1.00 12.90 | C |
| ATOM | 4033 | O | ASN | B | 139 | 47.504 | 34.573 | -30.340 | 1.00 12.05 | O |
| ATOM | 4034 | N | TRP | B | 140 | 45.848 | 33.420 | -29.319 | 1.00 11.82 | N |
| ATOM | 4035 | CA | TRP | B | 140 | 44.809 | 34.324 | -29.847 | 1.00 13.19 | C |
| ATOM | 4036 | CB | TRP | B | 140 | 43.405 | 33.752 | -29.635 | 1.00 11.12 | C |
| ATOM | 4037 | CG | TRP | B | 140 | 43.155 | 32.462 | -30.397 | 1.00 12.66 | C |

FIGURE 3TTT

```
ATOM   4038  CD1 TRP B 140      42.644  31.293 -29.891  1.00 16.48           C
ATOM   4039  NE1 TRP B 140      42.558  30.342 -30.882  1.00 14.36           N
ATOM   4040  CE2 TRP B 140      43.017  30.879 -32.058  1.00 14.16           C
ATOM   4041  CD2 TRP B 140      43.404  32.217 -31.790  1.00 15.14           C
ATOM   4042  CE3 TRP B 140      43.912  32.993 -32.850  1.00 13.62           C
ATOM   4043  CZ3 TRP B 140      44.019  32.416 -34.119  1.00 15.00           C
ATOM   4044  CH2 TRP B 140      43.617  31.088 -34.347  1.00 18.01           C
ATOM   4045  CZ2 TRP B 140      43.116  30.307 -33.335  1.00 17.08           C
ATOM   4046  C   TRP B 140      44.913  35.731 -29.256  1.00 16.30           C
ATOM   4047  O   TRP B 140      44.398  36.685 -29.841  1.00 15.78           O
ATOM   4048  N   ALA B 141      45.593  35.858 -28.116  1.00 12.13           N
ATOM   4049  CA  ALA B 141      45.774  37.165 -27.477  1.00 14.36           C
ATOM   4050  CB  ALA B 141      46.103  37.001 -25.987  1.00 16.40           C
ATOM   4051  C   ALA B 141      46.851  38.000 -28.183  1.00 19.14           C
ATOM   4052  O   ALA B 141      46.980  39.197 -27.924  1.00 21.14           O
ATOM   4053  N   GLY B 142      47.611  37.366 -29.075  1.00 14.88           N
ATOM   4054  CA  GLY B 142      48.638  38.044 -29.850  1.00 15.27           C
ATOM   4055  C   GLY B 142      48.149  38.553 -31.196  1.00 19.50           C
ATOM   4056  O   GLY B 142      46.937  38.669 -31.431  1.00 17.39           O
ATOM   4057  N   GLY B 143      49.088  38.886 -32.076  1.00 15.76           N
ATOM   4058  CA  GLY B 143      48.755  39.351 -33.421  1.00 15.95           C
ATOM   4059  C   GLY B 143      48.556  40.855 -33.563  1.00 18.42           C
ATOM   4060  O   GLY B 143      47.864  41.313 -34.478  1.00 19.31           O
ATOM   4061  N   LEU B 144      49.187  41.623 -32.675  1.00 16.41           N
ATOM   4062  CA  LEU B 144      49.009  43.074 -32.626  1.00 20.79           C
ATOM   4063  CB  LEU B 144      49.204  43.586 -31.193  1.00 22.27           C
ATOM   4064  CG  LEU B 144      48.111  43.345 -30.128  1.00 28.45           C
ATOM   4065  CD1 LEU B 144      46.702  43.732 -30.600  1.00 34.41           C
ATOM   4066  CD2 LEU B 144      48.129  41.903 -29.639  1.00 28.89           C
ATOM   4067  C   LEU B 144      49.940  43.787 -33.616  1.00 21.62           C
ATOM   4068  O   LEU B 144      50.965  44.380 -33.236  1.00 25.98           O
ATOM   4069  N   HIS B 145      49.533  43.766 -34.881  1.00 18.46           N
ATOM   4070  CA  HIS B 145      50.421  44.064 -36.004  1.00 17.78           C
ATOM   4071  CB  HIS B 145      49.974  43.321 -37.292  1.00 17.21           C
ATOM   4072  CG  HIS B 145      48.581  43.636 -37.768  1.00 15.61           C
ATOM   4073  ND1 HIS B 145      47.673  44.376 -37.042  1.00 22.18           N
ATOM   4074  CE1 HIS B 145      46.542  44.475 -37.720  1.00 16.36           C
ATOM   4075  NE2 HIS B 145      46.680  43.821 -38.859  1.00 19.81           N
ATOM   4076  CD2 HIS B 145      47.944  43.285 -38.913  1.00 13.59           C
ATOM   4077  C   HIS B 145      50.751  45.539 -36.303  1.00 16.71           C
ATOM   4078  O   HIS B 145      51.608  45.791 -37.138  1.00 17.33           O
ATOM   4079  N   HIS B 146      50.102  46.487 -35.621  1.00 17.20           N
ATOM   4080  CA  HIS B 146      50.325  47.920 -35.889  1.00 18.45           C
ATOM   4081  CB  HIS B 146      49.037  48.726 -35.718  1.00 15.34           C
ATOM   4082  CG  HIS B 146      47.938  48.295 -36.630  1.00 17.23           C
ATOM   4083  ND1 HIS B 146      48.091  48.235 -37.999  1.00 18.80           N
ATOM   4084  CE1 HIS B 146      46.966  47.814 -38.546  1.00 18.34           C
ATOM   4085  NE2 HIS B 146      46.094  47.589 -37.582  1.00 16.76           N
ATOM   4086  CD2 HIS B 146      46.676  47.881 -36.373  1.00 16.26           C
ATOM   4087  C   HIS B 146      51.411  48.584 -35.062  1.00 19.58           C
ATOM   4088  O   HIS B 146      51.899  49.652 -35.443  1.00 20.29           O
ATOM   4089  N   ALA B 147      51.790  47.978 -33.937  1.00 18.40           N
ATOM   4090  CA  ALA B 147      52.739  48.628 -33.029  1.00 18.60           C
ATOM   4091  CB  ALA B 147      52.917  47.818 -31.737  1.00 16.53           C
ATOM   4092  C   ALA B 147      54.078  48.858 -33.714  1.00 17.56           C
ATOM   4093  O   ALA B 147      54.565  48.000 -34.458  1.00 19.10           O
ATOM   4094  N   LYS B 148      54.664  50.025 -33.451  1.00 17.63           N
```

FIGURE 3UUU

```
ATOM   4095  CA   LYS B 148      55.906  50.442 -34.085  1.00 19.23           C
ATOM   4096  CB   LYS B 148      55.759  51.856 -34.663  1.00 22.61           C
ATOM   4097  CG   LYS B 148      54.585  52.023 -35.636  1.00 28.42           C
ATOM   4098  CD   LYS B 148      54.774  51.193 -36.896  1.00 31.24           C
ATOM   4099  CE   LYS B 148      53.568  51.292 -37.819  1.00 36.22           C
ATOM   4100  NZ   LYS B 148      53.774  52.320 -38.876  1.00 39.99           N
ATOM   4101  C    LYS B 148      57.035  50.417 -33.072  1.00 19.04           C
ATOM   4102  O    LYS B 148      56.797  50.275 -31.880  1.00 18.42           O
ATOM   4103  N    LYS B 149      58.263  50.571 -33.553  1.00 21.07           N
ATOM   4104  CA   LYS B 149      59.437  50.538 -32.691  1.00 23.20           C
ATOM   4105  CB   LYS B 149      60.683  50.924 -33.493  1.00 24.36           C
ATOM   4106  CG   LYS B 149      61.990  50.585 -32.802  1.00 32.03           C
ATOM   4107  CD   LYS B 149      63.177  50.763 -33.734  1.00 36.66           C
ATOM   4108  CE   LYS B 149      63.624  49.430 -34.324  1.00 42.35           C
ATOM   4109  NZ   LYS B 149      64.049  49.550 -35.753  1.00 42.21           N
ATOM   4110  C    LYS B 149      59.288  51.432 -31.451  1.00 21.61           C
ATOM   4111  O    LYS B 149      59.591  51.006 -30.334  1.00 19.98           O
ATOM   4112  N    SER B 150      58.801  52.656 -31.647  1.00 21.30           N
ATOM   4113  CA   SER B 150      58.707  53.629 -30.555  1.00 24.10           C
ATOM   4114  CB  ASER B 150      59.816  54.684 -30.682  0.65 22.77           C
ATOM   4115  OG  ASER B 150      61.044  54.088 -31.042  0.65 29.30           O
ATOM   4116  C    SER B 150      57.344  54.323 -30.436  1.00 24.98           C
ATOM   4117  O    SER B 150      57.252  55.422 -29.887  1.00 24.40           O
ATOM   4118  N    GLU B 151      56.286  53.698 -30.943  1.00 22.26           N
ATOM   4119  CA   GLU B 151      54.941  54.252 -30.766  1.00 22.72           C
ATOM   4120  CB   GLU B 151      54.653  55.385 -31.772  1.00 29.10           C
ATOM   4121  CG   GLU B 151      54.739  54.994 -33.236  1.00 38.98           C
ATOM   4122  CD   GLU B 151      54.644  56.182 -34.179  1.00 47.25           C
ATOM   4123  OE1  GLU B 151      53.782  56.150 -35.089  1.00 50.19           O
ATOM   4124  OE2  GLU B 151      55.430  57.143 -34.021  1.00 49.08           O
ATOM   4125  C    GLU B 151      53.846  53.202 -30.830  1.00 19.20           C
ATOM   4126  O    GLU B 151      53.961  52.218 -31.550  1.00 18.87           O
ATOM   4127  N    ALA B 152      52.782  53.437 -30.076  1.00 16.23           N
ATOM   4128  CA   ALA B 152      51.568  52.639 -30.188  1.00 19.59           C
ATOM   4129  CB   ALA B 152      50.683  52.862 -28.967  1.00 16.63           C
ATOM   4130  C    ALA B 152      50.824  53.034 -31.455  1.00 22.04           C
ATOM   4131  O    ALA B 152      50.929  54.175 -31.914  1.00 20.49           O
ATOM   4132  N    SER B 153      50.061  52.099 -32.014  1.00 19.18           N
ATOM   4133  CA   SER B 153      49.190  52.411 -33.146  1.00 19.29           C
ATOM   4134  CB   SER B 153      49.993  52.415 -34.450  1.00 17.10           C
ATOM   4135  OG   SER B 153      49.155  52.651 -35.566  1.00 21.52           O
ATOM   4136  C    SER B 153      48.073  51.391 -33.254  1.00 20.99           C
ATOM   4137  O    SER B 153      48.296  50.207 -33.020  1.00 18.70           O
ATOM   4138  N    GLY B 154      46.876  51.854 -33.609  1.00 18.94           N
ATOM   4139  CA   GLY B 154      45.791  50.962 -33.999  1.00 20.71           C
ATOM   4140  C    GLY B 154      45.400  49.910 -32.974  1.00 21.16           C
ATOM   4141  O    GLY B 154      45.158  48.748 -33.320  1.00 17.75           O
ATOM   4142  N    PHE B 155      45.329  50.337 -31.717  1.00 18.18           N
ATOM   4143  CA   PHE B 155      44.961  49.489 -30.574  1.00 18.20           C
ATOM   4144  CB   PHE B 155      43.734  48.592 -30.856  1.00 19.80           C
ATOM   4145  CG   PHE B 155      42.552  49.297 -31.498  1.00 19.51           C
ATOM   4146  CD1  PHE B 155      42.368  50.675 -31.386  1.00 18.36           C
ATOM   4147  CE1  PHE B 155      41.254  51.306 -31.985  1.00 17.39           C
ATOM   4148  CZ   PHE B 155      40.320  50.548 -32.689  1.00 17.59           C
ATOM   4149  CE2  PHE B 155      40.496  49.163 -32.803  1.00 17.13           C
ATOM   4150  CD2  PHE B 155      41.611  48.552 -32.211  1.00 15.19           C
ATOM   4151  C    PHE B 155      46.129  48.618 -30.087  1.00 17.37           C
```

FIGURE 3VVV

```
ATOM   4152  O    PHE B 155      45.968  47.858 -29.135  1.00 20.33           O
ATOM   4153  N    CYS B 156      47.289  48.732 -30.734  1.00 17.65           N
ATOM   4154  CA   CYS B 156      48.447  47.881 -30.427  1.00 19.90           C
ATOM   4155  CB   CYS B 156      49.037  47.288 -31.710  1.00 18.30           C
ATOM   4156  SG   CYS B 156      47.856  46.462 -32.794  1.00 22.07           S
ATOM   4157  C    CYS B 156      49.524  48.688 -29.716  1.00 20.01           C
ATOM   4158  O    CYS B 156      49.776  49.831 -30.084  1.00 19.37           O
ATOM   4159  N    TYR B 157      50.167  48.097 -28.714  1.00 15.17           N
ATOM   4160  CA   TYR B 157      51.223  48.802 -27.968  1.00 15.02           C
ATOM   4161  CB   TYR B 157      50.901  48.863 -26.469  1.00 17.53           C
ATOM   4162  CG   TYR B 157      49.555  49.471 -26.144  1.00 16.66           C
ATOM   4163  CD1  TYR B 157      48.395  48.692 -26.179  1.00 16.88           C
ATOM   4164  CE1  TYR B 157      47.153  49.232 -25.889  1.00 19.29           C
ATOM   4165  CZ   TYR B 157      47.056  50.574 -25.538  1.00 20.57           C
ATOM   4166  OH   TYR B 157      45.814  51.087 -25.253  1.00 19.73           O
ATOM   4167  CE2  TYR B 157      48.191  51.375 -25.487  1.00 16.22           C
ATOM   4168  CD2  TYR B 157      49.439  50.819 -25.786  1.00 17.93           C
ATOM   4169  C    TYR B 157      52.586  48.166 -28.188  1.00 17.53           C
ATOM   4170  O    TYR B 157      53.596  48.852 -28.369  1.00 17.53           O
ATOM   4171  N    VAL B 158      52.607  46.843 -28.180  1.00 14.98           N
ATOM   4172  CA   VAL B 158      53.845  46.087 -28.307  1.00 16.32           C
ATOM   4173  CB   VAL B 158      54.167  45.291 -27.003  1.00 15.65           C
ATOM   4174  CG1  VAL B 158      55.444  44.474 -27.155  1.00 17.08           C
ATOM   4175  CG2  VAL B 158      54.283  46.226 -25.801  1.00 19.56           C
ATOM   4176  C    VAL B 158      53.623  45.129 -29.463  1.00 18.28           C
ATOM   4177  O    VAL B 158      52.595  44.448 -29.516  1.00 19.65           O
ATOM   4178  N    ASN B 159      54.565  45.097 -30.396  1.00 15.80           N
ATOM   4179  CA   ASN B 159      54.416  44.242 -31.559  1.00 16.59           C
ATOM   4180  CB   ASN B 159      55.118  44.828 -32.792  1.00 16.58           C
ATOM   4181  CG   ASN B 159      54.543  44.288 -34.089  1.00 18.19           C
ATOM   4182  OD1  ASN B 159      54.402  43.072 -34.255  1.00 14.66           O
ATOM   4183  ND2  ASN B 159      54.206  45.183 -35.015  1.00 14.65           N
ATOM   4184  C    ASN B 159      54.903  42.836 -31.249  1.00 16.08           C
ATOM   4185  O    ASN B 159      56.064  42.493 -31.498  1.00 17.66           O
ATOM   4186  N    ASP B 160      53.994  42.027 -30.705  1.00 14.68           N
ATOM   4187  CA   ASP B 160      54.307  40.646 -30.332  1.00 15.45           C
ATOM   4188  CB   ASP B 160      53.103  39.991 -29.646  1.00 16.36           C
ATOM   4189  CG   ASP B 160      51.921  39.813 -30.592  1.00 24.07           C
ATOM   4190  OD1  ASP B 160      51.353  40.844 -31.027  1.00 23.12           O
ATOM   4191  OD2  ASP B 160      51.516  38.686 -30.977  1.00 21.12           O
ATOM   4192  C    ASP B 160      54.713  39.834 -31.552  1.00 15.23           C
ATOM   4193  O    ASP B 160      55.484  38.886 -31.428  1.00 16.20           O
ATOM   4194  N    ILE B 161      54.195  40.204 -32.726  1.00 14.70           N
ATOM   4195  CA   ILE B 161      54.512  39.484 -33.965  1.00 15.16           C
ATOM   4196  CB   ILE B 161      53.639  39.953 -35.151  1.00 15.93           C
ATOM   4197  CG1  ILE B 161      52.149  39.819 -34.813  1.00 18.50           C
ATOM   4198  CD1  ILE B 161      51.239  40.400 -35.848  1.00 19.98           C
ATOM   4199  CG2  ILE B 161      54.005  39.165 -36.419  1.00 17.10           C
ATOM   4200  C    ILE B 161      55.979  39.662 -34.318  1.00 15.12           C
ATOM   4201  O    ILE B 161      56.663  38.690 -34.610  1.00 13.76           O
ATOM   4202  N    VAL B 162      56.448  40.909 -34.306  1.00 13.03           N
ATOM   4203  CA   VAL B 162      57.849  41.188 -34.624  1.00 14.65           C
ATOM   4204  CB   VAL B 162      58.138  42.711 -34.667  1.00 14.18           C
ATOM   4205  CG1  VAL B 162      59.644  42.978 -34.803  1.00 15.44           C
ATOM   4206  CG2  VAL B 162      57.379  43.360 -35.824  1.00 14.61           C
ATOM   4207  C    VAL B 162      58.769  40.464 -33.629  1.00 15.85           C
ATOM   4208  O    VAL B 162      59.768  39.854 -34.022  1.00 16.21           O
```

FIGURE 3WWW

| | | | | | | | | | | |
|---|---|---|---|---|---|---|---|---|---|---|
| ATOM | 4209 | N | LEU | B | 163 | 58.413 | 40.510 | -32.352 | 1.00 14.48 | N |
| ATOM | 4210 | CA | LEU | B | 163 | 59.214 | 39.842 | -31.312 | 1.00 15.26 | C |
| ATOM | 4211 | CB | LEU | B | 163 | 58.718 | 40.227 | -29.914 | 1.00 14.84 | C |
| ATOM | 4212 | CG | LEU | B | 163 | 58.843 | 41.723 | -29.592 | 1.00 13.51 | C |
| ATOM | 4213 | CD1 | LEU | B | 163 | 58.045 | 42.085 | -28.371 | 1.00 16.18 | C |
| ATOM | 4214 | CD2 | LEU | B | 163 | 60.323 | 42.129 | -29.408 | 1.00 16.34 | C |
| ATOM | 4215 | C | LEU | B | 163 | 59.260 | 38.321 | -31.507 | 1.00 16.76 | C |
| ATOM | 4216 | O | LEU | B | 163 | 60.323 | 37.694 | -31.375 | 1.00 15.72 | O |
| ATOM | 4217 | N | ALA | B | 164 | 58.120 | 37.730 | -31.853 | 1.00 14.28 | N |
| ATOM | 4218 | CA | ALA | B | 164 | 58.064 | 36.289 | -32.121 | 1.00 16.54 | C |
| ATOM | 4219 | CB | ALA | B | 164 | 56.622 | 35.825 | -32.281 | 1.00 16.90 | C |
| ATOM | 4220 | C | ALA | B | 164 | 58.882 | 35.918 | -33.353 | 1.00 16.18 | C |
| ATOM | 4221 | O | ALA | B | 164 | 59.572 | 34.890 | -33.359 | 1.00 16.97 | O |
| ATOM | 4222 | N | ILE | B | 165 | 58.817 | 36.755 | -34.388 | 1.00 13.41 | N |
| ATOM | 4223 | CA | ILE | B | 165 | 59.583 | 36.511 | -35.617 | 1.00 14.54 | C |
| ATOM | 4224 | CB | ILE | B | 165 | 59.119 | 37.417 | -36.788 | 1.00 13.40 | C |
| ATOM | 4225 | CG1 | ILE | B | 165 | 57.734 | 36.966 | -37.281 | 1.00 15.86 | C |
| ATOM | 4226 | CD1 | ILE | B | 165 | 57.041 | 37.950 | -38.206 | 1.00 17.77 | C |
| ATOM | 4227 | CG2 | ILE | B | 165 | 60.105 | 37.332 | -37.971 | 1.00 13.71 | C |
| ATOM | 4228 | C | ILE | B | 165 | 61.079 | 36.643 | -35.342 | 1.00 14.98 | C |
| ATOM | 4229 | O | ILE | B | 165 | 61.869 | 35.845 | -35.835 | 1.00 15.82 | O |
| ATOM | 4230 | N | LEU | B | 166 | 61.467 | 37.627 | -34.534 | 1.00 16.07 | N |
| ATOM | 4231 | CA | LEU | B | 166 | 62.877 | 37.770 | -34.167 | 1.00 16.48 | C |
| ATOM | 4232 | CB | LEU | B | 166 | 63.100 | 39.013 | -33.309 | 1.00 17.43 | C |
| ATOM | 4233 | CG | LEU | B | 166 | 63.033 | 40.341 | -34.077 | 1.00 16.42 | C |
| ATOM | 4234 | CD1 | LEU | B | 166 | 62.972 | 41.501 | -33.087 | 1.00 18.97 | C |
| ATOM | 4235 | CD2 | LEU | B | 166 | 64.201 | 40.511 | -35.053 | 1.00 19.36 | C |
| ATOM | 4236 | C | LEU | B | 166 | 63.397 | 36.525 | -33.448 | 1.00 19.37 | C |
| ATOM | 4237 | O | LEU | B | 166 | 64.554 | 36.115 | -33.642 | 1.00 18.76 | O |
| ATOM | 4238 | N | GLU | B | 167 | 62.530 | 35.921 | -32.641 | 1.00 18.16 | N |
| ATOM | 4239 | CA | GLU | B | 167 | 62.853 | 34.674 | -31.949 | 1.00 18.56 | C |
| ATOM | 4240 | CB | GLU | B | 167 | 61.813 | 34.355 | -30.865 | 1.00 21.75 | C |
| ATOM | 4241 | CG | GLU | B | 167 | 62.116 | 33.122 | -30.018 | 1.00 25.50 | C |
| ATOM | 4242 | CD | GLU | B | 167 | 63.338 | 33.279 | -29.114 | 1.00 31.03 | C |
| ATOM | 4243 | OE1 | GLU | B | 167 | 64.035 | 32.270 | -28.900 | 1.00 38.02 | O |
| ATOM | 4244 | OE2 | GLU | B | 167 | 63.598 | 34.396 | -28.610 | 1.00 34.59 | O |
| ATOM | 4245 | C | GLU | B | 167 | 63.005 | 33.530 | -32.947 | 1.00 18.59 | C |
| ATOM | 4246 | O | GLU | B | 167 | 63.986 | 32.792 | -32.886 | 1.00 19.33 | O |
| ATOM | 4247 | N | LEU | B | 168 | 62.065 | 33.395 | -33.885 | 1.00 14.31 | N |
| ATOM | 4248 | CA | LEU | B | 168 | 62.192 | 32.380 | -34.933 | 1.00 14.91 | C |
| ATOM | 4249 | CB | LEU | B | 168 | 60.968 | 32.372 | -35.847 | 1.00 20.32 | C |
| ATOM | 4250 | CG | LEU | B | 168 | 59.666 | 31.861 | -35.231 | 1.00 19.21 | C |
| ATOM | 4251 | CD1 | LEU | B | 168 | 58.503 | 32.176 | -36.164 | 1.00 18.88 | C |
| ATOM | 4252 | CD2 | LEU | B | 168 | 59.723 | 30.348 | -34.920 | 1.00 20.69 | C |
| ATOM | 4253 | C | LEU | B | 168 | 63.469 | 32.549 | -35.770 | 1.00 19.16 | C |
| ATOM | 4254 | O | LEU | B | 168 | 64.095 | 31.556 | -36.174 | 1.00 19.27 | O |
| ATOM | 4255 | N | LEU | B | 169 | 63.854 | 33.801 | -36.014 | 1.00 13.78 | N |
| ATOM | 4256 | CA | LEU | B | 169 | 65.029 | 34.106 | -36.840 | 1.00 19.96 | C |
| ATOM | 4257 | CB | LEU | B | 169 | 65.094 | 35.592 | -37.184 | 1.00 14.44 | C |
| ATOM | 4258 | CG | LEU | B | 169 | 64.103 | 36.080 | -38.249 | 1.00 16.63 | C |
| ATOM | 4259 | CD1 | LEU | B | 169 | 64.029 | 37.596 | -38.218 | 1.00 15.92 | C |
| ATOM | 4260 | CD2 | LEU | B | 169 | 64.478 | 35.577 | -39.646 | 1.00 19.51 | C |
| ATOM | 4261 | C | LEU | B | 169 | 66.352 | 33.662 | -36.217 | 1.00 20.23 | C |
| ATOM | 4262 | O | LEU | B | 169 | 67.384 | 33.635 | -36.898 | 1.00 21.53 | O |
| ATOM | 4263 | N | LYS | B | 170 | 66.325 | 33.320 | -34.933 | 1.00 19.79 | N |
| ATOM | 4264 | CA | LYS | B | 170 | 67.499 | 32.731 | -34.286 | 1.00 21.39 | C |
| ATOM | 4265 | CB | LYS | B | 170 | 67.266 | 32.551 | -32.782 | 1.00 22.41 | C |

FIGURE 3XXX

```
ATOM   4266  CG   LYS B 170      67.201  33.857 -31.996  1.00 23.98           C
ATOM   4267  CD   LYS B 170      66.973  33.579 -30.523  1.00 27.04           C
ATOM   4268  CE   LYS B 170      66.832  34.867 -29.743  1.00 30.98           C
ATOM   4269  NZ   LYS B 170      66.524  34.590 -28.312  1.00 32.63           N
ATOM   4270  C    LYS B 170      67.872  31.388 -34.924  1.00 24.66           C
ATOM   4271  O    LYS B 170      69.059  31.092 -35.101  1.00 22.82           O
ATOM   4272  N    TYR B 171      66.858  30.595 -35.275  1.00 21.09           N
ATOM   4273  CA   TYR B 171      67.035  29.228 -35.778  1.00 22.71           C
ATOM   4274  CB   TYR B 171      66.193  28.241 -34.961  1.00 25.45           C
ATOM   4275  CG   TYR B 171      66.699  27.948 -33.566  1.00 31.79           C
ATOM   4276  CD1  TYR B 171      67.238  26.702 -33.250  1.00 38.76           C
ATOM   4277  CE1  TYR B 171      67.698  26.418 -31.961  1.00 41.31           C
ATOM   4278  CZ   TYR B 171      67.610  27.388 -30.977  1.00 42.48           C
ATOM   4279  OH   TYR B 171      68.060  27.114 -29.706  1.00 48.50           O
ATOM   4280  CE2  TYR B 171      67.074  28.634 -31.264  1.00 41.09           C
ATOM   4281  CD2  TYR B 171      66.614  28.905 -32.554  1.00 33.35           C
ATOM   4282  C    TYR B 171      66.669  29.056 -37.250  1.00 24.30           C
ATOM   4283  O    TYR B 171      67.083  28.077 -37.884  1.00 23.06           O
ATOM   4284  N    HIS B 172      65.884  29.990 -37.787  1.00 20.56           N
ATOM   4285  CA   HIS B 172      65.357  29.872 -39.143  1.00 19.52           C
ATOM   4286  CB   HIS B 172      63.819  29.935 -39.129  1.00 20.73           C
ATOM   4287  CG   HIS B 172      63.179  28.775 -38.435  1.00 16.68           C
ATOM   4288  ND1  HIS B 172      62.933  28.765 -37.081  1.00 22.02           N
ATOM   4289  CE1  HIS B 172      62.369  27.618 -36.747  1.00 19.46           C
ATOM   4290  NE2  HIS B 172      62.242  26.885 -37.836  1.00 20.14           N
ATOM   4291  CD2  HIS B 172      62.743  27.585 -38.905  1.00 17.63           C
ATOM   4292  C    HIS B 172      65.903  30.958 -40.057  1.00 20.92           C
ATOM   4293  O    HIS B 172      65.821  32.150 -39.742  1.00 19.96           O
ATOM   4294  N    GLN B 173      66.448  30.540 -41.195  1.00 21.33           N
ATOM   4295  CA   GLN B 173      67.019  31.472 -42.171  1.00 25.41           C
ATOM   4296  CB   GLN B 173      67.809  30.713 -43.245  1.00 29.83           C
ATOM   4297  CG   GLN B 173      68.841  31.569 -43.966  1.00 39.45           C
ATOM   4298  CD   GLN B 173      70.001  31.959 -43.067  1.00 44.42           C
ATOM   4299  OE1  GLN B 173      70.204  33.142 -42.791  1.00 48.77           O
ATOM   4300  NE2  GLN B 173      70.761  30.966 -42.605  1.00 48.73           N
ATOM   4301  C    GLN B 173      65.964  32.344 -42.843  1.00 23.31           C
ATOM   4302  O    GLN B 173      66.198  33.525 -43.103  1.00 25.49           O
ATOM   4303  N    ARG B 174      64.812  31.747 -43.138  1.00 21.98           N
ATOM   4304  CA   ARG B 174      63.731  32.450 -43.824  1.00 18.91           C
ATOM   4305  CB   ARG B 174      63.608  31.972 -45.272  1.00 18.26           C
ATOM   4306  CG   ARG B 174      64.756  32.421 -46.180  1.00 22.23           C
ATOM   4307  CD   ARG B 174      64.686  31.864 -47.597  1.00 24.18           C
ATOM   4308  NE   ARG B 174      64.511  30.415 -47.614  1.00 29.79           N
ATOM   4309  CZ   ARG B 174      65.488  29.528 -47.445  1.00 34.49           C
ATOM   4310  NH1  ARG B 174      65.207  28.233 -47.468  1.00 35.17           N
ATOM   4311  NH2  ARG B 174      66.743  29.928 -47.252  1.00 33.04           N
ATOM   4312  C    ARG B 174      62.427  32.192 -43.101  1.00 17.39           C
ATOM   4313  O    ARG B 174      62.063  31.043 -42.869  1.00 16.66           O
ATOM   4314  N    VAL B 175      61.746  33.270 -42.731  1.00 16.95           N
ATOM   4315  CA   VAL B 175      60.458  33.174 -42.052  1.00 16.64           C
ATOM   4316  CB   VAL B 175      60.485  33.814 -40.641  1.00 16.11           C
ATOM   4317  CG1  VAL B 175      59.103  33.761 -39.983  1.00 15.64           C
ATOM   4318  CG2  VAL B 175      61.523  33.113 -39.732  1.00 18.84           C
ATOM   4319  C    VAL B 175      59.423  33.859 -42.928  1.00 17.78           C
ATOM   4320  O    VAL B 175      59.660  34.945 -43.449  1.00 19.25           O
ATOM   4321  N    LEU B 176      58.283  33.202 -43.094  1.00 15.86           N
ATOM   4322  CA   LEU B 176      57.170  33.767 -43.833  1.00 15.37           C
```

FIGURE 3YYY

```
ATOM   4323  CB  LEU B 176      56.552  32.700 -44.737  1.00 15.89           C
ATOM   4324  CG  LEU B 176      55.249  33.040 -45.465  1.00 15.72           C
ATOM   4325  CD1 LEU B 176      55.414  34.267 -46.381  1.00 16.36           C
ATOM   4326  CD2 LEU B 176      54.776  31.833 -46.263  1.00 16.60           C
ATOM   4327  C   LEU B 176      56.114  34.289 -42.871  1.00 16.23           C
ATOM   4328  O   LEU B 176      55.692  33.583 -41.962  1.00 16.98           O
ATOM   4329  N   TYR B 177      55.685  35.527 -43.086  1.00 15.57           N
ATOM   4330  CA  TYR B 177      54.587  36.095 -42.318  1.00 15.26           C
ATOM   4331  CB  TYR B 177      55.015  37.438 -41.699  1.00 14.17           C
ATOM   4332  CG  TYR B 177      53.885  38.196 -41.046  1.00 15.07           C
ATOM   4333  CD1 TYR B 177      53.302  37.729 -39.871  1.00 14.88           C
ATOM   4334  CE1 TYR B 177      52.258  38.420 -39.260  1.00 14.81           C
ATOM   4335  CZ  TYR B 177      51.797  39.595 -39.824  1.00 15.17           C
ATOM   4336  OH  TYR B 177      50.770  40.269 -39.212  1.00 15.74           O
ATOM   4337  CE2 TYR B 177      52.360  40.089 -40.984  1.00 15.11           C
ATOM   4338  CD2 TYR B 177      53.401  39.380 -41.600  1.00 14.91           C
ATOM   4339  C   TYR B 177      53.387  36.283 -43.245  1.00 13.46           C
ATOM   4340  O   TYR B 177      53.523  36.851 -44.335  1.00 14.73           O
ATOM   4341  N   ILE B 178      52.224  35.786 -42.821  1.00 13.71           N
ATOM   4342  CA  ILE B 178      50.979  35.926 -43.584  1.00 13.68           C
ATOM   4343  CB  ILE B 178      50.448  34.545 -44.083  1.00 12.73           C
ATOM   4344  CG1 ILE B 178      51.513  33.791 -44.899  1.00 14.33           C
ATOM   4345  CD1 ILE B 178      51.267  32.287 -44.960  1.00 17.66           C
ATOM   4346  CG2 ILE B 178      49.169  34.723 -44.927  1.00 15.54           C
ATOM   4347  C   ILE B 178      49.935  36.602 -42.699  1.00 14.51           C
ATOM   4348  O   ILE B 178      49.769  36.239 -41.530  1.00 16.80           O
ATOM   4349  N   ASP B 179      49.227  37.577 -43.263  1.00 13.11           N
ATOM   4350  CA  ASP B 179      48.350  38.445 -42.483  1.00 15.74           C
ATOM   4351  CB  ASP B 179      49.023  39.829 -42.391  1.00 15.13           C
ATOM   4352  CG  ASP B 179      48.367  40.754 -41.384  1.00 16.21           C
ATOM   4353  OD1 ASP B 179      47.124  40.831 -41.340  1.00 16.48           O
ATOM   4354  OD2 ASP B 179      49.025  41.472 -40.604  1.00 21.55           O
ATOM   4355  C   ASP B 179      46.976  38.527 -43.167  1.00 14.82           C
ATOM   4356  O   ASP B 179      46.846  39.167 -44.217  1.00 14.10           O
ATOM   4357  N   ILE B 180      45.960  37.876 -42.586  1.00 14.20           N
ATOM   4358  CA  ILE B 180      44.596  37.889 -43.156  1.00 14.80           C
ATOM   4359  CB  ILE B 180      44.044  36.451 -43.383  1.00 13.54           C
ATOM   4360  CG1 ILE B 180      43.901  35.690 -42.061  1.00 12.68           C
ATOM   4361  CD1 ILE B 180      43.031  34.429 -42.159  1.00 18.60           C
ATOM   4362  CG2 ILE B 180      44.904  35.700 -44.396  1.00 13.84           C
ATOM   4363  C   ILE B 180      43.585  38.770 -42.388  1.00 15.18           C
ATOM   4364  O   ILE B 180      42.369  38.712 -42.629  1.00 15.75           O
ATOM   4365  N   ASP B 181      44.106  39.570 -41.461  1.00 13.87           N
ATOM   4366  CA  ASP B 181      43.378  40.694 -40.863  1.00 15.98           C
ATOM   4367  CB  ASP B 181      44.348  41.448 -39.946  1.00 13.69           C
ATOM   4368  CG  ASP B 181      43.666  42.438 -39.029  1.00 16.16           C
ATOM   4369  OD1 ASP B 181      43.601  42.197 -37.799  1.00 14.79           O
ATOM   4370  OD2 ASP B 181      43.208  43.510 -39.451  1.00 16.12           O
ATOM   4371  C   ASP B 181      42.910  41.600 -42.011  1.00 14.31           C
ATOM   4372  O   ASP B 181      43.580  41.679 -43.041  1.00 14.98           O
ATOM   4373  N   ILE B 182      41.766  42.264 -41.860  1.00 12.20           N
ATOM   4374  CA  ILE B 182      41.293  43.183 -42.904  1.00 12.44           C
ATOM   4375  CB  ILE B 182      39.824  43.628 -42.637  1.00 14.35           C
ATOM   4376  CG1 ILE B 182      39.176  44.146 -43.933  1.00 15.82           C
ATOM   4377  CD1 ILE B 182      37.688  44.508 -43.804  1.00 16.73           C
ATOM   4378  CG2 ILE B 182      39.768  44.670 -41.517  1.00 12.85           C
ATOM   4379  C   ILE B 182      42.231  44.396 -43.096  1.00 14.70           C
```

FIGURE 3ZZZ

```
ATOM   4380  O    ILE B 182      42.216  45.032 -44.146  1.00 13.36           O
ATOM   4381  N    HIS B 183      43.033  44.711 -42.077  1.00 13.84           N
ATOM   4382  CA   HIS B 183      43.975  45.828 -42.146  1.00 15.57           C
ATOM   4383  CB   HIS B 183      44.050  46.537 -40.789  1.00 13.95           C
ATOM   4384  CG   HIS B 183      42.728  47.054 -40.321  1.00 17.08           C
ATOM   4385  ND1  HIS B 183      41.977  46.412 -39.364  1.00 12.90           N
ATOM   4386  CE1  HIS B 183      40.852  47.078 -39.167  1.00 16.79           C
ATOM   4387  NE2  HIS B 183      40.842  48.126 -39.972  1.00 16.19           N
ATOM   4388  CD2  HIS B 183      42.004  48.132 -40.707  1.00 17.87           C
ATOM   4389  C    HIS B 183      45.351  45.356 -42.575  1.00 17.06           C
ATOM   4390  O    HIS B 183      45.716  44.211 -42.325  1.00 15.82           O
ATOM   4391  N    HIS B 184      46.103  46.236 -43.236  1.00 13.61           N
ATOM   4392  CA   HIS B 184      47.493  45.958 -43.591  1.00 14.81           C
ATOM   4393  CB   HIS B 184      48.037  47.090 -44.471  1.00 17.53           C
ATOM   4394  CG   HIS B 184      49.494  46.962 -44.798  1.00 16.56           C
ATOM   4395  ND1  HIS B 184      50.412  47.949 -44.513  1.00 18.71           N
ATOM   4396  CE1  HIS B 184      51.611  47.562 -44.915  1.00 18.71           C
ATOM   4397  NE2  HIS B 184      51.501  46.362 -45.457  1.00 18.41           N
ATOM   4398  CD2  HIS B 184      50.186  45.964 -45.393  1.00 14.71           C
ATOM   4399  C    HIS B 184      48.338  45.837 -42.325  1.00 17.15           C
ATOM   4400  O    HIS B 184      48.224  46.664 -41.423  1.00 16.26           O
ATOM   4401  N    GLY B 185      49.188  44.813 -42.259  1.00 18.04           N
ATOM   4402  CA   GLY B 185      50.073  44.642 -41.118  1.00 19.69           C
ATOM   4403  C    GLY B 185      51.300  45.528 -41.222  1.00 22.09           C
ATOM   4404  O    GLY B 185      52.405  45.046 -41.473  1.00 23.07           O
ATOM   4405  N    ASP B 186      51.104  46.826 -41.029  1.00 20.46           N
ATOM   4406  CA   ASP B 186      52.145  47.818 -41.317  1.00 20.39           C
ATOM   4407  CB   ASP B 186      51.546  49.233 -41.349  1.00 20.02           C
ATOM   4408  CG   ASP B 186      50.920  49.639 -40.032  1.00 24.42           C
ATOM   4409  OD1  ASP B 186      50.869  50.854 -39.756  1.00 25.43           O
ATOM   4410  OD2  ASP B 186      50.453  48.826 -39.206  1.00 27.51           O
ATOM   4411  C    ASP B 186      53.354  47.761 -40.378  1.00 20.38           C
ATOM   4412  O    ASP B 186      54.488  47.966 -40.817  1.00 19.75           O
ATOM   4413  N    GLY B 187      53.107  47.475 -39.102  1.00 17.39           N
ATOM   4414  CA   GLY B 187      54.160  47.389 -38.097  1.00 17.96           C
ATOM   4415  C    GLY B 187      55.115  46.246 -38.380  1.00 17.52           C
ATOM   4416  O    GLY B 187      56.322  46.374 -38.178  1.00 16.02           O
ATOM   4417  N    VAL B 188      54.572  45.120 -38.841  1.00 16.67           N
ATOM   4418  CA   VAL B 188      55.397  43.957 -39.176  1.00 15.50           C
ATOM   4419  CB   VAL B 188      54.546  42.663 -39.262  1.00 14.66           C
ATOM   4420  CG1  VAL B 188      55.439  41.444 -39.424  1.00 16.65           C
ATOM   4421  CG2  VAL B 188      53.660  42.526 -38.017  1.00 16.70           C
ATOM   4422  C    VAL B 188      56.151  44.208 -40.483  1.00 17.60           C
ATOM   4423  O    VAL B 188      57.355  43.941 -40.594  1.00 16.89           O
ATOM   4424  N    GLU B 189      55.445  44.738 -41.476  1.00 16.03           N
ATOM   4425  CA   GLU B 189      56.076  45.033 -42.759  1.00 18.78           C
ATOM   4426  CB   GLU B 189      55.063  45.588 -43.751  1.00 21.21           C
ATOM   4427  CG   GLU B 189      55.647  45.819 -45.137  1.00 23.84           C
ATOM   4428  CD   GLU B 189      54.615  46.348 -46.104  1.00 28.78           C
ATOM   4429  OE1  GLU B 189      53.859  45.524 -46.655  1.00 25.74           O
ATOM   4430  OE2  GLU B 189      54.545  47.585 -46.286  1.00 29.01           O
ATOM   4431  C    GLU B 189      57.247  46.011 -42.580  1.00 17.35           C
ATOM   4432  O    GLU B 189      58.327  45.797 -43.137  1.00 19.33           O
ATOM   4433  N    GLU B 190      57.029  47.048 -41.777  1.00 18.52           N
ATOM   4434  CA   GLU B 190      58.044  48.068 -41.495  1.00 22.18           C
ATOM   4435  CB   GLU B 190      57.465  49.188 -40.621  1.00 25.63           C
ATOM   4436  CG   GLU B 190      58.470  50.265 -40.223  1.00 31.22           C
```

FIGURE 3AAAA

```
ATOM   4437  CD   GLU B 190      57.835  51.424 -39.480  1.00 38.66           C
ATOM   4438  OE1  GLU B 190      57.980  51.496 -38.241  1.00 40.90           O
ATOM   4439  OE2  GLU B 190      57.191  52.270 -40.136  1.00 46.57           O
ATOM   4440  C    GLU B 190      59.296  47.481 -40.839  1.00 22.75           C
ATOM   4441  O    GLU B 190      60.411  47.799 -41.242  1.00 20.14           O
ATOM   4442  N    ALA B 191      59.105  46.628 -39.833  1.00 18.61           N
ATOM   4443  CA   ALA B 191      60.229  45.976 -39.157  1.00 20.17           C
ATOM   4444  CB   ALA B 191      59.722  45.038 -38.060  1.00 15.95           C
ATOM   4445  C    ALA B 191      61.136  45.212 -40.115  1.00 18.53           C
ATOM   4446  O    ALA B 191      62.353  45.204 -39.944  1.00 21.01           O
ATOM   4447  N    PHE B 192      60.534  44.568 -41.114  1.00 18.57           N
ATOM   4448  CA   PHE B 192      61.251  43.637 -41.981  1.00 18.09           C
ATOM   4449  CB   PHE B 192      60.647  42.230 -41.842  1.00 17.07           C
ATOM   4450  CG   PHE B 192      60.660  41.702 -40.423  1.00 15.61           C
ATOM   4451  CD1  PHE B 192      59.471  41.424 -39.756  1.00 18.72           C
ATOM   4452  CE1  PHE B 192      59.480  40.951 -38.438  1.00 18.23           C
ATOM   4453  CZ   PHE B 192      60.687  40.747 -37.781  1.00 17.49           C
ATOM   4454  CE2  PHE B 192      61.879  41.017 -38.429  1.00 18.64           C
ATOM   4455  CD2  PHE B 192      61.864  41.494 -39.751  1.00 20.17           C
ATOM   4456  C    PHE B 192      61.316  44.067 -43.456  1.00 17.09           C
ATOM   4457  O    PHE B 192      61.623  43.258 -44.332  1.00 20.00           O
ATOM   4458  N    TYR B 193      61.041  45.341 -43.714  1.00 17.73           N
ATOM   4459  CA   TYR B 193      60.967  45.861 -45.078  1.00 18.42           C
ATOM   4460  CB   TYR B 193      60.535  47.324 -45.070  1.00 18.17           C
ATOM   4461  CG   TYR B 193      59.830  47.754 -46.328  1.00 22.60           C
ATOM   4462  CD1  TYR B 193      60.385  48.732 -47.163  1.00 26.65           C
ATOM   4463  CE1  TYR B 193      59.729  49.142 -48.318  1.00 23.31           C
ATOM   4464  CZ   TYR B 193      58.501  48.580 -48.640  1.00 24.72           C
ATOM   4465  OH   TYR B 193      57.842  48.975 -49.777  1.00 27.26           O
ATOM   4466  CE2  TYR B 193      57.931  47.612 -47.831  1.00 24.84           C
ATOM   4467  CD2  TYR B 193      58.597  47.206 -46.681  1.00 23.52           C
ATOM   4468  C    TYR B 193      62.273  45.745 -45.849  1.00 19.32           C
ATOM   4469  O    TYR B 193      62.252  45.561 -47.066  1.00 21.59           O
ATOM   4470  N    THR B 194      63.395  45.854 -45.141  1.00 18.59           N
ATOM   4471  CA   THR B 194      64.713  45.841 -45.781  1.00 23.88           C
ATOM   4472  CB   THR B 194      65.599  46.984 -45.243  1.00 26.63           C
ATOM   4473  OG1  THR B 194      65.785  46.819 -43.834  1.00 25.59           O
ATOM   4474  CG2  THR B 194      64.894  48.334 -45.374  1.00 28.80           C
ATOM   4475  C    THR B 194      65.466  44.510 -45.664  1.00 25.04           C
ATOM   4476  O    THR B 194      66.661  44.443 -45.968  1.00 25.23           O
ATOM   4477  N    THR B 195      64.785  43.450 -45.242  1.00 22.14           N
ATOM   4478  CA   THR B 195      65.447  42.148 -45.156  1.00 22.13           C
ATOM   4479  CB   THR B 195      65.649  41.700 -43.684  1.00 24.66           C
ATOM   4480  OG1  THR B 195      66.299  40.420 -43.661  1.00 24.37           O
ATOM   4481  CG2  THR B 195      64.304  41.440 -42.989  1.00 19.81           C
ATOM   4482  C    THR B 195      64.769  41.061 -45.976  1.00 22.30           C
ATOM   4483  O    THR B 195      63.540  41.052 -46.135  1.00 17.75           O
ATOM   4484  N    ASP B 196      65.584  40.159 -46.517  1.00 20.16           N
ATOM   4485  CA   ASP B 196      65.070  39.007 -47.245  1.00 23.92           C
ATOM   4486  CB   ASP B 196      65.962  38.662 -48.449  1.00 27.14           C
ATOM   4487  CG   ASP B 196      67.414  38.383 -48.065  1.00 29.97           C
ATOM   4488  OD1  ASP B 196      67.806  38.579 -46.896  1.00 33.24           O
ATOM   4489  OD2  ASP B 196      68.245  37.963 -48.896  1.00 36.70           O
ATOM   4490  C    ASP B 196      64.868  37.793 -46.336  1.00 20.47           C
ATOM   4491  O    ASP B 196      64.422  36.745 -46.792  1.00 22.64           O
ATOM   4492  N    ARG B 197      65.175  37.946 -45.051  1.00 19.26           N
ATOM   4493  CA   ARG B 197      65.037  36.850 -44.085  1.00 21.36           C
```

FIGURE 3BBBB

```
ATOM   4494  CB   ARG B 197      66.030  37.026 -42.942  1.00 21.84           C
ATOM   4495  CG   ARG B 197      67.476  36.857 -43.402  1.00 27.60           C
ATOM   4496  CD   ARG B 197      68.449  36.480 -42.312  1.00 28.77           C
ATOM   4497  NE   ARG B 197      67.969  35.363 -41.501  1.00 25.50           N
ATOM   4498  CZ   ARG B 197      68.157  35.269 -40.194  1.00 27.91           C
ATOM   4499  NH1  ARG B 197      67.683  34.225 -39.535  1.00 27.06           N
ATOM   4500  NH2  ARG B 197      68.813  36.223 -39.541  1.00 25.26           N
ATOM   4501  C    ARG B 197      63.616  36.707 -43.542  1.00 18.54           C
ATOM   4502  O    ARG B 197      63.291  35.735 -42.860  1.00 19.46           O
ATOM   4503  N    VAL B 198      62.782  37.697 -43.836  1.00 18.33           N
ATOM   4504  CA   VAL B 198      61.357  37.623 -43.546  1.00 16.04           C
ATOM   4505  CB   VAL B 198      60.963  38.464 -42.312  1.00 16.04           C
ATOM   4506  CG1  VAL B 198      59.460  38.353 -42.031  1.00 17.84           C
ATOM   4507  CG2  VAL B 198      61.766  38.034 -41.084  1.00 16.15           C
ATOM   4508  C    VAL B 198      60.612  38.139 -44.768  1.00 18.66           C
ATOM   4509  O    VAL B 198      60.849  39.257 -45.219  1.00 18.06           O
ATOM   4510  N    MET B 199      59.732  37.311 -45.312  1.00 15.12           N
ATOM   4511  CA   MET B 199      58.807  37.763 -46.340  1.00 17.80           C
ATOM   4512  CB   MET B 199      58.614  36.703 -47.428  1.00 20.21           C
ATOM   4513  CG   MET B 199      57.533  37.085 -48.457  1.00 22.76           C
ATOM   4514  SD   MET B 199      57.461  36.017 -49.887  1.00 34.08           S
ATOM   4515  CE   MET B 199      58.906  36.506 -50.739  1.00 27.82           C
ATOM   4516  C    MET B 199      57.479  38.041 -45.665  1.00 18.23           C
ATOM   4517  O    MET B 199      56.991  37.217 -44.893  1.00 17.44           O
ATOM   4518  N    THR B 200      56.906  39.203 -45.941  1.00 14.34           N
ATOM   4519  CA   THR B 200      55.600  39.546 -45.388  1.00 16.48           C
ATOM   4520  CB   THR B 200      55.603  40.917 -44.654  1.00 17.31           C
ATOM   4521  OG1  THR B 200      56.150  41.936 -45.504  1.00 22.06           O
ATOM   4522  CG2  THR B 200      56.553  40.901 -43.463  1.00 18.84           C
ATOM   4523  C    THR B 200      54.581  39.527 -46.513  1.00 19.97           C
ATOM   4524  O    THR B 200      54.831  40.051 -47.611  1.00 19.06           O
ATOM   4525  N    VAL B 201      53.450  38.881 -46.244  1.00 14.00           N
ATOM   4526  CA   VAL B 201      52.372  38.773 -47.208  1.00 14.13           C
ATOM   4527  CB   VAL B 201      52.205  37.330 -47.743  1.00 15.28           C
ATOM   4528  CG1  VAL B 201      51.087  37.260 -48.769  1.00 18.38           C
ATOM   4529  CG2  VAL B 201      53.526  36.806 -48.341  1.00 16.94           C
ATOM   4530  C    VAL B 201      51.096  39.218 -46.516  1.00 18.48           C
ATOM   4531  O    VAL B 201      50.628  38.568 -45.579  1.00 16.84           O
ATOM   4532  N    SER B 202      50.550  40.344 -46.961  1.00 16.27           N
ATOM   4533  CA   SER B 202      49.316  40.856 -46.383  1.00 17.25           C
ATOM   4534  CB   SER B 202      49.553  42.214 -45.713  1.00 15.12           C
ATOM   4535  OG   SER B 202      48.338  42.727 -45.181  1.00 17.17           O
ATOM   4536  C    SER B 202      48.207  40.969 -47.418  1.00 19.64           C
ATOM   4537  O    SER B 202      48.408  41.500 -48.520  1.00 14.36           O
ATOM   4538  N    PHE B 203      47.037  40.459 -47.045  1.00 15.42           N
ATOM   4539  CA   PHE B 203      45.808  40.669 -47.796  1.00 16.52           C
ATOM   4540  CB   PHE B 203      45.070  39.345 -47.964  1.00 16.84           C
ATOM   4541  CG   PHE B 203      45.909  38.256 -48.580  1.00 18.57           C
ATOM   4542  CD1  PHE B 203      46.762  37.481 -47.796  1.00 18.97           C
ATOM   4543  CE1  PHE B 203      47.545  36.473 -48.372  1.00 19.40           C
ATOM   4544  CZ   PHE B 203      47.476  36.236 -49.747  1.00 19.02           C
ATOM   4545  CE2  PHE B 203      46.628  37.003 -50.537  1.00 20.36           C
ATOM   4546  CD2  PHE B 203      45.849  38.014 -49.945  1.00 20.45           C
ATOM   4547  C    PHE B 203      44.964  41.625 -46.972  1.00 14.94           C
ATOM   4548  O    PHE B 203      44.732  41.380 -45.803  1.00 16.25           O
ATOM   4549  N    HIS B 204      44.497  42.716 -47.569  1.00 15.10           N
ATOM   4550  CA   HIS B 204      43.826  43.746 -46.776  1.00 14.34           C
```

FIGURE 3CCCC

| | | | | | | | | | | |
|---|---|---|---|---|---|---|---|---|---|---|
| ATOM | 4551 | CB | HIS | B | 204 | 44.856 | 44.595 | -46.018 | 1.00 14.15 | C |
| ATOM | 4552 | CG | HIS | B | 204 | 45.996 | 45.041 | -46.872 | 1.00 18.06 | C |
| ATOM | 4553 | ND1 | HIS | B | 204 | 47.176 | 44.334 | -46.965 | 1.00 15.83 | N |
| ATOM | 4554 | CE1 | HIS | B | 204 | 47.986 | 44.945 | -47.810 | 1.00 19.08 | C |
| ATOM | 4555 | NE2 | HIS | B | 204 | 47.367 | 46.013 | -48.284 | 1.00 18.08 | N |
| ATOM | 4556 | CD2 | HIS | B | 204 | 46.120 | 46.096 | -47.714 | 1.00 15.80 | C |
| ATOM | 4557 | C | HIS | B | 204 | 42.977 | 44.658 | -47.640 | 1.00 16.49 | C |
| ATOM | 4558 | O | HIS | B | 204 | 43.217 | 44.780 | -48.851 | 1.00 14.56 | O |
| ATOM | 4559 | N | LYS | B | 205 | 41.979 | 45.270 | -47.006 | 1.00 14.90 | N |
| ATOM | 4560 | CA | LYS | B | 205 | 41.241 | 46.360 | -47.620 | 1.00 19.53 | C |
| ATOM | 4561 | CB | LYS | B | 205 | 40.045 | 46.789 | -46.763 | 1.00 22.09 | C |
| ATOM | 4562 | CG | LYS | B | 205 | 39.448 | 48.123 | -47.232 | 1.00 27.89 | C |
| ATOM | 4563 | CD | LYS | B | 205 | 38.027 | 48.333 | -46.767 | 1.00 34.79 | C |
| ATOM | 4564 | CE | LYS | B | 205 | 37.533 | 49.741 | -47.131 | 1.00 38.30 | C |
| ATOM | 4565 | NZ | LYS | B | 205 | 37.466 | 49.968 | -48.599 | 1.00 39.75 | N |
| ATOM | 4566 | C | LYS | B | 205 | 42.192 | 47.535 | -47.800 | 1.00 19.94 | C |
| ATOM | 4567 | O | LYS | B | 205 | 42.938 | 47.906 | -46.878 | 1.00 17.66 | O |
| ATOM | 4568 | N | TYR | B | 206 | 42.157 | 48.120 | -48.991 | 1.00 20.18 | N |
| ATOM | 4569 | CA | TYR | B | 206 | 43.010 | 49.246 | -49.316 | 1.00 17.30 | C |
| ATOM | 4570 | CB | TYR | B | 206 | 44.179 | 48.785 | -50.191 | 1.00 20.66 | C |
| ATOM | 4571 | CG | TYR | B | 206 | 45.196 | 49.861 | -50.482 | 1.00 25.57 | C |
| ATOM | 4572 | CD1 | TYR | B | 206 | 45.164 | 50.570 | -51.686 | 1.00 30.67 | C |
| ATOM | 4573 | CE1 | TYR | B | 206 | 46.097 | 51.565 | -51.960 | 1.00 31.11 | C |
| ATOM | 4574 | CZ | TYR | B | 206 | 47.069 | 51.862 | -51.029 | 1.00 30.46 | C |
| ATOM | 4575 | OH | TYR | B | 206 | 47.987 | 52.847 | -51.287 | 1.00 31.69 | O |
| ATOM | 4576 | CE2 | TYR | B | 206 | 47.124 | 51.174 | -49.819 | 1.00 28.88 | C |
| ATOM | 4577 | CD2 | TYR | B | 206 | 46.190 | 50.178 | -49.558 | 1.00 25.19 | C |
| ATOM | 4578 | C | TYR | B | 206 | 42.202 | 50.328 | -50.038 | 1.00 22.27 | C |
| ATOM | 4579 | O | TYR | B | 206 | 41.352 | 50.022 | -50.878 | 1.00 23.37 | O |
| ATOM | 4580 | N | GLY | B | 207 | 42.489 | 51.582 | -49.709 | 1.00 26.00 | N |
| ATOM | 4581 | CA | GLY | B | 207 | 41.824 | 52.722 | -50.315 | 1.00 26.82 | C |
| ATOM | 4582 | C | GLY | B | 207 | 41.146 | 53.557 | -49.252 | 1.00 28.96 | C |
| ATOM | 4583 | O | GLY | B | 207 | 39.996 | 53.294 | -48.899 | 1.00 32.68 | O |
| ATOM | 4584 | N | GLU | B | 208 | 41.873 | 54.546 | -48.734 | 1.00 32.89 | N |
| ATOM | 4585 | CA | GLU | B | 208 | 41.380 | 55.454 | -47.689 | 1.00 38.40 | C |
| ATOM | 4586 | CB | GLU | B | 208 | 40.322 | 56.411 | -48.252 | 1.00 44.37 | C |
| ATOM | 4587 | CG | GLU | B | 208 | 40.899 | 57.477 | -49.174 | 1.00 51.34 | C |
| ATOM | 4588 | CD | GLU | B | 208 | 39.843 | 58.406 | -49.746 | 1.00 56.00 | C |
| ATOM | 4589 | OE1 | GLU | B | 208 | 38.925 | 58.812 | -48.998 | 1.00 57.32 | O |
| ATOM | 4590 | OE2 | GLU | B | 208 | 39.935 | 58.736 | -50.948 | 1.00 58.73 | O |
| ATOM | 4591 | C | GLU | B | 208 | 40.867 | 54.690 | -46.463 | 1.00 37.69 | C |
| ATOM | 4592 | O | GLU | B | 208 | 39.778 | 54.949 | -45.944 | 1.00 38.26 | O |
| ATOM | 4593 | N | TYR | B | 209 | 41.680 | 53.738 | -46.017 | 1.00 31.97 | N |
| ATOM | 4594 | CA | TYR | B | 209 | 41.323 | 52.827 | -44.939 | 1.00 27.56 | C |
| ATOM | 4595 | CB | TYR | B | 209 | 40.946 | 51.470 | -45.534 | 1.00 27.63 | C |
| ATOM | 4596 | CG | TYR | B | 209 | 40.120 | 50.579 | -44.630 | 1.00 28.79 | C |
| ATOM | 4597 | CD1 | TYR | B | 209 | 40.631 | 49.369 | -44.166 | 1.00 28.55 | C |
| ATOM | 4598 | CE1 | TYR | B | 209 | 39.877 | 48.538 | -43.343 | 1.00 26.04 | C |
| ATOM | 4599 | CZ | TYR | B | 209 | 38.600 | 48.917 | -42.977 | 1.00 31.09 | C |
| ATOM | 4600 | OH | TYR | B | 209 | 37.862 | 48.096 | -42.163 | 1.00 37.08 | O |
| ATOM | 4601 | CE2 | TYR | B | 209 | 38.063 | 50.113 | -43.423 | 1.00 32.84 | C |
| ATOM | 4602 | CD2 | TYR | B | 209 | 38.825 | 50.936 | -44.251 | 1.00 32.55 | C |
| ATOM | 4603 | C | TYR | B | 209 | 42.537 | 52.688 | -44.035 | 1.00 23.31 | C |
| ATOM | 4604 | O | TYR | B | 209 | 43.669 | 52.674 | -44.523 | 1.00 23.94 | O |
| ATOM | 4605 | N | PHE | B | 210 | 42.310 | 52.590 | -42.726 | 1.00 21.06 | N |
| ATOM | 4606 | CA | PHE | B | 210 | 43.402 | 52.387 | -41.777 | 1.00 20.00 | C |
| ATOM | 4607 | CB | PHE | B | 210 | 42.851 | 52.225 | -40.350 | 1.00 21.32 | C |

FIGURE 3DDDD

```
ATOM   4608  CG  PHE B 210      43.914  52.248 -39.297  1.00 22.37           C
ATOM   4609  CD1 PHE B 210      44.475  51.057 -38.831  1.00 20.06           C
ATOM   4610  CE1 PHE B 210      45.482  51.073 -37.870  1.00 18.89           C
ATOM   4611  CZ  PHE B 210      45.946  52.284 -37.374  1.00 19.37           C
ATOM   4612  CE2 PHE B 210      45.399  53.486 -37.845  1.00 23.11           C
ATOM   4613  CD2 PHE B 210      44.396  53.457 -38.805  1.00 21.35           C
ATOM   4614  C   PHE B 210      44.236  51.151 -42.166  1.00 16.50           C
ATOM   4615  O   PHE B 210      43.664  50.154 -42.599  1.00 20.51           O
ATOM   4616  N   PRO B 211      45.566  51.192 -42.029  1.00 19.04           N
ATOM   4617  CA  PRO B 211      46.343  52.385 -41.670  1.00 18.95           C
ATOM   4618  CB  PRO B 211      47.544  51.782 -40.924  1.00 20.57           C
ATOM   4619  CG  PRO B 211      47.772  50.477 -41.608  1.00 21.47           C
ATOM   4620  CD  PRO B 211      46.429  50.002 -42.146  1.00 19.76           C
ATOM   4621  C   PRO B 211      46.844  53.210 -42.868  1.00 22.76           C
ATOM   4622  O   PRO B 211      47.636  54.133 -42.655  1.00 27.93           O
ATOM   4623  N   GLY B 212      46.402  52.883 -44.082  1.00 22.80           N
ATOM   4624  CA  GLY B 212      46.712  53.678 -45.263  1.00 25.36           C
ATOM   4625  C   GLY B 212      47.931  53.209 -46.033  1.00 28.41           C
ATOM   4626  O   GLY B 212      48.315  53.819 -47.034  1.00 26.92           O
ATOM   4627  N   THR B 213      48.540  52.121 -45.571  1.00 22.74           N
ATOM   4628  CA  THR B 213      49.727  51.566 -46.224  1.00 21.83           C
ATOM   4629  CB  THR B 213      50.837  51.323 -45.193  1.00 24.10           C
ATOM   4630  OG1 THR B 213      50.276  50.669 -44.053  1.00 20.79           O
ATOM   4631  CG2 THR B 213      51.365  52.651 -44.621  1.00 27.28           C
ATOM   4632  C   THR B 213      49.347  50.260 -46.913  1.00 20.41           C
ATOM   4633  O   THR B 213      48.177  49.875 -46.925  1.00 21.90           O
ATOM   4634  N   GLY B 214      50.329  49.575 -47.486  1.00 17.51           N
ATOM   4635  CA  GLY B 214      50.070  48.292 -48.110  1.00 17.30           C
ATOM   4636  C   GLY B 214      49.634  48.389 -49.556  1.00 18.39           C
ATOM   4637  O   GLY B 214      48.813  47.601 -50.024  1.00 19.22           O
ATOM   4638  N   ASP B 215      50.200  49.354 -50.274  1.00 19.22           N
ATOM   4639  CA  ASP B 215      49.972  49.455 -51.707  1.00 21.18           C
ATOM   4640  CB  ASP B 215      50.593  50.745 -52.257  1.00 21.43           C
ATOM   4641  CG  ASP B 215      50.106  51.077 -53.655  1.00 25.69           C
ATOM   4642  OD1 ASP B 215      50.508  50.385 -54.603  1.00 24.96           O
ATOM   4643  OD2 ASP B 215      49.318  52.007 -53.904  1.00 28.95           O
ATOM   4644  C   ASP B 215      50.574  48.238 -52.399  1.00 19.97           C
ATOM   4645  O   ASP B 215      51.570  47.676 -51.934  1.00 22.25           O
ATOM   4646  N   LEU B 216      49.954  47.835 -53.502  1.00 19.48           N
ATOM   4647  CA  LEU B 216      50.487  46.799 -54.389  1.00 20.76           C
ATOM   4648  CB  LEU B 216      49.657  46.786 -55.677  1.00 24.01           C
ATOM   4649  CG  LEU B 216      50.036  45.851 -56.821  1.00 26.06           C
ATOM   4650  CD1 LEU B 216      49.730  44.412 -56.436  1.00 30.00           C
ATOM   4651  CD2 LEU B 216      49.285  46.234 -58.087  1.00 30.84           C
ATOM   4652  C   LEU B 216      51.969  47.016 -54.735  1.00 18.98           C
ATOM   4653  O   LEU B 216      52.743  46.060 -54.886  1.00 21.02           O
ATOM   4654  N   ARG B 217      52.355  48.282 -54.864  1.00 18.76           N
ATOM   4655  CA  ARG B 217      53.701  48.637 -55.313  1.00 22.30           C
ATOM   4656  CB  ARG B 217      53.671  49.974 -56.055  1.00 24.03           C
ATOM   4657  CG  ARG B 217      52.927  49.908 -57.365  1.00 27.15           C
ATOM   4658  CD  ARG B 217      51.556  50.515 -57.276  1.00 37.44           C
ATOM   4659  NE  ARG B 217      51.512  51.790 -57.961  1.00 37.73           N
ATOM   4660  CZ  ARG B 217      50.786  52.837 -57.599  1.00 35.30           C
ATOM   4661  NH1 ARG B 217      50.010  52.815 -56.517  1.00 30.26           N
ATOM   4662  NH2 ARG B 217      50.848  53.925 -58.341  1.00 27.71           N
ATOM   4663  C   ARG B 217      54.721  48.695 -54.183  1.00 25.14           C
ATOM   4664  O   ARG B 217      55.917  48.883 -54.430  1.00 22.96           O
```

FIGURE 3EEEE

```
ATOM   4665  N    ASP B 218      54.252  48.553 -52.945  1.00 24.09           N
ATOM   4666  CA   ASP B 218      55.157  48.458 -51.806  1.00 23.29           C
ATOM   4667  CB   ASP B 218      54.439  48.831 -50.506  1.00 25.20           C
ATOM   4668  CG   ASP B 218      54.035  50.296 -50.467  1.00 30.62           C
ATOM   4669  OD1  ASP B 218      53.126  50.652 -49.680  1.00 26.04           O
ATOM   4670  OD2  ASP B 218      54.574  51.163 -51.191  1.00 30.27           O
ATOM   4671  C    ASP B 218      55.700  47.036 -51.761  1.00 25.43           C
ATOM   4672  O    ASP B 218      55.029  46.120 -51.288  1.00 23.11           O
ATOM   4673  N    ILE B 219      56.912  46.857 -52.278  1.00 22.50           N
ATOM   4674  CA   ILE B 219      57.467  45.516 -52.479  1.00 20.86           C
ATOM   4675  CB   ILE B 219      57.779  45.276 -53.981  1.00 24.87           C
ATOM   4676  CG1  ILE B 219      58.812  46.294 -54.488  1.00 26.63           C
ATOM   4677  CD1  ILE B 219      59.507  45.888 -55.774  1.00 33.02           C
ATOM   4678  CG2  ILE B 219      56.483  45.274 -54.802  1.00 27.46           C
ATOM   4679  C    ILE B 219      58.705  45.209 -51.641  1.00 19.36           C
ATOM   4680  O    ILE B 219      59.330  44.150 -51.812  1.00 20.33           O
ATOM   4681  N    GLY B 220      59.056  46.124 -50.743  1.00 19.84           N
ATOM   4682  CA   GLY B 220      60.279  45.997 -49.970  1.00 23.43           C
ATOM   4683  C    GLY B 220      61.352  46.918 -50.515  1.00 25.46           C
ATOM   4684  O    GLY B 220      61.161  47.541 -51.560  1.00 23.34           O
ATOM   4685  N    ALA B 221      62.476  47.010 -49.807  1.00 24.12           N
ATOM   4686  CA   ALA B 221      63.580  47.876 -50.221  1.00 24.96           C
ATOM   4687  CB   ALA B 221      63.464  49.245 -49.552  1.00 24.77           C
ATOM   4688  C    ALA B 221      64.915  47.220 -49.880  1.00 25.80           C
ATOM   4689  O    ALA B 221      64.990  46.402 -48.957  1.00 25.46           O
ATOM   4690  N    GLY B 222      65.957  47.566 -50.638  1.00 27.38           N
ATOM   4691  CA   GLY B 222      67.292  47.033 -50.421  1.00 29.04           C
ATOM   4692  C    GLY B 222      67.344  45.528 -50.580  1.00 26.37           C
ATOM   4693  O    GLY B 222      66.832  44.976 -51.557  1.00 28.24           O
ATOM   4694  N    LYS B 223      67.957  44.857 -49.611  1.00 28.06           N
ATOM   4695  CA   LYS B 223      68.002  43.398 -49.604  1.00 29.18           C
ATOM   4696  CB   LYS B 223      68.813  42.892 -48.406  1.00 32.72           C
ATOM   4697  CG   LYS B 223      69.500  41.560 -48.652  1.00 42.07           C
ATOM   4698  CD   LYS B 223      70.688  41.351 -47.720  1.00 45.41           C
ATOM   4699  CE   LYS B 223      71.481  40.114 -48.119  1.00 50.39           C
ATOM   4700  NZ   LYS B 223      72.751  39.995 -47.349  1.00 55.17           N
ATOM   4701  C    LYS B 223      66.588  42.808 -49.577  1.00 27.08           C
ATOM   4702  O    LYS B 223      66.368  41.687 -50.029  1.00 25.68           O
ATOM   4703  N    GLY B 224      65.638  43.582 -49.054  1.00 23.55           N
ATOM   4704  CA   GLY B 224      64.257  43.139 -48.931  1.00 24.66           C
ATOM   4705  C    GLY B 224      63.365  43.420 -50.129  1.00 21.44           C
ATOM   4706  O    GLY B 224      62.169  43.161 -50.062  1.00 19.70           O
ATOM   4707  N    LYS B 225      63.930  43.935 -51.225  1.00 22.44           N
ATOM   4708  CA   LYS B 225      63.138  44.184 -52.434  1.00 23.48           C
ATOM   4709  CB   LYS B 225      63.956  44.906 -53.514  1.00 27.44           C
ATOM   4710  CG   LYS B 225      63.101  45.718 -54.476  1.00 31.29           C
ATOM   4711  CD   LYS B 225      63.952  46.447 -55.505  1.00 39.08           C
ATOM   4712  CE   LYS B 225      63.109  46.938 -56.671  1.00 43.00           C
ATOM   4713  NZ   LYS B 225      63.029  48.426 -56.701  1.00 48.59           N
ATOM   4714  C    LYS B 225      62.557  42.888 -52.991  1.00 23.85           C
ATOM   4715  O    LYS B 225      63.286  41.920 -53.211  1.00 24.60           O
ATOM   4716  N    TYR B 226      61.239  42.894 -53.203  1.00 23.47           N
ATOM   4717  CA   TYR B 226      60.450  41.722 -53.613  1.00 24.71           C
ATOM   4718  CB   TYR B 226      61.089  40.980 -54.796  1.00 26.80           C
ATOM   4719  CG   TYR B 226      61.170  41.831 -56.040  1.00 31.24           C
ATOM   4720  CD1  TYR B 226      60.014  42.210 -56.720  1.00 34.45           C
ATOM   4721  CE1  TYR B 226      60.078  43.002 -57.863  1.00 39.19           C
```

FIGURE 3FFFF

| | | | | | | | | | |
|---|---|---|---|---|---|---|---|---|---|
| ATOM | 4722 | CZ | TYR B 226 | 61.309 | 43.427 | -58.329 | 1.00 | 41.37 | C |
| ATOM | 4723 | OH | TYR B 226 | 61.365 | 44.214 | -59.459 | 1.00 | 45.37 | O |
| ATOM | 4724 | CE2 | TYR B 226 | 62.475 | 43.069 | -57.668 | 1.00 | 37.82 | C |
| ATOM | 4725 | CD2 | TYR B 226 | 62.400 | 42.276 | -56.524 | 1.00 | 36.04 | C |
| ATOM | 4726 | C | TYR B 226 | 60.098 | 40.755 | -52.469 | 1.00 | 21.31 | C |
| ATOM | 4727 | O | TYR B 226 | 59.493 | 39.706 | -52.710 | 1.00 | 25.00 | O |
| ATOM | 4728 | N | TYR B 227 | 60.455 | 41.122 | -51.242 | 1.00 | 21.24 | N |
| ATOM | 4729 | CA | TYR B 227 | 60.144 | 40.295 | -50.068 | 1.00 | 22.04 | C |
| ATOM | 4730 | CB | TYR B 227 | 61.399 | 40.051 | -49.230 | 1.00 | 21.71 | C |
| ATOM | 4731 | CG | TYR B 227 | 62.392 | 39.212 | -49.980 | 1.00 | 20.76 | C |
| ATOM | 4732 | CD1 | TYR B 227 | 63.384 | 39.806 | -50.759 | 1.00 | 25.18 | C |
| ATOM | 4733 | CE1 | TYR B 227 | 64.299 | 39.034 | -51.476 | 1.00 | 26.24 | C |
| ATOM | 4734 | CZ | TYR B 227 | 64.217 | 37.655 | -51.426 | 1.00 | 28.58 | C |
| ATOM | 4735 | OH | TYR B 227 | 65.121 | 36.891 | -52.140 | 1.00 | 28.83 | O |
| ATOM | 4736 | CE2 | TYR B 227 | 63.233 | 37.037 | -50.664 | 1.00 | 25.59 | C |
| ATOM | 4737 | CD2 | TYR B 227 | 62.322 | 37.820 | -49.948 | 1.00 | 22.91 | C |
| ATOM | 4738 | C | TYR B 227 | 58.994 | 40.839 | -49.216 | 1.00 | 24.18 | C |
| ATOM | 4739 | O | TYR B 227 | 58.725 | 40.330 | -48.127 | 1.00 | 21.71 | O |
| ATOM | 4740 | N | ALA B 228 | 58.323 | 41.871 | -49.724 | 1.00 | 19.86 | N |
| ATOM | 4741 | CA | ALA B 228 | 57.058 | 42.326 | -49.150 | 1.00 | 18.28 | C |
| ATOM | 4742 | CB | ALA B 228 | 57.155 | 43.773 | -48.658 | 1.00 | 20.13 | C |
| ATOM | 4743 | C | ALA B 228 | 55.998 | 42.185 | -50.227 | 1.00 | 19.46 | C |
| ATOM | 4744 | O | ALA B 228 | 56.189 | 42.634 | -51.365 | 1.00 | 20.10 | O |
| ATOM | 4745 | N | VAL B 229 | 54.892 | 41.536 | -49.872 | 1.00 | 16.15 | N |
| ATOM | 4746 | CA | VAL B 229 | 53.849 | 41.197 | -50.826 | 1.00 | 17.32 | C |
| ATOM | 4747 | CB | VAL B 229 | 53.737 | 39.656 | -51.046 | 1.00 | 20.03 | C |
| ATOM | 4748 | CG1 | VAL B 229 | 52.663 | 39.324 | -52.076 | 1.00 | 21.62 | C |
| ATOM | 4749 | CG2 | VAL B 229 | 55.075 | 39.054 | -51.480 | 1.00 | 22.80 | C |
| ATOM | 4750 | C | VAL B 229 | 52.532 | 41.741 | -50.298 | 1.00 | 19.18 | C |
| ATOM | 4751 | O | VAL B 229 | 52.095 | 41.351 | -49.226 | 1.00 | 18.46 | O |
| ATOM | 4752 | N | ASN B 230 | 51.913 | 42.651 | -51.052 | 1.00 | 14.89 | N |
| ATOM | 4753 | CA | ASN B 230 | 50.654 | 43.261 | -50.641 | 1.00 | 17.60 | C |
| ATOM | 4754 | CB | ASN B 230 | 50.861 | 44.758 | -50.381 | 1.00 | 16.56 | C |
| ATOM | 4755 | CG | ASN B 230 | 51.675 | 45.010 | -49.125 | 1.00 | 18.84 | C |
| ATOM | 4756 | OD1 | ASN B 230 | 51.250 | 44.652 | -48.025 | 1.00 | 21.53 | O |
| ATOM | 4757 | ND2 | ASN B 230 | 52.868 | 45.589 | -49.284 | 1.00 | 18.48 | N |
| ATOM | 4758 | C | ASN B 230 | 49.536 | 43.032 | -51.645 | 1.00 | 18.01 | C |
| ATOM | 4759 | O | ASN B 230 | 49.693 | 43.321 | -52.836 | 1.00 | 17.76 | O |
| ATOM | 4760 | N | PHE B 231 | 48.420 | 42.486 | -51.160 | 1.00 | 15.46 | N |
| ATOM | 4761 | CA | PHE B 231 | 47.233 | 42.272 | -51.986 | 1.00 | 14.44 | C |
| ATOM | 4762 | CB | PHE B 231 | 46.774 | 40.811 | -51.973 | 1.00 | 16.00 | C |
| ATOM | 4763 | CG | PHE B 231 | 45.944 | 40.429 | -53.182 | 1.00 | 16.80 | C |
| ATOM | 4764 | CD1 | PHE B 231 | 46.334 | 39.382 | -54.004 | 1.00 | 17.53 | C |
| ATOM | 4765 | CE1 | PHE B 231 | 45.582 | 39.039 | -55.132 | 1.00 | 18.09 | C |
| ATOM | 4766 | CZ | PHE B 231 | 44.429 | 39.746 | -55.442 | 1.00 | 17.95 | C |
| ATOM | 4767 | CE2 | PHE B 231 | 44.025 | 40.800 | -54.633 | 1.00 | 20.66 | C |
| ATOM | 4768 | CD2 | PHE B 231 | 44.788 | 41.137 | -53.509 | 1.00 | 17.61 | C |
| ATOM | 4769 | C | PHE B 231 | 46.100 | 43.186 | -51.518 | 1.00 | 18.59 | C |
| ATOM | 4770 | O | PHE B 231 | 45.377 | 42.867 | -50.564 | 1.00 | 16.03 | O |
| ATOM | 4771 | N | PRO B 232 | 45.964 | 44.331 | -52.178 | 1.00 | 16.21 | N |
| ATOM | 4772 | CA | PRO B 232 | 44.927 | 45.297 | -51.825 | 1.00 | 18.79 | C |
| ATOM | 4773 | CB | PRO B 232 | 45.381 | 46.579 | -52.532 | 1.00 | 19.74 | C |
| ATOM | 4774 | CG | PRO B 232 | 46.302 | 46.151 | -53.618 | 1.00 | 20.63 | C |
| ATOM | 4775 | CD | PRO B 232 | 46.812 | 44.793 | -53.293 | 1.00 | 17.58 | C |
| ATOM | 4776 | C | PRO B 232 | 43.573 | 44.831 | -52.332 | 1.00 | 18.01 | C |
| ATOM | 4777 | O | PRO B 232 | 43.462 | 44.396 | -53.480 | 1.00 | 19.75 | O |
| ATOM | 4778 | N | MET B 233 | 42.566 | 44.903 | -51.467 | 1.00 | 17.52 | N |

FIGURE 3GGGG

```
ATOM   4779  CA  MET B 233      41.222  44.457 -51.800  1.00 15.99           C
ATOM   4780  CB  MET B 233      40.856  43.218 -50.975  1.00 18.25           C
ATOM   4781  CG  MET B 233      41.656  41.969 -51.327  1.00 24.52           C
ATOM   4782  SD  MET B 233      41.496  40.713 -50.050  1.00 27.92           S
ATOM   4783  CE  MET B 233      42.182  39.260 -50.886  1.00 29.30           C
ATOM   4784  C   MET B 233      40.201  45.557 -51.540  1.00 16.59           C
ATOM   4785  O   MET B 233      40.479  46.524 -50.838  1.00 23.57           O
ATOM   4786  N   ARG B 234      39.012  45.382 -52.110  1.00 18.03           N
ATOM   4787  CA  ARG B 234      37.906  46.302 -51.927  1.00 16.88           C
ATOM   4788  CB  ARG B 234      37.266  46.649 -53.283  1.00 23.35           C
ATOM   4789  CG  ARG B 234      38.232  47.141 -54.355  1.00 27.98           C
ATOM   4790  CD  ARG B 234      38.498  48.627 -54.310  1.00 34.85           C
ATOM   4791  NE  ARG B 234      39.791  48.897 -53.711  1.00 40.91           N
ATOM   4792  CZ  ARG B 234      40.891  49.243 -54.370  1.00 35.19           C
ATOM   4793  NH1 ARG B 234      41.998  49.443 -53.683  1.00 29.57           N
ATOM   4794  NH2 ARG B 234      40.902  49.397 -55.689  1.00 34.48           N
ATOM   4795  C   ARG B 234      36.862  45.656 -51.026  1.00 17.47           C
ATOM   4796  O   ARG B 234      36.945  44.459 -50.724  1.00 17.33           O
ATOM   4797  N   ASP B 235      35.880  46.452 -50.615  1.00 18.55           N
ATOM   4798  CA  ASP B 235      34.741  45.976 -49.815  1.00 19.36           C
ATOM   4799  CB  ASP B 235      33.642  47.049 -49.734  1.00 26.88           C
ATOM   4800  CG  ASP B 235      34.091  48.311 -49.050  1.00 36.13           C
ATOM   4801  OD1 ASP B 235      35.218  48.343 -48.525  1.00 38.24           O
ATOM   4802  OD2 ASP B 235      33.374  49.336 -48.990  1.00 41.04           O
ATOM   4803  C   ASP B 235      34.076  44.728 -50.368  1.00 20.75           C
ATOM   4804  O   ASP B 235      33.987  44.537 -51.583  1.00 19.34           O
ATOM   4805  N   GLY B 236      33.588  43.894 -49.454  1.00 16.84           N
ATOM   4806  CA  GLY B 236      32.646  42.846 -49.787  1.00 16.89           C
ATOM   4807  C   GLY B 236      33.218  41.565 -50.343  1.00 17.08           C
ATOM   4808  O   GLY B 236      32.461  40.733 -50.855  1.00 17.92           O
ATOM   4809  N   ILE B 237      34.538  41.389 -50.266  1.00 17.13           N
ATOM   4810  CA  ILE B 237      35.128  40.145 -50.752  1.00 18.09           C
ATOM   4811  CB  ILE B 237      36.681  40.163 -50.657  1.00 21.95           C
ATOM   4812  CG1 ILE B 237      37.269  39.062 -51.547  1.00 25.69           C
ATOM   4813  CD1 ILE B 237      38.596  39.407 -52.162  1.00 30.38           C
ATOM   4814  CG2 ILE B 237      37.156  40.000 -49.215  1.00 18.58           C
ATOM   4815  C   ILE B 237      34.499  38.941 -50.024  1.00 18.52           C
ATOM   4816  O   ILE B 237      34.219  39.005 -48.825  1.00 17.05           O
ATOM   4817  N   ASP B 238      34.245  37.868 -50.768  1.00 17.17           N
ATOM   4818  CA  ASP B 238      33.594  36.682 -50.219  1.00 20.94           C
ATOM   4819  CB  ASP B 238      32.281  36.370 -50.966  1.00 25.98           C
ATOM   4820  CG  ASP B 238      32.463  36.223 -52.480  1.00 34.97           C
ATOM   4821  OD1 ASP B 238      33.506  35.713 -52.944  1.00 34.59           O
ATOM   4822  OD2 ASP B 238      31.586  36.577 -53.297  1.00 40.46           O
ATOM   4823  C   ASP B 238      34.531  35.478 -50.226  1.00 19.85           C
ATOM   4824  O   ASP B 238      35.650  35.547 -50.741  1.00 21.00           O
ATOM   4825  N   ASP B 239      34.064  34.381 -49.642  1.00 19.25           N
ATOM   4826  CA  ASP B 239      34.837  33.148 -49.522  1.00 23.20           C
ATOM   4827  CB  ASP B 239      33.943  32.036 -48.985  1.00 22.49           C
ATOM   4828  CG  ASP B 239      33.557  32.235 -47.543  1.00 24.64           C
ATOM   4829  OD1 ASP B 239      34.095  33.151 -46.871  1.00 22.83           O
ATOM   4830  OD2 ASP B 239      32.722  31.492 -46.992  1.00 25.60           O
ATOM   4831  C   ASP B 239      35.453  32.667 -50.834  1.00 21.38           C
ATOM   4832  O   ASP B 239      36.643  32.356 -50.889  1.00 20.73           O
ATOM   4833  N   GLU B 240      34.623  32.583 -51.871  1.00 25.94           N
ATOM   4834  CA  GLU B 240      35.036  32.088 -53.183  1.00 30.48           C
ATOM   4835  CB  GLU B 240      33.829  32.031 -54.129  1.00 36.05           C
```

FIGURE 3HHHH

```
ATOM   4836  CG   GLU B 240      34.059  31.255 -55.420  1.00 48.26           C
ATOM   4837  CD   GLU B 240      32.828  31.217 -56.314  1.00 53.47           C
ATOM   4838  OE1  GLU B 240      32.400  32.289 -56.802  1.00 56.32           O
ATOM   4839  OE2  GLU B 240      32.286  30.112 -56.532  1.00 57.70           O
ATOM   4840  C    GLU B 240      36.163  32.939 -53.778  1.00 25.36           C
ATOM   4841  O    GLU B 240      37.188  32.404 -54.200  1.00 28.41           O
ATOM   4842  N    SER B 241      35.974  34.258 -53.778  1.00 22.49           N
ATOM   4843  CA   SER B 241      36.962  35.195 -54.313  1.00 25.95           C
ATOM   4844  CB   SER B 241      36.387  36.609 -54.374  1.00 27.19           C
ATOM   4845  OG   SER B 241      35.230  36.646 -55.190  1.00 32.80           O
ATOM   4846  C    SER B 241      38.275  35.193 -53.524  1.00 23.35           C
ATOM   4847  O    SER B 241      39.359  35.199 -54.110  1.00 23.32           O
ATOM   4848  N    TYR B 242      38.169  35.192 -52.198  1.00 20.82           N
ATOM   4849  CA   TYR B 242      39.340  35.151 -51.331  1.00 21.99           C
ATOM   4850  CB   TYR B 242      38.916  35.269 -49.869  1.00 19.70           C
ATOM   4851  CG   TYR B 242      39.973  35.836 -48.957  1.00 16.48           C
ATOM   4852  CD1  TYR B 242      39.956  37.186 -48.598  1.00 19.09           C
ATOM   4853  CE1  TYR B 242      40.926  37.718 -47.749  1.00 18.72           C
ATOM   4854  CZ   TYR B 242      41.914  36.890 -47.239  1.00 19.07           C
ATOM   4855  OH   TYR B 242      42.865  37.416 -46.393  1.00 20.07           O
ATOM   4856  CE2  TYR B 242      41.947  35.548 -47.569  1.00 19.76           C
ATOM   4857  CD2  TYR B 242      40.975  35.023 -48.422  1.00 18.85           C
ATOM   4858  C    TYR B 242      40.125  33.858 -51.543  1.00 20.42           C
ATOM   4859  O    TYR B 242      41.351  33.886 -51.683  1.00 22.59           O
ATOM   4860  N    GLY B 243      39.405  32.740 -51.582  1.00 21.71           N
ATOM   4861  CA   GLY B 243      39.997  31.424 -51.760  1.00 27.56           C
ATOM   4862  C    GLY B 243      40.755  31.286 -53.065  1.00 28.78           C
ATOM   4863  O    GLY B 243      41.831  30.685 -53.096  1.00 29.82           O
ATOM   4864  N    GLN B 244      40.195  31.867 -54.128  1.00 26.94           N
ATOM   4865  CA   GLN B 244      40.780  31.834 -55.468  1.00 31.15           C
ATOM   4866  CB   GLN B 244      39.782  32.360 -56.505  1.00 38.58           C
ATOM   4867  CG   GLN B 244      38.684  31.366 -56.912  1.00 49.05           C
ATOM   4868  CD   GLN B 244      39.223  30.107 -57.581  1.00 55.20           C
ATOM   4869  OE1  GLN B 244      40.097  30.178 -58.449  1.00 57.57           O
ATOM   4870  NE2  GLN B 244      38.700  28.954 -57.178  1.00 56.68           N
ATOM   4871  C    GLN B 244      42.074  32.636 -55.559  1.00 29.14           C
ATOM   4872  O    GLN B 244      42.860  32.454 -56.490  1.00 29.13           O
ATOM   4873  N    ILE B 245      42.281  33.534 -54.601  1.00 25.02           N
ATOM   4874  CA   ILE B 245      43.487  34.351 -54.573  1.00 25.49           C
ATOM   4875  CB   ILE B 245      43.115  35.846 -54.393  1.00 28.54           C
ATOM   4876  CG1  ILE B 245      43.318  36.586 -55.717  1.00 36.08           C
ATOM   4877  CD1  ILE B 245      42.615  35.960 -56.928  1.00 37.93           C
ATOM   4878  CG2  ILE B 245      43.901  36.514 -53.261  1.00 29.33           C
ATOM   4879  C    ILE B 245      44.508  33.860 -53.553  1.00 22.76           C
ATOM   4880  O    ILE B 245      45.706  33.835 -53.844  1.00 22.82           O
ATOM   4881  N    PHE B 246      44.034  33.445 -52.379  1.00 20.05           N
ATOM   4882  CA   PHE B 246      44.924  33.044 -51.290  1.00 18.46           C
ATOM   4883  CB   PHE B 246      44.125  32.812 -49.996  1.00 18.55           C
ATOM   4884  CG   PHE B 246      44.985  32.613 -48.772  1.00 17.14           C
ATOM   4885  CD1  PHE B 246      45.309  31.326 -48.333  1.00 17.04           C
ATOM   4886  CE1  PHE B 246      46.111  31.129 -47.195  1.00 17.11           C
ATOM   4887  CZ   PHE B 246      46.579  32.233 -46.484  1.00 14.31           C
ATOM   4888  CE2  PHE B 246      46.261  33.525 -46.917  1.00 15.82           C
ATOM   4889  CD2  PHE B 246      45.465  33.709 -48.051  1.00 16.40           C
ATOM   4890  C    PHE B 246      45.761  31.810 -51.641  1.00 17.34           C
ATOM   4891  O    PHE B 246      46.991  31.844 -51.538  1.00 18.76           O
ATOM   4892  N    LYS B 247      45.100  30.724 -52.036  1.00 17.85           N
```

FIGURE 3IIII

```
ATOM   4893  CA  LYS B 247      45.805  29.468 -52.318  1.00 21.78           C
ATOM   4894  CB  LYS B 247      44.830  28.339 -52.679  1.00 24.48           C
ATOM   4895  CG  LYS B 247      45.434  26.933 -52.571  1.00 31.18           C
ATOM   4896  CD  LYS B 247      44.458  25.866 -53.069  1.00 35.18           C
ATOM   4897  CE  LYS B 247      45.135  24.501 -53.194  1.00 42.83           C
ATOM   4898  NZ  LYS B 247      44.179  23.369 -52.978  1.00 45.92           N
ATOM   4899  C   LYS B 247      46.925  29.616 -53.370  1.00 20.54           C
ATOM   4900  O   LYS B 247      48.076  29.260 -53.081  1.00 20.22           O
ATOM   4901  N   PRO B 248      46.616  30.152 -54.558  1.00 23.86           N
ATOM   4902  CA  PRO B 248      47.639  30.354 -55.598  1.00 22.86           C
ATOM   4903  CB  PRO B 248      46.857  31.009 -56.744  1.00 24.35           C
ATOM   4904  CG  PRO B 248      45.467  30.620 -56.514  1.00 28.80           C
ATOM   4905  CD  PRO B 248      45.288  30.587 -55.024  1.00 21.86           C
ATOM   4906  C   PRO B 248      48.769  31.269 -55.147  1.00 22.88           C
ATOM   4907  O   PRO B 248      49.929  30.972 -55.443  1.00 21.91           O
ATOM   4908  N   ILE B 249      48.449  32.353 -54.440  1.00 18.88           N
ATOM   4909  CA  ILE B 249      49.489  33.270 -53.978  1.00 18.11           C
ATOM   4910  CB  ILE B 249      48.895  34.595 -53.415  1.00 19.58           C
ATOM   4911  CG1 ILE B 249      48.300  35.472 -54.539  1.00 20.29           C
ATOM   4912  CD1 ILE B 249      49.306  36.067 -55.517  1.00 25.47           C
ATOM   4913  CG2 ILE B 249      49.948  35.374 -52.612  1.00 20.69           C
ATOM   4914  C   ILE B 249      50.404  32.591 -52.955  1.00 17.96           C
ATOM   4915  O   ILE B 249      51.629  32.662 -53.071  1.00 18.75           O
ATOM   4916  N   ILE B 250      49.812  31.924 -51.968  1.00 19.03           N
ATOM   4917  CA  ILE B 250      50.613  31.275 -50.934  1.00 20.59           C
ATOM   4918  CB  ILE B 250      49.741  30.885 -49.703  1.00 20.98           C
ATOM   4919  CG1 ILE B 250      49.145  32.144 -49.049  1.00 19.25           C
ATOM   4920  CD1 ILE B 250      50.159  33.232 -48.628  1.00 19.38           C
ATOM   4921  CG2 ILE B 250      50.550  30.082 -48.681  1.00 19.80           C
ATOM   4922  C   ILE B 250      51.434  30.097 -51.493  1.00 20.96           C
ATOM   4923  O   ILE B 250      52.598  29.934 -51.137  1.00 17.63           O
ATOM   4924  N   SER B 251      50.843  29.308 -52.385  1.00 22.52           N
ATOM   4925  CA  SER B 251      51.585  28.252 -53.081  1.00 23.26           C
ATOM   4926  CB  SER B 251      50.682  27.510 -54.074  1.00 24.96           C
ATOM   4927  OG  SER B 251      49.503  27.050 -53.439  1.00 31.21           O
ATOM   4928  C   SER B 251      52.829  28.784 -53.803  1.00 21.46           C
ATOM   4929  O   SER B 251      53.907  28.189 -53.721  1.00 20.01           O
ATOM   4930  N   LYS B 252      52.681  29.911 -54.492  1.00 21.30           N
ATOM   4931  CA  LYS B 252      53.789  30.506 -55.238  1.00 23.80           C
ATOM   4932  CB  LYS B 252      53.266  31.567 -56.217  1.00 24.73           C
ATOM   4933  CG  LYS B 252      54.335  32.183 -57.121  1.00 31.92           C
ATOM   4934  CD  LYS B 252      54.482  31.431 -58.440  1.00 36.52           C
ATOM   4935  CE  LYS B 252      55.696  31.925 -59.222  1.00 41.18           C
ATOM   4936  NZ  LYS B 252      56.080  30.966 -60.299  1.00 44.70           N
ATOM   4937  C   LYS B 252      54.841  31.096 -54.298  1.00 25.06           C
ATOM   4938  O   LYS B 252      56.047  30.982 -54.543  1.00 23.09           O
ATOM   4939  N   VAL B 253      54.381  31.729 -53.220  1.00 20.49           N
ATOM   4940  CA  VAL B 253      55.292  32.218 -52.196  1.00 19.46           C
ATOM   4941  CB  VAL B 253      54.539  32.997 -51.081  1.00 22.23           C
ATOM   4942  CG1 VAL B 253      55.415  33.174 -49.855  1.00 20.97           C
ATOM   4943  CG2 VAL B 253      54.075  34.351 -51.597  1.00 20.79           C
ATOM   4944  C   VAL B 253      56.087  31.045 -51.613  1.00 21.42           C
ATOM   4945  O   VAL B 253      57.303  31.131 -51.475  1.00 19.78           O
ATOM   4946  N   MET B 254      55.403  29.942 -51.306  1.00 19.13           N
ATOM   4947  CA  MET B 254      56.072  28.775 -50.720  1.00 23.41           C
ATOM   4948  CB  MET B 254      55.054  27.690 -50.364  1.00 22.95           C
ATOM   4949  CG  MET B 254      54.168  28.044 -49.197  1.00 24.47           C
```

FIGURE 3JJJJ

```
ATOM   4950  SD  MET B 254      55.077  28.095 -47.665  1.00 25.93           S
ATOM   4951  CE  MET B 254      53.704  28.254 -46.509  1.00 26.92           C
ATOM   4952  C   MET B 254      57.135  28.211 -51.667  1.00 26.44           C
ATOM   4953  O   MET B 254      58.249  27.875 -51.242  1.00 28.89           O
ATOM   4954  N   GLU B 255      56.777  28.128 -52.946  1.00 31.10           N
ATOM   4955  CA  GLU B 255      57.658  27.622 -53.996  1.00 34.36           C
ATOM   4956  CB  GLU B 255      56.871  27.499 -55.307  1.00 38.50           C
ATOM   4957  CG  GLU B 255      57.543  26.671 -56.391  1.00 46.13           C
ATOM   4958  CD  GLU B 255      56.899  26.865 -57.754  1.00 51.89           C
ATOM   4959  OE1 GLU B 255      56.328  25.891 -58.289  1.00 54.54           O
ATOM   4960  OE2 GLU B 255      56.959  27.993 -58.294  1.00 54.00           O
ATOM   4961  C   GLU B 255      58.896  28.505 -54.189  1.00 31.88           C
ATOM   4962  O   GLU B 255      60.020  28.002 -54.250  1.00 30.93           O
ATOM   4963  N   MET B 256      58.690  29.817 -54.272  1.00 27.23           N
ATOM   4964  CA  MET B 256      59.787  30.747 -54.542  1.00 27.01           C
ATOM   4965  CB  MET B 256      59.263  32.037 -55.174  1.00 27.30           C
ATOM   4966  CG  MET B 256      58.538  31.855 -56.509  1.00 33.35           C
ATOM   4967  SD  MET B 256      59.548  31.029 -57.764  1.00 35.24           S
ATOM   4968  CE  MET B 256      60.863  32.209 -57.986  1.00 36.91           C
ATOM   4969  C   MET B 256      60.632  31.076 -53.310  1.00 26.75           C
ATOM   4970  O   MET B 256      61.857  31.130 -53.393  1.00 26.72           O
ATOM   4971  N   TYR B 257      59.976  31.304 -52.177  1.00 24.05           N
ATOM   4972  CA  TYR B 257      60.664  31.736 -50.962  1.00 23.73           C
ATOM   4973  CB  TYR B 257      59.744  32.632 -50.122  1.00 20.85           C
ATOM   4974  CG  TYR B 257      60.434  33.312 -48.976  1.00 20.86           C
ATOM   4975  CD1 TYR B 257      59.965  33.163 -47.670  1.00 20.45           C
ATOM   4976  CE1 TYR B 257      60.600  33.789 -46.608  1.00 17.38           C
ATOM   4977  CZ  TYR B 257      61.715  34.570 -46.850  1.00 20.33           C
ATOM   4978  OH  TYR B 257      62.345  35.187 -45.809  1.00 20.91           O
ATOM   4979  CE2 TYR B 257      62.202  34.730 -48.135  1.00 18.24           C
ATOM   4980  CD2 TYR B 257      61.560  34.108 -49.188  1.00 18.30           C
ATOM   4981  C   TYR B 257      61.223  30.589 -50.115  1.00 24.20           C
ATOM   4982  O   TYR B 257      62.253  30.742 -49.462  1.00 25.23           O
ATOM   4983  N   GLN B 258      60.535  29.450 -50.131  1.00 23.28           N
ATOM   4984  CA  GLN B 258      60.911  28.273 -49.332  1.00 24.39           C
ATOM   4985  CB  GLN B 258      62.076  27.520 -49.991  1.00 30.51           C
ATOM   4986  CG  GLN B 258      61.907  27.289 -51.481  1.00 35.96           C
ATOM   4987  CD  GLN B 258      62.528  25.991 -51.926  1.00 44.25           C
ATOM   4988  OE1 GLN B 258      63.600  25.986 -52.526  1.00 45.16           O
ATOM   4989  NE2 GLN B 258      61.862  24.881 -51.627  1.00 48.93           N
ATOM   4990  C   GLN B 258      61.257  28.599 -47.873  1.00 24.99           C
ATOM   4991  O   GLN B 258      62.397  28.390 -47.430  1.00 22.63           O
ATOM   4992  N   PRO B 259      60.286  29.091 -47.106  1.00 21.69           N
ATOM   4993  CA  PRO B 259      60.549  29.424 -45.704  1.00 19.82           C
ATOM   4994  CB  PRO B 259      59.302  30.223 -45.302  1.00 19.19           C
ATOM   4995  CG  PRO B 259      58.213  29.654 -46.156  1.00 20.39           C
ATOM   4996  CD  PRO B 259      58.872  29.316 -47.473  1.00 22.01           C
ATOM   4997  C   PRO B 259      60.649  28.138 -44.880  1.00 19.09           C
ATOM   4998  O   PRO B 259      60.161  27.098 -45.325  1.00 20.06           O
ATOM   4999  N   SER B 260      61.263  28.209 -43.704  1.00 20.01           N
ATOM   5000  CA  SER B 260      61.293  27.056 -42.802  1.00 24.22           C
ATOM   5001  CB  SER B 260      62.718  26.746 -42.345  1.00 22.33           C
ATOM   5002  OG  SER B 260      63.339  27.897 -41.815  1.00 24.56           O
ATOM   5003  C   SER B 260      60.359  27.212 -41.598  1.00 22.80           C
ATOM   5004  O   SER B 260      60.169  26.265 -40.830  1.00 19.42           O
ATOM   5005  N   ALA B 261      59.781  28.409 -41.445  1.00 20.76           N
ATOM   5006  CA  ALA B 261      58.769  28.671 -40.423  1.00 18.08           C
```

FIGURE 3KKKK

```
ATOM   5007  CB   ALA B 261      59.415  29.193 -39.131  1.00 17.69           C
ATOM   5008  C    ALA B 261      57.742  29.668 -40.949  1.00 19.15           C
ATOM   5009  O    ALA B 261      58.052  30.490 -41.817  1.00 16.74           O
ATOM   5010  N    VAL B 262      56.517  29.576 -40.442  1.00 15.53           N
ATOM   5011  CA   VAL B 262      55.446  30.479 -40.867  1.00 14.71           C
ATOM   5012  CB   VAL B 262      54.384  29.753 -41.743  1.00 17.22           C
ATOM   5013  CG1  VAL B 262      53.292  30.737 -42.203  1.00 14.73           C
ATOM   5014  CG2  VAL B 262      55.027  29.085 -42.952  1.00 17.20           C
ATOM   5015  C    VAL B 262      54.761  31.092 -39.644  1.00 16.40           C
ATOM   5016  O    VAL B 262      54.529  30.405 -38.646  1.00 13.68           O
ATOM   5017  N    VAL B 263      54.457  32.390 -39.724  1.00 15.38           N
ATOM   5018  CA   VAL B 263      53.631  33.060 -38.720  1.00 13.12           C
ATOM   5019  CB   VAL B 263      54.351  34.271 -38.070  1.00 13.11           C
ATOM   5020  CG1  VAL B 263      53.412  35.008 -37.097  1.00 14.14           C
ATOM   5021  CG2  VAL B 263      55.605  33.828 -37.347  1.00 13.44           C
ATOM   5022  C    VAL B 263      52.372  33.542 -39.420  1.00 15.83           C
ATOM   5023  O    VAL B 263      52.452  34.250 -40.429  1.00 14.61           O
ATOM   5024  N    LEU B 264      51.219  33.149 -38.893  1.00 13.07           N
ATOM   5025  CA   LEU B 264      49.939  33.489 -39.498  1.00 14.54           C
ATOM   5026  CB   LEU B 264      49.177  32.228 -39.925  1.00 15.81           C
ATOM   5027  CG   LEU B 264      47.751  32.362 -40.490  1.00 16.81           C
ATOM   5028  CD1  LEU B 264      47.698  33.199 -41.786  1.00 18.00           C
ATOM   5029  CD2  LEU B 264      47.164  30.979 -40.736  1.00 17.59           C
ATOM   5030  C    LEU B 264      49.102  34.329 -38.545  1.00 16.82           C
ATOM   5031  O    LEU B 264      48.703  33.879 -37.457  1.00 15.57           O
ATOM   5032  N    GLN B 265      48.864  35.566 -38.952  1.00 14.41           N
ATOM   5033  CA   GLN B 265      48.020  36.478 -38.191  1.00 12.39           C
ATOM   5034  CB   GLN B 265      48.511  37.924 -38.393  1.00 13.94           C
ATOM   5035  CG   GLN B 265      48.060  38.909 -37.326  1.00 14.21           C
ATOM   5036  CD   GLN B 265      46.717  39.577 -37.654  1.00 16.52           C
ATOM   5037  OE1  GLN B 265      45.967  39.097 -38.508  1.00 16.60           O
ATOM   5038  NE2  GLN B 265      46.428  40.694 -36.986  1.00 16.54           N
ATOM   5039  C    GLN B 265      46.596  36.272 -38.714  1.00 13.37           C
ATOM   5040  O    GLN B 265      46.336  36.448 -39.916  1.00 14.10           O
ATOM   5041  N    CYS B 266      45.691  35.869 -37.821  1.00 13.87           N
ATOM   5042  CA   CYS B 266      44.325  35.488 -38.186  1.00 10.87           C
ATOM   5043  CB   CYS B 266      43.967  34.125 -37.576  1.00 15.36           C
ATOM   5044  SG   CYS B 266      45.121  32.804 -37.967  1.00 20.01           S
ATOM   5045  C    CYS B 266      43.281  36.506 -37.720  1.00 13.88           C
ATOM   5046  O    CYS B 266      42.234  36.118 -37.192  1.00 16.49           O
ATOM   5047  N    GLY B 267      43.547  37.794 -37.927  1.00 13.78           N
ATOM   5048  CA   GLY B 267      42.599  38.834 -37.546  1.00 12.48           C
ATOM   5049  C    GLY B 267      41.203  38.509 -38.070  1.00 12.44           C
ATOM   5050  O    GLY B 267      41.034  38.192 -39.255  1.00 16.25           O
ATOM   5051  N    ALA B 268      40.215  38.579 -37.180  1.00 13.84           N
ATOM   5052  CA   ALA B 268      38.843  38.159 -37.483  1.00 13.06           C
ATOM   5053  CB   ALA B 268      38.222  37.461 -36.269  1.00 15.35           C
ATOM   5054  C    ALA B 268      37.957  39.321 -37.944  1.00 15.70           C
ATOM   5055  O    ALA B 268      36.762  39.145 -38.166  1.00 14.52           O
ATOM   5056  N    ASP B 269      38.548  40.501 -38.099  1.00 13.03           N
ATOM   5057  CA   ASP B 269      37.805  41.654 -38.599  1.00 12.46           C
ATOM   5058  CB   ASP B 269      38.432  42.980 -38.149  1.00 11.72           C
ATOM   5059  CG   ASP B 269      39.915  43.067 -38.433  1.00 19.15           C
ATOM   5060  OD1  ASP B 269      40.470  42.227 -39.195  1.00 18.12           O
ATOM   5061  OD2  ASP B 269      40.607  43.980 -37.938  1.00 17.56           O
ATOM   5062  C    ASP B 269      37.589  41.603 -40.119  1.00 15.51           C
ATOM   5063  O    ASP B 269      36.927  42.474 -40.683  1.00 15.04           O
```

FIGURE 3LLLL

```
ATOM   5064  N    SER B 270      38.129  40.570 -40.768  1.00 13.55           N
ATOM   5065  CA   SER B 270      37.846  40.310 -42.180  1.00 14.34           C
ATOM   5066  CB   SER B 270      39.048  39.633 -42.864  1.00 14.54           C
ATOM   5067  OG   SER B 270      39.617  38.666 -42.007  1.00 19.89           O
ATOM   5068  C    SER B 270      36.578  39.465 -42.359  1.00 17.11           C
ATOM   5069  O    SER B 270      36.215  39.130 -43.485  1.00 15.76           O
ATOM   5070  N    LEU B 271      35.899  39.130 -41.257  1.00 14.13           N
ATOM   5071  CA   LEU B 271      34.636  38.381 -41.333  1.00 13.69           C
ATOM   5072  CB   LEU B 271      34.331  37.667 -40.012  1.00 15.57           C
ATOM   5073  CG   LEU B 271      35.272  36.569 -39.519  1.00 14.97           C
ATOM   5074  CD1  LEU B 271      34.818  36.103 -38.135  1.00 16.75           C
ATOM   5075  CD2  LEU B 271      35.305  35.403 -40.501  1.00 15.33           C
ATOM   5076  C    LEU B 271      33.441  39.270 -41.659  1.00 16.39           C
ATOM   5077  O    LEU B 271      33.385  40.445 -41.261  1.00 14.87           O
ATOM   5078  N    SER B 272      32.476  38.685 -42.357  1.00 15.03           N
ATOM   5079  CA   SER B 272      31.157  39.298 -42.532  1.00 16.35           C
ATOM   5080  CB   SER B 272      30.191  38.296 -43.168  1.00 21.96           C
ATOM   5081  OG   SER B 272      28.911  38.893 -43.376  1.00 21.94           O
ATOM   5082  C    SER B 272      30.579  39.783 -41.203  1.00 20.45           C
ATOM   5083  O    SER B 272      30.611  39.063 -40.204  1.00 19.35           O
ATOM   5084  N    GLY B 273      30.067  41.012 -41.196  1.00 18.81           N
ATOM   5085  CA   GLY B 273      29.360  41.541 -40.043  1.00 20.75           C
ATOM   5086  C    GLY B 273      30.245  42.137 -38.965  1.00 17.21           C
ATOM   5087  O    GLY B 273      29.759  42.470 -37.881  1.00 20.15           O
ATOM   5088  N    ASP B 274      31.541  42.262 -39.242  1.00 16.89           N
ATOM   5089  CA   ASP B 274      32.434  42.873 -38.273  1.00 16.07           C
ATOM   5090  CB   ASP B 274      33.895  42.783 -38.696  1.00 16.64           C
ATOM   5091  CG   ASP B 274      34.829  43.320 -37.625  1.00 18.71           C
ATOM   5092  OD1  ASP B 274      35.114  42.575 -36.656  1.00 18.03           O
ATOM   5093  OD2  ASP B 274      35.294  44.478 -37.656  1.00 19.46           O
ATOM   5094  C    ASP B 274      32.047  44.337 -38.093  1.00 18.58           C
ATOM   5095  O    ASP B 274      31.693  45.016 -39.062  1.00 20.03           O
ATOM   5096  N    ARG B 275      32.131  44.801 -36.852  1.00 16.74           N
ATOM   5097  CA   ARG B 275      31.748  46.165 -36.485  1.00 23.49           C
ATOM   5098  CB   ARG B 275      31.871  46.357 -34.972  1.00 27.71           C
ATOM   5099  CG   ARG B 275      30.592  46.101 -34.201  1.00 36.02           C
ATOM   5100  CD  BARG B 275      30.709  46.316 -32.700  0.35 36.26           C
ATOM   5101  CD  AARG B 275      30.596  46.663 -32.773  0.65 38.18           C
ATOM   5102  NE  BARG B 275      30.025  45.268 -31.943  0.35 37.10           N
ATOM   5103  NE  AARG B 275      31.086  48.042 -32.715  0.65 41.71           N
ATOM   5104  CZ  BARG B 275      28.767  45.340 -31.520  0.35 39.46           C
ATOM   5105  CZ  AARG B 275      31.609  48.626 -31.638  0.65 40.69           C
ATOM   5106  NH1 BARG B 275      28.029  46.414 -31.774  0.35 40.25           N
ATOM   5107  NH1 AARG B 275      31.724  47.964 -30.491  0.65 39.56           N
ATOM   5108  NH2 BARG B 275      28.241  44.331 -30.840  0.35 39.76           N
ATOM   5109  NH2 AARG B 275      32.022  49.884 -31.709  0.65 41.50           N
ATOM   5110  C    ARG B 275      32.576  47.227 -37.198  1.00 23.99           C
ATOM   5111  O    ARG B 275      32.075  48.318 -37.472  1.00 24.68           O
ATOM   5112  N    LEU B 276      33.840  46.914 -37.489  1.00 20.37           N
ATOM   5113  CA   LEU B 276      34.749  47.885 -38.098  1.00 21.44           C
ATOM   5114  CB   LEU B 276      35.993  48.096 -37.220  1.00 22.48           C
ATOM   5115  CG   LEU B 276      35.826  48.602 -35.781  1.00 23.78           C
ATOM   5116  CD1  LEU B 276      37.182  48.937 -35.181  1.00 25.63           C
ATOM   5117  CD2  LEU B 276      34.892  49.804 -35.687  1.00 24.49           C
ATOM   5118  C    LEU B 276      35.187  47.510 -39.512  1.00 25.31           C
ATOM   5119  O    LEU B 276      35.770  48.332 -40.220  1.00 31.14           O
ATOM   5120  N    GLY B 277      34.925  46.270 -39.910  1.00 21.88           N
```

FIGURE 3MMMM

```
ATOM   5121  CA   GLY B 277      35.386  45.763  -41.192  1.00  21.01           C
ATOM   5122  C    GLY B 277      34.283  45.661  -42.227  1.00  25.39           C
ATOM   5123  O    GLY B 277      33.105  45.553  -41.887  1.00  27.07           O
ATOM   5124  N    CYS B 278      34.660  45.676  -43.499  1.00  21.26           N
ATOM   5125  CA   CYS B 278      33.667  45.610  -44.565  1.00  25.10           C
ATOM   5126  CB   CYS B 278      33.563  46.958  -45.275  1.00  33.96           C
ATOM   5127  SG   CYS B 278      35.175  47.695  -45.575  1.00  50.17           S
ATOM   5128  C    CYS B 278      33.924  44.487  -45.569  1.00  20.64           C
ATOM   5129  O    CYS B 278      33.639  44.638  -46.756  1.00  17.67           O
ATOM   5130  N    PHE B 279      34.473  43.370  -45.095  1.00  15.16           N
ATOM   5131  CA   PHE B 279      34.588  42.169  -45.919  1.00  12.73           C
ATOM   5132  CB   PHE B 279      35.870  41.381  -45.590  1.00  17.27           C
ATOM   5133  CG   PHE B 279      37.132  41.898  -46.252  1.00  17.32           C
ATOM   5134  CD1  PHE B 279      38.340  41.215  -46.058  1.00  15.52           C
ATOM   5135  CE1  PHE B 279      39.517  41.650  -46.654  1.00  18.39           C
ATOM   5136  CZ   PHE B 279      39.515  42.783  -47.456  1.00  17.28           C
ATOM   5137  CE2  PHE B 279      38.323  43.471  -47.670  1.00  16.47           C
ATOM   5138  CD2  PHE B 279      37.136  43.028  -47.072  1.00  17.01           C
ATOM   5139  C    PHE B 279      33.373  41.278  -45.664  1.00  16.55           C
ATOM   5140  O    PHE B 279      32.571  41.549  -44.762  1.00  19.59           O
ATOM   5141  N    ASN B 280      33.235  40.217  -46.455  1.00  17.36           N
ATOM   5142  CA   ASN B 280      32.078  39.326  -46.360  1.00  17.04           C
ATOM   5143  CB   ASN B 280      31.151  39.570  -47.554  1.00  18.86           C
ATOM   5144  CG   ASN B 280      29.720  39.127  -47.305  1.00  20.43           C
ATOM   5145  OD1  ASN B 280      29.294  38.929  -46.161  1.00  22.67           O
ATOM   5146  ND2  ASN B 280      28.959  38.967  -48.394  1.00  18.25           N
ATOM   5147  C    ASN B 280      32.479  37.850  -46.285  1.00  16.92           C
ATOM   5148  O    ASN B 280      31.819  36.981  -46.869  1.00  18.75           O
ATOM   5149  N    LEU B 281      33.574  37.569  -45.577  1.00  15.32           N
ATOM   5150  CA   LEU B 281      34.023  36.189  -45.386  1.00  14.56           C
ATOM   5151  CB   LEU B 281      35.508  36.143  -44.981  1.00  13.87           C
ATOM   5152  CG   LEU B 281      36.553  36.746  -45.921  1.00  17.99           C
ATOM   5153  CD1  LEU B 281      37.946  36.492  -45.341  1.00  18.33           C
ATOM   5154  CD2  LEU B 281      36.439  36.140  -47.316  1.00  19.02           C
ATOM   5155  C    LEU B 281      33.201  35.489  -44.314  1.00  16.37           C
ATOM   5156  O    LEU B 281      32.732  36.124  -43.361  1.00  16.39           O
ATOM   5157  N    THR B 282      33.026  34.179  -44.462  1.00  15.84           N
ATOM   5158  CA   THR B 282      32.476  33.389  -43.367  1.00  14.54           C
ATOM   5159  CB   THR B 282      31.587  32.244  -43.878  1.00  19.59           C
ATOM   5160  OG1  THR B 282      32.392  31.308  -44.600  1.00  20.46           O
ATOM   5161  CG2  THR B 282      30.562  32.751  -44.893  1.00  19.19           C
ATOM   5162  C    THR B 282      33.625  32.805  -42.575  1.00  18.29           C
ATOM   5163  O    THR B 282      34.793  32.948  -42.958  1.00  15.62           O
ATOM   5164  N    VAL B 283      33.287  32.131  -41.481  1.00  15.48           N
ATOM   5165  CA   VAL B 283      34.281  31.472  -40.647  1.00  15.83           C
ATOM   5166  CB   VAL B 283      33.648  30.931  -39.353  1.00  17.74           C
ATOM   5167  CG1  VAL B 283      34.575  29.921  -38.660  1.00  17.21           C
ATOM   5168  CG2  VAL B 283      33.324  32.095  -38.407  1.00  18.15           C
ATOM   5169  C    VAL B 283      34.985  30.372  -41.438  1.00  17.96           C
ATOM   5170  O    VAL B 283      36.205  30.226  -41.349  1.00  17.31           O
ATOM   5171  N    LYS B 284      34.217  29.617  -42.222  1.00  17.54           N
ATOM   5172  CA   LYS B 284      34.780  28.591  -43.101  1.00  23.06           C
ATOM   5173  CB   LYS B 284      33.671  27.838  -43.838  1.00  25.89           C
ATOM   5174  CG   LYS B 284      33.193  26.591  -43.133  1.00  32.21           C
ATOM   5175  CD   LYS B 284      32.000  25.995  -43.868  1.00  35.12           C
ATOM   5176  CE   LYS B 284      31.386  24.843  -43.086  1.00  39.97           C
ATOM   5177  NZ   LYS B 284      30.331  24.159  -43.881  1.00  36.74           N
```

FIGURE 3NNNN

| | | | | | | | | | |
|---|---|---|---|---|---|---|---|---|---|
| ATOM | 5178 | C   | LYS | B | 284 | 35.773 | 29.153 | -44.114 | 1.00 24.31 | C |
| ATOM | 5179 | O   | LYS | B | 284 | 36.810 | 28.541 | -44.374 | 1.00 22.47 | O |
| ATOM | 5180 | N   | GLY | B | 285 | 35.450 | 30.313 | -44.684 | 1.00 20.75 | N |
| ATOM | 5181 | CA  | GLY | B | 285 | 36.308 | 30.950 | -45.673 | 1.00 21.63 | C |
| ATOM | 5182 | C   | GLY | B | 285 | 37.598 | 31.472 | -45.073 | 1.00 20.89 | C |
| ATOM | 5183 | O   | GLY | B | 285 | 38.671 | 31.365 | -45.665 | 1.00 22.55 | O |
| ATOM | 5184 | N   | HIS | B | 286 | 37.479 | 32.044 | -43.884 | 1.00 16.20 | N |
| ATOM | 5185 | CA  | HIS | B | 286 | 38.617 | 32.527 | -43.114 | 1.00 16.17 | C |
| ATOM | 5186 | CB  | HIS | B | 286 | 38.073 | 33.221 | -41.862 | 1.00 17.20 | C |
| ATOM | 5187 | CG  | HIS | B | 286 | 39.042 | 34.145 | -41.187 | 1.00 18.96 | C |
| ATOM | 5188 | ND1 | HIS | B | 286 | 39.929 | 33.717 | -40.223 | 1.00 18.43 | N |
| ATOM | 5189 | CE1 | HIS | B | 286 | 40.622 | 34.749 | -39.774 | 1.00 18.98 | C |
| ATOM | 5190 | NE2 | HIS | B | 286 | 40.206 | 35.834 | -40.403 | 1.00 19.30 | N |
| ATOM | 5191 | CD2 | HIS | B | 286 | 39.214 | 35.485 | -41.288 | 1.00 16.96 | C |
| ATOM | 5192 | C   | HIS | B | 286 | 39.506 | 31.340 | -42.731 | 1.00 19.25 | C |
| ATOM | 5193 | O   | HIS | B | 286 | 40.714 | 31.374 | -42.924 | 1.00 18.99 | O |
| ATOM | 5194 | N   | ALA | B | 287 | 38.891 | 30.275 | -42.227 | 1.00 16.41 | N |
| ATOM | 5195 | CA  | ALA | B | 287 | 39.636 | 29.115 | -41.732 | 1.00 17.38 | C |
| ATOM | 5196 | CB  | ALA | B | 287 | 38.734 | 28.241 | -40.863 | 1.00 18.15 | C |
| ATOM | 5197 | C   | ALA | B | 287 | 40.295 | 28.278 | -42.832 | 1.00 18.28 | C |
| ATOM | 5198 | O   | ALA | B | 287 | 41.225 | 27.507 | -42.561 | 1.00 17.48 | O |
| ATOM | 5199 | N   | LYS | B | 288 | 39.806 | 28.423 | -44.061 | 1.00 18.30 | N |
| ATOM | 5200 | CA  | LYS | B | 288 | 40.408 | 27.782 | -45.231 | 1.00 22.26 | C |
| ATOM | 5201 | CB  | LYS | B | 288 | 39.584 | 28.086 | -46.492 | 1.00 25.45 | C |
| ATOM | 5202 | CG  | LYS | B | 288 | 40.127 | 27.486 | -47.790 | 1.00 34.52 | C |
| ATOM | 5203 | CD  | LYS | B | 288 | 39.340 | 26.259 | -48.216 | 1.00 40.60 | C |
| ATOM | 5204 | CE  | LYS | B | 288 | 39.386 | 26.076 | -49.729 | 1.00 47.72 | C |
| ATOM | 5205 | NZ  | LYS | B | 288 | 40.558 | 25.256 | -50.161 | 1.00 50.51 | N |
| ATOM | 5206 | C   | LYS | B | 288 | 41.864 | 28.230 | -45.400 | 1.00 20.63 | C |
| ATOM | 5207 | O   | LYS | B | 288 | 42.710 | 27.441 | -45.815 | 1.00 20.60 | O |
| ATOM | 5208 | N   | CYS | B | 289 | 42.145 | 29.491 | -45.067 | 1.00 19.34 | N |
| ATOM | 5209 | CA  | CYS | B | 289 | 43.513 | 30.015 | -45.040 | 1.00 19.68 | C |
| ATOM | 5210 | CB  | CYS | B | 289 | 43.524 | 31.480 | -44.591 | 1.00 19.84 | C |
| ATOM | 5211 | SG  | CYS | B | 289 | 42.666 | 32.562 | -45.728 | 1.00 21.65 | S |
| ATOM | 5212 | C   | CYS | B | 289 | 44.421 | 29.206 | -44.124 | 1.00 19.23 | C |
| ATOM | 5213 | O   | CYS | B | 289 | 45.545 | 28.873 | -44.497 | 1.00 18.43 | O |
| ATOM | 5214 | N   | VAL | B | 290 | 43.937 | 28.899 | -42.920 | 1.00 18.35 | N |
| ATOM | 5215 | CA  | VAL | B | 290 | 44.683 | 28.056 | -41.987 | 1.00 17.42 | C |
| ATOM | 5216 | CB  | VAL | B | 290 | 43.955 | 27.919 | -40.622 | 1.00 21.04 | C |
| ATOM | 5217 | CG1 | VAL | B | 290 | 44.738 | 27.025 | -39.667 | 1.00 21.48 | C |
| ATOM | 5218 | CG2 | VAL | B | 290 | 43.727 | 29.295 | -39.991 | 1.00 20.81 | C |
| ATOM | 5219 | C   | VAL | B | 290 | 44.934 | 26.678 | -42.608 | 1.00 20.82 | C |
| ATOM | 5220 | O   | VAL | B | 290 | 46.063 | 26.173 | -42.586 | 1.00 21.34 | O |
| ATOM | 5221 | N   | GLU | B | 291 | 43.881 | 26.086 | -43.165 | 1.00 16.33 | N |
| ATOM | 5222 | CA  | GLU | B | 291 | 43.976 | 24.777 | -43.824 | 1.00 22.93 | C |
| ATOM | 5223 | CB  | GLU | B | 291 | 42.636 | 24.391 | -44.463 | 1.00 27.17 | C |
| ATOM | 5224 | CG  | GLU | B | 291 | 41.558 | 23.939 | -43.487 | 1.00 37.64 | C |
| ATOM | 5225 | CD  | GLU | B | 291 | 40.191 | 23.780 | -44.139 | 1.00 45.14 | C |
| ATOM | 5226 | OE1 | GLU | B | 291 | 40.088 | 23.076 | -45.172 | 1.00 47.23 | O |
| ATOM | 5227 | OE2 | GLU | B | 291 | 39.212 | 24.359 | -43.614 | 1.00 47.93 | O |
| ATOM | 5228 | C   | GLU | B | 291 | 45.074 | 24.760 | -44.893 | 1.00 23.41 | C |
| ATOM | 5229 | O   | GLU | B | 291 | 45.903 | 23.851 | -44.923 | 1.00 23.31 | O |
| ATOM | 5230 | N   | VAL | B | 292 | 45.071 | 25.773 | -45.760 | 1.00 19.61 | N |
| ATOM | 5231 | CA  | VAL | B | 292 | 46.069 | 25.905 | -46.828 | 1.00 18.01 | C |
| ATOM | 5232 | CB  | VAL | B | 292 | 45.758 | 27.125 | -47.746 | 1.00 20.11 | C |
| ATOM | 5233 | CG1 | VAL | B | 292 | 46.907 | 27.413 | -48.724 | 1.00 19.73 | C |
| ATOM | 5234 | CG2 | VAL | B | 292 | 44.466 | 26.895 | -48.519 | 1.00 22.81 | C |

FIGURE 30000

```
ATOM   5235  C    VAL B 292      47.488  26.000 -46.258  1.00 21.55           C
ATOM   5236  O    VAL B 292      48.389  25.295 -46.709  1.00 19.81           O
ATOM   5237  N    VAL B 293      47.679  26.861 -45.257  1.00 18.96           N
ATOM   5238  CA   VAL B 293      49.000  27.059 -44.669  1.00 20.54           C
ATOM   5239  CB   VAL B 293      49.021  28.260 -43.683  1.00 21.91           C
ATOM   5240  CG1  VAL B 293      50.348  28.345 -42.951  1.00 20.08           C
ATOM   5241  CG2  VAL B 293      48.761  29.567 -44.432  1.00 21.78           C
ATOM   5242  C    VAL B 293      49.496  25.766 -44.017  1.00 23.93           C
ATOM   5243  O    VAL B 293      50.684  25.433 -44.100  1.00 23.42           O
ATOM   5244  N    LYS B 294      48.573  25.028 -43.406  1.00 20.91           N
ATOM   5245  CA   LYS B 294      48.895  23.744 -42.781  1.00 26.88           C
ATOM   5246  CB   LYS B 294      47.664  23.172 -42.084  1.00 27.99           C
ATOM   5247  CG   LYS B 294      47.563  23.540 -40.626  1.00 35.16           C
ATOM   5248  CD   LYS B 294      46.390  22.822 -39.978  1.00 38.41           C
ATOM   5249  CE   LYS B 294      46.827  21.487 -39.388  1.00 39.91           C
ATOM   5250  NZ   LYS B 294      45.901  20.403 -39.782  1.00 44.39           N
ATOM   5251  C    LYS B 294      49.456  22.699 -43.749  1.00 28.71           C
ATOM   5252  O    LYS B 294      50.314  21.903 -43.356  1.00 30.73           O
ATOM   5253  N    THR B 295      48.982  22.701 -45.000  1.00 26.76           N
ATOM   5254  CA   THR B 295      49.372  21.674 -45.977  1.00 29.75           C
ATOM   5255  CB   THR B 295      48.542  21.749 -47.288  1.00 33.10           C
ATOM   5256  OG1  THR B 295      48.865  22.946 -48.012  1.00 33.40           O
ATOM   5257  CG2  THR B 295      47.046  21.867 -47.003  1.00 33.09           C
ATOM   5258  C    THR B 295      50.862  21.682 -46.317  1.00 29.47           C
ATOM   5259  O    THR B 295      51.379  20.709 -46.850  1.00 30.01           O
ATOM   5260  N    PHE B 296      51.549  22.777 -46.006  1.00 24.77           N
ATOM   5261  CA   PHE B 296      52.974  22.889 -46.309  1.00 25.64           C
ATOM   5262  CB   PHE B 296      53.337  24.341 -46.628  1.00 25.71           C
ATOM   5263  CG   PHE B 296      52.694  24.834 -47.887  1.00 25.19           C
ATOM   5264  CD1  PHE B 296      53.282  24.588 -49.124  1.00 24.30           C
ATOM   5265  CE1  PHE B 296      52.668  25.015 -50.304  1.00 26.29           C
ATOM   5266  CZ   PHE B 296      51.450  25.689 -50.244  1.00 27.41           C
ATOM   5267  CE2  PHE B 296      50.848  25.922 -49.012  1.00 26.23           C
ATOM   5268  CD2  PHE B 296      51.468  25.489 -47.843  1.00 22.05           C
ATOM   5269  C    PHE B 296      53.880  22.281 -45.239  1.00 25.64           C
ATOM   5270  O    PHE B 296      55.103  22.236 -45.408  1.00 26.04           O
ATOM   5271  N    ASN B 297      53.266  21.808 -44.153  1.00 24.73           N
ATOM   5272  CA   ASN B 297      53.957  21.068 -43.095  1.00 27.58           C
ATOM   5273  CB   ASN B 297      54.387  19.677 -43.596  1.00 33.99           C
ATOM   5274  CG   ASN B 297      53.227  18.859 -44.121  1.00 38.33           C
ATOM   5275  OD1  ASN B 297      52.220  18.673 -43.434  1.00 42.35           O
ATOM   5276  ND2  ASN B 297      53.361  18.363 -45.348  1.00 40.05           N
ATOM   5277  C    ASN B 297      55.152  21.795 -42.496  1.00 27.86           C
ATOM   5278  O    ASN B 297      56.187  21.183 -42.237  1.00 28.10           O
ATOM   5279  N    LEU B 298      55.007  23.102 -42.282  1.00 23.99           N
ATOM   5280  CA   LEU B 298      56.061  23.907 -41.679  1.00 19.34           C
ATOM   5281  CB   LEU B 298      56.340  25.169 -42.521  1.00 22.23           C
ATOM   5282  CG   LEU B 298      56.885  24.986 -43.943  1.00 24.63           C
ATOM   5283  CD1  LEU B 298      56.854  26.311 -44.706  1.00 25.34           C
ATOM   5284  CD2  LEU B 298      58.299  24.396 -43.937  1.00 26.66           C
ATOM   5285  C    LEU B 298      55.651  24.311 -40.271  1.00 20.88           C
ATOM   5286  O    LEU B 298      54.459  24.485 -40.018  1.00 21.68           O
ATOM   5287  N    PRO B 299      56.621  24.455 -39.363  1.00 21.66           N
ATOM   5288  CA   PRO B 299      56.358  24.984 -38.019  1.00 21.78           C
ATOM   5289  CB   PRO B 299      57.754  25.279 -37.480  1.00 22.67           C
ATOM   5290  CG   PRO B 299      58.641  24.300 -38.186  1.00 26.16           C
ATOM   5291  CD   PRO B 299      58.051  24.143 -39.559  1.00 24.59           C
```

FIGURE 3PPPP

```
ATOM   5292  C   PRO B 299      55.557  26.277 -38.159  1.00 19.50           C
ATOM   5293  O   PRO B 299      55.925  27.143 -38.959  1.00 18.57           O
ATOM   5294  N   LEU B 300      54.467  26.372 -37.412  1.00 18.57           N
ATOM   5295  CA  LEU B 300      53.453  27.396 -37.648  1.00 14.91           C
ATOM   5296  CB  LEU B 300      52.239  26.772 -38.342  1.00 15.20           C
ATOM   5297  CG  LEU B 300      50.956  27.600 -38.535  1.00 17.81           C
ATOM   5298  CD1 LEU B 300      51.251  28.912 -39.291  1.00 17.60           C
ATOM   5299  CD2 LEU B 300      49.904  26.795 -39.282  1.00 19.72           C
ATOM   5300  C   LEU B 300      53.037  28.050 -36.339  1.00 17.91           C
ATOM   5301  O   LEU B 300      52.635  27.371 -35.400  1.00 14.72           O
ATOM   5302  N   LEU B 301      53.150  29.375 -36.287  1.00 15.86           N
ATOM   5303  CA  LEU B 301      52.646  30.158 -35.165  1.00 13.75           C
ATOM   5304  CB  LEU B 301      53.699  31.168 -34.709  1.00 14.99           C
ATOM   5305  CG  LEU B 301      53.298  32.134 -33.592  1.00 17.96           C
ATOM   5306  CD1 LEU B 301      52.976  31.392 -32.275  1.00 16.41           C
ATOM   5307  CD2 LEU B 301      54.404  33.141 -33.367  1.00 18.17           C
ATOM   5308  C   LEU B 301      51.386  30.884 -35.630  1.00 12.95           C
ATOM   5309  O   LEU B 301      51.437  31.649 -36.592  1.00 14.83           O
ATOM   5310  N   MET B 302      50.266  30.618 -34.963  1.00 13.69           N
ATOM   5311  CA  MET B 302      48.981  31.221 -35.308  1.00 13.43           C
ATOM   5312  CB  MET B 302      47.892  30.154 -35.406  1.00 15.16           C
ATOM   5313  CG  MET B 302      48.054  29.213 -36.587  1.00 23.53           C
ATOM   5314  SD  MET B 302      47.013  27.745 -36.396  1.00 28.97           S
ATOM   5315  CE  MET B 302      45.326  28.571 -36.434  1.00 21.22           C
ATOM   5316  C   MET B 302      48.607  32.236 -34.241  1.00 14.13           C
ATOM   5317  O   MET B 302      48.584  31.916 -33.054  1.00 13.51           O
ATOM   5318  N   LEU B 303      48.326  33.463 -34.671  1.00 10.22           N
ATOM   5319  CA  LEU B 303      48.049  34.554 -33.752  1.00  9.88           C
ATOM   5320  CB  LEU B 303      49.161  35.610 -33.833  1.00 13.07           C
ATOM   5321  CG  LEU B 303      50.595  35.089 -33.615  1.00 16.07           C
ATOM   5322  CD1 LEU B 303      51.605  36.192 -33.927  1.00 17.23           C
ATOM   5323  CD2 LEU B 303      50.768  34.569 -32.187  1.00 12.77           C
ATOM   5324  C   LEU B 303      46.697  35.191 -34.051  1.00 15.03           C
ATOM   5325  O   LEU B 303      46.135  34.990 -35.131  1.00 12.76           O
ATOM   5326  N   GLY B 304      46.179  35.941 -33.082  1.00 15.17           N
ATOM   5327  CA  GLY B 304      44.922  36.650 -33.244  1.00 15.19           C
ATOM   5328  C   GLY B 304      45.116  37.948 -34.018  1.00 16.85           C
ATOM   5329  O   GLY B 304      45.871  37.995 -34.983  1.00 17.24           O
ATOM   5330  N   GLY B 305      44.430  39.000 -33.593  1.00 16.64           N
ATOM   5331  CA  GLY B 305      44.508  40.287 -34.269  1.00 17.56           C
ATOM   5332  C   GLY B 305      43.210  41.032 -34.051  1.00 16.49           C
ATOM   5333  O   GLY B 305      42.606  40.917 -32.981  1.00 19.29           O
ATOM   5334  N   GLY B 306      42.775  41.785 -35.054  1.00 15.10           N
ATOM   5335  CA  GLY B 306      41.525  42.518 -34.963  1.00 16.89           C
ATOM   5336  C   GLY B 306      40.313  41.600 -34.911  1.00 19.47           C
ATOM   5337  O   GLY B 306      40.414  40.388 -35.119  1.00 21.06           O
ATOM   5338  N   GLY B 307      39.162  42.182 -34.610  1.00 14.53           N
ATOM   5339  CA  GLY B 307      37.916  41.436 -34.575  1.00 14.94           C
ATOM   5340  C   GLY B 307      37.031  42.090 -33.541  1.00 16.74           C
ATOM   5341  O   GLY B 307      37.373  42.107 -32.353  1.00 18.48           O
ATOM   5342  N   TYR B 308      35.887  42.596 -33.992  1.00 14.84           N
ATOM   5343  CA  TYR B 308      35.107  43.558 -33.211  1.00 16.38           C
ATOM   5344  CB  TYR B 308      35.307  44.976 -33.799  1.00 13.53           C
ATOM   5345  CG  TYR B 308      36.777  45.269 -33.922  1.00 16.01           C
ATOM   5346  CD1 TYR B 308      37.442  45.166 -35.152  1.00 14.32           C
ATOM   5347  CE1 TYR B 308      38.818  45.389 -35.235  1.00 15.56           C
ATOM   5348  CZ  TYR B 308      39.523  45.690 -34.070  1.00 17.41           C
```

FIGURE 3QQQQ

```
ATOM   5349  OH   TYR B 308      40.880  45.909 -34.090  1.00 19.81           C
ATOM   5350  CE2  TYR B 308      38.880  45.755 -32.852  1.00 17.64           C
ATOM   5351  CD2  TYR B 308      37.530  45.541 -32.785  1.00 17.59           C
ATOM   5352  C    TYR B 308      33.637  43.203 -33.033  1.00 17.03           C
ATOM   5353  O    TYR B 308      32.934  43.865 -32.286  1.00 18.01           O
ATOM   5354  N    THR B 309      33.182  42.155 -33.714  1.00 15.13           N
ATOM   5355  CA   THR B 309      31.877  41.563 -33.424  1.00 15.19           C
ATOM   5356  CB   THR B 309      31.099  41.268 -34.716  1.00 17.27           C
ATOM   5357  OG1  THR B 309      30.810  42.510 -35.364  1.00 19.64           O
ATOM   5358  CG2  THR B 309      29.717  40.706 -34.402  1.00 18.22           C
ATOM   5359  C    THR B 309      32.236  40.305 -32.673  1.00 16.42           C
ATOM   5360  O    THR B 309      32.563  39.272 -33.272  1.00 15.21           O
ATOM   5361  N    ILE B 310      32.230  40.409 -31.351  1.00 15.13           N
ATOM   5362  CA   ILE B 310      32.973  39.439 -30.547  1.00 18.62           C
ATOM   5363  CB   ILE B 310      33.234  39.963 -29.117  1.00 21.87           C
ATOM   5364  CG1  ILE B 310      31.925  40.194 -28.351  1.00 21.95           C
ATOM   5365  CD1  ILE B 310      32.132  40.706 -26.914  1.00 29.75           C
ATOM   5366  CG2  ILE B 310      34.064  41.256 -29.196  1.00 23.29           C
ATOM   5367  C    ILE B 310      32.413  38.019 -30.586  1.00 17.38           C
ATOM   5368  O    ILE B 310      33.174  37.056 -30.478  1.00 15.32           O
ATOM   5369  N    ARG B 311      31.102  37.880 -30.774  1.00 14.79           N
ATOM   5370  CA   ARG B 311      30.529  36.545 -30.989  1.00 17.18           C
ATOM   5371  CB   ARG B 311      28.998  36.600 -31.122  1.00 20.16           C
ATOM   5372  CG   ARG B 311      28.465  37.361 -32.336  1.00 22.10           C
ATOM   5373  CD   ARG B 311      26.941  37.321 -32.464  1.00 23.35           C
ATOM   5374  NE   ARG B 311      26.462  38.008 -33.664  1.00 25.63           N
ATOM   5375  CZ   ARG B 311      26.336  39.326 -33.778  1.00 27.53           C
ATOM   5376  NH1  ARG B 311      25.889  39.854 -34.910  1.00 31.46           N
ATOM   5377  NH2  ARG B 311      26.654  40.121 -32.767  1.00 27.66           N
ATOM   5378  C    ARG B 311      31.169  35.839 -32.197  1.00 16.34           C
ATOM   5379  O    ARG B 311      31.421  34.631 -32.159  1.00 14.64           O
ATOM   5380  N    ASN B 312      31.456  36.595 -33.254  1.00 12.89           N
ATOM   5381  CA   ASN B 312      32.041  36.005 -34.455  1.00 14.66           C
ATOM   5382  CB   ASN B 312      31.731  36.845 -35.684  1.00 14.46           C
ATOM   5383  CG   ASN B 312      30.257  36.821 -36.027  1.00 19.03           C
ATOM   5384  OD1  ASN B 312      29.515  35.952 -35.554  1.00 17.58           O
ATOM   5385  ND2  ASN B 312      29.825  37.767 -36.842  1.00 18.75           N
ATOM   5386  C    ASN B 312      33.526  35.767 -34.342  1.00 13.49           C
ATOM   5387  O    ASN B 312      34.051  34.853 -34.975  1.00 14.74           O
ATOM   5388  N    VAL B 313      34.190  36.605 -33.549  1.00 15.22           N
ATOM   5389  CA   VAL B 313      35.585  36.375 -33.197  1.00 13.86           C
ATOM   5390  CB   VAL B 313      36.139  37.505 -32.315  1.00 15.27           C
ATOM   5391  CG1  VAL B 313      37.563  37.192 -31.833  1.00 15.29           C
ATOM   5392  CG2  VAL B 313      36.114  38.817 -33.069  1.00 14.49           C
ATOM   5393  C    VAL B 313      35.719  35.037 -32.473  1.00 15.40           C
ATOM   5394  O    VAL B 313      36.562  34.224 -32.841  1.00 14.74           O
ATOM   5395  N    ALA B 314      34.877  34.808 -31.462  1.00 12.90           N
ATOM   5396  CA   ALA B 314      34.921  33.553 -30.710  1.00 13.25           C
ATOM   5397  CB   ALA B 314      33.922  33.568 -29.548  1.00 14.21           C
ATOM   5398  C    ALA B 314      34.685  32.344 -31.613  1.00 13.43           C
ATOM   5399  O    ALA B 314      35.399  31.342 -31.508  1.00 13.21           O
ATOM   5400  N    ARG B 315      33.691  32.434 -32.496  1.00 11.27           N
ATOM   5401  CA   ARG B 315      33.439  31.376 -33.489  1.00 13.03           C
ATOM   5402  CB   ARG B 315      32.275  31.761 -34.390  1.00 13.50           C
ATOM   5403  CG   ARG B 315      30.916  31.783 -33.730  1.00 13.80           C
ATOM   5404  CD   ARG B 315      29.865  32.533 -34.548  1.00 15.64           C
ATOM   5405  NE   ARG B 315      28.520  32.074 -34.204  1.00 16.30           N
```

FIGURE 3RRRR

| | | | | | | | | | |
|---|---|---|---|---|---|---|---|---|---|
| ATOM | 5406 | CZ | ARG | B | 315 | 27.490 | 32.868 | -33.935 | 1.00 16.69 | C |
| ATOM | 5407 | NH1 | ARG | B | 315 | 26.319 | 32.340 | -33.607 | 1.00 13.40 | N |
| ATOM | 5408 | NH2 | ARG | B | 315 | 27.616 | 34.188 | -34.003 | 1.00 19.30 | N |
| ATOM | 5409 | C | ARG | B | 315 | 34.658 | 31.116 | -34.382 | 1.00 14.08 | C |
| ATOM | 5410 | O | ARG | B | 315 | 35.080 | 29.972 | -34.579 | 1.00 14.61 | O |
| ATOM | 5411 | N | CYS | B | 316 | 35.203 | 32.189 | -34.941 | 1.00 12.98 | N |
| ATOM | 5412 | CA | CYS | B | 316 | 36.325 | 32.091 | -35.869 | 1.00 14.11 | C |
| ATOM | 5413 | CB | CYS | B | 316 | 36.750 | 33.491 | -36.318 | 1.00 11.80 | C |
| ATOM | 5414 | SG | CYS | B | 316 | 37.766 | 33.451 | -37.802 | 1.00 18.15 | S |
| ATOM | 5415 | C | CYS | B | 316 | 37.530 | 31.378 | -35.256 | 1.00 15.03 | C |
| ATOM | 5416 | O | CYS | B | 316 | 38.051 | 30.409 | -35.818 | 1.00 14.81 | O |
| ATOM | 5417 | N | TRP | B | 317 | 37.973 | 31.865 | -34.104 | 1.00 14.34 | N |
| ATOM | 5418 | CA | TRP | B | 317 | 39.190 | 31.339 | -33.502 | 1.00 12.85 | C |
| ATOM | 5419 | CB | TRP | B | 317 | 39.794 | 32.337 | -32.516 | 1.00 12.05 | C |
| ATOM | 5420 | CG | TRP | B | 317 | 40.311 | 33.573 | -33.212 | 1.00 13.03 | C |
| ATOM | 5421 | CD1 | TRP | B | 317 | 40.591 | 33.715 | -34.548 | 1.00 16.02 | C |
| ATOM | 5422 | NE1 | TRP | B | 317 | 41.044 | 34.988 | -34.808 | 1.00 13.77 | N |
| ATOM | 5423 | CE2 | TRP | B | 317 | 41.062 | 35.696 | -33.638 | 1.00 12.63 | C |
| ATOM | 5424 | CD2 | TRP | B | 317 | 40.600 | 34.837 | -32.612 | 1.00 10.95 | C |
| ATOM | 5425 | CE3 | TRP | B | 317 | 40.537 | 35.329 | -31.303 | 1.00 12.22 | C |
| ATOM | 5426 | CZ3 | TRP | B | 317 | 40.923 | 36.649 | -31.064 | 1.00 13.53 | C |
| ATOM | 5427 | CH2 | TRP | B | 317 | 41.365 | 37.477 | -32.114 | 1.00 13.00 | C |
| ATOM | 5428 | CZ2 | TRP | B | 317 | 41.441 | 37.020 | -33.398 | 1.00 14.60 | C |
| ATOM | 5429 | C | TRP | B | 317 | 38.970 | 29.956 | -32.894 | 1.00 11.81 | C |
| ATOM | 5430 | O | TRP | B | 317 | 39.885 | 29.140 | -32.879 | 1.00 13.28 | O |
| ATOM | 5431 | N | THR | B | 318 | 37.750 | 29.681 | -32.453 | 1.00 11.44 | N |
| ATOM | 5432 | CA | THR | B | 318 | 37.396 | 28.327 | -32.024 | 1.00 14.16 | C |
| ATOM | 5433 | CB | THR | B | 318 | 35.964 | 28.290 | -31.446 | 1.00 13.09 | C |
| ATOM | 5434 | OG1 | THR | B | 318 | 35.959 | 28.938 | -30.166 | 1.00 15.50 | O |
| ATOM | 5435 | CG2 | THR | B | 318 | 35.538 | 26.842 | -31.140 | 1.00 15.13 | C |
| ATOM | 5436 | C | THR | B | 318 | 37.537 | 27.364 | -33.199 | 1.00 15.73 | C |
| ATOM | 5437 | O | THR | B | 318 | 38.183 | 26.311 | -33.081 | 1.00 13.31 | O |
| ATOM | 5438 | N | TYR | B | 319 | 36.935 | 27.720 | -34.331 | 1.00 12.99 | N |
| ATOM | 5439 | CA | TYR | B | 319 | 36.991 | 26.848 | -35.509 | 1.00 13.73 | C |
| ATOM | 5440 | CB | TYR | B | 319 | 36.035 | 27.310 | -36.609 | 1.00 13.16 | C |
| ATOM | 5441 | CG | TYR | B | 319 | 35.916 | 26.330 | -37.759 | 1.00 14.46 | C |
| ATOM | 5442 | CD1 | TYR | B | 319 | 35.416 | 25.042 | -37.557 | 1.00 15.30 | C |
| ATOM | 5443 | CE1 | TYR | B | 319 | 35.304 | 24.142 | -38.612 | 1.00 21.07 | C |
| ATOM | 5444 | CZ | TYR | B | 319 | 35.699 | 24.529 | -39.879 | 1.00 22.51 | C |
| ATOM | 5445 | OH | TYR | B | 319 | 35.587 | 23.648 | -40.926 | 1.00 25.96 | O |
| ATOM | 5446 | CE2 | TYR | B | 319 | 36.197 | 25.807 | -40.106 | 1.00 19.53 | C |
| ATOM | 5447 | CD2 | TYR | B | 319 | 36.305 | 26.693 | -39.048 | 1.00 14.74 | C |
| ATOM | 5448 | C | TYR | B | 319 | 38.410 | 26.689 | -36.048 | 1.00 13.80 | C |
| ATOM | 5449 | O | TYR | B | 319 | 38.804 | 25.590 | -36.445 | 1.00 15.20 | O |
| ATOM | 5450 | N | GLU | B | 320 | 39.182 | 27.777 | -36.032 | 1.00 14.43 | N |
| ATOM | 5451 | CA | GLU | B | 320 | 40.575 | 27.728 | -36.485 | 1.00 12.69 | C |
| ATOM | 5452 | CB | GLU | B | 320 | 41.100 | 29.143 | -36.726 | 1.00 14.91 | C |
| ATOM | 5453 | CG | GLU | B | 320 | 40.444 | 29.635 | -38.006 | 1.00 14.81 | C |
| ATOM | 5454 | CD | GLU | B | 320 | 40.651 | 31.082 | -38.338 | 1.00 16.79 | C |
| ATOM | 5455 | OE1 | GLU | B | 320 | 41.030 | 31.890 | -37.462 | 1.00 18.96 | O |
| ATOM | 5456 | OE2 | GLU | B | 320 | 40.402 | 31.399 | -39.517 | 1.00 20.54 | O |
| ATOM | 5457 | C | GLU | B | 320 | 41.490 | 26.877 | -35.595 | 1.00 11.81 | C |
| ATOM | 5458 | O | GLU | B | 320 | 42.434 | 26.234 | -36.086 | 1.00 15.53 | O |
| ATOM | 5459 | N | THR | B | 321 | 41.193 | 26.857 | -34.302 | 1.00 13.03 | N |
| ATOM | 5460 | CA | THR | B | 321 | 41.871 | 25.951 | -33.374 | 1.00 14.46 | C |
| ATOM | 5461 | CB | THR | B | 321 | 41.440 | 26.238 | -31.934 | 1.00 13.74 | C |
| ATOM | 5462 | OG1 | THR | B | 321 | 41.701 | 27.617 | -31.612 | 1.00 15.54 | O |

FIGURE 3SSSS

```
ATOM   5463  CG2 THR B 321      42.304  25.444 -30.941  1.00 15.64           C
ATOM   5464  C   THR B 321      41.542  24.502 -33.743  1.00 12.50           C
ATOM   5465  O   THR B 321      42.430  23.649 -33.770  1.00 17.23           O
ATOM   5466  N   ALA B 322      40.269  24.234 -34.027  1.00 13.65           N
ATOM   5467  CA  ALA B 322      39.842  22.893 -34.450  1.00 17.14           C
ATOM   5468  CB  ALA B 322      38.318  22.844 -34.624  1.00 16.92           C
ATOM   5469  C   ALA B 322      40.550  22.470 -35.744  1.00 18.75           C
ATOM   5470  O   ALA B 322      40.977  21.313 -35.893  1.00 18.79           O
ATOM   5471  N   VAL B 323      40.672  23.411 -36.677  1.00 15.68           N
ATOM   5472  CA  VAL B 323      41.371  23.163 -37.936  1.00 17.47           C
ATOM   5473  CB  VAL B 323      41.287  24.388 -38.887  1.00 18.66           C
ATOM   5474  CG1 VAL B 323      42.281  24.254 -40.025  1.00 19.68           C
ATOM   5475  CG2 VAL B 323      39.871  24.548 -39.434  1.00 19.97           C
ATOM   5476  C   VAL B 323      42.834  22.792 -37.689  1.00 19.53           C
ATOM   5477  O   VAL B 323      43.357  21.858 -38.311  1.00 18.91           O
ATOM   5478  N   ALA B 324      43.487  23.524 -36.786  1.00 17.75           N
ATOM   5479  CA  ALA B 324      44.869  23.241 -36.418  1.00 20.56           C
ATOM   5480  CB  ALA B 324      45.405  24.310 -35.477  1.00 20.83           C
ATOM   5481  C   ALA B 324      45.001  21.853 -35.785  1.00 23.44           C
ATOM   5482  O   ALA B 324      46.030  21.198 -35.936  1.00 23.15           O
ATOM   5483  N   LEU B 325      43.950  21.414 -35.098  1.00 21.98           N
ATOM   5484  CA  LEU B 325      43.925  20.093 -34.451  1.00 20.94           C
ATOM   5485  CB  LEU B 325      43.043  20.137 -33.196  1.00 19.63           C
ATOM   5486  CG  LEU B 325      43.554  20.960 -32.014  1.00 21.72           C
ATOM   5487  CD1 LEU B 325      42.420  21.251 -31.063  1.00 19.78           C
ATOM   5488  CD2 LEU B 325      44.693  20.242 -31.290  1.00 23.00           C
ATOM   5489  C   LEU B 325      43.439  18.968 -35.375  1.00 24.71           C
ATOM   5490  O   LEU B 325      43.356  17.807 -34.954  1.00 25.42           O
ATOM   5491  N   ASP B 326      43.114  19.307 -36.622  1.00 23.10           N
ATOM   5492  CA  ASP B 326      42.584  18.342 -37.597  1.00 31.05           C
ATOM   5493  CB  ASP B 326      43.619  17.253 -37.910  1.00 38.06           C
ATOM   5494  CG  ASP B 326      44.502  17.610 -39.076  1.00 45.51           C
ATOM   5495  OD1 ASP B 326      45.743  17.581 -38.910  1.00 51.50           O
ATOM   5496  OD2 ASP B 326      44.049  17.929 -40.196  1.00 49.83           O
ATOM   5497  C   ASP B 326      41.288  17.701 -37.114  1.00 33.12           C
ATOM   5498  O   ASP B 326      41.016  16.529 -37.394  1.00 29.17           O
ATOM   5499  N   CYS B 327      40.496  18.489 -36.392  1.00 28.66           N
ATOM   5500  CA  CYS B 327      39.289  18.016 -35.735  1.00 34.57           C
ATOM   5501  CB  CYS B 327      39.421  18.265 -34.226  1.00 33.76           C
ATOM   5502  SG  CYS B 327      37.919  18.064 -33.252  1.00 50.64           S
ATOM   5503  C   CYS B 327      38.092  18.769 -36.304  1.00 34.49           C
ATOM   5504  O   CYS B 327      38.093  19.998 -36.331  1.00 36.80           O
ATOM   5505  N   GLU B 328      37.084  18.053 -36.793  1.00 31.02           N
ATOM   5506  CA  GLU B 328      35.846  18.740 -37.131  1.00 31.77           C
ATOM   5507  CB BGLU B 328      35.095  18.065 -38.283  0.35 30.05           C
ATOM   5508  CB AGLU B 328      35.106  18.058 -38.300  0.65 37.03           C
ATOM   5509  CG BGLU B 328      35.145  18.825 -39.610  0.35 26.45           C
ATOM   5510  CG AGLU B 328      34.753  16.588 -38.109  0.65 41.03           C
ATOM   5511  CD BGLU B 328      34.761  20.305 -39.824  0.35 25.50           C
ATOM   5512  CD AGLU B 328      33.894  16.033 -39.240  0.65 45.21           C
ATOM   5513  OE1BGLU B 328      34.136  20.743 -38.529  0.35 22.48           O
ATOM   5514  OE1AGLU B 328      32.673  15.858 -39.037  0.65 45.05           O
ATOM   5515  OE2BGLU B 328      35.088  21.043 -40.476  0.35 22.57           O
ATOM   5516  OE2AGLU B 328      34.437  15.764 -40.335  0.65 45.42           O
ATOM   5517  C   GLU B 328      34.977  18.835 -35.884  1.00 32.51           C
ATOM   5518  O   GLU B 328      34.929  17.909 -35.069  1.00 35.63           O
ATOM   5519  N   ILE B 329      34.349  19.989 -35.706  1.00 25.63           N
```

FIGURE 3TTTT

```
ATOM   5520  CA   ILE B 329      33.453  20.195 -34.580  1.00 22.60           C
ATOM   5521  CB   ILE B 329      33.991  21.297 -33.616  1.00 19.79           C
ATOM   5522  CG1  ILE B 329      34.337  22.592 -34.373  1.00 20.13           C
ATOM   5523  CD1  ILE B 329      34.767  23.753 -33.459  1.00 14.69           C
ATOM   5524  CG2  ILE B 329      35.200  20.761 -32.835  1.00 19.36           C
ATOM   5525  C    ILE B 329      32.058  20.509 -35.113  1.00 18.70           C
ATOM   5526  O    ILE B 329      31.930  21.066 -36.197  1.00 18.50           O
ATOM   5527  N    PRO B 330      31.017  20.111 -34.380  1.00 21.09           N
ATOM   5528  CA   PRO B 330      29.638  20.340 -34.836  1.00 19.32           C
ATOM   5529  CB   PRO B 330      28.779  19.661 -33.757  1.00 21.67           C
ATOM   5530  CG   PRO B 330      29.660  19.507 -32.577  1.00 27.05           C
ATOM   5531  CD   PRO B 330      31.066  19.384 -33.100  1.00 21.56           C
ATOM   5532  C    PRO B 330      29.269  21.816 -34.974  1.00 17.91           C
ATOM   5533  O    PRO B 330      29.758  22.660 -34.220  1.00 16.58           O
ATOM   5534  N    ASN B 331      28.412  22.114 -35.946  1.00 16.36           N
ATOM   5535  CA   ASN B 331      27.868  23.461 -36.106  1.00 17.06           C
ATOM   5536  CB   ASN B 331      27.071  23.573 -37.414  1.00 16.00           C
ATOM   5537  CG   ASN B 331      26.850  25.009 -37.824  1.00 17.08           C
ATOM   5538  OD1  ASN B 331      27.684  25.880 -37.549  1.00 17.36           O
ATOM   5539  ND2  ASN B 331      25.720  25.277 -38.463  1.00 18.80           N
ATOM   5540  C    ASN B 331      27.012  23.901 -34.914  1.00 19.61           C
ATOM   5541  O    ASN B 331      26.943  25.090 -34.587  1.00 18.03           O
ATOM   5542  N    GLU B 332      26.364  22.936 -34.265  1.00 19.11           N
ATOM   5543  CA   GLU B 332      25.568  23.212 -33.070  1.00 18.47           C
ATOM   5544  CB   GLU B 332      24.721  21.977 -32.727  1.00 23.36           C
ATOM   5545  CG   GLU B 332      23.833  22.133 -31.504  1.00 29.50           C
ATOM   5546  CD   GLU B 332      22.453  22.691 -31.817  1.00 36.55           C
ATOM   5547  OE1  GLU B 332      22.156  22.988 -33.000  1.00 37.06           O
ATOM   5548  OE2  GLU B 332      21.655  22.832 -30.862  1.00 39.05           O
ATOM   5549  C    GLU B 332      26.501  23.585 -31.914  1.00 15.92           C
ATOM   5550  O    GLU B 332      27.319  22.767 -31.487  1.00 17.24           O
ATOM   5551  N    LEU B 333      26.406  24.820 -31.424  1.00 17.14           N
ATOM   5552  CA   LEU B 333      27.265  25.252 -30.323  1.00 15.96           C
ATOM   5553  CB   LEU B 333      27.138  26.760 -30.063  1.00 17.06           C
ATOM   5554  CG   LEU B 333      27.659  27.703 -31.145  1.00 18.06           C
ATOM   5555  CD1  LEU B 333      27.220  29.127 -30.817  1.00 17.77           C
ATOM   5556  CD2  LEU B 333      29.179  27.604 -31.313  1.00 16.99           C
ATOM   5557  C    LEU B 333      26.955  24.488 -29.036  1.00 15.62           C
ATOM   5558  O    LEU B 333      25.787  24.280 -28.690  1.00 15.85           O
ATOM   5559  N    PRO B 334      27.988  24.084 -28.309  1.00 16.29           N
ATOM   5560  CA   PRO B 334      27.774  23.486 -26.991  1.00 15.45           C
ATOM   5561  CB   PRO B 334      29.168  22.993 -26.599  1.00 19.04           C
ATOM   5562  CG   PRO B 334      30.107  23.886 -27.341  1.00 19.34           C
ATOM   5563  CD   PRO B 334      29.417  24.164 -28.654  1.00 15.84           C
ATOM   5564  C    PRO B 334      27.344  24.586 -26.042  1.00 18.71           C
ATOM   5565  O    PRO B 334      27.682  25.752 -26.264  1.00 14.65           O
ATOM   5566  N    TYR B 335      26.616  24.233 -24.992  1.00 17.53           N
ATOM   5567  CA   TYR B 335      26.339  25.217 -23.959  1.00 16.92           C
ATOM   5568  CB   TYR B 335      25.451  24.640 -22.849  1.00 19.08           C
ATOM   5569  CG   TYR B 335      24.992  25.703 -21.891  1.00 19.10           C
ATOM   5570  CD1  TYR B 335      25.513  25.773 -20.600  1.00 21.31           C
ATOM   5571  CE1  TYR B 335      25.107  26.774 -19.721  1.00 20.68           C
ATOM   5572  CZ   TYR B 335      24.177  27.721 -20.145  1.00 17.67           C
ATOM   5573  OH   TYR B 335      23.774  28.711 -19.289  1.00 24.97           O
ATOM   5574  CE2  TYR B 335      23.651  27.672 -21.412  1.00 19.30           C
ATOM   5575  CD2  TYR B 335      24.062  26.668 -22.286  1.00 18.07           C
ATOM   5576  C    TYR B 335      27.664  25.760 -23.414  1.00 17.13           C
```

FIGURE 3UUUU

```
ATOM   5577  O    TYR B 335      28.670  25.049 -23.361  1.00 18.55           O
ATOM   5578  N    ASN B 336      27.667  27.035 -23.045  1.00 18.05           N
ATOM   5579  CA   ASN B 336      28.875  27.699 -22.575  1.00 16.35           C
ATOM   5580  CB   ASN B 336      29.802  28.038 -23.759  1.00 16.48           C
ATOM   5581  CG   ASN B 336      29.196  29.058 -24.706  1.00 18.25           C
ATOM   5582  OD1  ASN B 336      29.286  30.257 -24.470  1.00 19.82           O
ATOM   5583  ND2  ASN B 336      28.575  28.581 -25.784  1.00 16.30           N
ATOM   5584  C    ASN B 336      28.506  28.941 -21.768  1.00 14.85           C
ATOM   5585  O    ASN B 336      27.333  29.311 -21.706  1.00 16.32           O
ATOM   5586  N    ASP B 337      29.496  29.579 -21.152  1.00 17.37           N
ATOM   5587  CA   ASP B 337      29.244  30.706 -20.243  1.00 20.35           C
ATOM   5588  CB   ASP B 337      30.517  31.065 -19.465  1.00 26.24           C
ATOM   5589  CG   ASP B 337      30.806  30.104 -18.328  1.00 35.62           C
ATOM   5590  OD1  ASP B 337      29.876  29.405 -17.859  1.00 36.85           O
ATOM   5591  OD2  ASP B 337      31.948  29.986 -17.835  1.00 40.28           O
ATOM   5592  C    ASP B 337      28.711  31.964 -20.928  1.00 19.82           C
ATOM   5593  O    ASP B 337      28.209  32.876 -20.265  1.00 20.87           O
ATOM   5594  N    TYR B 338      28.833  32.008 -22.248  1.00 18.10           N
ATOM   5595  CA   TYR B 338      28.425  33.168 -23.042  1.00 15.43           C
ATOM   5596  CB   TYR B 338      29.674  33.795 -23.680  1.00 16.27           C
ATOM   5597  CG   TYR B 338      30.715  34.063 -22.621  1.00 21.96           C
ATOM   5598  CD1  TYR B 338      31.795  33.203 -22.442  1.00 21.12           C
ATOM   5599  CE1  TYR B 338      32.737  33.432 -21.433  1.00 23.94           C
ATOM   5600  CZ   TYR B 338      32.579  34.515 -20.587  1.00 26.73           C
ATOM   5601  OH   TYR B 338      33.500  34.743 -19.593  1.00 29.92           O
ATOM   5602  CE2  TYR B 338      31.502  35.372 -20.732  1.00 29.49           C
ATOM   5603  CD2  TYR B 338      30.573  35.139 -21.742  1.00 24.47           C
ATOM   5604  C    TYR B 338      27.392  32.783 -24.087  1.00 15.84           C
ATOM   5605  O    TYR B 338      27.259  33.443 -25.127  1.00 16.66           O
ATOM   5606  N    PHE B 339      26.634  31.725 -23.794  1.00 16.58           N
ATOM   5607  CA   PHE B 339      25.730  31.132 -24.772  1.00 16.85           C
ATOM   5608  CB   PHE B 339      24.904  30.013 -24.128  1.00 16.62           C
ATOM   5609  CG   PHE B 339      24.243  29.096 -25.124  1.00 15.56           C
ATOM   5610  CD1  PHE B 339      22.855  29.071 -25.244  1.00 15.90           C
ATOM   5611  CE1  PHE B 339      22.227  28.207 -26.156  1.00 18.93           C
ATOM   5612  CZ   PHE B 339      22.991  27.366 -26.957  1.00 17.30           C
ATOM   5613  CE2  PHE B 339      24.387  27.376 -26.840  1.00 16.36           C
ATOM   5614  CD2  PHE B 339      24.999  28.247 -25.921  1.00 17.94           C
ATOM   5615  C    PHE B 339      24.798  32.147 -25.436  1.00 17.05           C
ATOM   5616  O    PHE B 339      24.574  32.082 -26.646  1.00 16.14           O
ATOM   5617  N    GLU B 340      24.261  33.072 -24.637  1.00 15.10           N
ATOM   5618  CA   GLU B 340      23.326  34.093 -25.123  1.00 17.80           C
ATOM   5619  CB   GLU B 340      22.724  34.874 -23.944  1.00 19.38           C
ATOM   5620  CG   GLU B 340      23.686  35.848 -23.280  1.00 20.36           C
ATOM   5621  CD   GLU B 340      24.521  35.225 -22.182  1.00 26.26           C
ATOM   5622  OE1  GLU B 340      24.689  33.981 -22.151  1.00 23.37           O
ATOM   5623  OE2  GLU B 340      25.024  35.995 -21.342  1.00 25.07           O
ATOM   5624  C    GLU B 340      23.916  35.052 -26.175  1.00 18.64           C
ATOM   5625  O    GLU B 340      23.175  35.633 -26.976  1.00 18.12           O
ATOM   5626  N    TYR B 341      25.242  35.194 -26.187  1.00 15.98           N
ATOM   5627  CA   TYR B 341      25.924  36.032 -27.178  1.00 16.73           C
ATOM   5628  CB   TYR B 341      27.416  36.134 -26.845  1.00 19.05           C
ATOM   5629  CG   TYR B 341      27.758  37.052 -25.696  1.00 26.76           C
ATOM   5630  CD1  TYR B 341      27.329  36.776 -24.393  1.00 24.82           C
ATOM   5631  CE1  TYR B 341      27.658  37.622 -23.332  1.00 34.92           C
ATOM   5632  CZ   TYR B 341      28.436  38.751 -23.575  1.00 41.50           C
ATOM   5633  OH   TYR B 341      28.778  39.600 -22.546  1.00 46.34           O
```

FIGURE 3VVVV

```
ATOM   5634  CE2 TYR B 341      28.880  39.037 -24.858  1.00 39.25           C
ATOM   5635  CD2 TYR B 341      28.542  38.185 -25.909  1.00 33.79           C
ATOM   5636  C   TYR B 341      25.795  35.490 -28.599  1.00 17.17           C
ATOM   5637  O   TYR B 341      25.974  36.231 -29.565  1.00 17.06           O
ATOM   5638  N   PHE B 342      25.500  34.197 -28.723  1.00 14.52           N
ATOM   5639  CA  PHE B 342      25.503  33.514 -30.011  1.00 15.63           C
ATOM   5640  CB  PHE B 342      26.198  32.157 -29.879  1.00 14.35           C
ATOM   5641  CG  PHE B 342      27.601  32.254 -29.368  1.00 14.28           C
ATOM   5642  CD1 PHE B 342      27.890  31.970 -28.039  1.00 12.93           C
ATOM   5643  CE1 PHE B 342      29.192  32.062 -27.560  1.00 17.24           C
ATOM   5644  CZ  PHE B 342      30.223  32.447 -28.415  1.00 16.15           C
ATOM   5645  CE2 PHE B 342      29.946  32.733 -29.748  1.00 13.71           C
ATOM   5646  CD2 PHE B 342      28.638  32.649 -30.217  1.00 13.32           C
ATOM   5647  C   PHE B 342      24.120  33.348 -30.645  1.00 15.41           C
ATOM   5648  O   PHE B 342      23.972  32.656 -31.645  1.00 17.33           O
ATOM   5649  N   GLY B 343      23.109  33.987 -30.070  1.00 17.62           N
ATOM   5650  CA  GLY B 343      21.800  34.018 -30.700  1.00 17.69           C
ATOM   5651  C   GLY B 343      21.823  34.853 -31.973  1.00 20.72           C
ATOM   5652  O   GLY B 343      22.780  35.600 -32.194  1.00 21.53           O
ATOM   5653  N   PRO B 344      20.777  34.758 -32.795  1.00 22.21           N
ATOM   5654  CA  PRO B 344      19.593  33.925 -32.516  1.00 21.41           C
ATOM   5655  CB  PRO B 344      18.507  34.605 -33.356  1.00 25.40           C
ATOM   5656  CG  PRO B 344      19.247  35.132 -34.558  1.00 22.95           C
ATOM   5657  CD  PRO B 344      20.642  35.499 -34.064  1.00 23.41           C
ATOM   5658  C   PRO B 344      19.708  32.463 -32.950  1.00 22.19           C
ATOM   5659  O   PRO B 344      18.819  31.668 -32.634  1.00 22.73           O
ATOM   5660  N   ASP B 345      20.776  32.120 -33.665  1.00 19.79           N
ATOM   5661  CA  ASP B 345      20.925  30.794 -34.272  1.00 20.85           C
ATOM   5662  CB  ASP B 345      21.665  30.935 -35.603  1.00 23.79           C
ATOM   5663  CG  ASP B 345      22.993  31.662 -35.446  1.00 27.82           C
ATOM   5664  OD1 ASP B 345      22.977  32.900 -35.219  1.00 26.88           O
ATOM   5665  OD2 ASP B 345      24.094  31.071 -35.498  1.00 27.05           O
ATOM   5666  C   ASP B 345      21.658  29.770 -33.394  1.00 20.00           C
ATOM   5667  O   ASP B 345      21.391  28.568 -33.479  1.00 19.33           O
ATOM   5668  N   PHE B 346      22.596  30.249 -32.575  1.00 15.45           N
ATOM   5669  CA  PHE B 346      23.444  29.391 -31.733  1.00 16.59           C
ATOM   5670  CB  PHE B 346      22.627  28.754 -30.598  1.00 18.31           C
ATOM   5671  CG  PHE B 346      21.850  29.752 -29.803  1.00 17.16           C
ATOM   5672  CD1 PHE B 346      20.493  29.966 -30.060  1.00 17.32           C
ATOM   5673  CE1 PHE B 346      19.774  30.913 -29.333  1.00 16.00           C
ATOM   5674  CZ  PHE B 346      20.402  31.656 -28.351  1.00 17.43           C
ATOM   5675  CE2 PHE B 346      21.763  31.460 -28.089  1.00 16.60           C
ATOM   5676  CD2 PHE B 346      22.478  30.508 -28.818  1.00 17.69           C
ATOM   5677  C   PHE B 346      24.199  28.344 -32.545  1.00 17.04           C
ATOM   5678  O   PHE B 346      24.336  27.204 -32.119  1.00 15.05           O
ATOM   5679  N   LYS B 347      24.680  28.755 -33.719  1.00 13.94           N
ATOM   5680  CA  LYS B 347      25.537  27.914 -34.563  1.00 12.92           C
ATOM   5681  CB  LYS B 347      25.016  27.861 -36.006  1.00 15.71           C
ATOM   5682  CG  LYS B 347      23.581  27.343 -36.174  1.00 15.00           C
ATOM   5683  CD  LYS B 347      23.424  25.909 -35.698  1.00 19.25           C
ATOM   5684  CE  LYS B 347      21.972  25.437 -35.855  1.00 21.58           C
ATOM   5685  NZ  LYS B 347      21.775  24.059 -36.323  1.00 26.90           N
ATOM   5686  C   LYS B 347      26.951  28.454 -34.572  1.00 15.62           C
ATOM   5687  O   LYS B 347      27.182  29.648 -34.298  1.00 17.73           O
ATOM   5688  N   LEU B 348      27.903  27.581 -34.889  1.00 13.80           N
ATOM   5689  CA  LEU B 348      29.304  27.980 -34.981  1.00 12.59           C
ATOM   5690  CB  LEU B 348      30.195  26.730 -34.983  1.00 14.15           C
```

FIGURE 3WWWW

| | | | | | | | | | |
|---|---|---|---|---|---|---|---|---|---|
| ATOM | 5691 | CG | LEU | B | 348 | 31.701 | 26.988 | -35.138 | 1.00 18.02 | C |
| ATOM | 5692 | CD1 | LEU | B | 348 | 32.261 | 27.663 | -33.894 | 1.00 15.14 | C |
| ATOM | 5693 | CD2 | LEU | B | 348 | 32.424 | 25.683 | -35.436 | 1.00 18.12 | C |
| ATOM | 5694 | C | LEU | B | 348 | 29.558 | 28.801 | -36.250 | 1.00 14.60 | C |
| ATOM | 5695 | O | LEU | B | 348 | 30.281 | 29.803 | -36.237 | 1.00 17.18 | O |
| ATOM | 5696 | N | HIS | B | 349 | 28.975 | 28.351 | -37.355 | 1.00 17.56 | N |
| ATOM | 5697 | CA | HIS | B | 349 | 29.233 | 28.959 | -38.646 | 1.00 18.48 | C |
| ATOM | 5698 | CB | HIS | B | 349 | 29.255 | 27.886 | -39.734 | 1.00 19.04 | C |
| ATOM | 5699 | CG | HIS | B | 349 | 30.434 | 26.977 | -39.610 | 1.00 19.45 | C |
| ATOM | 5700 | ND1 | HIS | B | 349 | 31.701 | 27.354 | -40.003 | 1.00 20.11 | N |
| ATOM | 5701 | CE1 | HIS | B | 349 | 32.549 | 26.376 | -39.741 | 1.00 20.42 | C |
| ATOM | 5702 | NE2 | HIS | B | 349 | 31.885 | 25.393 | -39.161 | 1.00 20.96 | N |
| ATOM | 5703 | CD2 | HIS | B | 349 | 30.561 | 25.748 | -39.058 | 1.00 16.73 | C |
| ATOM | 5704 | C | HIS | B | 349 | 28.280 | 30.107 | -38.954 | 1.00 17.94 | C |
| ATOM | 5705 | O | HIS | B | 349 | 27.141 | 30.117 | -38.493 | 1.00 21.08 | O |
| ATOM | 5706 | N | ILE | B | 350 | 28.777 | 31.085 | -39.703 | 1.00 16.66 | N |
| ATOM | 5707 | CA | ILE | B | 350 | 28.010 | 32.291 | -40.019 | 1.00 18.20 | C |
| ATOM | 5708 | CB | ILE | B | 350 | 28.774 | 33.564 | -39.563 | 1.00 20.44 | C |
| ATOM | 5709 | CG1 | ILE | B | 350 | 30.085 | 33.723 | -40.360 | 1.00 17.04 | C |
| ATOM | 5710 | CD1 | ILE | B | 350 | 30.768 | 35.078 | -40.202 | 1.00 18.01 | C |
| ATOM | 5711 | CG2 | ILE | B | 350 | 29.034 | 33.523 | -38.046 | 1.00 17.62 | C |
| ATOM | 5712 | C | ILE | B | 350 | 27.700 | 32.370 | -41.513 | 1.00 23.57 | C |
| ATOM | 5713 | O | ILE | B | 350 | 28.431 | 31.829 | -42.342 | 1.00 21.67 | O |
| ATOM | 5714 | N | SER | B | 351 | 26.614 | 33.055 | -41.848 | 1.00 24.46 | N |
| ATOM | 5715 | CA | SER | B | 351 | 26.246 | 33.265 | -43.238 | 1.00 25.27 | C |
| ATOM | 5716 | CB | SER | B | 351 | 24.722 | 33.253 | -43.378 | 1.00 32.47 | C |
| ATOM | 5717 | OG | SER | B | 351 | 24.226 | 31.929 | -43.255 | 1.00 37.46 | O |
| ATOM | 5718 | C | SER | B | 351 | 26.818 | 34.597 | -43.729 | 1.00 23.00 | C |
| ATOM | 5719 | O | SER | B | 351 | 26.955 | 35.531 | -42.946 | 1.00 25.43 | O |
| ATOM | 5720 | N | PRO | B | 352 | 27.161 | 34.689 | -45.010 | 1.00 22.15 | N |
| ATOM | 5721 | CA | PRO | B | 352 | 27.561 | 35.979 | -45.581 | 1.00 22.55 | C |
| ATOM | 5722 | CB | PRO | B | 352 | 28.079 | 35.606 | -46.974 | 1.00 23.89 | C |
| ATOM | 5723 | CG | PRO | B | 352 | 27.444 | 34.311 | -47.301 | 1.00 27.43 | C |
| ATOM | 5724 | CD | PRO | B | 352 | 27.205 | 33.604 | -46.006 | 1.00 22.28 | C |
| ATOM | 5725 | C | PRO | B | 352 | 26.351 | 36.905 | -45.677 | 1.00 24.72 | C |
| ATOM | 5726 | O | PRO | B | 352 | 25.213 | 36.434 | -45.593 | 1.00 21.06 | O |
| ATOM | 5727 | N | SER | B | 353 | 26.601 | 38.203 | -45.819 | 1.00 22.24 | N |
| ATOM | 5728 | CA | SER | B | 353 | 25.536 | 39.175 | -46.027 | 1.00 27.42 | C |
| ATOM | 5729 | CB | SER | B | 353 | 25.919 | 40.507 | -45.387 | 1.00 29.63 | C |
| ATOM | 5730 | OG | SER | B | 353 | 26.965 | 41.121 | -46.115 | 1.00 29.30 | O |
| ATOM | 5731 | C | SER | B | 353 | 25.275 | 39.357 | -47.524 | 1.00 24.32 | C |
| ATOM | 5732 | O | SER | B | 353 | 25.951 | 38.747 | -48.354 | 1.00 21.86 | O |
| ATOM | 5733 | N | ASN | B | 354 | 24.294 | 40.190 | -47.868 | 1.00 25.41 | N |
| ATOM | 5734 | CA | ASN | B | 354 | 23.997 | 40.488 | -49.269 | 1.00 29.42 | C |
| ATOM | 5735 | CB | ASN | B | 354 | 22.496 | 40.738 | -49.457 | 1.00 31.23 | C |
| ATOM | 5736 | CG | ASN | B | 354 | 22.039 | 42.055 | -48.847 | 1.00 31.90 | C |
| ATOM | 5737 | OD1 | ASN | B | 354 | 22.561 | 42.499 | -47.825 | 1.00 34.12 | O |
| ATOM | 5738 | ND2 | ASN | B | 354 | 21.049 | 42.683 | -49.476 | 1.00 35.65 | N |
| ATOM | 5739 | C | ASN | B | 354 | 24.806 | 41.664 | -49.834 | 1.00 31.29 | C |
| ATOM | 5740 | O | ASN | B | 354 | 24.519 | 42.149 | -50.934 | 1.00 34.78 | O |
| ATOM | 5741 | N | MET | B | 355 | 25.810 | 42.118 | -49.066 | 1.00 27.29 | N |
| ATOM | 5742 | CA | MET | B | 355 | 26.679 | 43.198 | -49.548 | 1.00 26.07 | C |
| ATOM | 5743 | CB | MET | B | 355 | 27.676 | 43.610 | -48.454 | 1.00 24.64 | C |
| ATOM | 5744 | CG | MET | B | 355 | 28.919 | 42.733 | -48.344 | 1.00 25.29 | C |
| ATOM | 5745 | SD | MET | B | 355 | 30.126 | 43.349 | -47.146 | 1.00 29.03 | S |
| ATOM | 5746 | CE | MET | B | 355 | 30.445 | 44.986 | -47.746 | 1.00 26.12 | C |
| ATOM | 5747 | C | MET | B | 355 | 27.373 | 42.852 | -50.871 | 1.00 25.28 | C |

FIGURE 3XXXX

```
ATOM   5748  O    MET B 355      27.770  41.700 -51.111  1.00 23.84           O
ATOM   5749  N    THR B 356      27.494  43.844 -51.745  1.00 25.91           N
ATOM   5750  CA   THR B 356      28.084  43.604 -53.058  1.00 26.17           C
ATOM   5751  CB   THR B 356      27.727  44.736 -54.057  1.00 34.79           C
ATOM   5752  OG1  THR B 356      28.239  45.984 -53.577  1.00 40.69           O
ATOM   5753  CG2  THR B 356      26.221  44.969 -54.097  1.00 34.12           C
ATOM   5754  C    THR B 356      29.596  43.438 -52.948  1.00 24.79           C
ATOM   5755  O    THR B 356      30.258  44.139 -52.172  1.00 24.02           O
ATOM   5756  N    ASN B 357      30.122  42.486 -53.713  1.00 25.66           N
ATOM   5757  CA   ASN B 357      31.553  42.247 -53.782  1.00 23.29           C
ATOM   5758  CB   ASN B 357      31.826  40.772 -54.089  1.00 22.78           C
ATOM   5759  CG   ASN B 357      33.302  40.453 -54.181  1.00 22.26           C
ATOM   5760  OD1  ASN B 357      34.155  41.294 -53.901  1.00 21.65           O
ATOM   5761  ND2  ASN B 357      33.616  39.224 -54.578  1.00 25.78           N
ATOM   5762  C    ASN B 357      32.188  43.162 -54.832  1.00 27.66           C
ATOM   5763  O    ASN B 357      32.059  42.923 -56.032  1.00 28.42           O
ATOM   5764  N    GLN B 358      32.887  44.195 -54.369  1.00 23.90           N
ATOM   5765  CA   GLN B 358      33.490  45.191 -55.261  1.00 28.42           C
ATOM   5766  CB   GLN B 358      33.810  46.478 -54.495  1.00 30.86           C
ATOM   5767  CG BGLN B 358      32.595  47.174 -53.878  0.35 29.61           C
ATOM   5768  CG AGLN B 358      32.600  47.208 -53.947  0.65 36.48           C
ATOM   5769  CD BGLN B 358      31.579  47.660 -54.907  0.35 29.27           C
ATOM   5770  CD AGLN B 358      32.608  48.685 -54.293  0.65 40.09           C
ATOM   5771  OE1BGLN B 358      30.373  47.602 -54.664  0.35 30.72           O
ATOM   5772  OE1AGLN B 358      32.031  49.092 -55.300  0.65 41.77           O
ATOM   5773  NE2BGLN B 358      32.061  48.145 -56.046  0.35 28.09           N
ATOM   5774  NE2AGLN B 358      33.260  49.490 -53.460  0.65 42.44           N
ATOM   5775  C    GLN B 358      34.740  44.676 -55.984  1.00 28.04           C
ATOM   5776  O    GLN B 358      35.248  45.328 -56.896  1.00 30.40           O
ATOM   5777  N    ASN B 359      35.224  43.508 -55.567  1.00 24.95           N
ATOM   5778  CA   ASN B 359      36.350  42.836 -56.204  1.00 25.16           C
ATOM   5779  CB   ASN B 359      37.075  41.951 -55.187  1.00 24.25           C
ATOM   5780  CG   ASN B 359      37.422  42.696 -53.928  1.00 22.10           C
ATOM   5781  OD1  ASN B 359      36.602  42.809 -53.008  1.00 23.40           O
ATOM   5782  ND2  ASN B 359      38.624  43.246 -53.891  1.00 18.56           N
ATOM   5783  C    ASN B 359      35.912  41.978 -57.384  1.00 28.79           C
ATOM   5784  O    ASN B 359      35.515  40.819 -57.211  1.00 29.16           O
ATOM   5785  N    THR B 360      35.990  42.542 -58.583  1.00 25.53           N
ATOM   5786  CA   THR B 360      35.602  41.804 -59.783  1.00 25.94           C
ATOM   5787  CB   THR B 360      35.589  42.722 -61.022  1.00 22.16           C
ATOM   5788  OG1  THR B 360      36.909  43.235 -61.233  1.00 23.14           O
ATOM   5789  CG2  THR B 360      34.746  43.978 -60.783  1.00 23.10           C
ATOM   5790  C    THR B 360      36.588  40.659 -60.001  1.00 23.04           C
ATOM   5791  O    THR B 360      37.729  40.719 -59.532  1.00 24.19           O
ATOM   5792  N    PRO B 361      36.160  39.609 -60.696  1.00 24.77           N
ATOM   5793  CA   PRO B 361      37.074  38.517 -61.044  1.00 23.25           C
ATOM   5794  CB   PRO B 361      36.217  37.622 -61.948  1.00 26.99           C
ATOM   5795  CG   PRO B 361      34.828  37.887 -61.502  1.00 27.31           C
ATOM   5796  CD   PRO B 361      34.789  39.358 -61.181  1.00 24.82           C
ATOM   5797  C    PRO B 361      38.313  39.025 -61.784  1.00 22.09           C
ATOM   5798  O    PRO B 361      39.413  38.532 -61.541  1.00 23.23           O
ATOM   5799  N    GLU B 362      38.133  40.021 -62.651  1.00 20.42           N
ATOM   5800  CA   GLU B 362      39.229  40.566 -63.447  1.00 20.06           C
ATOM   5801  CB   GLU B 362      38.681  41.488 -64.548  1.00 23.85           C
ATOM   5802  CG   GLU B 362      37.759  40.801 -65.553  1.00 27.65           C
ATOM   5803  CD   GLU B 362      36.381  40.463 -64.999  1.00 31.94           C
ATOM   5804  OE1  GLU B 362      35.870  41.176 -64.102  1.00 27.43           O
```

FIGURE 3YYYY

| | | | | | | | | | |
|---|---|---|---|---|---|---|---|---|---|
| ATOM | 5805 | OE2 | GLU | B | 362 | 35.803 | 39.456 | -65.463 | 1.00 41.15 | O |
| ATOM | 5806 | C | GLU | B | 362 | 40.221 | 41.331 | -62.575 | 1.00 16.50 | C |
| ATOM | 5807 | O | GLU | B | 362 | 41.436 | 41.207 | -62.751 | 1.00 18.94 | O |
| ATOM | 5808 | N | TYR | B | 363 | 39.695 | 42.135 | -61.651 | 1.00 17.96 | N |
| ATOM | 5809 | CA | TYR | B | 363 | 40.532 | 42.843 | -60.680 | 1.00 16.41 | C |
| ATOM | 5810 | CB | TYR | B | 363 | 39.658 | 43.650 | -59.710 | 1.00 20.60 | C |
| ATOM | 5811 | CG | TYR | B | 363 | 40.413 | 44.276 | -58.550 | 1.00 21.67 | C |
| ATOM | 5812 | CD1 | TYR | B | 363 | 40.514 | 43.618 | -57.318 | 1.00 22.25 | C |
| ATOM | 5813 | CE1 | TYR | B | 363 | 41.206 | 44.189 | -56.247 | 1.00 18.66 | C |
| ATOM | 5814 | CZ | TYR | B | 363 | 41.803 | 45.433 | -56.403 | 1.00 23.16 | C |
| ATOM | 5815 | OH | TYR | B | 363 | 42.484 | 45.994 | -55.347 | 1.00 20.84 | O |
| ATOM | 5816 | CE2 | TYR | B | 363 | 41.711 | 46.114 | -57.615 | 1.00 21.06 | C |
| ATOM | 5817 | CD2 | TYR | B | 363 | 41.017 | 45.530 | -58.681 | 1.00 21.76 | C |
| ATOM | 5818 | C | TYR | B | 363 | 41.388 | 41.841 | -59.921 | 1.00 17.00 | C |
| ATOM | 5819 | O | TYR | B | 363 | 42.608 | 41.980 | -59.846 | 1.00 16.86 | O |
| ATOM | 5820 | N | MET | B | 364 | 40.737 | 40.817 | -59.374 | 1.00 17.71 | N |
| ATOM | 5821 | CA | MET | B | 364 | 41.428 | 39.805 | -58.570 | 1.00 21.33 | C |
| ATOM | 5822 | CB | MET | B | 364 | 40.447 | 38.729 | -58.082 | 1.00 23.52 | C |
| ATOM | 5823 | CG | MET | B | 364 | 39.391 | 39.204 | -57.073 | 1.00 31.29 | C |
| ATOM | 5824 | SD | MET | B | 364 | 40.027 | 40.094 | -55.625 | 1.00 41.93 | S |
| ATOM | 5825 | CE | MET | B | 364 | 40.861 | 38.764 | -54.724 | 1.00 40.02 | C |
| ATOM | 5826 | C | MET | B | 364 | 42.558 | 39.157 | -59.361 | 1.00 21.25 | C |
| ATOM | 5827 | O | MET | B | 364 | 43.680 | 39.033 | -58.868 | 1.00 20.57 | O |
| ATOM | 5828 | N | GLU | B | 365 | 42.269 | 38.760 | -60.598 | 1.00 24.03 | N |
| ATOM | 5829 | CA | GLU | B | 365 | 43.273 | 38.084 | -61.409 | 1.00 23.69 | C |
| ATOM | 5830 | CB | GLU | B | 365 | 42.631 | 37.349 | -62.583 | 1.00 26.85 | C |
| ATOM | 5831 | CG | GLU | B | 365 | 43.409 | 36.111 | -63.006 | 1.00 40.67 | C |
| ATOM | 5832 | CD | GLU | B | 365 | 43.209 | 34.914 | -62.085 | 1.00 40.61 | C |
| ATOM | 5833 | OE1 | GLU | B | 365 | 43.831 | 33.868 | -62.356 | 1.00 46.88 | O |
| ATOM | 5834 | OE2 | GLU | B | 365 | 42.438 | 35.001 | -61.105 | 1.00 40.92 | O |
| ATOM | 5835 | C | GLU | B | 365 | 44.384 | 39.019 | -61.882 | 1.00 22.51 | C |
| ATOM | 5836 | O | GLU | B | 365 | 45.544 | 38.611 | -61.977 | 1.00 20.81 | O |
| ATOM | 5837 | N | LYS | B | 366 | 44.037 | 40.274 | -62.158 | 1.00 19.77 | N |
| ATOM | 5838 | CA | LYS | B | 366 | 45.040 | 41.245 | -62.568 | 1.00 20.86 | C |
| ATOM | 5839 | CB | LYS | B | 366 | 44.379 | 42.558 | -63.009 | 1.00 21.02 | C |
| ATOM | 5840 | CG | LYS | B | 366 | 45.343 | 43.612 | -63.522 | 1.00 24.81 | C |
| ATOM | 5841 | CD | LYS | B | 366 | 46.024 | 43.171 | -64.799 | 1.00 24.80 | C |
| ATOM | 5842 | CE | LYS | B | 366 | 46.979 | 44.237 | -65.283 | 1.00 29.87 | C |
| ATOM | 5843 | NZ | LYS | B | 366 | 47.726 | 43.788 | -66.488 | 1.00 31.06 | N |
| ATOM | 5844 | C | LYS | B | 366 | 46.064 | 41.491 | -61.459 | 1.00 19.69 | C |
| ATOM | 5845 | O | LYS | B | 366 | 47.276 | 41.498 | -61.715 | 1.00 19.63 | O |
| ATOM | 5846 | N | ILE | B | 367 | 45.576 | 41.705 | -60.235 | 1.00 20.09 | N |
| ATOM | 5847 | CA | ILE | B | 367 | 46.462 | 41.907 | -59.087 | 1.00 16.38 | C |
| ATOM | 5848 | CB | ILE | B | 367 | 45.662 | 42.281 | -57.788 | 1.00 20.43 | C |
| ATOM | 5849 | CG1 | ILE | B | 367 | 44.787 | 43.539 | -57.981 | 1.00 20.60 | C |
| ATOM | 5850 | CD1 | ILE | B | 367 | 45.520 | 44.777 | -58.490 | 1.00 26.81 | C |
| ATOM | 5851 | CG2 | ILE | B | 367 | 46.610 | 42.463 | -56.572 | 1.00 20.03 | C |
| ATOM | 5852 | C | ILE | B | 367 | 47.319 | 40.656 | -58.873 | 1.00 17.91 | C |
| ATOM | 5853 | O | ILE | B | 367 | 48.530 | 40.755 | -58.669 | 1.00 18.33 | O |
| ATOM | 5854 | N | LYS | B | 368 | 46.688 | 39.488 | -58.947 | 1.00 19.12 | N |
| ATOM | 5855 | CA | LYS | B | 368 | 47.386 | 38.219 | -58.750 | 1.00 23.39 | C |
| ATOM | 5856 | CB | LYS | B | 368 | 46.396 | 37.056 | -58.848 | 1.00 24.64 | C |
| ATOM | 5857 | CG | LYS | B | 368 | 47.019 | 35.673 | -58.682 | 1.00 33.29 | C |
| ATOM | 5858 | CD | LYS | B | 368 | 46.033 | 34.670 | -58.084 | 1.00 39.24 | C |
| ATOM | 5859 | CE | LYS | B | 368 | 45.044 | 34.128 | -59.110 | 1.00 40.35 | C |
| ATOM | 5860 | NZ | LYS | B | 368 | 45.718 | 33.651 | -60.351 | 1.00 46.81 | N |
| ATOM | 5861 | C | LYS | B | 368 | 48.532 | 38.065 | -59.758 | 1.00 26.07 | C |

FIGURE 3ZZZZ

```
ATOM   5862  O    LYS B 368      49.649  37.683 -59.391  1.00 23.03           O
ATOM   5863  N    GLN B 369      48.261  38.399 -61.016  1.00 28.49           N
ATOM   5864  CA   GLN B 369      49.282  38.314 -62.061  1.00 30.11           C
ATOM   5865  CB   GLN B 369      48.655  38.458 -63.451  1.00 34.83           C
ATOM   5866  CG   GLN B 369      47.970  37.157 -63.914  1.00 42.09           C
ATOM   5867  CD   GLN B 369      47.366  37.232 -65.310  1.00 47.15           C
ATOM   5868  OE1  GLN B 369      47.622  38.173 -66.062  1.00 51.28           O
ATOM   5869  NE2  GLN B 369      46.562  36.231 -65.656  1.00 47.55           N
ATOM   5870  C    GLN B 369      50.443  39.287 -61.826  1.00 27.20           C
ATOM   5871  O    GLN B 369      51.601  38.937 -62.055  1.00 25.53           O
ATOM   5872  N    ARG B 370      50.142  40.486 -61.327  1.00 26.77           N
ATOM   5873  CA   ARG B 370      51.195  41.418 -60.906  1.00 27.77           C
ATOM   5874  CB   ARG B 370      50.603  42.763 -60.481  1.00 33.46           C
ATOM   5875  CG   ARG B 370      51.550  43.942 -60.666  1.00 42.22           C
ATOM   5876  CD   ARG B 370      51.253  44.785 -61.906  1.00 47.41           C
ATOM   5877  NE   ARG B 370      50.595  46.053 -61.577  1.00 48.46           N
ATOM   5878  CZ   ARG B 370      49.501  46.513 -62.175  1.00 49.43           C
ATOM   5879  NH1  ARG B 370      48.981  47.676 -61.807  1.00 48.54           N
ATOM   5880  NH2  ARG B 370      48.922  45.818 -63.143  1.00 50.52           N
ATOM   5881  C    ARG B 370      52.072  40.832 -59.784  1.00 29.39           C
ATOM   5882  O    ARG B 370      53.308  40.909 -59.842  1.00 26.86           O
ATOM   5883  N    LEU B 371      51.437  40.230 -58.779  1.00 26.22           N
ATOM   5884  CA   LEU B 371      52.179  39.633 -57.661  1.00 24.41           C
ATOM   5885  CB   LEU B 371      51.240  39.237 -56.514  1.00 20.96           C
ATOM   5886  CG   LEU B 371      50.478  40.375 -55.820  1.00 24.90           C
ATOM   5887  CD1  LEU B 371      49.713  39.841 -54.621  1.00 19.71           C
ATOM   5888  CD2  LEU B 371      51.397  41.502 -55.393  1.00 28.47           C
ATOM   5889  C    LEU B 371      53.018  38.436 -58.107  1.00 25.30           C
ATOM   5890  O    LEU B 371      54.147  38.255 -57.642  1.00 25.42           O
ATOM   5891  N    PHE B 372      52.460  37.623 -59.003  1.00 26.79           N
ATOM   5892  CA   PHE B 372      53.174  36.476 -59.563  1.00 27.25           C
ATOM   5893  CB   PHE B 372      52.288  35.709 -60.544  1.00 28.78           C
ATOM   5894  CG   PHE B 372      51.292  34.780 -59.896  1.00 31.97           C
ATOM   5895  CD1  PHE B 372      51.434  34.364 -58.575  1.00 36.19           C
ATOM   5896  CE1  PHE B 372      50.508  33.500 -57.995  1.00 33.85           C
ATOM   5897  CZ   PHE B 372      49.429  33.039 -58.736  1.00 37.46           C
ATOM   5898  CE2  PHE B 372      49.274  33.448 -60.059  1.00 39.08           C
ATOM   5899  CD2  PHE B 372      50.206  34.313 -60.628  1.00 36.53           C
ATOM   5900  C    PHE B 372      54.456  36.922 -60.276  1.00 27.24           C
ATOM   5901  O    PHE B 372      55.477  36.243 -60.201  1.00 28.64           O
ATOM   5902  N    GLU B 373      54.387  38.061 -60.965  1.00 27.76           N
ATOM   5903  CA   GLU B 373      55.540  38.636 -61.662  1.00 33.30           C
ATOM   5904  CB   GLU B 373      55.108  39.802 -62.560  1.00 38.12           C
ATOM   5905  CG   GLU B 373      54.440  39.374 -63.863  1.00 45.65           C
ATOM   5906  CD   GLU B 373      53.889  40.542 -64.676  1.00 51.54           C
ATOM   5907  OE1  GLU B 373      53.318  41.485 -64.082  1.00 53.94           O
ATOM   5908  OE2  GLU B 373      54.016  40.516 -65.920  1.00 52.44           O
ATOM   5909  C    GLU B 373      56.619  39.094 -60.682  1.00 33.67           C
ATOM   5910  O    GLU B 373      57.813  38.916 -60.940  1.00 33.16           O
ATOM   5911  N    ASN B 374      56.196  39.682 -59.562  1.00 27.10           N
ATOM   5912  CA   ASN B 374      57.122  40.072 -58.499  1.00 26.87           C
ATOM   5913  CB   ASN B 374      56.408  40.905 -57.419  1.00 26.49           C
ATOM   5914  CG   ASN B 374      55.968  42.276 -57.920  1.00 30.69           C
ATOM   5915  OD1  ASN B 374      56.424  42.750 -58.964  1.00 30.02           O
ATOM   5916  ND2  ASN B 374      55.075  42.921 -57.170  1.00 25.15           N
ATOM   5917  C    ASN B 374      57.791  38.860 -57.861  1.00 24.23           C
ATOM   5918  O    ASN B 374      58.975  38.896 -57.532  1.00 28.17           O
```

FIGURE 3AAAAA

| ATOM | 5919 | N | LEU | B | 375 | 57.018 | 37.793 | -57.681 | 1.00 | 24.17 | N |
|------|------|------|------|------|------|---------|---------|---------|------|-------|------|
| ATOM | 5920 | CA | LEU | B | 375 | 57.493 | 36.575 | -57.033 | 1.00 | 28.26 | C |
| ATOM | 5921 | CB | LEU | B | 375 | 56.317 | 35.643 | -56.729 | 1.00 | 27.42 | C |
| ATOM | 5922 | CG | LEU | B | 375 | 55.792 | 35.464 | -55.296 | 1.00 | 32.75 | C |
| ATOM | 5923 | CD1 | LEU | B | 375 | 56.436 | 36.390 | -54.264 | 1.00 | 30.58 | C |
| ATOM | 5924 | CD2 | LEU | B | 375 | 54.280 | 35.598 | -55.273 | 1.00 | 29.95 | C |
| ATOM | 5925 | C | LEU | B | 375 | 58.537 | 35.835 | -57.867 | 1.00 | 32.12 | C |
| ATOM | 5926 | O | LEU | B | 375 | 59.448 | 35.221 | -57.315 | 1.00 | 33.79 | O |
| ATOM | 5927 | N | ARG | B | 376 | 58.411 | 35.882 | -59.192 | 1.00 | 35.49 | N |
| ATOM | 5928 | CA | ARG | B | 376 | 59.414 | 35.235 | -60.041 | 1.00 | 38.79 | C |
| ATOM | 5929 | CB | ARG | B | 376 | 58.852 | 34.808 | -61.410 | 1.00 | 43.24 | C |
| ATOM | 5930 | CG | ARG | B | 376 | 58.226 | 35.905 | -62.258 | 1.00 | 48.80 | C |
| ATOM | 5931 | CD | ARG | B | 376 | 57.489 | 35.383 | -63.495 | 1.00 | 53.80 | C |
| ATOM | 5932 | NE | ARG | B | 376 | 56.433 | 34.430 | -63.145 | 1.00 | 56.93 | N |
| ATOM | 5933 | CZ | ARG | B | 376 | 55.136 | 34.599 | -63.403 | 1.00 | 58.64 | C |
| ATOM | 5934 | NH1 | ARG | B | 376 | 54.706 | 35.691 | -64.026 | 1.00 | 58.76 | N |
| ATOM | 5935 | NH2 | ARG | B | 376 | 54.263 | 33.668 | -63.037 | 1.00 | 58.42 | N |
| ATOM | 5936 | C | ARG | B | 376 | 60.714 | 36.046 | -60.154 | 1.00 | 38.60 | C |
| ATOM | 5937 | O | ARG | B | 376 | 61.686 | 35.586 | -60.757 | 1.00 | 40.47 | O |
| ATOM | 5938 | N | MET | B | 377 | 60.729 | 37.233 | -59.545 | 1.00 | 37.30 | N |
| ATOM | 5939 | CA | MET | B | 377 | 61.953 | 38.028 | -59.399 | 1.00 | 38.42 | C |
| ATOM | 5940 | CB | MET | B | 377 | 61.627 | 39.494 | -59.086 | 1.00 | 41.69 | C |
| ATOM | 5941 | CG | MET | B | 377 | 61.051 | 40.299 | -60.247 | 1.00 | 44.31 | C |
| ATOM | 5942 | SD | MET | B | 377 | 62.090 | 40.333 | -61.733 | 1.00 | 49.16 | S |
| ATOM | 5943 | CE | MET | B | 377 | 63.649 | 41.041 | -61.081 | 1.00 | 47.78 | C |
| ATOM | 5944 | C | MET | B | 377 | 62.897 | 37.474 | -58.321 | 1.00 | 37.34 | C |
| ATOM | 5945 | O | MET | B | 377 | 64.045 | 37.904 | -58.224 | 1.00 | 38.94 | O |
| ATOM | 5946 | N | LEU | B | 378 | 62.411 | 36.537 | -57.506 | 1.00 | 37.50 | N |
| ATOM | 5947 | CA | LEU | B | 378 | 63.251 | 35.871 | -56.505 | 1.00 | 40.07 | C |
| ATOM | 5948 | CB | LEU | B | 378 | 62.401 | 35.146 | -55.451 | 1.00 | 38.30 | C |
| ATOM | 5949 | CG | LEU | B | 378 | 61.461 | 35.889 | -54.485 | 1.00 | 38.69 | C |
| ATOM | 5950 | CD1 | LEU | B | 378 | 61.289 | 35.081 | -53.204 | 1.00 | 36.30 | C |
| ATOM | 5951 | CD2 | LEU | B | 378 | 61.910 | 37.304 | -54.158 | 1.00 | 37.32 | C |
| ATOM | 5952 | C | LEU | B | 378 | 64.200 | 34.877 | -57.181 | 1.00 | 39.73 | C |
| ATOM | 5953 | O | LEU | B | 378 | 65.232 | 34.509 | -56.618 | 1.00 | 44.95 | O |
| ATOM | 5954 | ZN | ZN | B | 379 | 42.346 | 44.764 | -38.237 | 1.00 | 17.93 | ZN |
| ATOM | 5955 | NA | NA | B | 380 | 46.027 | 41.848 | -43.569 | 1.00 | 9.14 | NA |
| ATOM | 5956 | O3 | TSS | B | 381 | 37.461 | 52.572 | -36.947 | 1.00 | 33.11 | O |
| ATOM | 5957 | C9 | TSS | B | 381 | 38.404 | 52.752 | -36.197 | 1.00 | 32.92 | C |
| ATOM | 5958 | C10 | TSS | B | 381 | 38.110 | 53.205 | -34.787 | 1.00 | 29.81 | C |
| ATOM | 5959 | C11 | TSS | B | 381 | 39.100 | 53.671 | -33.921 | 1.00 | 27.95 | C |
| ATOM | 5960 | C12 | TSS | B | 381 | 38.772 | 54.092 | -32.631 | 1.00 | 31.28 | C |
| ATOM | 5961 | C13 | TSS | B | 381 | 37.447 | 54.055 | -32.186 | 1.00 | 31.71 | C |
| ATOM | 5962 | N2 | TSS | B | 381 | 37.121 | 54.486 | -30.882 | 1.00 | 35.47 | N |
| ATOM | 5963 | C17 | TSS | B | 381 | 35.730 | 54.599 | -30.462 | 1.00 | 36.27 | C |
| ATOM | 5964 | C16 | TSS | B | 381 | 38.163 | 54.844 | -29.926 | 1.00 | 35.88 | C |
| ATOM | 5965 | C14 | TSS | B | 381 | 36.453 | 53.596 | -33.053 | 1.00 | 29.85 | C |
| ATOM | 5966 | C15 | TSS | B | 381 | 36.782 | 53.175 | -34.341 | 1.00 | 33.15 | C |
| ATOM | 5967 | C2 | TSS | B | 381 | 39.776 | 52.519 | -36.799 | 1.00 | 34.35 | C |
| ATOM | 5968 | C1 | TSS | B | 381 | 40.800 | 53.576 | -36.372 | 1.00 | 38.16 | C |
| ATOM | 5969 | C3 | TSS | B | 381 | 40.233 | 51.062 | -36.681 | 1.00 | 31.97 | C |
| ATOM | 5970 | C4 | TSS | B | 381 | 41.360 | 50.524 | -36.157 | 1.00 | 31.33 | C |
| ATOM | 5971 | C5 | TSS | B | 381 | 42.455 | 51.343 | -35.524 | 1.00 | 29.99 | C |
| ATOM | 5972 | C6 | TSS | B | 381 | 41.492 | 49.050 | -36.251 | 1.00 | 29.95 | C |
| ATOM | 5973 | C7 | TSS | B | 381 | 42.656 | 48.400 | -36.150 | 1.00 | 30.65 | C |
| ATOM | 5974 | C8 | TSS | B | 381 | 42.721 | 46.921 | -36.289 | 1.00 | 34.29 | C |
| ATOM | 5975 | O1 | TSS | B | 381 | 41.701 | 46.246 | -36.275 | 1.00 | 28.41 | O |

FIGURE 3BBBBB

```
ATOM   5976  N1   TSS B 381      43.901  46.324 -36.473  1.00 37.90           N
ATOM   5977  O2   TSS B 381      43.999  45.329 -37.223  1.00 27.54           O
ATOM   5978  N    LYS C  14      51.320  10.742  65.776  1.00 56.13           N
ATOM   5979  CA   LYS C  14      51.945  11.252  64.520  1.00 54.35           C
ATOM   5980  CB   LYS C  14      50.906  11.332  63.401  1.00 56.41           C
ATOM   5981  CG   LYS C  14      50.676  10.020  62.669  1.00 56.91           C
ATOM   5982  CD   LYS C  14      49.814  10.231  61.437  1.00 57.97           C
ATOM   5983  CE   LYS C  14      48.641   9.269  61.412  1.00 59.08           C
ATOM   5984  NZ   LYS C  14      47.844   9.411  60.163  1.00 59.01           N
ATOM   5985  C    LYS C  14      52.603  12.615  64.733  1.00 53.64           C
ATOM   5986  O    LYS C  14      51.982  13.537  65.265  1.00 52.34           O
ATOM   5987  N    LYS C  15      53.863  12.726  64.312  1.00 49.97           N
ATOM   5988  CA   LYS C  15      54.660  13.937  64.501  1.00 47.84           C
ATOM   5989  CB   LYS C  15      56.150  13.589  64.495  1.00 50.23           C
ATOM   5990  CG   LYS C  15      56.814  13.617  65.859  1.00 53.91           C
ATOM   5991  CD   LYS C  15      58.332  13.569  65.729  1.00 55.56           C
ATOM   5992  CE   LYS C  15      58.934  14.969  65.713  1.00 56.51           C
ATOM   5993  NZ   LYS C  15      60.420  14.932  65.609  1.00 57.29           N
ATOM   5994  C    LYS C  15      54.379  14.992  63.432  1.00 44.54           C
ATOM   5995  O    LYS C  15      54.270  14.676  62.243  1.00 43.90           O
ATOM   5996  N    VAL C  16      54.265  16.245  63.865  1.00 40.56           N
ATOM   5997  CA   VAL C  16      54.073  17.369  62.953  1.00 35.92           C
ATOM   5998  CB   VAL C  16      52.678  18.041  63.130  1.00 36.26           C
ATOM   5999  CG1  VAL C  16      52.532  19.287  62.238  1.00 34.82           C
ATOM   6000  CG2  VAL C  16      51.552  17.058  62.849  1.00 34.32           C
ATOM   6001  C    VAL C  16      55.181  18.396  63.172  1.00 38.43           C
ATOM   6002  O    VAL C  16      55.368  18.898  64.287  1.00 36.80           O
ATOM   6003  N    CYS C  17      55.928  18.678  62.109  1.00 34.12           N
ATOM   6004  CA   CYS C  17      56.909  19.758  62.119  1.00 35.98           C
ATOM   6005  CB   CYS C  17      58.241  19.303  61.523  1.00 38.13           C
ATOM   6006  SG   CYS C  17      59.189  18.232  62.630  1.00 48.14           S
ATOM   6007  C    CYS C  17      56.346  20.938  61.348  1.00 34.14           C
ATOM   6008  O    CYS C  17      55.773  20.778  60.270  1.00 33.22           O
ATOM   6009  N    TYR C  18      56.515  22.126  61.909  1.00 31.79           N
ATOM   6010  CA   TYR C  18      55.868  23.321  61.391  1.00 30.51           C
ATOM   6011  CB   TYR C  18      54.782  23.760  62.379  1.00 31.64           C
ATOM   6012  CG   TYR C  18      54.054  25.059  62.088  1.00 30.54           C
ATOM   6013  CD1  TYR C  18      54.609  26.291  62.444  1.00 31.33           C
ATOM   6014  CE1  TYR C  18      53.930  27.482  62.205  1.00 30.57           C
ATOM   6015  CZ   TYR C  18      52.673  27.445  61.625  1.00 31.75           C
ATOM   6016  OH   TYR C  18      51.996  28.620  61.394  1.00 36.63           O
ATOM   6017  CE2  TYR C  18      52.094  26.235  61.278  1.00 30.16           C
ATOM   6018  CD2  TYR C  18      52.782  25.052  61.520  1.00 30.00           C
ATOM   6019  C    TYR C  18      56.922  24.395  61.195  1.00 30.62           C
ATOM   6020  O    TYR C  18      57.765  24.615  62.066  1.00 28.76           O
ATOM   6021  N    TYR C  19      56.874  25.056  60.043  1.00 29.55           N
ATOM   6022  CA   TYR C  19      57.892  26.032  59.683  1.00 33.29           C
ATOM   6023  CB   TYR C  19      58.561  25.648  58.353  1.00 37.08           C
ATOM   6024  CG   TYR C  19      59.441  24.426  58.502  1.00 37.83           C
ATOM   6025  CD1  TYR C  19      58.920  23.145  58.335  1.00 37.23           C
ATOM   6026  CE1  TYR C  19      59.713  22.023  58.499  1.00 40.45           C
ATOM   6027  CZ   TYR C  19      61.045  22.169  58.839  1.00 40.52           C
ATOM   6028  OH   TYR C  19      61.827  21.049  58.997  1.00 43.89           O
ATOM   6029  CE2  TYR C  19      61.591  23.429  59.020  1.00 38.55           C
ATOM   6030  CD2  TYR C  19      60.785  24.550  58.857  1.00 37.99           C
ATOM   6031  C    TYR C  19      57.320  27.436  59.643  1.00 34.72           C
ATOM   6032  O    TYR C  19      56.267  27.679  59.049  1.00 33.04           O
```

FIGURE 3CCCCC

```
ATOM   6033  N    TYR C  20      58.014  28.355  60.303  1.00 34.11           N
ATOM   6034  CA   TYR C  20      57.608  29.752  60.311  1.00 36.91           C
ATOM   6035  CB   TYR C  20      56.538  29.990  61.379  1.00 39.51           C
ATOM   6036  CG   TYR C  20      56.064  31.424  61.490  1.00 40.24           C
ATOM   6037  CD1  TYR C  20      56.529  32.251  62.515  1.00 40.22           C
ATOM   6038  CE1  TYR C  20      56.095  33.568  62.631  1.00 40.05           C
ATOM   6039  CZ   TYR C  20      55.181  34.071  61.717  1.00 39.40           C
ATOM   6040  OH   TYR C  20      54.756  35.374  61.834  1.00 38.35           O
ATOM   6041  CE2  TYR C  20      54.701  33.269  60.686  1.00 39.14           C
ATOM   6042  CD2  TYR C  20      55.140  31.950  60.581  1.00 39.75           C
ATOM   6043  C    TYR C  20      58.807  30.642  60.570  1.00 38.24           C
ATOM   6044  O    TYR C  20      59.625  30.351  61.443  1.00 39.61           O
ATOM   6045  N    ASP C  21      58.911  31.714  59.791  1.00 38.63           N
ATOM   6046  CA   ASP C  21      59.870  32.775  60.070  1.00 43.47           C
ATOM   6047  CB   ASP C  21      60.817  33.001  58.889  1.00 43.17           C
ATOM   6048  CG   ASP C  21      61.911  34.006  59.208  1.00 45.80           C
ATOM   6049  OD1  ASP C  21      63.067  33.585  59.423  1.00 44.46           O
ATOM   6050  OD2  ASP C  21      61.700  35.236  59.280  1.00 46.10           O
ATOM   6051  C    ASP C  21      59.116  34.056  60.410  1.00 44.63           C
ATOM   6052  O    ASP C  21      58.243  34.486  59.653  1.00 46.69           O
ATOM   6053  N    GLY C  22      59.467  34.660  61.544  1.00 48.02           N
ATOM   6054  CA   GLY C  22      58.788  35.843  62.053  1.00 47.89           C
ATOM   6055  C    GLY C  22      58.770  37.052  61.132  1.00 49.14           C
ATOM   6056  O    GLY C  22      57.952  37.957  61.313  1.00 49.30           O
ATOM   6057  N    ASP C  23      59.666  37.063  60.146  1.00 47.56           N
ATOM   6058  CA   ASP C  23      59.792  38.187  59.217  1.00 46.80           C
ATOM   6059  CB   ASP C  23      61.258  38.387  58.818  1.00 51.43           C
ATOM   6060  CG   ASP C  23      62.037  39.193  59.844  1.00 55.39           C
ATOM   6061  OD1  ASP C  23      62.717  38.584  60.697  1.00 56.21           O
ATOM   6062  OD2  ASP C  23      62.025  40.441  59.874  1.00 56.78           O
ATOM   6063  C    ASP C  23      58.916  38.057  57.968  1.00 43.49           C
ATOM   6064  O    ASP C  23      58.708  39.039  57.248  1.00 39.90           O
ATOM   6065  N    ILE C  24      58.398  36.852  57.719  1.00 41.59           N
ATOM   6066  CA   ILE C  24      57.601  36.575  56.518  1.00 40.03           C
ATOM   6067  CB   ILE C  24      57.095  35.093  56.497  1.00 42.02           C
ATOM   6068  CG1  ILE C  24      56.699  34.673  55.077  1.00 42.60           C
ATOM   6069  CD1  ILE C  24      57.870  34.584  54.107  1.00 43.07           C
ATOM   6070  CG2  ILE C  24      55.942  34.870  57.482  1.00 43.14           C
ATOM   6071  C    ILE C  24      56.456  37.577  56.292  1.00 37.88           C
ATOM   6072  O    ILE C  24      56.230  38.023  55.165  1.00 37.83           O
ATOM   6073  N    GLY C  25      55.769  37.944  57.370  1.00 37.67           N
ATOM   6074  CA   GLY C  25      54.648  38.867  57.303  1.00 39.86           C
ATOM   6075  C    GLY C  25      55.018  40.318  57.037  1.00 40.03           C
ATOM   6076  O    GLY C  25      54.129  41.157  56.882  1.00 40.76           O
ATOM   6077  N    ASN C  26      56.317  40.612  56.978  1.00 40.10           N
ATOM   6078  CA   ASN C  26      56.803  41.981  56.771  1.00 42.47           C
ATOM   6079  CB   ASN C  26      58.086  42.230  57.575  1.00 45.32           C
ATOM   6080  CG   ASN C  26      57.864  42.140  59.072  1.00 47.53           C
ATOM   6081  OD1  ASN C  26      56.912  42.709  59.609  1.00 47.02           O
ATOM   6082  ND2  ASN C  26      58.746  41.418  59.755  1.00 48.52           N
ATOM   6083  C    ASN C  26      57.027  42.357  55.309  1.00 43.30           C
ATOM   6084  O    ASN C  26      57.258  43.526  54.990  1.00 43.41           O
ATOM   6085  N    TYR C  27      56.966  41.365  54.426  1.00 40.79           N
ATOM   6086  CA   TYR C  27      57.113  41.605  52.992  1.00 39.26           C
ATOM   6087  CB   TYR C  27      57.645  40.353  52.290  1.00 38.38           C
ATOM   6088  CG   TYR C  27      59.004  39.942  52.813  1.00 39.03           C
ATOM   6089  CD1  TYR C  27      59.126  38.972  53.809  1.00 39.67           C
```

FIGURE 3DDDDD

| | | | | | | | | | | |
|---|---|---|---|---|---|---|---|---|---|---|
| ATOM | 6090 | CE1 | TYR | C | 27 | 60.373 | 38.601 | 54.302 | 1.00 42.53 | C |
| ATOM | 6091 | CZ | TYR | C | 27 | 61.517 | 39.210 | 53.801 | 1.00 43.32 | C |
| ATOM | 6092 | OH | TYR | C | 27 | 62.755 | 38.849 | 54.285 | 1.00 45.81 | O |
| ATOM | 6093 | CE2 | TYR | C | 27 | 61.420 | 40.180 | 52.818 | 1.00 42.22 | C |
| ATOM | 6094 | CD2 | TYR | C | 27 | 60.166 | 40.544 | 52.332 | 1.00 39.21 | C |
| ATOM | 6095 | C | TYR | C | 27 | 55.806 | 42.094 | 52.378 | 1.00 40.23 | C |
| ATOM | 6096 | O | TYR | C | 27 | 54.724 | 41.621 | 52.730 | 1.00 39.76 | O |
| ATOM | 6097 | N | TYR | C | 28 | 55.920 | 43.052 | 51.465 | 1.00 38.98 | N |
| ATOM | 6098 | CA | TYR | C | 28 | 54.760 | 43.752 | 50.930 | 1.00 38.74 | C |
| ATOM | 6099 | CB | TYR | C | 28 | 54.726 | 45.178 | 51.495 | 1.00 42.26 | C |
| ATOM | 6100 | CG | TYR | C | 28 | 53.410 | 45.909 | 51.331 | 1.00 45.41 | C |
| ATOM | 6101 | CD1 | TYR | C | 28 | 52.226 | 45.394 | 51.867 | 1.00 47.50 | C |
| ATOM | 6102 | CE1 | TYR | C | 28 | 51.018 | 46.070 | 51.724 | 1.00 49.53 | C |
| ATOM | 6103 | CZ | TYR | C | 28 | 50.988 | 47.278 | 51.046 | 1.00 49.68 | C |
| ATOM | 6104 | OH | TYR | C | 28 | 49.798 | 47.957 | 50.901 | 1.00 51.36 | O |
| ATOM | 6105 | CE2 | TYR | C | 28 | 52.152 | 47.813 | 50.515 | 1.00 49.06 | C |
| ATOM | 6106 | CD2 | TYR | C | 28 | 53.354 | 47.126 | 50.659 | 1.00 44.61 | C |
| ATOM | 6107 | C | TYR | C | 28 | 54.808 | 43.797 | 49.412 | 1.00 33.90 | C |
| ATOM | 6108 | O | TYR | C | 28 | 55.757 | 44.335 | 48.843 | 1.00 31.76 | O |
| ATOM | 6109 | N | TYR | C | 29 | 53.783 | 43.238 | 48.764 | 1.00 31.72 | N |
| ATOM | 6110 | CA | TYR | C | 29 | 53.681 | 43.229 | 47.300 | 1.00 32.18 | C |
| ATOM | 6111 | CB | TYR | C | 29 | 52.600 | 42.245 | 46.834 | 1.00 31.72 | C |
| ATOM | 6112 | CG | TYR | C | 29 | 53.065 | 40.809 | 46.685 | 1.00 29.44 | C |
| ATOM | 6113 | CD1 | TYR | C | 29 | 52.975 | 40.154 | 45.457 | 1.00 29.70 | C |
| ATOM | 6114 | CE1 | TYR | C | 29 | 53.392 | 38.834 | 45.315 | 1.00 25.67 | C |
| ATOM | 6115 | CZ | TYR | C | 29 | 53.893 | 38.155 | 46.407 | 1.00 26.86 | C |
| ATOM | 6116 | OH | TYR | C | 29 | 54.295 | 36.841 | 46.271 | 1.00 28.91 | O |
| ATOM | 6117 | CE2 | TYR | C | 29 | 53.987 | 38.780 | 47.640 | 1.00 30.13 | C |
| ATOM | 6118 | CD2 | TYR | C | 29 | 53.567 | 40.098 | 47.774 | 1.00 30.07 | C |
| ATOM | 6119 | C | TYR | C | 29 | 53.401 | 44.613 | 46.703 | 1.00 35.73 | C |
| ATOM | 6120 | O | TYR | C | 29 | 53.648 | 44.846 | 45.516 | 1.00 36.83 | O |
| ATOM | 6121 | N | GLY | C | 30 | 52.895 | 45.526 | 47.528 | 1.00 36.66 | N |
| ATOM | 6122 | CA | GLY | C | 30 | 52.515 | 46.850 | 47.065 | 1.00 40.30 | C |
| ATOM | 6123 | C | GLY | C | 30 | 51.067 | 47.165 | 47.389 | 1.00 43.93 | C |
| ATOM | 6124 | O | GLY | C | 30 | 50.289 | 46.270 | 47.729 | 1.00 40.80 | O |
| ATOM | 6125 | N | GLN | C | 31 | 50.711 | 48.443 | 47.287 | 1.00 47.39 | N |
| ATOM | 6126 | CA | GLN | C | 31 | 49.357 | 48.910 | 47.580 | 1.00 48.51 | C |
| ATOM | 6127 | CB | GLN | C | 31 | 49.333 | 50.445 | 47.650 | 1.00 53.84 | C |
| ATOM | 6128 | CG | GLN | C | 31 | 47.954 | 51.089 | 47.511 | 1.00 60.02 | C |
| ATOM | 6129 | CD | GLN | C | 31 | 47.972 | 52.305 | 46.597 | 1.00 65.00 | C |
| ATOM | 6130 | OE1 | GLN | C | 31 | 47.793 | 52.179 | 45.383 | 1.00 66.36 | O |
| ATOM | 6131 | NE2 | GLN | C | 31 | 48.193 | 53.482 | 47.176 | 1.00 65.42 | N |
| ATOM | 6132 | C | GLN | C | 31 | 48.373 | 48.394 | 46.533 | 1.00 45.24 | C |
| ATOM | 6133 | O | GLN | C | 31 | 48.587 | 48.566 | 45.334 | 1.00 46.23 | O |
| ATOM | 6134 | N | GLY | C | 32 | 47.303 | 47.752 | 46.992 | 1.00 42.90 | N |
| ATOM | 6135 | CA | GLY | C | 32 | 46.267 | 47.269 | 46.097 | 1.00 40.42 | C |
| ATOM | 6136 | C | GLY | C | 32 | 46.495 | 45.863 | 45.563 | 1.00 40.39 | C |
| ATOM | 6137 | O | GLY | C | 32 | 45.621 | 45.303 | 44.897 | 1.00 38.98 | O |
| ATOM | 6138 | N | HIS | C | 33 | 47.663 | 45.290 | 45.844 | 1.00 37.69 | N |
| ATOM | 6139 | CA | HIS | C | 33 | 47.943 | 43.918 | 45.432 | 1.00 35.71 | C |
| ATOM | 6140 | CB | HIS | C | 33 | 49.448 | 43.662 | 45.317 | 1.00 34.11 | C |
| ATOM | 6141 | CG | HIS | C | 33 | 49.782 | 42.462 | 44.489 | 1.00 33.23 | C |
| ATOM | 6142 | ND1 | HIS | C | 33 | 49.584 | 41.173 | 44.938 | 1.00 32.29 | N |
| ATOM | 6143 | CE1 | HIS | C | 33 | 49.946 | 40.321 | 43.997 | 1.00 31.61 | C |
| ATOM | 6144 | NE2 | HIS | C | 33 | 50.369 | 41.010 | 42.951 | 1.00 32.32 | N |
| ATOM | 6145 | CD2 | HIS | C | 33 | 50.267 | 42.352 | 43.230 | 1.00 34.31 | C |
| ATOM | 6146 | C | HIS | C | 33 | 47.295 | 42.915 | 46.393 | 1.00 33.78 | C |

FIGURE 3EEEEE

| | | | | | | | | | | |
|---|---|---|---|---|---|---|---|---|---|---|
| ATOM | 6147 | O | HIS | C | 33 | 47.487 | 43.010 | 47.607 | 1.00 34.40 | O |
| ATOM | 6148 | N | PRO | C | 34 | 46.526 | 41.965 | 45.852 | 1.00 32.96 | N |
| ATOM | 6149 | CA | PRO | C | 34 | 45.781 | 40.997 | 46.679 | 1.00 31.81 | C |
| ATOM | 6150 | CB | PRO | C | 34 | 44.909 | 40.252 | 45.659 | 1.00 31.31 | C |
| ATOM | 6151 | CG | PRO | C | 34 | 45.591 | 40.440 | 44.354 | 1.00 31.72 | C |
| ATOM | 6152 | CD | PRO | C | 34 | 46.273 | 41.773 | 44.413 | 1.00 30.02 | C |
| ATOM | 6153 | C | PRO | C | 34 | 46.629 | 40.008 | 47.491 | 1.00 32.18 | C |
| ATOM | 6154 | O | PRO | C | 34 | 46.127 | 39.494 | 48.497 | 1.00 35.21 | O |
| ATOM | 6155 | N | MET | C | 35 | 47.869 | 39.743 | 47.083 | 1.00 30.65 | N |
| ATOM | 6156 | CA | MET | C | 35 | 48.726 | 38.832 | 47.846 | 1.00 32.37 | C |
| ATOM | 6157 | CB | MET | C | 35 | 49.851 | 38.257 | 46.975 | 1.00 34.98 | C |
| ATOM | 6158 | CG | MET | C | 35 | 50.748 | 37.231 | 47.676 | 1.00 36.00 | C |
| ATOM | 6159 | SD | MET | C | 35 | 49.880 | 35.830 | 48.432 | 1.00 39.50 | S |
| ATOM | 6160 | CE | MET | C | 35 | 49.830 | 34.670 | 47.053 | 1.00 37.79 | C |
| ATOM | 6161 | C | MET | C | 35 | 49.290 | 39.531 | 49.080 | 1.00 32.80 | C |
| ATOM | 6162 | O | MET | C | 35 | 50.061 | 40.486 | 48.968 | 1.00 32.06 | O |
| ATOM | 6163 | N | LYS | C | 36 | 48.898 | 39.045 | 50.254 | 1.00 33.47 | N |
| ATOM | 6164 | CA | LYS | C | 36 | 49.308 | 39.652 | 51.519 | 1.00 34.75 | C |
| ATOM | 6165 | CB | LYS | C | 36 | 48.092 | 40.243 | 52.237 | 1.00 38.77 | C |
| ATOM | 6166 | CG | LYS | C | 36 | 47.688 | 41.613 | 51.723 | 1.00 42.90 | C |
| ATOM | 6167 | CD | LYS | C | 36 | 46.183 | 41.738 | 51.597 | 1.00 46.54 | C |
| ATOM | 6168 | CE | LYS | C | 36 | 45.800 | 42.678 | 50.463 | 1.00 48.77 | C |
| ATOM | 6169 | NZ | LYS | C | 36 | 46.198 | 44.086 | 50.729 | 1.00 52.55 | N |
| ATOM | 6170 | C | LYS | C | 36 | 50.030 | 38.657 | 52.426 | 1.00 34.03 | C |
| ATOM | 6171 | O | LYS | C | 36 | 49.380 | 37.903 | 53.153 | 1.00 35.67 | O |
| ATOM | 6172 | N | PRO | C | 37 | 51.368 | 38.642 | 52.381 | 1.00 30.69 | N |
| ATOM | 6173 | CA | PRO | C | 37 | 52.161 | 37.737 | 53.228 | 1.00 29.96 | C |
| ATOM | 6174 | CB | PRO | C | 37 | 53.599 | 38.203 | 52.981 | 1.00 31.29 | C |
| ATOM | 6175 | CG | PRO | C | 37 | 53.559 | 38.765 | 51.593 | 1.00 30.69 | C |
| ATOM | 6176 | CD | PRO | C | 37 | 52.224 | 39.455 | 51.495 | 1.00 30.29 | C |
| ATOM | 6177 | C | PRO | C | 37 | 51.794 | 37.836 | 54.711 | 1.00 30.60 | C |
| ATOM | 6178 | O | PRO | C | 37 | 52.013 | 36.886 | 55.459 | 1.00 32.10 | O |
| ATOM | 6179 | N | HIS | C | 38 | 51.222 | 38.971 | 55.108 | 1.00 32.30 | N |
| ATOM | 6180 | CA | HIS | C | 38 | 50.700 | 39.179 | 56.458 | 1.00 36.07 | C |
| ATOM | 6181 | CB | HIS | C | 38 | 50.066 | 40.570 | 56.551 | 1.00 40.70 | C |
| ATOM | 6182 | CG | HIS | C | 38 | 49.728 | 40.992 | 57.946 | 1.00 48.92 | C |
| ATOM | 6183 | ND1 | HIS | C | 38 | 48.483 | 41.469 | 58.297 | 1.00 52.14 | N |
| ATOM | 6184 | CE1 | HIS | C | 38 | 48.474 | 41.763 | 59.585 | 1.00 54.24 | C |
| ATOM | 6185 | NE2 | HIS | C | 38 | 49.669 | 41.494 | 60.083 | 1.00 53.62 | N |
| ATOM | 6186 | CD2 | HIS | C | 38 | 50.471 | 41.010 | 59.078 | 1.00 51.31 | C |
| ATOM | 6187 | C | HIS | C | 38 | 49.694 | 38.102 | 56.900 | 1.00 33.63 | C |
| ATOM | 6188 | O | HIS | C | 38 | 49.542 | 37.845 | 58.092 | 1.00 35.64 | O |
| ATOM | 6189 | N | ARG | C | 39 | 49.023 | 37.465 | 55.940 | 1.00 35.23 | N |
| ATOM | 6190 | CA | ARG | C | 39 | 48.091 | 36.370 | 56.240 | 1.00 29.53 | C |
| ATOM | 6191 | CB | ARG | C | 39 | 47.313 | 35.959 | 54.982 | 1.00 31.89 | C |
| ATOM | 6192 | CG | ARG | C | 39 | 48.033 | 34.961 | 54.092 | 1.00 31.38 | C |
| ATOM | 6193 | CD | ARG | C | 39 | 47.812 | 35.165 | 52.607 | 1.00 33.64 | C |
| ATOM | 6194 | NE | ARG | C | 39 | 48.859 | 34.478 | 51.860 | 1.00 34.08 | N |
| ATOM | 6195 | CZ | ARG | C | 39 | 48.643 | 33.580 | 50.912 | 1.00 35.90 | C |
| ATOM | 6196 | NH1 | ARG | C | 39 | 47.404 | 33.261 | 50.556 | 1.00 31.85 | N |
| ATOM | 6197 | NH2 | ARG | C | 39 | 49.676 | 32.997 | 50.314 | 1.00 33.94 | N |
| ATOM | 6198 | C | ARG | C | 39 | 48.771 | 35.153 | 56.885 | 1.00 29.68 | C |
| ATOM | 6199 | O | ARG | C | 39 | 48.110 | 34.353 | 57.552 | 1.00 29.57 | O |
| ATOM | 6200 | N | ILE | C | 40 | 50.085 | 35.019 | 56.688 | 1.00 24.63 | N |
| ATOM | 6201 | CA | ILE | C | 40 | 50.852 | 33.944 | 57.320 | 1.00 27.45 | C |
| ATOM | 6202 | CB | ILE | C | 40 | 52.190 | 33.685 | 56.577 | 1.00 27.96 | C |
| ATOM | 6203 | CG1 | ILE | C | 40 | 51.927 | 33.385 | 55.100 | 1.00 33.79 | C |

FIGURE 3FFFFF

```
ATOM   6204  CD1 ILE C  40      53.061  33.808  54.183  1.00 38.17           C
ATOM   6205  CG2 ILE C  40      52.959  32.521  57.217  1.00 30.66           C
ATOM   6206  C   ILE C  40      51.084  34.243  58.806  1.00 28.04           C
ATOM   6207  O   ILE C  40      50.998  33.344  59.644  1.00 27.45           O
ATOM   6208  N   ARG C  41      51.375  35.505  59.115  1.00 31.89           N
ATOM   6209  CA  ARG C  41      51.511  35.965  60.500  1.00 31.28           C
ATOM   6210  CB  ARG C  41      51.969  37.428  60.537  1.00 36.38           C
ATOM   6211  CG  ARG C  41      52.289  37.952  61.941  1.00 41.97           C
ATOM   6212  CD  ARG C  41      53.350  39.045  61.991  1.00 45.76           C
ATOM   6213  NE  ARG C  41      53.010  40.189  61.146  1.00 50.70           N
ATOM   6214  CZ  ARG C  41      53.898  41.022  60.612  1.00 53.22           C
ATOM   6215  NH1 ARG C  41      55.198  40.852  60.828  1.00 53.30           N
ATOM   6216  NH2 ARG C  41      53.487  42.032  59.857  1.00 54.14           N
ATOM   6217  C   ARG C  41      50.191  35.792  61.262  1.00 29.80           C
ATOM   6218  O   ARG C  41      50.177  35.280  62.386  1.00 28.88           O
ATOM   6219  N   MET C  42      49.092  36.209  60.635  1.00 28.61           N
ATOM   6220  CA  MET C  42      47.748  36.021  61.185  1.00 33.28           C
ATOM   6221  CB  MET C  42      46.699  36.554  60.217  1.00 37.01           C
ATOM   6222  CG  MET C  42      46.518  38.050  60.263  1.00 40.51           C
ATOM   6223  SD  MET C  42      45.301  38.577  59.058  1.00 45.08           S
ATOM   6224  CE  MET C  42      43.784  37.848  59.746  1.00 33.97           C
ATOM   6225  C   MET C  42      47.443  34.559  61.492  1.00 33.95           C
ATOM   6226  O   MET C  42      46.899  34.243  62.556  1.00 33.67           O
ATOM   6227  N   THR C  43      47.787  33.676  60.552  1.00 27.78           N
ATOM   6228  CA  THR C  43      47.608  32.237  60.730  1.00 27.55           C
ATOM   6229  CB  THR C  43      48.037  31.465  59.450  1.00 27.61           C
ATOM   6230  OG1 THR C  43      47.202  31.850  58.355  1.00 25.98           O
ATOM   6231  CG2 THR C  43      47.752  29.983  59.600  1.00 27.27           C
ATOM   6232  C   THR C  43      48.404  31.754  61.929  1.00 27.77           C
ATOM   6233  O   THR C  43      47.856  31.096  62.823  1.00 29.09           O
ATOM   6234  N   HIS C  44      49.693  32.101  61.952  1.00 27.01           N
ATOM   6235  CA  HIS C  44      50.592  31.696  63.025  1.00 27.24           C
ATOM   6236  CB  HIS C  44      52.009  32.212  62.761  1.00 32.41           C
ATOM   6237  CG  HIS C  44      53.033  31.682  63.716  1.00 36.88           C
ATOM   6238  ND1 HIS C  44      53.702  32.486  64.613  1.00 40.76           N
ATOM   6239  CE1 HIS C  44      54.539  31.750  65.322  1.00 39.60           C
ATOM   6240  NE2 HIS C  44      54.433  30.496  64.921  1.00 41.04           N
ATOM   6241  CD2 HIS C  44      53.496  30.426  63.919  1.00 38.05           C
ATOM   6242  C   HIS C  44      50.103  32.177  64.396  1.00 30.21           C
ATOM   6243  O   HIS C  44      50.147  31.426  65.379  1.00 28.20           O
ATOM   6244  N   ASN C  45      49.638  33.423  64.447  1.00 30.01           N
ATOM   6245  CA  ASN C  45      49.130  34.017  65.680  1.00 32.74           C
ATOM   6246  CB  ASN C  45      48.884  35.515  65.477  1.00 34.57           C
ATOM   6247  CG  ASN C  45      48.650  36.258  66.784  1.00 38.90           C
ATOM   6248  OD1 ASN C  45      47.517  36.599  67.117  1.00 37.21           O
ATOM   6249  ND2 ASN C  45      49.725  36.524  67.520  1.00 35.99           N
ATOM   6250  C   ASN C  45      47.866  33.310  66.186  1.00 31.00           C
ATOM   6251  O   ASN C  45      47.722  33.071  67.387  1.00 32.09           O
ATOM   6252  N   LEU C  46      46.966  32.964  65.264  1.00 29.96           N
ATOM   6253  CA  LEU C  46      45.756  32.214  65.603  1.00 33.42           C
ATOM   6254  CB  LEU C  46      44.837  32.076  64.385  1.00 35.40           C
ATOM   6255  CG  LEU C  46      43.353  32.436  64.517  1.00 37.13           C
ATOM   6256  CD1 LEU C  46      42.526  31.716  63.453  1.00 31.44           C
ATOM   6257  CD2 LEU C  46      42.798  32.166  65.926  1.00 36.23           C
ATOM   6258  C   LEU C  46      46.095  30.835  66.161  1.00 34.66           C
ATOM   6259  O   LEU C  46      45.553  30.422  67.193  1.00 33.06           O
ATOM   6260  N   LEU C  47      47.006  30.144  65.478  1.00 35.52           N
```

FIGURE 3GGGGG

```
ATOM   6261  CA   LEU C  47      47.470  28.817  65.872  1.00 38.81           C
ATOM   6262  CB   LEU C  47      48.490  28.296  64.857  1.00 42.47           C
ATOM   6263  CG   LEU C  47      47.908  27.657  63.604  1.00 44.77           C
ATOM   6264  CD1  LEU C  47      48.989  27.467  62.565  1.00 42.82           C
ATOM   6265  CD2  LEU C  47      47.276  26.331  63.968  1.00 48.75           C
ATOM   6266  C    LEU C  47      48.093  28.786  67.260  1.00 37.66           C
ATOM   6267  O    LEU C  47      47.800  27.891  68.055  1.00 33.89           O
ATOM   6268  N    LEU C  48      48.959  29.759  67.539  1.00 37.85           N
ATOM   6269  CA   LEU C  48      49.627  29.860  68.833  1.00 37.36           C
ATOM   6270  CB   LEU C  48      50.625  31.026  68.843  1.00 40.20           C
ATOM   6271  CG   LEU C  48      51.915  30.960  68.016  1.00 42.05           C
ATOM   6272  CD1  LEU C  48      52.762  32.205  68.273  1.00 42.21           C
ATOM   6273  CD2  LEU C  48      52.725  29.690  68.277  1.00 41.54           C
ATOM   6274  C    LEU C  48      48.624  30.037  69.969  1.00 36.83           C
ATOM   6275  O    LEU C  48      48.761  29.425  71.025  1.00 40.04           O
ATOM   6276  N    ASN C  49      47.613  30.870  69.734  1.00 36.46           N
ATOM   6277  CA   ASN C  49      46.612  31.184  70.748  1.00 36.10           C
ATOM   6278  CB   ASN C  49      45.930  32.515  70.424  1.00 34.15           C
ATOM   6279  CG   ASN C  49      46.802  33.706  70.785  1.00 35.42           C
ATOM   6280  OD1  ASN C  49      47.107  33.927  71.955  1.00 34.95           O
ATOM   6281  ND2  ASN C  49      47.231  34.459  69.779  1.00 29.62           N
ATOM   6282  C    ASN C  49      45.598  30.069  70.985  1.00 35.25           C
ATOM   6283  O    ASN C  49      44.914  30.041  72.011  1.00 34.47           O
ATOM   6284  N    TYR C  50      45.518  29.140  70.037  1.00 33.96           N
ATOM   6285  CA   TYR C  50      44.760  27.911  70.228  1.00 35.45           C
ATOM   6286  CB   TYR C  50      44.368  27.314  68.878  1.00 33.16           C
ATOM   6287  CG   TYR C  50      42.967  27.641  68.411  1.00 32.45           C
ATOM   6288  CD1  TYR C  50      41.847  27.106  69.054  1.00 30.20           C
ATOM   6289  CE1  TYR C  50      40.556  27.400  68.613  1.00 27.65           C
ATOM   6290  CZ   TYR C  50      40.381  28.225  67.516  1.00 26.28           C
ATOM   6291  OH   TYR C  50      39.117  28.526  67.069  1.00 24.91           O
ATOM   6292  CE2  TYR C  50      41.479  28.764  66.860  1.00 26.27           C
ATOM   6293  CD2  TYR C  50      42.760  28.470  67.310  1.00 30.65           C
ATOM   6294  C    TYR C  50      45.602  26.909  71.018  1.00 38.03           C
ATOM   6295  O    TYR C  50      45.103  25.866  71.444  1.00 40.86           O
ATOM   6296  N    GLY C  51      46.883  27.233  71.199  1.00 37.84           N
ATOM   6297  CA   GLY C  51      47.812  26.396  71.940  1.00 40.86           C
ATOM   6298  C    GLY C  51      48.367  25.210  71.169  1.00 41.95           C
ATOM   6299  O    GLY C  51      48.886  24.265  71.769  1.00 43.30           O
ATOM   6300  N    LEU C  52      48.279  25.261  69.843  1.00 43.65           N
ATOM   6301  CA   LEU C  52      48.706  24.137  69.006  1.00 45.02           C
ATOM   6302  CB   LEU C  52      48.042  24.196  67.621  1.00 44.84           C
ATOM   6303  CG   LEU C  52      46.507  24.095  67.628  1.00 44.99           C
ATOM   6304  CD1  LEU C  52      45.936  24.223  66.233  1.00 45.90           C
ATOM   6305  CD2  LEU C  52      46.015  22.802  68.282  1.00 44.40           C
ATOM   6306  C    LEU C  52      50.230  23.985  68.913  1.00 44.79           C
ATOM   6307  O    LEU C  52      50.733  22.949  68.470  1.00 43.40           O
ATOM   6308  N    TYR C  53      50.952  25.012  69.360  1.00 45.25           N
ATOM   6309  CA   TYR C  53      52.411  24.966  69.458  1.00 48.37           C
ATOM   6310  CB   TYR C  53      52.972  26.351  69.797  1.00 50.70           C
ATOM   6311  CG   TYR C  53      52.647  26.846  71.191  1.00 53.81           C
ATOM   6312  CD1  TYR C  53      53.552  26.677  72.243  1.00 56.29           C
ATOM   6313  CE1  TYR C  53      53.261  27.133  73.524  1.00 57.54           C
ATOM   6314  CZ   TYR C  53      52.054  27.771  73.766  1.00 57.62           C
ATOM   6315  OH   TYR C  53      51.761  28.224  75.033  1.00 58.97           O
ATOM   6316  CE2  TYR C  53      51.140  27.953  72.740  1.00 56.80           C
ATOM   6317  CD2  TYR C  53      51.442  27.494  71.459  1.00 54.89           C
```

FIGURE 3HHHHH

```
ATOM   6318  C    TYR C  53      52.885  23.938  70.484  1.00 49.81           C
ATOM   6319  O    TYR C  53      54.018  23.455  70.417  1.00 50.68           O
ATOM   6320  N    ARG C  54      52.010  23.609  71.430  1.00 51.26           N
ATOM   6321  CA   ARG C  54      52.317  22.628  72.464  1.00 54.81           C
ATOM   6322  CB   ARG C  54      51.327  22.747  73.630  1.00 57.60           C
ATOM   6323  CG   ARG C  54      51.684  23.827  74.646  1.00 60.35           C
ATOM   6324  CD   ARG C  54      50.942  23.711  75.972  1.00 62.60           C
ATOM   6325  NE   ARG C  54      49.543  24.122  75.851  1.00 65.21           N
ATOM   6326  CZ   ARG C  54      48.543  23.636  76.580  1.00 67.23           C
ATOM   6327  NH1  ARG C  54      48.767  22.711  77.507  1.00 66.60           N
ATOM   6328  NH2  ARG C  54      47.308  24.081  76.384  1.00 67.60           N
ATOM   6329  C    ARG C  54      52.322  21.201  71.916  1.00 54.61           C
ATOM   6330  O    ARG C  54      52.825  20.287  72.572  1.00 56.11           O
ATOM   6331  N    LYS C  55      51.779  21.022  70.711  1.00 52.10           N
ATOM   6332  CA   LYS C  55      51.614  19.694  70.117  1.00 50.68           C
ATOM   6333  CB   LYS C  55      50.138  19.446  69.777  1.00 54.70           C
ATOM   6334  CG   LYS C  55      49.213  19.410  70.995  1.00 58.26           C
ATOM   6335  CD   LYS C  55      47.750  19.276  70.590  1.00 61.32           C
ATOM   6336  CE   LYS C  55      47.260  17.840  70.750  1.00 65.02           C
ATOM   6337  NZ   LYS C  55      45.782  17.761  70.948  1.00 66.27           N
ATOM   6338  C    LYS C  55      52.497  19.438  68.886  1.00 49.38           C
ATOM   6339  O    LYS C  55      52.467  18.345  68.311  1.00 46.69           O
ATOM   6340  N    MET C  56      53.279  20.439  68.486  1.00 46.45           N
ATOM   6341  CA   MET C  56      54.156  20.306  67.322  1.00 44.45           C
ATOM   6342  CB   MET C  56      53.441  20.763  66.040  1.00 44.89           C
ATOM   6343  CG   MET C  56      53.118  22.246  65.973  1.00 45.73           C
ATOM   6344  SD   MET C  56      52.048  22.667  64.581  1.00 47.72           S
ATOM   6345  CE   MET C  56      51.731  24.393  64.947  1.00 47.60           C
ATOM   6346  C    MET C  56      55.489  21.033  67.494  1.00 43.77           C
ATOM   6347  O    MET C  56      55.589  22.001  68.253  1.00 42.83           O
ATOM   6348  N    GLU C  57      56.509  20.553  66.787  1.00 41.61           N
ATOM   6349  CA   GLU C  57      57.812  21.202  66.785  1.00 43.07           C
ATOM   6350  CB   GLU C  57      58.921  20.188  66.498  1.00 46.03           C
ATOM   6351  CG   GLU C  57      59.729  19.806  67.727  1.00 53.50           C
ATOM   6352  CD   GLU C  57      60.089  18.333  67.754  1.00 57.45           C
ATOM   6353  OE1  GLU C  57      61.157  17.973  67.214  1.00 57.77           O
ATOM   6354  OE2  GLU C  57      59.306  17.537  68.317  1.00 60.20           O
ATOM   6355  C    GLU C  57      57.830  22.330  65.758  1.00 43.35           C
ATOM   6356  O    GLU C  57      57.587  22.103  64.569  1.00 43.55           O
ATOM   6357  N    ILE C  58      58.103  23.544  66.229  1.00 39.14           N
ATOM   6358  CA   ILE C  58      58.148  24.719  65.365  1.00 41.47           C
ATOM   6359  CB   ILE C  58      57.393  25.912  66.013  1.00 43.70           C
ATOM   6360  CG1  ILE C  58      55.884  25.637  66.047  1.00 43.45           C
ATOM   6361  CD1  ILE C  58      55.084  26.647  66.849  1.00 42.96           C
ATOM   6362  CG2  ILE C  58      57.693  27.230  65.273  1.00 44.09           C
ATOM   6363  C    ILE C  58      59.599  25.078  65.051  1.00 44.28           C
ATOM   6364  O    ILE C  58      60.413  25.264  65.963  1.00 41.74           O
ATOM   6365  N    TYR C  59      59.912  25.162  63.758  1.00 40.49           N
ATOM   6366  CA   TYR C  59      61.258  25.498  63.301  1.00 42.50           C
ATOM   6367  CB   TYR C  59      61.832  24.365  62.453  1.00 44.89           C
ATOM   6368  CG   TYR C  59      62.117  23.096  63.216  1.00 49.36           C
ATOM   6369  CD1  TYR C  59      63.307  22.940  63.931  1.00 51.41           C
ATOM   6370  CE1  TYR C  59      63.574  21.769  64.632  1.00 52.77           C
ATOM   6371  CZ   TYR C  59      62.647  20.740  64.619  1.00 53.53           C
ATOM   6372  OH   TYR C  59      62.907  19.578  65.308  1.00 54.32           O
ATOM   6373  CE2  TYR C  59      61.460  20.871  63.917  1.00 52.44           C
ATOM   6374  CD2  TYR C  59      61.203  22.044  63.219  1.00 51.40           C
```

FIGURE 3IIIII

```
ATOM   6375  C    TYR C  59      61.285  26.783  62.489  1.00 41.32           C
ATOM   6376  O    TYR C  59      60.362  27.063  61.727  1.00 39.22           O
ATOM   6377  N    ARG C  60      62.350  27.560  62.662  1.00 44.04           N
ATOM   6378  CA   ARG C  60      62.643  28.679  61.773  1.00 47.42           C
ATOM   6379  CB   ARG C  60      63.589  29.679  62.448  1.00 51.21           C
ATOM   6380  CG   ARG C  60      63.520  31.098  61.900  1.00 55.96           C
ATOM   6381  CD   ARG C  60      64.128  32.151  62.825  1.00 60.59           C
ATOM   6382  NE   ARG C  60      63.878  33.518  62.360  1.00 66.91           N
ATOM   6383  CZ   ARG C  60      63.128  34.417  63.001  1.00 70.06           C
ATOM   6384  NH1  ARG C  60      62.535  34.111  64.149  1.00 70.65           N
ATOM   6385  NH2  ARG C  60      62.966  35.633  62.491  1.00 70.49           N
ATOM   6386  C    ARG C  60      63.282  28.090  60.515  1.00 46.20           C
ATOM   6387  O    ARG C  60      64.248  27.328  60.612  1.00 44.53           O
ATOM   6388  N    PRO C  61      62.736  28.405  59.342  1.00 44.69           N
ATOM   6389  CA   PRO C  61      63.274  27.860  58.095  1.00 45.23           C
ATOM   6390  CB   PRO C  61      62.202  28.227  57.059  1.00 44.63           C
ATOM   6391  CG   PRO C  61      61.526  29.427  57.611  1.00 46.26           C
ATOM   6392  CD   PRO C  61      61.581  29.289  59.102  1.00 45.35           C
ATOM   6393  C    PRO C  61      64.607  28.510  57.746  1.00 41.77           C
ATOM   6394  O    PRO C  61      64.785  29.709  57.967  1.00 40.22           O
ATOM   6395  N    HIS C  62      65.535  27.713  57.232  1.00 44.44           N
ATOM   6396  CA   HIS C  62      66.747  28.246  56.629  1.00 46.90           C
ATOM   6397  CB   HIS C  62      67.725  27.110  56.293  1.00 52.30           C
ATOM   6398  CG   HIS C  62      67.319  26.287  55.107  1.00 55.86           C
ATOM   6399  ND1  HIS C  62      66.285  25.376  55.150  1.00 57.69           N
ATOM   6400  CE1  HIS C  62      66.155  24.802  53.967  1.00 56.50           C
ATOM   6401  NE2  HIS C  62      67.066  25.309  53.157  1.00 57.96           N
ATOM   6402  CD2  HIS C  62      67.808  26.239  53.845  1.00 57.75           C
ATOM   6403  C    HIS C  62      66.366  29.017  55.365  1.00 43.92           C
ATOM   6404  O    HIS C  62      65.308  28.778  54.776  1.00 43.41           O
ATOM   6405  N    LYS C  63      67.214  29.958  54.969  1.00 38.18           N
ATOM   6406  CA   LYS C  63      67.066  30.621  53.681  1.00 36.63           C
ATOM   6407  CB   LYS C  63      67.856  31.927  53.659  1.00 36.70           C
ATOM   6408  CG   LYS C  63      67.122  33.125  54.213  1.00 41.96           C
ATOM   6409  CD   LYS C  63      67.910  34.402  53.941  1.00 45.82           C
ATOM   6410  CE   LYS C  63      67.533  35.507  54.916  1.00 50.81           C
ATOM   6411  NZ   LYS C  63      66.315  36.252  54.479  1.00 55.25           N
ATOM   6412  C    LYS C  63      67.602  29.687  52.604  1.00 33.91           C
ATOM   6413  O    LYS C  63      68.745  29.225  52.692  1.00 33.93           O
ATOM   6414  N    ALA C  64      66.777  29.393  51.601  1.00 28.88           N
ATOM   6415  CA   ALA C  64      67.219  28.602  50.455  1.00 26.59           C
ATOM   6416  CB   ALA C  64      66.030  28.225  49.589  1.00 28.08           C
ATOM   6417  C    ALA C  64      68.218  29.434  49.658  1.00 25.42           C
ATOM   6418  O    ALA C  64      67.982  30.613  49.419  1.00 26.09           O
ATOM   6419  N    THR C  65      69.340  28.840  49.260  1.00 23.36           N
ATOM   6420  CA   THR C  65      70.319  29.586  48.472  1.00 23.80           C
ATOM   6421  CB   THR C  65      71.709  28.917  48.495  1.00 25.41           C
ATOM   6422  OG1  THR C  65      71.609  27.587  47.969  1.00 28.02           O
ATOM   6423  CG2  THR C  65      72.195  28.716  49.930  1.00 30.91           C
ATOM   6424  C    THR C  65      69.846  29.731  47.031  1.00 24.23           C
ATOM   6425  O    THR C  65      69.023  28.938  46.559  1.00 21.40           O
ATOM   6426  N    ALA C  66      70.378  30.742  46.347  1.00 19.59           N
ATOM   6427  CA   ALA C  66      70.196  30.908  44.911  1.00 22.36           C
ATOM   6428  CB   ALA C  66      70.956  32.128  44.421  1.00 23.82           C
ATOM   6429  C    ALA C  66      70.648  29.661  44.146  1.00 23.33           C
ATOM   6430  O    ALA C  66      70.014  29.275  43.170  1.00 21.16           O
ATOM   6431  N    GLU C  67      71.748  29.049  44.591  1.00 23.37           N
```

FIGURE 3JJJJJ

```
ATOM   6432  CA   GLU C  67      72.266  27.817  43.988  1.00 27.01           C
ATOM   6433  CB   GLU C  67      73.550  27.367  44.695  1.00 31.52           C
ATOM   6434  CG   GLU C  67      74.790  28.169  44.327  1.00 32.63           C
ATOM   6435  CD   GLU C  67      74.897  29.491  45.076  1.00 40.00           C
ATOM   6436  OE1  GLU C  67      75.604  30.392  44.578  1.00 42.09           O
ATOM   6437  OE2  GLU C  67      74.279  29.640  46.155  1.00 40.86           O
ATOM   6438  C    GLU C  67      71.229  26.695  44.049  1.00 25.65           C
ATOM   6439  O    GLU C  67      70.984  26.016  43.049  1.00 23.96           O
ATOM   6440  N    GLU C  68      70.631  26.513  45.225  1.00 20.71           N
ATOM   6441  CA   GLU C  68      69.571  25.523  45.426  1.00 24.52           C
ATOM   6442  CB   GLU C  68      69.142  25.488  46.901  1.00 30.41           C
ATOM   6443  CG   GLU C  68      67.685  25.115  47.173  1.00 40.89           C
ATOM   6444  CD   GLU C  68      67.430  23.615  47.170  1.00 48.71           C
ATOM   6445  OE1  GLU C  68      68.104  22.885  47.932  1.00 51.78           O
ATOM   6446  OE2  GLU C  68      66.541  23.162  46.411  1.00 48.39           O
ATOM   6447  C    GLU C  68      68.380  25.787  44.495  1.00 21.05           C
ATOM   6448  O    GLU C  68      67.797  24.855  43.948  1.00 19.99           O
ATOM   6449  N    MET C  69      68.032  27.057  44.301  1.00 20.34           N
ATOM   6450  CA   MET C  69      66.933  27.406  43.400  1.00 21.76           C
ATOM   6451  CB   MET C  69      66.618  28.897  43.477  1.00 19.55           C
ATOM   6452  CG   MET C  69      65.978  29.302  44.790  1.00 22.07           C
ATOM   6453  SD   MET C  69      65.871  31.083  44.874  1.00 23.24           S
ATOM   6454  CE   MET C  69      65.345  31.262  46.535  1.00 22.96           C
ATOM   6455  C    MET C  69      67.210  27.006  41.953  1.00 21.11           C
ATOM   6456  O    MET C  69      66.269  26.707  41.211  1.00 20.14           O
ATOM   6457  N    THR C  70      68.489  26.992  41.563  1.00 18.33           N
ATOM   6458  CA   THR C  70      68.866  26.631  40.189  1.00 17.88           C
ATOM   6459  CB   THR C  70      70.219  27.269  39.728  1.00 21.39           C
ATOM   6460  OG1  THR C  70      71.298  26.812  40.555  1.00 22.33           O
ATOM   6461  CG2  THR C  70      70.202  28.774  39.908  1.00 19.52           C
ATOM   6462  C    THR C  70      68.850  25.125  39.935  1.00 21.28           C
ATOM   6463  O    THR C  70      69.142  24.679  38.825  1.00 23.13           O
ATOM   6464  N    LYS C  71      68.495  24.348  40.956  1.00 20.33           N
ATOM   6465  CA   LYS C  71      68.206  22.930  40.763  1.00 21.20           C
ATOM   6466  CB   LYS C  71      67.866  22.250  42.089  1.00 22.84           C
ATOM   6467  CG   LYS C  71      69.078  21.998  42.991  1.00 27.11           C
ATOM   6468  CD   LYS C  71      68.681  21.190  44.218  1.00 29.87           C
ATOM   6469  CE   LYS C  71      69.835  21.067  45.211  1.00 34.62           C
ATOM   6470  NZ   LYS C  71      69.437  20.284  46.423  1.00 38.38           N
ATOM   6471  C    LYS C  71      67.049  22.800  39.786  1.00 21.09           C
ATOM   6472  O    LYS C  71      66.932  21.808  39.065  1.00 21.12           O
ATOM   6473  N    TYR C  72      66.200  23.821  39.756  1.00 17.81           N
ATOM   6474  CA   TYR C  72      65.091  23.847  38.820  1.00 17.96           C
ATOM   6475  CB   TYR C  72      63.750  23.759  39.558  1.00 17.45           C
ATOM   6476  CG   TYR C  72      62.593  23.739  38.594  1.00 19.83           C
ATOM   6477  CD1  TYR C  72      61.664  24.779  38.557  1.00 21.84           C
ATOM   6478  CE1  TYR C  72      60.611  24.757  37.642  1.00 23.48           C
ATOM   6479  CZ   TYR C  72      60.506  23.691  36.758  1.00 24.12           C
ATOM   6480  OH   TYR C  72      59.487  23.626  35.834  1.00 29.61           O
ATOM   6481  CE2  TYR C  72      61.428  22.665  36.781  1.00 25.40           C
ATOM   6482  CD2  TYR C  72      62.464  22.699  37.682  1.00 19.37           C
ATOM   6483  C    TYR C  72      65.112  25.072  37.908  1.00 19.91           C
ATOM   6484  O    TYR C  72      65.071  24.945  36.684  1.00 19.47           O
ATOM   6485  N    HIS C  73      65.175  26.257  38.509  1.00 18.51           N
ATOM   6486  CA   HIS C  73      65.073  27.497  37.751  1.00 17.37           C
ATOM   6487  CB   HIS C  73      64.720  28.650  38.689  1.00 18.17           C
ATOM   6488  CG   HIS C  73      63.358  28.529  39.292  1.00 17.68           C
```

FIGURE 3KKKKK

```
ATOM   6489  ND1 HIS C  73      62.212  28.885  38.617  1.00 16.57           N
ATOM   6490  CE1 HIS C  73      61.163  28.668  39.391  1.00 18.20           C
ATOM   6491  NE2 HIS C  73      61.589  28.180  40.542  1.00 18.06           N
ATOM   6492  CD2 HIS C  73      62.960  28.086  40.507  1.00 15.45           C
ATOM   6493  C   HIS C  73      66.356  27.813  37.002  1.00 21.42           C
ATOM   6494  O   HIS C  73      67.436  27.392  37.411  1.00 21.09           O
ATOM   6495  N   SER C  74      66.240  28.554  35.904  1.00 19.64           N
ATOM   6496  CA  SER C  74      67.435  28.946  35.155  1.00 22.05           C
ATOM   6497  CB  SER C  74      67.084  29.465  33.758  1.00 25.78           C
ATOM   6498  OG  SER C  74      66.548  30.771  33.799  1.00 26.55           O
ATOM   6499  C   SER C  74      68.267  29.965  35.930  1.00 22.28           C
ATOM   6500  O   SER C  74      67.726  30.779  36.689  1.00 21.78           O
ATOM   6501  N   ASP C  75      69.586  29.900  35.748  1.00 19.81           N
ATOM   6502  CA  ASP C  75      70.513  30.835  36.396  1.00 20.71           C
ATOM   6503  CB  ASP C  75      71.953  30.547  35.979  1.00 22.27           C
ATOM   6504  CG  ASP C  75      72.366  29.150  36.300  1.00 24.90           C
ATOM   6505  OD1 ASP C  75      73.224  28.971  37.195  1.00 23.94           O
ATOM   6506  OD2 ASP C  75      71.872  28.170  35.708  1.00 27.54           O
ATOM   6507  C   ASP C  75      70.202  32.289  36.074  1.00 21.42           C
ATOM   6508  O   ASP C  75      70.279  33.144  36.957  1.00 21.96           O
ATOM   6509  N   GLU C  76      69.884  32.552  34.806  1.00 20.51           N
ATOM   6510  CA  GLU C  76      69.586  33.904  34.325  1.00 23.83           C
ATOM   6511  CB  GLU C  76      69.357  33.893  32.806  1.00 31.92           C
ATOM   6512  CG  GLU C  76      70.357  33.045  32.012  1.00 40.28           C
ATOM   6513  CD  GLU C  76      69.887  31.604  31.789  1.00 45.03           C
ATOM   6514  OE1 GLU C  76      69.107  31.369  30.835  1.00 48.62           O
ATOM   6515  OE2 GLU C  76      70.299  30.699  32.561  1.00 37.28           O
ATOM   6516  C   GLU C  76      68.369  34.487  35.058  1.00 22.57           C
ATOM   6517  O   GLU C  76      68.358  35.665  35.435  1.00 21.69           O
ATOM   6518  N   TYR C  77      67.353  33.650  35.263  1.00 19.40           N
ATOM   6519  CA  TYR C  77      66.144  34.065  35.969  1.00 20.14           C
ATOM   6520  CB  TYR C  77      65.028  33.023  35.784  1.00 18.77           C
ATOM   6521  CG  TYR C  77      63.773  33.315  36.579  1.00 19.44           C
ATOM   6522  CD1 TYR C  77      63.127  34.550  36.472  1.00 21.82           C
ATOM   6523  CE1 TYR C  77      61.981  34.832  37.211  1.00 22.10           C
ATOM   6524  CZ  TYR C  77      61.465  33.866  38.065  1.00 22.25           C
ATOM   6525  OH  TYR C  77      60.331  34.145  38.793  1.00 22.05           O
ATOM   6526  CE2 TYR C  77      62.084  32.627  38.186  1.00 21.22           C
ATOM   6527  CD2 TYR C  77      63.241  32.361  37.448  1.00 18.33           C
ATOM   6528  C   TYR C  77      66.427  34.325  37.451  1.00 19.84           C
ATOM   6529  O   TYR C  77      65.987  35.335  38.004  1.00 21.50           O
ATOM   6530  N   ILE C  78      67.177  33.425  38.091  1.00 17.40           N
ATOM   6531  CA  ILE C  78      67.494  33.582  39.508  1.00 18.39           C
ATOM   6532  CB  ILE C  78      68.080  32.265  40.088  1.00 17.35           C
ATOM   6533  CG1 ILE C  78      67.012  31.157  40.098  1.00 20.32           C
ATOM   6534  CD1 ILE C  78      65.675  31.547  40.768  1.00 16.87           C
ATOM   6535  CG2 ILE C  78      68.657  32.479  41.482  1.00 19.10           C
ATOM   6536  C   ILE C  78      68.426  34.778  39.742  1.00 19.09           C
ATOM   6537  O   ILE C  78      68.282  35.495  40.733  1.00 21.49           O
ATOM   6538  N   LYS C  79      69.364  34.987  38.819  1.00 24.95           N
ATOM   6539  CA  LYS C  79      70.268  36.145  38.856  1.00 24.72           C
ATOM   6540  CB  LYS C  79      71.270  36.063  37.695  1.00 29.49           C
ATOM   6541  CG  LYS C  79      72.123  37.312  37.460  1.00 38.40           C
ATOM   6542  CD  LYS C  79      73.539  36.955  36.992  1.00 43.36           C
ATOM   6543  CE  LYS C  79      73.547  36.355  35.585  1.00 45.63           C
ATOM   6544  NZ  LYS C  79      73.681  34.870  35.616  1.00 48.38           N
ATOM   6545  C   LYS C  79      69.472  37.450  38.793  1.00 23.37           C
```

FIGURE 3LLLLL

```
ATOM   6546  O    LYS C  79      69.745  38.398  39.544  1.00 23.10           O
ATOM   6547  N    PHE C  80      68.487  37.480  37.900  1.00 22.63           N
ATOM   6548  CA   PHE C  80      67.554  38.606  37.785  1.00 24.07           C
ATOM   6549  CB   PHE C  80      66.614  38.386  36.591  1.00 24.48           C
ATOM   6550  CG   PHE C  80      65.436  39.327  36.546  1.00 27.52           C
ATOM   6551  CD1  PHE C  80      64.202  38.946  37.071  1.00 26.57           C
ATOM   6552  CE1  PHE C  80      63.107  39.812  37.028  1.00 29.04           C
ATOM   6553  CZ   PHE C  80      63.235  41.071  36.439  1.00 29.31           C
ATOM   6554  CE2  PHE C  80      64.457  41.459  35.901  1.00 27.52           C
ATOM   6555  CD2  PHE C  80      65.553  40.585  35.956  1.00 27.71           C
ATOM   6556  C    PHE C  80      66.764  38.819  39.079  1.00 23.77           C
ATOM   6557  O    PHE C  80      66.677  39.948  39.573  1.00 25.74           O
ATOM   6558  N    LEU C  81      66.196  37.745  39.635  1.00 20.26           N
ATOM   6559  CA   LEU C  81      65.402  37.855  40.868  1.00 21.83           C
ATOM   6560  CB   LEU C  81      64.806  36.504  41.290  1.00 22.09           C
ATOM   6561  CG   LEU C  81      63.611  35.934  40.523  1.00 22.29           C
ATOM   6562  CD1  LEU C  81      63.153  34.634  41.194  1.00 19.50           C
ATOM   6563  CD2  LEU C  81      62.451  36.932  40.422  1.00 22.44           C
ATOM   6564  C    LEU C  81      66.221  38.420  42.023  1.00 23.90           C
ATOM   6565  O    LEU C  81      65.703  39.175  42.851  1.00 22.21           O
ATOM   6566  N    ARG C  82      67.499  38.052  42.078  1.00 22.02           N
ATOM   6567  CA   ARG C  82      68.365  38.515  43.156  1.00 28.38           C
ATOM   6568  CB   ARG C  82      69.488  37.497  43.427  1.00 32.85           C
ATOM   6569  CG   ARG C  82      70.806  37.769  42.737  1.00 41.43           C
ATOM   6570  CD   ARG C  82      72.018  37.491  43.615  1.00 47.90           C
ATOM   6571  NE   ARG C  82      72.472  36.111  43.478  1.00 47.36           N
ATOM   6572  CZ   ARG C  82      73.324  35.505  44.300  1.00 47.23           C
ATOM   6573  NH1  ARG C  82      73.670  34.245  44.074  1.00 44.83           N
ATOM   6574  NH2  ARG C  82      73.832  36.146  45.345  1.00 45.37           N
ATOM   6575  C    ARG C  82      68.900  39.933  42.911  1.00 26.12           C
ATOM   6576  O    ARG C  82      69.382  40.582  43.839  1.00 30.78           O
ATOM   6577  N    SER C  83      68.775  40.411  41.674  1.00 25.30           N
ATOM   6578  CA   SER C  83      69.332  41.707  41.262  1.00 29.28           C
ATOM   6579  CB   SER C  83      70.016  41.584  39.896  1.00 27.16           C
ATOM   6580  OG   SER C  83      71.103  40.686  39.960  1.00 34.55           O
ATOM   6581  C    SER C  83      68.299  42.823  41.175  1.00 30.34           C
ATOM   6582  O    SER C  83      68.629  43.993  41.382  1.00 29.97           O
ATOM   6583  N    ILE C  84      67.059  42.464  40.850  1.00 30.87           N
ATOM   6584  CA   ILE C  84      66.016  43.451  40.580  1.00 30.79           C
ATOM   6585  CB   ILE C  84      64.834  42.816  39.778  1.00 30.97           C
ATOM   6586  CG1  ILE C  84      63.932  43.901  39.175  1.00 31.67           C
ATOM   6587  CD1  ILE C  84      64.450  44.502  37.898  1.00 30.59           C
ATOM   6588  CG2  ILE C  84      64.025  41.852  40.641  1.00 32.10           C
ATOM   6589  C    ILE C  84      65.538  44.185  41.835  1.00 31.63           C
ATOM   6590  O    ILE C  84      65.293  43.574  42.876  1.00 28.09           O
ATOM   6591  N    ARG C  85      65.425  45.508  41.714  1.00 32.91           N
ATOM   6592  CA   ARG C  85      65.001  46.376  42.808  1.00 35.61           C
ATOM   6593  CB   ARG C  85      66.214  47.082  43.420  1.00 39.52           C
ATOM   6594  CG   ARG C  85      67.101  46.195  44.279  1.00 46.31           C
ATOM   6595  CD   ARG C  85      68.398  46.854  44.705  1.00 54.25           C
ATOM   6596  NE   ARG C  85      69.199  47.299  43.561  1.00 61.12           N
ATOM   6597  CZ   ARG C  85      69.646  48.542  43.383  1.00 64.18           C
ATOM   6598  NH1  ARG C  85      70.367  48.839  42.308  1.00 64.22           N
ATOM   6599  NH2  ARG C  85      69.383  49.489  44.277  1.00 65.15           N
ATOM   6600  C    ARG C  85      64.016  47.419  42.272  1.00 34.69           C
ATOM   6601  O    ARG C  85      64.057  47.750  41.084  1.00 33.06           O
ATOM   6602  N    PRO C  86      63.127  47.932  43.125  1.00 36.52           N
```

FIGURE 3MMMMM

```
ATOM   6603  CA  PRO C  86      62.178  48.971  42.699  1.00 40.41           C
ATOM   6604  CB  PRO C  86      61.553  49.427  44.019  1.00 40.34           C
ATOM   6605  CG  PRO C  86      61.603  48.206  44.874  1.00 38.74           C
ATOM   6606  CD  PRO C  86      62.926  47.556  44.539  1.00 36.72           C
ATOM   6607  C   PRO C  86      62.849  50.143  41.974  1.00 42.31           C
ATOM   6608  O   PRO C  86      62.270  50.662  41.021  1.00 46.05           O
ATOM   6609  N   ASP C  87      64.057  50.516  42.394  1.00 47.22           N
ATOM   6610  CA  ASP C  87      64.751  51.681  41.837  1.00 51.71           C
ATOM   6611  CB  ASP C  87      65.624  52.360  42.903  1.00 56.62           C
ATOM   6612  CG  ASP C  87      66.658  51.424  43.500  1.00 61.71           C
ATOM   6613  OD1 ASP C  87      66.540  51.096  44.701  1.00 63.47           O
ATOM   6614  OD2 ASP C  87      67.624  50.972  42.850  1.00 64.75           O
ATOM   6615  C   ASP C  87      65.568  51.427  40.560  1.00 50.34           C
ATOM   6616  O   ASP C  87      65.912  52.380  39.854  1.00 51.47           O
ATOM   6617  N   ASN C  88      65.884  50.166  40.262  1.00 45.29           N
ATOM   6618  CA  ASN C  88      66.677  49.855  39.067  1.00 41.09           C
ATOM   6619  CB  ASN C  88      67.933  49.029  39.409  1.00 40.26           C
ATOM   6620  CG  ASN C  88      67.615  47.604  39.868  1.00 42.84           C
ATOM   6621  OD1 ASN C  88      66.504  47.099  39.683  1.00 39.64           O
ATOM   6622  ND2 ASN C  88      68.606  46.950  40.469  1.00 38.02           N
ATOM   6623  C   ASN C  88      65.882  49.239  37.915  1.00 41.91           C
ATOM   6624  O   ASN C  88      66.459  48.762  36.939  1.00 41.88           O
ATOM   6625  N   MET C  89      64.558  49.270  38.039  1.00 44.04           N
ATOM   6626  CA  MET C  89      63.645  48.647  37.081  1.00 46.28           C
ATOM   6627  CB  MET C  89      62.202  48.896  37.510  1.00 47.51           C
ATOM   6628  CG  MET C  89      61.578  47.742  38.261  1.00 48.49           C
ATOM   6629  SD  MET C  89      60.040  48.213  39.066  1.00 47.57           S
ATOM   6630  CE  MET C  89      59.050  48.771  37.665  1.00 51.37           C
ATOM   6631  C   MET C  89      63.825  49.091  35.630  1.00 49.09           C
ATOM   6632  O   MET C  89      63.721  48.275  34.709  1.00 48.97           O
ATOM   6633  N   SER C  90      64.089  50.384  35.437  1.00 52.40           N
ATOM   6634  CA  SER C  90      64.284  50.968  34.107  1.00 55.02           C
ATOM   6635  CB  SER C  90      64.495  52.483  34.214  1.00 58.10           C
ATOM   6636  OG  SER C  90      65.169  52.831  35.415  1.00 59.72           O
ATOM   6637  C   SER C  90      65.447  50.323  33.348  1.00 55.52           C
ATOM   6638  O   SER C  90      65.411  50.202  32.123  1.00 54.90           O
ATOM   6639  N   GLU C  91      66.465  49.903  34.094  1.00 57.12           N
ATOM   6640  CA  GLU C  91      67.644  49.247  33.536  1.00 58.98           C
ATOM   6641  CB  GLU C  91      68.776  49.264  34.570  1.00 64.10           C
ATOM   6642  CG  GLU C  91      70.177  49.130  33.995  1.00 71.27           C
ATOM   6643  CD  GLU C  91      70.907  47.914  34.534  1.00 75.28           C
ATOM   6644  OE1 GLU C  91      71.128  46.957  33.758  1.00 77.15           O
ATOM   6645  OE2 GLU C  91      71.259  47.913  35.736  1.00 77.13           O
ATOM   6646  C   GLU C  91      67.362  47.809  33.078  1.00 56.54           C
ATOM   6647  O   GLU C  91      68.063  47.287  32.209  1.00 54.98           O
ATOM   6648  N   TYR C  92      66.333  47.186  33.657  1.00 53.13           N
ATOM   6649  CA  TYR C  92      66.037  45.769  33.419  1.00 49.62           C
ATOM   6650  CB  TYR C  92      66.002  45.013  34.751  1.00 49.52           C
ATOM   6651  CG  TYR C  92      67.350  44.808  35.398  1.00 52.89           C
ATOM   6652  CD1 TYR C  92      67.789  45.651  36.422  1.00 53.13           C
ATOM   6653  CE1 TYR C  92      69.033  45.465  37.025  1.00 55.88           C
ATOM   6654  CZ  TYR C  92      69.849  44.424  36.604  1.00 57.29           C
ATOM   6655  OH  TYR C  92      71.080  44.232  37.191  1.00 56.51           O
ATOM   6656  CE2 TYR C  92      69.432  43.571  35.592  1.00 56.80           C
ATOM   6657  CD2 TYR C  92      68.187  43.766  34.997  1.00 54.86           C
ATOM   6658  C   TYR C  92      64.729  45.513  32.661  1.00 46.60           C
ATOM   6659  O   TYR C  92      64.146  44.431  32.779  1.00 41.05           O
```

FIGURE 3NNNNN

```
ATOM   6660  N    SER C  93      64.280  46.492  31.874  1.00 42.97           N
ATOM   6661  CA   SER C  93      62.977  46.410  31.208  1.00 42.92           C
ATOM   6662  CB   SER C  93      62.645  47.726  30.494  1.00 44.04           C
ATOM   6663  OG   SER C  93      63.253  47.790  29.216  1.00 45.92           O
ATOM   6664  C    SER C  93      62.837  45.209  30.254  1.00 43.21           C
ATOM   6665  O    SER C  93      61.770  44.593  30.177  1.00 41.98           O
ATOM   6666  N    LYS C  94      63.912  44.882  29.539  1.00 41.80           N
ATOM   6667  CA   LYS C  94      63.910  43.739  28.623  1.00 43.81           C
ATOM   6668  CB   LYS C  94      65.139  43.771  27.707  1.00 48.40           C
ATOM   6669  CG   LYS C  94      64.970  44.647  26.472  1.00 54.62           C
ATOM   6670  CD   LYS C  94      64.697  43.814  25.223  1.00 58.11           C
ATOM   6671  CE   LYS C  94      64.154  44.677  24.091  1.00 61.27           C
ATOM   6672  NZ   LYS C  94      62.674  44.856  24.180  1.00 61.18           N
ATOM   6673  C    LYS C  94      63.845  42.406  29.374  1.00 40.97           C
ATOM   6674  O    LYS C  94      63.180  41.460  28.933  1.00 36.46           O
ATOM   6675  N    GLN C  95      64.533  42.346  30.510  1.00 37.80           N
ATOM   6676  CA   GLN C  95      64.551  41.147  31.343  1.00 36.95           C
ATOM   6677  CB  BGLN C  95      65.711  41.193  32.342  0.35 35.46           C
ATOM   6678  CB  AGLN C  95      65.689  41.225  32.363  0.65 38.79           C
ATOM   6679  CG  BGLN C  95      66.917  40.355  31.921  0.35 36.14           C
ATOM   6680  CG  AGLN C  95      67.082  41.017  31.773  0.65 43.69           C
ATOM   6681  CD  BGLN C  95      68.146  40.597  32.782  0.35 35.55           C
ATOM   6682  CD  AGLN C  95      67.647  42.272  31.124  0.65 46.90           C
ATOM   6683  OE1 BGLN C  95      68.149  40.290  33.974  0.35 34.90           O
ATOM   6684  OE1 AGLN C  95      67.744  43.321  31.763  0.65 48.19           O
ATOM   6685  NE2 BGLN C  95      69.196  41.141  32.177  0.35 36.27           N
ATOM   6686  NE2 AGLN C  95      58.021  42.165  29.853  0.65 48.36           N
ATOM   6687  C    GLN C  95      63.211  40.966  32.059  1.00 32.27           C
ATOM   6688  O    GLN C  95      62.747  39.848  32.253  1.00 28.90           O
ATOM   6689  N    MET C  96      62.584  42.078  32.423  1.00 28.84           N
ATOM   6690  CA   MET C  96      61.261  42.053  33.034  1.00 34.15           C
ATOM   6691  CB   MET C  96      60.851  43.460  33.449  1.00 36.61           C
ATOM   6692  CG   MET C  96      61.429  43.880  34.791  1.00 40.23           C
ATOM   6693  SD   MET C  96      61.165  45.625  35.117  1.00 43.93           S
ATOM   6694  CE   MET C  96      59.502  45.596  35.750  1.00 43.59           C
ATOM   6695  C    MET C  96      60.207  41.437  32.112  1.00 33.53           C
ATOM   6696  O    MET C  96      59.340  40.689  32.568  1.00 32.97           O
ATOM   6697  N    GLN C  97      60.288  41.751  30.821  1.00 34.13           N
ATOM   6698  CA   GLN C  97      59.425  41.117  29.827  1.00 34.96           C
ATOM   6699  CB   GLN C  97      59.507  41.830  28.471  1.00 37.15           C
ATOM   6700  CG   GLN C  97      58.472  41.319  27.452  1.00 41.82           C
ATOM   6701  CD   GLN C  97      58.457  42.106  26.152  1.00 46.05           C
ATOM   6702  OE1  GLN C  97      58.649  43.326  26.149  1.00 47.37           O
ATOM   6703  NE2  GLN C  97      58.223  41.410  25.042  1.00 43.78           N
ATOM   6704  C    GLN C  97      59.782  39.643  29.666  1.00 31.93           C
ATOM   6705  O    GLN C  97      58.893  38.793  29.586  1.00 32.40           O
ATOM   6706  N    ARG C  98      61.080  39.345  29.619  1.00 28.77           N
ATOM   6707  CA   ARG C  98      61.551  37.964  29.487  1.00 29.76           C
ATOM   6708  CB   ARG C  98      63.080  37.914  29.425  1.00 31.45           C
ATOM   6709  CG   ARG C  98      63.632  36.607  28.871  1.00 38.28           C
ATOM   6710  CD   ARG C  98      65.134  36.422  29.061  1.00 44.58           C
ATOM   6711  NE   ARG C  98      65.890  36.659  27.827  1.00 53.60           N
ATOM   6712  CZ   ARG C  98      66.039  35.777  26.835  1.00 56.33           C
ATOM   6713  NH1  ARG C  98      66.751  36.103  25.765  1.00 59.20           N
ATOM   6714  NH2  ARG C  98      65.484  34.572  26.900  1.00 57.31           N
ATOM   6715  C    ARG C  98      61.053  37.063  30.621  1.00 28.22           C
ATOM   6716  O    ARG C  98      60.673  35.918  30.387  1.00 31.67           O
```

FIGURE 300000

```
ATOM   6717  N   PHE C  99      61.064  37.594  31.840  1.00 26.76           N
ATOM   6718  CA  PHE C  99      60.810  36.801  33.044  1.00 25.35           C
ATOM   6719  CB  PHE C  99      61.912  37.059  34.085  1.00 23.18           C
ATOM   6720  CG  PHE C  99      63.309  36.704  33.603  1.00 27.15           C
ATOM   6721  CD1 PHE C  99      63.569  35.470  33.004  1.00 27.70           C
ATOM   6722  CE1 PHE C  99      64.860  35.139  32.559  1.00 30.07           C
ATOM   6723  CZ  PHE C  99      65.895  36.057  32.702  1.00 27.13           C
ATOM   6724  CE2 PHE C  99      65.647  37.291  33.297  1.00 28.94           C
ATOM   6725  CD2 PHE C  99      64.358  37.608  33.743  1.00 28.32           C
ATOM   6726  C   PHE C  99      59.419  37.045  33.644  1.00 26.64           C
ATOM   6727  O   PHE C  99      59.090  36.486  34.695  1.00 29.14           O
ATOM   6728  N   ASN C 100      58.619  37.873  32.964  1.00 28.51           N
ATOM   6729  CA  ASN C 100      57.246  38.209  33.372  1.00 28.85           C
ATOM   6730  CB  ASN C 100      56.325  36.986  33.234  1.00 33.50           C
ATOM   6731  CG  ASN C 100      54.849  37.336  33.340  1.00 36.24           C
ATOM   6732  OD1 ASN C 100      54.384  38.312  32.749  1.00 38.95           O
ATOM   6733  ND2 ASN C 100      54.104  36.530  34.097  1.00 31.90           N
ATOM   6734  C   ASN C 100      57.158  38.833  34.772  1.00 29.73           C
ATOM   6735  O   ASN C 100      56.307  38.465  35.588  1.00 27.05           O
ATOM   6736  N   VAL C 101      58.051  39.780  35.046  1.00 26.04           N
ATOM   6737  CA  VAL C 101      58.082  40.453  36.341  1.00 31.33           C
ATOM   6738  CB  VAL C 101      59.448  40.254  37.045  1.00 31.40           C
ATOM   6739  CG1 VAL C 101      59.590  41.155  38.266  1.00 30.92           C
ATOM   6740  CG2 VAL C 101      59.630  38.793  37.457  1.00 30.63           C
ATOM   6741  C   VAL C 101      57.758  41.938  36.155  1.00 37.11           C
ATOM   6742  O   VAL C 101      58.294  42.582  35.250  1.00 34.11           O
ATOM   6743  N   GLY C 102      56.863  42.462  36.993  1.00 39.75           N
ATOM   6744  CA  GLY C 102      56.506  43.873  36.952  1.00 44.81           C
ATOM   6745  C   GLY C 102      55.023  44.204  37.008  1.00 47.01           C
ATOM   6746  O   GLY C 102      54.657  45.323  37.376  1.00 48.06           O
ATOM   6747  N   GLU C 103      54.175  43.243  36.644  1.00 48.24           N
ATOM   6748  CA  GLU C 103      52.726  43.449  36.614  1.00 49.54           C
ATOM   6749  CB  GLU C 103      52.164  43.129  35.225  1.00 54.62           C
ATOM   6750  CG  GLU C 103      52.395  44.224  34.194  1.00 60.36           C
ATOM   6751  CD  GLU C 103      51.309  45.282  34.214  1.00 64.34           C
ATOM   6752  OE1 GLU C 103      50.349  45.164  33.422  1.00 66.74           O
ATOM   6753  OE2 GLU C 103      51.414  46.233  35.020  1.00 66.91           O
ATOM   6754  C   GLU C 103      52.016  42.636  37.696  1.00 45.89           C
ATOM   6755  O   GLU C 103      51.883  43.098  38.831  1.00 45.41           O
ATOM   6756  N   ASP C 104      51.570  41.429  37.345  1.00 44.36           N
ATOM   6757  CA  ASP C 104      50.969  40.503  38.303  1.00 41.06           C
ATOM   6758  CB  ASP C 104      50.582  39.195  37.613  1.00 48.67           C
ATOM   6759  CG  ASP C 104      49.189  39.227  37.012  1.00 53.92           C
ATOM   6760  OD1 ASP C 104      48.474  40.242  37.170  1.00 56.33           O
ATOM   6761  OD2 ASP C 104      48.727  38.267  36.356  1.00 56.01           O
ATOM   6762  C   ASP C 104      51.951  40.188  39.420  1.00 37.77           C
ATOM   6763  O   ASP C 104      51.565  40.064  40.582  1.00 36.85           O
ATOM   6764  N   CYS C 105      53.221  40.048  39.046  1.00 30.82           N
ATOM   6765  CA  CYS C 105      54.292  39.738  39.977  1.00 28.07           C
ATOM   6766  CB  CYS C 105      55.050  38.501  39.506  1.00 30.49           C
ATOM   6767  SG  CYS C 105      53.958  37.149  39.013  1.00 31.80           S
ATOM   6768  C   CYS C 105      55.227  40.937  40.066  1.00 31.38           C
ATOM   6769  O   CYS C 105      56.223  41.008  39.342  1.00 30.00           O
ATOM   6770  N   PRO C 106      54.908  41.877  40.955  1.00 30.91           N
ATOM   6771  CA  PRO C 106      55.649  43.140  41.030  1.00 29.66           C
ATOM   6772  CB  PRO C 106      54.807  43.980  41.997  1.00 32.19           C
ATOM   6773  CG  PRO C 106      54.117  42.974  42.864  1.00 31.75           C
```

FIGURE 3PPPPP

```
ATOM   6774  CD  PRO C 106      53.835  41.805  41.967  1.00 32.10           C
ATOM   6775  C   PRO C 106      57.050  42.967  41.595  1.00 31.00           C
ATOM   6776  O   PRO C 106      57.337  41.965  42.253  1.00 28.23           O
ATOM   6777  N   VAL C 107      57.907  43.947  41.328  1.00 32.13           N
ATOM   6778  CA  VAL C 107      59.160  44.084  42.051  1.00 33.53           C
ATOM   6779  CB  VAL C 107      60.210  44.891  41.256  1.00 35.73           C
ATOM   6780  CG1 VAL C 107      61.555  44.869  41.969  1.00 37.66           C
ATOM   6781  CG2 VAL C 107      60.348  44.358  39.834  1.00 37.07           C
ATOM   6782  C   VAL C 107      58.858  44.801  43.365  1.00 35.11           C
ATOM   6783  O   VAL C 107      58.206  45.850  43.381  1.00 34.28           O
ATOM   6784  N   PHE C 108      59.309  44.218  44.468  1.00 35.01           N
ATOM   6785  CA  PHE C 108      59.215  44.877  45.763  1.00 32.91           C
ATOM   6786  CB  PHE C 108      57.950  44.447  46.524  1.00 31.70           C
ATOM   6787  CG  PHE C 108      57.795  42.952  46.688  1.00 32.36           C
ATOM   6788  CD1 PHE C 108      57.063  42.209  45.764  1.00 31.31           C
ATOM   6789  CE1 PHE C 108      56.896  40.828  45.923  1.00 32.19           C
ATOM   6790  CZ  PHE C 108      57.460  40.182  47.018  1.00 30.65           C
ATOM   6791  CE2 PHE C 108      58.189  40.915  47.952  1.00 32.50           C
ATOM   6792  CD2 PHE C 108      58.346  42.296  47.785  1.00 30.71           C
ATOM   6793  C   PHE C 108      60.481  44.650  46.579  1.00 34.69           C
ATOM   6794  O   PHE C 108      61.285  43.769  46.255  1.00 30.51           O
ATOM   6795  N   ASP C 109      60.657  45.453  47.627  1.00 35.25           N
ATOM   6796  CA  ASP C 109      61.843  45.372  48.473  1.00 36.14           C
ATOM   6797  CB  ASP C 109      61.894  46.555  49.446  1.00 41.72           C
ATOM   6798  CG  ASP C 109      62.140  47.885  48.744  1.00 46.61           C
ATOM   6799  OD1 ASP C 109      63.065  47.962  47.906  1.00 48.16           O
ATOM   6800  OD2 ASP C 109      61.462  48.912  48.971  1.00 49.82           O
ATOM   6801  C   ASP C 109      61.876  44.054  49.241  1.00 34.01           C
ATOM   6802  O   ASP C 109      60.888  43.666  49.868  1.00 32.23           O
ATOM   6803  N   GLY C 110      63.012  43.368  49.176  1.00 31.89           N
ATOM   6804  CA  GLY C 110      63.181  42.098  49.862  1.00 29.75           C
ATOM   6805  C   GLY C 110      62.577  40.924  49.107  1.00 30.18           C
ATOM   6806  O   GLY C 110      62.409  39.843  49.676  1.00 30.90           O
ATOM   6807  N   LEU C 111      62.264  41.135  47.827  1.00 27.41           N
ATOM   6808  CA  LEU C 111      61.663  40.098  46.980  1.00 27.95           C
ATOM   6809  CB  LEU C 111      61.552  40.574  45.521  1.00 26.73           C
ATOM   6810  CG  LEU C 111      61.236  39.529  44.440  1.00 28.82           C
ATOM   6811  CD1 LEU C 111      59.879  38.870  44.689  1.00 28.29           C
ATOM   6812  CD2 LEU C 111      61.277  40.136  43.049  1.00 28.23           C
ATOM   6813  C   LEU C 111      62.424  38.771  47.050  1.00 25.73           C
ATOM   6814  O   LEU C 111      61.828  37.713  47.293  1.00 25.43           O
ATOM   6815  N   PHE C 112      63.737  38.827  46.841  1.00 23.41           N
ATOM   6816  CA  PHE C 112      64.524  37.598  46.815  1.00 23.63           C
ATOM   6817  CB  PHE C 112      65.946  37.839  46.304  1.00 26.96           C
ATOM   6818  CG  PHE C 112      66.679  36.570  45.999  1.00 26.70           C
ATOM   6819  CD1 PHE C 112      66.278  35.763  44.937  1.00 29.91           C
ATOM   6820  CE1 PHE C 112      66.937  34.571  44.660  1.00 29.41           C
ATOM   6821  CZ  PHE C 112      68.000  34.170  45.460  1.00 30.30           C
ATOM   6822  CE2 PHE C 112      68.404  34.965  46.529  1.00 30.08           C
ATOM   6823  CD2 PHE C 112      67.738  36.156  46.795  1.00 27.87           C
ATOM   6824  C   PHE C 112      64.554  36.908  48.170  1.00 23.48           C
ATOM   6825  O   PHE C 112      64.371  35.689  48.266  1.00 23.72           O
ATOM   6826  N   GLU C 113      64.760  37.693  49.223  1.00 25.28           N
ATOM   6827  CA  GLU C 113      64.777  37.156  50.580  1.00 26.50           C
ATOM   6828  CB  GLU C 113      65.123  38.264  51.582  1.00 34.42           C
ATOM   6829  CG  GLU C 113      66.559  38.784  51.490  1.00 41.94           C
ATOM   6830  CD  GLU C 113      66.853  39.621  50.240  1.00 47.93           C
```

FIGURE 3QQQQQ

```
ATOM   6831  OE1 GLU C 113      68.044  39.708  49.858  1.00 50.38           O
ATOM   6832  OE2 GLU C 113      65.916  40.201  49.637  1.00 44.88           O
ATOM   6833  C   GLU C 113      63.432  36.497  50.910  1.00 24.53           C
ATOM   6834  O   GLU C 113      63.378  35.461  51.579  1.00 24.37           O
ATOM   6835  N   PHE C 114      62.352  37.098  50.420  1.00 23.45           N
ATOM   6836  CA  PHE C 114      61.011  36.525  50.542  1.00 27.29           C
ATOM   6837  CB  PHE C 114      59.989  37.469  49.900  1.00 31.23           C
ATOM   6838  CG  PHE C 114      58.590  36.925  49.845  1.00 35.45           C
ATOM   6839  CD1 PHE C 114      58.038  36.525  48.633  1.00 37.00           C
ATOM   6840  CE1 PHE C 114      56.735  36.029  48.570  1.00 41.27           C
ATOM   6841  CZ  PHE C 114      55.971  35.937  49.730  1.00 41.87           C
ATOM   6842  CE2 PHE C 114      56.511  36.342  50.948  1.00 40.74           C
ATOM   6843  CD2 PHE C 114      57.812  36.837  50.998  1.00 37.71           C
ATOM   6844  C   PHE C 114      60.961  35.127  49.912  1.00 27.80           C
ATOM   6845  O   PHE C 114      60.499  34.170  50.538  1.00 25.54           O
ATOM   6846  N   CYS C 115      61.475  35.016  48.687  1.00 26.56           N
ATOM   6847  CA  CYS C 115      61.545  33.737  47.978  1.00 27.28           C
ATOM   6848  CB  CYS C 115      62.091  33.935  46.563  1.00 26.29           C
ATOM   6849  SG  CYS C 115      61.035  34.976  45.539  1.00 30.90           S
ATOM   6850  C   CYS C 115      62.397  32.717  48.722  1.00 26.12           C
ATOM   6851  O   CYS C 115      62.053  31.535  48.767  1.00 26.73           O
ATOM   6852  N   GLN C 116      63.501  33.176  49.311  1.00 21.66           N
ATOM   6853  CA  GLN C 116      64.416  32.289  50.024  1.00 21.67           C
ATOM   6854  CB  GLN C 116      65.672  33.043  50.476  1.00 22.09           C
ATOM   6855  CG  GLN C 116      66.600  33.439  49.348  1.00 23.33           C
ATOM   6856  CD  GLN C 116      67.896  34.026  49.866  1.00 28.17           C
ATOM   6857  OE1 GLN C 116      67.952  35.210  50.181  1.00 29.37           O
ATOM   6858  NE2 GLN C 116      68.930  33.196  49.977  1.00 26.66           N
ATOM   6859  C   GLN C 116      63.747  31.647  51.226  1.00 20.65           C
ATOM   6860  O   GLN C 116      63.952  30.464  51.494  1.00 22.70           O
ATOM   6861  N   LEU C 117      62.956  32.437  51.947  1.00 21.28           N
ATOM   6862  CA  LEU C 117      62.302  31.971  53.171  1.00 27.80           C
ATOM   6863  CB  LEU C 117      61.842  33.160  54.014  1.00 29.06           C
ATOM   6864  CG  LEU C 117      62.940  33.981  54.691  1.00 30.85           C
ATOM   6865  CD1 LEU C 117      62.341  35.250  55.272  1.00 29.59           C
ATOM   6866  CD2 LEU C 117      63.657  33.167  55.770  1.00 32.44           C
ATOM   6867  C   LEU C 117      61.124  31.048  52.887  1.00 27.36           C
ATOM   6868  O   LEU C 117      60.950  30.028  53.559  1.00 27.76           O
ATOM   6869  N   SER C 118      60.316  31.416  51.896  1.00 28.94           N
ATOM   6870  CA  SER C 118      59.193  30.590  51.461  1.00 29.90           C
ATOM   6871  CB  SER C 118      58.413  31.312  50.350  1.00 34.15           C
ATOM   6872  OG  SER C 118      57.523  30.442  49.667  1.00 41.41           O
ATOM   6873  C   SER C 118      59.714  29.222  51.002  1.00 28.25           C
ATOM   6874  O   SER C 118      59.238  28.175  51.451  1.00 25.83           O
ATOM   6875  N   THR C 119      60.725  29.247  50.139  1.00 26.33           N
ATOM   6876  CA  THR C 119      61.359  28.036  49.622  1.00 24.92           C
ATOM   6877  CB  THR C 119      62.343  28.410  48.487  1.00 24.00           C
ATOM   6878  OG1 THR C 119      61.612  29.040  47.426  1.00 24.68           O
ATOM   6879  CG2 THR C 119      62.932  27.169  47.833  1.00 27.43           C
ATOM   6880  C   THR C 119      62.053  27.220  50.711  1.00 26.71           C
ATOM   6881  O   THR C 119      61.928  25.992  50.743  1.00 22.77           O
ATOM   6882  N   GLY C 120      62.777  27.905  51.597  1.00 23.47           N
ATOM   6883  CA  GLY C 120      63.475  27.261  52.699  1.00 25.53           C
ATOM   6884  C   GLY C 120      62.592  26.338  53.519  1.00 23.72           C
ATOM   6885  O   GLY C 120      62.969  25.194  53.800  1.00 24.50           O
ATOM   6886  N   GLY C 121      61.412  26.833  53.890  1.00 23.03           N
ATOM   6887  CA  GLY C 121      60.441  26.052  54.642  1.00 23.63           C
```

FIGURE 3RRRRR

```
ATOM   6888  C   GLY C 121      60.013  24.764  53.957  1.00 22.63           C
ATOM   6889  O   GLY C 121      59.902  23.713  54.610  1.00 25.23           O
ATOM   6890  N   SER C 122      59.775  24.842  52.647  1.00 20.95           N
ATOM   6891  CA  SER C 122      59.305  23.693  51.872  1.00 21.28           C
ATOM   6892  CB  SER C 122      58.779  24.146  50.512  1.00 20.48           C
ATOM   6893  OG  SER C 122      57.678  25.025  50.675  1.00 25.30           O
ATOM   6894  C   SER C 122      60.391  22.631  51.707  1.00 19.54           C
ATOM   6895  O   SER C 122      60.135  21.442  51.908  1.00 22.02           O
ATOM   6896  N   VAL C 123      61.597  23.062  51.338  1.00 20.21           N
ATOM   6897  CA  VAL C 123      62.741  22.151  51.214  1.00 20.95           C
ATOM   6898  CB  VAL C 123      63.949  22.837  50.506  1.00 24.13           C
ATOM   6899  CG1 VAL C 123      65.173  21.916  50.472  1.00 26.86           C
ATOM   6900  CG2 VAL C 123      63.569  23.259  49.077  1.00 22.88           C
ATOM   6901  C   VAL C 123      63.142  21.530  52.570  1.00 22.56           C
ATOM   6902  O   VAL C 123      63.417  20.327  52.654  1.00 23.36           O
ATOM   6903  N   ALA C 124      63.160  22.341  53.630  1.00 26.05           N
ATOM   6904  CA  ALA C 124      63.485  21.835  54.973  1.00 24.64           C
ATOM   6905  CB  ALA C 124      63.510  22.966  55.990  1.00 25.75           C
ATOM   6906  C   ALA C 124      62.494  20.761  55.403  1.00 24.40           C
ATOM   6907  O   ALA C 124      62.892  19.726  55.947  1.00 27.04           O
ATOM   6908  N   GLY C 125      61.209  21.023  55.152  1.00 24.22           N
ATOM   6909  CA  GLY C 125      60.139  20.070  55.401  1.00 24.71           C
ATOM   6910  C   GLY C 125      60.330  18.752  54.668  1.00 28.40           C
ATOM   6911  O   GLY C 125      60.141  17.678  55.256  1.00 25.40           O
ATOM   6912  N   ALA C 126      60.699  18.835  53.387  1.00 23.31           N
ATOM   6913  CA  ALA C 126      61.041  17.651  52.594  1.00 23.38           C
ATOM   6914  CB  ALA C 126      61.341  18.039  51.145  1.00 22.89           C
ATOM   6915  C   ALA C 126      62.221  16.875  53.191  1.00 25.11           C
ATOM   6916  O   ALA C 126      62.185  15.644  53.262  1.00 25.77           O
ATOM   6917  N   VAL C 127      63.252  17.601  53.619  1.00 25.67           N
ATOM   6918  CA  VAL C 127      64.443  16.999  54.221  1.00 28.70           C
ATOM   6919  CB  VAL C 127      65.548  18.058  54.484  1.00 29.69           C
ATOM   6920  CG1 VAL C 127      66.620  17.523  55.435  1.00 33.50           C
ATOM   6921  CG2 VAL C 127      66.187  18.512  53.173  1.00 30.01           C
ATOM   6922  C   VAL C 127      64.090  16.245  55.511  1.00 29.06           C
ATOM   6923  O   VAL C 127      64.589  15.142  55.744  1.00 30.11           O
ATOM   6924  N   LYS C 128      63.224  16.842  56.329  1.00 29.40           N
ATOM   6925  CA  LYS C 128      62.780  16.229  57.580  1.00 31.30           C
ATOM   6926  CB  LYS C 128      61.974  17.226  58.418  1.00 37.77           C
ATOM   6927  CG  LYS C 128      62.085  17.019  59.924  1.00 45.01           C
ATOM   6928  CD  LYS C 128      63.116  17.955  60.540  1.00 48.67           C
ATOM   6929  CE  LYS C 128      62.830  18.197  62.015  1.00 52.47           C
ATOM   6930  NZ  LYS C 128      63.334  17.093  62.884  1.00 53.86           N
ATOM   6931  C   LYS C 128      61.963  14.966  57.317  1.00 29.30           C
ATOM   6932  O   LYS C 128      62.109  13.969  58.025  1.00 29.69           O
ATOM   6933  N   LEU C 129      61.110  15.024  56.296  1.00 25.90           N
ATOM   6934  CA  LEU C 129      60.348  13.869  55.829  1.00 27.59           C
ATOM   6935  CB  LEU C 129      59.400  14.287  54.700  1.00 29.00           C
ATOM   6936  CG  LEU C 129      57.878  14.433  54.857  1.00 33.00           C
ATOM   6937  CD1 LEU C 129      57.339  14.152  56.264  1.00 29.48           C
ATOM   6938  CD2 LEU C 129      57.420  15.802  54.352  1.00 29.11           C
ATOM   6939  C   LEU C 129      61.284  12.768  55.333  1.00 31.36           C
ATOM   6940  O   LEU C 129      61.114  11.595  55.685  1.00 35.42           O
ATOM   6941  N   ASN C 130      62.271  13.154  54.521  1.00 29.71           N
ATOM   6942  CA  ASN C 130      63.277  12.226  53.999  1.00 30.07           C
ATOM   6943  CB  ASN C 130      64.275  12.961  53.091  1.00 27.87           C
ATOM   6944  CG  ASN C 130      63.737  13.201  51.681  1.00 28.22           C
```

FIGURE 3SSSSS

```
ATOM   6945  OD1  ASN C 130      62.712   12.648   51.280  1.00  26.43           O
ATOM   6946  ND2  ASN C 130      64.445   14.022   50.923  1.00  28.71           N
ATOM   6947  C    ASN C 130      64.040   11.499   55.112  1.00  34.00           C
ATOM   6948  O    ASN C 130      64.241   10.285   55.048  1.00  35.51           O
ATOM   6949  N    ARG C 131      64.452   12.250   56.130  1.00  35.18           N
ATOM   6950  CA   ARG C 131      65.237   11.709   57.239  1.00  40.35           C
ATOM   6951  CB   ARG C 131      66.050   12.822   57.908  1.00  41.46           C
ATOM   6952  CG   ARG C 131      67.203   13.343   57.063  1.00  45.97           C
ATOM   6953  CD   ARG C 131      67.857   14.598   57.613  1.00  49.78           C
ATOM   6954  NE   ARG C 131      68.947   15.061   56.756  1.00  54.97           N
ATOM   6955  CZ   ARG C 131      69.705   16.127   57.004  1.00  56.18           C
ATOM   6956  NH1  ARG C 131      70.669   16.461   56.158  1.00  57.36           N
ATOM   6957  NH2  ARG C 131      69.505   16.861   58.092  1.00  56.49           N
ATOM   6958  C    ARG C 131      64.374   10.984   58.275  1.00  41.23           C
ATOM   6959  O    ARG C 131      64.883   10.528   59.306  1.00  37.56           O
ATOM   6960  N    GLN C 132      63.074   10.883   57.988  1.00  42.12           N
ATOM   6961  CA   GLN C 132      62.098   10.205   58.847  1.00  45.95           C
ATOM   6962  CB   GLN C 132      62.297    8.679   58.814  1.00  47.73           C
ATOM   6963  CG   GLN C 132      61.797    8.025   57.533  1.00  51.66           C
ATOM   6964  CD   GLN C 132      62.011    6.523   57.513  1.00  55.87           C
ATOM   6965  OE1  GLN C 132      63.146    6.054   57.431  1.00  57.55           O
ATOM   6966  NE2  GLN C 132      60.921    5.766   57.585  1.00  57.31           N
ATOM   6967  C    GLN C 132      62.119   10.749   60.277  1.00  45.78           C
ATOM   6968  O    GLN C 132      61.986   10.002   61.250  1.00  44.29           O
ATOM   6969  N    GLN C 133      62.291   12.064   60.380  1.00  44.67           N
ATOM   6970  CA   GLN C 133      62.285   12.761   61.657  1.00  44.60           C
ATOM   6971  CB   GLN C 133      63.352   13.857   61.668  1.00  47.87           C
ATOM   6972  CG   GLN C 133      64.751   13.361   62.043  1.00  53.97           C
ATOM   6973  CD   GLN C 133      65.871   14.247   61.509  1.00  56.96           C
ATOM   6974  OE1  GLN C 133      65.680   15.444   61.287  1.00  59.27           O
ATOM   6975  NE2  GLN C 133      67.042   13.656   61.306  1.00  59.06           N
ATOM   6976  C    GLN C 133      60.898   13.335   61.966  1.00  43.38           C
ATOM   6977  O    GLN C 133      60.674   13.883   63.048  1.00  44.99           O
ATOM   6978  N    THR C 134      59.973   13.199   61.012  1.00  38.88           N
ATOM   6979  CA   THR C 134      58.582   13.626   61.187  1.00  35.79           C
ATOM   6980  CB   THR C 134      58.439   15.172   61.021  1.00  35.34           C
ATOM   6981  OG1  THR C 134      57.122   15.582   61.413  1.00  34.59           O
ATOM   6982  CG2  THR C 134      58.531   15.596   59.550  1.00  32.32           C
ATOM   6983  C    THR C 134      57.640   12.883   60.245  1.00  35.70           C
ATOM   6984  O    THR C 134      58.074   12.318   59.240  1.00  35.25           O
ATOM   6985  N    ASP C 135      56.351   12.889   60.578  1.00  35.15           N
ATOM   6986  CA   ASP C 135      55.330   12.257   59.749  1.00  34.99           C
ATOM   6987  CB   ASP C 135      54.261   11.609   60.630  1.00  40.85           C
ATOM   6988  CG   ASP C 135      54.821   10.500   61.497  1.00  44.88           C
ATOM   6989  OD1  ASP C 135      54.838   10.661   62.735  1.00  46.42           O
ATOM   6990  OD2  ASP C 135      55.270    9.433   61.026  1.00  47.04           O
ATOM   6991  C    ASP C 135      54.683   13.258   58.801  1.00  32.77           C
ATOM   6992  O    ASP C 135      54.272   12.906   57.690  1.00  29.31           O
ATOM   6993  N    MET C 136      54.588   14.500   59.266  1.00  29.59           N
ATOM   6994  CA   MET C 136      54.020   15.599   58.503  1.00  30.45           C
ATOM   6995  CB   MET C 136      52.602   15.913   58.978  1.00  33.27           C
ATOM   6996  CG   MET C 136      51.542   14.961   58.471  1.00  39.11           C
ATOM   6997  SD   MET C 136      50.033   15.040   59.459  1.00  43.11           S
ATOM   6998  CE   MET C 136      50.530   14.110   60.931  1.00  37.25           C
ATOM   6999  C    MET C 136      54.881   16.833   58.694  1.00  28.46           C
ATOM   7000  O    MET C 136      55.353   17.103   59.803  1.00  30.48           O
ATOM   7001  N    ALA C 137      55.093   17.571   57.608  1.00  27.42           N
```

FIGURE 3TTTTT

```
ATOM   7002  CA   ALA C 137      55.734  18.879  57.678  1.00  25.31           C
ATOM   7003  CB   ALA C 137      57.065  18.870  56.948  1.00  26.02           C
ATOM   7004  C    ALA C 137      54.805  19.935  57.096  1.00  25.10           C
ATOM   7005  O    ALA C 137      54.122  19.691  56.099  1.00  25.33           O
ATOM   7006  N    VAL C 138      54.789  21.111  57.718  1.00  24.13           N
ATOM   7007  CA   VAL C 138      53.866  22.173  57.343  1.00  23.18           C
ATOM   7008  CB   VAL C 138      52.782  22.410  58.439  1.00  21.18           C
ATOM   7009  CG1  VAL C 138      51.769  23.430  57.976  1.00  25.33           C
ATOM   7010  CG2  VAL C 138      52.077  21.108  58.801  1.00  23.89           C
ATOM   7011  C    VAL C 138      54.615  23.473  57.070  1.00  23.18           C
ATOM   7012  O    VAL C 138      55.422  23.923  57.885  1.00  24.37           O
ATOM   7013  N    ASN C 139      54.351  24.059  55.905  1.00  23.34           N
ATOM   7014  CA   ASN C 139      54.888  25.369  55.561  1.00  22.31           C
ATOM   7015  CB   ASN C 139      56.153  25.253  54.701  1.00  22.21           C
ATOM   7016  CG   ASN C 139      56.679  26.607  54.256  1.00  25.72           C
ATOM   7017  OD1  ASN C 139      56.593  27.592  54.993  1.00  26.13           O
ATOM   7018  ND2  ASN C 139      57.221  26.664  53.045  1.00  23.27           N
ATOM   7019  C    ASN C 139      53.840  26.207  54.855  1.00  25.88           C
ATOM   7020  O    ASN C 139      53.692  26.141  53.628  1.00  21.64           O
ATOM   7021  N    TRP C 140      53.116  27.008  55.633  1.00  24.47           N
ATOM   7022  CA   TRP C 140      52.043  27.822  55.075  1.00  21.50           C
ATOM   7023  CB   TRP C 140      51.111  28.349  56.178  1.00  23.35           C
ATOM   7024  CG   TRP C 140      50.360  27.255  56.920  1.00  22.62           C
ATOM   7025  CD1  TRP C 140      50.295  27.078  58.280  1.00  23.39           C
ATOM   7026  NE1  TRP C 140      49.520  25.982  58.580  1.00  22.42           N
ATOM   7027  CE2  TRP C 140      49.060  25.424  57.416  1.00  25.02           C
ATOM   7028  CD2  TRP C 140      49.573  26.194  56.347  1.00  22.89           C
ATOM   7029  CE3  TRP C 140      49.240  25.822  55.036  1.00  25.34           C
ATOM   7030  CZ3  TRP C 140      48.431  24.702  54.835  1.00  24.95           C
ATOM   7031  CH2  TRP C 140      47.939  23.961  55.919  1.00  27.91           C
ATOM   7032  CZ2  TRP C 140      48.244  24.301  57.213  1.00  23.85           C
ATOM   7033  C    TRP C 140      52.543  28.949  54.171  1.00  24.44           C
ATOM   7034  O    TRP C 140      51.785  29.462  53.352  1.00  23.81           O
ATOM   7035  N    ALA C 141      53.818  29.312  54.309  1.00  21.79           N
ATOM   7036  CA   ALA C 141      54.432  30.313  53.440  1.00  24.08           C
ATOM   7037  CB   ALA C 141      55.674  30.917  54.111  1.00  24.79           C
ATOM   7038  C    ALA C 141      54.776  29.783  52.039  1.00  25.95           C
ATOM   7039  O    ALA C 141      55.095  30.565  51.136  1.00  26.65           O
ATOM   7040  N    GLY C 142      54.698  28.463  51.858  1.00  23.38           N
ATOM   7041  CA   GLY C 142      54.993  27.838  50.579  1.00  26.19           C
ATOM   7042  C    GLY C 142      53.768  27.593  49.708  1.00  26.19           C
ATOM   7043  O    GLY C 142      52.690  28.144  49.950  1.00  27.02           O
ATOM   7044  N    GLY C 143      53.938  26.779  48.673  1.00  23.99           N
ATOM   7045  CA   GLY C 143      52.826  26.407  47.816  1.00  26.66           C
ATOM   7046  C    GLY C 143      52.658  27.322  46.620  1.00  26.00           C
ATOM   7047  O    GLY C 143      51.563  27.416  46.059  1.00  25.20           O
ATOM   7048  N    LEU C 144      53.751  27.977  46.225  1.00  24.52           N
ATOM   7049  CA   LEU C 144      53.762  28.916  45.103  1.00  25.64           C
ATOM   7050  CB   LEU C 144      54.948  29.886  45.227  1.00  27.75           C
ATOM   7051  CG   LEU C 144      55.074  30.684  46.528  1.00  35.85           C
ATOM   7052  CD1  LEU C 144      56.283  31.612  46.459  1.00  40.38           C
ATOM   7053  CD2  LEU C 144      53.805  31.468  46.825  1.00  38.49           C
ATOM   7054  C    LEU C 144      53.785  28.206  43.747  1.00  26.31           C
ATOM   7055  O    LEU C 144      54.804  28.203  43.043  1.00  23.50           O
ATOM   7056  N    HIS C 145      52.630  27.666  43.364  1.00  21.64           N
ATOM   7057  CA   HIS C 145      52.535  26.670  42.298  1.00  18.96           C
ATOM   7058  CB   HIS C 145      51.280  25.794  42.496  1.00  20.31           C
```

FIGURE 3UUUUU

```
ATOM   7059  CG   HIS C 145      49.984  26.553  42.479  1.00 23.25           C
ATOM   7060  ND1  HIS C 145      48.759  25.918  42.422  1.00 23.18           N
ATOM   7061  CE1  HIS C 145      47.796  26.822  42.419  1.00 22.75           C
ATOM   7062  NE2  HIS C 145      48.348  28.021  42.484  1.00 24.72           N
ATOM   7063  CD2  HIS C 145      49.716  27.881  42.525  1.00 23.02           C
ATOM   7064  C    HIS C 145      52.631  27.132  40.832  1.00 20.46           C
ATOM   7065  O    HIS C 145      52.743  26.285  39.946  1.00 22.21           O
ATOM   7066  N    HIS C 146      52.588  28.441  40.576  1.00 18.47           N
ATOM   7067  CA   HIS C 146      52.614  28.965  39.205  1.00 20.41           C
ATOM   7068  CB   HIS C 146      51.785  30.253  39.096  1.00 22.31           C
ATOM   7069  CG   HIS C 146      50.331  30.076  39.401  1.00 24.49           C
ATOM   7070  ND1  HIS C 146      49.523  29.204  38.702  1.00 23.92           N
ATOM   7071  CE1  HIS C 146      48.294  29.264  39.188  1.00 26.49           C
ATOM   7072  NE2  HIS C 146      48.276  30.150  40.167  1.00 26.31           N
ATOM   7073  CD2  HIS C 146      49.537  30.672  40.322  1.00 24.97           C
ATOM   7074  C    HIS C 146      53.999  29.276  38.640  1.00 19.68           C
ATOM   7075  O    HIS C 146      54.142  29.434  37.427  1.00 20.51           O
ATOM   7076  N    ALA C 147      54.996  29.434  39.505  1.00 21.32           N
ATOM   7077  CA   ALA C 147      56.327  29.842  39.047  1.00 20.73           C
ATOM   7078  CB   ALA C 147      57.267  30.042  40.235  1.00 21.40           C
ATOM   7079  C    ALA C 147      56.892  28.809  38.066  1.00 19.28           C
ATOM   7080  O    ALA C 147      56.789  27.602  38.299  1.00 18.06           O
ATOM   7081  N    LYS C 148      57.469  29.296  36.969  1.00 19.46           N
ATOM   7082  CA   LYS C 148      58.047  28.443  35.933  1.00 18.89           C
ATOM   7083  CB   LYS C 148      57.542  28.866  34.546  1.00 20.97           C
ATOM   7084  CG   LYS C 148      56.034  29.121  34.455  1.00 27.24           C
ATOM   7085  CD   LYS C 148      55.232  27.834  34.499  1.00 31.57           C
ATOM   7086  CE   LYS C 148      53.781  28.066  34.081  1.00 36.57           C
ATOM   7087  NZ   LYS C 148      53.070  29.056  34.960  1.00 39.16           N
ATOM   7088  C    LYS C 148      59.573  28.492  35.962  1.00 18.37           C
ATOM   7089  O    LYS C 148      60.159  29.264  36.718  1.00 18.13           O
ATOM   7090  N    LYS C 149      60.208  27.681  35.118  1.00 19.40           N
ATOM   7091  CA   LYS C 149      61.669  27.576  35.084  1.00 19.45           C
ATOM   7092  CB   LYS C 149      62.111  26.666  33.928  1.00 23.91           C
ATOM   7093  CG   LYS C 149      62.362  25.223  34.333  1.00 36.30           C
ATOM   7094  CD   LYS C 149      62.668  24.339  33.122  1.00 40.69           C
ATOM   7095  CE   LYS C 149      62.204  22.902  33.336  1.00 45.14           C
ATOM   7096  NZ   LYS C 149      60.717  22.733  33.194  1.00 46.77           N
ATOM   7097  C    LYS C 149      62.344  28.942  34.950  1.00 18.17           C
ATOM   7098  O    LYS C 149      63.300  29.247  35.666  1.00 19.54           O
ATOM   7099  N    SER C 150      61.826  29.758  34.038  1.00 17.12           N
ATOM   7100  CA   SER C 150      62.432  31.047  33.710  1.00 20.63           C
ATOM   7101  CB  ASER C 150      63.107  30.968  32.340  0.65 19.05           C
ATOM   7102  OG  ASER C 150      64.257  30.150  32.397  0.65 29.39           O
ATOM   7103  C    SER C 150      61.384  32.147  33.679  1.00 22.27           C
ATOM   7104  O    SER C 150      61.489  33.087  32.891  1.00 23.87           O
ATOM   7105  N    GLU C 151      60.363  32.027  34.520  1.00 21.40           N
ATOM   7106  CA   GLU C 151      59.252  32.974  34.479  1.00 26.55           C
ATOM   7107  CB   GLU C 151      58.276  32.599  33.353  1.00 32.51           C
ATOM   7108  CG   GLU C 151      57.410  33.756  32.883  1.00 44.26           C
ATOM   7109  CD   GLU C 151      56.455  33.393  31.757  1.00 49.04           C
ATOM   7110  OE1  GLU C 151      55.882  32.280  31.774  1.00 48.71           O
ATOM   7111  OE2  GLU C 151      56.267  34.239  30.856  1.00 53.70           O
ATOM   7112  C    GLU C 151      58.499  33.050  35.797  1.00 24.66           C
ATOM   7113  O    GLU C 151      58.159  32.021  36.389  1.00 24.54           O
ATOM   7114  N    ALA C 152      58.247  34.278  36.248  1.00 18.78           N
ATOM   7115  CA   ALA C 152      57.301  34.520  37.327  1.00 20.44           C
```

FIGURE 3VVVVV

```
ATOM   7116  CB  ALA C 152      57.534  35.882  37.955  1.00 20.98           C
ATOM   7117  C   ALA C 152      55.896  34.442  36.750  1.00 20.79           C
ATOM   7118  O   ALA C 152      55.676  34.766  35.581  1.00 24.62           O
ATOM   7119  N   SER C 153      54.947  34.021  37.577  1.00 23.32           N
ATOM   7120  CA  SER C 153      53.552  33.922  37.170  1.00 25.63           C
ATOM   7121  CB  SER C 153      53.334  32.651  36.342  1.00 26.95           C
ATOM   7122  OG  SER C 153      52.001  32.580  35.875  1.00 27.37           O
ATOM   7123  C   SER C 153      52.646  33.891  38.390  1.00 21.59           C
ATOM   7124  O   SER C 153      52.959  33.230  39.379  1.00 18.67           O
ATOM   7125  N   GLY C 154      51.533  34.619  38.322  1.00 23.59           N
ATOM   7126  CA  GLY C 154      50.480  34.521  39.322  1.00 21.52           C
ATOM   7127  C   GLY C 154      50.902  34.715  40.764  1.00 21.35           C
ATOM   7128  O   GLY C 154      50.499  33.946  41.648  1.00 22.74           O
ATOM   7129  N   PHE C 155      51.710  35.749  40.996  1.00 19.72           N
ATOM   7130  CA  PHE C 155      52.200  36.112  42.332  1.00 21.41           C
ATOM   7131  CB  PHE C 155      51.057  36.165  43.368  1.00 22.72           C
ATOM   7132  CG  PHE C 155      49.789  36.849  42.881  1.00 23.83           C
ATOM   7133  CD1 PHE C 155      49.819  37.815  41.875  1.00 29.94           C
ATOM   7134  CE1 PHE C 155      48.644  38.445  41.439  1.00 29.72           C
ATOM   7135  CZ  PHE C 155      47.429  38.111  42.020  1.00 29.34           C
ATOM   7136  CE2 PHE C 155      47.383  37.152  43.028  1.00 27.12           C
ATOM   7137  CD2 PHE C 155      48.562  36.527  43.456  1.00 25.61           C
ATOM   7138  C   PHE C 155      53.328  35.197  42.846  1.00 20.61           C
ATOM   7139  O   PHE C 155      53.774  35.339  43.988  1.00 23.49           O
ATOM   7140  N   CYS C 156      53.773  34.259  42.008  1.00 20.32           N
ATOM   7141  CA  CYS C 156      54.789  33.272  42.383  1.00 19.06           C
ATOM   7142  CB  CYS C 156      54.324  31.854  42.043  1.00 20.69           C
ATOM   7143  SG  CYS C 156      52.701  31.375  42.676  1.00 26.99           S
ATOM   7144  C   CYS C 156      56.074  33.541  41.605  1.00 20.50           C
ATOM   7145  O   CYS C 156      56.025  33.794  40.399  1.00 22.61           O
ATOM   7146  N   TYR C 157      57.214  33.476  42.288  1.00 17.82           N
ATOM   7147  CA  TYR C 157      58.492  33.766  41.644  1.00 18.77           C
ATOM   7148  CB  TYR C 157      59.219  34.913  42.352  1.00 21.59           C
ATOM   7149  CG  TYR C 157      58.407  36.183  42.469  1.00 22.70           C
ATOM   7150  CD1 TYR C 157      57.465  36.331  43.490  1.00 25.11           C
ATOM   7151  CE1 TYR C 157      56.710  37.485  43.610  1.00 23.29           C
ATOM   7152  CZ  TYR C 157      56.893  38.516  42.708  1.00 23.76           C
ATOM   7153  OH  TYR C 157      56.135  39.653  42.854  1.00 26.80           O
ATOM   7154  CE2 TYR C 157      57.821  38.404  41.678  1.00 26.50           C
ATOM   7155  CD2 TYR C 157      58.576  37.233  41.564  1.00 22.38           C
ATOM   7156  C   TYR C 157      59.379  32.535  41.604  1.00 18.48           C
ATOM   7157  O   TYR C 157      60.017  32.251  40.589  1.00 21.97           O
ATOM   7158  N   VAL C 158      59.418  31.810  42.714  1.00 18.43           N
ATOM   7159  CA  VAL C 158      60.221  30.603  42.812  1.00 15.87           C
ATOM   7160  CB  VAL C 158      61.361  30.754  43.861  1.00 19.22           C
ATOM   7161  CG1 VAL C 158      62.085  29.423  44.111  1.00 15.30           C
ATOM   7162  CG2 VAL C 158      62.360  31.817  43.410  1.00 18.32           C
ATOM   7163  C   VAL C 158      59.278  29.473  43.175  1.00 20.43           C
ATOM   7164  O   VAL C 158      58.430  29.615  44.063  1.00 18.42           O
ATOM   7165  N   ASN C 159      59.408  28.361  42.464  1.00 19.80           N
ATOM   7166  CA  ASN C 159      58.514  27.248  42.695  1.00 20.96           C
ATOM   7167  CB  ASN C 159      58.238  26.459  41.414  1.00 20.79           C
ATOM   7168  CG  ASN C 159      56.934  25.692  41.493  1.00 19.60           C
ATOM   7169  OD1 ASN C 159      56.692  24.968  42.464  1.00 15.97           O
ATOM   7170  ND2 ASN C 159      56.077  25.865  40.494  1.00 17.80           N
ATOM   7171  C   ASN C 159      59.029  26.361  43.805  1.00 21.03           C
ATOM   7172  O   ASN C 159      59.743  25.387  43.560  1.00 17.22           O
```

FIGURE 3WWWWW

```
ATOM   7173  N   ASP C 160      58.658  26.712  45.036  1.00 17.22           N
ATOM   7174  CA  ASP C 160      59.088  25.958  46.211  1.00 21.09           C
ATOM   7175  CB  ASP C 160      58.613  26.636  47.498  1.00 22.15           C
ATOM   7176  CG  ASP C 160      57.100  26.574  47.671  1.00 28.43           C
ATOM   7177  OD1 ASP C 160      56.377  27.229  46.882  1.00 28.06           O
ATOM   7178  OD2 ASP C 160      56.551  25.892  48.564  1.00 27.27           O
ATOM   7179  C   ASP C 160      58.611  24.509  46.175  1.00 20.02           C
ATOM   7180  O   ASP C 160      59.314  23.623  46.647  1.00 19.53           O
ATOM   7181  N   ILE C 161      57.419  24.278  45.621  1.00 19.53           N
ATOM   7182  CA  ILE C 161      56.847  22.925  45.547  1.00 20.29           C
ATOM   7183  CB  ILE C 161      55.422  22.951  44.935  1.00 22.80           C
ATOM   7184  CG1 ILE C 161      54.494  23.883  45.721  1.00 25.27           C
ATOM   7185  CD1 ILE C 161      53.150  24.103  45.071  1.00 25.18           C
ATOM   7186  CG2 ILE C 161      54.838  21.538  44.872  1.00 20.62           C
ATOM   7187  C   ILE C 161      57.741  21.999  44.715  1.00 17.29           C
ATOM   7188  O   ILE C 161      58.032  20.871  45.110  1.00 17.46           O
ATOM   7189  N   VAL C 162      58.147  22.480  43.545  1.00 17.09           N
ATOM   7190  CA  VAL C 162      58.985  21.694  42.643  1.00 15.53           C
ATOM   7191  CB  VAL C 162      59.205  22.437  41.302  1.00 16.77           C
ATOM   7192  CG1 VAL C 162      60.308  21.780  40.475  1.00 16.99           C
ATOM   7193  CG2 VAL C 162      57.896  22.485  40.499  1.00 18.38           C
ATOM   7194  C   VAL C 162      60.305  21.368  43.333  1.00 15.13           C
ATOM   7195  O   VAL C 162      60.775  20.224  43.306  1.00 17.01           O
ATOM   7196  N   LEU C 163      60.891  22.373  43.979  1.00 17.06           N
ATOM   7197  CA  LEU C 163      62.161  22.187  44.683  1.00 16.90           C
ATOM   7198  CB  LEU C 163      62.719  23.537  45.156  1.00 16.69           C
ATOM   7199  CG  LEU C 163      63.236  24.423  44.012  1.00 22.03           C
ATOM   7200  CD1 LEU C 163      63.370  25.875  44.474  1.00 21.01           C
ATOM   7201  CD2 LEU C 163      64.575  23.910  43.430  1.00 19.55           C
ATOM   7202  C   LEU C 163      62.049  21.204  45.848  1.00 18.62           C
ATOM   7203  O   LEU C 163      62.964  20.409  46.092  1.00 18.87           O
ATOM   7204  N   ALA C 164      60.919  21.240  46.547  1.00 18.00           N
ATOM   7205  CA  ALA C 164      60.683  20.308  47.652  1.00 20.50           C
ATOM   7206  CB  ALA C 164      59.492  20.749  48.479  1.00 19.04           C
ATOM   7207  C   ALA C 164      60.478  18.891  47.124  1.00 19.09           C
ATOM   7208  O   ALA C 164      60.988  17.925  47.706  1.00 18.67           O
ATOM   7209  N   ILE C 165      59.733  18.775  46.025  1.00 21.34           N
ATOM   7210  CA  ILE C 165      59.514  17.478  45.384  1.00 18.18           C
ATOM   7211  CB  ILE C 165      58.423  17.562  44.278  1.00 18.13           C
ATOM   7212  CG1 ILE C 165      57.049  17.820  44.908  1.00 18.87           C
ATOM   7213  CD1 ILE C 165      55.939  18.056  43.917  1.00 18.64           C
ATOM   7214  CG2 ILE C 165      58.384  16.278  43.450  1.00 18.97           C
ATOM   7215  C   ILE C 165      60.834  16.872  44.874  1.00 20.83           C
ATOM   7216  O   ILE C 165      61.080  15.674  45.056  1.00 22.41           O
ATOM   7217  N   LEU C 166      61.686  17.694  44.259  1.00 19.04           N
ATOM   7218  CA  LEU C 166      63.016  17.235  43.848  1.00 21.63           C
ATOM   7219  CB  LEU C 166      63.803  18.352  43.153  1.00 22.55           C
ATOM   7220  CG  LEU C 166      63.344  18.765  41.746  1.00 23.96           C
ATOM   7221  CD1 LEU C 166      64.204  19.921  41.254  1.00 24.61           C
ATOM   7222  CD2 LEU C 166      63.378  17.590  40.743  1.00 25.20           C
ATOM   7223  C   LEU C 166      63.813  16.672  45.032  1.00 23.98           C
ATOM   7224  O   LEU C 166      64.500  15.653  44.899  1.00 21.11           O
ATOM   7225  N   GLU C 167      63.707  17.328  46.187  1.00 23.51           N
ATOM   7226  CA  GLU C 167      64.327  16.823  47.407  1.00 24.54           C
ATOM   7227  CB  GLU C 167      64.239  17.854  48.535  1.00 30.09           C
ATOM   7228  CG  GLU C 167      65.056  17.505  49.774  1.00 37.28           C
ATOM   7229  CD  GLU C 167      66.535  17.282  49.482  1.00 43.46           C
```

FIGURE 3XXXXX

```
ATOM   7230  OE1 GLU C 167      67.101  16.305  50.020  1.00 46.60           O
ATOM   7231  OE2 GLU C 167      67.132  18.076  48.721  1.00 46.28           O
ATOM   7232  C   GLU C 167      63.722  15.482  47.837  1.00 24.61           C
ATOM   7233  O   GLU C 167      64.459  14.536  48.132  1.00 22.10           O
ATOM   7234  N   LEU C 168      62.391  15.403  47.856  1.00 19.17           N
ATOM   7235  CA  LEU C 168      61.679  14.162  48.182  1.00 20.32           C
ATOM   7236  CB  LEU C 168      60.159  14.383  48.136  1.00 21.36           C
ATOM   7237  CG  LEU C 168      59.552  15.191  49.292  1.00 20.90           C
ATOM   7238  CD1 LEU C 168      58.072  15.441  49.067  1.00 21.33           C
ATOM   7239  CD2 LEU C 168      59.780  14.507  50.640  1.00 20.43           C
ATOM   7240  C   LEU C 168      62.056  12.996  47.263  1.00 23.10           C
ATOM   7241  O   LEU C 168      62.161  11.847  47.707  1.00 21.44           O
ATOM   7242  N   LEU C 169      62.275  13.304  45.989  1.00 19.06           N
ATOM   7243  CA  LEU C 169      62.612  12.291  44.989  1.00 21.14           C
ATOM   7244  CB  LEU C 169      62.502  12.874  43.574  1.00 19.75           C
ATOM   7245  CG  LEU C 169      61.076  13.103  43.057  1.00 21.25           C
ATOM   7246  CD1 LEU C 169      61.087  14.001  41.821  1.00 21.38           C
ATOM   7247  CD2 LEU C 169      60.355  11.779  42.763  1.00 23.11           C
ATOM   7248  C   LEU C 169      63.977  11.627  45.202  1.00 23.12           C
ATOM   7249  O   LEU C 169      64.292  10.619  44.563  1.00 24.62           O
ATOM   7250  N   LYS C 170      64.782  12.184  46.104  1.00 24.79           N
ATOM   7251  CA  LYS C 170      66.033  11.538  46.503  1.00 26.97           C
ATOM   7252  CB  LYS C 170      66.912  12.496  47.308  1.00 29.47           C
ATOM   7253  CG  LYS C 170      67.710  13.450  46.441  1.00 33.54           C
ATOM   7254  CD  LYS C 170      67.842  14.810  47.085  1.00 39.30           C
ATOM   7255  CE  LYS C 170      69.212  15.413  46.822  1.00 39.75           C
ATOM   7256  NZ  LYS C 170      69.660  16.261  47.965  1.00 41.25           N
ATOM   7257  C   LYS C 170      65.771  10.243  47.286  1.00 28.83           C
ATOM   7258  O   LYS C 170      66.535   9.282  47.178  1.00 29.30           O
ATOM   7259  N   TYR C 171      64.671  10.217  48.040  1.00 26.82           N
ATOM   7260  CA  TYR C 171      64.354   9.111  48.944  1.00 29.54           C
ATOM   7261  CB  TYR C 171      64.240   9.630  50.383  1.00 31.39           C
ATOM   7262  CG  TYR C 171      65.560   9.956  51.043  1.00 36.26           C
ATOM   7263  CD1 TYR C 171      66.085   9.126  52.032  1.00 38.59           C
ATOM   7264  CE1 TYR C 171      67.293   9.421  52.646  1.00 41.65           C
ATOM   7265  CZ  TYR C 171      67.993  10.559  52.274  1.00 42.92           C
ATOM   7266  OH  TYR C 171      69.192  10.847  52.887  1.00 47.03           O
ATOM   7267  CE2 TYR C 171      67.495  11.403  51.296  1.00 38.03           C
ATOM   7268  CD2 TYR C 171      66.283  11.099  50.687  1.00 36.98           C
ATOM   7269  C   TYR C 171      63.062   8.392  48.570  1.00 30.77           C
ATOM   7270  O   TYR C 171      62.777   7.304  49.075  1.00 33.96           O
ATOM   7271  N   HIS C 172      62.273   9.006  47.697  1.00 27.99           N
ATOM   7272  CA  HIS C 172      60.968   8.462  47.344  1.00 26.92           C
ATOM   7273  CB  HIS C 172      59.855   9.404  47.806  1.00 27.87           C
ATOM   7274  CG  HIS C 172      59.863   9.644  49.282  1.00 27.80           C
ATOM   7275  ND1 HIS C 172      60.607  10.644  49.870  1.00 29.50           N
ATOM   7276  CE1 HIS C 172      60.435  10.607  51.179  1.00 28.94           C
ATOM   7277  NE2 HIS C 172      59.621   9.606  51.463  1.00 30.15           N
ATOM   7278  CD2 HIS C 172      59.258   8.980  50.295  1.00 29.13           C
ATOM   7279  C   HIS C 172      60.866   8.167  45.862  1.00 25.54           C
ATOM   7280  O   HIS C 172      61.093   9.044  45.028  1.00 23.17           O
ATOM   7281  N   GLN C 173      60.538   6.917  45.543  1.00 23.96           N
ATOM   7282  CA  GLN C 173      60.396   6.485  44.158  1.00 24.80           C
ATOM   7283  CB  BGLN C 173     60.174   4.969  44.091  0.35 28.49           C
ATOM   7284  CB  AGLN C 173     60.193   4.963  44.083  0.65 31.75           C
ATOM   7285  CG  BGLN C 173     61.442   4.146  44.262  0.35 29.43           C
ATOM   7286  CG  AGLN C 173     60.019   4.399  42.666  0.65 34.92           C
```

FIGURE 3YYYYY

```
ATOM   7287  CD  BGLN C 173      61.167   2.754  44.804  0.35 32.85           C
ATOM   7288  CD  AGLN C 173      61.236   4.610  41.770  0.65 39.62           C
ATOM   7289  OE1 BGLN C 173      60.952   1.817  44.037  0.35 33.02           O
ATOM   7290  OE1 AGLN C 173      61.093   5.000  40.610  0.65 40.62           O
ATOM   7291  NE2 BGLN C 173      61.177   2.618  46.126  0.35 32.91           N
ATOM   7292  NE2 AGLN C 173      62.428   4.346  42.301  0.65 41.63           N
ATOM   7293  C   GLN  C 173      59.252   7.218  43.454  1.00 24.52           C
ATOM   7294  O   GLN  C 173      59.400   7.649  42.310  1.00 23.73           O
ATOM   7295  N   ARG  C 174      58.125   7.358  44.149  1.00 23.97           N
ATOM   7296  CA  ARG  C 174      56.923   7.972  43.595  1.00 24.56           C
ATOM   7297  CB  ARG  C 174      55.865   6.905  43.286  1.00 27.65           C
ATOM   7298  CG  ARG  C 174      56.122   6.124  41.993  1.00 31.90           C
ATOM   7299  CD  ARG  C 174      55.102   5.016  41.690  1.00 35.00           C
ATOM   7300  NE  ARG  C 174      54.816   4.186  42.860  1.00 39.03           N
ATOM   7301  CZ  ARG  C 174      55.580   3.182  43.283  1.00 41.28           C
ATOM   7302  NH1 ARG  C 174      55.229   2.502  44.366  1.00 40.68           N
ATOM   7303  NH2 ARG  C 174      56.692   2.853  42.632  1.00 39.36           N
ATOM   7304  C   ARG  C 174      56.363   9.010  44.561  1.00 26.31           C
ATOM   7305  O   ARG  C 174      56.145   8.723  45.744  1.00 28.75           O
ATOM   7306  N   VAL  C 175      56.151  10.224  44.056  1.00 23.11           N
ATOM   7307  CA  VAL  C 175      55.600  11.310  44.868  1.00 20.10           C
ATOM   7308  CB  VAL  C 175      56.612  12.494  45.020  1.00 22.50           C
ATOM   7309  CG1 VAL  C 175      55.996  13.655  45.783  1.00 22.30           C
ATOM   7310  CG2 VAL  C 175      57.888  12.038  45.724  1.00 21.59           C
ATOM   7311  C   VAL  C 175      54.289  11.792  44.254  1.00 19.28           C
ATOM   7312  O   VAL  C 175      54.199  12.011  43.043  1.00 22.33           O
ATOM   7313  N   LEU  C 176      53.268  11.933  45.092  1.00 19.18           N
ATOM   7314  CA  LEU  C 176      51.970  12.412  44.647  1.00 21.31           C
ATOM   7315  CB  LEU  C 176      50.854  11.541  45.234  1.00 20.22           C
ATOM   7316  CG  LEU  C 176      49.418  11.998  44.968  1.00 22.60           C
ATOM   7317  CD1 LEU  C 176      49.089  12.011  43.470  1.00 21.68           C
ATOM   7318  CD2 LEU  C 176      48.429  11.126  45.728  1.00 24.91           C
ATOM   7319  C   LEU  C 176      51.769  13.867  45.070  1.00 18.66           C
ATOM   7320  O   LEU  C 176      51.911  14.199  46.245  1.00 22.56           O
ATOM   7321  N   TYR  C 177      51.426  14.715  44.105  1.00 19.35           N
ATOM   7322  CA  TYR  C 177      51.124  16.120  44.366  1.00 20.12           C
ATOM   7323  CB  TYR  C 177      51.933  17.019  43.421  1.00 20.48           C
ATOM   7324  CG  TYR  C 177      51.546  18.481  43.489  1.00 20.06           C
ATOM   7325  CD1 TYR  C 177      51.893  19.258  44.595  1.00 20.96           C
ATOM   7326  CE1 TYR  C 177      51.533  20.589  44.674  1.00 21.74           C
ATOM   7327  CZ  TYR  C 177      50.828  21.172  43.634  1.00 19.84           C
ATOM   7328  OH  TYR  C 177      50.484  22.502  43.719  1.00 20.42           O
ATOM   7329  CE2 TYR  C 177      50.472  20.430  42.521  1.00 20.46           C
ATOM   7330  CD2 TYR  C 177      50.832  19.083  42.456  1.00 21.11           C
ATOM   7331  C   TYR  C 177      49.635  16.366  44.170  1.00 19.62           C
ATOM   7332  O   TYR  C 177      49.086  16.057  43.108  1.00 20.04           O
ATOM   7333  N   ILE  C 178      48.982  16.917  45.193  1.00 20.86           N
ATOM   7334  CA  ILE  C 178      47.552  17.233  45.124  1.00 21.59           C
ATOM   7335  CB  ILE  C 178      46.740  16.427  46.173  1.00 20.87           C
ATOM   7336  CG1 ILE  C 178      46.968  14.921  46.009  1.00 22.29           C
ATOM   7337  CD1 ILE  C 178      46.615  14.111  47.252  1.00 20.02           C
ATOM   7338  CG2 ILE  C 178      45.232  16.757  46.085  1.00 21.09           C
ATOM   7339  C   ILE  C 178      47.383  18.728  45.354  1.00 20.24           C
ATOM   7340  O   ILE  C 178      47.985  19.282  46.271  1.00 19.47           O
ATOM   7341  N   ASP  C 179      46.577  19.366  44.508  1.00 21.59           N
ATOM   7342  CA  ASP  C 179      46.439  20.819  44.484  1.00 22.34           C
ATOM   7343  CB  ASP  C 179      47.029  21.340  43.163  1.00 24.36           C
```

FIGURE 3ZZZZZ

```
ATOM   7344  CG  ASP C 179      47.327  22.832  43.182  1.00 28.02           C
ATOM   7345  OD1 ASP C 179      46.457  23.623  43.601  1.00 25.23           O
ATOM   7346  OD2 ASP C 179      48.398  23.314  42.750  1.00 26.56           O
ATOM   7347  C   ASP C 179      44.962  21.220  44.610  1.00 24.49           C
ATOM   7348  O   ASP C 179      44.191  21.048  43.659  1.00 21.23           O
ATOM   7349  N   ILE C 180      44.576  21.770  45.765  1.00 21.97           N
ATOM   7350  CA  ILE C 180      43.178  22.178  46.003  1.00 23.05           C
ATOM   7351  CB  ILE C 180      42.582  21.514  47.278  1.00 23.12           C
ATOM   7352  CG1 ILE C 180      43.287  21.999  48.552  1.00 23.80           C
ATOM   7353  CD1 ILE C 180      42.602  21.563  49.840  1.00 24.48           C
ATOM   7354  CG2 ILE C 180      42.621  19.995  47.156  1.00 22.97           C
ATOM   7355  C   ILE C 180      42.964  23.696  45.999  1.00 27.03           C
ATOM   7356  O   ILE C 180      41.877  24.194  46.326  1.00 24.86           O
ATOM   7357  N   ASP C 181      44.016  24.421  45.623  1.00 24.47           N
ATOM   7358  CA  ASP C 181      43.911  25.818  45.227  1.00 22.04           C
ATOM   7359  CB  ASP C 181      45.274  26.273  44.700  1.00 22.18           C
ATOM   7360  CG  ASP C 181      45.394  27.763  44.596  1.00 25.92           C
ATOM   7361  OD1 ASP C 181      46.039  28.381  45.481  1.00 25.43           O
ATOM   7362  OD2 ASP C 181      44.882  28.398  43.655  1.00 22.17           O
ATOM   7363  C   ASP C 181      42.860  25.935  44.120  1.00 23.98           C
ATOM   7364  O   ASP C 181      42.681  24.996  43.325  1.00 21.78           O
ATOM   7365  N   ILE C 182      42.172  27.072  44.042  1.00 18.61           N
ATOM   7366  CA  ILE C 182      41.178  27.263  42.985  1.00 19.52           C
ATOM   7367  CB  ILE C 182      40.283  28.506  43.255  1.00 22.35           C
ATOM   7368  CG1 ILE C 182      38.973  28.374  42.470  1.00 24.38           C
ATOM   7369  CD1 ILE C 182      38.030  29.568  42.602  1.00 25.20           C
ATOM   7370  CG2 ILE C 182      41.010  29.809  42.895  1.00 18.01           C
ATOM   7371  C   ILE C 182      41.799  27.304  41.578  1.00 21.11           C
ATOM   7372  O   ILE C 182      41.121  27.038  40.584  1.00 20.87           O
ATOM   7373  N   HIS C 183      43.086  27.654  41.504  1.00 22.00           N
ATOM   7374  CA  HIS C 183      43.792  27.773  40.230  1.00 21.81           C
ATOM   7375  CB  HIS C 183      44.739  28.981  40.246  1.00 22.70           C
ATOM   7376  CG  HIS C 183      44.052  30.280  40.530  1.00 20.36           C
ATOM   7377  ND1 HIS C 183      44.109  30.901  41.761  1.00 20.70           N
ATOM   7378  CE1 HIS C 183      43.408  32.022  41.715  1.00 22.77           C
ATOM   7379  NE2 HIS C 183      42.909  32.154  40.499  1.00 23.39           N
ATOM   7380  CD2 HIS C 183      43.300  31.079  39.738  1.00 22.59           C
ATOM   7381  C   HIS C 183      44.573  26.504  39.918  1.00 20.26           C
ATOM   7382  O   HIS C 183      44.987  25.770  40.827  1.00 23.33           O
ATOM   7383  N   HIS C 184      44.762  26.237  38.630  1.00 20.73           N
ATOM   7384  CA  HIS C 184      45.511  25.066  38.197  1.00 20.10           C
ATOM   7385  CB  HIS C 184      45.386  24.894  36.685  1.00 21.04           C
ATOM   7386  CG  HIS C 184      46.244  23.803  36.129  1.00 21.66           C
ATOM   7387  ND1 HIS C 184      47.186  24.025  35.151  1.00 22.38           N
ATOM   7388  CE1 HIS C 184      47.789  22.886  34.855  1.00 25.95           C
ATOM   7389  NE2 HIS C 184      47.276  21.935  35.616  1.00 23.89           N
ATOM   7390  CD2 HIS C 184      46.310  22.483  36.424  1.00 24.26           C
ATOM   7391  C   HIS C 184      46.983  25.231  38.585  1.00 20.57           C
ATOM   7392  O   HIS C 184      47.565  26.291  38.366  1.00 22.12           O
ATOM   7393  N   GLY C 185      47.568  24.183  39.162  1.00 20.01           N
ATOM   7394  CA  GLY C 185      48.981  24.189  39.524  1.00 19.93           C
ATOM   7395  C   GLY C 185      49.862  23.943  38.313  1.00 18.69           C
ATOM   7396  O   GLY C 185      50.513  22.905  38.220  1.00 22.24           O
ATOM   7397  N   ASP C 186      49.865  24.895  37.387  1.00 21.46           N
ATOM   7398  CA  ASP C 186      50.527  24.729  36.098  1.00 22.12           C
ATOM   7399  CB  ASP C 186      50.112  25.829  35.110  1.00 23.90           C
ATOM   7400  CG  ASP C 186      50.474  27.225  35.587  1.00 26.98           C
```

FIGURE 3AAAAAA

```
ATOM   7401  OD1 ASP C 186      50.590  28.125  34.726  1.00 29.01           O
ATOM   7402  OD2 ASP C 186      50.653  27.518  36.789  1.00 27.06           O
ATOM   7403  C   ASP C 186      52.051  24.622  36.191  1.00 22.36           C
ATOM   7404  O   ASP C 186      52.650  23.863  35.441  1.00 20.33           O
ATOM   7405  N   GLY C 187      52.669  25.377  37.099  1.00 20.83           N
ATOM   7406  CA  GLY C 187      54.119  25.305  37.285  1.00 17.69           C
ATOM   7407  C   GLY C 187      54.596  23.932  37.736  1.00 19.92           C
ATOM   7408  O   GLY C 187      55.617  23.432  37.268  1.00 19.79           O
ATOM   7409  N   VAL C 188      53.853  23.316  38.648  1.00 17.70           N
ATOM   7410  CA  VAL C 188      54.210  21.988  39.154  1.00 17.26           C
ATOM   7411  CB  VAL C 188      53.459  21.657  40.467  1.00 18.34           C
ATOM   7412  CG1 VAL C 188      53.896  20.297  41.026  1.00 16.90           C
ATOM   7413  CG2 VAL C 188      53.696  22.770  41.503  1.00 16.87           C
ATOM   7414  C   VAL C 188      53.957  20.919  38.091  1.00 20.99           C
ATOM   7415  O   VAL C 188      54.804  20.050  37.859  1.00 21.21           O
ATOM   7416  N   GLU C 189      52.794  20.995  37.449  1.00 19.83           N
ATOM   7417  CA  GLU C 189      52.448  20.066  36.380  1.00 22.49           C
ATOM   7418  CB  GLU C 189      51.053  20.365  35.835  1.00 24.00           C
ATOM   7419  CG  GLU C 189      50.635  19.464  34.686  1.00 26.09           C
ATOM   7420  CD  GLU C 189      49.317  19.889  34.077  1.00 30.16           C
ATOM   7421  OE1 GLU C 189      48.263  19.571  34.669  1.00 31.79           O
ATOM   7422  OE2 GLU C 189      49.340  20.548  33.017  1.00 29.94           O
ATOM   7423  C   GLU C 189      53.479  20.101  35.248  1.00 21.81           C
ATOM   7424  O   GLU C 189      53.882  19.054  34.752  1.00 22.91           O
ATOM   7425  N   GLU C 190      53.905  21.303  34.862  1.00 21.62           N
ATOM   7426  CA  GLU C 190      54.895  21.466  33.798  1.00 25.08           C
ATOM   7427  CB  GLU C 190      55.070  22.945  33.441  1.00 28.29           C
ATOM   7428  CG  GLU C 190      55.864  23.188  32.167  1.00 37.14           C
ATOM   7429  CD  GLU C 190      56.179  24.657  31.938  1.00 42.38           C
ATOM   7430  OE1 GLU C 190      56.608  25.338  32.892  1.00 42.50           O
ATOM   7431  OE2 GLU C 190      56.004  25.129  30.794  1.00 48.28           O
ATOM   7432  C   GLU C 190      56.243  20.846  34.180  1.00 23.96           C
ATOM   7433  O   GLU C 190      56.877  20.174  33.359  1.00 22.70           O
ATOM   7434  N   ALA C 191      56.671  21.051  35.424  1.00 20.50           N
ATOM   7435  CA  ALA C 191      57.964  20.523  35.869  1.00 18.25           C
ATOM   7436  CB  ALA C 191      58.245  20.922  37.302  1.00 20.41           C
ATOM   7437  C   ALA C 191      58.012  19.009  35.741  1.00 19.75           C
ATOM   7438  O   ALA C 191      59.049  18.450  35.393  1.00 19.34           O
ATOM   7439  N   PHE C 192      56.887  18.353  36.025  1.00 15.16           N
ATOM   7440  CA  PHE C 192      56.869  16.893  36.100  1.00 17.47           C
ATOM   7441  CB  PHE C 192      56.459  16.463  37.513  1.00 18.89           C
ATOM   7442  CG  PHE C 192      57.383  16.978  38.582  1.00 19.86           C
ATOM   7443  CD1 PHE C 192      56.942  17.918  39.506  1.00 22.01           C
ATOM   7444  CE1 PHE C 192      57.803  18.405  40.497  1.00 19.42           C
ATOM   7445  CZ  PHE C 192      59.128  17.964  40.540  1.00 17.93           C
ATOM   7446  CE2 PHE C 192      59.579  17.026  39.613  1.00 19.47           C
ATOM   7447  CD2 PHE C 192      58.710  16.547  38.639  1.00 21.48           C
ATOM   7448  C   PHE C 192      55.995  16.234  35.032  1.00 17.79           C
ATOM   7449  O   PHE C 192      55.563  15.092  35.192  1.00 17.44           O
ATOM   7450  N   TYR C 193      55.756  16.957  33.943  1.00 19.66           N
ATOM   7451  CA  TYR C 193      54.827  16.523  32.902  1.00 19.80           C
ATOM   7452  CB  TYR C 193      54.645  17.611  31.839  1.00 20.13           C
ATOM   7453  CG  TYR C 193      53.318  17.521  31.115  1.00 23.73           C
ATOM   7454  CD1 TYR C 193      53.259  17.182  29.763  1.00 24.52           C
ATOM   7455  CE1 TYR C 193      52.028  17.107  29.087  1.00 25.58           C
ATOM   7456  CZ  TYR C 193      50.854  17.359  29.780  1.00 28.10           C
ATOM   7457  OH  TYR C 193      49.637  17.273  29.142  1.00 30.86           O
```

FIGURE 3BBBBBB

```
ATOM   7458  CE2 TYR C 193      50.890  17.687  31.130  1.00 29.89           C
ATOM   7459  CD2 TYR C 193      52.119  17.764  31.788  1.00 24.79           C
ATOM   7460  C   TYR C 193      55.238  15.215  32.236  1.00 21.50           C
ATOM   7461  O   TYR C 193      54.374  14.418  31.864  1.00 19.68           O
ATOM   7462  N   THR C 194      56.549  14.994  32.106  1.00 18.37           N
ATOM   7463  CA  THR C 194      57.051  13.831  31.370  1.00 19.71           C
ATOM   7464  CB  THR C 194      58.083  14.256  30.297  1.00 22.65           C
ATOM   7465  OG1 THR C 194      59.179  14.934  30.925  1.00 24.40           O
ATOM   7466  CG2 THR C 194      57.494  15.308  29.356  1.00 22.15           C
ATOM   7467  C   THR C 194      57.627  12.738  32.272  1.00 20.22           C
ATOM   7468  O   THR C 194      58.284  11.814  31.793  1.00 23.17           O
ATOM   7469  N   THR C 195      57.375  12.830  33.572  1.00 20.54           N
ATOM   7470  CA  THR C 195      57.814  11.767  34.485  1.00 21.02           C
ATOM   7471  CB  THR C 195      58.861  12.275  35.521  1.00 22.46           C
ATOM   7472  OG1 THR C 195      59.262  11.186  36.371  1.00 24.54           O
ATOM   7473  CG2 THR C 195      58.238  13.270  36.506  1.00 20.85           C
ATOM   7474  C   THR C 195      56.671  11.041  35.184  1.00 23.69           C
ATOM   7475  O   THR C 195      55.670  11.652  35.574  1.00 21.32           O
ATOM   7476  N   ASP C 196      56.846   9.733  35.356  1.00 22.82           N
ATOM   7477  CA  ASP C 196      55.913   8.931  36.141  1.00 26.04           C
ATOM   7478  CB  ASP C 196      55.760   7.510  35.563  1.00 29.12           C
ATOM   7479  CG  ASP C 196      57.073   6.733  35.506  1.00 33.20           C
ATOM   7480  OD1 ASP C 196      58.149   7.295  35.804  1.00 32.15           O
ATOM   7481  OD2 ASP C 196      57.118   5.533  35.151  1.00 33.43           O
ATOM   7482  C   ASP C 196      56.304   8.887  37.620  1.00 24.57           C
ATOM   7483  O   ASP C 196      55.607   8.280  38.425  1.00 28.45           O
ATOM   7484  N   ARG C 197      57.409   9.548  37.974  1.00 22.80           N
ATOM   7485  CA  ARG C 197      57.870   9.587  39.365  1.00 22.28           C
ATOM   7486  CB  ARG C 197      59.385   9.795  39.440  1.00 23.51           C
ATOM   7487  CG  ARG C 197      60.187   8.622  38.900  1.00 27.97           C
ATOM   7488  CD  ARG C 197      61.632   8.580  39.369  1.00 27.50           C
ATOM   7489  NE  ARG C 197      61.751   8.651  40.826  1.00 25.31           N
ATOM   7490  CZ  ARG C 197      62.841   9.051  41.471  1.00 26.93           C
ATOM   7491  NH1 ARG C 197      62.854   9.087  42.797  1.00 26.76           N
ATOM   7492  NH2 ARG C 197      63.921   9.415  40.793  1.00 25.61           N
ATOM   7493  C   ARG C 197      57.157  10.644  40.194  1.00 19.00           C
ATOM   7494  O   ARG C 197      57.282  10.667  41.417  1.00 20.82           O
ATOM   7495  N   VAL C 198      56.427  11.527  39.522  1.00 19.16           N
ATOM   7496  CA  VAL C 198      55.563  12.492  40.200  1.00 20.14           C
ATOM   7497  CB  VAL C 198      56.149  13.927  40.187  1.00 19.38           C
ATOM   7498  CG1 VAL C 198      55.249  14.888  40.985  1.00 20.86           C
ATOM   7499  CG2 VAL C 198      57.559  13.941  40.746  1.00 17.19           C
ATOM   7500  C   VAL C 198      54.226  12.485  39.482  1.00 19.04           C
ATOM   7501  O   VAL C 198      54.175  12.677  38.271  1.00 21.59           O
ATOM   7502  N   MET C 199      53.156  12.216  40.221  1.00 20.36           N
ATOM   7503  CA  MET C 199      51.816  12.362  39.683  1.00 21.56           C
ATOM   7504  CB  MET C 199      50.922  11.191  40.095  1.00 23.09           C
ATOM   7505  CG  MET C 199      49.474  11.361  39.642  1.00 31.48           C
ATOM   7506  SD  MET C 199      48.489   9.876  39.842  1.00 41.47           S
ATOM   7507  CE  MET C 199      48.407   9.300  38.191  1.00 37.68           C
ATOM   7508  C   MET C 199      51.244  13.662  40.229  1.00 21.55           C
ATOM   7509  O   MET C 199      51.308  13.903  41.430  1.00 21.48           O
ATOM   7510  N   THR C 200      50.710  14.496  39.345  1.00 22.67           N
ATOM   7511  CA  THR C 200      50.096  15.759  39.758  1.00 22.30           C
ATOM   7512  CB  THR C 200      50.714  16.952  38.985  1.00 21.81           C
ATOM   7513  OG1 THR C 200      50.514  16.777  37.576  1.00 21.09           O
ATOM   7514  CG2 THR C 200      52.248  16.950  39.128  1.00 19.11           C
```

FIGURE 3CCCCCC

```
ATOM   7515  C    THR C 200      48.583  15.699  39.557  1.00 21.94           C
ATOM   7516  O    THR C 200      48.105  15.328  38.485  1.00 26.33           O
ATOM   7517  N    VAL C 201      47.839  16.059  40.601  1.00 18.95           N
ATOM   7518  CA   VAL C 201      46.376  16.020  40.577  1.00 18.55           C
ATOM   7519  CB   VAL C 201      45.798  14.944  41.539  1.00 22.30           C
ATOM   7520  CG1  VAL C 201      44.264  14.853  41.417  1.00 22.13           C
ATOM   7521  CG2  VAL C 201      46.437  13.572  41.294  1.00 21.04           C
ATOM   7522  C    VAL C 201      45.885  17.398  40.997  1.00 19.73           C
ATOM   7523  O    VAL C 201      46.105  17.812  42.136  1.00 20.42           O
ATOM   7524  N    SER C 202      45.254  18.110  40.068  1.00 20.47           N
ATOM   7525  CA   SER C 202      44.723  19.443  40.338  1.00 19.60           C
ATOM   7526  CB   SER C 202      45.458  20.505  39.505  1.00 19.91           C
ATOM   7527  OG   SER C 202      44.975  21.810  39.799  1.00 22.96           O
ATOM   7528  C    SER C 202      43.214  19.549  40.109  1.00 21.19           C
ATOM   7529  O    SER C 202      42.691  19.139  39.071  1.00 24.32           O
ATOM   7530  N    PHE C 203      42.535  20.114  41.102  1.00 20.19           N
ATOM   7531  CA   PHE C 203      41.126  20.492  41.009  1.00 21.78           C
ATOM   7532  CB   PHE C 203      40.357  20.011  42.249  1.00 22.93           C
ATOM   7533  CG   PHE C 203      40.509  18.542  42.531  1.00 23.37           C
ATOM   7534  CD1  PHE C 203      41.570  18.073  43.308  1.00 24.86           C
ATOM   7535  CE1  PHE C 203      41.722  16.710  43.568  1.00 25.25           C
ATOM   7536  CZ   PHE C 203      40.795  15.798  43.052  1.00 25.99           C
ATOM   7537  CE2  PHE C 203      39.728  16.256  42.279  1.00 24.65           C
ATOM   7538  CD2  PHE C 203      39.589  17.626  42.026  1.00 26.81           C
ATOM   7539  C    PHE C 203      41.093  22.010  40.936  1.00 20.23           C
ATOM   7540  O    PHE C 203      41.683  22.683  41.791  1.00 19.02           O
ATOM   7541  N    HIS C 204      40.439  22.559  39.919  1.00 20.36           N
ATOM   7542  CA   HIS C 204      40.507  24.003  39.698  1.00 24.48           C
ATOM   7543  CB   HIS C 204      41.829  24.359  39.017  1.00 22.06           C
ATOM   7544  CG   HIS C 204      42.168  23.444  37.891  1.00 23.01           C
ATOM   7545  ND1  HIS C 204      42.910  22.296  38.068  1.00 24.44           N
ATOM   7546  CE1  HIS C 204      43.031  21.672  36.909  1.00 24.65           C
ATOM   7547  NE2  HIS C 204      42.383  22.368  35.991  1.00 26.61           N
ATOM   7548  CD2  HIS C 204      41.827  23.477  36.582  1.00 24.89           C
ATOM   7549  C    HIS C 204      39.382  24.509  38.833  1.00 24.71           C
ATOM   7550  O    HIS C 204      38.796  23.753  38.062  1.00 27.67           O
ATOM   7551  N    LYS C 205      39.101  25.804  38.961  1.00 23.84           N
ATOM   7552  CA   LYS C 205      38.231  26.516  38.037  1.00 28.98           C
ATOM   7553  CB   LYS C 205      37.929  27.924  38.577  1.00 32.39           C
ATOM   7554  CG   LYS C 205      37.406  28.923  37.551  1.00 42.28           C
ATOM   7555  CD   LYS C 205      35.890  28.924  37.441  1.00 47.57           C
ATOM   7556  CE   LYS C 205      35.447  29.586  36.138  1.00 51.03           C
ATOM   7557  NZ   LYS C 205      34.409  28.786  35.424  1.00 54.84           N
ATOM   7558  C    LYS C 205      38.897  26.573  36.662  1.00 29.80           C
ATOM   7559  O    LYS C 205      40.119  26.750  36.558  1.00 28.05           O
ATOM   7560  N    TYR C 206      38.097  26.406  35.611  1.00 28.06           N
ATOM   7561  CA   TYR C 206      38.620  26.372  34.245  1.00 35.03           C
ATOM   7562  CB   TYR C 206      38.830  24.921  33.795  1.00 36.34           C
ATOM   7563  CG   TYR C 206      39.471  24.763  32.427  1.00 39.71           C
ATOM   7564  CD1  TYR C 206      38.694  24.500  31.298  1.00 39.23           C
ATOM   7565  CE1  TYR C 206      39.278  24.359  30.039  1.00 41.35           C
ATOM   7566  CZ   TYR C 206      40.653  24.476  29.908  1.00 41.29           C
ATOM   7567  OH   TYR C 206      41.233  24.338  28.669  1.00 41.80           O
ATOM   7568  CE2  TYR C 206      41.447  24.739  31.013  1.00 38.87           C
ATOM   7569  CD2  TYR C 206      40.855  24.876  32.265  1.00 37.49           C
ATOM   7570  C    TYR C 206      37.708  27.105  33.265  1.00 40.96           C
ATOM   7571  O    TYR C 206      36.481  27.029  33.366  1.00 41.60           O
```

FIGURE 3DDDDDD

```
ATOM   7572  N    GLY C  207      38.326  27.798  32.310  1.00 45.36           N
ATOM   7573  CA   GLY C  207      37.612  28.559  31.300  1.00 49.28           C
ATOM   7574  C    GLY C  207      37.486  30.013  31.703  1.00 52.65           C
ATOM   7575  O    GLY C  207      36.965  30.311  32.780  1.00 55.83           O
ATOM   7576  N    GLU C  208      37.973  30.911  30.846  1.00 55.33           N
ATOM   7577  CA   GLU C  208      37.932  32.357  31.099  1.00 58.48           C
ATOM   7578  CB   GLU C  208      36.480  32.864  31.051  1.00 63.63           C
ATOM   7579  CG   GLU C  208      36.307  34.299  30.568  1.00 68.24           C
ATOM   7580  CD   GLU C  208      34.846  34.695  30.410  1.00 70.99           C
ATOM   7581  OE1  GLU C  208      34.546  35.495  29.498  1.00 73.25           O
ATOM   7582  OE2  GLU C  208      33.995  34.212  31.193  1.00 71.18           O
ATOM   7583  C    GLU C  208      38.592  32.698  32.443  1.00 56.36           C
ATOM   7584  O    GLU C  208      38.143  33.595  33.165  1.00 58.55           O
ATOM   7585  N    TYR C  209      39.662  31.972  32.766  1.00 50.67           N
ATOM   7586  CA   TYR C  209      40.272  32.036  34.089  1.00 45.52           C
ATOM   7587  CB   TYR C  209      39.576  31.047  35.027  1.00 45.45           C
ATOM   7588  CG   TYR C  209      39.410  31.531  36.451  1.00 48.28           C
ATOM   7589  CD1  TYR C  209      40.101  30.919  37.499  1.00 48.18           C
ATOM   7590  CE1  TYR C  209      39.942  31.350  38.815  1.00 49.59           C
ATOM   7591  CZ   TYR C  209      39.085  32.408  39.090  1.00 51.54           C
ATOM   7592  OH   TYR C  209      38.930  32.843  40.386  1.00 54.81           O
ATOM   7593  CE2  TYR C  209      38.385  33.031  38.069  1.00 50.70           C
ATOM   7594  CD2  TYR C  209      38.546  32.588  36.757  1.00 50.19           C
ATOM   7595  C    TYR C  209      41.769  31.738  34.055  1.00 41.54           C
ATOM   7596  O    TYR C  209      42.234  30.906  33.269  1.00 39.29           O
ATOM   7597  N    PHE C  210      42.506  32.426  34.925  1.00 38.15           N
ATOM   7598  CA   PHE C  210      43.939  32.219  35.117  1.00 31.21           C
ATOM   7599  CB   PHE C  210      44.466  33.272  36.107  1.00 31.52           C
ATOM   7600  CG   PHE C  210      45.950  33.234  36.303  1.00 29.64           C
ATOM   7601  CD1  PHE C  210      46.509  32.512  37.353  1.00 28.18           C
ATOM   7602  CE1  PHE C  210      47.895  32.464  37.522  1.00 25.87           C
ATOM   7603  CZ   PHE C  210      48.719  33.142  36.640  1.00 26.92           C
ATOM   7604  CE2  PHE C  210      48.172  33.863  35.595  1.00 29.06           C
ATOM   7605  CD2  PHE C  210      46.794  33.908  35.430  1.00 28.56           C
ATOM   7606  C    PHE C  210      44.199  30.805  35.655  1.00 32.37           C
ATOM   7607  O    PHE C  210      43.411  30.308  36.464  1.00 33.33           O
ATOM   7608  N    PRO C  211      45.284  30.148  35.228  1.00 29.69           N
ATOM   7609  CA   PRO C  211      46.200  30.639  34.189  1.00 29.92           C
ATOM   7610  CB   PRO C  211      47.541  30.049  34.628  1.00 30.95           C
ATOM   7611  CG   PRO C  211      47.172  28.752  35.296  1.00 29.69           C
ATOM   7612  CD   PRO C  211      45.736  28.860  35.782  1.00 29.37           C
ATOM   7613  C    PRO C  211      45.874  30.160  32.770  1.00 33.32           C
ATOM   7614  O    PRO C  211      46.710  30.319  31.874  1.00 36.53           O
ATOM   7615  N    GLY C  212      44.699  29.570  32.571  1.00 29.52           N
ATOM   7616  CA   GLY C  212      44.281  29.136  31.245  1.00 29.40           C
ATOM   7617  C    GLY C  212      44.663  27.714  30.882  1.00 29.68           C
ATOM   7618  O    GLY C  212      44.434  27.274  29.752  1.00 32.43           O
ATOM   7619  N    THR C  213      45.225  26.991  31.845  1.00 27.08           N
ATOM   7620  CA   THR C  213      45.702  25.629  31.626  1.00 26.81           C
ATOM   7621  CB   THR C  213      47.197  25.538  31.969  1.00 27.96           C
ATOM   7622  OG1  THR C  213      47.425  26.176  33.231  1.00 28.66           O
ATOM   7623  CG2  THR C  213      48.039  26.359  30.995  1.00 31.02           C
ATOM   7624  C    THR C  213      44.918  24.641  32.493  1.00 26.91           C
ATOM   7625  O    THR C  213      44.010  25.031  33.230  1.00 27.78           O
ATOM   7626  N    GLY C  214      45.276  23.364  32.412  1.00 22.31           N
ATOM   7627  CA   GLY C  214      44.652  22.350  33.243  1.00 23.22           C
ATOM   7628  C    GLY C  214      43.400  21.766  32.621  1.00 25.46           C
```

FIGURE 3EEEEEE

```
ATOM   7629  O   GLY C 214      42.431  21.461  33.320  1.00 22.98           O
ATOM   7630  N   ASP C 215      43.429  21.614  31.301  1.00 27.80           N
ATOM   7631  CA  ASP C 215      42.369  20.937  30.566  1.00 29.96           C
ATOM   7632  CB  ASP C 215      42.605  21.074  29.056  1.00 33.13           C
ATOM   7633  CG  ASP C 215      41.358  20.781  28.238  1.00 37.94           C
ATOM   7634  OD1 ASP C 215      41.081  19.596  27.961  1.00 42.21           O
ATOM   7635  OD2 ASP C 215      40.594  21.672  27.827  1.00 43.89           O
ATOM   7636  C   ASP C 215      42.332  19.463  30.958  1.00 29.48           C
ATOM   7637  O   ASP C 215      43.358  18.873  31.300  1.00 28.38           O
ATOM   7638  N   LEU C 216      41.138  18.882  30.913  1.00 30.02           N
ATOM   7639  CA  LEU C 216      40.935  17.459  31.166  1.00 29.57           C
ATOM   7640  CB  LEU C 216      39.450  17.107  30.953  1.00 33.16           C
ATOM   7641  CG  LEU C 216      38.994  15.649  31.045  1.00 34.64           C
ATOM   7642  CD1 LEU C 216      39.049  15.151  32.481  1.00 35.08           C
ATOM   7643  CD2 LEU C 216      37.586  15.495  30.475  1.00 35.23           C
ATOM   7644  C   LEU C 216      41.827  16.580  30.277  1.00 24.16           C
ATOM   7645  O   LEU C 216      42.251  15.498  30.688  1.00 25.98           O
ATOM   7646  N   ARG C 217      42.112  17.055  29.068  1.00 27.68           N
ATOM   7647  CA  ARG C 217      42.907  16.299  28.098  1.00 31.90           C
ATOM   7648  CB  ARG C 217      42.574  16.742  26.672  1.00 35.87           C
ATOM   7649  CG  ARG C 217      41.268  16.164  26.146  1.00 42.66           C
ATOM   7650  CD  ARG C 217      40.173  17.198  25.929  1.00 46.68           C
ATOM   7651  NE  ARG C 217      38.837  16.623  26.093  1.00 50.27           N
ATOM   7652  CZ  ARG C 217      37.743  17.317  26.401  1.00 52.47           C
ATOM   7653  NH1 ARG C 217      37.804  18.632  26.589  1.00 53.82           N
ATOM   7654  NH2 ARG C 217      36.578  16.694  26.523  1.00 53.61           N
ATOM   7655  C   ARG C 217      44.416  16.385  28.345  1.00 34.37           C
ATOM   7656  O   ARG C 217      45.195  15.661  27.713  1.00 32.26           O
ATOM   7657  N   ASP C 218      44.823  17.266  29.259  1.00 31.81           N
ATOM   7658  CA  ASP C 218      46.232  17.381  29.638  1.00 30.92           C
ATOM   7659  CB  ASP C 218      46.539  18.771  30.206  1.00 29.08           C
ATOM   7660  CG  ASP C 218      46.207  19.891  29.232  1.00 36.38           C
ATOM   7661  OD1 ASP C 218      45.987  21.035  29.693  1.00 35.31           O
ATOM   7662  OD2 ASP C 218      46.137  19.728  27.991  1.00 36.55           O
ATOM   7663  C   ASP C 218      46.580  16.278  30.637  1.00 28.51           C
ATOM   7664  O   ASP C 218      46.352  16.408  31.841  1.00 28.99           O
ATOM   7665  N   ILE C 219      47.115  15.178  30.118  1.00 23.44           N
ATOM   7666  CA  ILE C 219      47.295  13.964  30.906  1.00 23.50           C
ATOM   7667  CB  ILE C 219      46.538  12.772  30.250  1.00 27.96           C
ATOM   7668  CG1 ILE C 219      47.015  12.552  28.807  1.00 30.42           C
ATOM   7669  CD1 ILE C 219      46.830  11.137  28.293  1.00 35.22           C
ATOM   7670  CG2 ILE C 219      45.020  13.007  30.297  1.00 32.60           C
ATOM   7671  C   ILE C 219      48.759  13.603  31.122  1.00 19.96           C
ATOM   7672  O   ILE C 219      49.060  12.582  31.731  1.00 21.29           O
ATOM   7673  N   GLY C 220      49.670  14.442  30.637  1.00 21.18           N
ATOM   7674  CA  GLY C 220      51.091  14.133  30.727  1.00 19.90           C
ATOM   7675  C   GLY C 220      51.600  13.600  29.405  1.00 21.84           C
ATOM   7676  O   GLY C 220      50.811  13.322  28.497  1.00 21.54           O
ATOM   7677  N   ALA C 221      52.918  13.456  29.291  1.00 22.69           N
ATOM   7678  CA  ALA C 221      53.532  12.956  28.058  1.00 25.94           C
ATOM   7679  CB  ALA C 221      53.972  14.120  27.175  1.00 24.79           C
ATOM   7680  C   ALA C 221      54.706  12.031  28.360  1.00 21.90           C
ATOM   7681  O   ALA C 221      55.261  12.059  29.460  1.00 22.78           O
ATOM   7682  N   GLY C 222      55.078  11.211  27.381  1.00 21.92           N
ATOM   7683  CA  GLY C 222      56.167  10.260  27.541  1.00 21.73           C
ATOM   7684  C   GLY C 222      55.887   9.276  28.656  1.00 22.68           C
ATOM   7685  O   GLY C 222      54.761   8.796  28.792  1.00 23.34           O
```

FIGURE 3FFFFFF

```
ATOM   7686  N   LYS C 223      56.904   8.991  29.468  1.00 21.97           N
ATOM   7687  CA  LYS C 223      56.735   8.139  30.646  1.00 27.37           C
ATOM   7688  CB  LYS C 223      58.062   7.986  31.399  1.00 33.27           C
ATOM   7689  CG  LYS C 223      59.116   7.165  30.660  1.00 41.30           C
ATOM   7690  CD  LYS C 223      60.277   6.795  31.574  1.00 45.09           C
ATOM   7691  CE  LYS C 223      61.581   6.676  30.796  1.00 50.54           C
ATOM   7692  NZ  LYS C 223      62.646   7.566  31.352  1.00 53.12           N
ATOM   7693  C   LYS C 223      55.657   8.690  31.591  1.00 24.41           C
ATOM   7694  O   LYS C 223      55.030   7.938  32.333  1.00 23.80           O
ATOM   7695  N   GLY C 224      55.438  10.000  31.542  1.00 23.35           N
ATOM   7696  CA  GLY C 224      54.457  10.645  32.395  1.00 19.57           C
ATOM   7697  C   GLY C 224      53.048  10.674  31.834  1.00 21.16           C
ATOM   7698  O   GLY C 224      52.169  11.284  32.435  1.00 20.55           O
ATOM   7699  N   LYS C 225      52.824  10.039  30.680  1.00 20.69           N
ATOM   7700  CA  LYS C 225      51.478   9.975  30.108  1.00 22.11           C
ATOM   7701  CB  LYS C 225      51.482   9.297  28.735  1.00 27.15           C
ATOM   7702  CG  LYS C 225      50.296   9.664  27.853  1.00 33.28           C
ATOM   7703  CD  LYS C 225      50.408   8.984  26.491  1.00 39.16           C
ATOM   7704  CE  LYS C 225      49.481   9.621  25.472  1.00 43.97           C
ATOM   7705  NZ  LYS C 225      49.797   9.170  24.084  1.00 48.53           N
ATOM   7706  C   LYS C 225      50.538   9.246  31.068  1.00 22.07           C
ATOM   7707  O   LYS C 225      50.822   8.121  31.489  1.00 23.24           O
ATOM   7708  N   TYR C 226      49.440   9.926  31.408  1.00 25.17           N
ATOM   7709  CA  TYR C 226      48.433   9.500  32.395  1.00 27.54           C
ATOM   7710  CB  TYR C 226      48.028   8.022  32.224  1.00 30.35           C
ATOM   7711  CG  TYR C 226      47.414   7.705  30.875  1.00 34.83           C
ATOM   7712  CD1 TYR C 226      46.154   8.196  30.522  1.00 37.41           C
ATOM   7713  CE1 TYR C 226      45.587   7.902  29.279  1.00 40.27           C
ATOM   7714  CZ  TYR C 226      46.286   7.108  28.380  1.00 42.03           C
ATOM   7715  OH  TYR C 226      45.736   6.815  27.152  1.00 46.14           O
ATOM   7716  CE2 TYR C 226      47.538   6.607  28.709  1.00 39.19           C
ATOM   7717  CD2 TYR C 226      48.093   6.904  29.953  1.00 36.64           C
ATOM   7718  C   TYR C 226      48.800   9.812  33.853  1.00 27.30           C
ATOM   7719  O   TYR C 226      48.042   9.485  34.765  1.00 26.26           O
ATOM   7720  N   TYR C 227      49.944  10.465  34.069  1.00 24.38           N
ATOM   7721  CA  TYR C 227      50.366  10.831  35.418  1.00 22.39           C
ATOM   7722  CB  TYR C 227      51.822  10.431  35.667  1.00 21.64           C
ATOM   7723  CG  TYR C 227      52.044   8.934  35.658  1.00 24.63           C
ATOM   7724  CD1 TYR C 227      52.301   8.253  34.465  1.00 26.45           C
ATOM   7725  CE1 TYR C 227      52.501   6.873  34.451  1.00 27.88           C
ATOM   7726  CZ  TYR C 227      52.442   6.166  35.637  1.00 28.61           C
ATOM   7727  OH  TYR C 227      52.644   4.807  35.633  1.00 30.42           O
ATOM   7728  CE2 TYR C 227      52.187   6.817  36.833  1.00 28.42           C
ATOM   7729  CD2 TYR C 227      51.985   8.198  36.837  1.00 27.00           C
ATOM   7730  C   TYR C 227      50.119  12.312  35.745  1.00 24.12           C
ATOM   7731  O   TYR C 227      50.572  12.815  36.771  1.00 23.83           O
ATOM   7732  N   ALA C 228      49.410  13.005  34.859  1.00 22.02           N
ATOM   7733  CA  ALA C 228      48.864  14.316  35.174  1.00 23.15           C
ATOM   7734  CB  ALA C 228      49.338  15.368  34.187  1.00 21.80           C
ATOM   7735  C   ALA C 228      47.344  14.181  35.154  1.00 26.08           C
ATOM   7736  O   ALA C 228      46.768  13.661  34.190  1.00 25.35           O
ATOM   7737  N   VAL C 229      46.711  14.613  36.239  1.00 22.23           N
ATOM   7738  CA  VAL C 229      45.264  14.497  36.404  1.00 21.88           C
ATOM   7739  CB  VAL C 229      44.900  13.556  37.586  1.00 22.10           C
ATOM   7740  CG1 VAL C 229      43.378  13.474  37.799  1.00 22.71           C
ATOM   7741  CG2 VAL C 229      45.491  12.154  37.392  1.00 25.22           C
ATOM   7742  C   VAL C 229      44.688  15.895  36.645  1.00 23.86           C
```

FIGURE 3GGGGGG

```
ATOM   7743  O    VAL C 229      45.122  16.598  37.560  1.00 23.46           O
ATOM   7744  N    ASN C 230      43.724  16.283  35.813  1.00 23.74           N
ATOM   7745  CA   ASN C 230      43.078  17.589  35.905  1.00 21.48           C
ATOM   7746  CB   ASN C 230      43.506  18.479  34.730  1.00 21.69           C
ATOM   7747  CG   ASN C 230      44.951  18.939  34.849  1.00 23.80           C
ATOM   7748  OD1  ASN C 230      45.320  19.608  35.816  1.00 22.70           O
ATOM   7749  ND2  ASN C 230      45.778  18.566  33.878  1.00 25.30           N
ATOM   7750  C    ASN C 230      41.556  17.481  35.963  1.00 24.23           C
ATOM   7751  O    ASN C 230      40.936  16.851  35.099  1.00 22.63           O
ATOM   7752  N    PHE C 231      40.969  18.091  36.991  1.00 23.13           N
ATOM   7753  CA   PHE C 231      39.615  18.201  37.108  1.00 21.59           C
ATOM   7754  CB   PHE C 231      39.031  17.589  38.421  1.00 23.22           C
ATOM   7755  CG   PHE C 231      37.574  17.200  38.410  1.00 24.99           C
ATOM   7756  CD1  PHE C 231      37.194  15.892  38.683  1.00 26.17           C
ATOM   7757  CE1  PHE C 231      35.846  15.523  38.669  1.00 26.36           C
ATOM   7758  CZ   PHE C 231      34.871  16.470  38.388  1.00 25.00           C
ATOM   7759  CE2  PHE C 231      35.235  17.785  38.112  1.00 27.53           C
ATOM   7760  CD2  PHE C 231      36.584  18.144  38.130  1.00 25.47           C
ATOM   7761  C    PHE C 231      39.103  19.674  37.013  1.00 23.17           C
ATOM   7762  O    PHE C 231      39.110  20.392  38.017  1.00 23.57           O
ATOM   7763  N    PRO C 232      38.771  20.124  35.804  1.00 23.05           N
ATOM   7764  CA   PRO C 232      38.300  21.495  35.590  1.00 25.35           C
ATOM   7765  CB   PRO C 232      38.369  21.654  34.067  1.00 27.46           C
ATOM   7766  CG   PRO C 232      38.222  20.266  33.522  1.00 26.45           C
ATOM   7767  CD   PRO C 232      38.828  19.353  34.546  1.00 27.22           C
ATOM   7768  C    PRO C 232      36.869  21.672  36.109  1.00 29.02           C
ATOM   7769  O    PRO C 232      36.012  20.813  35.880  1.00 27.62           O
ATOM   7770  N    MET C 233      36.632  22.767  36.824  1.00 27.97           N
ATOM   7771  CA   MET C 233      35.346  23.025  37.463  1.00 29.37           C
ATOM   7772  CB   MET C 233      35.494  22.995  38.988  1.00 31.11           C
ATOM   7773  CG   MET C 233      35.511  21.602  39.615  1.00 35.22           C
ATOM   7774  SD   MET C 233      36.353  21.604  41.231  1.00 38.62           S
ATOM   7775  CE   MET C 233      36.308  19.858  41.641  1.00 37.47           C
ATOM   7776  C    MET C 233      34.791  24.378  37.031  1.00 33.15           C
ATOM   7777  O    MET C 233      35.522  25.225  36.516  1.00 32.82           O
ATOM   7778  N    ARG C 234      33.493  24.572  37.237  1.00 32.33           N
ATOM   7779  CA   ARG C 234      32.856  25.863  36.998  1.00 33.50           C
ATOM   7780  CB   ARG C 234      31.538  25.680  36.246  1.00 36.25           C
ATOM   7781  CG   ARG C 234      31.703  25.550  34.743  1.00 42.43           C
ATOM   7782  CD   ARG C 234      30.873  24.437  34.123  1.00 50.34           C
ATOM   7783  NE   ARG C 234      31.161  24.282  32.696  1.00 56.45           N
ATOM   7784  CZ   ARG C 234      30.339  23.728  31.808  1.00 58.05           C
ATOM   7785  NH1  ARG C 234      30.710  23.641  30.537  1.00 59.79           N
ATOM   7786  NH2  ARG C 234      29.151  23.258  32.178  1.00 57.83           N
ATOM   7787  C    ARG C 234      32.622  26.576  38.328  1.00 32.08           C
ATOM   7788  O    ARG C 234      32.895  26.013  39.398  1.00 27.38           O
ATOM   7789  N    ASP C 235      32.126  27.812  38.251  1.00 31.97           N
ATOM   7790  CA   ASP C 235      31.793  28.615  39.432  1.00 35.89           C
ATOM   7791  CB   ASP C 235      31.073  29.903  39.012  1.00 42.65           C
ATOM   7792  CG   ASP C 235      31.956  30.851  38.221  1.00 50.99           C
ATOM   7793  OD1  ASP C 235      33.172  30.594  38.101  1.00 54.01           O
ATOM   7794  OD2  ASP C 235      31.516  31.889  37.681  1.00 52.23           O
ATOM   7795  C    ASP C 235      30.886  27.880  40.416  1.00 33.10           C
ATOM   7796  O    ASP C 235      29.993  27.134  40.009  1.00 31.23           O
ATOM   7797  N    GLY C 236      31.128  28.096  41.707  1.00 29.95           N
ATOM   7798  CA   GLY C 236      30.141  27.821  42.739  1.00 32.05           C
ATOM   7799  C    GLY C 236      30.089  26.441  43.362  1.00 32.08           C
```

FIGURE 3HHHHHH

```
ATOM   7800  O    GLY C 236      29.131  26.132  44.077  1.00  29.53           O
ATOM   7801  N    ILE C 237      31.102  25.613  43.111  1.00  29.02           N
ATOM   7802  CA   ILE C 237      31.148  24.288  43.722  1.00  30.75           C
ATOM   7803  CB   ILE C 237      32.406  23.494  43.273  1.00  32.33           C
ATOM   7804  CG1  ILE C 237      32.229  22.001  43.567  1.00  31.61           C
ATOM   7805  CD1  ILE C 237      32.304  21.152  42.344  1.00  34.57           C
ATOM   7806  CG2  ILE C 237      33.685  24.029  43.935  1.00  26.93           C
ATOM   7807  C    ILE C 237      31.066  24.398  45.244  1.00  33.67           C
ATOM   7808  O    ILE C 237      31.704  25.267  45.850  1.00  32.02           O
ATOM   7809  N    ASP C 238      30.260  23.532  45.850  1.00  34.63           N
ATOM   7810  CA   ASP C 238      30.076  23.540  47.298  1.00  34.77           C
ATOM   7811  CB   ASP C 238      28.585  23.651  47.671  1.00  39.13           C
ATOM   7812  CG   ASP C 238      27.732  22.531  47.084  1.00  44.74           C
ATOM   7813  OD1  ASP C 238      28.279  21.508  46.616  1.00  45.72           O
ATOM   7814  OD2  ASP C 238      26.485  22.591  47.055  1.00  48.25           O
ATOM   7815  C    ASP C 238      30.723  22.326  47.952  1.00  31.34           C
ATOM   7816  O    ASP C 238      31.259  21.456  47.262  1.00  30.89           O
ATOM   7817  N    ASP C 239      30.655  22.282  49.280  1.00  30.05           N
ATOM   7818  CA   ASP C 239      31.263  21.233  50.098  1.00  32.47           C
ATOM   7819  CB   ASP C 239      30.833  21.407  51.558  1.00  35.34           C
ATOM   7820  CG   ASP C 239      31.643  22.459  52.296  1.00  39.09           C
ATOM   7821  OD1  ASP C 239      32.659  22.959  51.755  1.00  38.69           O
ATOM   7822  OD2  ASP C 239      31.330  22.837  53.442  1.00  36.06           O
ATOM   7823  C    ASP C 239      30.912  19.810  49.661  1.00  35.54           C
ATOM   7824  O    ASP C 239      31.802  18.962  49.534  1.00  33.03           O
ATOM   7825  N    GLU C 240      29.618  19.554  49.463  1.00  34.62           N
ATOM   7826  CA   GLU C 240      29.127  18.214  49.125  1.00  38.42           C
ATOM   7827  CB   GLU C 240      27.588  18.132  49.208  1.00  42.18           C
ATOM   7828  CG   GLU C 240      26.823  18.962  48.176  1.00  51.64           C
ATOM   7829  CD   GLU C 240      25.339  18.624  48.097  1.00  56.37           C
ATOM   7830  OE1  GLU C 240      24.836  18.409  46.970  1.00  58.02           O
ATOM   7831  OE2  GLU C 240      24.667  18.585  49.153  1.00  59.74           O
ATOM   7832  C    GLU C 240      29.635  17.727  47.765  1.00  35.32           C
ATOM   7833  O    GLU C 240      30.138  16.608  47.656  1.00  36.83           O
ATOM   7834  N    SER C 241      29.515  18.579  46.748  1.00  35.39           N
ATOM   7835  CA   SER C 241      29.912  18.243  45.382  1.00  34.94           C
ATOM   7836  CB   SER C 241      29.471  19.336  44.413  1.00  34.90           C
ATOM   7837  OG   SER C 241      28.059  19.389  44.327  1.00  43.24           O
ATOM   7838  C    SER C 241      31.416  18.029  45.271  1.00  34.48           C
ATOM   7839  O    SER C 241      31.866  17.124  44.568  1.00  33.38           O
ATOM   7840  N    TYR C 242      32.183  18.862  45.976  1.00  30.03           N
ATOM   7841  CA   TYR C 242      33.642  18.771  45.970  1.00  27.72           C
ATOM   7842  CB   TYR C 242      34.260  19.969  46.695  1.00  27.30           C
ATOM   7843  CG   TYR C 242      35.719  20.222  46.370  1.00  26.43           C
ATOM   7844  CD1  TYR C 242      36.086  21.194  45.436  1.00  28.25           C
ATOM   7845  CE1  TYR C 242      37.430  21.442  45.141  1.00  26.95           C
ATOM   7846  CZ   TYR C 242      38.418  20.713  45.787  1.00  27.25           C
ATOM   7847  OH   TYR C 242      39.745  20.950  45.494  1.00  26.58           O
ATOM   7848  CE2  TYR C 242      38.081  19.745  46.719  1.00  28.45           C
ATOM   7849  CD2  TYR C 242      36.734  19.505  47.009  1.00  27.66           C
ATOM   7850  C    TYR C 242      34.087  17.480  46.629  1.00  29.13           C
ATOM   7851  O    TYR C 242      34.932  16.762  46.089  1.00  28.88           O
ATOM   7852  N    GLY C 243      33.504  17.186  47.790  1.00  28.46           N
ATOM   7853  CA   GLY C 243      33.827  15.988  48.545  1.00  30.69           C
ATOM   7854  C    GLY C 243      33.494  14.701  47.808  1.00  34.14           C
ATOM   7855  O    GLY C 243      34.233  13.716  47.912  1.00  34.47           O
ATOM   7856  N    GLN C 244      32.393  14.713  47.059  1.00  36.35           N
```

FIGURE 3IIIIII

```
ATOM   7857  CA   GLN C 244      31.947  13.545  46.292  1.00 40.00           C
ATOM   7858  CB   GLN C 244      30.479  13.694  45.882  1.00 43.26           C
ATOM   7859  CG   GLN C 244      29.491  13.396  46.999  1.00 49.53           C
ATOM   7860  CD   GLN C 244      28.046  13.506  46.545  1.00 53.70           C
ATOM   7861  OE1  GLN C 244      27.509  14.609  46.419  1.00 56.27           O
ATOM   7862  NE2  GLN C 244      27.412  12.363  46.302  1.00 55.69           N
ATOM   7863  C    GLN C 244      32.815  13.305  45.055  1.00 40.98           C
ATOM   7864  O    GLN C 244      32.689  12.278  44.382  1.00 39.10           O
ATOM   7865  N    ILE C 245      33.693  14.260  44.763  1.00 39.23           N
ATOM   7866  CA   ILE C 245      34.630  14.128  43.656  1.00 38.22           C
ATOM   7867  CB   ILE C 245      34.524  15.363  42.712  1.00 41.77           C
ATOM   7868  CG1  ILE C 245      33.773  14.985  41.430  1.00 44.28           C
ATOM   7869  CD1  ILE C 245      32.314  14.595  41.629  1.00 49.76           C
ATOM   7870  CG2  ILE C 245      35.896  15.971  42.387  1.00 43.30           C
ATOM   7871  C    ILE C 245      36.049  13.872  44.173  1.00 36.94           C
ATOM   7872  O    ILE C 245      36.758  13.009  43.648  1.00 32.61           O
ATOM   7873  N    PHE C 246      36.431  14.596  45.227  1.00 32.22           N
ATOM   7874  CA   PHE C 246      37.771  14.511  45.799  1.00 29.36           C
ATOM   7875  CB   PHE C 246      37.973  15.575  46.891  1.00 26.09           C
ATOM   7876  CG   PHE C 246      39.391  15.669  47.392  1.00 24.54           C
ATOM   7877  CD1  PHE C 246      39.797  14.956  48.513  1.00 24.43           C
ATOM   7878  CE1  PHE C 246      41.107  15.036  48.979  1.00 27.43           C
ATOM   7879  CZ   PHE C 246      42.034  15.842  48.314  1.00 26.43           C
ATOM   7880  CE2  PHE C 246      41.638  16.557  47.191  1.00 24.41           C
ATOM   7881  CD2  PHE C 246      40.320  16.472  46.738  1.00 26.14           C
ATOM   7882  C    PHE C 246      38.084  13.125  46.348  1.00 29.11           C
ATOM   7883  O    PHE C 246      39.106  12.540  45.996  1.00 28.42           O
ATOM   7884  N    LYS C 247      37.210  12.608  47.209  1.00 29.31           N
ATOM   7885  CA   LYS C 247      37.452  11.322  47.866  1.00 33.49           C
ATOM   7886  CB   LYS C 247      36.417  11.044  48.969  1.00 36.75           C
ATOM   7887  CG   LYS C 247      36.892  10.051  50.029  1.00 43.28           C
ATOM   7888  CD   LYS C 247      35.895   9.929  51.178  1.00 46.76           C
ATOM   7889  CE   LYS C 247      35.871   8.511  51.745  1.00 50.62           C
ATOM   7890  NZ   LYS C 247      34.486   7.944  51.798  1.00 50.63           N
ATOM   7891  C    LYS C 247      37.584  10.128  46.897  1.00 31.93           C
ATOM   7892  O    LYS C 247      38.549   9.373  47.011  1.00 31.70           O
ATOM   7893  N    PRO C 248      36.640   9.938  45.970  1.00 34.74           N
ATOM   7894  CA   PRO C 248      36.757   8.857  44.976  1.00 35.75           C
ATOM   7895  CB   PRO C 248      35.481   9.010  44.142  1.00 36.77           C
ATOM   7896  CG   PRO C 248      34.538   9.706  45.043  1.00 38.33           C
ATOM   7897  CD   PRO C 248      35.380  10.689  45.799  1.00 35.90           C
ATOM   7898  C    PRO C 248      37.994   8.987  44.077  1.00 33.39           C
ATOM   7899  O    PRO C 248      38.694   7.993  43.876  1.00 30.43           O
ATOM   7900  N    ILE C 249      38.257  10.186  43.556  1.00 32.73           N
ATOM   7901  CA   ILE C 249      39.416  10.404  42.688  1.00 31.14           C
ATOM   7902  CB   ILE C 249      39.409  11.838  42.084  1.00 34.48           C
ATOM   7903  CG1  ILE C 249      38.286  11.994  41.048  1.00 35.61           C
ATOM   7904  CD1  ILE C 249      38.465  11.195  39.755  1.00 42.58           C
ATOM   7905  CG2  ILE C 249      40.783  12.211  41.487  1.00 33.95           C
ATOM   7906  C    ILE C 249      40.723  10.101  43.425  1.00 31.62           C
ATOM   7907  O    ILE C 249      41.558   9.334  42.929  1.00 31.70           O
ATOM   7908  N    ILE C 250      40.884  10.679  44.616  1.00 29.58           N
ATOM   7909  CA   ILE C 250      42.110  10.499  45.399  1.00 27.49           C
ATOM   7910  CB   ILE C 250      42.194  11.541  46.560  1.00 26.02           C
ATOM   7911  CG1  ILE C 250      42.345  12.970  46.000  1.00 28.41           C
ATOM   7912  CD1  ILE C 250      43.600  13.226  45.124  1.00 24.20           C
ATOM   7913  CG2  ILE C 250      43.306  11.193  47.545  1.00 27.40           C
```

FIGURE 3JJJJJJJ

```
ATOM   7914  C    ILE C 250      42.276   9.062  45.899  1.00 28.26           C
ATOM   7915  O    ILE C 250      43.392   8.553  45.955  1.00 26.53           O
ATOM   7916  N    SER C 251      41.172   8.404  46.250  1.00 26.19           N
ATOM   7917  CA   SER C 251      41.242   6.994  46.630  1.00 28.60           C
ATOM   7918  CB   SER C 251      39.885   6.493  47.135  1.00 30.08           C
ATOM   7919  OG   SER C 251      39.575   7.097  48.379  1.00 36.51           O
ATOM   7920  C    SER C 251      41.753   6.129  45.467  1.00 26.24           C
ATOM   7921  O    SER C 251      42.614   5.275  45.662  1.00 30.22           O
ATOM   7922  N    LYS C 252      41.237   6.379  44.266  1.00 29.04           N
ATOM   7923  CA   LYS C 252      41.647   5.638  43.074  1.00 31.86           C
ATOM   7924  CB   LYS C 252      40.706   5.934  41.901  1.00 34.07           C
ATOM   7925  CG   LYS C 252      40.903   5.037  40.680  1.00 39.92           C
ATOM   7926  CD   LYS C 252      39.992   3.819  40.712  1.00 45.03           C
ATOM   7927  CE   LYS C 252      39.910   3.161  39.334  1.00 49.14           C
ATOM   7928  NZ   LYS C 252      40.540   1.807  39.321  1.00 49.66           N
ATOM   7929  C    LYS C 252      43.109   5.932  42.705  1.00 33.22           C
ATOM   7930  O    LYS C 252      43.863   5.021  42.355  1.00 29.80           O
ATOM   7931  N    VAL C 253      43.504   7.201  42.804  1.00 29.39           N
ATOM   7932  CA   VAL C 253      44.897   7.595  42.588  1.00 27.87           C
ATOM   7933  CB   VAL C 253      45.079   9.129  42.733  1.00 28.61           C
ATOM   7934  CG1  VAL C 253      46.553   9.498  42.874  1.00 26.41           C
ATOM   7935  CG2  VAL C 253      44.458   9.858  41.548  1.00 28.23           C
ATOM   7936  C    VAL C 253      45.847   6.842  43.529  1.00 29.22           C
ATOM   7937  O    VAL C 253      46.860   6.297  43.085  1.00 29.47           O
ATOM   7938  N    MET C 254      45.508   6.797  44.820  1.00 28.66           N
ATOM   7939  CA   MET C 254      46.330   6.097  45.810  1.00 31.78           C
ATOM   7940  CB   MET C 254      45.750   6.265  47.216  1.00 33.16           C
ATOM   7941  CG   MET C 254      45.912   7.660  47.791  1.00 34.69           C
ATOM   7942  SD   MET C 254      47.608   8.026  48.258  1.00 34.16           S
ATOM   7943  CE   MET C 254      47.396   9.694  48.937  1.00 35.33           C
ATOM   7944  C    MET C 254      46.473   4.610  45.486  1.00 33.25           C
ATOM   7945  O    MET C 254      47.569   4.050  45.572  1.00 31.39           O
ATOM   7946  N    GLU C 255      45.357   3.992  45.108  1.00 33.62           N
ATOM   7947  CA   GLU C 255      45.308   2.578  44.743  1.00 36.43           C
ATOM   7948  CB   GLU C 255      43.853   2.164  44.487  1.00 40.73           C
ATOM   7949  CG   GLU C 255      43.645   0.691  44.167  1.00 50.44           C
ATOM   7950  CD   GLU C 255      42.247   0.389  43.649  1.00 55.06           C
ATOM   7951  OE1  GLU C 255      41.629   1.271  43.008  1.00 57.22           O
ATOM   7952  OE2  GLU C 255      41.763  -0.739  43.880  1.00 57.85           O
ATOM   7953  C    GLU C 255      46.169   2.273  43.518  1.00 36.40           C
ATOM   7954  O    GLU C 255      46.939   1.313  43.520  1.00 38.27           O
ATOM   7955  N    MET C 256      46.033   3.100  42.484  1.00 34.77           N
ATOM   7956  CA   MET C 256      46.712   2.883  41.214  1.00 32.53           C
ATOM   7957  CB   MET C 256      45.970   3.601  40.081  1.00 32.00           C
ATOM   7958  CG   MET C 256      44.550   3.097  39.814  1.00 38.42           C
ATOM   7959  SD   MET C 256      44.431   1.296  39.623  1.00 42.06           S
ATOM   7960  CE   MET C 256      45.248   1.073  38.038  1.00 41.93           C
ATOM   7961  C    MET C 256      48.180   3.322  41.238  1.00 32.56           C
ATOM   7962  O    MET C 256      49.040   2.642  40.685  1.00 31.39           O
ATOM   7963  N    TYR C 257      48.458   4.457  41.878  1.00 29.12           N
ATOM   7964  CA   TYR C 257      49.793   5.051  41.843  1.00 27.80           C
ATOM   7965  CB   TYR C 257      49.709   6.587  41.829  1.00 25.69           C
ATOM   7966  CG   TYR C 257      51.037   7.273  41.583  1.00 25.43           C
ATOM   7967  CD1  TYR C 257      51.531   8.224  42.483  1.00 24.74           C
ATOM   7968  CE1  TYR C 257      52.748   8.857  42.261  1.00 26.34           C
ATOM   7969  CZ   TYR C 257      53.486   8.546  41.132  1.00 27.73           C
ATOM   7970  OH   TYR C 257      54.694   9.168  40.912  1.00 26.72           O
```

FIGURE 3KKKKKK

```
ATOM   7971  CE2 TYR C 257      53.025   7.600  40.224  1.00 25.98           C
ATOM   7972  CD2 TYR C 257      51.799   6.977  40.452  1.00 26.03           C
ATOM   7973  C   TYR C 257      50.714   4.564  42.958  1.00 29.04           C
ATOM   7974  O   TYR C 257      51.922   4.449  42.758  1.00 28.60           O
ATOM   7975  N   GLN C 258      50.139   4.271  44.124  1.00 29.61           N
ATOM   7976  CA  GLN C 258      50.895   3.829  45.301  1.00 30.48           C
ATOM   7977  CB  GLN C 258      51.317   2.360  45.175  1.00 36.43           C
ATOM   7978  CG  GLN C 258      50.184   1.389  44.904  1.00 43.68           C
ATOM   7979  CD  GLN C 258      50.682   0.114  44.263  1.00 50.00           C
ATOM   7980  OE1 GLN C 258      50.710   0.000  43.036  1.00 54.55           O
ATOM   7981  NE2 GLN C 258      51.095  -0.844  45.088  1.00 49.03           N
ATOM   7982  C   GLN C 258      52.122   4.699  45.597  1.00 30.14           C
ATOM   7983  O   GLN C 258      53.255   4.202  45.599  1.00 26.83           O
ATOM   7984  N   PRO C 259      51.903   5.990  45.854  1.00 26.91           N
ATOM   7985  CA  PRO C 259      53.012   6.904  46.161  1.00 25.70           C
ATOM   7986  CB  PRO C 259      52.337   8.281  46.162  1.00 25.75           C
ATOM   7987  CG  PRO C 259      50.904   7.998  46.542  1.00 24.78           C
ATOM   7988  CD  PRO C 259      50.595   6.675  45.888  1.00 25.39           C
ATOM   7989  C   PRO C 259      53.614   6.602  47.534  1.00 28.24           C
ATOM   7990  O   PRO C 259      52.930   6.020  48.378  1.00 30.52           O
ATOM   7991  N   SER C 260      54.870   6.979  47.760  1.00 27.65           N
ATOM   7992  CA  SER C 260      55.467   6.819  49.087  1.00 28.16           C
ATOM   7993  CB  SER C 260      56.822   6.105  49.010  1.00 34.12           C
ATOM   7994  OG  SER C 260      57.678   6.713  48.065  1.00 39.53           O
ATOM   7995  C   SER C 260      55.571   8.139  49.854  1.00 27.93           C
ATOM   7996  O   SER C 260      55.994   8.161  51.009  1.00 25.87           O
ATOM   7997  N   ALA C 261      55.176   9.234  49.202  1.00 23.37           N
ATOM   7998  CA  ALA C 261      55.130  10.559  49.824  1.00 25.56           C
ATOM   7999  CB  ALA C 261      56.504  11.224  49.795  1.00 24.30           C
ATOM   8000  C   ALA C 261      54.097  11.434  49.136  1.00 24.44           C
ATOM   8001  O   ALA C 261      53.796  11.251  47.948  1.00 23.67           O
ATOM   8002  N   VAL C 262      53.538  12.380  49.885  1.00 22.61           N
ATOM   8003  CA  VAL C 262      52.494  13.238  49.344  1.00 23.65           C
ATOM   8004  CB  VAL C 262      51.090  12.845  49.873  1.00 23.38           C
ATOM   8005  CG1 VAL C 262      49.992  13.709  49.247  1.00 22.24           C
ATOM   8006  CG2 VAL C 262      50.804  11.364  49.607  1.00 27.99           C
ATOM   8007  C   VAL C 262      52.781  14.708  49.647  1.00 21.56           C
ATOM   8008  O   VAL C 262      53.195  15.059  50.752  1.00 22.52           O
ATOM   8009  N   VAL C 263      52.568  15.547  48.642  1.00 22.31           N
ATOM   8010  CA  VAL C 263      52.614  16.995  48.800  1.00 19.80           C
ATOM   8011  CB  VAL C 263      53.616  17.657  47.820  1.00 19.48           C
ATOM   8012  CG1 VAL C 263      53.580  19.181  47.960  1.00 20.93           C
ATOM   8013  CG2 VAL C 263      55.014  17.142  48.057  1.00 18.31           C
ATOM   8014  C   VAL C 263      51.220  17.533  48.538  1.00 20.20           C
ATOM   8015  O   VAL C 263      50.665  17.329  47.458  1.00 24.47           O
ATOM   8016  N   LEU C 264      50.649  18.212  49.532  1.00 20.59           N
ATOM   8017  CA  LEU C 264      49.321  18.796  49.393  1.00 21.73           C
ATOM   8018  CB  LEU C 264      48.376  18.265  50.467  1.00 23.68           C
ATOM   8019  CG  LEU C 264      46.943  18.807  50.595  1.00 25.20           C
ATOM   8020  CD1 LEU C 264      46.109  18.509  49.362  1.00 26.73           C
ATOM   8021  CD2 LEU C 264      46.263  18.244  51.841  1.00 26.62           C
ATOM   8022  C   LEU C 264      49.400  20.321  49.427  1.00 21.69           C
ATOM   8023  O   LEU C 264      49.803  20.913  50.436  1.00 24.86           O
ATOM   8024  N   GLN C 265      49.032  20.947  48.313  1.00 19.20           N
ATOM   8025  CA  GLN C 265      48.938  22.395  48.248  1.00 20.54           C
ATOM   8026  CB  GLN C 265      49.224  22.882  46.827  1.00 19.06           C
ATOM   8027  CG  GLN C 265      49.654  24.344  46.721  1.00 21.26           C
```

FIGURE 3LLLLLL

```
ATOM   8028  CD   GLN C 265      48.494  25.282  46.408  1.00 23.47           C
ATOM   8029  OE1  GLN C 265      47.333  24.956  46.676  1.00 28.18           O
ATOM   8030  NE2  GLN C 265      48.802  26.447  45.840  1.00 19.56           N
ATOM   8031  C    GLN C 265      47.523  22.765  48.676  1.00 21.51           C
ATOM   8032  O    GLN C 265      46.554  22.350  48.042  1.00 23.35           O
ATOM   8033  N    CYS C 266      47.415  23.536  49.757  1.00 22.92           N
ATOM   8034  CA   CYS C 266      46.126  23.831  50.382  1.00 24.39           C
ATOM   8035  CB   CYS C 266      46.201  23.584  51.893  1.00 26.10           C
ATOM   8036  SG   CYS C 266      46.732  21.937  52.377  1.00 29.06           S
ATOM   8037  C    CYS C 266      45.674  25.266  50.150  1.00 24.88           C
ATOM   8038  O    CYS C 266      45.189  25.918  51.081  1.00 26.00           O
ATOM   8039  N    GLY C 267      45.833  25.751  48.921  1.00 23.48           N
ATOM   8040  CA   GLY C 267      45.412  27.094  48.555  1.00 24.37           C
ATOM   8041  C    GLY C 267      43.996  27.378  49.029  1.00 28.37           C
ATOM   8042  O    GLY C 267      43.069  26.616  48.742  1.00 22.56           O
ATOM   8043  N    ALA C 268      43.837  28.481  49.755  1.00 24.97           N
ATOM   8044  CA   ALA C 268      42.581  28.799  50.423  1.00 25.61           C
ATOM   8045  CB   ALA C 268      42.860  29.373  51.811  1.00 26.74           C
ATOM   8046  C    ALA C 268      41.685  29.738  49.611  1.00 24.93           C
ATOM   8047  O    ALA C 268      40.646  30.188  50.093  1.00 25.14           O
ATOM   8048  N    ASP C 269      42.068  30.018  48.370  1.00 21.96           N
ATOM   8049  CA   ASP C 269      41.222  30.836  47.503  1.00 22.63           C
ATOM   8050  CB   ASP C 269      42.033  31.554  46.421  1.00 19.25           C
ATOM   8051  CG   ASP C 269      43.019  30.641  45.708  1.00 24.43           C
ATOM   8052  OD1  ASP C 269      42.976  29.396  45.875  1.00 20.41           O
ATOM   8053  OD2  ASP C 269      43.888  31.108  44.950  1.00 23.10           O
ATOM   8054  C    ASP C 269      40.068  30.039  46.885  1.00 20.93           C
ATOM   8055  O    ASP C 269      39.299  30.564  46.081  1.00 21.23           O
ATOM   8056  N    SER C 270      39.971  28.770  47.267  1.00 21.50           N
ATOM   8057  CA   SER C 270      38.838  27.931  46.901  1.00 24.44           C
ATOM   8058  CB   SER C 270      39.282  26.476  46.707  1.00 21.59           C
ATOM   8059  OG   SER C 270      40.119  26.052  47.769  1.00 23.39           O
ATOM   8060  C    SER C 270      37.721  28.024  47.950  1.00 26.05           C
ATOM   8061  O    SER C 270      36.701  27.339  47.841  1.00 26.93           O
ATOM   8062  N    LEU C 271      37.918  28.878  48.954  1.00 25.05           N
ATOM   8063  CA   LEU C 271      36.921  29.086  50.005  1.00 25.99           C
ATOM   8064  CB   LEU C 271      37.581  29.608  51.282  1.00 23.60           C
ATOM   8065  CG   LEU C 271      38.445  28.649  52.107  1.00 26.00           C
ATOM   8066  CD1  LEU C 271      39.012  29.367  53.315  1.00 25.41           C
ATOM   8067  CD2  LEU C 271      37.667  27.413  52.540  1.00 27.51           C
ATOM   8068  C    LEU C 271      35.820  30.049  49.580  1.00 27.72           C
ATOM   8069  O    LEU C 271      36.042  30.960  48.776  1.00 24.33           O
ATOM   8070  N    SER C 272      34.624  29.838  50.132  1.00 28.75           N
ATOM   8071  CA   SER C 272      33.527  30.779  49.990  1.00 26.57           C
ATOM   8072  CB   SER C 272      32.353  30.348  50.870  1.00 29.43           C
ATOM   8073  OG   SER C 272      31.235  31.187  50.653  1.00 32.58           O
ATOM   8074  C    SER C 272      33.984  32.165  50.423  1.00 24.07           C
ATOM   8075  O    SER C 272      34.682  32.304  51.423  1.00 28.83           O
ATOM   8076  N    GLY C 273      33.597  33.177  49.657  1.00 27.95           N
ATOM   8077  CA   GLY C 273      33.867  34.559  50.013  1.00 31.38           C
ATOM   8078  C    GLY C 273      35.276  35.041  49.716  1.00 31.85           C
ATOM   8079  O    GLY C 273      35.672  36.113  50.184  1.00 28.59           O
ATOM   8080  N    ASP C 274      36.040  34.268  48.944  1.00 29.37           N
ATOM   8081  CA   ASP C 274      37.385  34.709  48.580  1.00 28.85           C
ATOM   8082  CB   ASP C 274      38.220  33.587  47.959  1.00 28.61           C
ATOM   8083  CG   ASP C 274      39.672  33.990  47.792  1.00 32.21           C
ATOM   8084  OD1  ASP C 274      40.454  33.825  48.756  1.00 32.02           O
```

FIGURE 3MMMMMM

| ATOM | 8085 | OD2 | ASP | C | 274 | 40.107 | 34.511 | 46.742 | 1.00 | 30.75 | O |
|------|------|-----|-----|---|-----|--------|--------|--------|------|-------|---|
| ATOM | 8086 | C | ASP | C | 274 | 37.326 | 35.903 | 47.640 | 1.00 | 29.31 | C |
| ATOM | 8087 | O | ASP | C | 274 | 36.488 | 35.954 | 46.741 | 1.00 | 29.37 | O |
| ATOM | 8088 | N | ARG | C | 275 | 38.231 | 36.855 | 47.859 | 1.00 | 29.73 | N |
| ATOM | 8089 | CA | ARG | C | 275 | 38.302 | 38.083 | 47.070 | 1.00 | 35.74 | C |
| ATOM | 8090 | CB | ARG | C | 275 | 39.447 | 38.962 | 47.580 | 1.00 | 38.60 | C |
| ATOM | 8091 | CG | ARG | C | 275 | 39.146 | 40.448 | 47.588 | 1.00 | 49.39 | C |
| ATOM | 8092 | CD | ARG | C | 275 | 40.170 | 41.275 | 48.348 | 1.00 | 53.24 | C |
| ATOM | 8093 | NE | ARG | C | 275 | 40.480 | 42.530 | 47.664 | 1.00 | 59.13 | N |
| ATOM | 8094 | CZ | ARG | C | 275 | 41.571 | 43.262 | 47.878 | 1.00 | 61.48 | C |
| ATOM | 8095 | NH1 | ARG | C | 275 | 42.485 | 42.878 | 48.762 | 1.00 | 60.41 | N |
| ATOM | 8096 | NH2 | ARG | C | 275 | 41.750 | 44.390 | 47.203 | 1.00 | 63.30 | N |
| ATOM | 8097 | C | ARG | C | 275 | 38.467 | 37.830 | 45.569 | 1.00 | 35.11 | C |
| ATOM | 8098 | O | ARG | C | 275 | 37.892 | 38.551 | 44.753 | 1.00 | 35.20 | O |
| ATOM | 8099 | N | LEU | C | 276 | 39.244 | 36.805 | 45.216 | 1.00 | 32.99 | N |
| ATOM | 8100 | CA | LEU | C | 276 | 39.523 | 36.478 | 43.815 | 1.00 | 33.48 | C |
| ATOM | 8101 | CB | LEU | C | 276 | 41.037 | 36.364 | 43.579 | 1.00 | 32.85 | C |
| ATOM | 8102 | CG | LEU | C | 276 | 41.911 | 37.588 | 43.897 | 1.00 | 33.08 | C |
| ATOM | 8103 | CD1 | LEU | C | 276 | 43.339 | 37.356 | 43.442 | 1.00 | 32.13 | C |
| ATOM | 8104 | CD2 | LEU | C | 276 | 41.354 | 38.874 | 43.280 | 1.00 | 35.12 | C |
| ATOM | 8105 | C | LEU | C | 276 | 38.823 | 35.207 | 43.329 | 1.00 | 34.90 | C |
| ATOM | 8106 | O | LEU | C | 276 | 38.602 | 35.038 | 42.127 | 1.00 | 38.61 | O |
| ATOM | 8107 | N | GLY | C | 277 | 38.480 | 34.320 | 44.259 | 1.00 | 31.77 | N |
| ATOM | 8108 | CA | GLY | C | 277 | 37.896 | 33.032 | 43.918 | 1.00 | 31.85 | C |
| ATOM | 8109 | C | GLY | C | 277 | 36.387 | 33.051 | 43.732 | 1.00 | 37.11 | C |
| ATOM | 8110 | O | GLY | C | 277 | 35.715 | 34.006 | 44.128 | 1.00 | 35.84 | O |
| ATOM | 8111 | N | CYS | C | 278 | 35.861 | 31.985 | 43.131 | 1.00 | 33.17 | N |
| ATOM | 8112 | CA | CYS | C | 278 | 34.427 | 31.854 | 42.877 | 1.00 | 37.35 | C |
| ATOM | 8113 | CB | CYS | C | 278 | 34.110 | 32.189 | 41.415 | 1.00 | 42.61 | C |
| ATOM | 8114 | SG | CYS | C | 278 | 35.244 | 31.433 | 40.227 | 1.00 | 56.01 | S |
| ATOM | 8115 | C | CYS | C | 278 | 33.880 | 30.469 | 43.244 | 1.00 | 33.64 | C |
| ATOM | 8116 | O | CYS | C | 278 | 32.852 | 30.040 | 42.715 | 1.00 | 33.08 | O |
| ATOM | 8117 | N | PHE | C | 279 | 34.578 | 29.773 | 44.142 | 1.00 | 29.85 | N |
| ATOM | 8118 | CA | PHE | C | 279 | 34.088 | 28.524 | 44.714 | 1.00 | 27.75 | C |
| ATOM | 8119 | CB | PHE | C | 279 | 35.253 | 27.564 | 44.998 | 1.00 | 26.59 | C |
| ATOM | 8120 | CG | PHE | C | 279 | 35.748 | 26.802 | 43.780 | 1.00 | 26.30 | C |
| ATOM | 8121 | CD1 | PHE | C | 279 | 36.740 | 25.828 | 43.916 | 1.00 | 25.91 | C |
| ATOM | 8122 | CE1 | PHE | C | 279 | 37.201 | 25.108 | 42.808 | 1.00 | 24.24 | C |
| ATOM | 8123 | CZ | PHE | C | 279 | 36.677 | 25.361 | 41.548 | 1.00 | 22.25 | C |
| ATOM | 8124 | CE2 | PHE | C | 279 | 35.682 | 26.331 | 41.393 | 1.00 | 27.56 | C |
| ATOM | 8125 | CD2 | PHE | C | 279 | 35.225 | 27.046 | 42.510 | 1.00 | 25.82 | C |
| ATOM | 8126 | C | PHE | C | 279 | 33.290 | 28.829 | 45.994 | 1.00 | 27.95 | C |
| ATOM | 8127 | O | PHE | C | 279 | 33.261 | 29.974 | 46.446 | 1.00 | 27.07 | O |
| ATOM | 8128 | N | ASN | C | 280 | 32.653 | 27.805 | 46.563 | 1.00 | 29.39 | N |
| ATOM | 8129 | CA | ASN | C | 280 | 31.781 | 27.950 | 47.733 | 1.00 | 29.61 | C |
| ATOM | 8130 | CB | ASN | C | 280 | 30.303 | 27.864 | 47.298 | 1.00 | 32.12 | C |
| ATOM | 8131 | CG | ASN | C | 280 | 29.343 | 28.527 | 48.294 | 1.00 | 36.48 | C |
| ATOM | 8132 | OD1 | ASN | C | 280 | 29.746 | 29.346 | 49.126 | 1.00 | 34.24 | O |
| ATOM | 8133 | ND2 | ASN | C | 280 | 28.060 | 28.166 | 48.207 | 1.00 | 35.36 | N |
| ATOM | 8134 | C | ASN | C | 280 | 32.086 | 26.927 | 48.833 | 1.00 | 28.57 | C |
| ATOM | 8135 | O | ASN | C | 280 | 31.176 | 26.395 | 49.479 | 1.00 | 29.42 | O |
| ATOM | 8136 | N | LEU | C | 281 | 33.369 | 26.646 | 49.050 | 1.00 | 26.62 | N |
| ATOM | 8137 | CA | LEU | C | 281 | 33.766 | 25.709 | 50.101 | 1.00 | 26.52 | C |
| ATOM | 8138 | CB | LEU | C | 281 | 35.108 | 25.039 | 49.773 | 1.00 | 26.76 | C |
| ATOM | 8139 | CG | LEU | C | 281 | 35.316 | 24.279 | 48.453 | 1.00 | 29.90 | C |
| ATOM | 8140 | CD1 | LEU | C | 281 | 36.705 | 23.645 | 48.437 | 1.00 | 25.82 | C |
| ATOM | 8141 | CD2 | LEU | C | 281 | 34.252 | 23.215 | 48.236 | 1.00 | 30.26 | C |

FIGURE 3NNNNNN

```
ATOM   8142  C    LEU C 281      33.870  26.412  51.451  1.00 29.26           C
ATOM   8143  O    LEU C 281      34.238  27.583  51.523  1.00 31.12           O
ATOM   8144  N    THR C 282      33.545  25.686  52.516  1.00 30.02           N
ATOM   8145  CA   THR C 282      33.773  26.168  53.874  1.00 29.16           C
ATOM   8146  CB   THR C 282      32.677  25.664  54.837  1.00 31.07           C
ATOM   8147  OG1  THR C 282      32.661  24.232  54.827  1.00 30.15           O
ATOM   8148  CG2  THR C 282      31.288  26.056  54.348  1.00 30.54           C
ATOM   8149  C    THR C 282      35.118  25.648  54.345  1.00 29.74           C
ATOM   8150  O    THR C 282      35.759  24.844  53.656  1.00 30.20           O
ATOM   8151  N    VAL C 283      35.531  26.094  55.528  1.00 29.42           N
ATOM   8152  CA   VAL C 283      36.776  25.645  56.140  1.00 29.21           C
ATOM   8153  CB   VAL C 283      37.123  26.497  57.389  1.00 30.05           C
ATOM   8154  CG1  VAL C 283      38.201  25.838  58.242  1.00 29.58           C
ATOM   8155  CG2  VAL C 283      37.571  27.893  56.958  1.00 28.11           C
ATOM   8156  C    VAL C 283      36.711  24.143  56.446  1.00 34.16           C
ATOM   8157  O    VAL C 283      37.707  23.428  56.306  1.00 31.84           O
ATOM   8158  N    LYS C 284      35.528  23.671  56.831  1.00 33.82           N
ATOM   8159  CA   LYS C 284      35.307  22.248  57.069  1.00 35.83           C
ATOM   8160  CB   LYS C 284      33.954  22.018  57.751  1.00 39.93           C
ATOM   8161  CG   LYS C 284      34.054  21.817  59.259  1.00 44.87           C
ATOM   8162  CD   LYS C 284      32.691  21.560  59.882  1.00 48.64           C
ATOM   8163  CE   LYS C 284      32.713  21.806  61.386  1.00 51.12           C
ATOM   8164  NZ   LYS C 284      31.372  22.209  61.897  1.00 52.36           N
ATOM   8165  C    LYS C 284      35.408  21.426  55.781  1.00 31.70           C
ATOM   8166  O    LYS C 284      36.025  20.360  55.773  1.00 33.92           O
ATOM   8167  N    GLY C 285      34.800  21.924  54.706  1.00 31.39           N
ATOM   8168  CA   GLY C 285      34.849  21.263  53.412  1.00 34.56           C
ATOM   8169  C    GLY C 285      36.270  21.182  52.886  1.00 33.53           C
ATOM   8170  O    GLY C 285      36.728  20.123  52.445  1.00 31.68           O
ATOM   8171  N    HIS C 286      36.965  22.314  52.958  1.00 30.67           N
ATOM   8172  CA   HIS C 286      38.364  22.425  52.561  1.00 29.94           C
ATOM   8173  CB   HIS C 286      38.836  23.863  52.778  1.00 30.45           C
ATOM   8174  CG   HIS C 286      39.995  24.267  51.923  1.00 29.92           C
ATOM   8175  ND1  HIS C 286      41.305  24.126  52.329  1.00 30.44           N
ATOM   8176  CE1  HIS C 286      42.108  24.588  51.388  1.00 30.91           C
ATOM   8177  NE2  HIS C 286      41.367  25.025  50.385  1.00 32.96           N
ATOM   8178  CD2  HIS C 286      40.042  24.843  50.698  1.00 30.44           C
ATOM   8179  C    HIS C 286      39.238  21.454  53.353  1.00 28.13           C
ATOM   8180  O    HIS C 286      40.001  20.690  52.769  1.00 30.44           O
ATOM   8181  N    ALA C 287      39.109  21.474  54.679  1.00 27.70           N
ATOM   8182  CA   ALA C 287      39.952  20.656  55.557  1.00 27.83           C
ATOM   8183  CB   ALA C 287      39.874  21.153  56.981  1.00 30.89           C
ATOM   8184  C    ALA C 287      39.679  19.148  55.510  1.00 27.52           C
ATOM   8185  O    ALA C 287      40.518  18.358  55.952  1.00 28.89           O
ATOM   8186  N    LYS C 288      38.510  18.758  55.001  1.00 30.57           N
ATOM   8187  CA   LYS C 288      38.179  17.343  54.791  1.00 36.81           C
ATOM   8188  CB   LYS C 288      36.727  17.189  54.315  1.00 42.03           C
ATOM   8189  CG   LYS C 288      36.240  15.738  54.239  1.00 46.30           C
ATOM   8190  CD   LYS C 288      34.730  15.637  54.418  1.00 53.03           C
ATOM   8191  CE   LYS C 288      34.186  14.343  53.819  1.00 55.60           C
ATOM   8192  NZ   LYS C 288      33.949  14.460  52.347  1.00 57.47           N
ATOM   8193  C    LYS C 288      39.141  16.698  53.764  1.00 35.10           C
ATOM   8194  O    LYS C 288      39.418  15.496  53.850  1.00 34.42           O
ATOM   8195  N    CYS C 289      39.645  17.510  52.857  1.00 34.86           N
ATOM   8196  CA   CYS C 289      40.660  17.077  51.900  1.00 31.43           C
ATOM   8197  CB   CYS C 289      40.958  18.198  50.908  1.00 31.88           C
ATOM   8198  SG   CYS C 289      39.550  18.673  49.887  1.00 35.55           S
```

FIGURE 3000000

```
ATOM   8199  C   CYS C 289      41.939  16.658  52.617  1.00 31.12           C
ATOM   8200  O   CYS C 289      42.525  15.620  52.300  1.00 32.32           O
ATOM   8201  N   VAL C 290      42.363  17.472  53.583  1.00 30.50           N
ATOM   8202  CA  VAL C 290      43.504  17.153  54.442  1.00 31.14           C
ATOM   8203  CB  VAL C 290      43.817  18.312  55.435  1.00 30.38           C
ATOM   8204  CG1 VAL C 290      44.990  17.962  56.335  1.00 31.91           C
ATOM   8205  CG2 VAL C 290      44.102  19.606  54.678  1.00 27.09           C
ATOM   8206  C   VAL C 290      43.250  15.850  55.202  1.00 32.02           C
ATOM   8207  O   VAL C 290      44.133  14.982  55.280  1.00 31.94           O
ATOM   8208  N   GLU C 291      42.042  15.723  55.753  1.00 31.71           N
ATOM   8209  CA  GLU C 291      41.629  14.530  56.487  1.00 34.68           C
ATOM   8210  CB  GLU C 291      40.198  14.693  57.012  1.00 40.12           C
ATOM   8211  CG  GLU C 291      40.018  14.306  58.472  1.00 50.33           C
ATOM   8212  CD  GLU C 291      38.709  14.810  59.060  1.00 57.09           C
ATOM   8213  OE1 GLU C 291      37.639  14.546  58.462  1.00 60.65           O
ATOM   8214  OE2 GLU C 291      38.747  15.469  60.125  1.00 58.67           O
ATOM   8215  C   GLU C 291      41.722  13.282  55.609  1.00 32.89           C
ATOM   8216  O   GLU C 291      42.289  12.269  56.021  1.00 31.14           O
ATOM   8217  N   VAL C 292      41.178  13.379  54.399  1.00 30.54           N
ATOM   8218  CA  VAL C 292      41.183  12.275  53.440  1.00 33.46           C
ATOM   8219  CB  VAL C 292      40.364  12.628  52.169  1.00 34.14           C
ATOM   8220  CG1 VAL C 292      40.679  11.681  51.011  1.00 36.49           C
ATOM   8221  CG2 VAL C 292      38.869  12.601  52.481  1.00 33.60           C
ATOM   8222  C   VAL C 292      42.612  11.828  53.105  1.00 33.26           C
ATOM   8223  O   VAL C 292      42.922  10.636  53.167  1.00 33.34           O
ATOM   8224  N   VAL C 293      43.478  12.789  52.782  1.00 30.56           N
ATOM   8225  CA  VAL C 293      44.886  12.503  52.480  1.00 30.95           C
ATOM   8226  CB  VAL C 293      45.639  13.778  52.006  1.00 28.29           C
ATOM   8227  CG1 VAL C 293      47.133  13.507  51.833  1.00 26.02           C
ATOM   8228  CG2 VAL C 293      45.048  14.276  50.712  1.00 25.73           C
ATOM   8229  C   VAL C 293      45.605  11.846  53.664  1.00 31.43           C
ATOM   8230  O   VAL C 293      46.346  10.875  53.489  1.00 29.13           O
ATOM   8231  N   LYS C 294      45.357  12.373  54.861  1.00 33.87           N
ATOM   8232  CA  LYS C 294      45.932  11.857  56.106  1.00 37.15           C
ATOM   8233  CB  LYS C 294      45.380  12.651  57.293  1.00 40.01           C
ATOM   8234  CG  LYS C 294      46.315  13.704  57.838  1.00 42.85           C
ATOM   8235  CD  LYS C 294      45.800  14.243  59.163  1.00 45.28           C
ATOM   8236  CE  LYS C 294      46.531  13.604  60.331  1.00 46.91           C
ATOM   8237  NZ  LYS C 294      45.592  13.033  61.327  1.00 48.09           N
ATOM   8238  C   LYS C 294      45.694  10.362  56.359  1.00 36.15           C
ATOM   8239  O   LYS C 294      46.568   9.685  56.905  1.00 38.99           O
ATOM   8240  N   THR C 295      44.521   9.856  55.967  1.00 36.58           N
ATOM   8241  CA  THR C 295      44.133   8.470  56.272  1.00 41.63           C
ATOM   8242  CB  THR C 295      42.627   8.205  55.990  1.00 42.30           C
ATOM   8243  OG1 THR C 295      42.309   8.565  54.641  1.00 43.99           O
ATOM   8244  CG2 THR C 295      41.734   9.106  56.834  1.00 44.39           C
ATOM   8245  C   THR C 295      44.978   7.412  55.562  1.00 42.13           C
ATOM   8246  O   THR C 295      44.929   6.235  55.925  1.00 43.13           O
ATOM   8247  N   PHE C 296      45.749   7.825  54.558  1.00 38.67           N
ATOM   8248  CA  PHE C 296      46.602   6.888  53.827  1.00 37.45           C
ATOM   8249  CB  PHE C 296      46.757   7.317  52.362  1.00 36.64           C
ATOM   8250  CG  PHE C 296      45.468   7.282  51.590  1.00 36.32           C
ATOM   8251  CD1 PHE C 296      45.010   6.090  51.026  1.00 36.57           C
ATOM   8252  CE1 PHE C 296      43.810   6.049  50.321  1.00 37.70           C
ATOM   8253  CZ  PHE C 296      43.050   7.207  50.172  1.00 37.45           C
ATOM   8254  CE2 PHE C 296      43.496   8.405  50.736  1.00 37.34           C
ATOM   8255  CD2 PHE C 296      44.698   8.433  51.443  1.00 34.49           C
```

FIGURE 3PPPPPP

```
ATOM   8256  C   PHE C 296      47.954   6.674  54.509  1.00 36.26           C
ATOM   8257  O   PHE C 296      48.735   5.815  54.093  1.00 37.47           O
ATOM   8258  N   ASN C 297      48.207   7.451  55.563  1.00 36.03           N
ATOM   8259  CA  ASN C 297      49.383   7.296  56.430  1.00 38.21           C
ATOM   8260  CB  ASN C 297      49.276   6.019  57.278  1.00 43.25           C
ATOM   8261  CG  ASN C 297      48.108   6.061  58.247  1.00 47.88           C
ATOM   8262  OD1 ASN C 297      48.139   6.781  59.244  1.00 49.17           O
ATOM   8263  ND2 ASN C 297      47.067   5.292  57.951  1.00 49.38           N
ATOM   8264  C   ASN C 297      50.727   7.364  55.703  1.00 38.07           C
ATOM   8265  O   ASN C 297      51.667   6.619  56.017  1.00 36.95           O
ATOM   8266  N   LEU C 298      50.805   8.271  54.734  1.00 33.92           N
ATOM   8267  CA  LEU C 298      52.029   8.505  53.978  1.00 31.96           C
ATOM   8268  CB  LEU C 298      51.712   8.591  52.481  1.00 32.36           C
ATOM   8269  CG  LEU C 298      51.259   7.299  51.786  1.00 31.43           C
ATOM   8270  CD1 LEU C 298      50.695   7.598  50.410  1.00 29.08           C
ATOM   8271  CD2 LEU C 298      52.396   6.288  51.701  1.00 31.17           C
ATOM   8272  C   LEU C 298      52.682   9.799  54.455  1.00 29.64           C
ATOM   8273  O   LEU C 298      51.972  10.729  54.854  1.00 28.28           O
ATOM   8274  N   PRO C 299      54.018   9.864  54.424  1.00 28.27           N
ATOM   8275  CA  PRO C 299      54.732  11.110  54.728  1.00 27.47           C
ATOM   8276  CB  PRO C 299      56.144  10.840  54.209  1.00 27.93           C
ATOM   8277  CG  PRO C 299      56.313   9.359  54.357  1.00 32.17           C
ATOM   8278  CD  PRO C 299      54.948   8.763  54.104  1.00 30.66           C
ATOM   8279  C   PRO C 299      54.097  12.250  53.952  1.00 26.74           C
ATOM   8280  O   PRO C 299      53.844  12.109  52.751  1.00 25.90           O
ATOM   8281  N   LEU C 300      53.820  13.354  54.634  1.00 25.46           N
ATOM   8282  CA  LEU C 300      52.996  14.401  54.051  1.00 24.61           C
ATOM   8283  CB  LEU C 300      51.571  14.321  54.615  1.00 28.92           C
ATOM   8284  CG  LEU C 300      50.543  15.394  54.245  1.00 28.04           C
ATOM   8285  CD1 LEU C 300      50.297  15.449  52.736  1.00 28.48           C
ATOM   8286  CD2 LEU C 300      49.238  15.132  54.985  1.00 30.82           C
ATOM   8287  C   LEU C 300      53.575  15.790  54.267  1.00 25.23           C
ATOM   8288  O   LEU C 300      53.848  16.192  55.399  1.00 25.15           O
ATOM   8289  N   LEU C 301      53.759  16.510  53.164  1.00 21.49           N
ATOM   8290  CA  LEU C 301      54.150  17.912  53.201  1.00 20.74           C
ATOM   8291  CB  LEU C 301      55.304  18.179  52.219  1.00 23.24           C
ATOM   8292  CG  LEU C 301      55.852  19.611  52.093  1.00 25.06           C
ATOM   8293  CD1 LEU C 301      56.530  20.101  53.379  1.00 22.54           C
ATOM   8294  CD2 LEU C 301      56.813  19.715  50.911  1.00 22.94           C
ATOM   8295  C   LEU C 301      52.932  18.749  52.849  1.00 21.05           C
ATOM   8296  O   LEU C 301      52.361  18.594  51.772  1.00 23.29           O
ATOM   8297  N   MET C 302      52.521  19.618  53.774  1.00 21.69           N
ATOM   8298  CA  MET C 302      51.359  20.473  53.561  1.00 21.29           C
ATOM   8299  CB  MET C 302      50.388  20.389  54.744  1.00 27.46           C
ATOM   8300  CG  MET C 302      49.780  19.010  54.979  1.00 32.03           C
ATOM   8301  SD  MET C 302      48.944  18.906  56.588  1.00 40.42           S
ATOM   8302  CE  MET C 302      47.817  20.334  56.455  1.00 30.58           C
ATOM   8303  C   MET C 302      51.808  21.917  53.365  1.00 21.90           C
ATOM   8304  O   MET C 302      52.554  22.460  54.184  1.00 21.74           O
ATOM   8305  N   LEU C 303      51.335  22.550  52.286  1.00 21.80           N
ATOM   8306  CA  LEU C 303      51.774  23.865  51.883  1.00 23.91           C
ATOM   8307  CB  LEU C 303      52.579  23.779  50.577  1.00 20.98           C
ATOM   8308  CG  LEU C 303      53.778  22.826  50.602  1.00 22.27           C
ATOM   8309  CD1 LEU C 303      54.353  22.612  49.213  1.00 21.27           C
ATOM   8310  CD2 LEU C 303      54.855  23.343  51.565  1.00 23.23           C
ATOM   8311  C   LEU C 303      50.596  24.802  51.696  1.00 24.83           C
ATOM   8312  O   LEU C 303      49.462  24.358  51.495  1.00 25.87           O
```

FIGURE 3QQQQQQ

```
ATOM   8313  N    GLY C 304      50.872  26.104  51.745  1.00 23.97           N
ATOM   8314  CA   GLY C 304      49.853  27.108  51.500  1.00 20.69           C
ATOM   8315  C    GLY C 304      49.605  27.321  50.022  1.00 21.16           C
ATOM   8316  O    GLY C 304      49.641  26.379  49.243  1.00 26.61           O
ATOM   8317  N    GLY C 305      49.355  28.563  49.633  1.00 22.00           N
ATOM   8318  CA   GLY C 305      49.013  28.884  48.259  1.00 22.76           C
ATOM   8319  C    GLY C 305      48.191  30.153  48.221  1.00 25.11           C
ATOM   8320  O    GLY C 305      48.411  31.055  49.029  1.00 24.31           O
ATOM   8321  N    GLY C 306      47.241  30.218  47.293  1.00 24.44           N
ATOM   8322  CA   GLY C 306      46.344  31.358  47.177  1.00 23.55           C
ATOM   8323  C    GLY C 306      45.467  31.536  48.403  1.00 24.84           C
ATOM   8324  O    GLY C 306      45.424  30.675  49.289  1.00 26.96           O
ATOM   8325  N    GLY C 307      44.771  32.665  48.456  1.00 25.02           N
ATOM   8326  CA   GLY C 307      43.872  32.968  49.559  1.00 23.82           C
ATOM   8327  C    GLY C 307      43.910  34.458  49.799  1.00 26.96           C
ATOM   8328  O    GLY C 307      44.945  34.987  50.211  1.00 22.52           O
ATOM   8329  N    TYR C 308      42.793  35.136  49.541  1.00 23.76           N
ATOM   8330  CA   TYR C 308      42.814  36.597  49.416  1.00 27.77           C
ATOM   8331  CB   TYR C 308      42.693  36.989  47.940  1.00 26.83           C
ATOM   8332  CG   TYR C 308      43.753  36.283  47.117  1.00 28.07           C
ATOM   8333  CD1  TYR C 308      43.452  35.127  46.388  1.00 26.78           C
ATOM   8334  CE1  TYR C 308      44.442  34.458  45.660  1.00 26.57           C
ATOM   8335  CZ   TYR C 308      45.744  34.945  45.679  1.00 29.46           C
ATOM   8336  OH   TYR C 308      46.737  34.306  44.982  1.00 29.72           O
ATOM   8337  CE2  TYR C 308      46.066  36.076  46.408  1.00 28.66           C
ATOM   8338  CD2  TYR C 308      45.076  36.730  47.127  1.00 27.76           C
ATOM   8339  C    TYR C 308      41.813  37.327  50.312  1.00 29.75           C
ATOM   8340  O    TYR C 308      41.809  38.563  50.395  1.00 28.15           O
ATOM   8341  N    THR C 309      40.972  36.546  50.978  1.00 25.30           N
ATOM   8342  CA   THR C 309      40.192  37.033  52.105  1.00 27.14           C
ATOM   8343  CB   THR C 309      38.749  36.516  52.006  1.00 23.72           C
ATOM   8344  OG1  THR C 309      38.129  37.116  50.866  1.00 23.76           O
ATOM   8345  CG2  THR C 309      37.907  37.015  53.170  1.00 27.85           C
ATOM   8346  C    THR C 309      40.913  36.508  53.333  1.00 24.55           C
ATOM   8347  O    THR C 309      40.725  35.358  53.737  1.00 27.78           O
ATOM   8348  N    ILE C 310      41.763  37.356  53.911  1.00 24.18           N
ATOM   8349  CA   ILE C 310      42.811  36.867  54.802  1.00 24.94           C
ATOM   8350  CB   ILE C 310      43.986  37.884  54.944  1.00 30.16           C
ATOM   8351  CG1  ILE C 310      43.556  39.153  55.687  1.00 31.78           C
ATOM   8352  CD1  ILE C 310      44.703  40.139  55.940  1.00 38.21           C
ATOM   8353  CG2  ILE C 310      44.586  38.210  53.564  1.00 31.59           C
ATOM   8354  C    ILE C 310      42.311  36.337  56.148  1.00 24.14           C
ATOM   8355  O    ILE C 310      42.940  35.459  56.733  1.00 25.35           O
ATOM   8356  N    ARG C 311      41.173  36.842  56.626  1.00 25.85           N
ATOM   8357  CA   ARG C 311      40.578  36.286  57.842  1.00 28.37           C
ATOM   8358  CB   ARG C 311      39.365  37.103  58.323  1.00 30.47           C
ATOM   8359  CG   ARG C 311      38.216  37.214  57.335  1.00 33.72           C
ATOM   8360  CD   ARG C 311      37.079  38.113  57.802  1.00 39.28           C
ATOM   8361  NE   ARG C 311      36.342  38.683  56.675  1.00 43.97           N
ATOM   8362  CZ   ARG C 311      35.250  38.153  56.141  1.00 45.14           C
ATOM   8363  NH1  ARG C 311      34.738  37.026  56.628  1.00 49.98           N
ATOM   8364  NH2  ARG C 311      34.662  38.751  55.116  1.00 46.49           N
ATOM   8365  C    ARG C 311      40.211  34.812  57.639  1.00 25.42           C
ATOM   8366  O    ARG C 311      40.403  33.993  58.537  1.00 25.65           O
ATOM   8367  N    ASN C 312      39.710  34.480  56.451  1.00 24.42           N
ATOM   8368  CA   ASN C 312      39.326  33.099  56.143  1.00 27.36           C
ATOM   8369  CB   ASN C 312      38.312  33.056  54.998  1.00 26.48           C
```

FIGURE 3RRRRRR

```
ATOM   8370  CG   ASN C 312      36.979  33.675  55.384  1.00  29.35           C
ATOM   8371  OD1  ASN C 312      36.667  33.810  56.572  1.00  31.57           O
ATOM   8372  ND2  ASN C 312      36.192  34.065  54.388  1.00  30.14           N
ATOM   8373  C    ASN C 312      40.521  32.184  55.875  1.00  26.47           C
ATOM   8374  O    ASN C 312      40.485  30.994  56.199  1.00  27.55           O
ATOM   8375  N    VAL C 313      41.587  32.747  55.314  1.00  28.64           N
ATOM   8376  CA   VAL C 313      42.835  32.002  55.128  1.00  23.01           C
ATOM   8377  CB   VAL C 313      43.876  32.834  54.344  1.00  26.01           C
ATOM   8378  CG1  VAL C 313      45.243  32.154  54.338  1.00  25.30           C
ATOM   8379  CG2  VAL C 313      43.400  33.060  52.933  1.00  19.87           C
ATOM   8380  C    VAL C 313      43.398  31.589  56.486  1.00  26.54           C
ATOM   8381  O    VAL C 313      43.768  30.426  56.698  1.00  25.19           O
ATOM   8382  N    ALA C 314      43.436  32.545  57.413  1.00  23.30           N
ATOM   8383  CA   ALA C 314      43.903  32.279  58.767  1.00  25.85           C
ATOM   8384  CB   ALA C 314      43.874  33.560  59.612  1.00  24.53           C
ATOM   8385  C    ALA C 314      43.077  31.169  59.419  1.00  22.71           C
ATOM   8386  O    ALA C 314      43.639  30.267  60.041  1.00  27.68           O
ATOM   8387  N    ARG C 315      41.754  31.231  59.261  1.00  24.64           N
ATOM   8388  CA   ARG C 315      40.856  30.202  59.796  1.00  26.07           C
ATOM   8389  CB   ARG C 315      39.398  30.546  59.498  1.00  26.37           C
ATOM   8390  CG   ARG C 315      38.814  31.678  60.314  1.00  29.61           C
ATOM   8391  CD   ARG C 315      37.536  32.235  59.711  1.00  28.44           C
ATOM   8392  NE   ARG C 315      36.728  32.924  60.712  1.00  31.85           N
ATOM   8393  CZ   ARG C 315      36.136  34.099  60.526  1.00  32.64           C
ATOM   8394  NH1  ARG C 315      35.425  34.639  61.512  1.00  32.15           N
ATOM   8395  NH2  ARG C 315      36.243  34.737  59.366  1.00  29.26           N
ATOM   8396  C    ARG C 315      41.161  28.841  59.172  1.00  22.89           C
ATOM   8397  O    ARG C 315      41.313  27.841  59.876  1.00  24.17           O
ATOM   8398  N    CYS C 316      41.242  28.831  57.843  1.00  23.64           N
ATOM   8399  CA   CYS C 316      41.482  27.618  57.065  1.00  24.73           C
ATOM   8400  CB   CYS C 316      41.552  27.952  55.573  1.00  26.69           C
ATOM   8401  SG   CYS C 316      41.290  26.544  54.470  1.00  30.04           S
ATOM   8402  C    CYS C 316      42.751  26.893  57.502  1.00  25.39           C
ATOM   8403  O    CYS C 316      42.699  25.732  57.896  1.00  23.75           O
ATOM   8404  N    TRP C 317      43.889  27.582  57.445  1.00  23.33           N
ATOM   8405  CA   TRP C 317      45.164  26.935  57.746  1.00  24.51           C
ATOM   8406  CB   TRP C 317      46.332  27.739  57.175  1.00  23.81           C
ATOM   8407  CG   TRP C 317      46.293  27.797  55.662  1.00  25.22           C
ATOM   8408  CD1  TRP C 317      45.608  26.956  54.822  1.00  26.01           C
ATOM   8409  NE1  TRP C 317      45.813  27.321  53.512  1.00  26.68           N
ATOM   8410  CE2  TRP C 317      46.642  28.412  53.478  1.00  24.30           C
ATOM   8411  CD2  TRP C 317      46.962  28.742  54.820  1.00  22.41           C
ATOM   8412  CE3  TRP C 317      47.813  29.832  55.058  1.00  22.65           C
ATOM   8413  CZ3  TRP C 317      48.301  30.556  53.964  1.00  25.31           C
ATOM   8414  CH2  TRP C 317      47.956  30.204  52.648  1.00  23.16           C
ATOM   8415  CZ2  TRP C 317      47.125  29.141  52.385  1.00  23.29           C
ATOM   8416  C    TRP C 317      45.356  26.604  59.226  1.00  24.23           C
ATOM   8417  O    TRP C 317      46.081  25.668  59.564  1.00  24.12           O
ATOM   8418  N    THR C 318      44.696  27.365  60.100  1.00  25.22           N
ATOM   8419  CA   THR C 318      44.627  27.014  61.520  1.00  25.36           C
ATOM   8420  CB   THR C 318      43.884  28.109  62.312  1.00  28.36           C
ATOM   8421  OG1  THR C 318      44.701  29.282  62.367  1.00  28.30           O
ATOM   8422  CG2  THR C 318      43.721  27.712  63.782  1.00  30.23           C
ATOM   8423  C    THR C 318      43.923  25.670  61.707  1.00  22.36           C
ATOM   8424  O    THR C 318      44.442  24.771  62.381  1.00  24.76           O
ATOM   8425  N    TYR C 319      42.742  25.549  61.108  1.00  23.19           N
ATOM   8426  CA   TYR C 319      41.941  24.343  61.246  1.00  28.45           C
```

FIGURE 3SSSSSS

```
ATOM   8427  CB   TYR C 319      40.547  24.533  60.647  1.00 30.63           C
ATOM   8428  CG   TYR C 319      39.605  23.392  60.961  1.00 33.37           C
ATOM   8429  CD1  TYR C 319      39.354  23.008  62.283  1.00 35.05           C
ATOM   8430  CE1  TYR C 319      38.488  21.950  62.575  1.00 38.13           C
ATOM   8431  CZ   TYR C 319      37.870  21.269  61.537  1.00 40.49           C
ATOM   8432  OH   TYR C 319      37.014  20.226  61.812  1.00 42.40           O
ATOM   8433  CE2  TYR C 319      38.105  21.632  60.221  1.00 37.55           C
ATOM   8434  CD2  TYR C 319      38.972  22.689  59.942  1.00 36.45           C
ATOM   8435  C    TYR C 319      42.646  23.158  60.599  1.00 32.30           C
ATOM   8436  O    TYR C 319      42.611  22.043  61.126  1.00 31.07           O
ATOM   8437  N    GLU C 320      43.306  23.412  59.472  1.00 28.79           N
ATOM   8438  CA   GLU C 320      44.046  22.364  58.781  1.00 28.13           C
ATOM   8439  CB   GLU C 320      44.311  22.752  57.318  1.00 30.85           C
ATOM   8440  CG   GLU C 320      43.032  22.616  56.494  1.00 31.27           C
ATOM   8441  CD   GLU C 320      43.058  23.256  55.117  1.00 34.25           C
ATOM   8442  OE1  GLU C 320      44.011  23.989  54.777  1.00 33.04           O
ATOM   8443  OE2  GLU C 320      42.093  23.017  54.358  1.00 36.70           O
ATOM   8444  C    GLU C 320      45.287  21.909  59.555  1.00 27.42           C
ATOM   8445  O    GLU C 320      45.651  20.737  59.495  1.00 30.99           O
ATOM   8446  N    THR C 321      45.901  22.815  60.319  1.00 27.18           N
ATOM   8447  CA   THR C 321      46.977  22.438  61.239  1.00 27.40           C
ATOM   8448  CB   THR C 321      47.675  23.692  61.831  1.00 26.91           C
ATOM   8449  OG1  THR C 321      48.178  24.514  60.767  1.00 28.72           O
ATOM   8450  CG2  THR C 321      48.935  23.314  62.586  1.00 28.08           C
ATOM   8451  C    THR C 321      46.418  21.546  62.356  1.00 28.31           C
ATOM   8452  O    THR C 321      47.030  20.540  62.725  1.00 30.60           O
ATOM   8453  N    ALA C 322      45.244  21.913  62.865  1.00 28.58           N
ATOM   8454  CA   ALA C 322      44.563  21.130  63.893  1.00 29.50           C
ATOM   8455  CB   ALA C 322      43.335  21.873  64.398  1.00 27.76           C
ATOM   8456  C    ALA C 322      44.195  19.730  63.387  1.00 30.46           C
ATOM   8457  O    ALA C 322      44.348  18.749  64.115  1.00 31.98           O
ATOM   8458  N    VAL C 323      43.729  19.649  62.140  1.00 32.98           N
ATOM   8459  CA   VAL C 323      43.435  18.367  61.488  1.00 33.03           C
ATOM   8460  CB   VAL C 323      42.818  18.566  60.077  1.00 34.28           C
ATOM   8461  CG1  VAL C 323      42.842  17.263  59.267  1.00 36.51           C
ATOM   8462  CG2  VAL C 323      41.390  19.084  60.182  1.00 33.51           C
ATOM   8463  C    VAL C 323      44.687  17.475  61.426  1.00 36.88           C
ATOM   8464  O    VAL C 323      44.634  16.291  61.782  1.00 36.53           O
ATOM   8465  N    ALA C 324      45.807  18.053  60.996  1.00 35.61           N
ATOM   8466  CA   ALA C 324      47.090  17.350  60.972  1.00 35.88           C
ATOM   8467  CB   ALA C 324      48.201  18.272  60.464  1.00 37.43           C
ATOM   8468  C    ALA C 324      47.458  16.787  62.344  1.00 38.24           C
ATOM   8469  O    ALA C 324      47.997  15.680  62.447  1.00 35.86           O
ATOM   8470  N    LEU C 325      47.152  17.550  63.391  1.00 36.01           N
ATOM   8471  CA   LEU C 325      47.492  17.166  64.760  1.00 40.20           C
ATOM   8472  CB   LEU C 325      47.765  18.417  65.605  1.00 38.38           C
ATOM   8473  CG   LEU C 325      49.002  19.261  65.297  1.00 38.03           C
ATOM   8474  CD1  LEU C 325      48.823  20.658  65.858  1.00 35.65           C
ATOM   8475  CD2  LEU C 325      50.256  18.616  65.867  1.00 38.43           C
ATOM   8476  C    LEU C 325      46.426  16.305  65.451  1.00 40.24           C
ATOM   8477  O    LEU C 325      46.590  15.946  66.620  1.00 43.40           O
ATOM   8478  N    ASP C 326      45.352  15.978  64.730  1.00 44.20           N
ATOM   8479  CA   ASP C 326      44.185  15.278  65.292  1.00 49.09           C
ATOM   8480  CB   ASP C 326      44.509  13.811  65.611  1.00 51.36           C
ATOM   8481  CG   ASP C 326      44.542  12.937  64.374  1.00 54.85           C
ATOM   8482  OD1  ASP C 326      45.484  12.125  64.247  1.00 57.40           O
ATOM   8483  OD2  ASP C 326      43.674  12.985  63.476  1.00 56.93           O
```

FIGURE 3TTTTTT

```
ATOM   8484  C    ASP C 326      43.644  15.999  66.531  1.00 50.29           C
ATOM   8485  O    ASP C 326      43.376  15.384  67.569  1.00 47.29           O
ATOM   8486  N    CYS C 327      43.486  17.311  66.402  1.00 49.92           N
ATOM   8487  CA   CYS C 327      43.100  18.160  67.515  1.00 53.49           C
ATOM   8488  CB   CYS C 327      44.250  19.106  67.871  1.00 55.45           C
ATOM   8489  SG   CYS C 327      44.170  19.826  69.526  1.00 63.76           S
ATOM   8490  C    CYS C 327      41.855  18.946  67.141  1.00 53.25           C
ATOM   8491  O    CYS C 327      41.941  19.977  66.473  1.00 54.36           O
ATOM   8492  N    GLU C 328      40.694  18.444  67.554  1.00 52.30           N
ATOM   8493  CA   GLU C 328      39.442  19.148  67.311  1.00 52.70           C
ATOM   8494  CB   GLU C 328      38.231  18.237  67.541  1.00 55.40           C
ATOM   8495  CG   GLU C 328      36.889  18.877  67.207  1.00 60.34           C
ATOM   8496  CD   GLU C 328      36.721  19.167  65.725  1.00 64.30           C
ATOM   8497  OE1  GLU C 328      36.976  20.319  65.306  1.00 65.17           O
ATOM   8498  OE2  GLU C 328      36.328  18.244  64.979  1.00 66.01           O
ATOM   8499  C    GLU C 328      39.395  20.384  68.203  1.00 52.07           C
ATOM   8500  O    GLU C 328      39.210  20.283  69.419  1.00 55.49           O
ATOM   8501  N    ILE C 329      39.594  21.544  67.586  1.00 46.54           N
ATOM   8502  CA   ILE C 329      39.683  22.809  68.315  1.00 41.76           C
ATOM   8503  CB   ILE C 329      40.785  23.730  67.705  1.00 37.62           C
ATOM   8504  CG1  ILE C 329      40.618  23.872  66.186  1.00 37.69           C
ATOM   8505  CD1  ILE C 329      41.455  24.993  65.566  1.00 37.31           C
ATOM   8506  CG2  ILE C 329      42.177  23.210  68.086  1.00 36.35           C
ATOM   8507  C    ILE C 329      38.325  23.510  68.380  1.00 39.05           C
ATOM   8508  O    ILE C 329      37.508  23.347  67.474  1.00 40.28           O
ATOM   8509  N    PRO C 330      38.082  24.274  69.448  1.00 39.42           N
ATOM   8510  CA   PRO C 330      36.784  24.935  69.655  1.00 39.82           C
ATOM   8511  CB   PRO C 330      36.973  25.675  70.984  1.00 39.09           C
ATOM   8512  CG   PRO C 330      38.108  24.989  71.652  1.00 41.56           C
ATOM   8513  CD   PRO C 330      39.022  24.559  70.549  1.00 40.96           C
ATOM   8514  C    PRO C 330      36.439  25.931  68.548  1.00 39.03           C
ATOM   8515  O    PRO C 330      37.335  26.594  68.016  1.00 38.11           O
ATOM   8516  N    ASN C 331      35.154  26.022  68.211  1.00 36.42           N
ATOM   8517  CA   ASN C 331      34.674  26.968  67.206  1.00 34.58           C
ATOM   8518  CB   ASN C 331      33.208  26.694  66.856  1.00 36.22           C
ATOM   8519  CG   ASN C 331      32.746  27.460  65.624  1.00 37.46           C
ATOM   8520  OD1  ASN C 331      33.508  27.651  64.670  1.00 37.09           O
ATOM   8521  ND2  ASN C 331      31.495  27.904  65.638  1.00 34.95           N
ATOM   8522  C    ASN C 331      34.838  28.423  67.635  1.00 35.55           C
ATOM   8523  O    ASN C 331      34.972  29.311  66.795  1.00 36.91           O
ATOM   8524  N    GLU C 332      34.810  28.656  68.945  1.00 34.21           N
ATOM   8525  CA   GLU C 332      35.028  29.984  69.508  1.00 34.85           C
ATOM   8526  CB   GLU C 332      34.567  30.030  70.971  1.00 40.46           C
ATOM   8527  CG   GLU C 332      33.058  29.939  71.164  1.00 45.24           C
ATOM   8528  CD   GLU C 332      32.512  28.543  70.914  1.00 50.50           C
ATOM   8529  OE1  GLU C 332      31.511  28.422  70.172  1.00 52.83           O
ATOM   8530  OE2  GLU C 332      33.087  27.567  71.452  1.00 52.24           O
ATOM   8531  C    GLU C 332      36.509  30.319  69.410  1.00 32.41           C
ATOM   8532  O    GLU C 332      37.349  29.621  69.987  1.00 33.80           O
ATOM   8533  N    LEU C 333      36.827  31.380  68.670  1.00 30.05           N
ATOM   8534  CA   LEU C 333      38.215  31.815  68.514  1.00 30.56           C
ATOM   8535  CB   LEU C 333      38.314  32.934  67.473  1.00 31.86           C
ATOM   8536  CG   LEU C 333      38.074  32.557  66.013  1.00 33.66           C
ATOM   8537  CD1  LEU C 333      37.955  33.807  65.179  1.00 33.35           C
ATOM   8538  CD2  LEU C 333      39.183  31.652  65.472  1.00 34.63           C
ATOM   8539  C    LEU C 333      38.811  32.295  69.836  1.00 30.79           C
ATOM   8540  O    LEU C 333      38.128  32.952  70.616  1.00 32.89           O
```

FIGURE 3UUUUUU

```
ATOM   8541  N    PRO C 334      40.073  31.960  70.096  1.00 32.79           N
ATOM   8542  CA   PRO C 334      40.766  32.501  71.265  1.00 32.39           C
ATOM   8543  CB   PRO C 334      42.007  31.618  71.380  1.00 33.56           C
ATOM   8544  CG   PRO C 334      42.273  31.146  69.978  1.00 35.90           C
ATOM   8545  CD   PRO C 334      40.940  31.068  69.304  1.00 33.11           C
ATOM   8546  C    PRO C 334      41.159  33.936  70.952  1.00 33.60           C
ATOM   8547  O    PRO C 334      41.241  34.303  69.771  1.00 31.89           O
ATOM   8548  N    TYR C 335      41.381  34.749  71.978  1.00 31.33           N
ATOM   8549  CA   TYR C 335      41.855  36.093  71.725  1.00 29.19           C
ATOM   8550  CB   TYR C 335      41.972  36.921  73.003  1.00 27.53           C
ATOM   8551  CG   TYR C 335      42.297  38.360  72.695  1.00 25.81           C
ATOM   8552  CD1  TYR C 335      43.604  38.845  72.791  1.00 29.54           C
ATOM   8553  CE1  TYR C 335      43.900  40.162  72.478  1.00 29.98           C
ATOM   8554  CZ   TYR C 335      42.877  40.996  72.055  1.00 29.81           C
ATOM   8555  OH   TYR C 335      43.130  42.304  71.731  1.00 36.01           O
ATOM   8556  CE2  TYR C 335      41.584  40.528  71.946  1.00 29.63           C
ATOM   8557  CD2  TYR C 335      41.301  39.224  72.261  1.00 28.71           C
ATOM   8558  C    TYR C 335      43.205  36.016  71.022  1.00 30.83           C
ATOM   8559  O    TYR C 335      44.013  35.137  71.311  1.00 32.65           O
ATOM   8560  N    ASN C 336      43.426  36.935  70.091  1.00 32.83           N
ATOM   8561  CA   ASN C 336      44.679  37.006  69.353  1.00 34.43           C
ATOM   8562  CB   ASN C 336      44.664  36.019  68.172  1.00 32.04           C
ATOM   8563  CG   ASN C 336      43.570  36.320  67.175  1.00 32.29           C
ATOM   8564  OD1  ASN C 336      43.749  37.142  66.282  1.00 32.64           O
ATOM   8565  ND2  ASN C 336      42.423  35.665  67.329  1.00 29.81           N
ATOM   8566  C    ASN C 336      44.963  38.435  68.892  1.00 33.05           C
ATOM   8567  O    ASN C 336      44.099  39.311  68.999  1.00 31.87           O
ATOM   8568  N    ASP C 337      46.170  38.661  68.377  1.00 36.08           N
ATOM   8569  CA   ASP C 337      46.605  39.994  67.946  1.00 40.47           C
ATOM   8570  CB   ASP C 337      48.084  39.968  67.549  1.00 44.94           C
ATOM   8571  CG   ASP C 337      48.999  39.725  68.729  1.00 50.05           C
ATOM   8572  OD1  ASP C 337      48.665  40.169  69.849  1.00 52.95           O
ATOM   8573  OD2  ASP C 337      50.076  39.101  68.629  1.00 52.85           O
ATOM   8574  C    ASP C 337      45.782  40.589  66.806  1.00 37.80           C
ATOM   8575  O    ASP C 337      45.880  41.785  66.526  1.00 35.43           O
ATOM   8576  N    TYR C 338      44.976  39.752  66.154  1.00 36.18           N
ATOM   8577  CA   TYR C 338      44.172  40.175  65.009  1.00 36.49           C
ATOM   8578  CB   TYR C 338      44.707  39.524  63.723  1.00 38.72           C
ATOM   8579  CG   TYR C 338      46.193  39.753  63.541  1.00 41.96           C
ATOM   8580  CD1  TYR C 338      47.120  38.779  63.914  1.00 41.96           C
ATOM   8581  CE1  TYR C 338      48.488  38.994  63.771  1.00 44.34           C
ATOM   8582  CZ   TYR C 338      48.938  40.200  63.254  1.00 48.33           C
ATOM   8583  OH   TYR C 338      50.288  40.419  63.107  1.00 50.63           O
ATOM   8584  CE2  TYR C 338      48.037  41.189  62.888  1.00 47.29           C
ATOM   8585  CD2  TYR C 338      46.672  40.961  63.034  1.00 45.76           C
ATOM   8586  C    TYR C 338      42.691  39.874  65.218  1.00 34.69           C
ATOM   8587  O    TYR C 338      41.928  39.761  64.257  1.00 32.26           O
ATOM   8588  N    PHE C 339      42.297  39.786  66.489  1.00 33.64           N
ATOM   8589  CA   PHE C 339      40.952  39.364  66.890  1.00 33.03           C
ATOM   8590  CB   PHE C 339      40.798  39.454  68.413  1.00 33.42           C
ATOM   8591  CG   PHE C 339      39.600  38.721  68.950  1.00 34.26           C
ATOM   8592  CD1  PHE C 339      38.468  39.420  69.355  1.00 36.45           C
ATOM   8593  CE1  PHE C 339      37.356  38.750  69.861  1.00 36.86           C
ATOM   8594  CZ   PHE C 339      37.374  37.356  69.962  1.00 37.50           C
ATOM   8595  CE2  PHE C 339      38.500  36.650  69.561  1.00 34.28           C
ATOM   8596  CD2  PHE C 339      39.605  37.331  69.060  1.00 33.51           C
ATOM   8597  C    PHE C 339      39.813  40.113  66.192  1.00 32.32           C
```

FIGURE 3VVVVVV

```
ATOM   8598  O    PHE C 339      38.808  39.505  65.817  1.00 30.54           O
ATOM   8599  N    GLU C 340      39.983  41.422  66.009  1.00 32.55           N
ATOM   8600  CA   GLU C 340      38.955  42.275  65.401  1.00 34.45           C
ATOM   8601  CB   GLU C 340      39.331  43.757  65.558  1.00 35.59           C
ATOM   8602  CG   GLU C 340      40.504  44.212  64.693  1.00 38.97           C
ATOM   8603  CD   GLU C 340      41.859  44.064  65.370  1.00 43.04           C
ATOM   8604  OE1  GLU C 340      42.000  43.243  66.305  1.00 43.35           O
ATOM   8605  OE2  GLU C 340      42.799  44.779  64.962  1.00 46.15           O
ATOM   8606  C    GLU C 340      38.659  41.951  63.927  1.00 35.57           C
ATOM   8607  O    GLU C 340      37.576  42.260  63.428  1.00 37.95           O
ATOM   8608  N    TYR C 341      39.627  41.338  63.244  1.00 39.03           N
ATOM   8609  CA   TYR C 341      39.501  40.967  61.830  1.00 42.08           C
ATOM   8610  CB   TYR C 341      40.853  40.487  61.294  1.00 47.90           C
ATOM   8611  CG   TYR C 341      41.819  41.576  60.877  1.00 54.36           C
ATOM   8612  CD1  TYR C 341      42.432  42.400  61.823  1.00 56.81           C
ATOM   8613  CE1  TYR C 341      43.329  43.393  61.438  1.00 60.63           C
ATOM   8614  CZ   TYR C 341      43.628  43.559  60.093  1.00 62.30           C
ATOM   8615  OH   TYR C 341      44.515  44.535  59.701  1.00 65.85           O
ATOM   8616  CE2  TYR C 341      43.041  42.745  59.136  1.00 60.87           C
ATOM   8617  CD2  TYR C 341      42.145  41.759  59.532  1.00 56.88           C
ATOM   8618  C    TYR C 341      38.482  39.845  61.629  1.00 39.93           C
ATOM   8619  O    TYR C 341      37.985  39.635  60.521  1.00 41.18           O
ATOM   8620  N    PHE C 342      38.182  39.131  62.709  1.00 36.70           N
ATOM   8621  CA   PHE C 342      37.350  37.936  62.654  1.00 37.05           C
ATOM   8622  CB   PHE C 342      37.946  36.853  63.548  1.00 35.37           C
ATOM   8623  CG   PHE C 342      39.320  36.408  63.129  1.00 33.29           C
ATOM   8624  CD1  PHE C 342      39.490  35.570  62.026  1.00 32.65           C
ATOM   8625  CE1  PHE C 342      40.761  35.154  61.636  1.00 28.04           C
ATOM   8626  CZ   PHE C 342      41.879  35.571  62.350  1.00 28.92           C
ATOM   8627  CE2  PHE C 342      41.721  36.409  63.454  1.00 31.78           C
ATOM   8628  CD2  PHE C 342      40.442  36.822  63.834  1.00 29.81           C
ATOM   8629  C    PHE C 342      35.901  38.209  63.047  1.00 39.88           C
ATOM   8630  O    PHE C 342      35.114  37.277  63.226  1.00 37.14           O
ATOM   8631  N    GLY C 343      35.557  39.490  63.170  1.00 41.44           N
ATOM   8632  CA   GLY C 343      34.203  39.897  63.508  1.00 44.55           C
ATOM   8633  C    GLY C 343      33.270  39.823  62.313  1.00 45.92           C
ATOM   8634  O    GLY C 343      33.738  39.662  61.181  1.00 46.33           O
ATOM   8635  N    PRO C 344      31.961  39.951  62.546  1.00 48.16           N
ATOM   8636  CA   PRO C 344      31.397  40.167  63.886  1.00 48.81           C
ATOM   8637  CB   PRO C 344      30.136  40.982  63.587  1.00 50.73           C
ATOM   8638  CG   PRO C 344      29.704  40.522  62.213  1.00 50.48           C
ATOM   8639  CD   PRO C 344      30.910  39.923  61.513  1.00 49.58           C
ATOM   8640  C    PRO C 344      31.025  38.880  64.637  1.00 49.58           C
ATOM   8641  O    PRO C 344      30.491  38.959  65.749  1.00 49.01           O
ATOM   8642  N    ASP C 345      31.309  37.722  64.041  1.00 46.99           N
ATOM   8643  CA   ASP C 345      30.943  36.430  64.624  1.00 43.81           C
ATOM   8644  CB   ASP C 345      30.626  35.420  63.516  1.00 44.94           C
ATOM   8645  CG   ASP C 345      31.812  35.171  62.597  1.00 44.06           C
ATOM   8646  OD1  ASP C 345      32.007  35.955  61.643  1.00 44.07           O
ATOM   8647  OD2  ASP C 345      32.612  34.227  62.768  1.00 42.52           O
ATOM   8648  C    ASP C 345      32.013  35.865  65.564  1.00 41.00           C
ATOM   8649  O    ASP C 345      31.687  35.187  66.542  1.00 43.10           O
ATOM   8650  N    PHE C 346      33.283  36.134  65.250  1.00 38.71           N
ATOM   8651  CA   PHE C 346      34.436  35.662  66.031  1.00 32.58           C
ATOM   8652  CB   PHE C 346      34.511  36.382  67.382  1.00 35.82           C
ATOM   8653  CG   PHE C 346      34.528  37.883  67.261  1.00 36.67           C
ATOM   8654  CD1  PHE C 346      33.378  38.627  67.506  1.00 40.29           C
```

FIGURE 3WWWWWW

| ATOM | 8655 | CE1 | PHE | C | 346 | 33.389 | 40.025 | 67.390 | 1.00 | 39.18 | C |
|------|------|-----|-----|---|-----|--------|--------|--------|------|-------|---|
| ATOM | 8656 | CZ | PHE | C | 346 | 34.560 | 40.681 | 67.023 | 1.00 | 35.88 | C |
| ATOM | 8657 | CE2 | PHE | C | 346 | 35.714 | 39.946 | 66.772 | 1.00 | 38.17 | C |
| ATOM | 8658 | CD2 | PHE | C | 346 | 35.691 | 38.551 | 66.885 | 1.00 | 35.04 | C |
| ATOM | 8659 | C | PHE | C | 346 | 34.498 | 34.137 | 66.188 | 1.00 | 33.71 | C |
| ATOM | 8660 | O | PHE | C | 346 | 34.945 | 33.611 | 67.214 | 1.00 | 32.51 | O |
| ATOM | 8661 | N | LYS | C | 347 | 34.052 | 33.438 | 65.147 | 1.00 | 32.83 | N |
| ATOM | 8662 | CA | LYS | C | 347 | 34.085 | 31.977 | 65.120 | 1.00 | 32.84 | C |
| ATOM | 8663 | CB | LYS | C | 347 | 32.700 | 31.408 | 64.791 | 1.00 | 34.07 | C |
| ATOM | 8664 | CG | LYS | C | 347 | 31.577 | 31.872 | 65.726 | 1.00 | 37.23 | C |
| ATOM | 8665 | CD | LYS | C | 347 | 31.746 | 31.335 | 67.144 | 1.00 | 38.90 | C |
| ATOM | 8666 | CE | LYS | C | 347 | 30.538 | 31.668 | 68.014 | 1.00 | 44.03 | C |
| ATOM | 8667 | NZ | LYS | C | 347 | 29.327 | 30.899 | 67.593 | 1.00 | 44.06 | N |
| ATOM | 8668 | C | LYS | C | 347 | 35.114 | 31.483 | 64.107 | 1.00 | 31.93 | C |
| ATOM | 8669 | O | LYS | C | 347 | 35.476 | 32.205 | 63.179 | 1.00 | 33.36 | O |
| ATOM | 8670 | N | LEU | C | 348 | 35.579 | 30.254 | 64.300 | 1.00 | 31.88 | N |
| ATOM | 8671 | CA | LEU | C | 348 | 36.566 | 29.645 | 63.417 | 1.00 | 31.43 | C |
| ATOM | 8672 | CB | LEU | C | 348 | 37.211 | 28.432 | 64.100 | 1.00 | 31.19 | C |
| ATOM | 8673 | CG | LEU | C | 348 | 38.273 | 27.646 | 63.318 | 1.00 | 32.95 | C |
| ATOM | 8674 | CD1 | LEU | C | 348 | 39.596 | 28.406 | 63.257 | 1.00 | 31.00 | C |
| ATOM | 8675 | CD2 | LEU | C | 348 | 38.470 | 26.255 | 63.926 | 1.00 | 33.21 | C |
| ATOM | 8676 | C | LEU | C | 348 | 35.959 | 29.251 | 62.066 | 1.00 | 32.39 | C |
| ATOM | 8677 | O | LEU | C | 348 | 36.561 | 29.482 | 61.017 | 1.00 | 30.78 | O |
| ATOM | 8678 | N | HIS | C | 349 | 34.763 | 28.670 | 62.096 | 1.00 | 30.08 | N |
| ATOM | 8679 | CA | HIS | C | 349 | 34.138 | 28.150 | 60.882 | 1.00 | 32.82 | C |
| ATOM | 8680 | CB | HIS | C | 349 | 33.371 | 26.864 | 61.194 | 1.00 | 34.71 | C |
| ATOM | 8681 | CG | HIS | C | 349 | 34.265 | 25.747 | 61.633 | 1.00 | 35.14 | C |
| ATOM | 8682 | ND1 | HIS | C | 349 | 35.007 | 24.998 | 60.744 | 1.00 | 35.01 | N |
| ATOM | 8683 | CE1 | HIS | C | 349 | 35.722 | 24.109 | 61.411 | 1.00 | 33.83 | C |
| ATOM | 8684 | NE2 | HIS | C | 349 | 35.481 | 24.262 | 62.700 | 1.00 | 34.38 | N |
| ATOM | 8685 | CD2 | HIS | C | 349 | 34.578 | 25.285 | 62.867 | 1.00 | 35.31 | C |
| ATOM | 8686 | C | HIS | C | 349 | 33.286 | 29.186 | 60.151 | 1.00 | 34.74 | C |
| ATOM | 8687 | O | HIS | C | 349 | 32.824 | 30.163 | 60.748 | 1.00 | 39.52 | O |
| ATOM | 8688 | N | ILE | C | 350 | 33.112 | 28.976 | 58.849 | 1.00 | 34.38 | N |
| ATOM | 8689 | CA | ILE | C | 350 | 32.423 | 29.933 | 57.984 | 1.00 | 35.22 | C |
| ATOM | 8690 | CB | ILE | C | 350 | 33.401 | 30.557 | 56.942 | 1.00 | 37.53 | C |
| ATOM | 8691 | CG1 | ILE | C | 350 | 34.066 | 29.473 | 56.080 | 1.00 | 36.30 | C |
| ATOM | 8692 | CD1 | ILE | C | 350 | 34.379 | 29.917 | 54.659 | 1.00 | 37.14 | C |
| ATOM | 8693 | CG2 | ILE | C | 350 | 34.449 | 31.432 | 57.630 | 1.00 | 37.38 | C |
| ATOM | 8694 | C | ILE | C | 350 | 31.227 | 29.302 | 57.280 | 1.00 | 35.44 | C |
| ATOM | 8695 | O | ILE | C | 350 | 31.176 | 28.086 | 57.085 | 1.00 | 35.53 | O |
| ATOM | 8696 | N | SER | C | 351 | 30.268 | 30.142 | 56.907 | 1.00 | 39.33 | N |
| ATOM | 8697 | CA | SER | C | 351 | 29.083 | 29.699 | 56.187 | 1.00 | 42.04 | C |
| ATOM | 8698 | CB | SER | C | 351 | 27.856 | 30.495 | 56.643 | 1.00 | 44.97 | C |
| ATOM | 8699 | OG | SER | C | 351 | 27.483 | 30.139 | 57.964 | 1.00 | 49.58 | O |
| ATOM | 8700 | C | SER | C | 351 | 29.279 | 29.866 | 54.682 | 1.00 | 41.12 | C |
| ATOM | 8701 | O | SER | C | 351 | 29.916 | 30.827 | 54.241 | 1.00 | 38.64 | O |
| ATOM | 8702 | N | PRO | C | 352 | 28.726 | 28.943 | 53.893 | 1.00 | 40.74 | N |
| ATOM | 8703 | CA | PRO | C | 352 | 28.739 | 29.087 | 52.432 | 1.00 | 40.60 | C |
| ATOM | 8704 | CB | PRO | C | 352 | 28.213 | 27.739 | 51.940 | 1.00 | 39.61 | C |
| ATOM | 8705 | CG | PRO | C | 352 | 27.381 | 27.214 | 53.066 | 1.00 | 40.32 | C |
| ATOM | 8706 | CD | PRO | C | 352 | 28.033 | 27.712 | 54.325 | 1.00 | 40.29 | C |
| ATOM | 8707 | C | PRO | C | 352 | 27.796 | 30.207 | 52.003 | 1.00 | 42.80 | C |
| ATOM | 8708 | O | PRO | C | 352 | 26.869 | 30.539 | 52.746 | 1.00 | 42.50 | O |
| ATOM | 8709 | N | SER | C | 353 | 28.040 | 30.790 | 50.834 | 1.00 | 44.13 | N |
| ATOM | 8710 | CA | SER | C | 353 | 27.136 | 31.791 | 50.280 | 1.00 | 47.20 | C |
| ATOM | 8711 | CB | SER | C | 353 | 27.886 | 32.748 | 49.348 | 1.00 | 48.01 | C |

FIGURE 3XXXXXX

```
ATOM   8712  OG   SER C 353      28.079  32.181  48.064  1.00 46.91           O
ATOM   8713  C    SER C 353      25.988  31.092  49.552  1.00 47.59           C
ATOM   8714  O    SER C 353      26.013  29.874  49.362  1.00 44.88           O
ATOM   8715  N    ASN C 354      24.983  31.864  49.151  1.00 50.60           N
ATOM   8716  CA   ASN C 354      23.834  31.317  48.434  1.00 53.75           C
ATOM   8717  CB   ASN C 354      22.543  32.058  48.830  1.00 58.82           C
ATOM   8718  CG   ASN C 354      22.484  33.485  48.294  1.00 63.28           C
ATOM   8719  OD1  ASN C 354      21.541  33.852  47.593  1.00 65.63           O
ATOM   8720  ND2  ASN C 354      23.484  34.297  48.635  1.00 64.34           N
ATOM   8721  C    ASN C 354      24.028  31.272  46.911  1.00 51.90           C
ATOM   8722  O    ASN C 354      23.063  31.094  46.159  1.00 53.56           O
ATOM   8723  N    MET C 355      25.279  31.419  46.471  1.00 47.81           N
ATOM   8724  CA   MET C 355      25.629  31.392  45.049  1.00 42.74           C
ATOM   8725  CB   MET C 355      27.113  31.739  44.839  1.00 42.75           C
ATOM   8726  CG   MET C 355      28.087  30.576  45.032  1.00 42.95           C
ATOM   8727  SD   MET C 355      29.830  31.033  44.824  1.00 44.30           S
ATOM   8728  CE   MET C 355      29.842  31.629  43.113  1.00 44.66           C
ATOM   8729  C    MET C 355      25.290  30.052  44.397  1.00 38.21           C
ATOM   8730  O    MET C 355      25.333  29.000  45.046  1.00 35.04           O
ATOM   8731  N    THR C 356      24.953  30.108  43.113  1.00 38.49           N
ATOM   8732  CA   THR C 356      24.567  28.922  42.358  1.00 41.03           C
ATOM   8733  CB   THR C 356      23.717  29.309  41.106  1.00 46.21           C
ATOM   8734  OG1  THR C 356      23.943  28.371  40.044  1.00 51.18           O
ATOM   8735  CG2  THR C 356      24.181  30.635  40.505  1.00 48.29           C
ATOM   8736  C    THR C 356      25.791  28.087  41.969  1.00 38.27           C
ATOM   8737  O    THR C 356      26.792  28.621  41.488  1.00 32.56           O
ATOM   8738  N    ASN C 357      25.702  26.782  42.206  1.00 35.95           N
ATOM   8739  CA   ASN C 357      26.700  25.839  41.720  1.00 34.19           C
ATOM   8740  CB   ASN C 357      26.577  24.506  42.467  1.00 33.24           C
ATOM   8741  CG   ASN C 357      27.685  23.519  42.114  1.00 34.86           C
ATOM   8742  OD1  ASN C 357      28.522  23.775  41.245  1.00 31.99           O
ATOM   8743  ND2  ASN C 357      27.688  22.378  42.793  1.00 34.38           N
ATOM   8744  C    ASN C 357      26.507  25.641  40.223  1.00 35.33           C
ATOM   8745  O    ASN C 357      25.493  25.092  39.793  1.00 34.28           O
ATOM   8746  N    GLN C 358      27.474  26.097  39.427  1.00 29.79           N
ATOM   8747  CA   GLN C 358      27.360  25.999  37.972  1.00 28.78           C
ATOM   8748  CB   GLN C 358      28.080  27.164  37.276  1.00 32.26           C
ATOM   8749  CG   GLN C 358      27.583  28.557  37.675  1.00 40.52           C
ATOM   8750  CD   GLN C 358      26.236  28.933  37.062  1.00 45.27           C
ATOM   8751  OE1  GLN C 358      25.571  29.853  37.544  1.00 48.83           O
ATOM   8752  NE2  GLN C 358      25.839  28.237  36.002  1.00 46.22           N
ATOM   8753  C    GLN C 358      27.822  24.651  37.404  1.00 30.32           C
ATOM   8754  O    GLN C 358      27.724  24.419  36.196  1.00 32.38           O
ATOM   8755  N    ASN C 359      28.312  23.771  38.277  1.00 26.38           N
ATOM   8756  CA   ASN C 359      28.700  22.418  37.894  1.00 27.23           C
ATOM   8757  CB   ASN C 359      29.773  21.875  38.840  1.00 27.10           C
ATOM   8758  CG   ASN C 359      31.009  22.740  38.880  1.00 29.36           C
ATOM   8759  OD1  ASN C 359      31.103  23.678  39.679  1.00 33.70           O
ATOM   8760  ND2  ASN C 359      31.963  22.437  38.016  1.00 27.64           N
ATOM   8761  C    ASN C 359      27.498  21.480  37.934  1.00 28.33           C
ATOM   8762  O    ASN C 359      27.092  21.042  39.013  1.00 31.39           O
ATOM   8763  N    THR C 360      26.943  21.167  36.767  1.00 26.04           N
ATOM   8764  CA   THR C 360      25.796  20.255  36.679  1.00 26.73           C
ATOM   8765  CB   THR C 360      25.187  20.252  35.260  1.00 24.65           C
ATOM   8766  OG1  THR C 360      26.157  19.767  34.326  1.00 27.73           O
ATOM   8767  CG2  THR C 360      24.883  21.662  34.769  1.00 27.93           C
ATOM   8768  C    THR C 360      26.220  18.832  37.048  1.00 26.70           C
```

FIGURE 3YYYYYY

```
ATOM   8769  O    THR C 360      27.375  18.456  36.841  1.00 21.46           O
ATOM   8770  N    PRO C 361      25.299  18.036  37.595  1.00 25.02           N
ATOM   8771  CA   PRO C 361      25.581  16.623  37.866  1.00 24.96           C
ATOM   8772  CB   PRO C 361      24.211  16.071  38.265  1.00 24.81           C
ATOM   8773  CG   PRO C 361      23.499  17.242  38.834  1.00 26.04           C
ATOM   8774  CD   PRO C 361      23.945  18.422  38.037  1.00 25.45           C
ATOM   8775  C    PRO C 361      26.117  15.889  36.636  1.00 24.79           C
ATOM   8776  O    PRO C 361      27.016  15.065  36.786  1.00 27.05           O
ATOM   8777  N    GLU C 362      25.581  16.192  35.451  1.00 24.05           N
ATOM   8778  CA   GLU C 362      26.018  15.557  34.207  1.00 25.65           C
ATOM   8779  CB   GLU C 362      25.118  15.980  33.044  1.00 29.94           C
ATOM   8780  CG   GLU C 362      25.454  15.332  31.708  1.00 34.93           C
ATOM   8781  CD   GLU C 362      24.667  15.925  30.549  1.00 40.08           C
ATOM   8782  OE1  GLU C 362      24.340  15.163  29.614  1.00 41.88           O
ATOM   8783  OE2  GLU C 362      24.378  17.145  30.567  1.00 38.41           O
ATOM   8784  C    GLU C 362      27.487  15.892  33.903  1.00 27.87           C
ATOM   8785  O    GLU C 362      28.279  15.001  33.593  1.00 27.18           O
ATOM   8786  N    TYR C 363      27.828  17.175  34.011  1.00 26.45           N
ATOM   8787  CA   TYR C 363      29.203  17.646  33.826  1.00 29.99           C
ATOM   8788  CB   TYR C 363      29.271  19.166  34.009  1.00 33.11           C
ATOM   8789  CG   TYR C 363      30.672  19.731  33.921  1.00 35.45           C
ATOM   8790  CD1  TYR C 363      31.384  20.061  35.076  1.00 38.97           C
ATOM   8791  CE1  TYR C 363      32.681  20.576  35.002  1.00 38.23           C
ATOM   8792  CZ   TYR C 363      33.269  20.762  33.759  1.00 41.41           C
ATOM   8793  OH   TYR C 363      34.546  21.266  33.674  1.00 40.86           O
ATOM   8794  CE2  TYR C 363      32.581  20.435  32.598  1.00 40.33           C
ATOM   8795  CD2  TYR C 363      31.289  19.922  32.685  1.00 38.07           C
ATOM   8796  C    TYR C 363      30.188  16.941  34.768  1.00 28.66           C
ATOM   8797  O    TYR C 363      31.201  16.399  34.321  1.00 29.10           O
ATOM   8798  N    MET C 364      29.870  16.937  36.062  1.00 24.40           N
ATOM   8799  CA   MET C 364      30.709  16.325  37.093  1.00 27.10           C
ATOM   8800  CB   BMET C 364     30.142  16.602  38.489  0.35 25.63           C
ATOM   8801  CB   AMET C 364     30.112  16.573  38.485  0.65 29.18           C
ATOM   8802  CG   BMET C 364     30.017  18.082  38.821  0.35 24.55           C
ATOM   8803  CG   AMET C 364     30.108  18.032  38.920  0.65 31.47           C
ATOM   8804  SD   BMET C 364     29.861  18.393  40.580  0.35 24.51           S
ATOM   8805  SD   AMET C 364     31.777  18.701  39.052  0.65 36.22           S
ATOM   8806  CE   BMET C 364     28.066  18.300  40.786  0.35 25.88           C
ATOM   8807  CE   AMET C 364     32.225  18.150  40.670  0.65 36.05           C
ATOM   8808  C    MET C 364      30.886  14.825  36.879  1.00 30.02           C
ATOM   8809  O    MET C 364      31.977  14.287  37.075  1.00 32.87           O
ATOM   8810  N    GLU C 365      29.810  14.158  36.471  1.00 28.55           N
ATOM   8811  CA   GLU C 365      29.842  12.724  36.222  1.00 34.09           C
ATOM   8812  CB   GLU C 365      28.420  12.180  36.016  1.00 38.22           C
ATOM   8813  CG   GLU C 365      28.287  10.670  36.176  1.00 48.60           C
ATOM   8814  CD   GLU C 365      28.743  10.166  37.536  1.00 53.71           C
ATOM   8815  OE1  GLU C 365      29.303   9.049  37.595  1.00 57.35           O
ATOM   8816  OE2  GLU C 365      28.543  10.879  38.546  1.00 56.65           O
ATOM   8817  C    GLU C 365      30.723  12.396  35.022  1.00 29.29           C
ATOM   8818  O    GLU C 365      31.505  11.445  35.072  1.00 30.73           O
ATOM   8819  N    LYS C 366      30.592  13.193  33.961  1.00 31.30           N
ATOM   8820  CA   LYS C 366      31.352  12.996  32.727  1.00 32.64           C
ATOM   8821  CB   LYS C 366      30.895  13.976  31.633  1.00 38.20           C
ATOM   8822  CG   LYS C 366      29.617  13.600  30.857  1.00 46.84           C
ATOM   8823  CD   LYS C 366      29.226  12.129  30.987  1.00 51.40           C
ATOM   8824  CE   LYS C 366      29.388  11.389  29.669  1.00 54.94           C
ATOM   8825  NZ   LYS C 366      29.295   9.917  29.859  1.00 55.32           N
```

FIGURE 3ZZZZZZ

```
ATOM   8826  C    LYS C 366      32.857  13.142  32.973  1.00 30.07           C
ATOM   8827  O    LYS C 366      33.652  12.345  32.467  1.00 27.35           O
ATOM   8828  N    ILE C 367      33.243  14.158  33.746  1.00 24.90           N
ATOM   8829  CA   ILE C 367      34.660  14.372  34.078  1.00 26.40           C
ATOM   8830  CB   ILE C 367      34.891  15.755  34.774  1.00 25.26           C
ATOM   8831  CG1  ILE C 367      34.304  16.915  33.946  1.00 25.22           C
ATOM   8832  CD1  ILE C 367      35.006  17.238  32.633  1.00 29.95           C
ATOM   8833  CG2  ILE C 367      36.387  15.967  35.112  1.00 24.89           C
ATOM   8834  C    ILE C 367      35.196  13.227  34.937  1.00 27.55           C
ATOM   8835  O    ILE C 367      36.252  12.656  34.637  1.00 30.22           O
ATOM   8836  N    LYS C 368      34.462  12.896  35.998  1.00 26.55           N
ATOM   8837  CA   LYS C 368      34.800  11.778  36.877  1.00 30.59           C
ATOM   8838  CB   LYS C 368      33.699  11.591  37.925  1.00 33.67           C
ATOM   8839  CG   LYS C 368      34.119  10.862  39.187  1.00 43.17           C
ATOM   8840  CD   LYS C 368      33.019  10.916  40.249  1.00 48.23           C
ATOM   8841  CE   LYS C 368      32.136   9.671  40.208  1.00 53.08           C
ATOM   8842  NZ   LYS C 368      32.408   8.746  41.349  1.00 56.41           N
ATOM   8843  C    LYS C 368      35.000  10.492  36.068  1.00 31.49           C
ATOM   8844  O    LYS C 368      35.991   9.780  36.255  1.00 28.13           O
ATOM   8845  N    GLN C 369      34.071  10.221  35.153  1.00 34.61           N
ATOM   8846  CA   GLN C 369      34.142   9.037  34.293  1.00 37.01           C
ATOM   8847  CB   GLN C 369      32.930   8.972  33.360  1.00 42.79           C
ATOM   8848  CG   GLN C 369      31.756   8.179  33.923  1.00 49.74           C
ATOM   8849  CD   GLN C 369      30.649   7.955  32.900  1.00 53.23           C
ATOM   8850  OE1  GLN C 369      30.807   7.163  31.967  1.00 53.94           O
ATOM   8851  NE2  GLN C 369      29.528   8.648  33.075  1.00 55.10           N
ATOM   8852  C    GLN C 369      35.438   8.990  33.480  1.00 35.42           C
ATOM   8853  O    GLN C 369      36.113   7.958  33.439  1.00 36.55           O
ATOM   8854  N    ARG C 370      35.779  10.111  32.847  1.00 32.88           N
ATOM   8855  CA   ARG C 370      36.987  10.215  32.029  1.00 34.79           C
ATOM   8856  CB   ARG C 370      37.017  11.548  31.271  1.00 37.55           C
ATOM   8857  CG   ARG C 370      38.335  11.841  30.552  1.00 43.62           C
ATOM   8858  CD   ARG C 370      38.447  11.230  29.159  1.00 48.26           C
ATOM   8859  NE   ARG C 370      38.075  12.200  28.130  1.00 55.59           N
ATOM   8860  CZ   ARG C 370      37.273  11.944  27.102  1.00 57.51           C
ATOM   8861  NH1  ARG C 370      36.998  12.906  26.230  1.00 57.41           N
ATOM   8862  NH2  ARG C 370      36.748  10.734  26.937  1.00 58.85           N
ATOM   8863  C    ARG C 370      38.266  10.035  32.849  1.00 32.90           C
ATOM   8864  O    ARG C 370      39.211   9.388  32.390  1.00 31.24           O
ATOM   8865  N    LEU C 371      38.290  10.609  34.050  1.00 30.31           N
ATOM   8866  CA   LEU C 371      39.454  10.522  34.934  1.00 30.07           C
ATOM   8867  CB   LEU C 371      39.327  11.497  36.115  1.00 32.28           C
ATOM   8868  CG   LEU C 371      39.523  12.994  35.836  1.00 34.88           C
ATOM   8869  CD1  LEU C 371      39.585  13.776  37.134  1.00 35.56           C
ATOM   8870  CD2  LEU C 371      40.772  13.250  35.023  1.00 37.08           C
ATOM   8871  C    LEU C 371      39.684   9.105  35.442  1.00 30.09           C
ATOM   8872  O    LEU C 371      40.816   8.626  35.454  1.00 28.26           O
ATOM   8873  N    PHE C 372      38.608   8.440  35.863  1.00 31.51           N
ATOM   8874  CA   PHE C 372      38.680   7.037  36.274  1.00 34.04           C
ATOM   8875  CB   PHE C 372      37.308   6.546  36.755  1.00 37.33           C
ATOM   8876  CG   PHE C 372      37.113   6.659  38.242  1.00 41.54           C
ATOM   8877  CD1  PHE C 372      36.951   7.903  38.846  1.00 43.59           C
ATOM   8878  CE1  PHE C 372      36.773   8.013  40.225  1.00 44.36           C
ATOM   8879  CZ   PHE C 372      36.755   6.868  41.014  1.00 47.87           C
ATOM   8880  CE2  PHE C 372      36.915   5.617  40.421  1.00 47.38           C
ATOM   8881  CD2  PHE C 372      37.096   5.520  39.042  1.00 45.61           C
ATOM   8882  C    PHE C 372      39.202   6.150  35.141  1.00 32.88           C
```

FIGURE 3AAAAAAA

```
ATOM   8883  O    PHE C 372      39.962   5.209  35.383  1.00 35.67           O
ATOM   8884  N    GLU C 373      38.799   6.473  33.912  1.00 32.54           N
ATOM   8885  CA   GLU C 373      39.275   5.789  32.707  1.00 37.04           C
ATOM   8886  CB   GLU C 373      38.525   6.292  31.468  1.00 40.53           C
ATOM   8887  CG   GLU C 373      37.171   5.635  31.225  1.00 49.73           C
ATOM   8888  CD   GLU C 373      36.301   6.402  30.238  1.00 54.59           C
ATOM   8889  OE1  GLU C 373      36.848   7.143  29.390  1.00 56.54           O
ATOM   8890  OE2  GLU C 373      35.059   6.263  30.305  1.00 58.53           O
ATOM   8891  C    GLU C 373      40.779   5.989  32.511  1.00 36.57           C
ATOM   8892  O    GLU C 373      41.503   5.043  32.192  1.00 34.92           O
ATOM   8893  N    ASN C 374      41.240   7.226  32.701  1.00 33.51           N
ATOM   8894  CA   ASN C 374      42.666   7.544  32.615  1.00 30.80           C
ATOM   8895  CB   ASN C 374      42.884   9.058  32.672  1.00 31.02           C
ATOM   8896  CG   ASN C 374      42.389   9.764  31.429  1.00 31.50           C
ATOM   8897  OD1  ASN C 374      42.218   9.147  30.376  1.00 32.31           O
ATOM   8898  ND2  ASN C 374      42.149  11.067  31.542  1.00 32.48           N
ATOM   8899  C    ASN C 374      43.490   6.839  33.683  1.00 30.70           C
ATOM   8900  O    ASN C 374      44.594   6.357  33.407  1.00 32.78           O
ATOM   8901  N    LEU C 375      42.939   6.766  34.893  1.00 30.93           N
ATOM   8902  CA   LEU C 375      43.594   6.109  36.024  1.00 34.20           C
ATOM   8903  CB   LEU C 375      42.812   6.367  37.314  1.00 35.18           C
ATOM   8904  CG   LEU C 375      43.266   7.467  38.285  1.00 39.23           C
ATOM   8905  CD1  LEU C 375      44.305   8.428  37.695  1.00 35.69           C
ATOM   8906  CD2  LEU C 375      42.061   8.234  38.808  1.00 36.54           C
ATOM   8907  C    LEU C 375      43.776   4.603  35.823  1.00 37.14           C
ATOM   8908  O    LEU C 375      44.733   4.020  36.333  1.00 36.46           O
ATOM   8909  N    ARG C 376      42.862   3.974  35.089  1.00 40.26           N
ATOM   8910  CA   ARG C 376      42.960   2.531  34.851  1.00 46.56           C
ATOM   8911  CB   ARG C 376      41.579   1.914  34.554  1.00 50.72           C
ATOM   8912  CG   ARG C 376      41.183   1.833  33.090  1.00 57.54           C
ATOM   8913  CD   ARG C 376      40.602   0.481  32.683  1.00 63.53           C
ATOM   8914  NE   ARG C 376      39.169   0.378  32.964  1.00 66.74           N
ATOM   8915  CZ   ARG C 376      38.203   0.782  32.141  1.00 69.78           C
ATOM   8916  NH1  ARG C 376      38.501   1.330  30.968  1.00 71.02           N
ATOM   8917  NH2  ARG C 376      36.930   0.641  32.492  1.00 70.27           N
ATOM   8918  C    ARG C 376      44.028   2.165  33.801  1.00 45.97           C
ATOM   8919  O    ARG C 376      44.328   0.985  33.599  1.00 47.43           O
ATOM   8920  N    MET C 377      44.611   3.184  33.167  1.00 44.00           N
ATOM   8921  CA   MET C 377      45.718   3.011  32.223  1.00 45.62           C
ATOM   8922  CB   MET C 377      45.779   4.187  31.237  1.00 47.70           C
ATOM   8923  CG   MET C 377      44.545   4.364  30.355  1.00 51.55           C
ATOM   8924  SD   MET C 377      44.326   3.054  29.125  1.00 57.23           S
ATOM   8925  CE   MET C 377      45.639   3.448  27.935  1.00 55.61           C
ATOM   8926  C    MET C 377      47.091   2.840  32.899  1.00 46.62           C
ATOM   8927  O    MET C 377      48.071   2.490  32.236  1.00 47.82           O
ATOM   8928  N    LEU C 378      47.163   3.086  34.208  1.00 46.64           N
ATOM   8929  CA   LEU C 378      48.432   3.014  34.939  1.00 49.02           C
ATOM   8930  CB   LEU C 378      48.301   3.640  36.334  1.00 47.46           C
ATOM   8931  CG   LEU C 378      47.929   5.118  36.529  1.00 48.42           C
ATOM   8932  CD1  LEU C 378      48.356   5.572  37.922  1.00 46.15           C
ATOM   8933  CD2  LEU C 378      48.507   6.045  35.462  1.00 45.37           C
ATOM   8934  C    LEU C 378      48.966   1.583  35.058  1.00 51.02           C
ATOM   8935  O    LEU C 378      48.212   0.650  35.344  1.00 51.68           O
ATOM   8936  ZN   ZN  C 379      45.073  30.367  43.523  1.00 24.79          ZN
ATOM   8937  NA   NA  C 380      44.126  23.480  42.024  1.00 14.49          NA
ATOM   8938  O3   TSS C 381      42.639  38.468  39.619  1.00 38.82           O
ATOM   8939  C9   TSS C 381      43.849  38.536  39.429  1.00 39.14           C
```

FIGURE 3BBBBBBB

```
ATOM   8940  C10  TSS C 381      44.581  39.798  39.814  1.00 39.18           C
ATOM   8941  C11  TSS C 381      45.878  40.059  39.358  1.00 38.67           C
ATOM   8942  C12  TSS C 381      46.531  41.236  39.727  1.00 39.06           C
ATOM   8943  C13  TSS C 381      45.897  42.167  40.559  1.00 39.46           C
ATOM   8944  N2   TSS C 381      46.548  43.359  40.938  1.00 40.32           N
ATOM   8945  C17  TSS C 381      45.806  44.435  41.587  1.00 42.42           C
ATOM   8946  C16  TSS C 381      47.970  43.548  40.681  1.00 42.37           C
ATOM   8947  C14  TSS C 381      44.602  41.905  41.010  1.00 38.55           C
ATOM   8948  C15  TSS C 381      43.949  40.730  40.640  1.00 40.81           C
ATOM   8949  C2   TSS C 381      44.584  37.366  38.816  1.00 38.81           C
ATOM   8950  C1   TSS C 381      43.837  36.863  37.579  1.00 39.28           C
ATOM   8951  C3   TSS C 381      44.708  36.223  39.807  1.00 37.07           C
ATOM   8952  C4   TSS C 381      45.827  35.491  40.008  1.00 34.62           C
ATOM   8953  C5   TSS C 381      47.088  35.761  39.232  1.00 38.13           C
ATOM   8954  C6   TSS C 381      45.776  34.396  41.006  1.00 31.96           C
ATOM   8955  C7   TSS C 381      46.840  33.760  41.508  1.00 32.37           C
ATOM   8956  C8   TSS C 381      46.662  32.669  42.498  1.00 35.58           C
ATOM   8957  O1   TSS C 381      45.803  32.772  43.359  1.00 30.40           O
ATOM   8958  N1   TSS C 381      47.431  31.574  42.442  1.00 41.90           N
ATOM   8959  O2   TSS C 381      47.022  30.446  42.809  1.00 31.67           O
ATOM   8960  O    HOH C 382      42.993  41.607 -26.943  1.00 17.67           O
ATOM   8961  O    HOH C 383      13.666  41.274  -2.996  1.00 20.00           O
ATOM   8962  O    HOH C 384      42.332  39.904 -45.320  1.00 15.94           O
ATOM   8963  O    HOH C 385      31.205  29.899 -41.463  1.00 19.49           O
ATOM   8964  O    HOH C 386      60.974  43.086 -47.606  1.00 18.75           O
ATOM   8965  O    HOH C 387       4.145  41.659  -7.452  1.00 23.97           O
ATOM   8966  O    HOH C 388      23.063  28.587  -9.004  1.00 17.44           O
ATOM   8967  O    HOH C 389      31.835  39.581 -37.715  1.00 20.29           O
ATOM   8968  O    HOH C 390      50.032  44.968 -27.371  1.00 27.35           O
ATOM   8969  O    HOH C 391      16.930  38.193  -7.487  1.00 17.91           O
ATOM   8970  O    HOH C 392      44.482  48.423 -44.477  1.00 17.37           O
ATOM   8971  O    HOH C 393      14.559  30.476 -10.298  1.00 18.22           O
ATOM   8972  O    HOH C 394      37.178  44.941 -63.139  1.00 21.87           O
ATOM   8973  O    HOH C 395      20.640  35.385 -27.785  1.00 22.32           O
ATOM   8974  O    HOH C 396      36.917  43.486 -29.902  1.00 18.98           O
ATOM   8975  O    HOH C 397      53.315  44.022 -53.158  1.00 21.82           O
ATOM   8976  O    HOH C 398       8.773  24.561  10.462  1.00 23.82           O
ATOM   8977  O    HOH C 399      44.467  39.317 -30.469  1.00 19.02           O
ATOM   8978  O    HOH C 400      20.249  36.028  11.372  1.00 20.34           O
ATOM   8979  O    HOH C 401      31.531  34.563 -48.224  1.00 20.80           O
ATOM   8980  O    HOH C 402      30.759  30.050  13.559  1.00 30.88           O
ATOM   8981  O    HOH C 403      17.178  36.489   5.166  1.00 19.83           O
ATOM   8982  O    HOH C 404      -0.414  42.258  15.077  1.00 33.13           O
ATOM   8983  O    HOH C 405       4.701  27.638   6.762  1.00 18.04           O
ATOM   8984  O    HOH C 406      37.773  46.945 -23.792  1.00 22.34           O
ATOM   8985  O    HOH C 407      52.789  34.606  51.060  1.00 32.51           O
ATOM   8986  O    HOH C 408       8.687  18.768  19.372  1.00 20.89           O
ATOM   8987  O    HOH C 409      13.156  28.878   4.503  1.00 18.67           O
ATOM   8988  O    HOH C 410      36.558  30.614  46.062  1.00 22.17           O
ATOM   8989  O    HOH C 411      25.853  32.064 -36.930  1.00 21.91           O
ATOM   8990  O    HOH C 412      45.889  34.872 -23.168  1.00 22.04           O
ATOM   8991  O    HOH C 413      30.162  42.356 -30.344  1.00 31.65           O
ATOM   8992  O    HOH C 414      52.916  13.408  34.015  1.00 22.20           O
ATOM   8993  O    HOH C 415      42.737  27.562  36.837  1.00 23.67           O
ATOM   8994  O    HOH C 416      19.420  19.280 -17.451  1.00 23.01           O
ATOM   8995  O    HOH C 417      30.894  26.627 -18.908  1.00 29.48           O
ATOM   8996  O    HOH C 418      59.962  29.204  31.923  1.00 25.04           O
```

FIGURE 3CCCCCCC

```
ATOM   8997  O   HOH C 419      18.193  11.802 -11.724  1.00 21.16           O
ATOM   8998  O   HOH C 420      41.923  47.426 -17.542  1.00 23.28           O
ATOM   8999  O   HOH C 421      48.825  35.141 -24.253  1.00 23.03           O
ATOM   9000  O   HOH C 422      29.948  39.995 -50.957  1.00 21.16           O
ATOM   9001  O   HOH C 423       8.711  48.206   0.296  1.00 25.11           O
ATOM   9002  O   HOH C 424      17.149  15.518 -18.185  1.00 24.36           O
ATOM   9003  O   HOH C 425      13.308  38.098 -29.537  1.00 29.63           O
ATOM   9004  O   HOH C 426      44.173  52.236 -47.273  1.00 24.41           O
ATOM   9005  O   HOH C 427      27.223  35.446 -20.105  1.00 25.18           O
ATOM   9006  O   HOH C 428      -1.597  16.299  13.373  1.00 40.01           O
ATOM   9007  O   HOH C 429      40.177  23.332  44.113  1.00 26.07           O
ATOM   9008  O   HOH C 430      35.707  48.724 -24.559  1.00 22.87           O
ATOM   9009  O   HOH C 431      16.249  43.174   4.263  1.00 32.42           O
ATOM   9010  O   HOH C 432       8.421  27.391  11.431  1.00 22.85           O
ATOM   9011  O   HOH C 433      56.933  41.544 -53.866  1.00 25.84           O
ATOM   9012  O   HOH C 434      25.462  27.960 -39.633  1.00 22.78           O
ATOM   9013  O   HOH C 435      18.008  19.277 -10.869  1.00 24.54           O
ATOM   9014  O   HOH C 436      46.475  56.682 -29.048  1.00 27.15           O
ATOM   9015  O   HOH C 437      25.787  21.535 -25.063  1.00 27.64           O
ATOM   9016  O   HOH C 438      32.217  22.757 -38.287  1.00 27.97           O
ATOM   9017  O   HOH C 439      17.558  14.059  -9.824  1.00 29.34           O
ATOM   9018  O   HOH C 440      58.495  54.096 -34.032  1.00 26.18           O
ATOM   9019  O   HOH C 441      24.791  34.875 -34.063  1.00 26.90           O
ATOM   9020  O   HOH C 442      27.569  25.194 -42.977  1.00 38.06           O
ATOM   9021  O   HOH C 443      53.651  43.007 -46.571  1.00 26.76           O
ATOM   9022  O   HOH C 444      43.416  57.336 -22.170  1.00 38.02           O
ATOM   9023  O   HOH C 445      19.206  23.337   8.181  1.00 29.68           O
ATOM   9024  O   HOH C 446      69.843  26.413  36.340  1.00 27.48           O
ATOM   9025  O   HOH C 447      58.844  42.593 -45.634  1.00 28.16           O
ATOM   9026  O   HOH C 448       9.602  41.113 -13.834  1.00 26.63           O
ATOM   9027  O   HOH C 449      72.613  32.632  40.578  1.00 43.52           O
ATOM   9028  O   HOH C 450      12.051   9.940  16.135  1.00 25.74           O
ATOM   9029  O   HOH C 451      37.179  33.300  51.761  1.00 28.73           O
ATOM   9030  O   HOH C 452      27.434  20.381 -29.739  1.00 33.54           O
ATOM   9031  O   HOH C 453      28.634  27.292   1.774  1.00 26.97           O
ATOM   9032  O   HOH C 455      57.022  48.085 -36.312  1.00 33.15           O
ATOM   9033  O   HOH C 456      40.035  39.572  55.838  1.00 34.45           O
ATOM   9034  O   HOH C 457      54.026  45.638 -57.353  1.00 24.87           O
ATOM   9035  O   HOH C 458      52.420  42.646 -43.557  1.00 27.73           O
ATOM   9036  O   HOH C 459      36.431  43.743 -22.960  1.00 32.12           O
ATOM   9037  O   HOH C 460      33.923  26.012  58.083  1.00 33.57           O
ATOM   9038  O   HOH C 461      21.429  18.472 -21.586  1.00 29.02           O
ATOM   9039  O   HOH C 463      65.062  28.826 -43.486  1.00 32.73           O
ATOM   9040  O   HOH C 464      27.179  28.812 -11.577  1.00 26.39           O
ATOM   9041  O   HOH C 465      53.858  26.888  58.607  1.00 28.29           O
ATOM   9042  O   HOH C 466      24.527  19.893 -11.439  1.00 32.24           O
ATOM   9043  O   HOH C 467      31.635  32.656 -51.586  1.00 34.93           O
ATOM   9044  O   HOH C 468      45.608  11.199  33.601  1.00 26.92           O
ATOM   9045  O   HOH C 469      63.781  42.701 -18.377  1.00 26.15           O
ATOM   9046  O   HOH C 470      43.594  40.449  49.381  1.00 31.24           O
ATOM   9047  O   HOH C 471      43.830  15.077  33.103  1.00 32.11           O
ATOM   9048  O   HOH C 472      46.452  37.437  50.401  1.00 32.18           O
ATOM   9049  O   HOH C 473      50.487  46.875 -15.427  1.00 27.88           O
ATOM   9050  O   HOH C 474      66.455  31.670  31.215  1.00 36.01           O
ATOM   9051  O   HOH C 475      22.882  29.782 -39.436  1.00 38.99           O
ATOM   9052  O   HOH C 476       7.276  28.070   8.732  1.00 26.38           O
ATOM   9053  O   HOH C 477       5.698  31.073   8.165  1.00 31.60           O
```

FIGURE 3DDDDDDD

```
ATOM   9054  O   HOH C  478      61.348  23.792 -40.791  1.00 30.95           O
ATOM   9055  O   HOH C  479      43.207  43.021 -14.505  1.00 43.58           O
ATOM   9056  O   HOH C  480      69.533  26.043  50.093  1.00 37.99           O
ATOM   9057  O   HOH C  481      38.669  31.200 -48.498  1.00 33.86           O
ATOM   9058  O   HOH C  482       6.005  21.610  18.512  1.00 30.48           O
ATOM   9059  O   HOH C  483      17.384  13.499  18.652  1.00 35.98           O
ATOM   9060  O   HOH C  484      14.982  42.681 -16.273  1.00 25.60           O
ATOM   9061  O   HOH C  485      58.072  58.046 -30.377  1.00 32.26           O
ATOM   9062  O   HOH C  486      48.099  18.197  37.103  1.00 29.41           O
ATOM   9063  O   HOH C  487      57.449  31.373  57.296  1.00 37.85           O
ATOM   9064  O   HOH C  488      20.499  32.051  17.827  1.00 26.78           O
ATOM   9065  O   HOH C  489      51.011  36.575  36.018  1.00 33.98           O
ATOM   9066  O   HOH C  490       2.047  15.155  10.069  1.00 24.57           O
ATOM   9067  O   HOH C  491      57.164  49.242 -56.774  1.00 31.69           O
ATOM   9068  O   HOH C  492      52.696  24.824 -42.433  1.00 31.70           O
ATOM   9069  O   HOH C  493       5.818  31.166 -14.164  1.00 34.91           O
ATOM   9070  O   HOH C  494      -6.054  45.515  -4.001  1.00 39.06           O
ATOM   9071  O   HOH C  495      -7.307  26.480  -2.833  1.00 32.15           O
ATOM   9072  O   HOH C  496      24.544  37.259 -16.076  1.00 34.49           O
ATOM   9073  O   HOH C  497      15.948  30.042 -29.992  1.00 29.79           O
ATOM   9074  O   HOH C  498      52.655  52.747 -60.720  1.00 30.26           O
ATOM   9075  O   HOH C  499      26.993  46.746 -50.631  1.00 41.55           O
ATOM   9076  O   HOH C  500      58.908  16.052  33.553  1.00 30.95           O
ATOM   9077  O   HOH C  501      65.541  20.751  45.794  1.00 30.84           O
ATOM   9078  O   HOH C  502      42.577  32.107 -26.332  1.00 32.70           O
ATOM   9079  O   HOH C  503      22.728  23.688  18.872  1.00 30.29           O
ATOM   9080  O   HOH C  504      25.257  34.338 -39.674  1.00 37.21           O
ATOM   9081  O   HOH C  505      58.951  26.373  32.438  1.00 39.66           O
ATOM   9082  O   HOH C  506      -5.227  34.494  -5.616  1.00 40.06           O
ATOM   9083  O   HOH C  507      69.499  36.106 -36.407  1.00 40.14           O
ATOM   9084  O   HOH C  508      56.642  46.245  39.780  1.00 40.53           O
ATOM   9085  O   HOH C  509      41.347  34.491  40.037  1.00 38.19           O
ATOM   9086  O   HOH C  510      -7.541  25.053   3.347  1.00 36.23           O
ATOM   9087  O   HOH C  511      62.253  23.635 -45.177  1.00 45.33           O
ATOM   9088  O   HOH C  512      55.531  35.825 -15.778  1.00 35.64           O
ATOM   9089  O   HOH C  514      17.460  20.463  -8.034  1.00 27.70           O
ATOM   9090  O   HOH C  515      23.256  38.798 -30.953  1.00 47.83           O
ATOM   9091  O   HOH C  516      27.164  33.703  15.710  1.00 48.52           O
ATOM   9092  O   HOH C  517       5.200   2.627  -3.645  1.00 49.55           O
ATOM   9093  O   HOH C  518      -6.818  43.078   4.377  1.00 34.31           O
ATOM   9094  O   HOH C  519       8.659  45.822  14.107  1.00 29.00           O
ATOM   9095  O   HOH C  520      58.581  22.743 -34.796  1.00 35.61           O
ATOM   9096  O   HOH C  521       1.946  47.658  -5.653  1.00 34.92           O
ATOM   9097  O   HOH C  522      65.223  41.490  46.641  1.00 36.87           O
ATOM   9098  O   HOH C  523      64.201  45.178 -42.157  1.00 31.56           O
ATOM   9099  O   HOH C  524      60.388  56.867 -21.290  1.00 39.05           O
ATOM   9100  O   HOH C  525      48.190  37.078 -14.738  1.00 48.06           O
ATOM   9101  O   HOH C  526      65.468  30.537 -51.480  1.00 47.78           O
ATOM   9102  O   HOH C  527      65.284  24.486 -39.491  1.00 48.15           O
ATOM   9103  O   HOH C  528      16.522  34.952 -37.456  1.00 44.72           O
ATOM   9104  O   HOH C  529      40.263  35.969 -19.463  1.00 33.91           O
ATOM   9105  O   HOH C  530      -4.753  38.703  -4.856  1.00 38.61           O
ATOM   9106  O   HOH C  531      23.309  39.654 -25.166  1.00 56.03           O
ATOM   9107  O   HOH C  532      42.244  33.288 -64.629  1.00 53.49           O
ATOM   9108  O   HOH C  533      41.527  51.895 -16.477  1.00 38.62           O
ATOM   9109  O   HOH C  534      15.981  30.595  20.424  1.00 49.04           O
ATOM   9110  O   HOH C  535      47.703  22.013  31.417  1.00 37.87           O
```

FIGURE 3EEEEEEE

```
ATOM   9111  O   HOH C 536      28.418   41.385  -55.613  1.00 39.33           O
ATOM   9112  O   HOH C 537      51.300   42.582   50.169  1.00 34.75           O
ATOM   9113  O   HOH C 538      72.070   32.603   47.992  1.00 37.78           O
ATOM   9114  O   HOH C 539      64.554    6.239   45.659  1.00 44.01           O
ATOM   9115  O   HOH C 540      62.263   16.457   36.918  1.00 42.37           O
ATOM   9116  O   HOH C 541       0.029   21.907   16.390  1.00 43.42           O
ATOM   9117  O   HOH C 542       8.616    7.344  -15.337  1.00 53.68           O
ATOM   9118  O   HOH C 543      47.137   21.105  -21.290  1.00 34.96           O
ATOM   9119  O   HOH C 544      55.823   27.801  -22.676  1.00 44.07           O
ATOM   9120  O   HOH C 545       9.970   25.481   19.549  1.00 37.32           O
ATOM   9121  O   HOH C 546      37.690   37.892   40.945  1.00 55.82           O
ATOM   9122  O   HOH C 547       7.808   43.009   16.999  1.00 49.27           O
ATOM   9123  O   HOH C 548      51.269   10.137   58.377  1.00 48.71           O
ATOM   9124  O   HOH C 549      -0.220   20.040   -7.945  1.00 34.42           O
ATOM   9125  O   HOH C 550      29.344   19.765  -17.560  1.00 52.22           O
ATOM   9126  O   HOH C 551      51.558   30.491   50.735  1.00 30.50           O
ATOM   9127  O   HOH C 552      69.975   37.628  -45.551  1.00 45.55           O
ATOM   9128  O   HOH C 553      30.707   13.406   15.078  1.00 35.17           O
ATOM   9129  O   HOH C 554      62.728    8.224   53.667  1.00 39.39           O
ATOM   9130  O   HOH C 555      40.908   30.651  -16.628  1.00 43.98           O
ATOM   9131  O   HOH C 556      25.433   13.361   20.867  1.00 51.69           O
ATOM   9132  O   HOH C 557      61.110   43.343   54.720  1.00 43.96           O
ATOM   9133  O   HOH C 558      35.929   54.054  -19.720  1.00 41.12           O
ATOM   9134  O   HOH C 559      40.926   28.519   32.697  1.00 36.71           O
ATOM   9135  O   HOH C 560      29.727   33.814  -16.315  1.00 51.29           O
ATOM   9136  O   HOH C 561      12.032   45.912   -5.023  1.00 51.45           O
ATOM   9137  O   HOH C 562      26.707   38.905  -29.046  1.00 36.88           O
ATOM   9138  O   HOH C 563      42.476   29.424  -50.344  1.00 34.36           O
ATOM   9139  O   HOH C 564      26.929   38.382   15.969  1.00 42.65           O
ATOM   9140  O   HOH C 565      44.153   33.590   31.871  1.00 52.99           O
ATOM   9141  O   HOH C 566      20.078    8.903   -5.956  1.00 32.32           O
ATOM   9142  O   HOH C 567      16.330   40.436  -23.255  1.00 45.20           O
ATOM   9143  O   HOH C 568      62.450   38.034  -29.670  1.00 34.67           O
ATOM   9144  O   HOH C 569      34.566   25.186  -18.898  1.00 42.79           O
ATOM   9145  O   HOH C 570      54.308   40.409   36.230  1.00 34.04           O
ATOM   9146  O   HOH C 571      -1.350   11.336   -6.164  1.00 40.28           O
ATOM   9147  O   HOH C 572      67.507   34.723  -47.828  1.00 50.31           O
ATOM   9148  O   HOH C 573       3.844   28.712   17.302  1.00 40.94           O
ATOM   9149  O   HOH C 574      18.489    8.051   -1.743  1.00 52.32           O
ATOM   9150  O   HOH C 575      36.692   29.673  -19.227  1.00 41.99           O
ATOM   9151  O   HOH C 576      51.702   21.862  -39.934  1.00 44.78           O
ATOM   9152  O   HOH C 577      17.562   41.582   -7.787  1.00 36.67           O
ATOM   9153  O   HOH C 578      16.734   38.103   17.325  1.00 54.60           O
ATOM   9154  O   HOH C 579      30.018   46.606  -51.010  1.00 37.68           O
ATOM   9155  O   HOH C 580      33.546   38.635  -58.059  1.00 43.54           O
ATOM   9156  O   HOH C 581      38.319   35.374  -64.728  1.00 59.72           O
ATOM   9157  O   HOH C 582      -1.252    8.491   -0.256  1.00 41.47           O
ATOM   9158  O   HOH C 583      38.646   20.532   30.047  1.00 43.68           O
ATOM   9159  O   HOH C 584      -9.044   42.030   -2.839  1.00 51.63           O
ATOM   9160  O   HOH C 585       7.997   40.826  -17.485  1.00 36.39           O
ATOM   9161  O   HOH C 586      22.507   46.255  -50.389  1.00 55.11           O
ATOM   9162  O   HOH C 587      24.895   32.538   18.897  1.00 40.58           O
ATOM   9163  O   HOH C 588      29.706   24.913   -3.153  1.00 56.40           O
ATOM   9164  O   HOH C 589      11.251   33.017  -25.336  1.00 38.03           O
ATOM   9165  O   HOH C 590      38.697   29.084   72.967  1.00 50.30           O
ATOM   9166  O   HOH C 591      48.156   18.554  -29.768  1.00 35.98           O
ATOM   9167  O   HOH C 592      23.180   10.741   15.405  1.00 42.07           O
```

FIGURE 3FFFFFFF

```
ATOM   9168  O   HOH C 593      67.612  50.979 -48.853  1.00 60.56           O
ATOM   9169  O   HOH C 594      64.838  40.850  53.585  1.00 49.06           O
ATOM   9170  O   HOH C 595      34.481  43.383 -19.555  1.00 56.41           O
ATOM   9171  O   HOH C 596      58.077   4.835  39.257  1.00 45.60           O
ATOM   9172  O   HOH C 597       8.735  17.857 -27.231  1.00 55.69           O
ATOM   9173  O   HOH C 598      51.999   5.561  30.306  1.00 45.82           O
ATOM   9174  O   HOH C 599      50.741  34.333 -16.568  1.00 38.29           O
ATOM   9175  O   HOH C 600      23.235  16.349 -21.971  1.00 38.31           O
ATOM   9176  O   HOH C 601      33.049  18.347 -23.244  1.00 55.03           O
ATOM   9177  O   HOH C 602      32.954  33.027  60.363  1.00 39.75           O
ATOM   9178  O   HOH C 603      -9.513  26.371   9.666  1.00 48.18           O
ATOM   9179  O   HOH C 604      39.492  53.167 -41.512  1.00 40.11           O
ATOM   9180  O   HOH C 605      43.604  67.840 -14.245  1.00 50.28           O
ATOM   9181  O   HOH C 606      25.931   6.463 -23.252  1.00 50.33           O
ATOM   9182  O   HOH C 607      28.449  14.931   2.110  1.00 31.20           O
ATOM   9183  O   HOH C 608      12.201  50.256   3.893  1.00 42.76           O
ATOM   9184  O   HOH C 609      39.476  41.789  40.587  1.00 46.15           O
ATOM   9185  O   HOH C 610      43.801  25.044  28.476  1.00 37.10           O
ATOM   9186  O   HOH C 611      21.454   4.191 -10.790  1.00 39.05           O
ATOM   9187  O   HOH C 612      72.142  45.284  39.398  1.00 43.82           O
ATOM   9188  O   HOH C 613      28.732  20.063 -24.504  1.00 31.77           O
ATOM   9189  O   HOH C 614       4.829  34.476  15.995  1.00 42.97           O
ATOM   9190  O   HOH C 615      66.566  22.536 -31.858  1.00 51.04           O
ATOM   9191  O   HOH C 616      29.251  18.235  29.566  1.00 58.32           O
ATOM   9192  O   HOH C 617      30.666  45.433 -58.565  1.00 48.65           O
ATOM   9193  O   HOH C 618       9.099  47.628  -5.680  1.00 41.83           O
ATOM   9194  O   HOH C 619      42.053   4.334  53.007  1.00 57.04           O
ATOM   9195  O   HOH C 620      67.225  18.487  45.882  1.00 47.25           O
ATOM   9196  O   HOH C 621      -1.235  10.514 -10.101  1.00 49.24           O
ATOM   9197  O   HOH C 622      56.031  51.804 -47.304  1.00 54.42           O
ATOM   9198  O   HOH C 623      47.977  50.350 -14.341  1.00 35.72           O
ATOM   9199  O   HOH C 624       9.660   4.657 -11.323  1.00 47.03           O
ATOM   9200  O   HOH C 625      38.623  20.581 -39.511  1.00 40.81           O
ATOM   9201  O   HOH C 626       4.404  22.639 -25.240  1.00 50.21           O
ATOM   9202  O   HOH C 627      69.805  52.013  39.157  1.00 57.57           O
ATOM   9203  O   HOH C 628      16.442  49.332   4.901  1.00 54.37           O
ATOM   9204  O   HOH C 629      15.749  44.041 -20.809  1.00 55.68           O
ATOM   9205  O   HOH C 630      38.559  36.046 -57.246  1.00 53.79           O
ATOM   9206  O   HOH C 631      66.047  28.144 -27.519  1.00 46.85           O
ATOM   9207  O   HOH C 632      27.868  35.984 -11.519  1.00 62.89           O
ATOM   9208  O   HOH C 633      59.484  44.846  61.781  1.00 50.06           O
ATOM   9209  O   HOH C 634      41.929  26.657 -19.083  1.00 42.01           O
ATOM   9210  O   HOH C 635      67.013  40.907 -39.062  1.00 59.81           O
ATOM   9211  O   HOH C 636      31.357  17.300 -27.658  1.00 46.47           O
ATOM   9212  O   HOH C 637      49.062  20.444  39.006  1.00 35.06           O
ATOM   9213  O   HOH C 638      24.723   7.557 -16.552  1.00 39.07           O
ATOM   9214  O   HOH C 639      26.773  16.826 -23.037  1.00 56.73           O
ATOM   9215  O   HOH C 640      61.021  52.221 -50.275  1.00 47.36           O
ATOM   9216  O   HOH C 641      33.479  32.749  46.353  1.00 42.07           O
ATOM   9217  O   HOH C 642      34.459  36.805  60.059  1.00 40.83           O
ATOM   9218  O   HOH C 643      52.578  53.857 -52.909  1.00 56.57           O
ATOM   9219  O   HOH C 644      18.109   4.832   8.675  1.00 50.23           O
ATOM   9220  O   HOH C 645      -5.736  26.139  12.409  1.00 38.83           O
ATOM   9221  O   HOH C 646      58.517  44.293  51.086  1.00 37.38           O
ATOM   9222  O   HOH C 647      27.352  38.051 -39.177  1.00 44.71           O
ATOM   9223  O   HOH C 648      64.509  24.411 -35.092  1.00 36.51           O
ATOM   9224  O   HOH C 649      31.364  49.031 -27.117  1.00 47.19           O
```

FIGURE 3GGGGGGG

```
ATOM   9225  O   HOH C 650      57.949  50.716 -12.681  1.00 51.79           O
ATOM   9226  O   HOH C 651      57.245  28.789  73.229  1.00 61.16           O
ATOM   9227  O   HOH C 652      52.834  -3.284  48.395  1.00 51.25           O
ATOM   9228  O   HOH C 653      26.287  36.397 -50.912  1.00 48.63           O
ATOM   9229  O   HOH C 654      -5.827  38.270  14.601  1.00 54.99           O
ATOM   9230  O   HOH C 655      49.420  -0.487  32.114  1.00 56.90           O
ATOM   9231  O   HOH C 656       3.170  19.391 -22.771  1.00 54.97           O
ATOM   9232  O   HOH C 657      24.493  42.075 -28.989  1.00 59.24           O
ATOM   9233  O   HOH C 658      30.509  35.982  -0.486  1.00 51.93           O
ATOM   9234  O   HOH C 659      31.480  23.702  -8.486  1.00 49.63           O
ATOM   9235  O   HOH C 660      58.110   8.993  62.013  1.00 56.97           O
ATOM   9236  O   HOH C 661      71.925  35.612  48.427  1.00 51.67           O
ATOM   9237  O   HOH C 662      32.337  22.924 -14.504  1.00 55.86           O
ATOM   9238  O   HOH C 663      32.982  47.653 -61.694  1.00 56.82           O
ATOM   9239  O   HOH C 664      54.185  45.827  56.148  1.00 55.79           O
ATOM   9240  O   HOH C 665      -0.171   7.138  -4.852  1.00 48.57           O
ATOM   9241  O   HOH C 666      24.478  18.178  -7.616  1.00 47.63           O
ATOM   9242  O   HOH C 667      26.387  41.713 -41.835  1.00 50.95           O
ATOM   9243  O   HOH C 668      15.283  49.970  -8.955  1.00 60.41           O
ATOM   9244  O   HOH C 669      32.532  33.961  53.105  1.00 57.25           O
ATOM   9245  O   HOH C 670      42.616  45.366 -13.809  1.00 45.10           O
ATOM   9246  O   HOH C 671      23.274  25.328  42.872  1.00 47.39           O
ATOM   9247  O   HOH C 672      66.926  37.156 -33.813  1.00 40.35           O
ATOM   9248  O   HOH C 673      60.208   4.774  48.014  1.00 46.65           O
ATOM   9249  O   HOH C 674     -10.285  18.343 -12.587  1.00 56.29           O
ATOM   9250  O   HOH C 675      41.567  13.128  29.505  1.00 37.25           O
ATOM   9251  O   HOH C 676       2.307   6.135  -6.818  1.00 46.41           O
ATOM   9252  O   HOH C 677      27.042  26.924  45.632  1.00 34.23           O
ATOM   9253  O   HOH C 678      54.939  36.457  64.309  1.00 50.15           O
ATOM   9254  O   HOH C 679      48.379  13.444  64.322  1.00 49.58           O
ATOM   9255  O   HOH C 680      30.493  28.667 -14.999  1.00 44.75           O
ATOM   9256  O   HOH C 681      -8.558  26.615  -0.148  1.00 35.32           O
ATOM   9257  O   HOH C 682      18.478  30.638  21.503  1.00 45.79           O
ATOM   9258  O   HOH C 683      16.722  36.836  12.233  1.00 45.40           O
ATOM   9259  O   HOH C 684      22.062  38.034  10.709  1.00 25.68           O
ATOM   9260  O   HOH C 685      19.515  39.944   4.618  1.00 29.08           O
ATOM   9261  O   HOH C 686     -10.202  35.951   4.908  1.00 49.78           O
ATOM   9262  O   HOH C 687      -6.551  17.469   9.269  1.00 50.81           O
ATOM   9263  O   HOH C 688      -6.071  28.353  11.361  1.00 43.03           O
ATOM   9264  O   HOH C 689      10.433  17.816  21.140  1.00 30.06           O
ATOM   9265  O   HOH C 690      12.372  10.947   5.860  1.00 36.82           O
ATOM   9266  O   HOH C 691      12.844  11.799   8.278  1.00 38.77           O
ATOM   9267  O   HOH C 692      22.364  16.199  -0.328  1.00 34.75           O
ATOM   9268  O   HOH C 693      25.830  14.330  -0.150  1.00 42.15           O
ATOM   9269  O   HOH C 694      27.020  22.091  -5.828  1.00 38.23           O
ATOM   9270  O   HOH C 695      25.351  27.383 -10.025  1.00 25.30           O
ATOM   9271  O   HOH C 696      28.850  23.348 -13.424  1.00 35.22           O
ATOM   9272  O   HOH C 697      27.918  21.112 -12.794  1.00 35.78           O
ATOM   9273  O   HOH C 698      31.331  28.249   3.936  1.00 48.98           O
ATOM   9274  O   HOH C 699      30.532  27.314   6.794  1.00 29.58           O
ATOM   9275  O   HOH C 700       3.623  43.329  -9.405  1.00 33.09           O
ATOM   9276  O   HOH C 701       6.058  47.129  -2.750  1.00 33.68           O
ATOM   9277  O   HOH C 702      10.520  46.596  -1.811  1.00 43.94           O
ATOM   9278  O   HOH C 703      13.669  44.287   4.103  1.00 24.01           O
ATOM   9279  O   HOH C 704      22.411  40.094 -45.443  1.00 30.95           O
ATOM   9280  O   HOH C 705      20.072  34.327 -42.419  1.00 47.24           O
ATOM   9281  O   HOH C 706      26.188  29.080 -41.980  1.00 33.72           O
```

FIGURE 3HHHHHHH

```
ATOM   9282  O   HOH C 707      29.497  24.775  50.678  1.00 35.74           O
ATOM   9283  O   HOH C 708      27.427  21.397  50.255  1.00 42.20           O
ATOM   9284  O   HOH C 709      44.772  44.231  67.775  1.00 40.74           O
ATOM   9285  O   HOH C 710      40.982  40.437  53.572  1.00 35.93           O
ATOM   9286  O   HOH C 711      39.752  32.789  51.017  1.00 29.99           O
ATOM   9287  O   HOH C 712      40.163  16.875  63.352  1.00 42.37           O
ATOM   9288  O   HOH C 713      43.583  20.621 -40.933  1.00 48.50           O
ATOM   9289  O   HOH C 714      -3.109  40.919  -4.538  1.00 34.61           O
ATOM   9290  O   HOH C 715      -5.912  47.341  -2.023  1.00 38.85           O
ATOM   9291  O   HOH C 716      -5.711  45.242   3.768  1.00 43.37           O
ATOM   9292  O   HOH C 717      -5.099  47.375   8.540  1.00 37.06           O
ATOM   9293  O   HOH C 718      24.087  34.538  -4.373  1.00 32.99           O
ATOM   9294  O   HOH C 719      13.935  38.803  -1.851  1.00 21.23           O
ATOM   9295  O   HOH C 720      38.499  49.696 -39.899  1.00 33.79           O
ATOM   9296  O   HOH C 721      46.055  54.572 -33.983  1.00 26.48           O
ATOM   9297  O   HOH C 722      34.383  39.923 -36.667  1.00 19.35           O
ATOM   9298  O   HOH C 723      34.763  42.506 -42.406  1.00 14.29           O
ATOM   9299  O   HOH C 724      33.563  45.882 -30.611  1.00 24.96           O
ATOM   9300  O   HOH C 725      29.003  39.985 -30.440  1.00 21.29           O
ATOM   9301  O   HOH C 726      19.485  36.450 -30.013  1.00 35.64           O
ATOM   9302  O   HOH C 727      26.155  43.105 -34.175  1.00 46.58           O
ATOM   9303  O   HOH C 728      37.557  43.189 -20.621  1.00 32.11           O
ATOM   9304  O   HOH C 729      13.658  31.269 -30.791  1.00 33.58           O
ATOM   9305  O   HOH C 730      17.446  17.945 -19.103  1.00 27.11           O
ATOM   9306  O   HOH C 731      54.551  41.883 -54.672  1.00 28.92           O
ATOM   9307  O   HOH C 732      43.325  12.176  33.783  1.00 33.38           O
ATOM   9308  O   HOH C 733      43.021  27.309  34.143  1.00 28.09           O
ATOM   9309  O   HOH C 734      57.432  25.133  36.529  1.00 39.26           O
ATOM   9310  O   HOH C 735      57.536  19.314  31.129  1.00 40.76           O
ATOM   9311  O   HOH C 736      54.139  13.447  36.054  1.00 13.73           O
ATOM   9312  O   HOH C 737      60.852  14.313  33.300  1.00 34.82           O
ATOM   9313  O   HOH C 738      61.207  41.484 -45.803  1.00 12.89           O
ATOM   9314  O   HOH C 739      16.598  11.635  -9.895  1.00 15.74           O
ATOM   9315  O   HOH C 740      15.284  30.418   8.113  1.00 17.10           O
```

CRYSTALLIZATION OF HISTONE DEACETYLASE 2

FIELD OF THE INVENTION

The present invention relates to histone deacetylases ("HDAC") and more specifically to a particular HDAC known as HDAC-2. Provided is HDAC-2 in crystalline form, methods of forming crystals comprising HDAC-2, methods of using crystals comprising HDAC-2, a crystal structure of HDAC-2, and methods of using the crystal structure.

BACKGROUND OF THE INVENTION

A general approach to designing inhibitors that are selective for a given protein is to determine how a putative inhibitor interacts with a three dimensional structure of that protein. For this reason it is useful to obtain the protein in crystalline form and perform X-ray diffraction techniques to determine the protein's three dimensional structure coordinates. Various methods for preparing crystalline proteins are known in the art.

Once protein crystals are produced, crystallographic data can be generated using the crystals to provide useful structural information that assists in the design of small molecules that bind to the active site of the protein and inhibit the protein's activity in vivo. If the protein is crystallized as a complex with a ligand, one can determine both the shape of the protein's binding pocket when bound to the ligand, as well as the amino acid residues that are capable of close contact with the ligand. By knowing the shape and amino acid residues comprised in the binding pocket, one may design new ligands that will interact favorably with the protein. With such structural information, available computational methods may be used to predict how strong the ligand binding interaction will be. Such methods aid in the design of inhibitors that bind strongly, as well as selectively to the protein.

SUMMARY OF THE INVENTION

The present invention is directed to crystals comprising HDAC-2 and particularly crystals comprising HDAC-2 that have sufficient size and quality to obtain useful information about the structural properties of HDAC-2 and molecules or complexes that may associate with HDAC-2.

In one embodiment, a composition is provided that comprises a protein in crystalline form wherein at least a portion of the protein has 55%, 65%, 75%, 85%, 90%, 95%, 97%, 99% or greater identity with SEQ. ID No. 4.

In one embodiment, a composition is provided that comprises a protein in crystalline form wherein at least a portion of the protein has 55%, 65%, 75%, 85%, 90%, 95%, 97%, 99% or greater identity with SEQ. ID No. 5.

In one variation, the protein has activity characteristic of HDAC-2. For example, the protein may optionally be inhibited by inhibitors of wild type HDAC-2. The protein crystal may also diffract X-rays for a determination of structure coordinates to a resolution of 4 Å, 3.5 Å, 3.0 Å or less.

In one variation, the protein crystal has a crystal lattice in a $P2_1$ space group. The protein crystal may also have a crystal lattice having unit cell dimensions, +/−5%, of a=79.9 Å, b=56.9 Å, c=95.2 Å, $\alpha=90°$, $\beta=90.5°$, and $\gamma=90°$.

In one variation, the protein crystal has a crystal lattice in a $P2_12_12_1$ space group. The protein crystal may also have a crystal lattice having unit cell dimensions, +/−5%, of a=92.1 Å, b=97.6 Å, c=138.9 Å, and $\alpha=\beta=\gamma=90°$.

The present invention is also directed to crystallizing HDAC-2. The present invention is also directed to the conditions useful for crystallizing HDAC-2. It should be recognized that a wide variety of crystallization methods can be used in combination with the crystallization conditions to form crystals comprising HDAC-2 including, but not limited to, vapor diffusion, batch, dialysis, and other methods of contacting the protein solution for the purpose of crystallization.

In one embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with SEQ. ID No. 4; and storing the crystallization volume under conditions suitable for crystal formation.

In one variation, the crystallization volume comprises the protein in a concentration between 1 mg/ml and 50 mg/ml, and 5-50% w/v of precipitant wherein the precipitant comprises one or more members of the group consisting of PEG having a molecular weight range between 200-20000, 2-methyl-2,4-pentanediol (MPD) and isopropanol, and wherein the crystallization volume has a pH between pH 4 and pH 10.

In one embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with SEQ. ID No. 5; and storing the crystallization volume under conditions suitable for crystal formation.

In one variation, the crystallization volume comprises the protein in a concentration between 1 mg/ml and 50 mg/ml, and 5-50% w/v of precipitant wherein the precipitant comprises one or more members of the group consisting of PEG having a molecular weight range between 200-20000, 2-methyl-2,4-pentanediol (MPD) and isopropanol, and wherein the crystallization volume has a pH between pH 4 and pH 10.

The method may optionally further comprise forming a protein crystal that has a crystal lattice in a $P2_1$ space group. The method also optionally further comprises forming a protein crystal that has a crystal lattice having unit cell dimensions, +/−5%, of a=79.9 Å, b=56.9 Å, c=95.2 Å, $\alpha=90°$, $\beta=90.5°$, and $\gamma=90°$. of. The invention also relates to protein crystals formed by these methods.

The method may optionally further comprise forming a protein crystal that has a crystal lattice in a $P2_12_12_1$ space group. The method also optionally further comprises forming a protein crystal that has a crystal lattice having unit cell dimensions, +/−5%, of a=92.1 Å, b=97.6 Å, c=138.9 Å, and $\alpha=\beta=\gamma=90°$. The invention also relates to protein crystals formed by these methods.

The present invention is also directed to a composition comprising an isolated protein that comprises or consists of one or more of the protein sequence(s) of HDAC-2 taught herein for crystallizing HDAC-2. The present invention is also directed to a composition comprising an isolated nucleic acid molecule that comprises or consists of the nucleotides for expressing the protein sequence of HDAC-2 taught herein for crystallizing HDAC-2.

The present invention is also directed to an expression vector that may be used to express the isolated proteins taught herein for crystallizing HDAC-2. In one variation, the expression vector comprises a promoter that promotes expression of the isolated protein.

The present invention is also directed to a cell line transformed or transfected by an isolated nucleic acid molecule or expression vector of the present invention.

The present invention is also directed to structure coordinates for HDAC-2 as well as structure coordinates that are comparatively similar to these structure coordinates. It is noted that these comparatively similar structure coordinates may encompass proteins with similar sequences and/or structures, such as other histone deacetylases. For example, machine-readable data storage media is provided having data storage material encoded with machine-readable data that comprises structure coordinates that are comparatively similar to the structure coordinates of HDAC-2. The present invention is also directed to a machine readable data storage medium having data storage material encoded with machine readable data, which, when read by an appropriate machine, can display a three dimensional representation of all or a portion of a structure of HDAC-2 or a model that is comparatively similar to the structure of all or a portion of HDAC-2.

Various embodiments of machine readable data storage medium are provided that comprise data storage material encoded with machine readable data. The machine readable data comprises: structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1. The amino acids being overlayed and compared need not be identical when the RMSD calculation is performed on alpha carbons and main chain atoms but the amino acids being overlayed and compared must have identical side chains when the RMSD calculation is performed on all non-hydrogen atoms.

For example, in one embodiment where the comparison is based on the 10 Angstrom set of amino acid residues (Column 1) and is based on superimposing alpha-carbon atoms (Column 2), the structure coordinates may have a root mean square deviation equal to or less than 0.45 when compared to the structure coordinates of FIG. 3.

interacting with HDAC-2. Ligands that interact with HDAC-2 may be any type of atom, compound, protein or chemical group that binds to or otherwise associates with the protein. Examples of types of ligands include natural substrates for HDAC-2, inhibitors of HDAC-2, and heavy atoms. The inhibitors of HDAC-2 may optionally be used as drugs to treat therapeutic indications by modifying the in vivo activity of HDAC-2.

In various embodiments, methods are provided for displaying a three dimensional representation of a structure of a protein comprising:

taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

computing a three dimensional representation of a structure based on the structure coordinates; and displaying the three dimensional representation.

The present invention is also directed to a method for solving a three-dimensional crystal structure of a target protein using the structure of HDAC-2.

In various embodiments, computational methods are provided comprising: taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

TABLE 1

| AA RESIDUES TO USE TO PERFORM RMSD COMPARISON | PORTION OF EACH AA RESIDUE USED TO PERFORM RMSD COMPARISON | RMSD VALUE LESS THAN OR EQUAL TO | | |
|---|---|---|---|---|
| Table 2 | alpha-carbon atoms[1] | 0.33 | 0.22 | 0.17 |
| (4 Angstrom set) | main-chain atoms[1] | 0.35 | 0.24 | 0.18 |
|  | all non-hydrogen[2] | 0.49 | 0.33 | 0.25 |
| Table 3 | alpha-carbon atoms[1] | 0.39 | 0.26 | 0.20 |
| (7 Angstrom set) | main-chain atoms[1] | 0.44 | 0.30 | 0.22 |
|  | all non-hydrogen[2] | 0.60 | 0.40 | 0.30 |
| Table 4 | alpha-carbon atoms[1] | 0.45 | 0.30 | 0.23 |
| (10 Angstrom set) | main-chain atoms[1] | 0.51 | 0.34 | 0.25 |
|  | all non-hydrogen[2] | 0.63 | 0.42 | 0.31 |
| SEQ. ID No. 3 | alpha-carbon atoms[1] | 1.13 | 0.75 | 0.56 |
|  | main-chain atoms[1] | 1.11 | 0.74 | 0.56 |
|  | all non-hydrogen[2] | 1.24 | 0.82 | 0.62 |

[1] the RMSD computed between the atoms of all amino acids that are common to both the target and the reference in the aligned and superposed structure. The amino acids need not be identical.
[2] the RMSD computed only between identical amino acids, which are common to both the target and the reference in the aligned and superposed structure.

The present invention is also directed to a three-dimensional structure of all or a portion of HDAC-2. This three-dimensional structure may be used to identify binding sites, to provide mutants having desirable binding properties, and ultimately, to design, characterize, or identify ligands capable of computing phases based on the structural coordinates;

computing an electron density map based on the computed phases; and determining a three-dimensional crystal structure based on the computed electron density map.

In various embodiments, computational methods are provided comprising: taking an X-ray diffraction pattern of a crystal of the target protein; and computing a three-dimensional electron density map from the X-ray diffraction pattern by molecular replacement, wherein structure coordinates used as a molecular replacement model comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

These methods may optionally further comprise determining a three-dimensional crystal structure based upon the computed three-dimensional electron density map.

The present invention is also directed to using a crystal structure of HDAC-2, in particular the structure coordinates of HDAC-2 and the surface contour defined by them, in methods for screening, designing, or optimizing molecules or other chemical entities that interact with and preferably inhibit HDAC-2.

One skilled in the art will appreciate the numerous uses of the inventions described herein, particularly in the areas of drug design, screening and optimization of drug candidates, as well as in determining additional unknown crystal structures. For example, a further aspect of the present invention relates to using a three-dimensional crystal structure of all or a portion of HDAC-2 and/or its structure coordinates to evaluate the ability of entities to associate with HDAC-2. The entities may be any entity that may function as a ligand and thus may be any type of atom, compound, protein (such as antibodies) or chemical group that can bind to or otherwise associate with a protein.

In various embodiments, methods are provided for evaluating a potential of an entity to associate with a protein comprising:

creating a computer model of a protein structure using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

performing a fitting operation between the entity and the computer model; and analyzing results of the fitting operation to quantify an association between the entity and the model.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

employing the three-dimensional structure to design or select an entity that can associate with the protein; and contacting the entity with a protein wherein at least a portion of the protein has 55%, 65%, 75%, 85%, 90%, 95%, 97%, 99% or greater identity with SEQ. ID No. 4.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

employing the three-dimensional structure to design or select an entity that can associate with the protein; and contacting the entity with a protein wherein at least a portion of the protein has 55%, 65%, 75%, 85%, 90%, 95%, 97%, 99% or greater identity with SEQ. ID No. 5.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1; and employing the three-dimensional structure to design or select an entity that can associate with the protein.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1);

employing the computer model to design or select an entity that can associate with the protein; and contacting the entity with a protein wherein at least a portion of the protein has 55%, 65%, 75%, 85%, 90%, 95%, 97%, 99% or greater identity with SEQ. ID No. 4.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1);

employing the computer model to design or select an entity that can associate with the protein; and contacting the entity with a protein wherein at least a portion of the protein has 55%, 65%, 75%, 85%, 90%, 95%, 97%, 99% or greater identity with SEQ. ID No. 5.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and employing the computer model to design or select an entity that can associate with the protein.

In other embodiments, methods are provided for evaluating the ability of an entity to associate with a protein, the method comprising:

constructing a computer model defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

selecting an entity to be evaluated by a method selected from the group consisting of (i) assembling molecular fragments into the entity, (ii) selecting an entity from a small molecule database, (iii) de novo ligand design of the entity, and (iv) modifying a known ligand for HDAC-2, or a portion thereof;

performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In other embodiments, methods are provided for evaluating the ability of an entity to associate with a protein, the method comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1);

selecting an entity to be evaluated by a method selected from the group consisting of (i) assembling molecular fragments into the entity, (ii) selecting an entity from a small molecule database, (iii) de novo ligand design of the entity, and (iv) modifying a known ligand for HDAC-2, or a portion thereof;

performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In regard to each of these embodiments, the protein may optionally have activity characteristic of HDAC-2. For example, the protein may optionally be inhibited by inhibitors of wild type HDAC-2.

In another embodiment, a method is provided for identifying an entity that associates with a protein comprising: taking structure coordinates from diffraction data obtained from a crystal of a protein wherein at least a portion of the protein has 55%, 65%, 75%, 85%, 90%, 95%, 97%, 99% or greater identity with SEQ. ID No. 4; and performing rational drug design using a three dimensional structure that is based on the obtained structure coordinates.

In another embodiment, a method is provided for identifying an entity that associates with a protein comprising: taking structure coordinates from diffraction data obtained from a crystal of a protein wherein at least a portion of the protein has 55%, 65%, 75%, 85%, 90%, 95%, 97%, 99% or greater identity with SEQ. ID No. 5; and performing rational drug design using a three dimensional structure that is based on the obtained structure coordinates.

The protein crystals may optionally have a crystal lattice with a P2$_1$ space group and unit cell dimensions, +/−5%, of a=79.9 Å, b=56.9 Å, c=95.2 Å, α=90°, β=90.5°, and γ=90°.

The protein crystals may optionally have a crystal lattice with a P2$_1$2$_1$2$_1$ space group and unit cell dimensions, +/−5%, of a=92.1 Å, b=97.6 Å, c=138.9 Å, and α=β=γ=90°.

The method may optionally further comprise selecting one or more entities based on the rational drug design and contacting the selected entities with the protein. The method may also optionally further comprise measuring an activity of the protein when contacted with the one or more entities. The method also may optionally further comprise comparing activity of the protein in a presence of and in the absence of the one or more entities; and selecting entities where activity of the protein changes depending whether a particular entity is present. The method also may optionally further comprise contacting cells expressing the protein with the one or more entities and detecting a change in a phenotype of the cells when a particular entity is present.

BRIEF DESCRIPTION OF THE FIGURES

FIG. 1 illustrates SEQ. ID Nos. 1, 2, 3, 4, and 5 referred to in this application.

FIG. 3 lists a set of atomic structure coordinates as derived by X-ray crystallography from a crystal that comprises three molecules of HDAC-2 protein in the asymmetric. The listed amino acids represent the residues of each of the three molecules of HDAC-2 for which structure coordinates are reported, the amino acid number ("E") being derived from the corresponding amino acid position for HDAC-2 in SEQ ID NO:5. The following abbreviations are used in FIG. 3: "X, Y, Z" crystallographically define the atomic position of the element measured; "B" is a thermal factor that measures movement of the atom around its atomic center; "Occ" is an occupancy factor that refers to the fraction of the molecules in which each atom occupies the position specified by the coordinates (a value of "1" indicates that each atom has the same conformation, i.e., the same position, in all molecules of the crystal).

DETAILED DESCRIPTION OF THE INVENTION

Figure 2A:
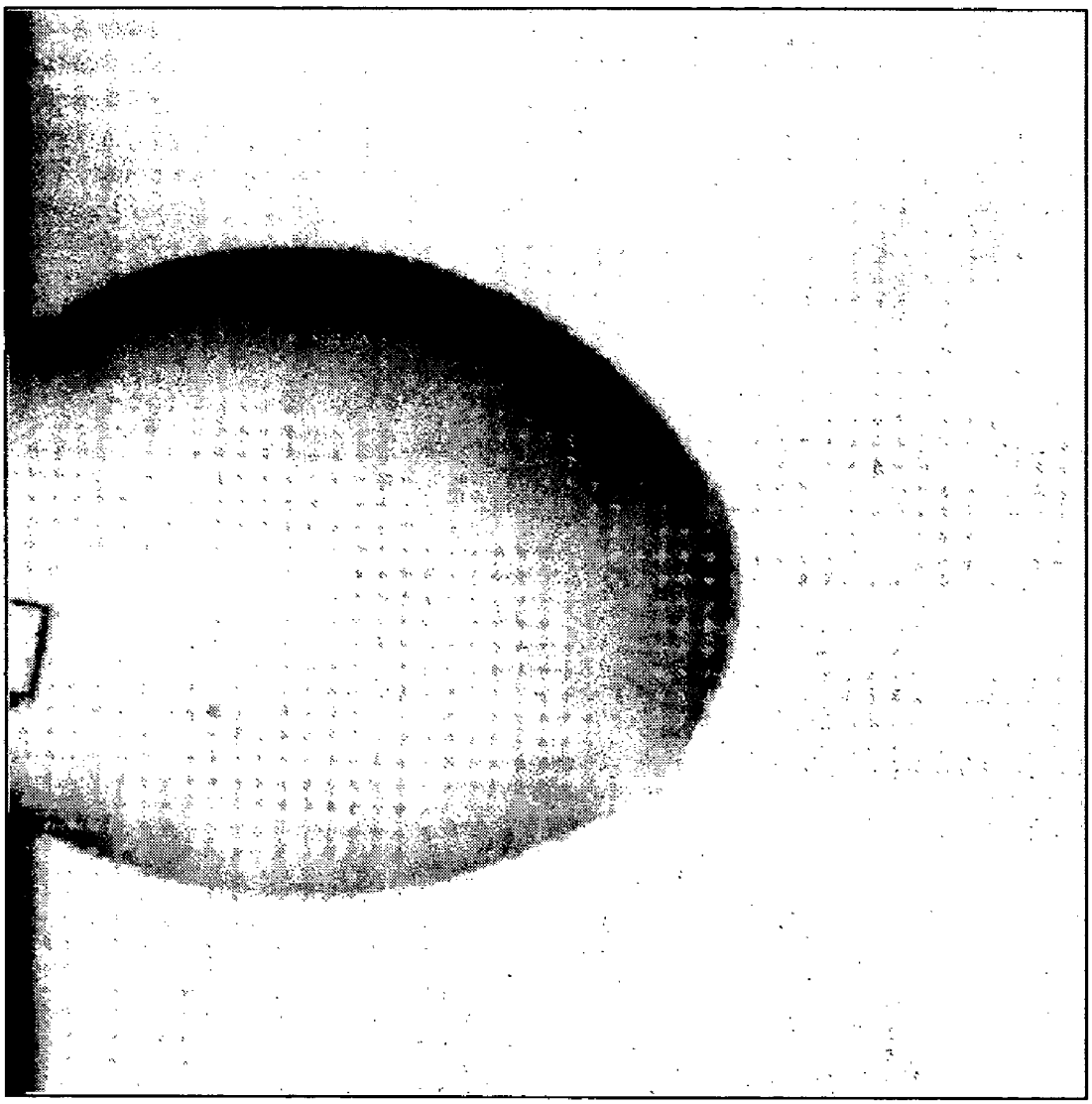
FIG. 2A illustrates a crystal formed according to Example 1 with a crystal lattice in a $P2_1$ space group.

The present invention relates to a member of the histone deacetylase (HDAC) family known as HDAC-2. More specifically, present invention relates to HDAC-2 in crystalline form, methods of forming crystals comprising HDAC-2, methods of using crystals comprising HDAC-2, a crystal structure of HDAC-2, and methods of using the crystal structure.

In describing protein structure and function herein, reference is made to amino acids comprising the protein. The amino acids may also be referred to by their conventional abbreviations; A=Ala=Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; and H=His=Histidine.

1. HDAC-2

Histone deacetylases (HDACs) play important roles in the modulation of chromatin structure and the regulation of gene expression. HDACs are involved in cell-cycle progression and differentiation, and their deregulation is associated with several different forms of cancer. HDACs are known to acetylate the ε-amino group of lysine residues.

Seventeen human genes that encode proven or putative histone deacetylases (HDACs) have been identified to date, some of which are described in Johnstone, R. W., "Histone-Deacetylase Inhibitors: Novel Drugs for the Treatment of Cancer", Nature Reviews, Volume I, pp. 287-299, (2002) and PCT Publication Nos. 00/10583, 01/18045, 01/42437 and 02/08273.

HDACs have been categorized into three distinct classes based on size and sequence homology. Class I of the HDAC family includes HDACs 1, 2, 3 and 8.

HDAC-2 is a 488 residue, 55 kDa protein localized to the nucleus of a wide array of tissues, as well as several human tumor cell lines. The wild-type form of full length HDAC-2 is set forth as SEQ. ID No. 1 (GenBank Accession Number NM 001527; Furukawa, Y. et al. "Isolation and mapping of a human gene (RPD3L1) that is homologous to RPD3, a transcription factor in *Saccharomyces cerevisiae*" Cryogenet. Cell Genet. 73 (1-2), 130-133 (1996)). $Zn^{2+}$ is likely native to the protein and required for HDAC-2 activity. All class I HDACs (including HDAC-2) appear to be sensitive to inhibition by trichostatin A (TSA), which is the ligand present in the structure described herein.

It should be understood that the methods and compositions provided relating to HDAC-2 are not intended to be limited to the wild type, full length form of HDAC-2. Instead, the present invention also relates to fragments and variants of HDAC-2 as described herein.

In one embodiment, HDAC-2 comprises the wild-type form of full length HDAC-2, set forth herein as SEQ. ID No. 1.

It should be recognized that the invention may be readily extended to various variants of wild-type HDAC-2 and variants of fragments thereof. In another embodiment, HDAC-2 comprises a sequence that has at least 65% identity, preferably at least 70%, 80%, 90%, 95% or higher identity with SEQ. ID No. 1. In another embodiment, HDAC-2 comprises a sequence that has at least 65% identity, preferably at least 70%, 80%, 90%, 95% or higher identity with SEQ. ID No. 4. In yet another embodiment, HDAC-2 comprises a sequence that has at least 65% identity, preferably at least 70%, 80%, 90%, 95% or higher identity with SEQ. ID No. 5.

It is also noted that the above sequences of HDAC-2 is also intended to encompass isoforms, mutants and fusion proteins of these sequences. An example of a fusion protein is provided by SEQ ID NO:3 which includes a 7 residue C-terminal tag (GHHHHHH) (residues 489-495 of SEQ ID NO:3 that may be used to facilitate purification of the protein.

With the crystal structure provided herein, where amino acid residues are positioned in the structure are now known. As a result, the impact of different substitutions can be more easily predicted and understood.

Figure 5:
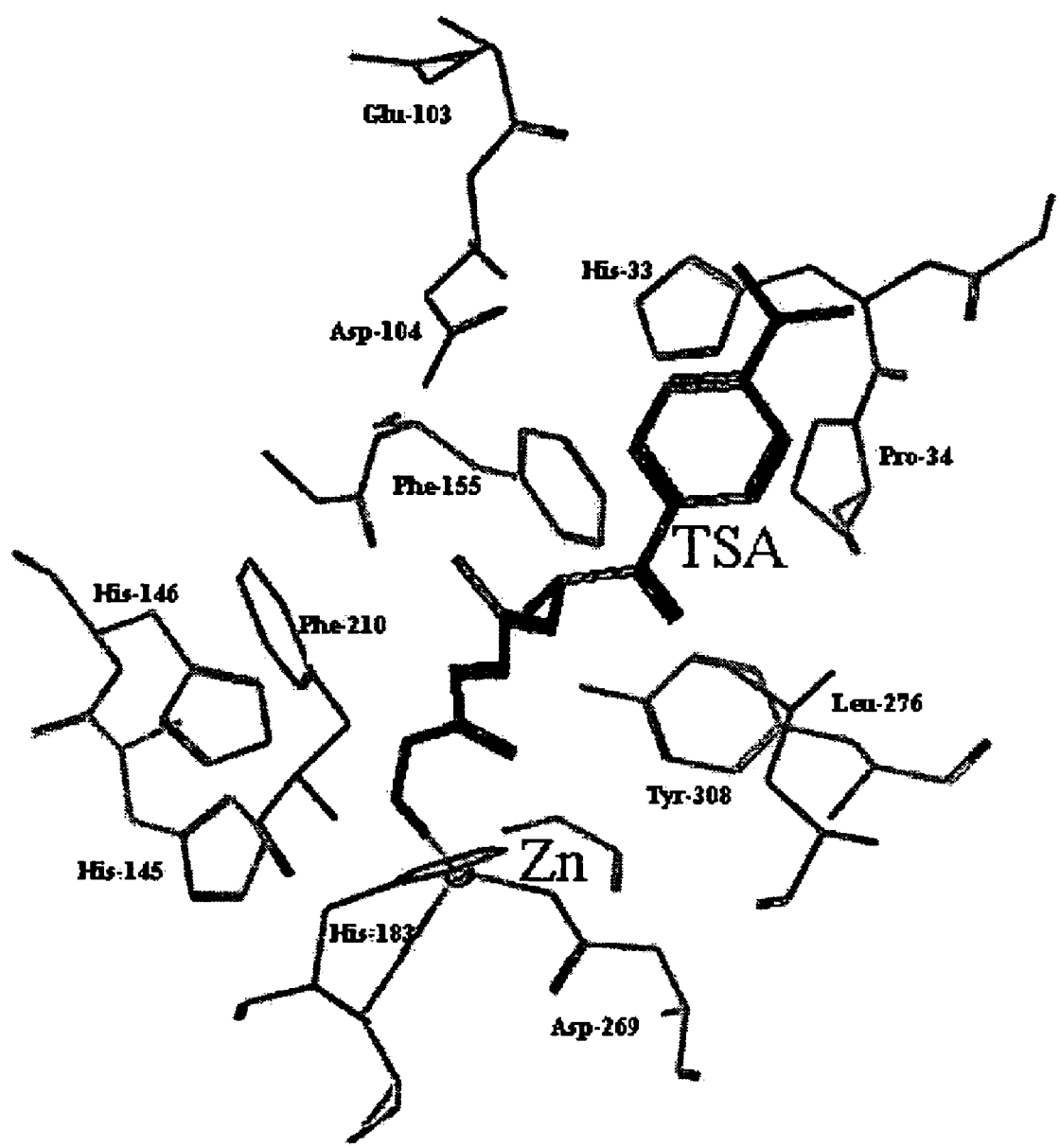
FIG. 5 illustrates key interactions between groups in the binding pocket and the TSA molecule.

For example, based on the crystal structure, applicants have determined that HDAC-2 has one binding pocket capable of binding to a TSA molecule. FIG. 5 illustrates a TSA molecule bound to the HDAC-2 binding pocket.

The amino acids shown in Table 2 were found to be within 4 Angstroms of the binding pocket and therefore close enough to interact with TSA. Applicants have also determined that the amino acids of Table 3 are within 7 Angstroms of TSA bound in the binding pocket and therefore are also close enough to interact with that substrate or analogs thereof. Further it has been determined that the amino acids of Table 4 are within 10 Angstroms of the bound TSA in the binding pocket.

One or more of these sets of amino acids is preferably conserved in a variant of HDAC-2. Hence, HDAC-2 may optionally comprise a sequence wherein at least a portion of the protein that has at least 65% identity, preferably at least 70%, 80%, 90%, 95% or higher identity with any one of the above sequences (e.g., all of SEQ. ID No. 1, SEQ. ID No. 4, or SEQ. ID No. 5), where at least the residues shown in Tables 2, 3, and 4 are conserved with the exception of 0, 1, 2, 3, or 4 residues. It should be recognized that one might optionally vary some of the binding site residues in order to determine the effect such changes have on structure or activity.

TABLE 2

Amino Acids encompassed by a 4-Angstrom radius around the HDAC-2 active site.

| GLY 32 | HIS 33 | PRO 34 |
| ASP 104 | HIS 145 | HIS 146 |
| GLY 154 | PHE 155 | ASP 181 |
| HIS 183 | PHE 210 | ASP 269 |
| LEU 276 | TYR 308 | |

TABLE 3

Amino Acids encompassed by a 7-Angstrom radius around the HDAC-2 active site.

| GLN 31 | GLY 32 | HIS 33 |
| PRO 34 | MET 35 | GLU 103 |
| ASP 104 | CYS 105 | PRO 106 |
| GLY 143 | HIS 145 | HIS 146 |
| SER 153 | GLY 154 | PHE 155 |
| CYS 156 | ASP 179 | ASP 181 |
| ILE 182 | HIS 183 | HIS 184 |
| TYR 209 | PHE 210 | GLN 265 |
| GLY 267 | ASP 269 | ASP 274 |
| ARG 275 | LEU 276 | GLY 305 |
| GLY 306 | GLY 307 | TYR 308 |

TABLE 4

Amino Acids encompassed by a 4-Angstrom radius around the HDAC-2 active site.

| TYR 29 | GLY 30 | GLN 31 |
| GLY 32 | HIS 33 | PRO 34 |
| MET 35 | LYS 36 | ARG 39 |
| ASN 100 | GLY 102 | GLU 103 |
| ASP 104 | CYS 105 | PRO 106 |
| GLY 142 | GLY 143 | LEU 144 |
| HIS 145 | HIS 146 | ALA 147 |
| LYS 148 | ALA 153 | SER 153 |
| GLY 154 | PHE 155 | CYS 156 |
| TYR 157 | ILE 161 | TYR 177 |
| ASP 179 | ILE 180 | ASP 181 |
| ILE 182 | HIS 183 | HIS 184 |
| GLY 185 | ASP 186 | GLY 187 |
| SER 202 | PHE 203 | HIS 204 |
| GLU 208 | TYR 209 | PHE 210 |
| PRO 211 | GLY 212 | GLN 265 |
| CYS 266 | GLY 267 | ALA 268 |
| ASP 269 | SER 270 | ASP 274 |
| ARG 275 | LEU 276 | GLY 277 |
| CYS 278 | GLY 304 | GLY 305 |
| GLY 306 | GLY 307 | TYR 308 |
| THR 309 | VAL 313 | TRP 317 |

With the benefit of the crystal structure and guidance provided by Tables 2, 3, and 4, a wide variety of HDAC-2 variants (e.g., insertions, deletions, substitutions, etc.) that fall within the above specified identity ranges may be designed and manufactured utilizing recombinant DNA techniques well known to those skilled in the art, particularly in view of the knowledge of the crystal structure provided herein. These modifications can be used in a number of combinations to produce the variants. The present invention is useful for crystallizing and then solving the structure of the range of variants of HDAC-2.

Variants of HDAC-2 may be insertional variants in which one or more amino acid residues are introduced into a predetermined site in the HDAC-2 sequence. For instance, insertional variants can be fusions of heterologous proteins or polypeptides to the amino or carboxyl terminus of the subunits.

Variants of HDAC-2 also may be substitutional variants in which at least one residue has been removed and a different residue inserted in its place. Non-natural amino acids (i.e. amino acids not normally found in native proteins), as well as isosteric analogs (amino acid or otherwise) may optionally be employed in substitutional variants. Examples of suitable substitutions are well known in the art, such as Glu→Asp, Ser→Cys, Cys→Ser, and His→Ala for example.

Another class of variants is deletional variants, which are characterized by the removal of one or more amino acid residues from the HDAC-2 sequence.

Other variants may be produced by chemically modifying amino acids of the native protein (e.g., diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution of bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; 0-methylisourea; 2,4-pentanedione; and transaminase catalyzed reaction with glyoxylate; and N-hydroxysuccinamide esters of polyethylene glycol or other bulky substitutions.

Arginyl residues may be modified by reaction with a number of reagents, including phenylglyoxal; 2,3-butanedione; 1,2-cyclohexanedione; and ninhydrin. Modification of arginine residues requires that the reaction be performed in alkaline conditions because of the high $pK_a$ of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming 0-acetyl tyrosyl species and 3-nitro derivatives, respectively. Tyrosyl residues may also be iodinated using $^{125}I$ or $^{131}I$ to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, *Proteins: Struc-* ture and Molecular Properties, W.H. Freeman & Co., San Francisco, pp. 79-86, 1983), acetylation of the N-terminal amine and amidation of any C-terminal carboxyl group.

As can be seen, modifications of the nucleic sequence encoding HDAC-2 may be accomplished by a variety of well-known techniques, such as site-directed mutagenesis (see, Gillman and Smith, Gene 8:81-97 (1979) and Roberts, S. et al., Nature 328:731-734 (1987)). When modifications are made, these modifications may optionally be evaluated for there affect on a variety of different properties including, for example, solubility, crystallizability and a modification to the protein's structure and activity.

In one variation, the variant and/or fragment of wild-type HDAC-2 is functional in the sense that the resulting protein is capable of associating with at least one same chemical entity that is also capable of selectively associating with a protein comprising SEQ. ID No. 1 since this common associative ability evidences that at least a portion of the native structure has been conserved. That chemical entity may optionally be TSA.

It is noted that the activity of the native protein need not necessarily be conserved. Rather, amino acid substitutions, additions or deletions that interfere with native activity but which do not significantly alter the three-dimensional structure of the domain are specifically contemplated by the invention. Crystals comprising such variants of HDAC-2, and the atomic structure coordinates obtained therefrom, can be used to identify compounds that bind to the native domain. These compounds may affect the activity or the native domain.

Amino acid substitutions, deletions and additions that do not significantly interfere with the three-dimensional structure of HDAC-2 will depend, in part, on the region where the substitution, addition or deletion occurs in the crystal structure. These modifications to the protein can now be made far more intelligently with the crystal structure information provided herein. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine; isoleucine; valine; glycine; alanine; asparagines; glutamine; serine; threonine; phenylalanine; and tyrosine. Other conservative amino acid substitutions are well known in the art.

It should be understood that the protein may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of HDAC-2 will be apparent to those having skills in the art, particularly in view of the three dimensional structure of HDAC-2 provided herein.

2. Cloning, Expression and Purification of HDAC-2

The gene encoding HDAC-2 can be isolated from RNA, cDNA or cDNA libraries. In this case, the portion of the gene encoding amino acid residues 1-488 was isolated and is shown as SEQ. I.D. No. 2.

Construction of expression vectors and recombinant proteins from the DNA sequence encoding HDAC-2 may be performed by various methods well known in the art. For example, these techniques may be performed according to Sambrook et al., Molecular Cloning—A Laboratory Manual, Cold Spring Harbor, N.Y. (1989), and Kriegler, M., Gene Transfer and Expression, A Laboratory Manual, Stockton Press, New York (1990).

A variety of expression systems and hosts may be used for the expression of HDAC-2. Example 1 provides one such expression system.

Once expressed, purification steps are employed to produce HDAC-2 in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography, (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

HDAC-2 may optionally be affinity labeled during cloning, preferably with a poly-histidine ($His_6$) region, in order to facilitate purification. With the use of an affinity label, it is possible to perform a one-step purification process on a purification column that has a unique affinity for the label. The affinity label may be optionally removed after purification. These and other purification methods are known and will be apparent to one of skill in the art.

3. Crystallization & Crystals Comprising HDAC-2

One aspect of the present invention relates to methods for forming crystals comprising HDAC-2 as well as crystals comprising HDAC-2.

In one embodiment, a method for forming crystals comprising HDAC-2 is provided comprising forming a crystallization volume comprising HDAC-2, one or more precipitants, optionally a buffer, optionally a monovalent or divalent salt and optionally an organic solvent; and storing the crystallization volume under conditions suitable for crystal formation.

In yet another embodiment, a method for forming crystals comprising HDAC-2 is provided comprising forming a crystallization volume comprising HDAC-2 in solution comprising the components shown in Table 5; and storing the crystallization volume under conditions suitable for crystal formation.

TABLE 5

Precipitant 5-50% w/v comprising one or more of any of the PEGs from the 200-20000 molecular weight range, 2-methyl-2,4-pentanediol (MPD) or isopropanol

TABLE 5-continued pH pH 4-10. Buffers that may be used include, but are not limited to imidazole, acetate, hepes, citrate, tris, CHES, MES and combinations thereof.

Additives 0.01 mM-3 M comprising one or more of any monovalent or divalent cation, including, but not limited to, $Ca^{2+}$, $Zn^{2+}$, $Mg^{2+}$, $Mn^{2+}$, $Na^+$ or $K^+$, and/or ammonium sulfate.

Protein Concentration 1 mg/ml-50 mg/ml

Temperature

1° C.-25° C.

In yet another embodiment, a method for forming crystals comprising HDAC-2 is provided comprising forming a crystallization volume comprising HDAC-2; introducing crystals comprising HDAC-2 as nucleation sites, and storing the crystallization volume under conditions suitable for crystal formation.

Crystallization experiments may optionally be performed in volumes commonly used in the art, for example typically 15, 10, 5, 2 microliters or less. It is noted that the crystallization volume optionally has a volume of less than 1 microliter, optionally 500, 250, 150, 100, 50 or less nanoliters.

It is also noted that crystallization may be performed by any crystallization method including, but not limited to batch, dialysis and vapor diffusion (e.g., sitting drop and hanging drop) methods. Micro and/or macro seeding of crystals may also be performed to facilitate crystallization.

It should be understood that forming crystals comprising HDAC-2 and crystals comprising HDAC-2 according to the invention are not intended to be limited to the wild-type, full length HDAC-2 shown in SEQ. ID No. 1. Rather, it should be recognized that the invention may be extended to various other fragments and variants of wild-type HDAC-2 as described above.

It should also be understood that forming crystals comprising HDAC-2 and crystals comprising HDAC-2 according to the invention may be such that HDAC-2 is complexed with one or more ligands and one or more copies of the same ligand. The ligand used to form the complex may be any ligand capable of binding to HDAC-2. In one variation, the ligand is a natural substrate. In another variation, the ligand is an inhibitor, such as trichostatin A (TSA). In one particular variation, the ligand binds to the binding pocket of the protein. Examples of such ligands include, but are not limited to, small molecule inhibitors of HDAC-2 such as trichostatin A (TSA). In one particular variation, the crystallizable compositions of this invention comprise one or more copies of TSA as the substrate.

Optionally, the HDAC-2 complex may further comprise divalent cations, especially zinc which may be introduced in any suitable manner. For example, the cations may be introduced by incubating the desired divalent cation with a suitable metal salt such as $MgCl_2$ prior to incubation with the HDAC-2 protein.

In one particular embodiment, HDAC-2 crystals have a crystal lattice in the $P2_1$ space group. HDAC-2 crystals may also optionally have unit cell dimensions, +/−5%, of a=79.9 Å, b=56.9 Å, c=95.2 Å, α=90°, β=90.5°, and γ=90°.

In one particular embodiment, HDAC-2 crystals have a crystal lattice in a $P2_12_12_1$ space group. HDAC-2 crystals may also optionally have unit cell dimensions, +/−5%, of a=92.1 Å, b=97.6 Å, c=138.9 Å, and α=β=γ=90°.

HDAC-2 crystals also preferably are capable of diffracting X-rays for determination of atomic coordinates to a resolution of 4 Å, 3 Å, 2.5 Å, 2 Å or greater.

Crystals comprising HDAC-2 may be formed by a variety of different methods known in the art. For example, crystallizations may be performed by batch, dialysis, and vapor diffusion (sitting drop and hanging drop) methods. A detailed description of basic protein crystallization setups may be found in McRee, D. and David. P., *Practical Protein Crystallography*, $2^{nd}$ Ed. (1999), Academic Press Inc. Further descriptions regarding performing crystallization experiments are provided in Stevens, et al. (2000) *Curr. Opin. Struct. Biol.*: 10(5):558-63, and U.S. Pat. Nos. 6,296,673, 5,419,278, and 5,096,676.

In one variation, crystals comprising HDAC-2 are formed by mixing substantially pure HDAC-2 with an aqueous buffer containing a precipitant at a concentration just below a concentration necessary to precipitate the protein. One suitable precipitant for crystallizing HDAC-2 is polyethylene glycol (PEG), which combines some of the characteristics of the salts and other organic precipitants (see, for example, Ward et al., *J. Mol. Biol.* 98:161, 1975, and McPherson, *J. Biol. Chem.* 251:6300, 1976).

During a crystallization experiment, water is removed by diffusion or evaporation to increase the concentration of the precipitant, thus creating precipitating conditions for the protein. In one particular variation, crystals are grown by vapor diffusion in hanging drops or sitting drops. According to these methods, a protein/precipitant solution is formed and then allowed to equilibrate in a closed container with a larger aqueous reservoir having a precipitant concentration for producing crystals. The protein/precipitant solution continues to equilibrate until crystals grow.

By performing submicroliter volume sized crystallization experiments, as detailed in U.S. Pat. No. 6,296,673, effective crystallization conditions for forming crystals of HDAC-2 complexed with a range of compounds were obtained. In order to accomplish this, systematic broad screen crystallization trials were performed on HDAC-2 using the sitting drop technique. In each experiment, a 100 nL mixture of HDAC-2 complexed with different inhibitors and precipitant was placed on a platform positioned over a well containing 50-100 µL of the precipitating solution. Precipitate and crystal formation was detected in the sitting drops. Fine screening was then carried out for those crystallization conditions that appeared to produce precipitate and/or crystal in the drops.

Figure 2B:
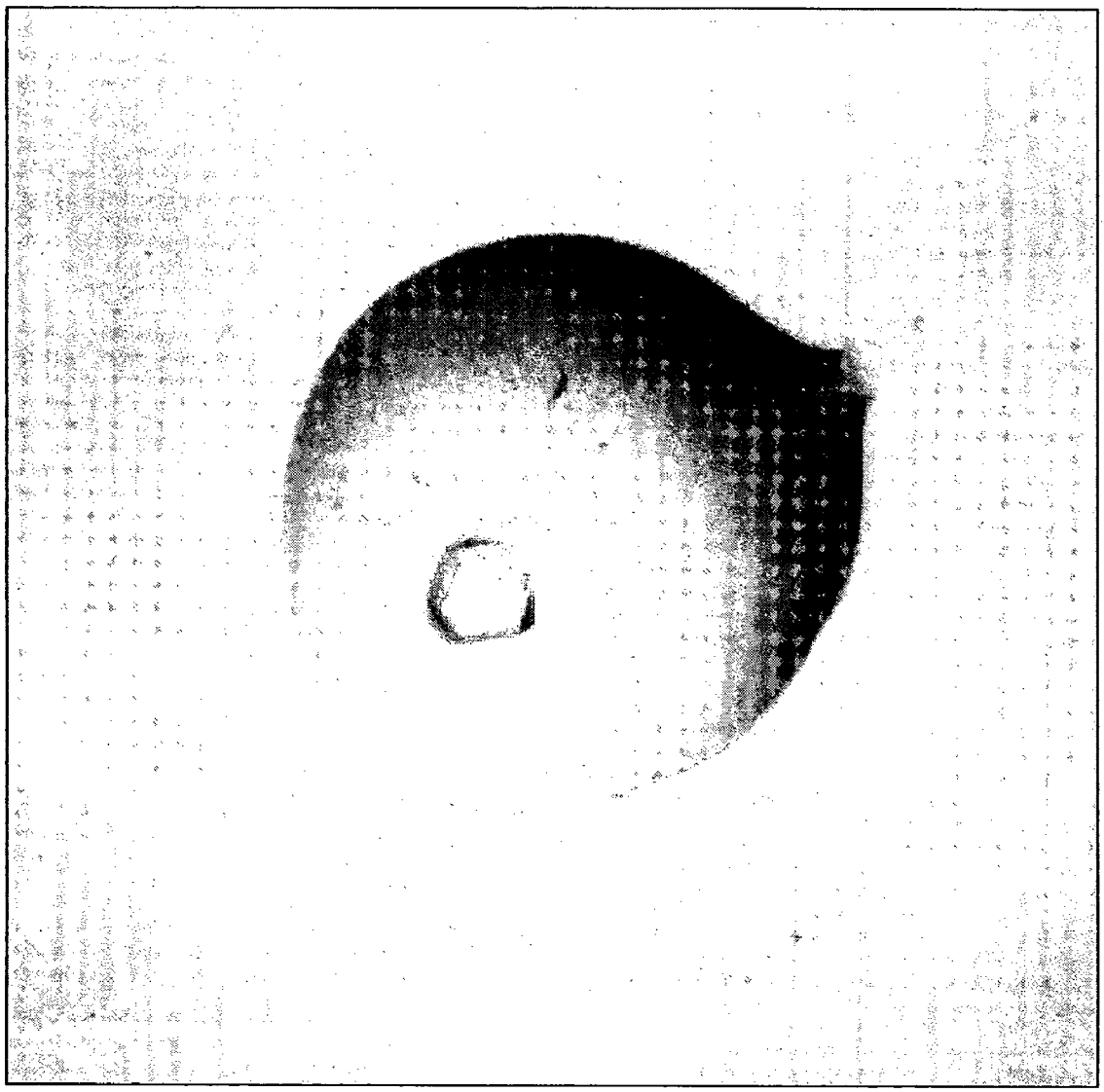
FIG. 2B illustrates a crystal formed according to Example 2 with a crystal lattice in a $P2_12_12$ space group.

Based on the crystallization experiments that were performed, a thorough understanding of how different crystallization conditions affect HDAC-2 crystallization was obtained. Based on this understanding, a series of crystallization conditions were identified that may be used to form crystals comprising HDAC-2. These conditions are summarized in Table 5. Particular examples of crystallization conditions that may be used to form diffraction quality crystals of HDAC-2 are detailed in Examples 1-2. FIGS. 2A-2B illustrate crystals of HDAC-2 complexes formed using the crystallization conditions provided in Table 5.

One skilled in the art will recognize that the crystallization conditions provided in Table 5 and Examples 1-2 can be varied and still yield protein crystals comprising HDAC-2. For example, it is noted that variations on the crystallization conditions described herein can be readily determined by taking the conditions provided in Table 5 and performing fine screens around those conditions by varying the type and concentration of the components in order to determine additional suitable conditions for crystallizing HDAC-2, variants of HDAC-2, and ligand complexes thereof.

Crystals comprising HDAC-2 have a wide range of uses. For example, now that crystals comprising HDAC-2 have been produced, it is noted that crystallizations may be performed using such crystals as a nucleation site within a concentrated protein solution. According to this variation, a concentrated protein solution is prepared and a crystalline material (microcrystals) is used to 'seed' the protein solution to assist nucleation for crystal growth. If the concentrations of the protein and any precipitants are optimal for crystal growth, the seed crystal will provide a nucleation site around which a larger crystal forms. Given the ability to form crystals comprising HDAC-2 according to the present invention, the crystals so formed can be used by this crystallization technique to initiate crystal growth of other HDAC-2 comprising crystals, including HDAC-2 complexed to other ligands.

As will be described herein in greater detail, crystals may also be used to perform X-ray or neutron diffraction analysis in order to determine the three-dimensional structure of HDAC-2 and, in particular, to assist in the identification of its active site. Knowledge of the binding site region allows rational design and construction of ligands including inhibitors. Crystallization and structural determination of HDAC-2 mutants having altered bioactivity allows the evaluation of whether such changes are caused by general structure deformation or by side chain alterations at the substitution site.

4. X-Ray Data Collection and Structure Determination

Crystals comprising HDAC-2 may be obtained as described above in Section 3. As described herein, these crystals may then be used to perform x-ray data collection and for structure determination.

In one embodiment, described in Example 1, crystals of an HDAC-2-$Zn^{2+}$-SAHA complex were obtained where HDAC-2 has the sequence of residues shown in SEQ. ID No. 4. These particular crystals were used to determine the three dimensional structure of HDAC-2. However, it is noted that other crystals comprising HDAC-2 including different HDAC-2 variants, fragments, and complexes thereof may also be used.

Diffraction data was collected from cryocooled crystals (100K) of the HDAC-2-$Zn^{2+}$-SAHA complex at the Advanced Light Source beam line 5.0.2 (Berkeley, Calif.) using an ADSC CCD detector. The diffraction pattern of the HDAC-2-$Zn^{2+}$-SAHA complex displayed symmetry consistent with space group $P2_1$ with unit cell dimensions a=79.9 Å b=56.9 Å and c=95.2 Å α=90° β=90.5° γ=90°. Data were collected and integrated to 1.8 Å with DENZO and scaled with SCALEPACK (Z. Ostwinowski and W. Minor "Processing of X-ray Diffraction Data Collected in Oscillation Mode", Methods in Enzymology, Volume 276: Macromolecular Crystallography, Part A, pages 307-326, 1997, C. W. Carter, Jr. & R. M. Sweet, Eds. Academic Press.).

All crystallographic calculations were performed using the CCP4 program package (Collaborative Computational Project, N. The CCP4 Suite: Programs for Protein Crystallography. *Acta Cryst.* D50, 760-763 (1994)). The initial phases for HDAC-2-$Zn^{2+}$-SAHA complex were obtained by the molecular replacement method using the program MOL-REP. The coordinates of histone deacetylase HDAC-8 previously determined and disclosed in U.S. application Ser. Nos. 10/601,335 and 10/601,058, filed on Jun. 20, 2003, were used as a search model for the solution of the HDAC-2-$Zn^{2+}$-SAHA structure. The highest solution from the translation function was subjected to a rigid body refinement against the maximum likelihood target function as implemented in REFMAC (CCP4). Rigid body refinement was followed by 50 cycles of iterative map/model/phase improvement using ARP_WARP map improvement (Perrakis, A., Morris, R. J. & Lamzin, V. S. This was followed by alternating cycles of manual rebuilding of the model with Xfit (McRee, D. E. XtalView/Xfit-A versatile program for manipulating atomic coordinates and electron density *J. Struct. Biol.* 125, 156-65 (1999)), ARP_WARP map improvement (Perrakis, A., Morris, R. J. & Lamzin, V. S. Automated protein model building combined with iterative structure refinement) and geometrically restrained refinement against a maximum likelihood target function as implemented in REFMAC (CCP4) until the refinement reached convergence. All stages of model refinement were carried with bulk solvent correction and anisotropic scaling. The data collection and data refinement statistics are given in Table 6A.

TABLE 6A

| Crystal data | | |
|---|---|---|
| Ligands | | SAHA, water, $Zn^{2+}$, $Na^{2+}$, $SO_4^{2+}$ |
| Space group | | $P2_1$ |
| Unit cell dimensions | | a = 79.9 Å b = 56.9 Å and c = 95.2 Å α = 90° β = 90.5° γ = 90° |
| Data collection | | HDAC-2-$Zn^{2+}$-SAHA |
| X-ray source | | ALS 5.0.2 |
| Wavelength [Å] | | 1.0 |
| Resolution [Å] | | 50-1.8 |
| Observations (unique) | | 256208 (76785) |
| Redundancy | | 3 |
| Completeness | overall (outer shell) | 96.7% (72.4%) |
| I/σ(I) | overall (outer shell) | 11.4 (1.8) |
| $R_{symm}^1$ | overall (outer shell) | 0.108 (0.39) |
| Refinement | | |
| Reflections used | | 72932 |
| R-factor | | 19.1% |
| $R_{free}$ | | 22.1% |
| r.m.s bonds | | 0.008 |
| r.m.s angles | | 1.06 |

$^1R_{symm} = \Sigma_{hkl}\Sigma_i | I(hkl)_i - <I(hkl)> |/\Sigma_{hkl}\Sigma_i <I(hkl)_i>$ over I observations of a reflection hkl.

During structure determination, where the unit cell dimensions were a=79.9 Å, b=56.9 Å, c=95.2 Å, and α=90° β=90.5° γ=90°, it was realized that the asymmetric unit comprised two HDAC-2-$Zn^{2+}$-SAHA molecules.

In one embodiment, described in Example 2, crystals of an HDAC-2-$Zn^{2+}$-TSA complex were obtained where HDAC-2 has the sequence of residues shown in SEQ. ID No. 5. These particular crystals were used to determine the three dimensional structure of HDAC-2. However, it is noted that other crystals comprising HDAC-2 including different HDAC-2 variants, fragments, and complexes thereof may also be used.

Diffraction data was collected from cryocooled crystals (100K) of the HDAC-2-$Zn^{2+}$-TSA complex at the Advanced Light Source beam line 5.0.3 (Berkeley, Calif.) using an ADSC CCD detector. The diffraction pattern of the HDAC-2-$Zn^{2+}$-TSA complex displayed symmetry consistent with space group $P2_12_12_1$ with unit cell dimensions a=92.1 b=97.6 Å and c=138.9 Å α=β=γ=90°. Data were collected and integrated to 1.85 Å with DENZO and scaled with SCALEPACK (Z. Ostwinowski and W. Minor "Processing of X-ray Diffraction Data Collected in Oscillation Mode", Methods in Enzymology, Volume 276: Macromolecular Crystallography, Part A, pages 307-326, 1997, C. W. Carter, Jr. & R. M. Sweet, Eds. Academic Press.).

All crystallographic calculations were performed using the CCP4 program package (Collaborative Computational Project, N. The CCP4 Suite: Programs for Protein Crystallography. *Acta Cryst.* D50, 760-763 (1994)). The initial phases for HDAC-2-$Zn^{2+}$-TSA complex were obtained by the molecular replacement method using the program MOLREP. The coordinates of histone deacetylase HDAC-8 previously determined and disclosed in U.S. application Ser. Nos. 10/601,335 and 10/601,058, filed on Jun. 20, 2003, were used as a search model for the solution of the HDAC-2-$Zn^{2+}$-TSA structure. The highest solution from the translation function was subjected to a rigid body refinement against the maximum likelihood target function as implemented in REFMAC (CCP4). Rigid body refinement was followed by 50 cycles of iterative map/model/phase improvement using ARP_WARP map improvement (Perrakis, A., Morris, R. J. & Lanzin, V. S. This was followed by alternating cycles of manual rebuilding of the model with Xfit (McRee, D. E. XtalView/Xfit-A versatile program for manipulating atomic coordinates and electron density *J. Struct. Biol.* 125, 156-65 (1999)), ARP_WARP map improvement (Perrakis, A., Morris, R. J. & Lamzin, V. S. Automated protein model building combined with iterative structure refinement) and geometrically restrained refinement against a maximum likelihood target function as implemented in REFMAC (CCP4) until the refinement reached convergence. All stages of model refinement were carried with bulk solvent correction and anisotropic scaling. The data collection and data refinement statistics are given in Table 6B.

TABLE 6B

| Crystal data | |
|---|---|
| Ligands | TSA, water, $Zn^{2+}$, $Na^{2+}$, |
| Space group | $P2_12_12_1$ |
| Unit cell dimensions | a = 92.1 b = 97.6 Å and |
| | c = 138.9 Å $\alpha = \beta = \gamma = 90°$ |
| Data collection | HDAC-2-$Zn^{2+}$-TSA |
| X-ray source | ALS 5.0.3 |
| Wavelength [Å] | 1.0 |
| Resolution [Å] | 50-1.84 |
| Observations (unique) | 361033 (107684) |
| Redundancy | 3 |
| Completeness overall (outer shell) | 99.6% (99%) |
| I/σ(I) overall (outer shell) | 15 (2) |
| $R_{symm}$[1] overall (outer shell) | 0.069 (0.58) |
| Refinement | |
| Reflections used | 102236 |
| R-factor | 18.66% |
| $R_{free}$ | 21.79% |
| r.m.s bonds | 0.007 |
| r.m.s angles | 1.01 |

[1]$R_{symm} = \Sigma_{hkl}\Sigma_i | I(hkl)_i - <I(hkl)> |/\Sigma_{hkl}\Sigma_i <I(hkl)_i>$ over I observations of a reflection hkl.

During structure determination, where the unit cell dimensions were a=92.1 Å, b=97.6 Å, c=138.9 Å, and $\alpha=\beta=\gamma=90°$, it was realized that the asymmetric unit comprised three HDAC-2-$Zn^{2+}$-TSA molecules. Structure coordinates were determined for this complex and the resultant set of structural coordinates from the refinement are presented in FIG. 3.

The binding pocket, shown in FIG. 5, was observed in this structure with one TSA molecule bound in the pocket. TSA binds with its hydroxamate moiety ligating the zinc ion bound at the bottom of the pocket. Key interactions between groups in the binding pockets and the TSA molecules are depicted in and described in FIG. 5.

It is noted that the sequence of the structure coordinates presented in FIG. 3 differ in some regards from the sequence shown in SEQ. ID NO:5. It is noted structure coordinates are not reported for some residues because the electron density obtained was insufficient to identify the position of these residues. For FIG. 3, chain A, structure coordinates for residues 1-11 and 379-409 (using numbering from SEQ ID NO:5) are not reported. For FIG. 3, chain B, structure coordinates for residues 1-13 and 379-409 are not reported. For FIG. 3, chain C, structure coordinates for residues 1-13 and 379-409 are not reported.

Those of skill in the art understand that a set of structure coordinates (such as those in FIG. 3) for a protein or a protein-complex or a portion thereof, is a relative set of points that define a shape in three dimensions. Thus, it is possible that an entirely different set of structure coordinates could define a similar or identical shape. Moreover, slight variations in the individual coordinates may have little effect on overall shape. In terms of binding pockets, these variations would not be expected to significantly alter the nature of ligands that could associate with those pockets. The term "binding pocket" as used herein refers to a region of the protein that, as a result of its shape, favorably associates with a ligand.

These variations in coordinates may be generated because of mathematical manipulations of the HDAC-2 structure coordinates. For example, the sets of structure coordinates shown in FIG. 3 could be manipulated by crystallographic permutations of the structure coordinates, fractionalization of the structure coordinates, application of a rotation matrix, integer additions or subtractions to sets of the structure coordinates, inversion of the structure coordinates or any combination of the above.

Alternatively, modifications in the crystal structure due to mutations, additions, substitutions, and/or deletions of amino acids or other changes in any of the components that make up the crystal could also account for variations in structure coordinates. If such variations are within an acceptable standard error as compared to the original coordinates, the resulting three-dimensional shape should be considered to be the same. Thus, for example, a ligand that bound to the active site binding pocket of HDAC-2 would also be expected to bind to another binding pocket whose structure coordinates defined a shape that fell within the acceptable error.

Various computational methods may be used to determine whether a particular protein or a portion thereof (referred to here as the "target protein"), typically the binding pocket, has a high degree of three-dimensional spatial similarity to another protein (referred to here as the "reference protein") against which the target protein is being compared.

The process of comparing a target protein structure to a reference protein structure may generally be divided into three steps: 1) defining the equivalent residues and/or atoms for the target and reference proteins, 2) performing a fitting operation between the proteins; and 3) analyzing the results. These steps are described in more detail below. All structure comparisons reported herein and the structure comparisons claimed are intended to be based on the particular comparison procedure described below.

Equivalent residues or atoms can be determined based upon an alignment of primary sequences of the proteins, an alignment of their structural domains or as a combination of both. Sequence alignments generally implement the dynamic programming algorithm of Needleman and Wunsch [*J. Mol. Biol.* 48: 442-453, 1970]. For the purpose of this invention the sequence alignment was performed using the publicly available software program MOE (Chemical Computing Group Inc.) package version 2002.3. When using the MOE program, alignment was performed in the sequence editor window using the ALIGN option utilizing the following program parameters: Initial pairwise Build-up: ON, Substitution Matrix: Blosum62, Round Robin: ON, Gap Start: 7, Gap Extend: 1, Iterative Refinement: ON, Build-up: TREE-BASED, Secondary Structure: NONE, Structural Alignment: ENABLED, Gap Start: 1, Gap Extend: 0.1.

Once aligned, a rigid body fitting operation is performed where the structure for the target protein is translated and rotated to obtain an optimum fit relative to the structure of the reference protein. The fitting operation uses an algorithm that computes the optimum translation and rotation to be applied to the moving structure, such that the root mean square deviation of the fit over the specified pairs of equivalent atoms is an absolute minimum. For the purpose of fitting operations made herein, the publicly available software program MOE (Chemical Computing Group Inc.) v. 2002.3 was used.

The results from this process are typically reported as an RMSD value between two sets of atoms. The term "root mean square deviation" means the square root of the arithmetic mean of the squares of deviations. It is a way to express the deviation or variation from a trend or object. As used herein, an RMSD value refers to a calculated value based on variations in the atomic coordinates of a target protein from the atomic coordinates of a reference protein or portions of thereof. The structure coordinates for HDAC-2, provided in FIG. 3, are used as the reference protein in these calculations.

The same set of atoms was used for initial fitting of the structures and for computing root mean square deviation values. For example, if a root mean square deviation (RMSD) between Cα atoms of two proteins is needed, the proteins in question should be superposed only on the Cα atoms and not on any other set of atoms. Similarly, if an RMSD calculation for all atoms is required, the superposition of two structures should be performed on all atoms.

Based on a review of protein structures deposited in the Protein Databank (PDB), 1C3R was identified as having the smallest RMSD values relative to the structure coordinates provided herein. Table 7 below provides a series of RMSD values that were calculated by the above described process using the structure coordinates in FIG. 3 as the reference protein and the structure coordinates from PDB code: 1C3R (Histone deacetylase like protein, HDLP) as the target protein.

TABLE 7

| AA RESIDUES USED TO PERFORM RMSD COMPARISON WITH PDB:1C3R | PORTION OF EACH AA RESIDUE USED TO PERFORM RMSD COMPARISON WITH PDB:1C3R | RMSD [Å] |
|---|---|---|
| Table 2 (4 Angstrom set) | alpha-carbon atoms[1] | 0.67 |
|  | main-chain atoms[1] | 0.71 |
|  | all non-hydrogen[2] | 0.99 |
| Table 3 (7 Angstrom set) | alpha-carbon atoms[1] | 0.78 |
|  | main-chain atoms[1] | 0.89 |
|  | all non-hydrogen[2] | 1.20 |
| Table 4 (10 Angstrom set) | alpha-carbon atoms[1] | 0.91 |
|  | main-chain atoms[1] | 1.02 |
|  | all non-hydrogen[2] | 1.25 |
| SEQ. ID No. 3 | alpha-carbon atoms[1] | 2.25 |
|  | main-chain atoms[1] | 2.21 |
|  | all non-hydrogen[2] | 2.47 |

[1]the RMSD computed between the atoms of all amino acids that are common to both the target and the reference in the aligned and superposed structure. The amino acids need not be identical.
[2]the RMSD computed only between identical amino acids, which are common to both the target and the reference in the aligned and superposed structure.

It is noted that mutants and variants of HDAC-2 as well as other histone deacetylases are likely to have similar structures despite having different sequences. For example, the binding pockets of these related proteins are likely to have similar contours. Accordingly, it should be recognized that the structure coordinates and binding pocket models provided herein have utility for these other related proteins.

Accordingly, in one embodiment, the invention relates to data, computer readable media comprising data, and uses of the data where the data comprises all or a portion of the structure coordinates shown in FIG. 3 or structure coordinates having a root mean square deviation (RMSD) equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

As noted, there are many different ways to express the surface contours of the HDAC-2 structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

5. HDAC-2-$Zn^{2+}$-TSA Structure

The present invention is also directed to a three-dimensional crystal structure of HDAC-2. This crystal structure may be used to identify binding sites, to provide mutants having desirable binding properties, and ultimately, to design, characterize, or identify ligands that interact with HDAC-2.

The three-dimensional crystal structure of HDAC-2 may be generated, as is known in the art, from the structure coordinates shown in FIG. 3 and similar such coordinates.

The refined crystal structure of HDAC-2-$Zn^{2+}$-TSA determined according to the present invention contains amino acids residues 13-378 as numbered according to SEQ. ID No. 5 (based on the coordinates of FIG. 3), one bound TSA molecule, and one $Zn^+$ ion. A total of 359 water molecules were included.

Figure 4A:
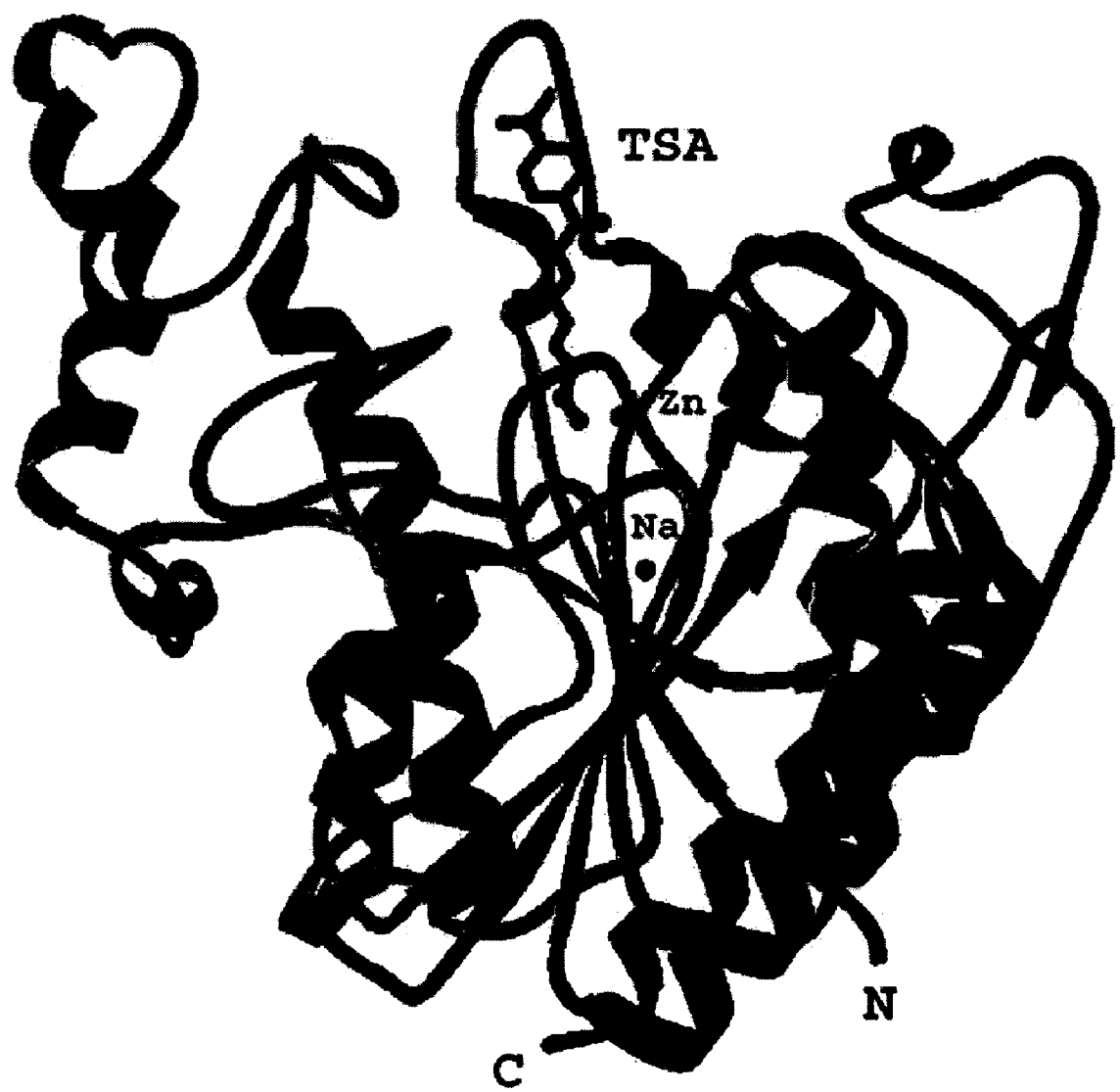
FIG. 4A illustrates a ribbon diagram overview of the structure of HDAC-2, highlighting the secondary structural elements of the protein.
Figure 4B:
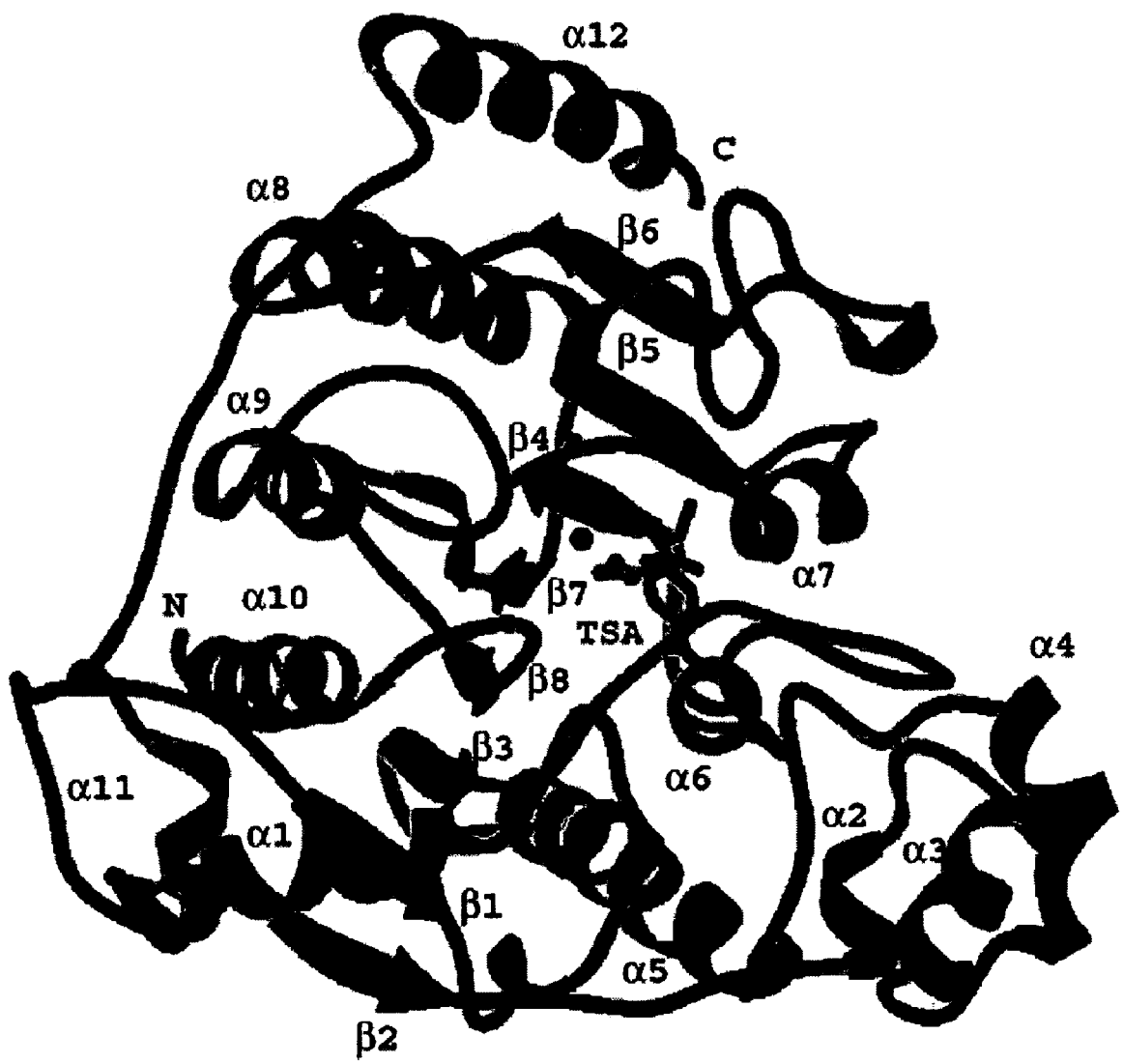
FIG. 4B illustrates a ribbon diagram overview of the structure of HDAC-2 rotated 90° with respect to the view in FIG. 4A, highlighting the secondary structural elements of the protein.

FIG. 4A, and FIG. 4B, a 90° rotation thereof, illustrate a ribbon diagram overview of the structure of HDAC-2, highlighting the secondary structural elements of the protein. HDAC-2 adopts an open-faced α/β structure consisting of 8 central parallel β-sheets sandwiched between 12 α-helices. The ligand binding cleft lies almost in the plane of the central β-sheet, and is formed primarily by loops emanating from the carboxy-terminal ends of the β-strands comprising the sheet. Residues which form loop regions extending between β-strand 1 and α-helix 1 and between α-helix 4 and α-helix 5, provide key surface interactions with bound ligands. Residues which form loop regions extending between β-strand 3 and α-helix 6 and between β-strand 4 and α-helix 7 and between β-strand 8 and α-helix 10 play important roles in defining the shape of the ligand binding pocket, and are involved in a number of key interactions with the bound ligands.

The only other protein that possesses a high degree of structural and topological homology to HDAC-2 is histone deacetylase from *A. Aeolicus* (HDLP, pdb entry 1C3P). The structure of this protein is reported in PCT Publication No. WO 01/18045. Based on data from this publication, the two structures can be superimposed with a Cα RMSD of 2.25 Å. However, HDAC-2 only possesses 12 α-helices while HDLP contains 16. Also, the HDAC-2 structure differs significantly from HDLP in a number of key aspects, particularly in the relative spatial dispositions of the active site loops, the structural landscape in the vicinity of the active site. FIG. 5 illustrates a representation of the active site of HDAC-2 and the relative orientations of the bound TSA molecule based on the structure coordinates shown in FIG. 3. The catalytic machinery residing at the bottom of the active site pocket is identical to that observed in HDLP. A 7 Å×5 Å "foot pocket" extends into the protein interior from the bottom of the catalytic pocket in a perpendicular direction to the active site pocket. The central region of the active site pocket is lined with a hydrophobic band of residues, including F155, F210 and L276. The active site pocket of HDAC-2 is narrower than its counterpart in HDLP, and the residues lining the pocket are likely more conformationally restricted.

6. HDAC-2 Binding Pocket and Ligand Interaction

The terms "binding site" or "binding pocket", as used herein, refer to a region of a protein that, as a result of its shape, favorably associates with a ligand or substrate. The term "HDAC-2-like binding pocket" refers to a portion of a molecule or molecular complex whose shape is sufficiently similar to the HDAC-2 binding pockets as to bind common ligands. This commonality of shape may be quantitatively defined by a root mean square deviation (RMSD) from the structure coordinates of the backbone atoms of the amino acids that make up the binding pockets in HDAC-2 (as set forth in FIG. 3).

The "active site binding pocket" (FIG. 5) or "active site" of HDAC-2 refers to the area on the surface of HDAC-2 where the substrate (a TSA inhibitor molecule) binds. FIG. 5 illustrates TSA bound in the active site of HDAC-2 based on the crystal structure of the present invention. TSA binds with its hydroxamate moiety ligating the zinc ion bound at the bottom of the pocket. Key interactions between groups in the binding pockets and the TSA molecule are depicted in and described in FIG. 5.

To date, the active site binding pocket of histone deacetylases (based on the structure of HDLP) has been the only target for the design of small molecule inhibitors. A number of key substrate binding and catalytic residues observed in the active site binding pocket of HDAC-2 appear well conserved among all class I histone deacetylases. However, when the overall sequence of the TSA binding pocket in the HDAC-2-$Zn^{2+}$-TSA complex are compared with the aligned sequences of other HDACs, significant sequence variability is observed, which is reflective of diversity among members of the HDAC family. The binding pocket likely shows subtle differences in shape and chemical content that may be explored to confer specificity of inhibition.

In resolving the crystal structure of HDAC-2 in complex with $Zn^{2+}$-TSA, applicants determined that HDAC-2 amino acids in Tables 2 (above) are within 4 Angstroms of and therefore close enough to interact with the two TSA molecules. Applicants have also determined that the amino acids of Tables 3 (above) are within 7 Angstroms of bound TSA molecules and therefore are also close enough to interact with that inhibitor or analogs thereof. Further it has been determined that the amino acids of Tables 4 (above) are within 10 Angstroms of bound TSA molecules and therefore are also close enough to interact with that inhibitor or analogs thereof. The 4, 7, and/or 10 Angstroms sets of amino acids are preferably conserved in variants of HDAC-2. While it is desirable to largely conserve these residues, it should be recognized however that variants may also involve varying 1, 2, 3, 4 or more of the residues set forth in Tables 2, 3, and 4 in order to evaluate the roles these amino acids play in the binding pocket.

With the knowledge of the HDAC-2 crystal structure provided herein, Applicants define the HDAC-2 binding pocket as binding pockets where the relative positioning of the 4, 7, and/or 10 Angstroms sets of amino acids are substantially conserved. Again, it is noted that it may be desirable to form variants where 1, 2, 3, 4 or more of the residues set forth in Tables 2, 3, and 4 are varied in order to evaluate the roles these amino acids play in the binding pockets. Accordingly, any set of structure coordinates for a protein from any source having a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

As noted previously, the root mean square deviation is intended to be limited to only those alpha-carbon atoms or non-hydrogen atoms of amino acid residues that are common to both the protein fragments represented in FIG. 3, and the protein whose structure coordinates are being compared to the coordinates shown in FIG. 3, since the sequence of the protein may be varied somewhat.

Accordingly, in various embodiments, the invention relates to data, computer readable media comprising data, and uses of the data where the data comprises structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

As noted above, there are many different ways to express the surface contours of HDAC-2 structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

It is again noted that the root mean square deviation calculation may optionally be based on a comparison of non-hydrogen atoms. Also, the root mean square deviation of alpha-carbon atoms or non-hydrogen atoms may optionally be less than 2.7 Å, 2.5 Å, 2.0 Å, 1.5 Å, 1 Å, 0.5 Å, or less.

It will be readily apparent to those of skill in the art that the numbering of amino acids in other isoforms of HDAC-2 may be different than that set forth for HDAC-2. Corresponding amino acids in other isoforms of HDAC-2 are easily identified by visual inspection of the amino acid sequences or by using commercially available homology software programs, as further described below.

7. System for Displaying the Three Dimensional Structure of HDAC-2

The present invention is also directed to machine-readable data storage media having data storage material encoded with machine-readable data that comprises structure coordinates for HDAC-2. The present invention is also directed to a machine readable data storage media having data storage material encoded with machine readable data, which, when read by an appropriate machine, can display a three dimensional representation of a structure of HDAC-2.

All or a portion of the HDAC-2 coordinate data shown in FIG. 3, when used in conjunction with a computer programmed with software to translate those coordinates into the three-dimensional structure of HDAC-2 may be used for a variety of purposes, especially for purposes relating to drug discovery. Software for generating three-dimensional graphical representations are known and commercially available. The ready use of the coordinate data requires that it be stored in a computer-readable format. Thus, in accordance with the present invention, data capable of being displayed as the three-dimensional structure of HDAC-2 and/or portions thereof and/or their structurally similar variants may be stored in a machine-readable storage medium, which is capable of displaying a graphical three-dimensional representation of the structure.

For example, in various embodiments, a computer is provided for producing a three-dimensional representation of at least an HDAC-2-like binding pocket, the computer comprising:

machine readable data storage medium comprising a data storage material encoded with machine-readable data, the machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

a working memory for storing instructions for processing the machine-readable data;

a central-processing unit coupled to the working memory and to the machine-readable data storage medium, for processing the machine-readable data into the three-dimensional representation; and an output hardware coupled to the central processing unit, for receiving the three dimensional representation.

Another embodiment of this invention provides a machine-readable data storage medium, comprising a data storage material encoded with machine readable data which, when used by a machine programmed with instructions for using said data, displays a graphical three-dimensional representation comprising HDAC-2 or a portion or variant thereof.

In various variations, the machine readable data comprises data for representing a protein based on structure coordinates where the structure coordinates have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

According to another embodiment, the machine-readable data storage medium comprises a data storage material encoded with a first set of machine readable data which comprises the Fourier transform of structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1, and which, when using a machine programmed with instructions for using said data, can be combined with a second set of machine readable data comprising the X-ray diffraction pattern of another molecule or molecular complex to determine at least a portion of the structure coordinates corresponding to the second set of machine readable data. For example, the Fourier transform of the structure coordinates set forth in FIG. 3 may be used to determine at least a portion of the structure coordinates of other HDAC-2-like enzymes, and isoforms of HDAC-2.

Optionally, a computer system is provided in combination with the machine-readable data storage medium provided herein. In one embodiment, the computer system comprises a working memory for storing instructions for processing the machine-readable data; a processing unit coupled to the working memory and to the machine-readable data storage medium, for processing the machine-readable data into the three-dimensional representation; and an output hardware coupled to the processing unit, for receiving the three-dimensional representation.

Figure 6:
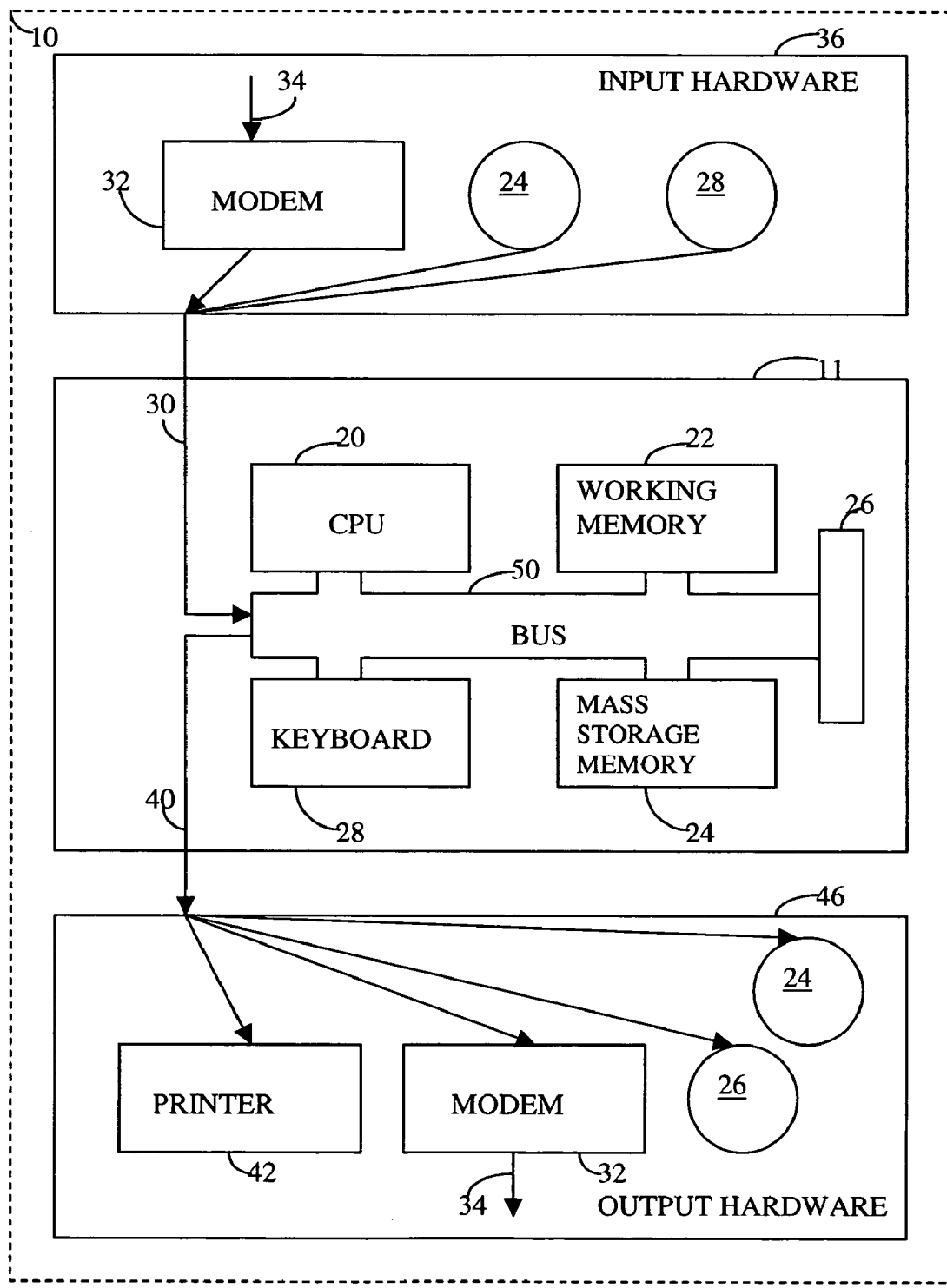
FIG. 6 illustrates a system that may be used to carry out instructions for displaying a crystal structure of HDAC-2 encoded on a storage medium.

FIG. 6 illustrates an example of a computer system that may be used in combination with storage media according to the present invention. As illustrated, the computer system 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Conventional devices, coupled to computer 11 by output lines 40, may similarly implement output hardware 46. By way of example, output hardware 46 may include CRT display terminal 26 for displaying a graphical representation of a binding pocket of this invention using a program such as MOE as described herein. Output hardware might also include a printer 42, so that hard copy output may be produced, or a disk drive 24, to store system output for later use.

In operation, CPU 20 coordinates the use of the various input and output devices 36, 46 coordinates data accesses from mass storage 24 and accesses to and from working memory 22; and determines the sequence of data processing steps. A number of programs may be used to process the machine-readable data of this invention. Such programs are discussed in reference to using the three dimensional structure of HDAC-2 described herein.

The storage medium encoded with machine-readable data according to the present invention can be any conventional data storage device known in the art. For example, the storage medium can be a conventional floppy diskette or hard disk. The storage medium can also be an optically readable data storage medium, such as a CD-ROM or a DVD-ROM, or a rewritable medium such as a magneto-optical disk that is optically readable and magneto-optically writable.

8. Uses of the Three Dimensional Structure of HDAC-2

The three-dimensional crystal structure of the present invention may be used to identify HDAC-2 binding sites, be used as a molecular replacement model to solve the structure of unknown crystallized proteins, to design mutants having desirable binding properties, and ultimately, to design, characterize, and identify entities capable of interacting with HDAC-2 and other structurally similar proteins as well as other uses that would be recognized by one of ordinary skill in the art. Such entities may be chemical entities or proteins. The term "chemical entity," as used herein, refers to chemical compounds, complexes of at least two chemical compounds, and fragments of such compounds.

The HDAC-2 structure coordinates provided herein are useful for screening and identifying drugs that inhibit HDAC-2 and other structurally similar proteins. For example, the structure encoded by the data may be computationally evaluated for its ability to associate with putative substrates or ligands. Such compounds that associate with HDAC-2 may inhibit HDAC-2, and are potential drug candidates. Additionally or alternatively, the structure encoded by the data may be displayed in a graphical three-dimensional representation on a computer screen. This allows visual inspection of the structure, as well as visual inspection of the structure's association with the compounds.

Thus, according to another embodiment of the present invention, a method is provided for evaluating the potential of an entity to associate with HDAC-2 or a fragment or variant thereof by using all or a portion of the structure coordinates provided in FIG. 3 or functional equivalents thereof. A method is also provided for evaluating the potential of an entity to associate with HDAC-2 or a fragment or variant thereof by using structure coordinates similar to all or a portion of the structure coordinates provided in FIG. 3 or functional equivalents thereof.

The method may optionally comprise the steps of: creating a computer model of all or a portion of a protein structure (e.g., a binding pocket) using structure coordinates according to the present invention; performing a fitting operation between the entity and the computer model; and analyzing the results of the fitting operation to quantify the association between the entity and the model. The portion of the protein structure used optionally comprises all of the amino acids listed in Tables 2, 3, and 4 that are present in the structure coordinates being used.

It is noted that the computer model may not necessarily directly use the structure coordinates. Rather, a computer model can be formed that defines a surface contour that is the same or similar to the surface contour defined by the structure coordinates.

The structure coordinates provided herein can also be utilized in a method for identifying a ligand (e.g., entities capable of associating with a protein) of a protein comprising an HDAC-2-like binding pocket. One embodiment of the method comprises: using all or a portion of the structure coordinates provided herein to generate a three-dimensional structure of an HDAC-2-like binding pocket; employing the three-dimensional structure to design or select a potential ligand; synthesizing the potential ligand; and contacting the synthesized potential ligand with a protein comprising an HDAC-2-like binding pocket to determine the ability of the potential ligand to interact with the protein. According to this method, the structure coordinates used may have a root mean square deviation equal to or less than the RMSD values specified in Columns 3, 4 or 5 of Table 1 when compared to the structure coordinates of FIG. 3 according to the RMSD calculation method set forth herein, provided that the portion of amino acid residues specified in Column 2 of Table 1 of each set of structure coordinates are superimposed and the root mean square deviation is calculated based only on those amino acid residues in the structure coordinates that are also present in the portion of the protein specified in Column 1 of Table 1. The portion of the protein structure used optionally comprises all of the amino acids listed in Tables 2, 3, and 4 that are present.

As noted previously, the three-dimensional structure of an HDAC-2-like binding pocket need not be generated directly from structure coordinates. Rather, a computer model can be formed that defines a surface contour that is the same or similar to the surface contour defined by the structure coordinates.

A method is also provided for evaluating the ability of an entity, such as a compound or a protein to associate with an HDAC-2-like binding pocket, the method comprising: constructing a computer model of a binding pocket defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1; selecting an entity to be evaluated by a method selected from the group consisting of (i) assembling molecular fragments into the entity, (ii) selecting an entity from a small molecule database, (iii) de novo ligand design of the entity, and (iv) modifying a known ligand for HDAC-2, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

The computer model of a binding pocket used in this embodiment need not be generated directly from structure coordinates. Rather, a computer model can be formed that defines a surface contour that is the same or similar to the surface contour defined by the structure coordinates.

Also according to the method, the method may further include synthesizing the entity; and contacting a protein having an HDAC-2-like binding pocket with the synthesized entity.

With the structure provided herein, the present invention for the first time permits the use of molecular design techniques to identify, select or design potential inhibitors of HDAC-2, based on the structure of an HDA2-like binding pocket. Such a predictive model is valuable in light of the high costs associated with the preparation and testing of the many diverse compounds that may possibly bind to the HDAC-2 protein.

According to this invention, a potential HDAC-2 inhibitor may now be evaluated for its ability to bind an HDAC-2-like binding pocket prior to its actual synthesis and testing. If a proposed entity is predicted to have insufficient interaction or association with the binding pocket, preparation and testing of the entity can be obviated. However, if the computer modeling indicates a strong interaction, the entity may then be obtained and tested for its ability to bind.

A potential inhibitor of an HDAC-2-like binding pocket may be computationally evaluated using a series of steps in which chemical entities or fragments are screened and selected for their ability to associate with the HDAC-2-like binding pockets.

One skilled in the art may use one of several methods to screen entities (whether chemical or protein) for their ability to associate with an HDAC-2-like binding pocket. This process may begin by visual inspection of, for example, an HDAC-2-like binding pocket on a computer screen based on the HDAC-2 structure coordinates in FIG. 3 or other coordinates which define a similar shape generated from the machine-readable storage medium. Selected fragments or chemical entities may then be positioned in a variety of orientations, or docked, within that binding pocket as defined above. Docking may be accomplished using software such as Quanta and Sybyl, followed by energy minimization and molecular dynamics with standard molecular mechanics force fields, such as CHARMM and AMBER.

Specialized computer programs may also assist in the process of selecting entities. These include: GRID (P. J. Goodford, "A Computational Procedure for Determining Energetically Favorable Binding Sites on Biologically Important Macromolecules", J. Med. Chem., 28, pp. 849-857 (1985)). GRID is available from Oxford University, Oxford, UK; MCSS (A. Miranker et al., "Functionality Maps of Binding Sites: A Multiple Copy Simultaneous Search Method." Proteins: Structure, Function and Genetics, 11, pp. 29-34 (1991)). MCSS is available from Molecular Simulations, San Diego, Calif.; AUTODOCK (D. S. Goodsell et al., "Automated Docking of Substrates to Proteins by Simulated Annealing", Proteins: Structure, Function, and Genetics, 8, pp. 195-202 (1990)). AUTODOCK is available from Scripps Research Institute, La Jolla, Calif.; & DOCK (I. D. Kuntz et al., "A Geometric Approach to Macromolecule-Ligand Interactions", J. Mol. Biol., 161, pp. 269-288 (1982)). DOCK is available from University of California, San Francisco, Calif.

Once suitable entities have been selected, they can be designed or assembled. Assembly may be preceded by visual inspection of the relationship of the fragments to each other on the three-dimensional image displayed on a computer screen in relation to the structure coordinates of HDAC-2. This may then be followed by manual model building using software such as MOE, QUANTA or Sybyl [Tripos Associates, St. Louis, Mo].

Useful programs to aid one of skill in the art in connecting the individual chemical entities or fragments include: CAVEAT (P. A. Bartlett et al, "CAVEAT: A Program to Facilitate the Structure-Derived Design of Biologically Active Molecules", in "Molecular Recognition in Chemical and Biological Problems", Special Pub., Royal Chem. Soc., 78, pp. 182-196 (1989); G. Lauri and P. A. Bartlett, "CAVEAT: a Program to Facilitate the Design of Organic Molecules", J. Comput. Aided Mol. Des., 8, pp. 51-66 (1994)). CAVEAT is available from the University of California, Berkeley, Calif.; 3D Database systems such as ISIS (MDL Information Systems, San Leandro, Calif.). This area is reviewed in Y. C. Martin, "3D Database Searching in Drug Design", J. Med. Chem., 35, pp. 2145-2154 (1992); HOOK (M. B. Eisen et al, "HOOK: A Program for Finding Novel Molecular Architectures that Satisfy the Chemical and Steric Requirements of a Macromolecule Binding Site", Proteins: Struct., Funct., Genet., 19, pp. 199-221 (1994). HOOK is available from Molecular Simulations, San Diego, Calif.

Instead of proceeding to build an inhibitor of an HDAC-2-like binding pocket in a step-wise fashion one fragment or entity at a time as described above, inhibitory or other HDAC-2 binding compounds may be designed as a whole or "de novo" using either an empty binding site or optionally including some portion(s) of a known inhibitor(s). There are many de novo ligand design methods including: LUDI (H.-J. Bohm, "The Computer Program LUDI: A New Method for the De Novo Design of Enzyme Inhibitors", J. Comp. Aid. Molec. Design, 6, pp. 61-78 (1992)). LUDI is available from Molecular Simulations Incorporated, San Diego, Calif.; LEGEND (Y. Nishibata et al., Tetrahedron, 47, p. 8985 (1991)). LEGEND is available from Molecular Simulations Incorporated, San Diego, Calif.; LEAPFROG (available from Tripos Associates, St. Louis, Mo.); & SPROUT (V. Gillet et al, "SPROUT: A Program for Structure Generation", J. Comput. Aided Mol. Design, 7, pp. 127-153 (1993)). SPROUT is available from the University of Leeds, UK.

Other molecular modeling techniques may also be employed in accordance with this invention (see, e.g., Cohen et al., "Molecular Modeling Software and Methods for Medicinal Chemistry", J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)).

Once an entity has been designed or selected, for example, by the above methods, the efficiency with which that entity may bind to an HDAC-2 binding pocket may be tested and optimized by computational evaluation. For example, an effective HDAC-2 binding pocket inhibitor preferably demonstrates a relatively small difference in energy between its bound and free states (i.e., a small deformation energy of binding). Thus, the most efficient HDAC-2 binding pocket inhibitors should preferably be designed with deformation energy of binding of not greater than about 10 kcal/mole, and more preferably, not greater than 7 kcal/mole. HDAC-2 binding pocket inhibitors may interact with the binding pocket in more than one of multiple conformations that are similar in overall binding energy. In those cases, the deformation energy of binding is taken to be the difference between the energy of the free entity and the average energy of the conformations observed when the inhibitor binds to the protein.

An entity designed or selected as binding to an HDAC-2 binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. COPYRGT. 1995); AMBER, version 4.1 (P. A. Kollman, University of California at San Francisco, COPYRGT 1995); QUANTA/CHARMM (Molecular Simulations, Inc., San Diego, Calif. COPYRGT. 1995); Insight II/Discover (Molecular Simulations, Inc., San Diego, Calif. COPYRGT. 1995); DelPhi (Molecular Simulations, Inc., San Diego, Calif. COPYRGT. 1995); and AMSOL (Quantum Chemistry Program Exchange, Indiana University). These programs may be implemented, for instance, using a Silicon Graphics workstation such as an Indigo.sup.2 with "IMPACT" graphics. Other hardware systems and software packages will be known to those skilled in the art.

Another approach provided by this invention, is the computational screening of small molecule databases for chemical entities or compounds that can bind in whole, or in part, to an HDAC-2 binding pocket. In this screening, the quality of fit of such entities to the binding site may be judged either by shape complementarities or by estimated interaction energy [E. C. Meng et al., J. Comp. Chem., 13, 505-524 (1992)].

According to another embodiment, the invention provides compounds that associate with an HDAC-2-like binding pocket produced or identified by various methods set forth above.

The structure coordinates set forth in FIG. 3 can also be used to aid in obtaining structural information about another crystallized molecule or molecular complex. This may be achieved by any of a number of well-known techniques, including molecular replacement.

For example, a method is also provided for utilizing molecular replacement to obtain structural information about a protein whose structure is unknown comprising the steps of: generating an X-ray diffraction pattern of a crystal of the protein whose structure is unknown; generating a three-dimensional electron density map of the protein whose structure is unknown from the X-ray diffraction pattern by using at least a portion of the structure coordinates set forth in FIG. 3 as a molecular replacement model.

By using molecular replacement, all or part of the structure coordinates of the HDAC-2 provided by this invention (and set forth in FIG. 3) can be used to determine the structure of another crystallized molecule or molecular complex more quickly and efficiently than attempting an ab initio structure determination. One particular use includes use with other structurally similar proteins. Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of HDAC-2 according to FIG. 3 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in Meth. Enzymol., 115, pp. 55-77 (1985); M. G. Rossmann, ed., "The Molecular Replacement Method", Int. Sci. Rev. Ser., No. 13, Gordon & Breach, New York (1972)].

The structure of any portion of any crystallized molecule or molecular complex that is sufficiently homologous to any portion of HDAC-2 can be resolved by this method.

In one embodiment, the method of molecular replacement is utilized to obtain structural information about the present invention and any other HDAC-2-like molecule. The structure coordinates of HDAC-2, as provided by this invention, are particularly useful in solving the structure of other isoforms of HDAC-2 or HDAC-2 complexes.

The structure coordinates of HDAC-2 as provided by this invention are useful in solving the structure of HDAC-2 variants that have amino acid substitutions, additions and/or deletions (referred to collectively as "HDAC-2 mutants", as compared to naturally occurring HDAC-2). These HDAC-2 mutants may optionally be crystallized in co-complex with a ligand, such as an inhibitor, substrate analogue or a suicide substrate. The crystal structures of a series of such complexes may then be solved by molecular replacement and compared with that of HDAC-2. Potential sites for modification within the various binding sites of the enzyme may thus be identified. This information provides an additional tool for determining the most efficient binding interactions such as, for example, increased hydrophobic interactions, between HDAC-2 and a ligand. It is noted that the ligand may be the protein's natural ligand or may be a potential agonist or antagonist of a protein.

All of the complexes referred to above may be studied using well-known X-ray diffraction techniques and may be refined versus 1.5-3 Å resolution X-ray data to an R value of about 0.22 or less using computer software, such as X-PLOR [Yale University, COPYRIGHT. 1992, distributed by Molecular Simulations, Inc.; see, e.g., Blundell & Johnson, supra; Meth. Enzymol., Vol. 114 & 115, H. W. Wyckoff et al., eds., Academic Press (1985)]. This information may thus be used to optimize known HDAC-2 inhibitors, and more importantly, to design new HDAC-2 inhibitors.

The structure coordinates described above may also be used to derive the dihedral angles, phi and psi, that define the conformation of the amino acids in the protein backbone. As will be understood by those skilled in the art, the $phi_n$ angle refers to the rotation around the bond between the alpha-carbon and the nitrogen, and the $psi_n$ angle refers to the rotation around the bond between the carbonyl carbon and the alpha-carbon. The subscript "n" identifies the amino acid whose conformation is being described [for a general reference, see Blundell and Johnson, Protein Crystallography, Academic Press, London, 1976].

9. Uses of the Crystal and Diffraction Pattern of HDAC-2

Crystals, crystallization conditions and the diffraction pattern of HDAC-2 that can be generated from the crystals also have a range of uses. One particular use relates to screening entities that are not known ligands of HDAC-2 for their ability to bind to HDAC-2. For example, with the availability of crystallization conditions, crystals and diffraction patterns of HDAC-2 provided according to the present invention, it is possible to take a crystal of HDAC-2; expose the crystal to one or more entities that may be a ligand of HDAC-2; and determine whether a ligand/HDAC-2 complex is formed. The crystals of HDAC-2 may be exposed to potential ligands by various methods, including but not limited to, soaking a crystal in a solution of one or more potential ligands or co-crystallizing HDAC-2 in the presence of one or more potential ligands. Given the structure coordinates provided herein, once a ligand complex is formed, the structure coordinates can be used as a model in molecular replacement in order to determine the structure of the ligand complex.

Once one or more ligands are identified, structural information from the ligand/HDAC-2 complex(es) may be used to design new ligands that bind tighter, bind more specifically, have better biological activity or have better safety profiles than known ligands.

In one embodiment, a method is provided for identifying a ligand that binds to HDAC-2 comprising: (a) attempting to crystallize a protein that comprises a sequence wherein at least a portion of the sequence has 55%, 65%, 75%, 85%, 90%, 95%, 97%, 99% or greater identity with SEQ. ID No. 4 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In one embodiment, a method is provided for identifying a ligand that binds to HDAC-2 comprising: (a) attempting to crystallize a protein that comprises a sequence wherein at least a portion of the sequence has 55%, 65%, 75%, 85%, 90%, 95%, 97%, 99% or greater identity with SEQ. ID No. 5 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In another embodiment, a method is provided for identifying a ligand that binds to HDAC-2 comprising: soaking a crystal of a protein wherein at least a portion of the protein has 55%, 65%, 75%, 85%, 90%, 95%, 97%, 99% or greater identity with SEQ. ID No. 4 with one or more entities; determining whether a ligand/protein complex was formed by comparing an X-ray diffraction pattern of a crystal of the protein that has not been soaked with the one or more entities to the crystal that has been soaked with the one or more entities.

In another embodiment, a method is provided for identifying a ligand that binds to HDAC-2 comprising: soaking a crystal of a protein wherein at least a portion of the protein has 55%, 65%, 75%, 85%, 90%, 95%, 97%, 99% or greater identity with SEQ. ID No. 5 with one or more entities; determining whether a ligand/protein complex was formed by comparing an X-ray diffraction pattern of a crystal of the protein that has not been soaked with the one or more entities to the crystal that has been soaked with the one or more entities.

Optionally, the method may further comprise converting the diffraction patterns into electron density maps using phases of the protein crystal and comparing the electron density maps.

Libraries of "shape-diverse" compounds may optionally be used to allow direct identification of the ligand-receptor complex even when the ligand is exposed as part of a mixture. According to this variation, the need for time-consuming de-convolution of a hit from the mixture is avoided. More specifically, the calculated electron density function reveals the binding event, identifies the bound compound and provides a detailed 3-D structure of the ligand-receptor complex. Once a hit is found, one may optionally also screen a number of analogs or derivatives of the hit for tighter binding or better biological activity by traditional screening methods. The hit and information about the structure of the target may also be used to develop analogs or derivatives with tighter binding or better biological activity. It is noted that the ligand-HDAC-2 complex may optionally be exposed to additional iterations of potential ligands so that two or more hits can be linked together to make a more potent ligand. Screening for potential ligands by co-crystallization and/or soaking is further described in U.S. Pat. No. 6,297,021, which is incorporated herein by reference.

EXAMPLES

Example 1

Expression, Purification and Crystallization of HDAC-2 ($P2_1$ Crystal Form)

This example describes the expression, purification and crystallization of HDAC-2 that resulted in a $P2_1$ crystal form.

The portion of the gene encoding residues 1-488 (from SEQ. ID No. 1) which corresponds to the entire sequence of human HDAC-2 was amplified by PCR and cloned into the BamHI/SmaI site of pFastbac (Invitrogen) with a 6-histidine tag at the C-terminus. This DNA sequence is presented in FIG. 1 as SEQ. ID No. 2.

Expression in this vector generated a fusion of HDAC-2 residues 1-488 with a C-terminal 6×-histidine tag, the amino acid sequence of which is shown in FIG. 1 as SEQ. ID. 3. Recombinant baculoviruses incorporating the HDAC-2 constructs were generated by transposition using the Bac-to-Bac system (Invitrogen). High-titer viral stocks were generated by infection of *Spodoptera frugiperda* Sf9 cells and the expression of recombinant protein was carried out by infection of Sf9 cells (Invitrogen) in 10 L Wave Bioreactors (Wave Biotech). Recombinant proteins were isolated from cellular extracts by passage over ProBond (InVitrogen) resin. Purified HDAC-2 protein samples were incubated in the presence of a known HDAC-2 inhibitor such as SAHA or TSA before subjecting samples to limited proteolysis utilizing cross linked enzyme crystals CLEC™-BL (Altus). The protein samples were incubated with CLEC and shaken for 90 minutes at 25° C. to yield fragments of SEQ. ID No. 4. Cleavage reactions were terminated by centrifugation at 900 g for 5 min and supernatants were tested for cleavage by mass spectroscopy. Samples were further purified over a POROS-S column (Applied Biosystems) followed by size exclusion chromatography through passage over BioSep S3000 resin (Phenomenex). The HDAC-2 protein purity as determined on denaturing SDS-PAGE gel was 90-95%. HDAC-2 was concentrated to a final concentration of 11 mg/ml and stored at 4° C. in a buffer containing 25 mM TRIS-HCl pH 7.6, 250 mM NaCl and 0.125 mM TCEP.

HDAC-2 protein samples were incubated with 1 mM Benzamidine and 5 mM $CaCl_2$ before setting up crystallization trials. Crystals were obtained after an extensive and broad screen of conditions, followed by optimization.

Diffraction quality crystals were grown as in 100 nL sitting droplets using the vapor diffusion method. 50 nL comprising the HDAC-2-inhibitor complex (15 mg/ml) was mixed with 50 nL from a reservoir solution (100 μL) comprising 0.1M CHES pH=9.25, 17.5 mM Ammonium Sulfate and 18% PEG MME 2000. The resulting solution was incubated over a period of one week at 4° C.

Crystals typically appeared after 24-48 hours and grew to a maximum size within 72 hours. Single crystals were transferred, briefly, into a cryoprotecting solution containing the reservoir solution supplemented with 30% v/v ethylene glycol. Crystals were then flash frozen by immersion in liquid nitrogen and then stored under liquid nitrogen.

A crystal of HDAC-2 produced as described is illustrated in FIG. 2A. The protein crystal was found to have a crystal lattice in a $P2_1$ space group. The protein crystal may also have a crystal lattice having unit cell dimensions, +/−5%, of a=79.9 Å, b=56.9 Å, c=95.2 Å, α=90°, β=90.5°, and γ=90°. Crystals of this crystal form were subjected to x-ray diffraction experiments in order to arrive at the structure coordinates reported herein.

Example 2

Expression, Purification and Crystallization of HDAC-2 ($P2_12_12_1$ Crystal Form)

This example describes the expression, purification and crystallization of HDAC-2 that resulted in a $P2_12_12_1$ crystal form.

The portion of the gene encoding residues 1-488 (from SEQ. ID No. 1) which corresponds to the entire sequence of human HDAC-2 was amplified by PCR and cloned into the BamHI/SmaI site of pFastbac (Invitrogen) with a 6-histidine tag at the C-terminus. This DNA sequence is presented in FIG. 1 as SEQ. ID No. 2.

Expression in this vector generated a fusion of HDAC-2 residues 1-488 with a C-terminal 6x-histidine tag, the amino acid sequence of which is shown in FIG. 1 as SEQ. ID. 3. Recombinant baculoviruses incorporating the HDAC-2 constructs were generated by transposition using the Bac-to-Bac system (Invitrogen). High-titer viral stocks were generated by infection of *Spodoptera frugiperda* Sf9 cells and the expression of recombinant protein was carried out by infection of Sf9 cells (Invitrogen) in 10 L Wave Bioreactors (Wave Biotech). Recombinant proteins were isolated from cellular extracts by passage over ProBond (InVitrogen) resin. Purified HDAC-2 protein samples were incubated in the presence of a known HDAC-2 inhibitor such as SAHA or TSA before subjecting samples to limited proteolysis utilizing Immobilized TPCK-Trypsin (Pierce). The protein samples were incubated with Immobilized TPCK-Trypsin and shaken for 90 minutes at 25° C. to yield fragments of SEQ. ID No. 5. Cleavage reactions were terminated by centrifugation at 900 g for 5 min and supernatants were tested for cleavage by mass spectroscopy. Samples were further purified through size exclusion chromatography by passage over BioSep S3000 resin (Phenomenex). The HDAC-2 protein purity as determined on denaturing SDS-PAGE gel was 90-95%. HDAC-2 was concentrated to a final concentration of 11 mg/ml and stored at 4° C. in a buffer containing 25 mM TRIS-HCl pH 7.6, 250 mM NaCl and 0.125 mM TCEP.

HDAC-2 protein samples were incubated 0.5 mM Benzamidine and 5 mM $CaCl_2$ before setting up crystallization trials. Crystals were obtained after an extensive and broad screen of conditions, followed by optimization.

Diffraction quality crystals were grown as in 100 nL sitting droplets using the vapor diffusion method. 50 nL comprising the resulting HDAC-2 complex (11.0 mg/ml) was mixed with 50 nL from a reservoir solution (100 μL) comprising 0.1M CHES pH=9.5 and 40% PEG 600. The resulting solution was incubated over a period of one week at 20° C. Crystals typically appeared after 24-48 hours and grew to a maximum size within 72 hours. Single crystals were separated from their parent cluster (if necessary) and incubated in reservoir solution supplemented with 5 mM TSA for a period of 3 hours. Crystals were then flash frozen directly from reservoir solution by immersion in liquid nitrogen and then stored under liquid nitrogen.

A crystal of HDAC-2 produced as described is illustrated in FIG. 2B. The protein crystal was found to have a crystal lattice in a $P2_12_12_1$ space group. The protein crystal may also have a crystal lattice having unit cell dimensions, +/−5%, of a=92.1 Å, b=97.6 Å, c=138.9 Å, and α=β=γ=90°.

While the present invention is disclosed with reference to certain embodiments and examples detailed above, it is to be understood that these embodiments and examples are intended to be illustrative rather than limiting, as it is contemplated that modifications will readily occur to those skilled in the art, which modifications are intended to be within the scope of the invention and the appended claims. All patents, papers, and books cited in this application are incorporated herein in their entirety.

We claim:

1. A composition comprising a protein in crystalline form wherein the protein consists of SEQ ID NO: 5, wherein said protein is in complex with trichostatin A and wherein the protein crystal has a crystal lattice in a P2$_1$2$_1$2$_1$ space group and unit cell dimensions, +/−5%, of a=92.1 Å, b=97.6 Å, c=138.9 Å, and α=β=γ=90°.

2. The composition according to claim 1 wherein the asymmetric unit of the crystal comprises three molecules of the protein.

3. The composition according to claim 1 wherein the protein crystal diffracts X-rays for a determination of structure coordinates to a resolution of a value equal to or less than 3.0 Angstroms.

4. A method for forming a protein crystal comprising:
   forming a crystallization volume comprising a precipitant solution and a protein that consists of SEQ ID NO:5, wherein said protein is in complex with trichostatin A; and
   storing the crystallization volume under conditions suitable for crystal formation of the protein; and
   forming a protein crystal, wherein the protein crystal has a crystal lattice in a P2$_1$2$_1$2$_1$ space group and unit cell dimensions, +/−5%, of a=92.1 Å, b=97.6 Å, c=138.9 Å, and α=β=γ=90°.

5. The method according to claim 4, wherein the asymmetric unit of the crystal comprises three molecules of the protein.

6. The method according to claim 4, wherein the protein crystal diffracts X-rays for a determination of structure coordinates to a resolution of a value equal to or less than 3.0 Angstroms.

7. A method for solving the structure of the protein of SEQ ID NO:5, the method comprising:

diffracting the protein crystal of claim 1 with X-rays to produce a diffraction pattern; and
solving the structure of the protein from the diffraction pattern, thereby solving the structure of the protein of SEQ ID NO:5.

8. A method of rational drug design, the method comprising:
   diffracting the protein crystal of claim 1 with X-rays to produce a diffraction pattern;
   solving the structure of the protein from the diffraction pattern, thereby solving the structure of the protein of SEQ ID NO:5;
   performing rational drug design using the solved structure;
   identifying one or more entities that potentially associates with the protein; and
   selecting the one or more entities based on the rational drug design.

9. The method according to claim 8, the method further comprising measuring an activity of the protein when contacted with the one or more entities.

10. The method according to claim 8, the method further comprising:
    comparing activity of the protein in the presence of and in the absence of the one or more entities; and
    selecting entities where activity of the protein changes depending on whether or not a particular entity is present.

11. The method according to claim 8, the method further comprising contacting cells expressing the protein with the one or more entities and detecting a change in a phenotype of the cells when a particular entity is present.

* * * * *

SEQUENCE LISTING

```
<160> NUMBER OF SEQ ID NOS: 5

<210> SEQ ID NO 1
<211> LENGTH: 488
<212> TYPE: PRT
<213> ORGANISM: Homo sapiens
<220> FEATURE:
<221> NAME/KEY: Amino acid sequence for full length human HDAC-2
<222> LOCATION: (1)..(488)

<400> SEQUENCE: 1
```

-continued

```
Met Ala Tyr Ser Gln Gly Gly Lys Lys Val Cys Tyr Tyr
1               5                   10                  15

Asp Gly Asp Ile Gly Asn Tyr Tyr Gly Gln Gly His Pro Met Lys
            20                  25                  30

Pro His Arg Ile Arg Met Thr His Asn Leu Leu Leu Asn Tyr Gly Leu
        35                  40                  45

Tyr Arg Lys Met Glu Ile Tyr Arg Pro His Lys Ala Thr Ala Glu Glu
    50                  55                  60

Met Thr Lys Tyr His Ser Asp Glu Tyr Ile Lys Phe Leu Arg Ser Ile
65                  70                  75                  80

Arg Pro Asp Asn Met Ser Glu Tyr Ser Lys Gln Met Gln Arg Phe Asn
                85                  90                  95

Val Gly Glu Asp Cys Pro Val Phe Asp Gly Leu Phe Glu Phe Cys Gln
            100                 105                 110

Leu Ser Thr Gly Gly Ser Val Ala Gly Ala Val Lys Leu Asn Arg Gln
        115                 120                 125

Gln Thr Asp Met Ala Val Asn Trp Ala Gly Gly Leu His His Ala Lys
    130                 135                 140

Lys Ser Glu Ala Ser Gly Phe Cys Tyr Val Asn Asp Ile Val Leu Ala
145                 150                 155                 160

Ile Leu Glu Leu Leu Lys Tyr His Gln Arg Val Leu Tyr Ile Asp Ile
                165                 170                 175

Asp Ile His His Gly Asp Gly Val Glu Glu Ala Phe Tyr Thr Thr Asp
            180                 185                 190

Arg Val Met Thr Val Ser Phe His Lys Tyr Gly Glu Tyr Phe Pro Gly
        195                 200                 205

Thr Gly Asp Leu Arg Asp Ile Gly Ala Gly Lys Gly Lys Tyr Tyr Ala
    210                 215                 220

Val Asn Phe Pro Met Arg Asp Gly Ile Asp Asp Glu Ser Tyr Gly Gln
225                 230                 235                 240

Ile Phe Lys Pro Ile Ile Ser Lys Val Met Glu Met Tyr Gln Pro Ser
                245                 250                 255

Ala Val Val Leu Gln Cys Gly Ala Asp Ser Leu Ser Gly Asp Arg Leu
            260                 265                 270

Gly Cys Phe Asn Leu Thr Val Lys Gly His Ala Lys Cys Val Glu Val
        275                 280                 285

Val Lys Thr Phe Asn Leu Pro Leu Leu Met Leu Gly Gly Gly Gly Tyr
    290                 295                 300

Thr Ile Arg Asn Val Ala Arg Cys Trp Thr Tyr Glu Thr Ala Val Ala
305                 310                 315                 320

Leu Asp Cys Glu Ile Pro Asn Glu Leu Pro Tyr Asn Asp Tyr Phe Glu
                325                 330                 335

Tyr Phe Gly Pro Asp Phe Lys Leu His Ile Ser Pro Ser Asn Met Thr
            340                 345                 350

Asn Gln Asn Thr Pro Glu Tyr Met Glu Lys Ile Lys Gln Arg Leu Phe
        355                 360                 365

Glu Asn Leu Arg Met Leu Pro His Ala Pro Gly Val Gln Met Gln Ala
    370                 375                 380

Ile Pro Glu Asp Ala Val His Glu Asp Ser Gly Asp Glu Asp Gly Glu
385                 390                 395                 400

Asp Pro Asp Lys Arg Ile Ser Ile Arg Ala Ser Asp Lys Arg Ile Ala
                405                 410                 415

Cys Asp Glu Glu Phe Ser Asp Ser Glu Asp Glu Gly Glu Gly Gly Arg
```

|     |     |     |     | 420 |     |     |     | 425 |     |     |     | 430 |     |
| --- | --- | --- | --- | --- | --- | --- | --- | --- | --- | --- | --- | --- | --- |
| Arg | Asn | Val | Ala | Asp | His | Lys | Lys | Gly | Ala | Lys | Ala | Arg | Ile | Glu |
|     |     |     | 435 |     |     |     | 440 |     |     |     | 445 |     |     |
| Glu | Asp | Lys | Lys | Glu | Thr | Glu | Asp | Lys | Lys | Thr | Asp | Val | Lys | Glu | Glu |
|     |     | 450 |     |     |     | 455 |     |     |     | 460 |     |     |     |
| Asp | Lys | Ser | Lys | Asp | Asn | Ser | Gly | Glu | Lys | Thr | Asp | Thr | Lys | Gly | Thr |
| 465 |     |     |     | 470 |     |     |     | 475 |     |     |     | 480 |     |
| Lys | Ser | Glu | Gln | Leu | Ser | Asn | Pro |
|     |     |     |     | 485 |     |     |     |

```
<210> SEQ ID NO 2
<211> LENGTH: 1497
<212> TYPE: DNA
<213> ORGANISM: Homo sapiens
<220> FEATURE:
<221> NAME/KEY: Human cDNA sequence encoding HDAC-2
<222> LOCATION: (1)..(1497)

<400> SEQUENCE: 2
atgggatcca tggcgtacag tcaaggaggc ggcaaaaaaa aagtctgcta ctactacgac    60
ggtgatattg gaaattatta ttatggacag ggtcatccca tgaagcctca tagaatccgc   120
atgacccata acttgctgtt aaattatggc ttatacagaa aaatggaaat atataggccc   180
cataaagcca ctgccgaaga atgacaaaa tatcacagtg atgagtatat caaatttcta   240
cggtcaataa gaccagataa catgtctgag tatagtaagc agatgcagag atttaatgtt   300
ggagaagatt gtccagtgtt tgatggactc tttgagtttt gtcagctctc aactggcggt   360
tcagttgctg gagctgtgaa gttaaaccga caacagactg atatggctgt taattgggct   420
ggaggattac atcatgctaa gaaatcagaa gcatcaggat tctgttacgt taatgatatt   480
gtgcttgcca tccttgaatt actaaagtat catcagagag tcttatatat tgatatagat   540
attcatcatg gtgatggtgt tgaagaagct ttttatacaa cagatcgtgt aatgacggta   600
tcattccata aatatgggga atactttcct ggcacaggag acttgaggga tattggtgct   660
ggaaaaggca atactatgc tgtcaatttt ccaatgagag atggtataga tgatgagtca   720
tatgggcaga tatttaagcc tattatctca aaggtgatgg agatgtatca acctagtgct   780
gtggtattac agtgtggtgc agactcatta tctggtgata actgggttg tttcaatcta   840 acagtcaaag gtcatgctaa atgtgtagaa gttgtaaaaa ctttaactt accattactg   900 atgcttggag gaggtggcta cacaatccgt aatgttgctc gatgttggac atatgagact   960
gcagttgccc ttgattgtga gattcccaat gagttgccat ataatgatta ctttgagtat  1020
tttggaccag acttcaaact gcatattagt ccttcaaaca tgacaaacca gaacactcca  1080
gaatatatgg aaaagataaa acagcgtttg tttgaaaatt tgcgcatgtt acctcatgca  1140
cctggtgtcc agatgcaagc tattccagaa gatgctgttc atgaagacag tggagatgaa  1200
gatggagaag atccagacaa gagaatttct attcgagcat cagacaagcg gatagcttgt  1260
gatgaagaat tctcagattc tgaggatgaa ggagaaggag tcgaagaaa tgtggctgat  1320 cataagaaag gagcaaagaa agctagaatt gaagaagata agaaagaaac agaggacaaa  1380
aaaacagacg ttaaggaaga agataaatcc aaggacaaca gtggtgaaaa aacagatacc  1440
aaaggaacca atcagaaca gctcagcaac cccgggcatc accatcacca tcactaa       1497

<210> SEQ ID NO 3
<211> LENGTH: 495
<212> TYPE: PRT
```

<213> ORGANISM: Artificial sequence
<220> FEATURE:
<223> OTHER INFORMATION: Amino acid sequence for full length human HDAC-2 with a C-terminal 6x-histidine tag

<400> SEQUENCE: 3

```
Met Ala Tyr Ser Gln Gly Gly Gly Lys Lys Val Cys Tyr Tyr Tyr
1               5                   10                  15

Asp Gly Asp Ile Gly Asn Tyr Tyr Tyr Gly Gln Gly His Pro Met Lys
            20                  25                  30

Pro His Arg Ile Arg Met Thr His Asn Leu Leu Leu Asn Tyr Gly Leu
        35                  40                  45

Tyr Arg Lys Met Glu Ile Tyr Arg Pro His Lys Ala Thr Ala Glu Glu
    50                  55                  60

Met Thr Lys Tyr His Ser Asp Glu Tyr Ile Lys Phe Leu Arg Ser Ile
65                  70                  75                  80

Arg Pro Asp Asn Met Ser Glu Tyr Ser Lys Gln Met Gln Arg Phe Asn
                85                  90                  95

Val Gly Glu Asp Cys Pro Val Phe Asp Gly Leu Phe Glu Phe Cys Gln
            100                 105                 110

Leu Ser Thr Gly Gly Ser Val Ala Gly Ala Val Lys Leu Asn Arg Gln
        115                 120                 125

Gln Thr Asp Met Ala Val Asn Trp Ala Gly Gly Leu His His Ala Lys
    130                 135                 140

Lys Ser Glu Ala Ser Gly Phe Cys Tyr Val Asn Asp Ile Val Leu Ala
145                 150                 155                 160

Ile Leu Glu Leu Leu Lys Tyr His Gln Arg Val Leu Tyr Ile Asp Ile
                165                 170                 175

Asp Ile His His Gly Asp Gly Val Glu Glu Ala Phe Tyr Thr Thr Asp
            180                 185                 190

Arg Val Met Thr Val Ser Phe His Lys Tyr Gly Glu Tyr Phe Pro Gly
        195                 200                 205

Thr Gly Asp Leu Arg Asp Ile Gly Ala Gly Lys Gly Lys Tyr Tyr Ala
    210                 215                 220

Val Asn Phe Pro Met Arg Asp Gly Ile Asp Asp Glu Ser Tyr Gly Gln
225                 230                 235                 240

Ile Phe Lys Pro Ile Ile Ser Lys Val Met Glu Met Tyr Gln Pro Ser
                245                 250                 255

Ala Val Val Leu Gln Cys Gly Ala Asp Ser Leu Ser Gly Asp Arg Leu
            260                 265                 270

Gly Cys Phe Asn Leu Thr Val Lys Gly His Ala Lys Cys Val Glu Val
        275                 280                 285

Val Lys Thr Phe Asn Leu Pro Leu Leu Met Leu Gly Gly Gly Gly Tyr
    290                 295                 300

Thr Ile Arg Asn Val Ala Arg Cys Trp Thr Tyr Glu Thr Ala Val Ala
305                 310                 315                 320

Leu Asp Cys Glu Ile Pro Asn Glu Leu Pro Tyr Asn Asp Tyr Phe Glu
                325                 330                 335

Tyr Phe Gly Pro Asp Phe Lys Leu His Ile Ser Pro Ser Asn Met Thr
            340                 345                 350

Asn Gln Asn Thr Pro Glu Tyr Met Glu Lys Ile Lys Gln Arg Leu Phe
        355                 360                 365

Glu Asn Leu Arg Met Leu Pro His Ala Pro Gly Val Gln Met Gln Ala
    370                 375                 380
```

```
Ile Pro Glu Asp Ala Val His Glu Asp Ser Gly Asp Glu Asp Gly Glu
385                 390                 395                 400

Asp Pro Asp Lys Arg Ile Ser Ile Arg Ala Ser Asp Lys Arg Ile Ala
                405                 410                 415

Cys Asp Glu Glu Phe Ser Asp Ser Glu Asp Gly Glu Gly Gly Arg
            420                 425                 430

Arg Asn Val Ala Asp His Lys Lys Gly Ala Lys Lys Ala Arg Ile Glu
                435                 440                 445

Glu Asp Lys Lys Glu Thr Glu Asp Lys Lys Thr Asp Val Lys Glu Glu
            450                 455                 460

Asp Lys Ser Lys Asp Asn Ser Gly Glu Lys Thr Asp Thr Lys Gly Thr
465                 470                 475                 480

Lys Ser Glu Gln Leu Ser Asn Pro Gly His His His His His
                485                 490                 495

<210> SEQ ID NO 4
<211> LENGTH: 378
<212> TYPE: PRT
<213> ORGANISM: Homo sapiens
<220> FEATURE:
<221> NAME/KEY: Amino acid sequence for CLEC fragment of human HDAC-2
<222> LOCATION: (1)..(378)

<400> SEQUENCE: 4

Ser Gln Gly Gly Gly Lys Lys Lys Val Cys Tyr Tyr Tyr Asp Gly Asp
1               5                   10                  15

Ile Gly Asn Tyr Tyr Gly Gln Gly His Pro Met Lys Pro His Arg
            20                  25                  30

Ile Arg Met Thr His Asn Leu Leu Leu Asn Tyr Gly Leu Tyr Arg Lys
            35                  40                  45

Met Glu Ile Tyr Arg Pro His Lys Ala Thr Ala Glu Glu Met Thr Lys
        50                  55                  60

Tyr His Ser Asp Glu Tyr Ile Lys Phe Leu Arg Ser Ile Arg Pro Asp
65                  70                  75                  80

Asn Met Ser Glu Tyr Ser Lys Gln Met Gln Arg Phe Asn Val Gly Glu
                85                  90                  95

Asp Cys Pro Val Phe Asp Gly Leu Phe Glu Phe Cys Gln Leu Ser Thr
            100                 105                 110

Gly Gly Ser Val Ala Gly Ala Val Lys Leu Asn Arg Gln Gln Thr Asp
        115                 120                 125

Met Ala Val Asn Trp Ala Gly Gly Leu His His Ala Lys Lys Ser Glu
    130                 135                 140

Ala Ser Gly Phe Cys Tyr Val Asn Asp Ile Val Leu Ala Ile Leu Glu
145                 150                 155                 160

Leu Leu Lys Tyr His Gln Arg Val Leu Tyr Ile Asp Ile Asp Ile His
                165                 170                 175

His Gly Asp Gly Val Glu Glu Ala Phe Tyr Thr Thr Asp Arg Val Met
            180                 185                 190

Thr Val Ser Phe His Lys Tyr Gly Glu Tyr Phe Pro Gly Thr Gly Asp
        195                 200                 205

Leu Arg Asp Ile Gly Ala Gly Lys Gly Lys Tyr Tyr Ala Val Asn Phe
    210                 215                 220

Pro Met Arg Asp Gly Ile Asp Asp Glu Ser Tyr Gly Gln Ile Phe Lys
225                 230                 235                 240

Pro Ile Ile Ser Lys Val Met Glu Met Tyr Gln Pro Ser Ala Val Val
                245                 250                 255
```

```
Leu Gln Cys Gly Ala Asp Ser Leu Ser Gly Asp Arg Leu Gly Cys Phe
            260                 265                 270

Asn Leu Thr Val Lys Gly His Ala Lys Cys Val Glu Val Lys Thr
        275                 280                 285

Phe Asn Leu Pro Leu Met Leu Gly Gly Gly Tyr Thr Ile Arg
        290                 295                 300

Asn Val Ala Arg Cys Trp Thr Tyr Glu Thr Ala Val Ala Leu Asp Cys
305                 310                 315                 320

Glu Ile Pro Asn Glu Leu Pro Tyr Asn Asp Tyr Phe Glu Tyr Phe Gly
                325                 330                 335

Pro Asp Phe Lys Leu His Ile Ser Pro Ser Asn Met Thr Asn Gln Asn
                340                 345                 350

Thr Pro Glu Tyr Met Glu Lys Ile Lys Gln Arg Leu Phe Glu Asn Leu
                355                 360                 365

Arg Met Leu Pro His Ala Pro Gly Val Gln
                370                 375
```

```
<210> SEQ ID NO 5
<211> LENGTH: 405
<212> TYPE: PRT
<213> ORGANISM: Homo sapiens
<220> FEATURE:
<221> NAME/KEY: Amino acid sequence for immobilized Trypsin fragment of
      human HDAC-2
<222> LOCATION: (1)..(405)

<400> SEQUENCE: 5

Met Ala Tyr Ser Gln Gly Gly Lys Lys Lys Val Cys Tyr Tyr Tyr
1               5                   10                  15

Asp Gly Asp Ile Gly Asn Tyr Tyr Gly Gln Gly His Pro Met Lys
                20                  25                  30

Pro His Arg Ile Arg Met Thr His Asn Leu Leu Leu Asn Tyr Gly Leu
            35                  40                  45

Tyr Arg Lys Met Glu Ile Tyr Arg Pro His Lys Ala Thr Ala Glu Glu
    50                  55                  60

Met Thr Lys Tyr His Ser Asp Glu Tyr Ile Lys Phe Leu Arg Ser Ile
65                  70                  75                  80

Arg Pro Asp Asn Met Ser Glu Tyr Ser Lys Gln Met Gln Arg Phe Asn
                85                  90                  95

Val Gly Glu Asp Cys Pro Val Phe Asp Gly Leu Phe Glu Phe Cys Gln
            100                 105                 110

Leu Ser Thr Gly Gly Ser Val Ala Gly Ala Val Lys Leu Asn Arg Gln
        115                 120                 125

Gln Thr Asp Met Ala Val Asn Trp Ala Gly Gly Leu His His Ala Lys
    130                 135                 140

Lys Ser Glu Ala Ser Gly Phe Cys Tyr Val Asn Asp Ile Val Leu Ala
145                 150                 155                 160

Ile Leu Glu Leu Leu Lys Tyr His Gln Arg Val Leu Tyr Ile Asp Ile
                165                 170                 175

Asp Ile His His Gly Asp Gly Val Glu Glu Ala Phe Tyr Thr Thr Asp
            180                 185                 190

Arg Val Met Thr Val Ser Phe His Lys Tyr Gly Glu Tyr Phe Pro Gly
        195                 200                 205

Thr Gly Asp Leu Arg Asp Ile Gly Ala Gly Lys Gly Lys Tyr Tyr Ala
    210                 215                 220
```

-continued

```
Val Asn Phe Pro Met Arg Asp Gly Ile Asp Asp Glu Ser Tyr Gly Gln
225                 230                 235                 240

Ile Phe Lys Pro Ile Ile Ser Lys Val Met Glu Met Tyr Gln Pro Ser
                245                 250                 255

Ala Val Val Leu Gln Cys Gly Ala Asp Ser Leu Ser Gly Asp Arg Leu
            260                 265                 270

Gly Cys Phe Asn Leu Thr Val Lys Gly His Ala Lys Cys Val Glu Val
        275                 280                 285

Val Lys Thr Phe Asn Leu Pro Leu Leu Met Leu Gly Gly Gly Gly Tyr
        290                 295                 300

Thr Ile Arg Asn Val Ala Arg Cys Trp Thr Tyr Glu Thr Ala Val Ala
305                 310                 315                 320

Leu Asp Cys Glu Ile Pro Asn Glu Leu Pro Tyr Asn Asp Tyr Phe Glu
                325                 330                 335

Tyr Phe Gly Pro Asp Phe Lys Leu His Ile Ser Pro Ser Asn Met Thr
            340                 345                 350

Asn Gln Asn Thr Pro Glu Tyr Met Glu Lys Ile Lys Gln Arg Leu Phe
        355                 360                 365

Glu Asn Leu Arg Met Leu Pro His Ala Pro Gly Val Gln Met Gln Ala
    370                 375                 380

Ile Pro Glu Asp Ala Val His Glu Asp Ser Gly Asp Glu Asp Gly Glu
385                 390                 395                 400

Asp Pro Asp Lys Arg
                405
```